(12) United States Patent
Liu et al.

(10) Patent No.: US 10,927,107 B2
(45) Date of Patent: Feb. 23, 2021

(54) PHENYL [A]INDOLE[2,3-G]QUINOLIZINE COMPOUNDS, PREPARATION METHOD THEREFOR, PHARMACEUTICAL COMPOSITION, AND APPLICATIONS THEREOF

(71) Applicant: Shanghai Institute of Materia Medica, Chinese Academy of Sciences, Shanghai (CN)

(72) Inventors: Hong Liu, Shanghai (CN); Yiping Wang, Shanghai (CN); Fei Zhao, Shanghai (CN); Jing Zhao, Shanghai (CN); Jiang Wang, Shanghai (CN); Cong Xi, Shanghai (CN); Chenglin Wu, Shanghai (CN); Hao Shen, Shanghai (CN); Xu Han, Shanghai (CN); Hualiang Jiang, Shanghai (CN); Kaixian Chen, Shanghai (CN)

(73) Assignee: Shanghai Institute of Materia Medica, Chinese Academy of Sciences, Shanghai (CN)

(*) Notice: Subject to any disclaimer, the term of this patent is extended or adjusted under 35 U.S.C. 154(b) by 0 days.

(21) Appl. No.: 16/089,713

(22) PCT Filed: Mar. 29, 2017

(86) PCT No.: PCT/CN2017/078616
§ 371 (c)(1),
(2) Date: Jan. 17, 2019

(87) PCT Pub. No.: WO2017/167202
PCT Pub. Date: Oct. 5, 2017

(65) Prior Publication Data
US 2019/0194185 A1 Jun. 27, 2019

(30) Foreign Application Priority Data
Mar. 30, 2016 (CN) .......................... 201610192571.9

(51) Int. Cl.
| C07D 459/00 | (2006.01) |
| C07D 495/22 | (2006.01) |
| A61K 31/4745 | (2006.01) |
| C07D 491/22 | (2006.01) |
| C07D 471/14 | (2006.01) |
| A61P 3/06 | (2006.01) |

(52) U.S. Cl.
CPC ........ *C07D 459/00* (2013.01); *A61K 31/4745* (2013.01); *A61P 3/06* (2018.01); *C07D 471/14* (2013.01); *C07D 491/22* (2013.01); *C07D 495/22* (2013.01)

(58) Field of Classification Search
CPC .. C07D 459/00; C07D 471/14; C07D 491/22; C07D 495/22; A61P 3/06; A61K 31/4745
See application file for complete search history.

(56) References Cited

U.S. PATENT DOCUMENTS 3,772,306 A 11/1973 Morrison et al.

FOREIGN PATENT DOCUMENTS

| CN | 103664974 | * | 3/2014 |
| CN | 103664974 A | | 3/2014 |

OTHER PUBLICATIONS

International Search Report and Written Opinion for Application No. PCT/CN2017/078616, dated Jul. 4, 2017.
International Preliminary Report on Patentability for Application No. PCT/CN2017/078916, dated Oct. 11, 2018.
Guo et al., Design, Synthesis, and Biological Evaluation of Novel Tetrahydroprotoberberine Derivatives (THPBs) as Selective α(1A)-Adrenoceptor Antagonists. J Med Chem. Oct. 27, 2016;59(20):9489-9502. Abstract Only.
Liu et al., Inhibition of proprotein convertase subtilisin/kexin type 9: a novel mechanism of berberine and 8-hydroxy dihydroberberine against hyperlipidemia. Chin J Intergr Med. Feb. 2015;21(2):132-8. doi: 10.1007/s11655-014-1775-1. Epub Jun. 3, 2014. Abstract Only.

* cited by examiner

*Primary Examiner* — Timothy R Rozof
(74) *Attorney, Agent, or Firm* — Wolf, Greenfield & Sacks, P.C.

(57) ABSTRACT

The present invention relates to phenyl [a]indole[2,3-g] quinolizine compounds represented by formula (I), a preparation method therefor, a pharmaceutical composition, and applications thereof. Specific applications are applications in the preparation of drugs for treating diseases related to a proprotein convertase subtilisin Kexin-9 (PCSK9), comprising the applications in the preparation of drugs for treating hyperlipemia, hypercholesterolemia, hypertriglyceridemia, fatty liver deformation, atherosclerosis, obesity and other metabolic diseases.

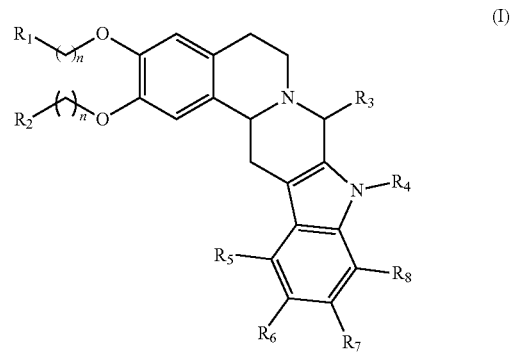

(I)

17 Claims, No Drawings

PHENYL [A]INDOLE[2,3-G]QUINOLIZINE COMPOUNDS, PREPARATION METHOD THEREFOR, PHARMACEUTICAL COMPOSITION, AND APPLICATIONS THEREOF

CROSS-REFERENCE TO RELATED APPLICATIONS

This Application is a national stage filing under 35 U.S.C. § 371 of International Patent Application Serial No. PCT/CN2017/078616, filed Mar. 29, 2017, which claims the benefit of priority to Chinese Patent Application Serial Number 201610192571.9, filed Mar. 30, 2016, the entire contents of each of which are incorporated by reference herein.

FIELD OF THE INVENTION

The invention relates to the field of medicinal chemistry and chemotherapy. Specifically, the present invention relates to a phenyl [a] indole [2,3-g] quinazine compound of formula (I) and a derivative thereof, a preparation method thereof, a pharmaceutical composition and the application thereof in the prevention and treatment of hyperlipidemia, hypercholesterolemia, hypertriglyceridemia, fatty liver deformation, atherosclerosis, obesity and other metabolic diseases thereof.

BACKGROUND OF THE INVENTION

Hyperlipidemia is a major risk factor for cardiovascular disease. High blood lipid levels can directly cause diseases that seriously endanger human health, such as atherosclerosis, coronary heart disease and so on. The clinical manifestations of hyperlipidemia are mainly yellow tumors caused by the deposition of lipid in the dermis and the arteriosclerosis caused by deposition of lipids in the vascular endothelium. Although hyperlipidemia can cause yellow tumors, it is of low incidence; and the occurrence and development of atherosclerosis is a slow and gradual process. Therefore, under normal circumstances, most patients do not show obvious symptoms and abnormal signs. Many people were found to have elevated levels of plasma lipoproteins when they were tested for blood biochemistry for other reasons. Deaths from cardiovascular disease account for a quarter of all deaths, which is equivalent to one death from cardiovascular disease every three minutes.

At present, the main lipid-lowering drugs are statins. However, during clinical use, it was found that approximately 20% of patients were unable to tolerate side effects of statins, such as muscle soreness and forgetfulness.

In recent years, new lipid-lowering targets represented by PCSK9 have received more and more attention. Remarkable progresses in the research of PCSK9 inhibitors have also been achieved, and they are expected to become new revolutionary lipid-lowering drugs. PCSK9 is mainly regulated by the transcription factor, Sterol Response Element Binding Protein-2 (SREBP-2), and exists as a precursor of soluble zymogen in the endoplasmic reticulum of hepatocytes and the like, and form mature PCSK9 through self-catalyzation and hydrolyzation and secreted into plasma. Plasma LDL-c is uptaken by LDLR expressed on the surface of hepatocytes, endocytosed into cells, and degraded in lysosomes. PCSK9 can compete with LDL-c for binding to LDLR, thereby mediating the degradation of LDLR and causing elevated plasma LDL-c levels. Therefore, PCSK9 plays a key regulatory role in maintaining cholesterol homeostasis. Inhibition of PCSK9 can significantly reduce LDL-C levels in vivo. These findings have attracted interest in the development of PCSK9 inhibitors.

There are currently about 10 pharmaceutical companies producing or developing PCSK9 inhibitors, including Sanofi, Amgen, Novartis, Pfizer and Bristol-Myers Squibb. Among them, about half of the PCSK9 inhibitors are monoclonal antibodies, and at the leading stage of drug clinical research. As a lipid-lowering drug, PCSK9 monoclonal antibody has many advantages, such as high specificity to target, longer half-life, and greatly reduced drug frequency. More importantly, PCSK9 monoclonal antibodies have shown promising results in previous clinical trials. According to the 2015 American Lipid Association (NLA) Clinical Lipid Annual Summary Report, 270 patients with hyperlipidemia and coronary heart disease were investigated in domestic hospitals. PCSK9 can rapidly and stably reduce the plasma LDL-C level, whenever used as an adjunct to statins or as a monotherapy, and none of the 270 cases showed significant adverse reactions, and there was no discomfort or ineffectiveness caused by statin tolerance. PCSK9 monoclonal antibodies can also improve other lipoprotein indicators that cause cardiovascular risk, such as non-HDL-C, apolipoprotein B, lipoprotein a, etc. Taking the possibility of gradually expanding the scope of treatment into consideration, such as treatment of early onset coronary heart disease and increased levels of lipoprotein B and lipoprotein a, even the patients can be extended to patients with diabetes and metabolic syndrome. In future, it is especially suitable for high-risk patients who do not achieve lipid-lowering goals by using statins or who cannot tolerate statins, as well as familial hypercholesterolemia patients. There are two problems for monoclonal antibody drugs: too expensive for patients, and it can not be taken orally (single dosage form), which lead to problems that whether many patients, especially asymptomatic hyperlipidemia, can accept long-term treatment with subcutaneous or intravenous every 2 or 4 weeks. However, the development of small molecule PCSK9 inhibitors is relatively rare, and the development of a novel structure of PCSK9 small molecule inhibitors is currently a research hotspot of lipid-lowering drugs.

SUMMARY OF THE INVENTION

The present invention relates to a novel phenyl [a]indole [2,3-g]quinolizine compound and a preparation method thereof, while some of the compounds show their use in the prevention and treatment of hyperlipidemia, hypercholesterolemia, hypertriglyceridemia, fatty liver deformation, atherosclerosis, obesity and other metabolic diseases thereof. The compounds disclosed herein also reduce total cholesterol, LDL-cholesterol and triglycerides, and increase hepatic LDL receptor expression, inhibit PCSK9 expression, and activate AMP-activated protein kinases.

In the first aspect of the present invention, a phenyl [a] indole [2,3-g] quinazine compound of formula (I), or a enantiomer, diastereomer, racemate, and mixture thereof, a pharmaceutically acceptable salt, crystalline hydrate and solvate thereof is provided,

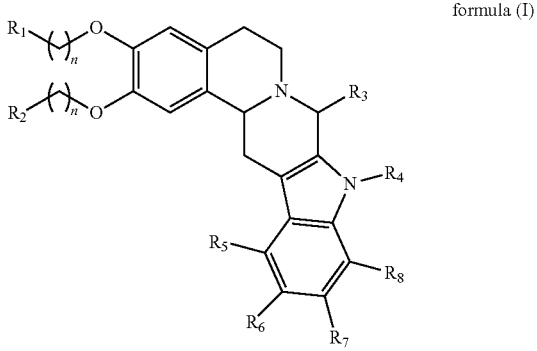

formula (I)

wherein $R_1$ and $R_2$ are each independently selected from the group consisting of hydrogen, deuterium, tritium, halogen, a substituted or unsubstituted C1-C6 alkyl, substituted or unsubstituted C1-C6 alkoxy, substituted or unsubstituted C6-C10 aryl, substituted or unsubstituted 5-7 membered heterocyclic ring, substituted or unsubstituted C1-C6 alkylphenyl, substituted or unsubstituted C1-C6 alkyl (5-7 membered heteroaryl), substituted or unsubstituted C3-C12 cycloalkyl, substituted or unsubstituted C2-C10 acyl, substituted or unsubstituted C2-C10 ester group, amino group, substituted or unsubstituted C1-C6 amide group, —$SO_2R_9$, —$OSO_2R_9$, —$OCOR_9$; and not both of $R_1$ and $R_2$ are hydrogen;

or the $R_1$ and $R_2$ and the adjacent —$(CH_2)_n$—O and C=C together form a substituted or unsubstituted 5-7 membered heterocyclic ring, wherein the heterocyclic ring is a fully saturated heterocyclic ring, partially unsaturated heterocyclic ring or aromatic heterocyclic ring;

$R_3$, $R_4$ are each independently selected from the group consisting of hydrogen, deuterium, tritium, halogen, amine, hydroxy, a substituted or unsubstituted C1-C6 alkyl, substituted or unsubstituted C1-C6 alkoxy, substituted or unsubstituted C6-C10 aryl, substituted or unsubstituted 5-7 membered heterocyclic ring, substituted or unsubstituted C1-C6 alkylphenyl, substituted or unsubstituted C3-C12 cycloalkyl, substituted or unsubstituted C2-C10 acyl, substituted or unsubstituted C2-C10 ester group, amino, C1-C6 alkylamino, substituted or unsubstituted C1-C6 amide group, —$SO_2R_9$, —$OSO_2R_9$, —$OCOR_9$;

$R_5$, $R_6$, $R_7$ and $R_8$ are each independently selected from the group consisting of hydrogen, deuterium, tritium, halogen, hydroxy, a substituted or unsubstituted C1-C6 alkyl, substituted or unsubstituted C1-C6 alkoxy, substituted or unsubstituted C3-C12 cycloalkyl, cyano, nitro, carboxyl, sulfydryl, —$NR_9R_{10}$, —$NCOR_9R_{10}$, —$SO_2R_9$, —$SO_2NR_9R_{10}$, —$OSO_2R_9$ and —$OCOR_9$;

$R_9$ and $R_{10}$ are independently hydrogen, deuterium, tritium, halogen, an unsubstituted or 1-3 halogen substituted C1-C6 alkyl, or C3-C6 cycloalkane unsubstituted or substituted by 1-3 halogens, C6-C10 aryl unsubstituted or substituted by 1 to 3 halogens, C1-C3 alkyl-(C6-C10 aryl) unsubstituted or substituted by 1-3 halogens, 5-7 membered heteroaryl unsubstituted or substituted by 1-3 halogens;

And when both of $R_3$ and $R_4$ are hydrogen, at least one of $R_1$, $R_2$, $R_6$, $R_7$ is a group selected from the group consisting of a substituted C6-C10 aryl, substituted 5-7-membered heterocyclic ring, —$OSO_2R_9$;

wherein the "substituted" refers to one or more hydrogen atoms on the group are substituted with a substituent selected from the group consisting of halogen, a C1-C6 alkyl unsubstituted or substituted by halogen or C3-C6 (preferably C1-C4) cycloalkyl, C1-C4 alkoxy, C3-C6 cycloalkyl, C1-C4 linear or branched alkyl-substituted amine group, hydroxy, cyano, nitro, oxygen atom (=O), hydroxy-C1-C6 alkyl, carboxyl, sulfydryl, C6-C10 aryl unsubstituted or substituted by 1 to 3 halogens or hydroxy groups, unsubstituted or halogenated 5-7 membered heterocyclic ring, unsubstituted or halogenated C2-C6 acyl, C1-C6 hydroxyalkyl, —$NR_9R_{10}$, —$NCOR_9R_{10}$, —$SO_2R_9$, —$OSO_2R_9$, —$SO_2NR_9R_{10}$, —$COOR_9$ and —$OCOR_9$;

n is 0 or 1.

In another preferred embodiment, the phenyl[a]indolo[2,3-g]quinoline compound has the following formula R-(I) or formula S-(I):

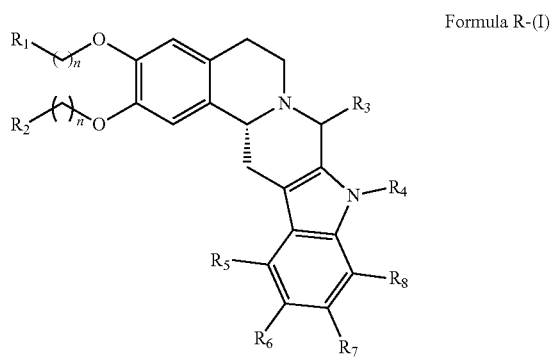

Formula R-(I)

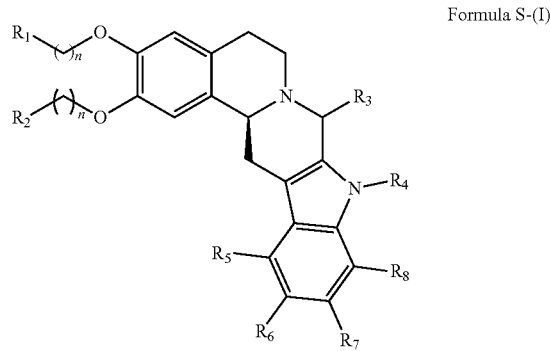

Formula S-(I)

In another preferred embodiment, the $R_3$ is hydrogen or a substituted or unsubstituted C1-C6 alkyl, and the $R_4$ is selected from the group consisting of a substituted or unsubstituted C1-C6 alkyl, substituted or unsubstituted C1-C6 alkoxy, substituted or unsubstituted C1-C6 alkylphenyl, substituted or unsubstituted 5-7-membered heterocyclic ring, substituted or unsubstituted C3-C12 cycloalkyl, substituted or unsubstituted C2-C10 acyl, substituted or unsubstituted C2-C10 ester group, —$OSO_2R_9$.

In another preferred embodiment, the $R_4$ is a C1-C6 alkyl substituted with a group selected from the group consisting of hydroxyl, —$OCOR_9$, —$OSO_2R_9$; preferably, the $R_9$ is halogen (preferably F)-substituted phenyl.

In another preferred embodiment, the $R_4$ is hydrogen, and the $R_3$ is selected from the group consisting of a substituted or unsubstituted C6-C10 aryl, substituted or unsubstituted 5-7 membered heterocyclic ring, substituted or unsubstituted C1-C6 alkylphenyl, substituted or unsubstituted C3-C12 cycloalkyl.

In another preferred embodiment, in the $R_3$, the aryl is phenyl group, and the heterocyclic ring is 5-membered heteroaryl ring.

In another preferred embodiment, the $R_3$ and $R_4$ are H, and at least one of $R_1$ and $R_2$ is a group selected from the group consisting of a substituted or unsubstituted C6-C10 aryl, substituted or unsubstituted 5-7 membered heterocyclic ring, substituted or unsubstituted C1-C6 alkylphenyl group, substituted or unsubstituted C1-C6 alkyl-(5-7 membered heteroaryl), substituted or unsubstituted C3-C12 cycloalkyl, —SO$_2$R$_9$; or at least one of $R_5$, $R_6$, $R_7$ and $R_8$ is a group selected from the group consisting of a substituted or unsubstituted C6-C10 aryl, substituted or unsubstituted 5-7 membered heterocyclic ring, substituted or unsubstituted C1-C6 alkylphenyl, substituted or unsubstituted C1-C6 alkyl-(5-7 membered heteroaryl), substituted or unsubstituted C3-C12 cycloalkyl, —OSO$_2$R$_9$.

In another preferred embodiment, $R_1$ and $R_2$ are independently selected from the group consisting of hydrogen, deuterium, tritium, halogen, a substituted or unsubstituted C1-C6 alkyl, substituted or unsubstituted C6-C10 aryl;

or the $R_1$ and $R_2$ together form a substituted or unsubstituted 5-7 membered heterocyclic ring, wherein the heterocyclic ring is fully saturated heterocyclic ring, partially unsaturated heterocyclic ring or aromatic heterocyclic ring;

$R_3$ is selected from the group consisting of hydrogen, deuterium, tritium, halogen, a substituted or unsubstituted C6-C10 aryl, substituted or unsubstituted 5-7 membered heterocyclic ring;

$R_4$ is hydrogen, deuterium, tritium, halogen, a substituted or unsubstituted hydroxy-C1-C6 alkyl, substituted or unsubstituted C1-C6 alkylene-C2-C6 oxyacyl, substituted or unsubstituted C1-C6 alkylene-C2-C6 oxy (3-7 membered carbocyclic or heterocyclic sulfonyl);

$R_5$, $R_6$, $R_7$ and $R_8$ are each independently hydrogen, deuterium, tritium, halogen, a substituted or unsubstituted C1-C12 alkyl, substituted or unsubstituted C1-C12 alkoxy, substituted or unsubstituted C3-C6 cycloalkyl, C1-C6 alkoxy-substituted C1-C6 alkyl, C3-C6 cycloalkyl-substituted C1-C6 alkyl, hydroxyl, cyano, nitro, C1-C6 straight or branched hydroxyalkyl, carboxyl, sulfydryl, —NR$_9$R$_{10}$, —NCOR$_9$R$_{10}$, —SO$_2$R$_9$, —SO$_2$NR$_9$R$_{10}$, or —OCOR$_9$.

In another preferred embodiment, the compound is a compound selected from the table 1.

In a second aspect of the invention, a PCSK9 inhibitor is provided, which comprises a compound according to the first aspect of the invention, or a enantiomer, diastereomer, racemate, or mixture thereof, and a pharmaceutically acceptable salt, crystalline hydrate and solvate thereof.

In another preferred embodiment, the inhibitor is in vitro or in vivo inhibitor.

In the third aspect of the present invention, a preparation method of compound (I) of the first aspect of the present invention is provided, which comprises the following steps:

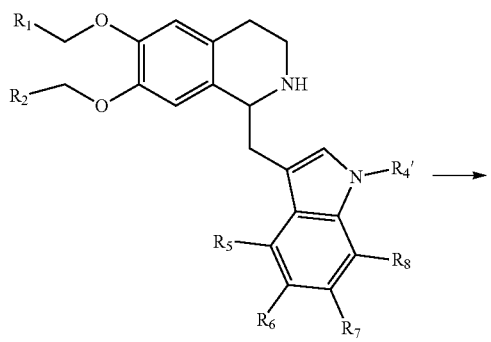

I-7

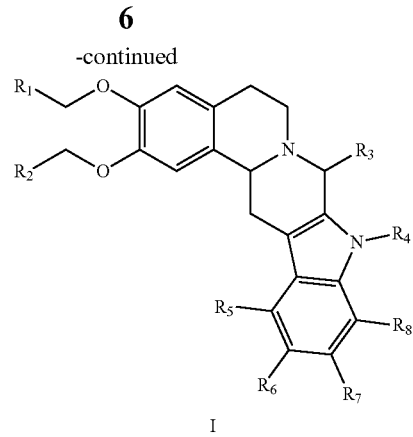

I

In an inert solvent, $R_3$—CHO reacts with a compound of formula I-7 to obtain a compound of formula I in the presence of formic acid;

Wherein $R_4'$ is of the same definition of $R_4$, while they may be the same or different;

While the remaining groups are defined as in the first aspect of the present invention.

In another preferred embodiment, the method comprises the following steps:

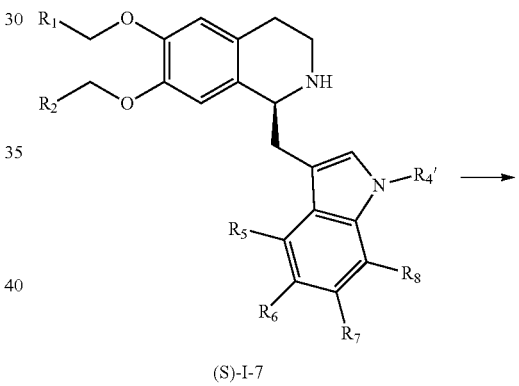

(S)-I-7

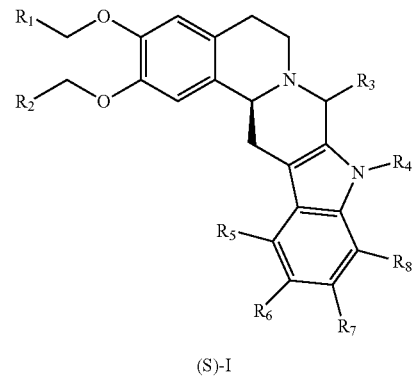

(S)-I

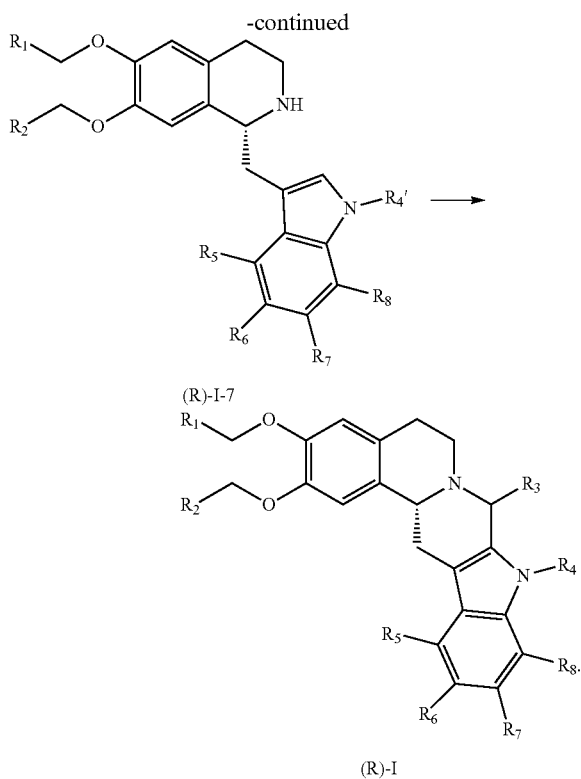

In the fourth aspect of the invention, a pharmaceutical composition is provided, which comprises (A) therapeutically efficient amount of one or more of a compound according to the first aspect of the invention, a enantiomer, diastereomer, racemate, mixtures thereof, and a pharmaceutically acceptable salt, crystalline hydrate and solvate thereof; and (B) a pharmaceutically acceptable carrier.

In the fifth aspect of the invention, the use of a compound according to the first aspect of the invention, or a enantiomer, diastereomer, racemate, or mixture thereof, and a pharmaceutically acceptable salt, crystalline hydrate and solvate thereof is provided, for the preparation of:

(i) a medicament for treating a disease associated with a preprotein convertase subtilisin Kexin-9 (PCSK9), wherein the PCSK9-related diseases include prevention and treatment of metabolic diseases such as hyperlipidemia, hypercholesterolemia, hypertriglyceridemia, fatty liver deformation, atherosclerosis, and obesity;

(ii) a medicament that reduces total cholesterol, LDL-cholesterol, and/or triglycerides;

(iii) a medicament that increases liver LDL receptor expression, inhibits PCSK9 expression, and/or activates AMP-activated protein kinase.

It should be understood that, in the present invention, each of the technical features specifically described above and below (such as those in the Examples) can be combined with each other, thereby constituting new or preferred technical solutions which need not be specified again herein.

EMBODIMENTS FOR CARRYING OUT THE INVENTION

After long-term and intensive research, the present inventors have unexpectedly discovered that phenyl[a]indolo[2,3-g]quinolizine compounds can be used as highly effective PCSK9 inhibitors, and can also lower total cholesterol, LDL-cholesterol and triglycerides, increase hepatic LDL receptor expression and activate protein kinases that activated by AMP. Moreover, the inhibitory activity of this type of inhibitor on α1A-AR is rather weak, so it can be used for prevention and treatment of metabolic diseases such as hyperlipidemia, hypercholesterolemia, hypertriglyceridemia, fatty liver deformation, atherosclerosis, and obesity. The present invention is completed based on the above findingd.

Terms

As used herein, unless otherwise specified, the term "substituted" means that one or more hydrogen atoms on the group are substituted with a substituent selected from the group consisting of halogen, amino, hydroxy, nitro, cyano, trifluoromethyl, a $C_1$-$C_{12}$ alkyl or cycloalkyl, $C_1$-$C_{12}$ alkoxy, oxygen atom (i.e., =O), $C_1$-$C_{12}$ alkylamino unsubstituted or substituted by $C_1$-$C_4$ alkylamino, $C_2$-$C_6$ acyl, $C_2$-$C_6$ amide group, sulfo-$C_1$-$C_{12}$ alkyl, carboxyl, $C_5$-$C_{12}$ aryl or heteroaryl, $C_5$-$C_{12}$ heterocyclic group (containing 1-5, preferably 1-3 heteroatoms selected from N, O or S).

Term "$C_1$-$C_{12}$ alkyl" refers to a linear or branched alkyl with 1 to 12 carbon atoms, such as methyl, ethyl, propyl, isopropyl, butyl, isobutyl, sec-butyl, tert-butyl, or similar groups.

Term "$C_1$-$C_{12}$ cycloalkyl" refers to a cyclic alkyl with 1-12, preferably 3-12 carbon atoms (i.e., $C_{3-12}$) such as cyclopropyl, cyclobutyl, cyclopentyl, cycloheptyl, or the like.

The term "$C_1$-$C_{12}$ alkoxy" refers to a straight or branched chain alkyl having 1 to 12 carbon atoms, such as methoxy, ethoxy, propoxy, isopropoxy, butoxy, iso-butoxy, sec-butoxy, tert-butoxy, or the like.

The term "halogen" refers to F, Cl, Br or I.

The term "$C_1$-$C_{12}$ alkylamino" refers to a $C_1$-$C_{12}$ alkyl substituted by amino, for example, a group having structure of "$C_1$-$C_{12}$ alkyl-NH—" or "(alkyl)$_2$-N-(the total number of carbon atoms is 1-12)", "—$C_1$-$C_{12}$ alkylene-NH$_2$", "alkyl-N-alkylene-(total number of carbon atoms is 1-12)", or "(alkyl)$_2$-N-alkylene-(the total number of carbon atoms is 1-12)", such as $CH_3NH$—, $C_2H_5NH$—, $C_3H_7NH$—, $(CH_3)_2N$—, —$CH_2NH_2$, —$C_2H_5NH_2$, —$C_3H_7NH_2$, —$C_2H_4N(CH_3)_2$, or the like. Among them, the definition of the C1-12 alkyl group is as described above.

The term "$C_2$-$C_6$ ester group" refers to a substituent in a form of "linear or branched alkyl/cycloalkyl/aryl/heteroaryl-carbonyl-oxy- with 1 to 5 carbon atoms", such as ethyl ester group, propyl ester group, butyl ester group, or the like.

As used herein, the term "$C_1$-$C_6$ acylamino" refers to a substituent in a form of "linear or branched alkyl/cycloalkyl/aryl/heteroaryl-carbonyl-amino- with 0-5 carbon atoms", such as acetamino group, propionamide group, butyramide group, or the like.

The term "$C_6$-$C_{10}$ aryl" refers to an aryl with 1-12 (preferably 6-10, i.e., $C_6$-10) carbon atoms, such as phenyl, naphthyl, or the like, the aryl can be substituted or unsubstituted.

The term "$C_1$-$C_{12}$ heteroaryl" refers to a heteroaryl having 1-12 carbon atoms and one or more (preferably 1-3) heteroatoms selected from O, S and/or N, preferably C5-C8 heteroaryl. The heteroaryl may be substituted or unsubstituted.

The term "5-7 membered heterocyclic ring" refers to a cyclic saturated, partially unsaturated or aromatic group having 5-7 members, wherein the heterocyclic ring has at least one ring atom selected from the group consisting of O, S and/or N.

The term "5-7 membered heteroaryl" refers to a cyclic aromatic group having 5-7 members, wherein the heterocyclic ring has at least one ring atom selected from the group consisting of O, S and/or N.

In particular, the expression "C1-Cn" means that a group has 1-n carbon atoms, for example, the expression "C1-C12" means that a group has 1, 2, 3, 4, 5, 6, 7, 8, 9, 10, 11 or 12 carbon atoms; "C6-C10" means that a group has 6, 7, 8, 9 or 10 carbon atoms.

The present invention, the term "pharmaceutically acceptable" component refers to substances which are suitable for applying to humans and/or animals without undue harmful side reactions (such as toxicity, stimulation or allergy), that is, substances of reasonable benefit/risk ratio.

In the present invention, the term "effective amount" refers to an amount in which the therapeutic agents can treat, relieve or prevent the target disease, or exhibit detectable therapeutic or preventive effects. The exact effective amount for a subject will depend on the size and health condition of the subject, the nature and extent of the disorder, and the the therapeutic agent and/or therapeutic agent combination selected for administration. Therefore, it is useless to specify an accurate effective amount in advance. However, for a given situation, the effective amount may be determined by routine experimentation, which can be determined by clinicians.

Unless otherwise indicated, all compounds in the invention are intended to include all possible optical isomers, such as single chiral compounds, or mixtures of various chiral compounds (i.e., racemates). In compounds of the present invention, each chiral carbon atom may optionally be in R configuration or S configuration, or the mixture of R configuration and S configuration.

As used herein, the term "compound of the invention" refers to formula I compound. The term also comprises the crystal forms, pharmaceutically acceptable salts, hydrates or solvates of compound of formula I.

As used herein, the term "pharmaceutically acceptable salts" refers to salts suitable for use in pharmaceutical which is formed by compound of the present invention with an acid or base. The pharmaceutically acceptable salts include inorganic and organic salts. A preferred type of salts are salts formed by the compounds of the present invention and acid. Suitable salt-forming acids include, but are not limited to: inorganic acids such as hydrochloric acid, hydrobromic acid, hydrofluoric acid, sulfuric acid, nitric acid, phosphoric acid; organic acids such as formic acid, acetic acid, propionic acid, oxalic acid, malonic acid, succinic acid, fumaric acid, maleic acid, lactic acid, malic acid, tartaric acid, citric acid, picric acid, methanesulfonic acid, toluenesulfonic acid, benzenesulfonic acid and the like; and acidic amino acids such as aspartic acid, glutamic acid.

Compound of Formula (I)

The present invention provides a compound of formula (I):

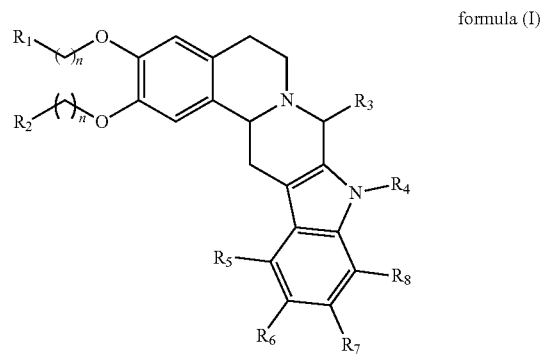

formula (I)

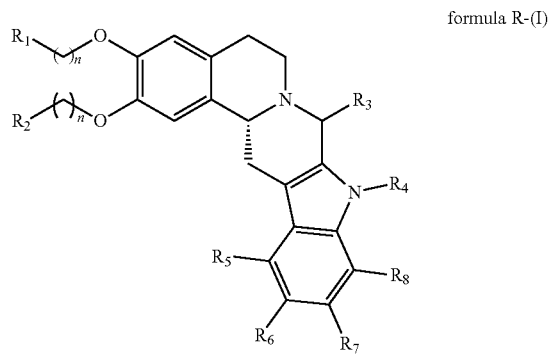

formula R-(I)

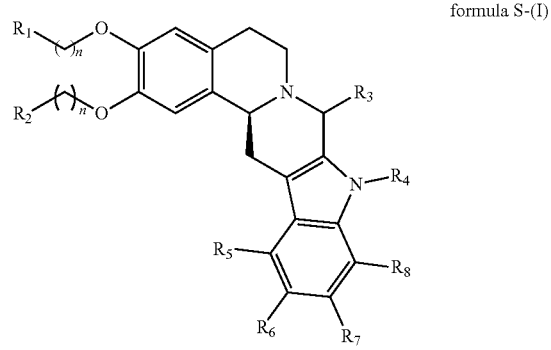

formula S-(I)

In another preferred embodiment, $R_1$, $R_2$, $R_3$, $R_4$, $R_5$, $R_6$, $R_7$, $R_8$, $R_9$ and $R_{10}$ and n are each independently the groups shown in the specific examples.

Meanwhile, the chiral carbon atom in the compound of formula (I) is R type and/or S type.

More preferably, the phenyl[a]indolo[2,3-g]quinolizine compound of the present invention is selected from the following compounds:

TABLE 1

| No. | Name | Structure |
|-----|------|-----------|
| A1 | (2-(benzyloxy)-3,12-dimethoxy-5,6,14,14a-tetrahydroindolo[3',2':4,5]pyridine[2,1-a]isoquinoline-9(8H)-yl)methanol | 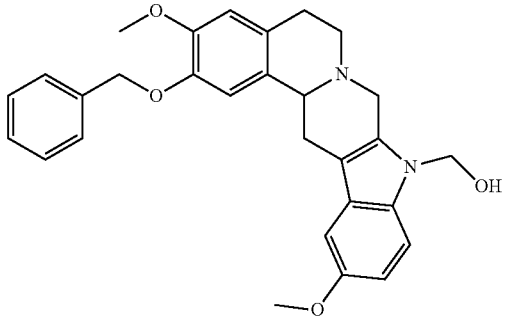 [SMILES: COc1ccc2c(c1)c1c(n2CO)CN2CCc3cc(OC)c(OCc4ccccc4)cc3C2C1]<br>A1 |
| A2 | (2-(benzyloxy)-3-methoxy-5,6,14,14a-tetrahydroindolo[3',2':4,5]pyridine[2,1-a]isoquinoline-9(8H)-yl)methanol | 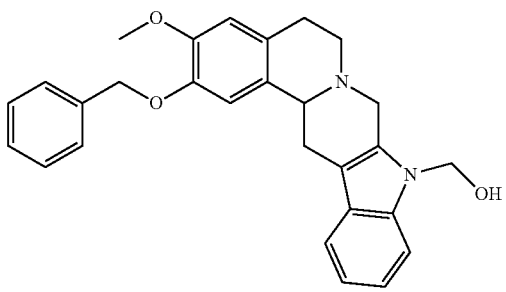 [SMILES: COc1cc2c(cc1OCc1ccccc1)C1Cc3c(n(CO)c4ccccc34)CN1CC2]<br>A2 |
| A3 | (3,12-dimethoxy-2-((4-(trifluoromethyl)benzyl)oxy)-5,6,14,14a-tetrahydroindolo[3',2':4,5]pyridine[2,1-a]isoquinoline-9(8H)-yl)methanol | 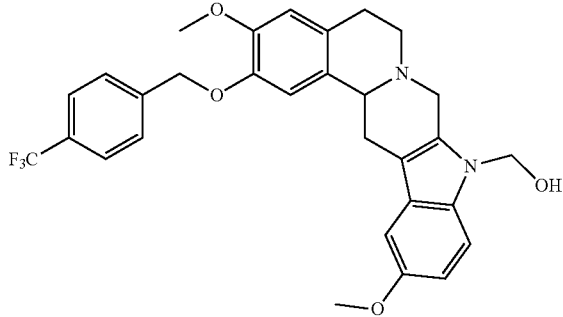 [SMILES: COc1ccc2c(c1)c1c(n2CO)CN2CCc3cc(OC)c(OCc4ccc(C(F)(F)F)cc4)cc3C2C1]<br>A3 |
| A4 | (3-methoxy-2-((4-(trifluoromethyl)benzyl)oxy)-5,6,14,14a-tetrahydroindolo[3',2':4,5]pyridine[2,1-a]isoquinoline-9(8H)-yl)methanol | 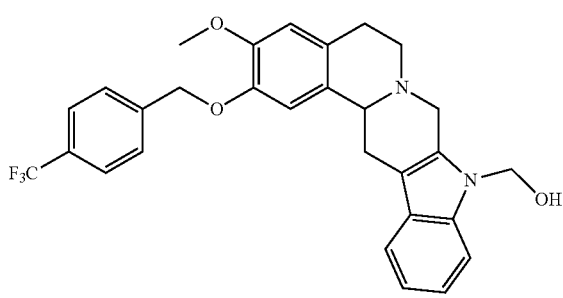 [SMILES: COc1cc2c(cc1OCc1ccc(C(F)(F)F)cc1)C1Cc3c(n(CO)c4ccccc34)CN1CC2]<br>A4 |

TABLE 1-continued

| No. | Name | Structure |
|---|---|---|
| A5 | (2-((4-fluorobenzyl)oxy)-3,12-dimethoxy-5,6,14,14a-tetrahydroindolo[3',2':4,5]pyridine[2,1-a]isoquinoline-9(8H)-yl)methanol | 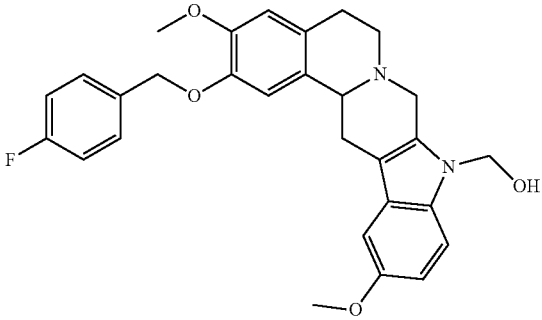 [SMILES: COc1ccc2c(c1)c1c(n2CO)CN2CCc3cc(OC)c(OCc4ccc(F)cc4)cc3C2C1]<br>A5 |
| A6 | (2-((4-fluorobenzyl)oxy)-3-methoxy-5,6,14,14a-tetrahydroindolo[3',2':4,5]pyridine[2,1-a]isoquinoline-9(8H)-yl)methanol | 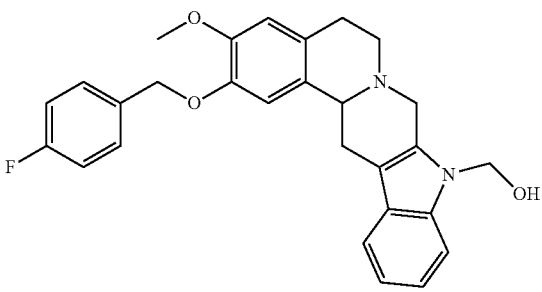<br>A6 |
| A7 | (2-((3-fluorobenzyl)oxy)-3,12-dimethoxy-5,6,14,14a-tetrahydroindolo[3',2':4,5]pyridine[2,1-a]isoquinoline-9(8H)-yl)methanol | 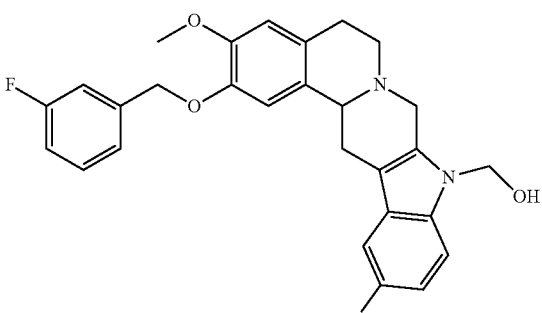<br>A7 |
| A8 | (2-((3-fluorobenzyl)oxy)-3-methoxy-5,6,14,14a-tetrahydroindolo[3',2':4,5]pyridine[2,1-a]isoquinoline-9(8H)-yl)methanol | 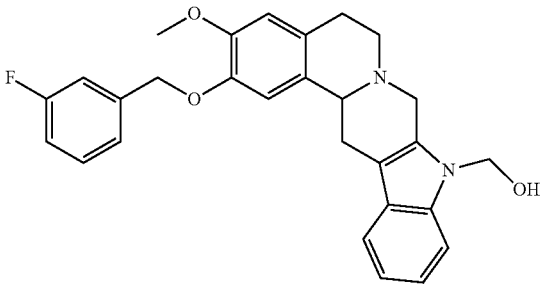 [SMILES: COc1cc2c(cc1OCc1cccc(F)c1)C1Cc3c(n(CO)c4ccccc34)CN1CC2]<br>A8 |

TABLE 1-continued

| No. | Name | Structure |
|---|---|---|
| A9 | (2-((2-fluorobenzyl)oxy)-3,12-dimethoxy-5,6,14,14a-tetrahydroindolo[3',2':4,5]pyridine[2,1-a]isoquinoline-9(8H)-yl)methanol | A9 |
| A10 | (2-((2-fluorobenzyl)oxy)-3-methoxy-5,6,14,14a-tetrahydroindolo[3',2':4,5]pyridine[2,1-a]isoquinoline-9(8H)-yl)methanol | A10 |
| A11 | (3,12-dimethoxy-2-((4-methoxybenzyl)oxy)-5,6,14,14a-tetrahydroindolo[3',2':4,5]pyridine[2,1-a]isoquinoline-9(8H)-yl)methanol | A11 |
| A12 | (3-methoxy-2-((4-methoxybenzyl)oxy)-5,6,14,14a-tetrahydroindolo[3',2':4,5]pyridine[2,1-a]isoquinoline-9(8H)-yl)methanol | A12 |

TABLE 1-continued

| No. | Name | Structure |
| --- | --- | --- |
| A13 | (3,12-dimethoxy-2-((3-methoxybenzyl)oxy)-5,6,14,14a-tetrahydroindolo[3',2':4,5]pyridine[2,1-a]isoquinoline-9(8H)-yl)methanol | 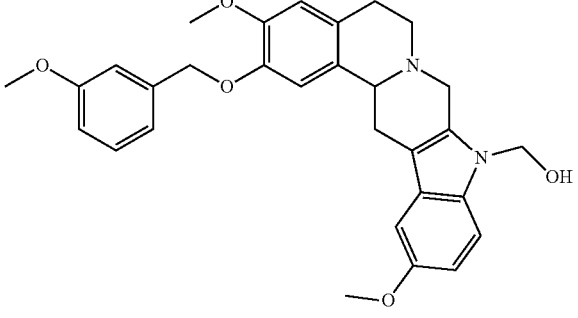<br>A13 |
| A14 | (3-methoxy-2-((3-methoxybenzyl)oxy)-5,6,14,14a-tetrahydroindolo[3',2':4,5]pyridine[2,1-a]isoquinoline-9(8H)-yl)methanol | 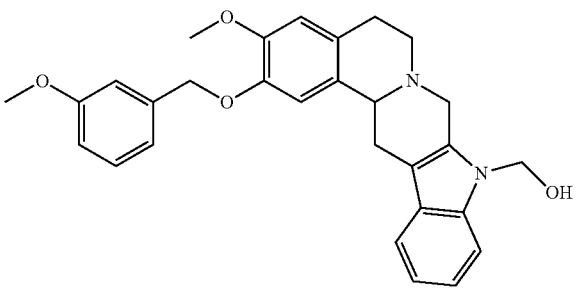 [SMILES: COc1cccc(COc2cc3c(cc2OC)CCN2Cc4c(c5ccccc5n4CO)CC32)c1]<br>A14 |
| A15 | (3,12-dimethoxy-2-((4-methylbenzyl)oxy)-5,6,14,14a-tetrahydroindolo[3',2':4,5]pyridine[2,1-a]isoquinoline-9(8H)-yl)methanol | 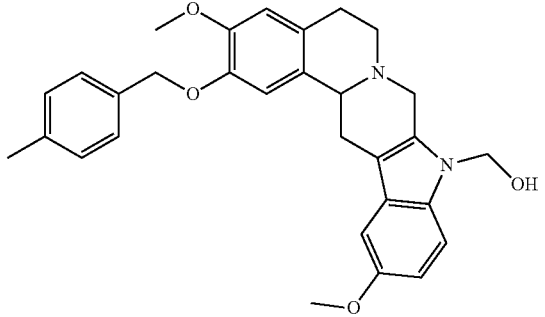 [SMILES: COc1ccc2c(c1)c1c(n2CO)CN2CCc3cc(OC)c(OCc4ccc(C)cc4)cc3C2C1]<br>A15 |
| A16 | (3-methoxy-2-((4-methylbenzyl)oxy)-5,6,14,14a-tetrahydroindolo[3',2':4,5]pyridine[2,1-a]isoquinoline-9(8H)-yl)methanol | 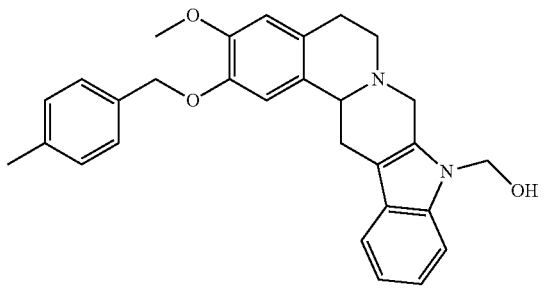 [SMILES: COc1cc2c(cc1OCc1ccc(C)cc1)C1Cc3c(n(CO)c4ccccc34)CN1CC2]<br>A16 |

TABLE 1-continued

| No. | Name | Structure |
|---|---|---|
| A17 | (2-((4-chlorobenzyl)oxy)-3,12-dimethoxy-5,6,14,14a-tetrahydroindolo[3',2':4,5]pyridine[2,1-a]isoquinoline-9(8H)-yl)methanol | 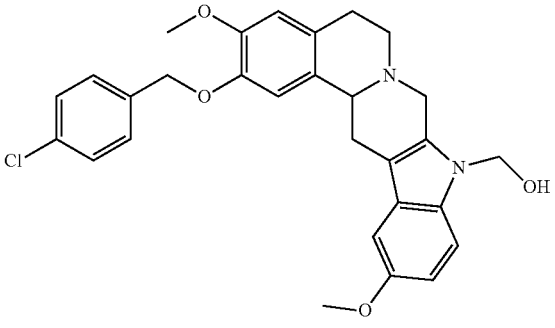 [SMILES: COc1ccc2c(c1)c1c(n2CO)CN2CCc3cc(OC)c(OCc4ccc(Cl)cc4)cc3C2C1]<br>A17 |
| A18 | (2-((4-chlorobenzyl)oxy)-3-methoxy-5,6,14,14a-tetrahydroindolo[3',2':4,5]pyridine[2,1-a]isoquinoline-9(8H)-yl)methanol | 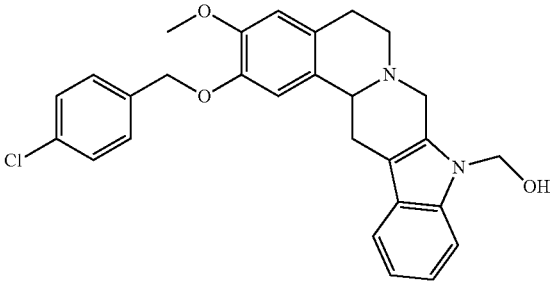 [SMILES: COc1cc2c(cc1OCc1ccc(Cl)cc1)C1Cc3c(n(CO)c4ccccc34)CN1CC2]<br>A18 |
| A19 | 4-(((9-(hydroxymethyl)-3,12-dimethoxy-5,6,8,9,14,14a-hexahydroindolo[3',2':4,5]pyridine[2,1-a]isoquinoline-2-yl)oxy)methyl)benzonitrile | 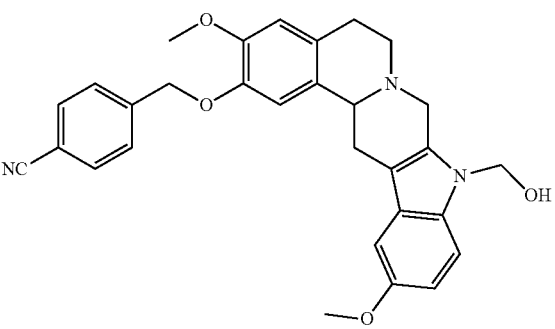 [SMILES: COc1ccc2c(c1)c1c(n2CO)CN2CCc3cc(OC)c(OCc4ccc(C#N)cc4)cc3C2C1]<br>A19 |
| A20 | 4-(((9-(hydroxymethyl)-3-methoxy-5,6,8,9,14,14a-hexahydroindolo[3',2':4,5]pyridine[2,1-a]isoquinoline-2-yl)oxy)methyl)benzonitrile | 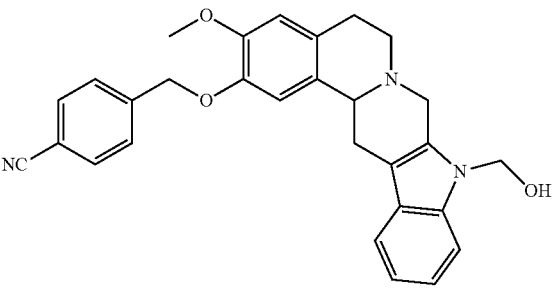 [SMILES: COc1cc2c(cc1OCc1ccc(C#N)cc1)C1Cc3c(n(CO)c4ccccc34)CN1CC2]<br>A20 |

TABLE 1-continued

| No. | Name | Structure |
|---|---|---|
| A21 | (2-((4-bromobenzyl)oxy)-3,12-dimethoxy-5,6,14,14a-tetrahydroindolo[3',2':4,5]pyridine[2,1-a]isoquinoline-9(8H)-yl)methanol | 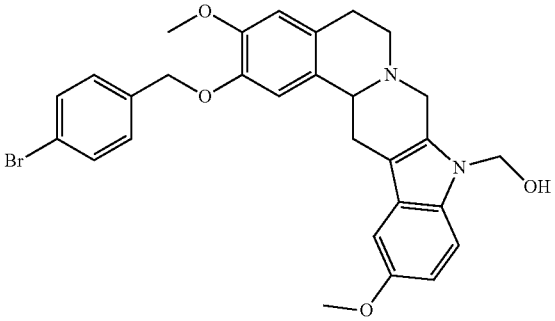<br>A21 |
| A22 | (2-((4-bromobenzyl)oxy)-3-methoxy-5,6,14,14a-tetrahydroindolo[3',2':4,5]pyridine[2,1-a]isoquinoline-9(8H)-yl)methanol | 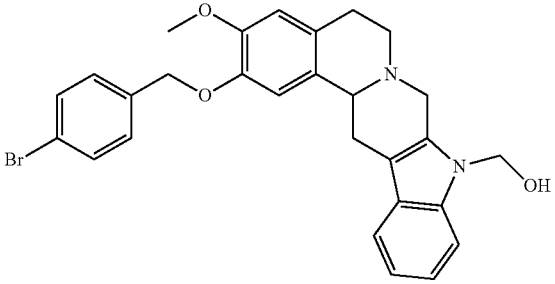<br>A22 |
| A23 | (2-((3-fluoro-4-(trifluoromethyl)benzyl)oxy)-3,12-dimethoxy-5,6,14,14a-tetrahydroindolo[3',2':4,5]pyridine[2,1-a]isoquinoline-9(8H)-yl)methanol | 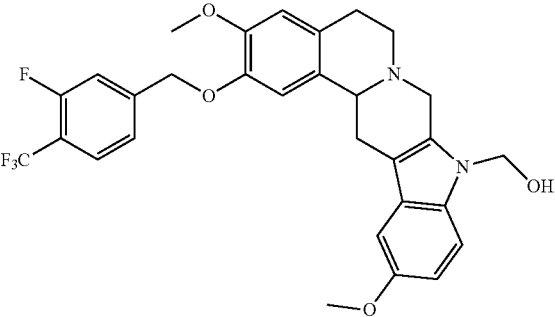 [SMILES: COc1ccc2c(c1)c1c(n2CO)CN2CCc3cc(OC)c(OCc4ccc(C(F)(F)F)c(F)c4)cc3C2C1]<br>A23 |
| A24 | (2-((3-fluoro-4-(trifluoromethyl)benzyl)oxy)-3-methoxy-5,6,14,14a-tetrahydroindolo[3',2':4,5]pyridine[2,1-a]isoquinoline-9(8H)-yl)methanol | 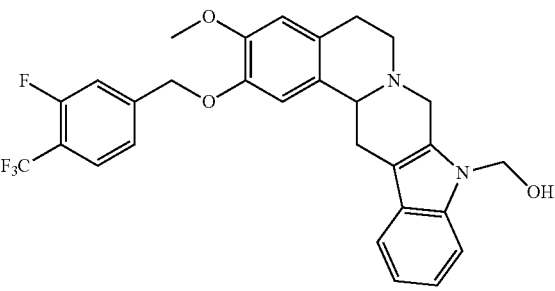 [SMILES: COc1cc2c(cc1OCc1ccc(C(F)(F)F)c(F)c1)C1Cc3c(n(CO)c4ccccc34)CN1CC2]<br>A24 |

TABLE 1-continued

| No. | Name | Structure |
|---|---|---|
| A25 | (2-((2-fluoro-4-(trifluoromethyl)benzyl)oxy)-3,12-dimethoxy-5,6,14,14a-tetrahydroindolo[3',2':4,5]pyridine[2,1-a]isoquinoline-9(8H)-yl)methanol | 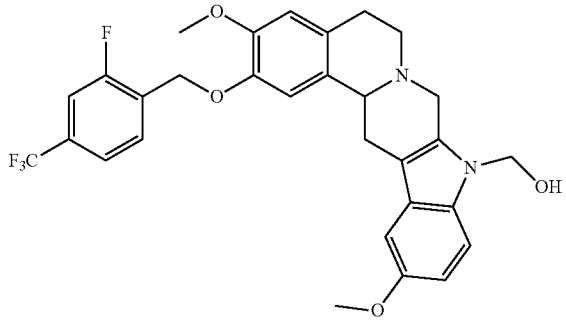 A25 |
| A26 | (2-((2-fluoro-4-(trifluoromethyl)benzyl)oxy)-3-methoxy-5,6,14,14a-tetrahydroindolo[3',2':4,5]pyridine[2,1-a]isoquinoline-9(8H)-yl)methanol | 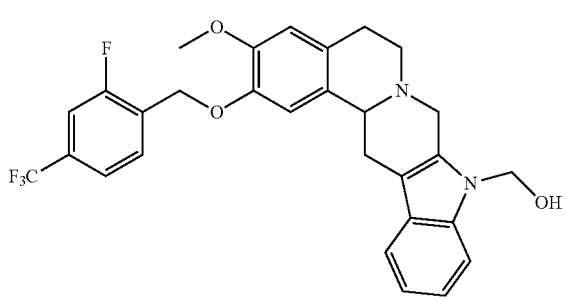 A26 |
| A27 | (3,12-dimethoxy-2-((4-ethylbenzyl)oxy)-5,6,14,14a-tetrahydroindolo[3',2':4,5]pyridine[2,1-a]isoquinoline-9(8H)-yl)methanol | 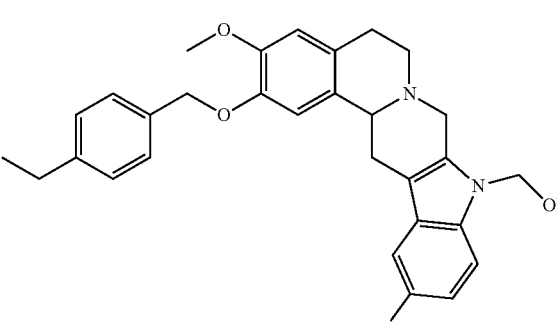 A27 |
| A28 | (3-methoxy-2-((4-ethylbenzyl)oxy)-5,6,14,14a-tetrahydroindolo[3',2':4,5]pyridine[2,1-a]isoquinoline-9(8H)-yl)methanol | 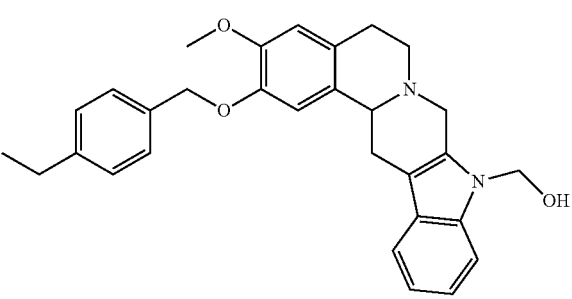 A28 |

TABLE 1-continued

| No. | Name | Structure |
|---|---|---|
| A29 | (3,12-dimethoxy-2-(naphthalen-2-ylmethoxy)-5,6,14,14a-tetrahydroindolo[3',2':4,5]pyridine[2,1-a]isoquinoline-9(8H)-yl)methanol | 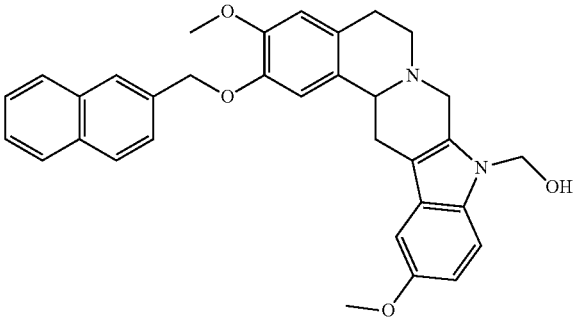 A29 |
| A30 | (3-methoxy-2-(naphthalen-2-ylmethoxy)-5,6,14,14a-tetrahydroindolo[3',2':4,5]pyridine[2,1-a]isoquinoline-9(8H)-yl)methanol | 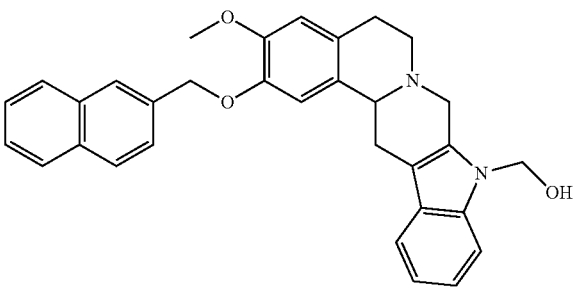 A30 |
| A31 | 4-(((9-(hydroxymethyl)-3,12-dimethoxy-5,6,8,9,14,14a-hexahydroindolo[3',2':4,5]pyridine[2,1-a]isoquinoline-2-yl)oxo)methyl)benzoate | 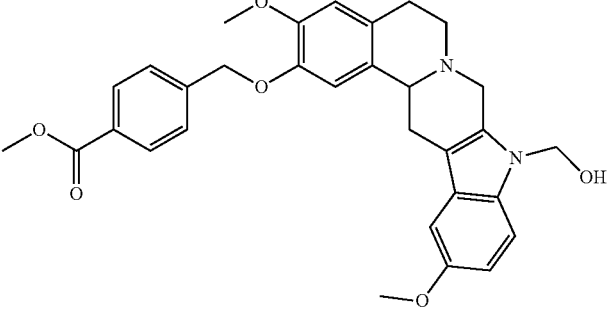 A31 |
| A32 | 4-(((9-(hydroxymethyl)-3-methoxy-5,6,8,9,14,14a-hexahydroindolo[3',2':4,5]pyridine[2,1-a]isoquinoline-2-yl)oxo)methyl)benzoate | 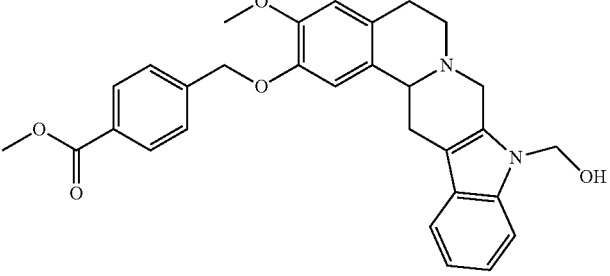 A32 |

TABLE 1-continued

| No. | Name | Structure |
| --- | --- | --- |
| A33 | (2-((4-(1H-pyrazol-1-yl)benzyl)oxy)-3,12-dimethoxy-5,6,14,14a-tetrahydroindolo[3',2':4,5]pyridine[2,1-a]isoquinoline-9(8H)-yl)methanol | 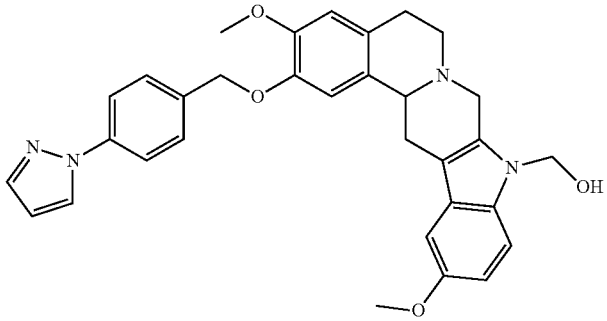 A33 |
| A34 | (2-((4-(1H-pyrazol-1-yl)benzyl)oxy)-3-methoxy-5,6,14,14a-tetrahydroindolo[3',2':4,5]pyridine[2,1-a]isoquinoline-9(8H)-yl)methanol | 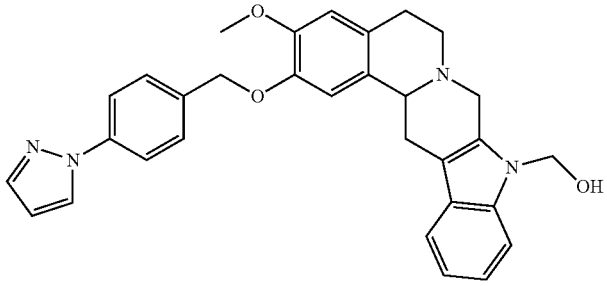 A34 |
| A35 | (2-butoxy-3,12-dimethoxy-5,6,14,14a-tetrahydroindolo[3',2':4,5]pyridine[2,1-a]isoquinoline-9(8H)-yl)methanol | 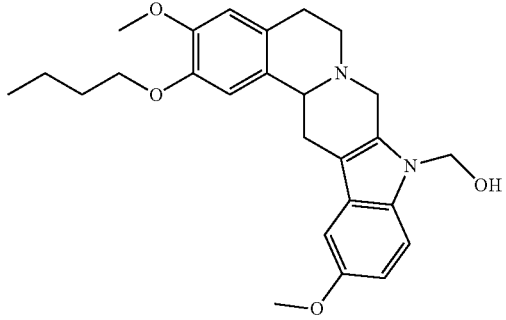 A35 |
| A36 | (2-butoxy-3-methoxy-5,6,14,14a-tetrahydroindolo[3',2':4,5]pyridine[2,1-a]isoquinoline-9(8H)-yl)methanol | 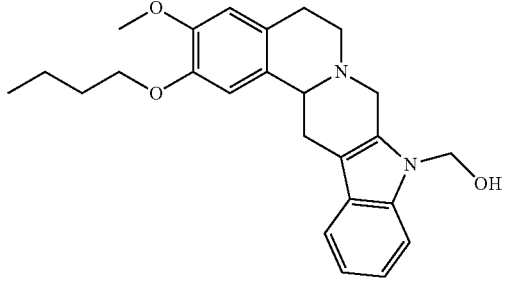 A36 |

TABLE 1-continued

| No. | Name | Structure |
|---|---|---|
| A37 | (2,3,12-trimethoxy-5,6,14,14a-tetrahydroindolo[3',2':4,5]pyridine[2,1-a]isoquinoline-9(8H)-yl)methanol | A37 |
| A38 | (2,3-dimethoxy-5,6,14,14a-tetrahydroindolo[3',2':4,5]pyridine[2,1-a]isoquinoline-9(8H)-yl)methanol | A38 |
| A39 | (3,12-dimethoxy-2-(2,2,2-trifluoroethoxy)-5,6,14,14a-tetrahydroindolo[3',2':4,5]pyridine[2,1-a]isoquinoline-9(8H)-yl)methanol | A39 |
| A40 | (3-methoxy-2-(2,2,2-trifluoroethoxy)-5,6,14,14a-tetrahydroindolo[3',2':4,5]pyridine[2,1-a]isoquinoline-9(8H)-yl)methanol | A40 |

TABLE 1-continued

| No. | Name | Structure |
|---|---|---|
| A41 | (3,12-dimethoxy-2-((4-(methylsulfonyl)benzyl)oxy)-5,6,14,14a-tetrahydroindolo[3',2':4,5]pyridine[2,1-a]isoquinoline-9(8H)-yl)methanol | 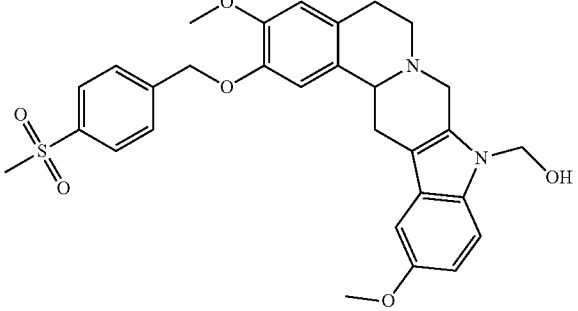 A41 |
| A42 | (3-methoxy-2-((4-(methylsulfonyl)benzyl)oxy)-5,6,14,14a-tetrahydroindolo[3',2':4,5]pyridine[2,1-a]isoquinoline-9(8H)-yl)methanol | 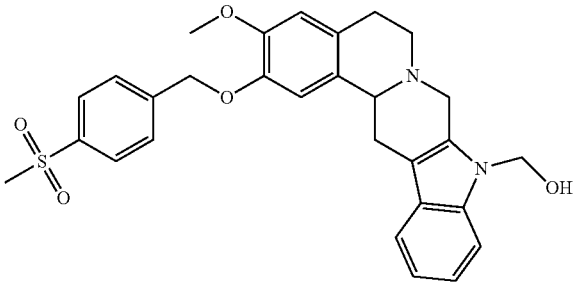 A42 |
| A43 | (2-(benzyloxy)-11-fluoro-3-methoxy-5,6,14,14a-tetrahydroindolo[3',2':4,5]pyridine[2,1-a]isoquinoline-9(8H)-yl)methanol | 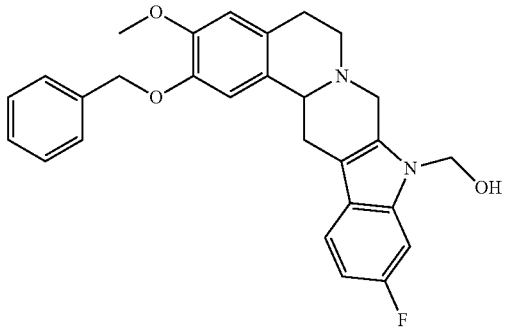 A43 |
| A44 | (2-(benzyloxy)-12-fluoro-3-methoxy-5,6,14,14a-tetrahydroindolo[3',2':4,5]pyridine[2,1-a]isoquinoline-9(8H)-yl)methanol | 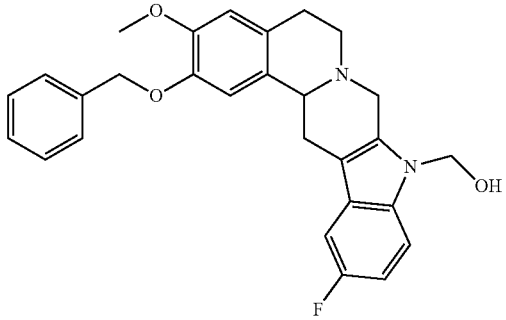 A44 |

TABLE 1-continued

| No. | Name | Structure |
|---|---|---|
| A45 | (2-(benzyloxy)-13-fluoro-3-methoxy-5,6,14,14a-tetrahydroindolo[3',2':4,5]pyridine[2,1-a]isoquinoline-9(8H)-yl)methanol | A45 |
| A46 | (2-(benzyloxy)-11-chloro-3-methoxy-5,6,14,14a-tetrahydroindolo[3',2':4,5]pyridine[2,1-a]isoquinoline-9(8H)-yl)methanol | A46 |
| A47 | (2-(benzyloxy)-12-chloro-3-methoxy-5,6,14,14a-tetrahydroindolo[3',2':4,5]pyridine[2,1-a]isoquinoline-9(8H)-yl)methanol | A47 |
| A48 | (2-(benzyloxy)-13-chloro-3-methoxy-5,6,14,14a-tetrahydroindolo[3',2':4,5]pyridine[2,1-a]isoquinoline-9(8H)-yl)methanol | A48 |

TABLE 1-continued

| No. | Name | Structure |
|---|---|---|
| A49 | (2-(benzyloxy)-11-bromo-3-methoxy-5,6,14,14a-tetrahydroindolo[3',2':4,5]pyridine[2,1-a]isoquinoline-9(8H)-yl)methanol | 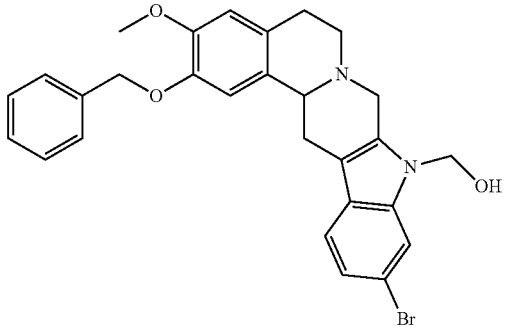 [SMILES: COc1cc2c(cc1OCc1ccccc1)C1Cc3c(n(CO)c4cc(Br)ccc34)CN1CC2]<br>A49 |
| A50 | (2-(benzyloxy)-12-bromo-3-methoxy-5,6,14,14a-tetrahydroindolo[3',2':4,5]pyridine[2,1-a]isoquinoline-9(8H)-yl)methanol | 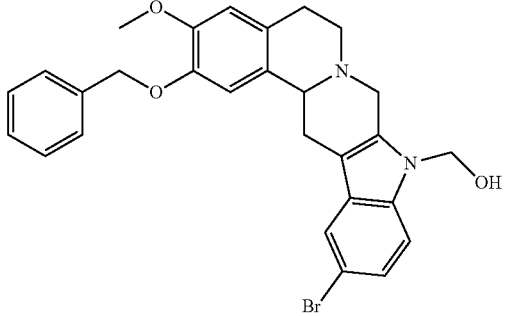<br>A50 |
| A51 | (2-(benzyloxy)-13-bromo-3-methoxy-5,6,14,14a-tetrahydroindolo[3',2':4,5]pyridine[2,1-a]isoquinoline-9(8H)-yl)methanol | 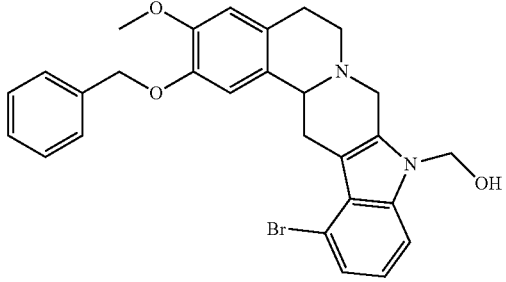 [SMILES: COc1cc2c(cc1OCc1ccccc1)C1Cc3c(n(CO)c4cccc(Br)c34)CN1CC2]<br>A51 |
| A52 | 2-(benzyloxy)-9-(hydroxymethyl)-3-methoxy-5,6,8,9,14,14a-hexahydroindolo[3',2':4,5]pyridine[2,1-a]isoquinoline-12-phenol | 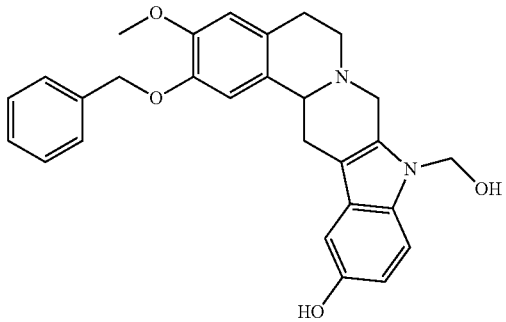 [SMILES: COc1cc2c(cc1OCc1ccccc1)C1Cc3c(n(CO)c4ccc(O)cc34)CN1CC2]<br>A52 |

TABLE 1-continued

| No. | Name | Structure |
|---|---|---|
| A53 | (2-(benzyloxy)-3-methoxy-11-methyl-5,6,14,14a-tetrahydroindolo[3',2':4,5]pyridine[2,1-a]isoquinoline-9(8H)-yl)methanol | A53 |
| A54 | (2-(benzyloxy)-12-ethyl-3-methoxy-5,6,14,14a-tetrahydroindolo[3',2':4,5]pyridine[2,1-a]isoquinoline-9(8H)-yl)methanol | A54 |
| A55 | (3-(benzyloxy)-2,12-dimethoxy-5,6,14,14a-tetrahydroindolo[3',2':4,5]pyridine[2,1-a]isoquinoline-9(8H)-yl)methanol | A55 |
| A56 | (3-(benzyloxy)-2-methoxy-5,6,14,14a-tetrahydroindolo[3',2':4,5]pyridine[2,1-a]isoquinoline-9(8H)-yl)methanol | A56 |

TABLE 1-continued
| No. | Name | Structure |
|---|---|---|
| A57 | (2,12-dimethoxy-3-((4-(trifluoromethyl)benzyl)oxy)-5,6,14,14a-tetrahydroindolo[3',2':4,5]pyridine[2,1-a]isoquinoline-9(8H)-yl)methanol | 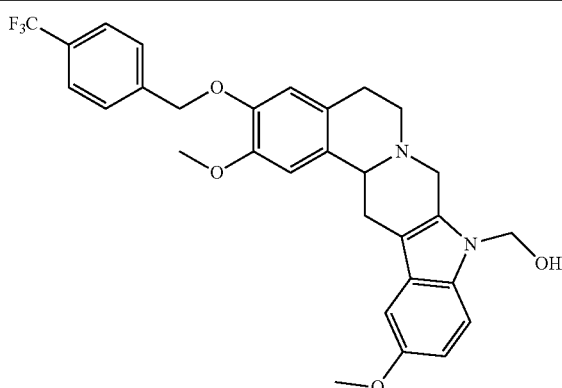<br>A57 |
| A58 | (2-methoxy-3-((4-(trifluoromethyl)benzyl)oxy)-5,6,14,14a-tetrahydroindolo[3',2':4,5]pyridine[2,1-a]isoquinoline-9(8H)-yl)methanol | 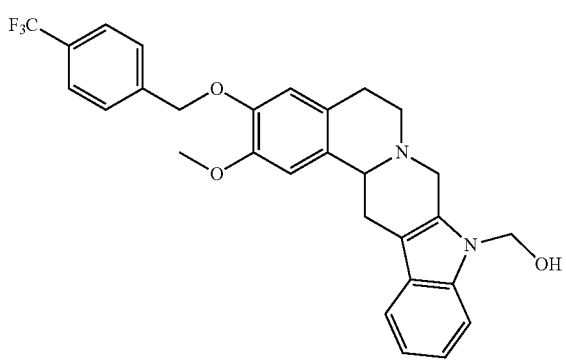 [SMILES: COc1cc2c(cc1OCc1ccc(C(F)(F)F)cc1)CCN1Cc3c(c4ccccc4n3CO)CC21]<br>A58 |
| A59 | (3-((4-fluorobenzyl)oxy)-2,12-dimethoxy-5,6,14,14a-tetrahydroindolo[3',2':4,5]pyridine[2,1-a]isoquinoline-9(8H)-yl)methanol | 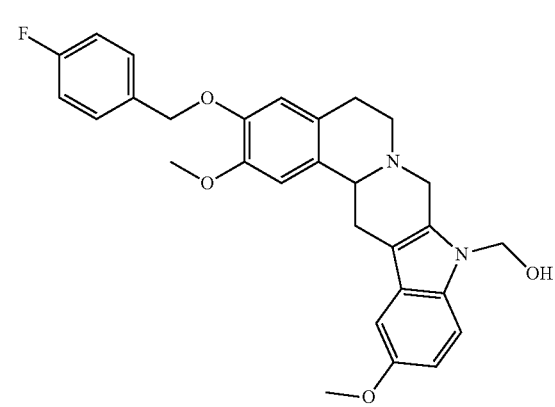 [SMILES: COc1ccc2c(c1)c1c(n2CO)CN2CCc3cc(OCc4ccc(F)cc4)c(OC)cc3C2C1]<br>A59 |

TABLE 1-continued
| No. | Name | Structure |
|---|---|---|
| A60 | (3-((4-fluorobenzyl)oxy)-2-methoxy-5,6,14,14a-tetrahydroindolo[3',2':4,5]pyridine[2,1-a]isoquinoline-9(8H)-yl)methanol | 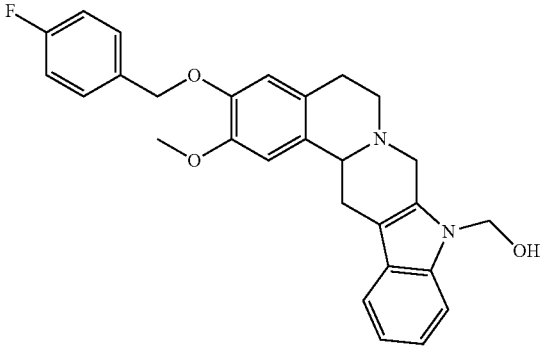 [SMILES: COc1cc2c(cc1OCc1ccc(F)cc1)CCN1Cc3c(c4ccccc4n3CO)CC21]<br>A60 |
| A61 | (3-((3-fluorobenzyl)oxy)-2,12-dimethoxy-5,6,14,14a-tetrahydroindolo[3',2':4,5]pyridine[2,1-a]isoquinoline-9(8H)-yl)methanol | 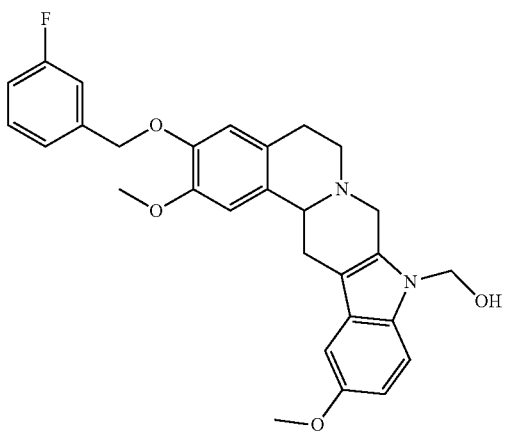 [SMILES: COc1ccc2c(c1)c1c(n2CO)CN2CCc3cc(OCc4cccc(F)c4)c(OC)cc3C2C1]<br>A61 |
| A62 | (3-((3-fluorobenzyl)oxy)-2-methoxy-5,6,14,14a-tetrahydroindolo[3',2':4,5]pyridine[2,1-a]isoquinoline-9(8H)-yl)methanol | 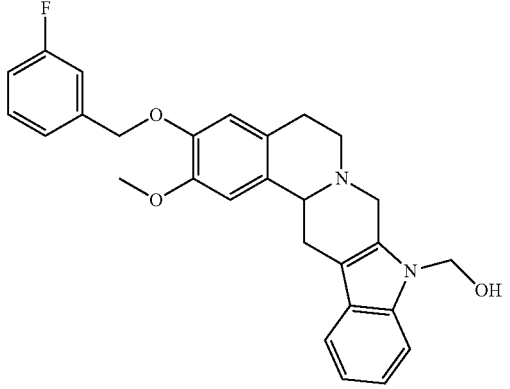 [SMILES: COc1cc2c(cc1OCc1cccc(F)c1)CCN1Cc3c(c4ccccc4n3CO)CC21]<br>A62 |

TABLE 1-continued
| No. | Name | Structure |
|---|---|---|
| A63 | (3-((2-fluorobenzyl)oxy)-2,12-dimethoxy-5,6,14,14a-tetrahydroindolo[3',2':4,5]pyridine[2,1-a]isoquinoline-9(8H)-yl)methanol | 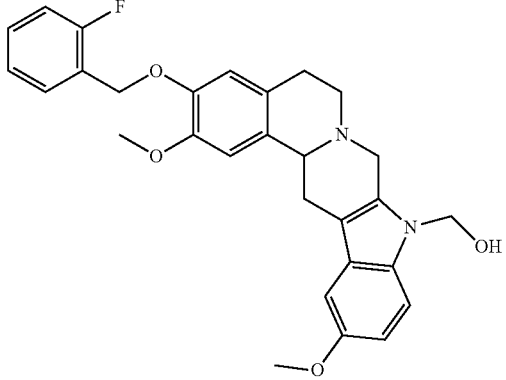 A63 |
| A64 | (3-((2-fluorobenzyl)oxy)-2-dimethoxy-5,6,14,14a-tetrahydroindolo[3',2':4,5]pyridine[2,1-a]isoquinoline-9(8H)-yl)methanol | 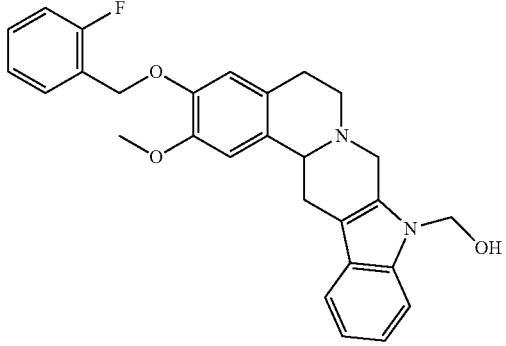 A64 |
| A65 | (2,12-dimethoxy-3-((4-methoxybenzyl)oxy)-5,6,14,14a-tetrahydroindolo[3',2':4,5]pyridine[2,1-a]isoquinoline-9(8H)-yl)methanol | 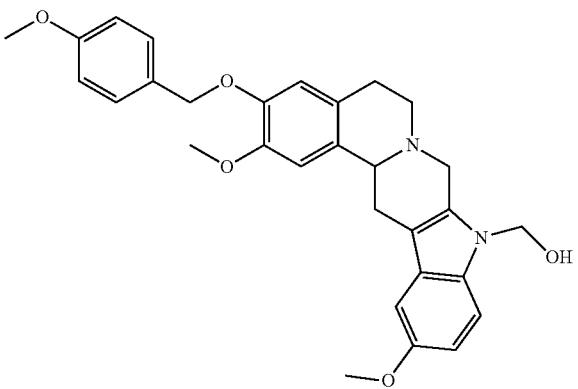 A65 |

TABLE 1-continued
| No. | Name | Structure |
|---|---|---|
| A66 | (2-methoxy-3-((4-methoxybenzyl)oxy)-5,6,14,14a-tetrahydroindolo[3',2':4,5]pyridine[2,1-a]isoquinoline-9(8H)-yl)methanol | 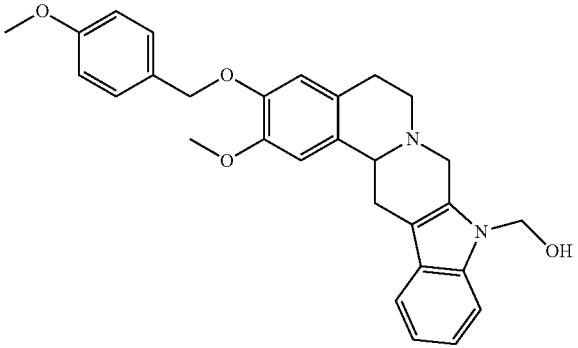 [SMILES: COc1ccc(COc2cc3c(cc2OC)C2Cc4c(n(CO)c5ccccc45)CN2CC3)cc1]<br>A66 |
| A67 | (2,12-dimethoxy-3-((3-methoxybenzyl)oxy)-5,6,14,14a-tetrahydroindolo[3',2':4,5]pyridine[2,1-a]isoquinoline-9(8H)-yl)methanol | 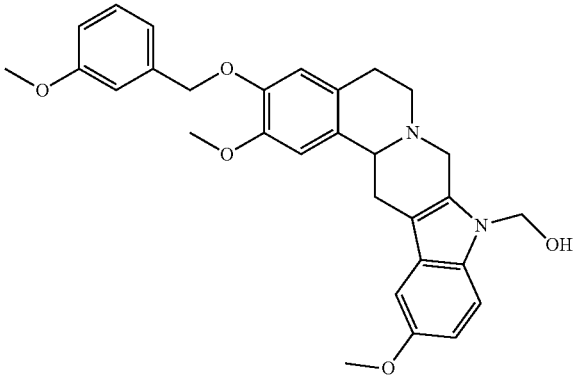 [SMILES: COc1cccc(COc2cc3c(cc2OC)C2Cc4c(n(CO)c5ccc(OC)cc45)CN2CC3)c1]<br>A67 |
| A68 | (2-methoxy-3-((3-methoxybenzyl)oxy)-5,6,14,14a-tetrahydroindolo[3',2':4,5]pyridine[2,1-a]isoquinoline-9(8H)-yl)methanol | 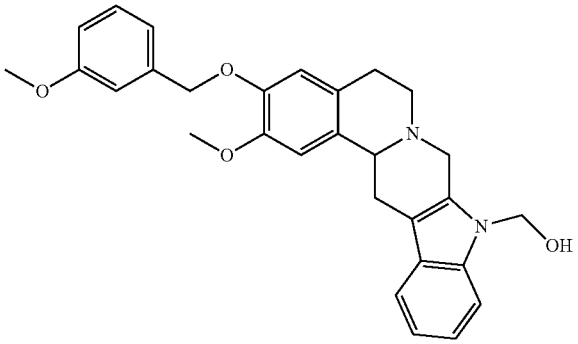 [SMILES: COc1cccc(COc2cc3c(cc2OC)C2Cc4c(n(CO)c5ccccc45)CN2CC3)c1]<br>A68 |

TABLE 1-continued
| No. | Name | Structure |
|---|---|---|
| A69 | (2,12-dimethoxy-3-((4-methylbenzyl)oxy)-5,6,14,14a-tetrahydroindolo[3',2':4,5]pyridine[2,1-a]isoquinoline-9(8H)-yl)methanol | 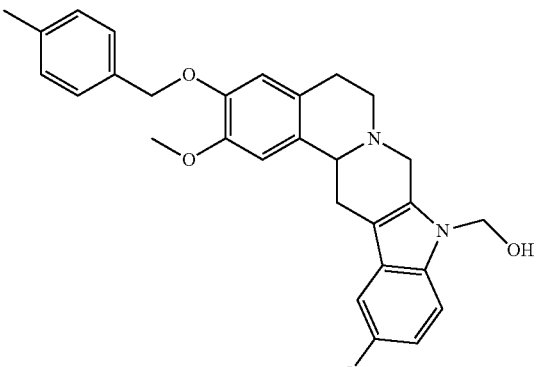<br>A69 |
| A70 | (2-methoxy-3-((4-methylbenzyl)oxy)-5,6,14,14a-tetrahydroindolo[3',2':4,5]pyridine[2,1-a]isoquinoline-9(8H)-yl)methanol | 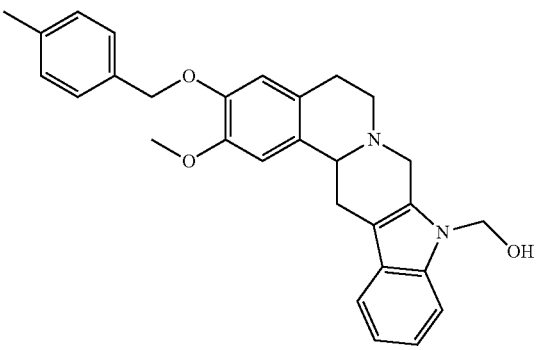 [SMILES: COc1cc2c(cc1OCc1ccc(C)cc1)CCN1Cc3c(c4ccccc4n3CO)CC21]<br>A70 |
| A71 | (3-((4-chlorobenzyl)oxy)-2,12-dimethoxy-5,6,14,14a-tetrahydroindolo[3',2':4,5]pyridine[2,1-a]isoquinoline-9(8H)-yl)methanol | 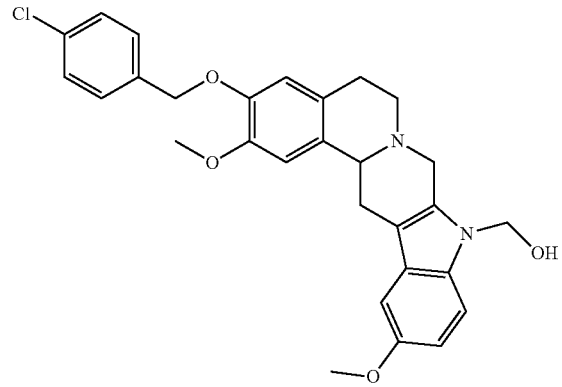 [SMILES: COc1ccc2c(c1)c1c(n2CO)CN2CCc3cc(OCc4ccc(Cl)cc4)c(OC)cc3C2C1]<br>A71 |

TABLE 1-continued
| No. | Name | Structure |
|---|---|---|
| A72 | (3-((4-chlorobenzyl)oxy)-2-methoxy-5,6,14,14a-tetrahydroindolo[3',2':4,5]pyridine[2,1-a]isoquinoline-9(8H)-yl)methanol | 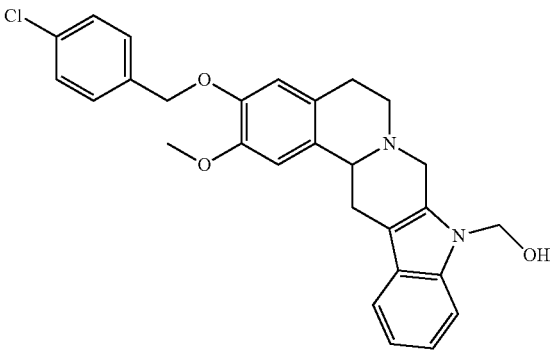 [SMILES: COc1cc2c(cc1OCc1ccc(Cl)cc1)CCN1Cc3c(c4ccccc4n3CO)CC21] |
| A73 | 4-(((9-(hydroxymethyl)-2,12-dimethoxy-5,6,8,9,14,14a-hexahydroindolo[3',2':4,5]pyridine[2,1-a]isoquinoline-3-yl)oxy)methyl)benzonitrile | 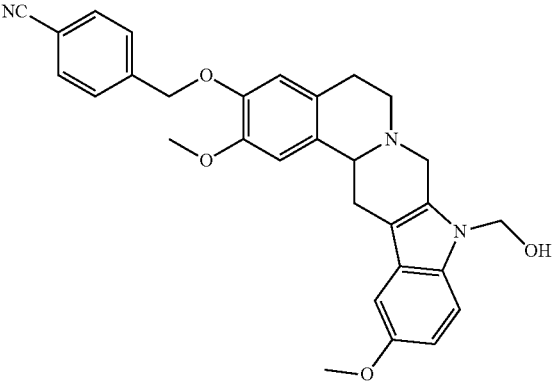 |
| A74 | 4-(((9-(hydroxymethyl)-2-methoxy-5,6,8,9,14,14a-hexahydroindolo[3',2':4,5]pyridine[2,1-a]isoquinoline-3-yl)oxy)methyl)benzonitrile | 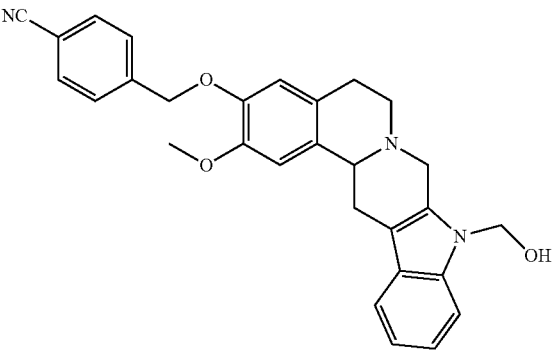 [SMILES: COc1cc2c(cc1OCc1ccc(C#N)cc1)CCN1Cc3c(c4ccccc4n3CO)CC21] |

TABLE 1-continued
| No. | Name | Structure |
|---|---|---|
| A75 | (3-((4-bromobenzyl)oxy)-2,12-dimethoxy-5,6,14,14a-tetrahydroindolo[3',2':4,5]pyridine[2,1-a]isoquinoline-9(8H)-yl)methanol | 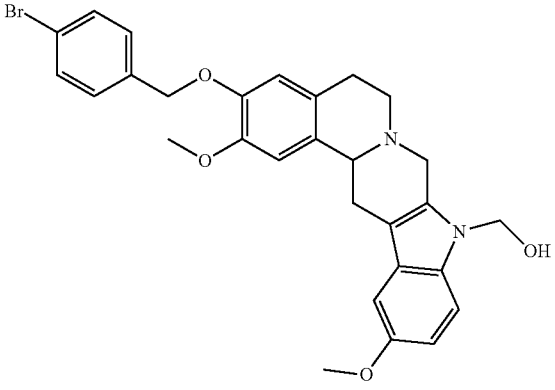 |
| A76 | (3-((4-iodobenzyl)oxy)-2-methoxy-5,6,14,14a-tetrahydroindolo[3',2':4,5]pyridine[2,1-a]isoquinoline-9(8H)-yl)methanol | 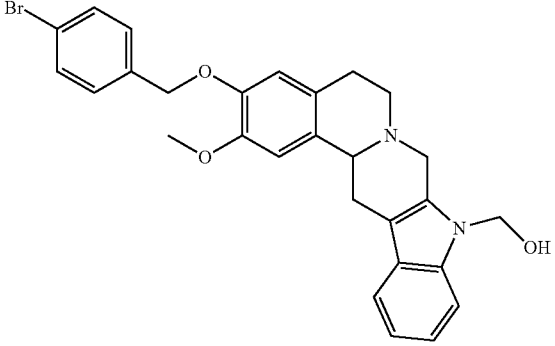 |
| A77 | (3-((3-fluoro-4-(trifluoromethyl)benzyl)oxy)-2,12-dimethoxy-5,6,14,14a-tetrahydroindolo[3',2':4,5]pyridine[2,1-a]isoquinoline-9(8H)-yl)methanol | 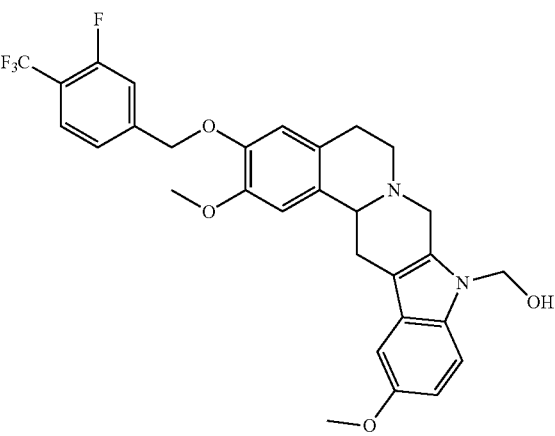 [SMILES: COc1ccc2c(c1)c1c(n2CO)CN2CCc3cc(OCc4ccc(C(F)(F)F)c(F)c4)c(OC)cc3C2C1] |

TABLE 1-continued

| No. | Name | Structure |
|---|---|---|
| A78 | (3-((3-fluoro-4-(trifluoromethyl)benzyl) oxy)-2-methoxy-5,6,14,14a-tetrahydroindolo [3',2':4,5]pyridine[2,1-a]isoquinoline-9(8H)-yl)methanol | 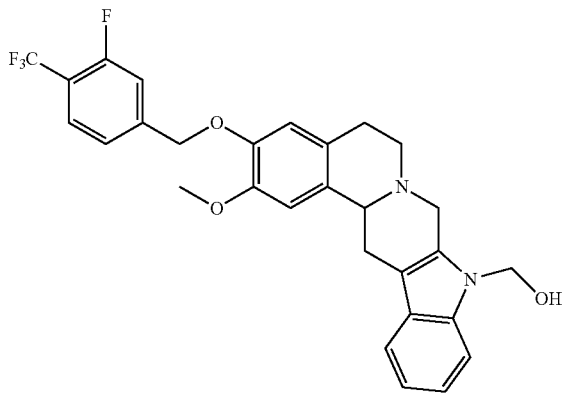 A78 |
| A79 | (3-((2-fluoro-4-(trifluoromethyl)benzyl) oxy)-2,12-dimethoxy-5,6,14,14a-tetrahydroindolo[3',2':4,5]pyridine[2,1-a]isoquinoline-9(8H)-yl)methanol | 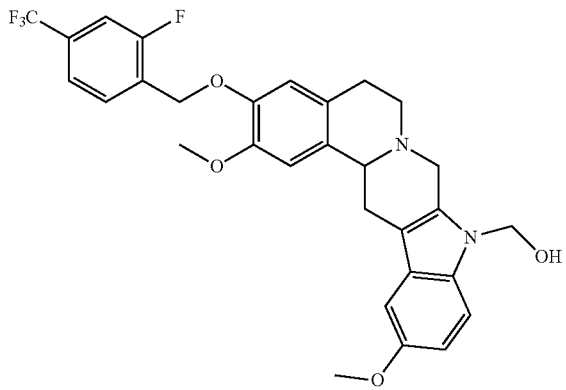 A79 |
| A80 | (3-((2-fluoro-4-(trifluoromethyl)benzyl) oxy)-2-methoxy-5,6,14,14a-tetrahydroindolo [3',2':4,5]pyridine[2,1-a]isoquinoline-9(8H)-yl)methanol | 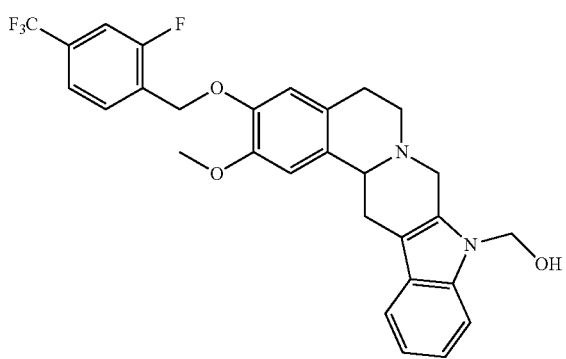 A80 |

TABLE 1-continued
| No. | Name | Structure |
|---|---|---|
| A81 | (2,12-dimethoxy-3-((4-ethylbenzyl)oxy)-5,6,14,14a-tetrahydroindolo[3',2':4,5]pyridine[2,1-a]isoquinoline-9(8H)-yl)methanol | 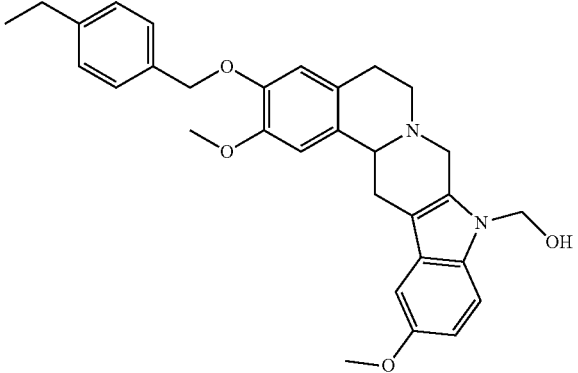 [SMILES: CCc1ccc(COc2cc3c(cc2OC)C2Cc4c(n(CO)c5ccc(OC)cc45)CN2CC3)cc1]<br>A81 |
| A82 | (2-methoxy-3-((4-ethylbenzyl)oxy)-5,6,14,14a-tetrahydroindolo[3',2':4,5]pyridine[2,1-a]isoquinoline-9(8H)-yl)methanol | 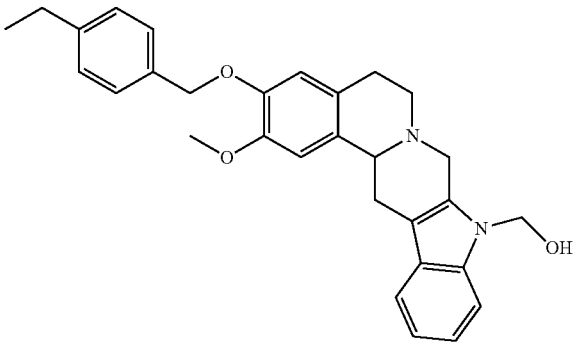 [SMILES: CCc1ccc(COc2cc3c(cc2OC)C2Cc4c(n(CO)c5ccccc45)CN2CC3)cc1]<br>A82 |
| A83 | (2,12-dimethoxy-3-(naphthalen-2-ylmethoxy)-5,6,14,14a-tetrahydroindolo[3',2':4,5]pyridine[2,1-a]isoquinoline-9(8H)-yl)methanol | 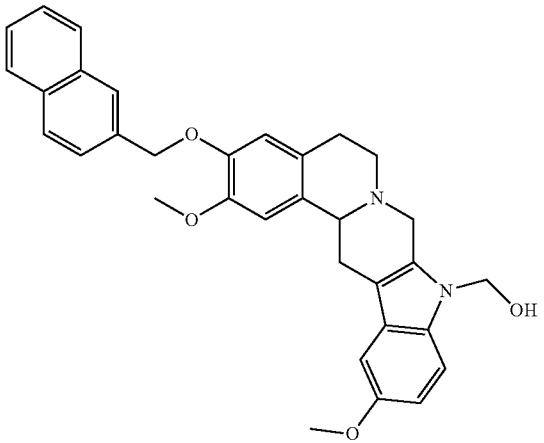 [SMILES: COc1ccc2c(c1)c1c(n2CO)CN2CCc3cc(OCc4ccc5ccccc5c4)c(OC)cc3C2C1]<br>A83 |

TABLE 1-continued
| No. | Name | Structure |
|---|---|---|
| A84 | (2-methoxy-3-(naphthalen-2-ylmethoxy)-5,6,14,14a-tetrahydroindolo[3',2':4,5]pyridine[2,1-a]isoquinoline-9(8H)-yl)methanol | 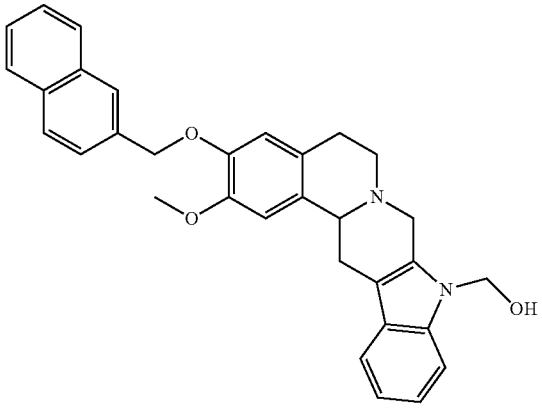 A84 |
| A85 | 4-(((9-(hydroxymethyl)-2,12-dimethoxy-5,6,8,9,14,14a-hexahydroindolo[3',2':4,5]pyridine[2,1-a]isoquinoline-3-yl)oxo)methyl)benzoate | 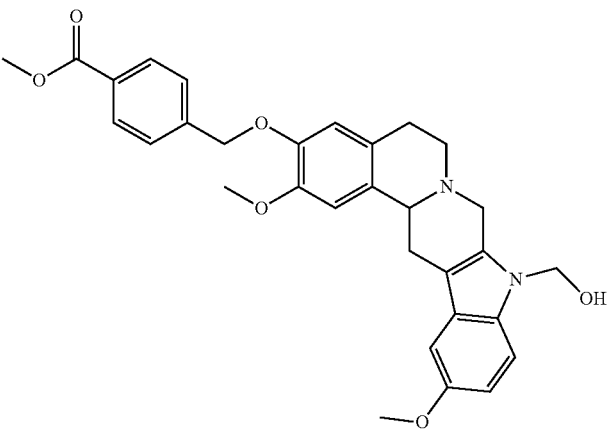 A85 |
| A86 | 4-(((9-(hydroxymethyl)-2-methoxy-5,6,8,9,14,14a-hexahydroindolo[3',2':4,5]pyridine[2,1-a]isoquinoline-3-yl)oxo)methyl)benzoate | 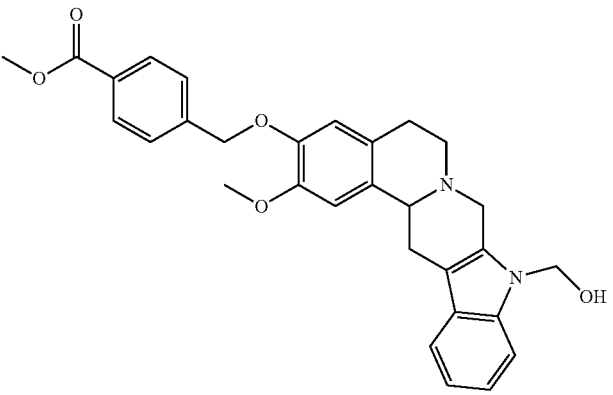 A86 |

TABLE 1-continued
| No. | Name | Structure |
|---|---|---|
| A87 | (3-((4-(1H-pyrazol-1-yl)benzyl)oxy)-2,12-dimethoxy-5,6,14,14a-tetrahydroindolo[3',2':4,5]pyridine[2,1-a]isoquinoline-9(8H)-yl)methanol | 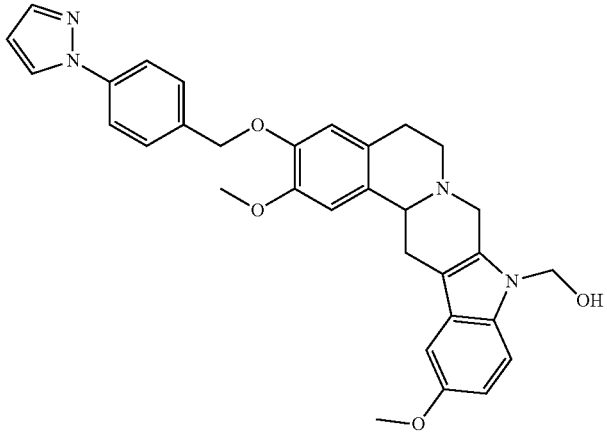 A87 |
| A88 | (3-((4-(1H-pyrazol-1-yl)benzyl)oxy)-2-methoxy-5,6,14,14a-tetrahydroindolo[3',2':4,5]pyridine[2,1-a]isoquinoline-9(8H)-yl)methanol | 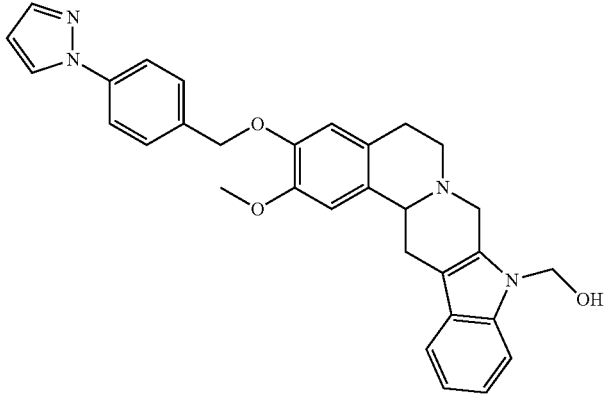 A88 |
| A89 | (3-butoxy-2,12-dimethoxy-5,6,14,14a-tetrahydroindolo[3',2':4,5]pyridine[2,1-a]isoquinoline-9(8H)-yl)methanol | 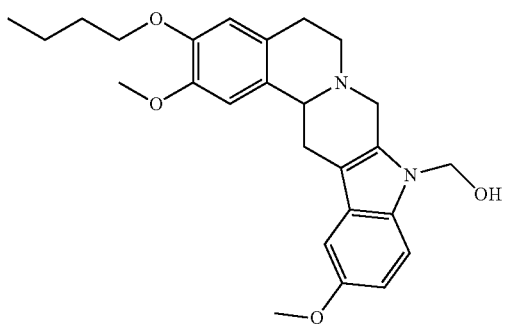 A89 |

TABLE 1-continued

| No. | Name | Structure |
|---|---|---|
| A90 | (3-butoxy-2-methoxy-5,6,14,14a-tetrahydroindolo[3',2':4,5]pyridine[2,1-a]isoquinoline-9(8H)-yl)methanol | 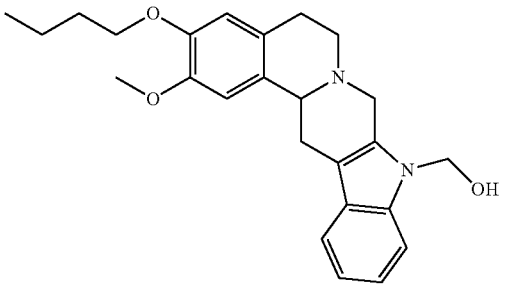 [SMILES: CCCCOc1cc2c(cc1OC)C1Cc3c(n(CO)c4ccccc34)CN1CC2]<br>A90 |
| A91 | (12-fluoro-2,3-dimethoxy-5,6,14,14a-tetrahydroindolo[3',2':4,5]pyridine[2,1-a]isoquinoline-9(8H)-yl)methanol | 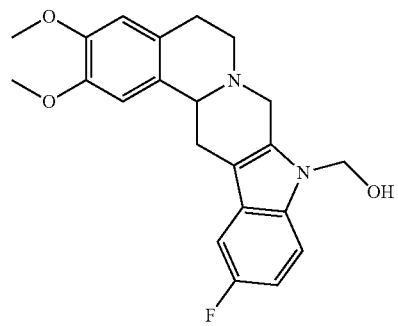 [SMILES: COc1cc2c(cc1OC)C1Cc3c(n(CO)c4ccc(F)cc34)CN1CC2]<br>A91 |
| A92 | (12-methyl-2,3-dimethoxy-5,6,14,14a-tetrahydroindolo[3',2':4,5]pyridine[2,1-a]isoquinoline-9(8H)-yl)methanol | 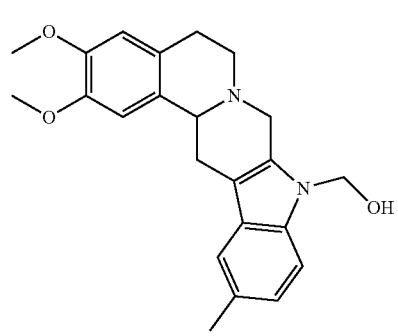 [SMILES: COc1cc2c(cc1OC)C1Cc3c(n(CO)c4ccc(C)cc34)CN1CC2]<br>A92 |
| A93 | (2,12-dimethoxy-3-(2,2,2-trifluoroethoxy)-5,6,14,14a-tetrahydroindolo[3',2':4,5]pyridine[2,1-a]isoquinoline-9(8H)-yl)methanol | 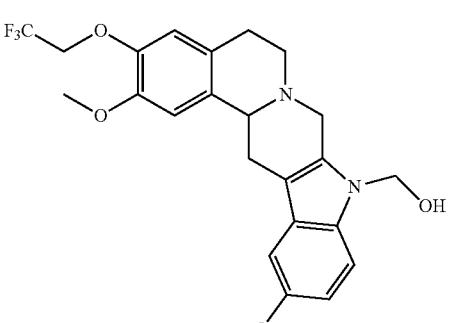<br>A93 |

TABLE 1-continued
| No. | Name | Structure |
|---|---|---|
| A94 | (2-methoxy-3-(2,2,2-trifluoroethoxy)-5,6,14,14a-tetrahydroindolo[3',2':4,5]pyridine[2,1-a]isoquinoline-9(8H)-yl)methanol | 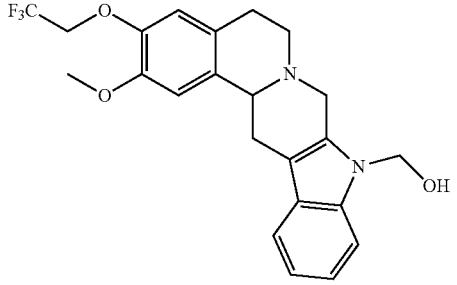 [SMILES: COc1cc2c(cc1OCC(F)(F)F)CCN1Cc3c(c4ccccc4n3CO)CC21]<br>A94 |
| A95 | (2,12-dimethoxy-3-((4-(methylsulfonyl)benzyl)oxy)-5,6,14,14a-tetrahydroindolo[3',2':4,5]pyridine[2,1-a]isoquinoline-9(8H)-yl)methanol | 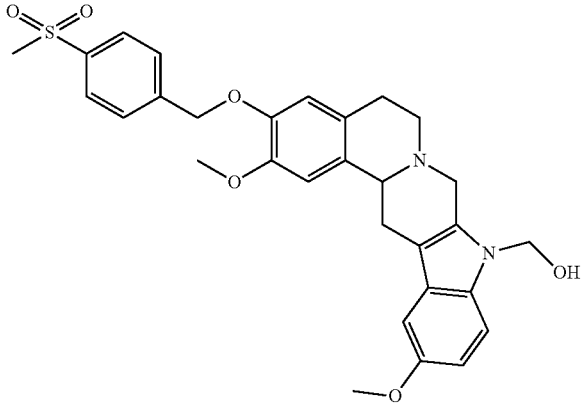 [SMILES: COc1ccc2c(c1)c1c(n2CO)CN2CCc3cc(OCc4ccc(S(C)(=O)=O)cc4)c(OC)cc3C2C1]<br>A95 |
| A96 | (2-methoxy-3-((4-(methylsulfonyl)benzyl)oxy)-5,6,14,14a-tetrahydroindolo[3',2':4,5]pyridine[2,1-a]isoquinoline-9(8H)-yl)methanol | 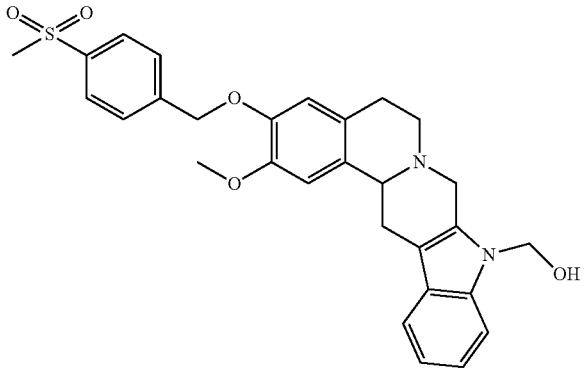 [SMILES: COc1cc2c(cc1OCc1ccc(S(C)(=O)=O)cc1)CCN1Cc3c(c4ccccc4n3CO)CC21]<br>A96 |

TABLE 1-continued

| No. | Name | Structure |
|---|---|---|
| A97 | (3-(benzyloxy)-11-fluoro-2-methoxy-5,6,14,14a-tetrahydroindolo[3',2':4,5]pyridine[2,1-a]isoquinoline-9(8H)-yl)methanol | A97 |
| A98 | (3-(benzyloxy)-12-fluoro-2-methoxy-5,6,14,14a-tetrahydroindolo[3',2':4,5]pyridine[2,1-a]isoquinoline-9(8H)-yl)methanol | A98 |
| A99 | (3-(benzyloxy)-13-fluoro-2-methoxy-5,6,14,14a-tetrahydroindolo[3',2':4,5]pyridine[2,1-a]isoquinoline-9(8H)-yl)methanol | A99 |

TABLE 1-continued
| No. | Name | Structure |
|---|---|---|
| A100 | (3-(benzyloxy)-11-chloro-2-methoxy-5,6,14,14a-tetrahydroindolo[3',2':4,5]pyridine[2,1-a]isoquinoline-9(8H)-yl)methanol | 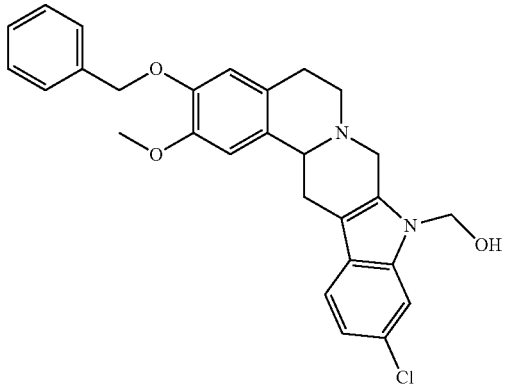 A100 |
| A101 | (3-(benzyloxy)-12-chloro-2-methoxy-5,6,14,14a-tetrahydroindolo[3',2':4,5]pyridine[2,1-a]isoquinoline-9(8H)-yl)methanol | 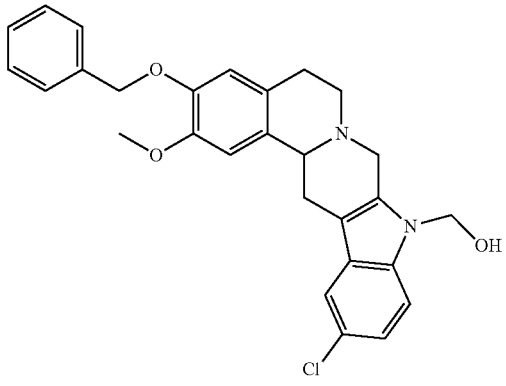 A101 |
| A102 | (3-(benzyloxy)-13-chloro-2-methoxy-5,6,14,14a-tetrahydroindolo[3',2':4,5]pyridine[2,1-a]isoquinoline-9(8H)-yl)methanol | 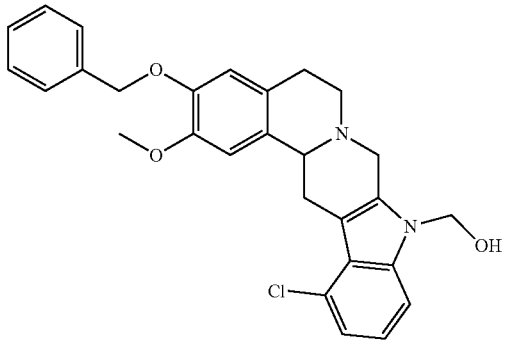 A102 |

TABLE 1-continued
| No. | Name | Structure |
|---|---|---|
| A103 | (3-(benzyloxy)-11-bromo-2-methoxy-5,6,14,14a-tetrahydroindolo[3',2':4,5]pyridine[2,1-a]isoquinoline-9(8H)-yl)methanol | 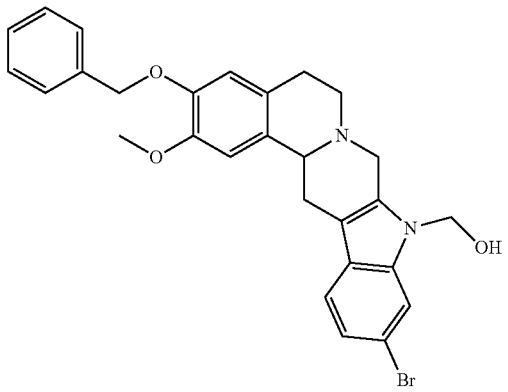 [SMILES: COc1cc2c(cc1OCc1ccccc1)CCN1Cc3c(c4ccc(Br)cc4n3CO)CC21]<br>A103 |
| A104 | (3-(benzyloxy)-12-bromo-2-methoxy-5,6,14,14a-tetrahydroindolo[3',2':4,5]pyridine[2,1-a]isoquinoline-9(8H)-yl)methanol | 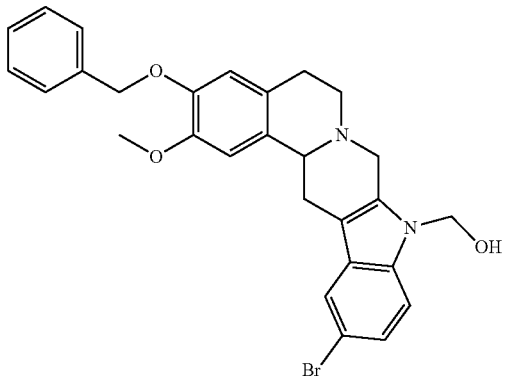<br>A104 |
| A105 | (3-(benzyloxy)-13-bromo-2-methoxy-5,6,14,14a-tetrahydroindolo[3',2':4,5]pyridine[2,1-a]isoquinoline-9(8H)-yl)methanol | 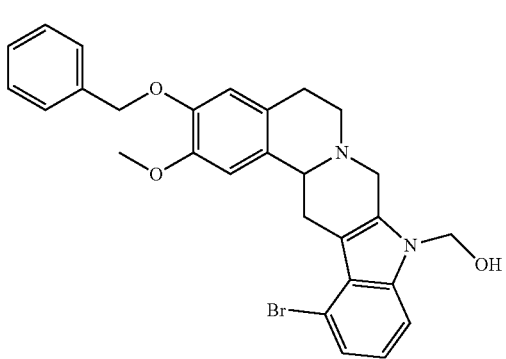 [SMILES: COc1cc2c(cc1OCc1ccccc1)CCN1Cc3c(c4c(Br)cccc4n3CO)CC21]<br>A105 |

TABLE 1-continued

| No. | Name | Structure |
| --- | --- | --- |
| A106 | (3-(benzyloxy)-11-methyl-5,6,14,14a-tetrahydroindolo[3',2':4,5]pyridine[2,1-a]isoquinoline-9(8H)-yl)methanol | A106 |
| A107 | (3-(benzyloxy)-12-ethyl-5,6,14,14a-tetrahydroindolo[3',2':4,5]pyridine[2,1-a]isoquinoline-9(8H)-yl)methanol | A107 |
| A108 | (12-methoxy-5,6,14,14a-tetrahydro-[1,3]dioxazo[4,5-g]indolo[3',2':4,5]pyridine[2,1-a]isoquinoline-9(8H)-yl)methanol | A108 |
| A109 | (5,6,14,14a-tetrahydro-[1,3]dioxazo[4,5-g]indolo[3',2':4,5]pyridine[2,1-a]isoquinoline-9(8H)-yl)methanol | A109 |

TABLE 1-continued

| No. | Name | Structure |
|---|---|---|
| A110 | (12-methoxy-5,6,14,14a-tetrahydro-[1,3]dioxazo[4,5-g]indolo[3',2':4,5]pyridine[2,1-a]isoquinoline-9(8H)-yl)methanol | 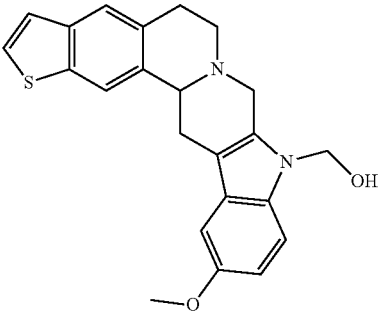 A110 |
| A111 | (5,6,14,14a-tetrahydro-[1,3]dioxazo[4,5-g]indolo[3',2':4,5]pyridine[2,1-a]isoquinoline-9(8H)-yl)methanol | 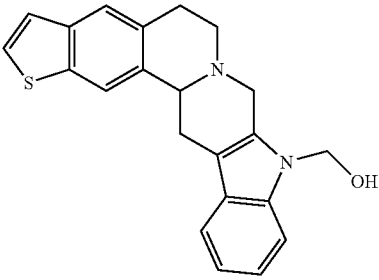 A111 |
| A112 | methyl (2-(benzyloxy)-3,12-dimethoxy-5,6,14,14a-tetrahydroindolo[3',2':4,5]pyridine[2,1-a]isoquinoline-9(8H)-yl)acetate | 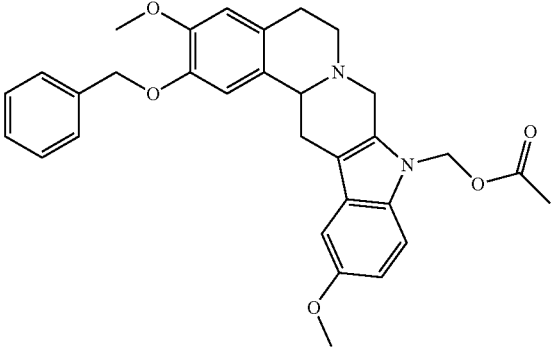 |
| A113 | methyl (2-(benzyloxy)-3,12-dimethoxy-5,6,14,14a-tetrahydroindolo[3',2':4,5]pyridine[2,1-a]isoquinoline-9(8H)-yl)cyclohexylsulfonate | 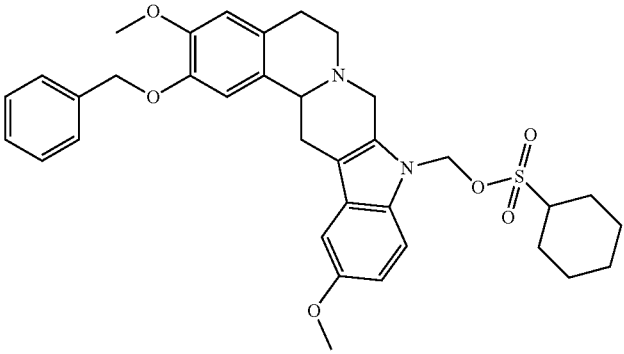 |

TABLE 1-continued

| No. | Name | Structure |
|---|---|---|
| A114 | methyl (2-(benzyloxy)-3,12-dimethoxy-5,6,14,14a-tetrahydroindolo[3',2':4,5]pyridine[2,1-a]isoquinoline-9(8H)-yl)benzenesulfonate | 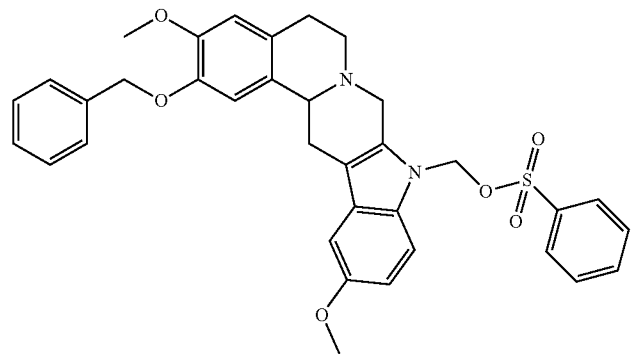 [SMILES: COc1ccc2c(c1)c1c(n2COS(=O)(=O)c2ccccc2)CN2CCc3cc(OC)c(OCc4ccccc4)cc3C2C1] |
| A115 | methyl (2-(benzyloxy)-3,12-dimethoxy-5,6,14,14a-tetrahydroindolo[3',2':4,5]pyridine[2,1-a]isoquinoline-9(8H)-yl)4-fluorobenzenesulfonate | 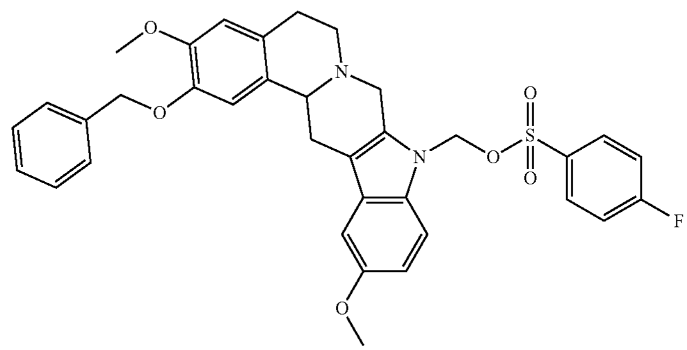 [SMILES: COc1ccc2c(c1)c1c(n2COS(=O)(=O)c2ccc(F)cc2)CN2CCc3cc(OC)c(OCc4ccccc4)cc3C2C1] |
| A116 | methyl (2-(benzyloxy)-3,12-dimethoxy-5,6,14,14a-tetrahydroindolo[3',2':4,5]pyridine[2,1-a]isoquinoline-9(8H)-yl)3-fluorobenzenesulfonate | 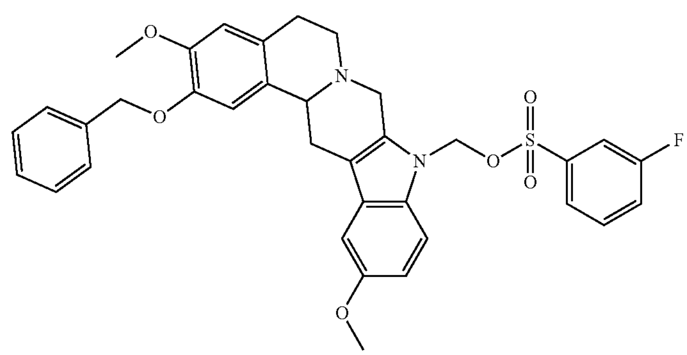 [SMILES: COc1ccc2c(c1)c1c(n2COS(=O)(=O)c2cccc(F)c2)CN2CCc3cc(OC)c(OCc4ccccc4)cc3C2C1] |
| A117 | methyl (2-(benzyloxy)-3,12-dimethoxy-5,6,14,14a-tetrahydroindolo[3',2':4,5]pyridine[2,1-a]isoquinoline-9(8H)-yl)2-fluorobenzenesulfonate | 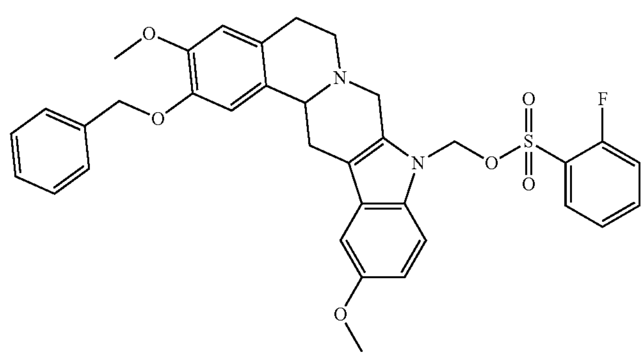 [SMILES: COc1ccc2c(c1)c1c(n2COS(=O)(=O)c2ccccc2F)CN2CCc3cc(OC)c(OCc4ccccc4)cc3C2C1] |

TABLE 1-continued

| No. | Name | Structure |
|---|---|---|
| A118 | methyl (2-(benzyloxy)-3,12-dimethoxy-5,6,14,14a-tetrahydroindolo[3',2':4,5]pyridine[2,1-a]isoquinoline-9(8H)-yl)benzylbenzenesulfonate | 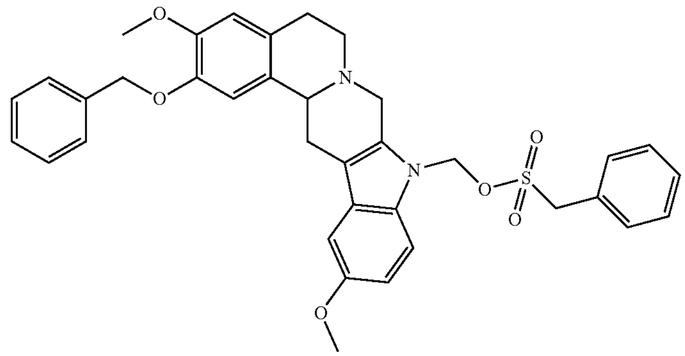 [SMILES: COc1ccc2c(c1)c1c(n2COS(=O)(=O)Cc2ccccc2)CN2CCc3cc(OC)c(OCc4ccccc4)cc3C2C1] |
| A119 | methyl (2-(benzyloxy)-3,12-dimethoxy-5,6,14,14a-tetrahydroindolo[3',2':4,5]pyridine[2,1-a]isoquinoline-9(8H)-yl)benzoate | 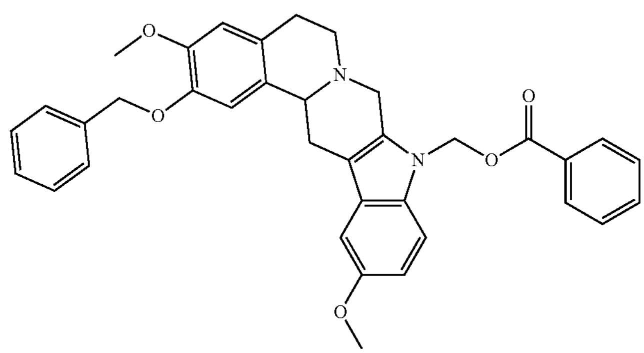 [SMILES: COc1ccc2c(c1)c1c(n2COC(=O)c2ccccc2)CN2CCc3cc(OC)c(OCc4ccccc4)cc3C2C1] |
| A120 | methyl (2-(benzyloxy)-3,12-dimethoxy-5,6,14,14a-tetrahydroindolo[3',2':4,5]pyridine[2,1-a]isoquinoline-9(8H)-yl)N,N-dimethylformate | 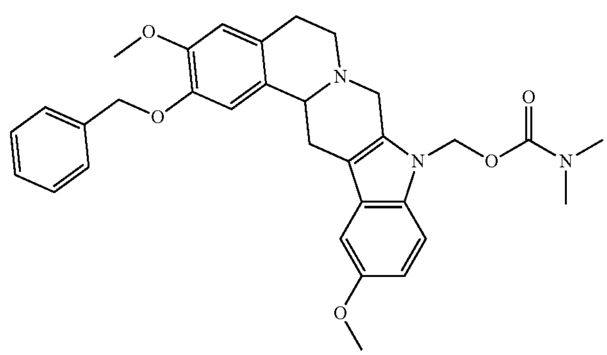 [SMILES: COc1ccc2c(c1)c1c(n2COC(=O)N(C)C)CN2CCc3cc(OC)c(OCc4ccccc4)cc3C2C1] |
| A121 | methyl (2-(benzyloxy)-3,12-dimethoxy-5,6,14,14a-tetrahydroindolo[3',2':4,5]pyridine[2,1-a]isoquinoline-9(8H)-yl)4-fluorobenzoate | 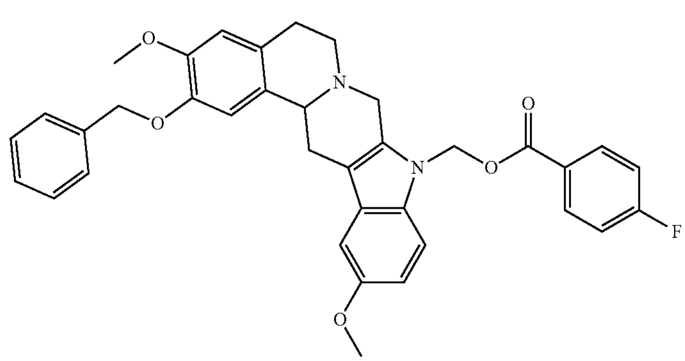 [SMILES: COc1ccc2c(c1)c1c(n2COC(=O)c2ccc(F)cc2)CN2CCc3cc(OC)c(OCc4ccccc4)cc3C2C1] |

TABLE 1-continued

| No. | Name | Structure |
|---|---|---|
| A122 | methyl (2-(benzyloxy)-3,12-dimethoxy-5,6,14,14a-tetrahydroindolo[3',2':4,5]pyridine[2,1-a]isoquinoline-9(8H)-yl)3-fluorobenzoate | 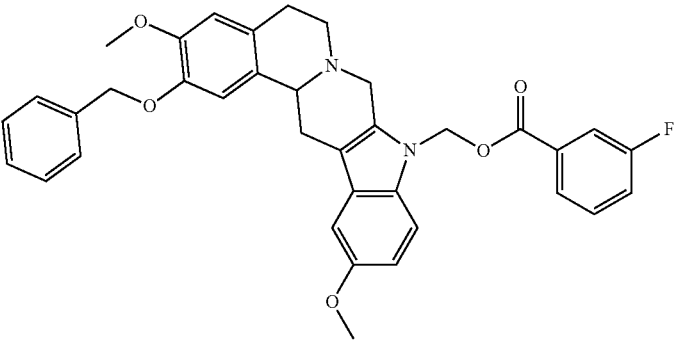 [SMILES: COc1ccc2c(c1)c1c(n2COC(=O)c2cccc(F)c2)CN2CCc3cc(OC)c(OCc4ccccc4)cc3C2C1] |
| A123 | methyl (2-(benzyloxy)-3,12-dimethoxy-5,6,14,14a-tetrahydroindolo[3',2':4,5]pyridine[2,1-a]isoquinoline-9(8H)-yl)2-fluorobenzoate | 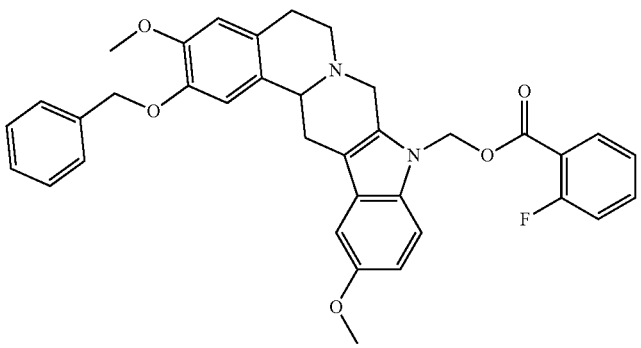 [SMILES: COc1ccc2c(c1)c1c(n2COC(=O)c2ccccc2F)CN2CCc3cc(OC)c(OCc4ccccc4)cc3C2C1] |
| A124 | 9-(hydroxymethyl)-2,12-dimethoxy-5,6,8,9,14,14a-hexahydroindolo[3',2':4,5]pyridine[2,1-a]isoquinoline-3-ylbenzenesulfonate | 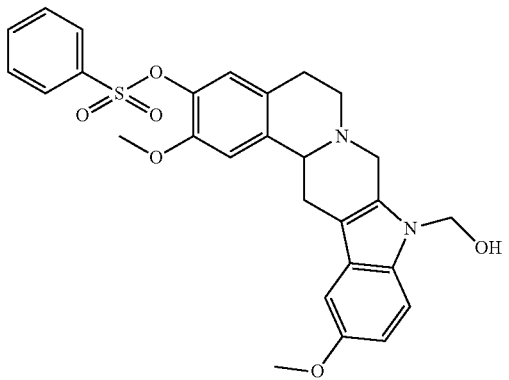 [SMILES: COc1ccc2c(c1)c1c(n2CO)CN2CCc3cc(OS(=O)(=O)c4ccccc4)c(OC)cc3C2C1] |
| A125 | 9-(hydroxymethyl)-3,12-dimethoxy-5,6,8,9,14,14a-hexahydroindolo[3',2':4,5]pyridine[2,1-a]isoquinoline-2-ylbenzenesulfonate | 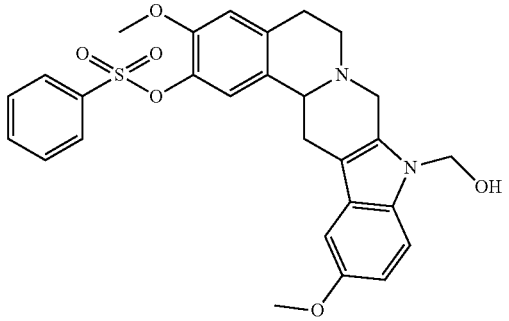 [SMILES: COc1ccc2c(c1)c1c(n2CO)CN2CCc3cc(OC)c(OS(=O)(=O)c4ccccc4)cc3C2C1] |

TABLE 1-continued

| No. | Name |
|---|---|
| A130 | (3-(benzyloxy)-8-isopropyl-2,12-dimethoxy-5,6,14,14a-tetrahydroindolo[3',2':4,5]pyridine[2,1-a]isoquinoline-9(8H)-yl)methanol |
| A131 | (2-(benzyloxy)-8-isopropyl-3,12-dimethoxy-5,6,14,14a-tetrahydroindolo[3',2':4,5]pyridine[2,1-a]isoquinoline-9(8H)-yl)methanol |
| A132 | 2-(benzyloxy)-3,12-dimethoxy-9-(benzenesulfonyl)-5,6,8,9,14,14a-hexahydroindolo[3',2':4,5]pyridine[2,1-a]isoquinoline |
| A133 | 3-(benzyloxy)-2,12-dimethoxy-9-(benzenesulfonyl)-5,6,8,9,14,14a-hexahydroindolo[3',2':4,5]pyridine[2,1-a]isoquinoline |

TABLE 1-continued

| No. | Name |
|---|---|
| A134 | (2-((4-aminobenzyl)oxy)-3,12-dimethoxy-5,6,14,14a-tetrahydroindolo[3',2':4,5]pyridine[2,1-a]isoquinoline-9(8H)-yl)methanol |
| A135 | (3-((4-aminobenzyl)oxy)-2,12-dimethoxy-5,6,14,14a-tetrahydroindolo[3',2':4,5]pyridine[2,1-a]isoquinoline-9(8H)-yl)methanol |
| A136 | 4-(((9-(hydroxymethyl)-3,12-dimethoxy-5,6,8,9,14,14a-hexahydroindolo[3',2':4,5]pyridine[2,1-a]isoquinoline-2-yl)oxo)methyl)phenol |
| A137 | 4-(((9-(hydroxymethyl)-2,12-dimethoxy-5,6,8,9,14,14a-hexahydroindolo[3',2':4,5]pyridine[2,1-a]isoquinoline-3-yl)oxo)methyl)phenol |

TABLE 1-continued

| No. | Name | Structure |
|---|---|---|
| A138 | 4-(((9-(Hydroxymethyl)-3,12-dimethoxy-5,6,8,9,14,14a-hexahydroindole[3',2':4,5]pyridine[2,1-a]isoquinolin-2-yl)oxo)methyl)benzoic acid | 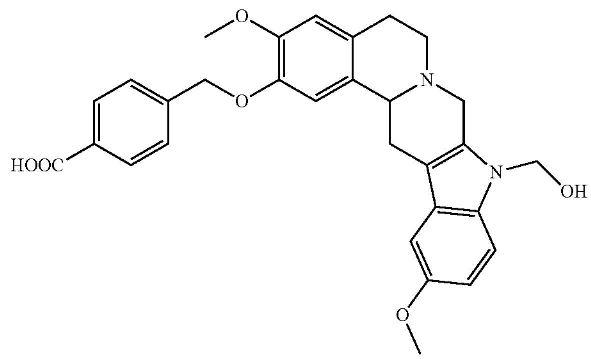 [SMILES: COc1ccc2c(c1)c1c(n2CO)CN2CCc3cc(OC)c(OCc4ccc(C(=O)O)cc4)cc3C2C1] |
| A139 | 4-(((9-(Hydroxymethyl)-2,12-dimethoxy-5,6,8,9,14,14a-hexahydroindole[3',2':4,5]pyridine[2,1-a]isoquinolin-3-yl)oxo)methyl)benzoic acid | 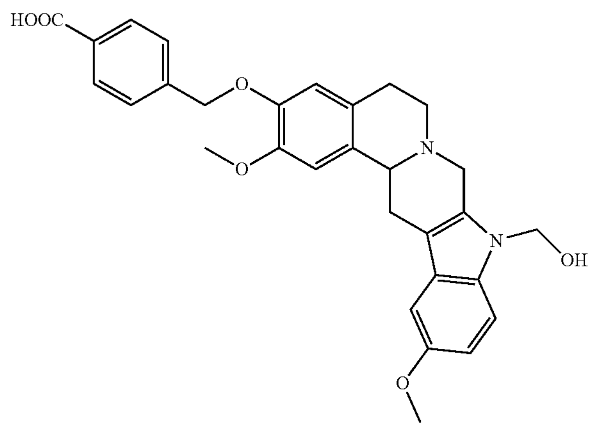 [SMILES: COc1ccc2c(c1)c1c(n2CO)CN2CCc3cc(OCc4ccc(C(=O)O)cc4)c(OC)cc3C2C1] |
| (S)-A55 | S)-(3-(Benzyloxy)-2,12-dimethoxy-5,6,14,14a-tetrahydroindole[3',2':4,5]pyridine[2,1-a]isoquinoline-9(8H)-yl)methanol | 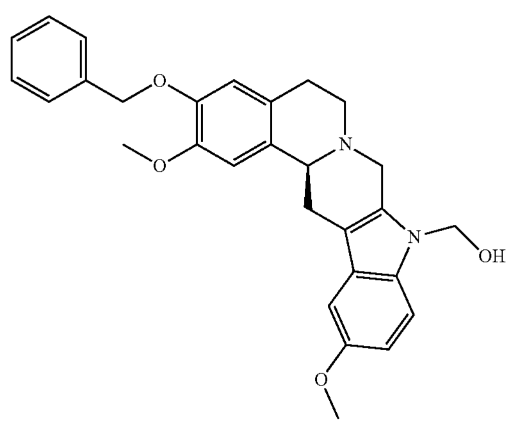 [SMILES: COc1ccc2c(c1)c1c(n2CO)CN2CCc3cc(OCc4ccccc4)c(OC)cc3[C@@H]2C1] |
| (R)-A55 | R)-(3-(Benzyloxy)-2,12-dimethoxy-5,6,14,14a-tetrahydroindole[3',2':4,5]pyridine[2,1-a]isoquinoline-9(8H)-yl)methanol | 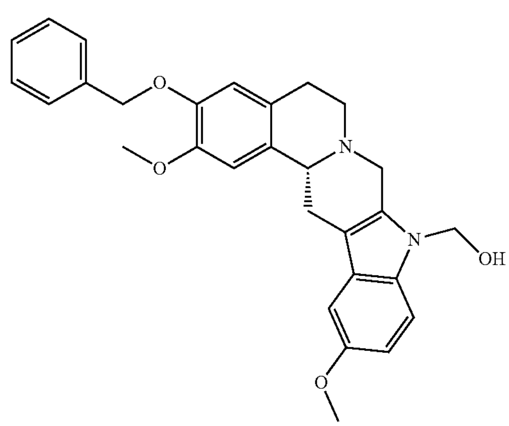 [SMILES: COc1ccc2c(c1)c1c(n2CO)CN2CCc3cc(OCc4ccccc4)c(OC)cc3[C@H]2C1] |

TABLE 1-continued

| No. | Name | Structure |
|---|---|---|
| (S)-A1 | S)-(2-(benzyloxy)-3,12-dimethoxy-5,8,14,14a-tetrahydroindole[3',2':4,5]pyridine[2,1-a]isoquinoline-9(6H)-yl)methanol | 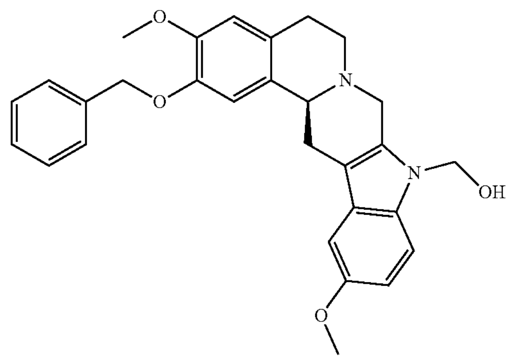 [SMILES: COc1ccc2c(c1)c1c(n2CO)CN2CCc3cc(OC)c(OCc4ccccc4)cc3[C@@H]2C1] |
| (R)-A1 | R)-(2-(benzyloxy)-3,12-dimethoxy-5,8,14,14a-tetrahydroindole[3',2':4,5]pyridine[2,1-a]isoquinoline-9(6H)-yl)methanol | 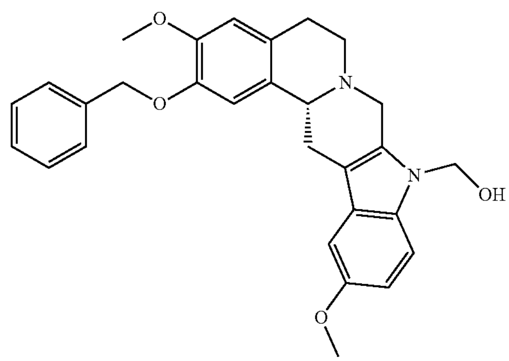 [SMILES: COc1ccc2c(c1)c1c(n2CO)CN2CCc3cc(OC)c(OCc4ccccc4)cc3[C@H]2C1] |
| A140 | (2,12-dimethoxy-3-((2-methoxybenzyl)oxy)-5,6,14,14a-tetrahydroindolo[3',2':4,5]pyridine[2,1-a]isoquinoline-9(8H)-yl)methanol | A140 |
| A141 | (2-methoxy-3-((2-methoxybenzyl)oxy)-5,6,14,14a-tetrahydroindolo[3',2':4,5]pyridine[2,1-a]isoquinoline-9(8H)-yl)methanol | A141 |

TABLE 1-continued

| No. | Name | Structure |
|---|---|---|
| A142 | (2,12-dimethoxy-3-((3-methylbenzyl)oxy)-5,6,14,14a-tetrahydroindolo[3',2':4,5]pyridine[2,1-a]isoquinoline-9(8H)-yl)methanol | 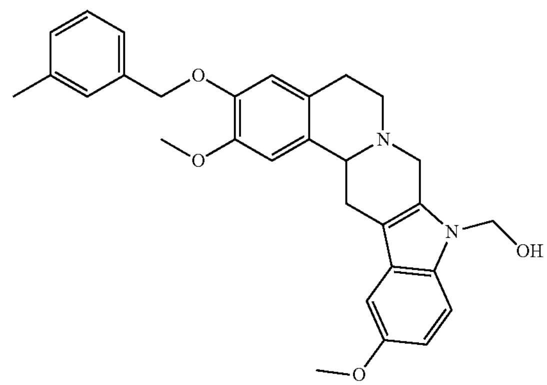 [SMILES: COc1ccc2c(c1)c1c(n2CO)CN2CCc3cc(OCc4cccc(C)c4)c(OC)cc3C2C1] |
| A143 | (2-methoxy-3-((3-methylbenzyl)oxy)-5,6,14,14a-tetrahydroindolo[3',2':4,5]pyridine[2,1-a]isoquinoline-9(8H)-yl)methanol | 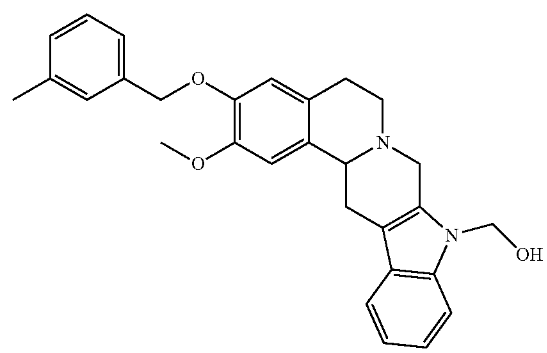 [SMILES: COc1cc2c(cc1OCc1cccc(C)c1)CCN1Cc3c(c4ccccc4n3CO)CC21] |
| A144 | (2,12-dimethoxy-3-((2-methylbenzyl)oxy)-5,6,14,14a-tetrahydroindolo[3',2':4,5]pyridine[2,1-a]isoquinoline-9(8H)-yl)methanol | 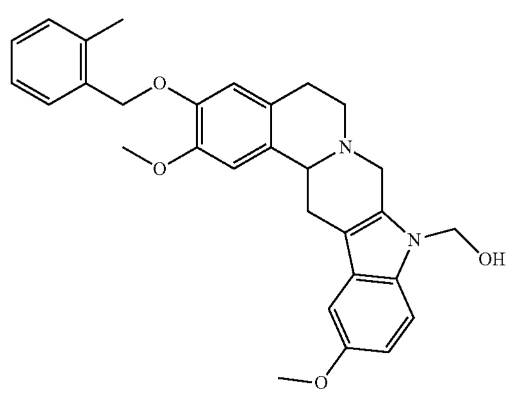 [SMILES: COc1ccc2c(c1)c1c(n2CO)CN2CCc3cc(OCc4ccccc4C)c(OC)cc3C2C1] |

TABLE 1-continued

| No. | Name | Structure |
|---|---|---|
| A145 | (2-methoxy-3-((2-methylbenzyl)oxy)-5,6,14,14a-tetrahydroindolo[3',2':4,5]pyridine[2,1-a]isoquinoline-9(8H)-yl)methanol | 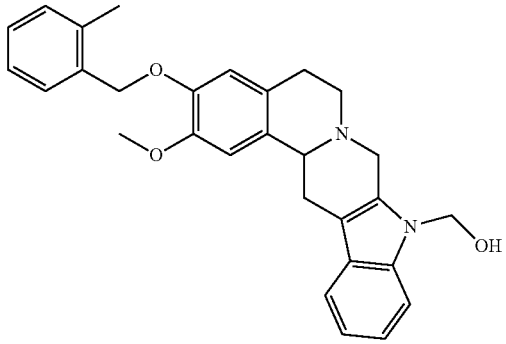 [SMILES: COc1cc2c(cc1OCc1ccccc1C)CCN1Cc3c(c4ccccc4n3CO)CC21]<br>A145 |
| A146 | (3,12-dimethoxy-2-((2-methoxybenzyl)oxy)-5,6,14,14a-tetrahydroindolo[3',2':4,5]pyridine[2,1-a]isoquinoline-9(8H)-yl)methanol | 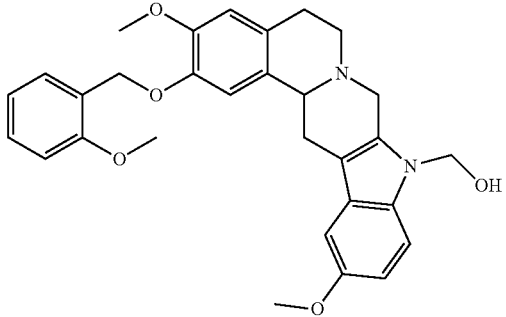 [SMILES: COc1ccc2c(c1)c1c(n2CO)CN2CCc3cc(OC)c(OCc4ccccc4OC)cc3C2C1]<br>A146 |
| A147 | (3-methoxy-2-((2-methoxybenzyl)oxy)-5,6,14,14a-tetrahydroindolo[3',2':4,5]pyridine[2,1-a]isoquinoline-9(8H)-yl)methanol | 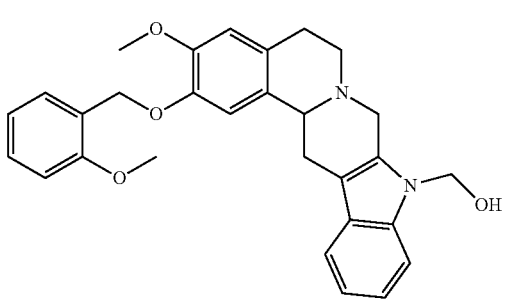 [SMILES: COc1ccccc1COc1cc2c(cc1OC)CCN1Cc3c(c4ccccc4n3CO)CC21]<br>A147 |
| A148 | (3,12-dimethoxy-2-((3-methylbenzyl)oxy)-5,6,14,14a-tetrahydroindolo[3',2':4,5]pyridine[2,1-a]isoquinoline-9(8H)-yl)methanol | 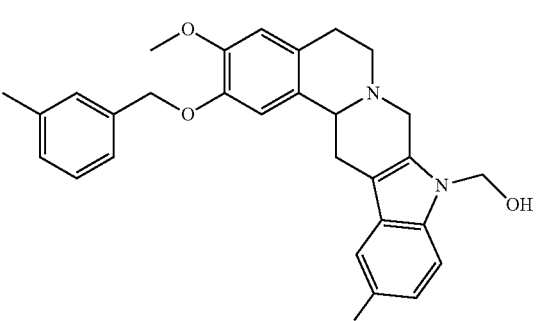<br>A148 |

TABLE 1-continued

| No. | Name | Structure |
|---|---|---|
| A149 | (3-methoxy-2-((3-methylbenzyl)oxy)-5,6,14,14a-tetrahydroindolo[3',2':4,5]pyridine[2,1-a]isoquinoline-9(8H)-yl)methanol | 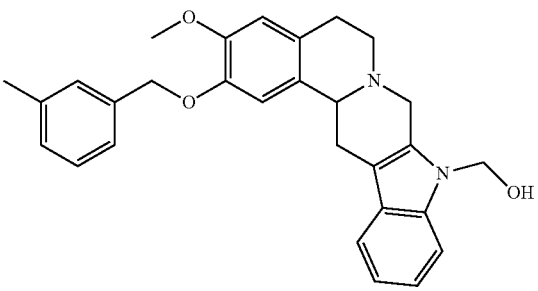 A149 |
| A150 | (3,12-dimethoxy-2-((2-methylbenzyl)oxy)-5,6,14,14a-tetrahydroindolo[3',2':4,5]pyridine[2,1-a]isoquinoline-9(8H)-yl)methanol | 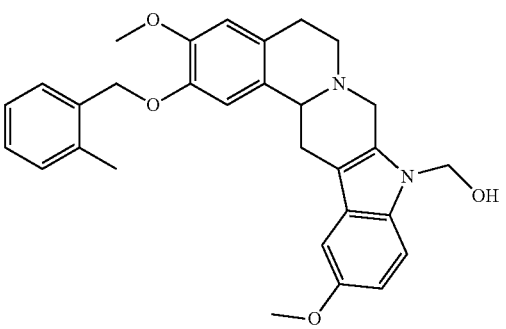 A150 |
| A151 | (3-methoxy-2-((2-methylbenzyl)oxy)-5,6,14,14a-tetrahydroindolo[3',2':4,5]pyridine[2,1-a]isoquinoline-9(8H)-yl)methanol | 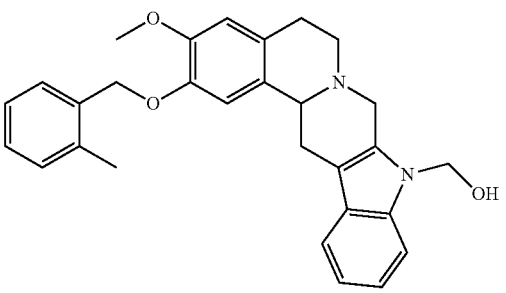 A151 |
| A152 | (2-methoxy-3-((3,4-difluorobenzyl)oxy)-5,6,14,14a-tetrahydroindolo[3',2':4,5]pyridine[2,1-a]isoquinoline-9(8H)-yl)methanol | 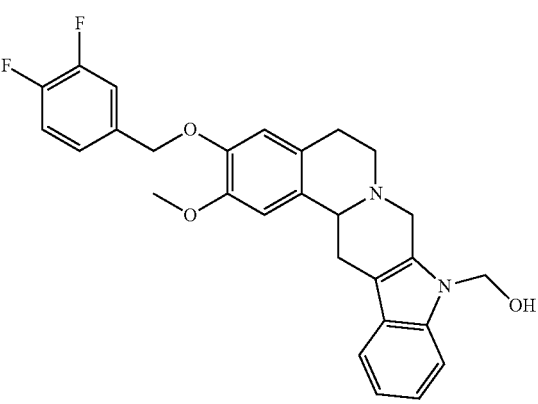 A152 |

TABLE 1-continued
| No. | Name | Structure |
|---|---|---|
| A153 | (2,12-dimethoxy-3-((3,4-difluorobenzyl)oxy)-5,6,14,14a-tetrahydroindolo[3',2':4,5]pyridine[2,1-a]isoquinoline-9(8H)-yl)methanol | 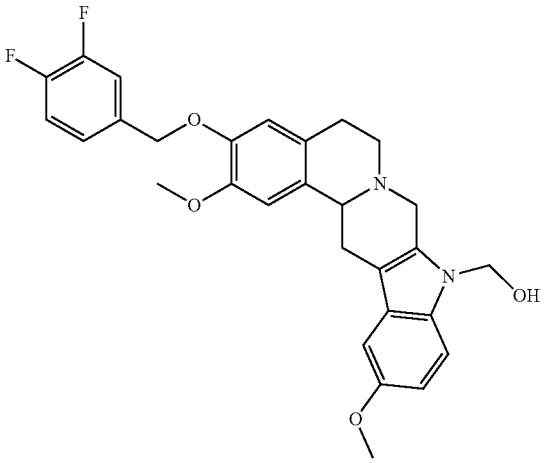 [SMILES: COc1ccc2c(c1)c1c(n2CO)CN2CCc3cc(OCc4ccc(F)c(F)c4)c(OC)cc3C2C1]<br>A153 |
| A154 | (2-methoxy-3-((3,5-difluorobenzyl)oxy)-5,6,14,14a-tetrahydroindolo[3',2':4,5]pyridine[2,1-a]isoquinoline-9(8H)-yl)methanol | 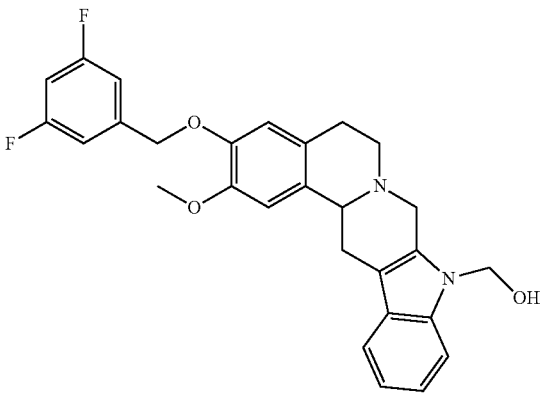 [SMILES: COc1cc2c(cc1OCc1cc(F)cc(F)c1)CCN1Cc3c(c4ccccc4n3CO)CC21]<br>A154 |
| A155 | (2,12-dimethoxy-3-((3,5-difluorobenzyl)oxy)-5,6,14,14a-tetrahydroindolo[3',2':4,5]pyridine[2,1-a]isoquinoline-9(8H)-yl)methanol | 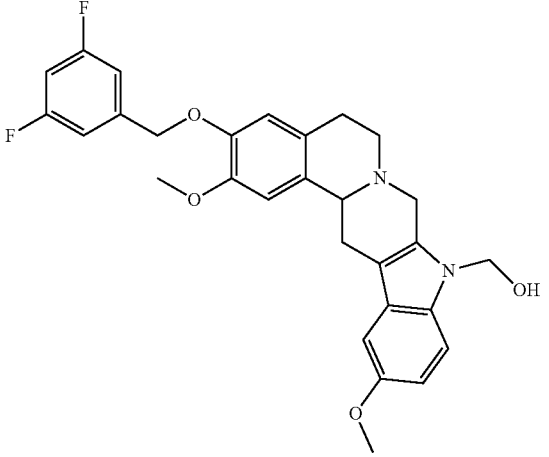 [SMILES: COc1ccc2c(c1)c1c(n2CO)CN2CCc3cc(OCc4cc(F)cc(F)c4)c(OC)cc3C2C1]<br>A155 |

TABLE 1-continued
| No. | Name | Structure |
|---|---|---|
| A156 | (2-methoxy-3-((3,4,5-trifluorobenzyl)oxy)-5,6,14,14a-tetrahydroindolo[3',2':4,5]pyridine[2,1-a]isoquinoline-9(8H)-yl)methanol | 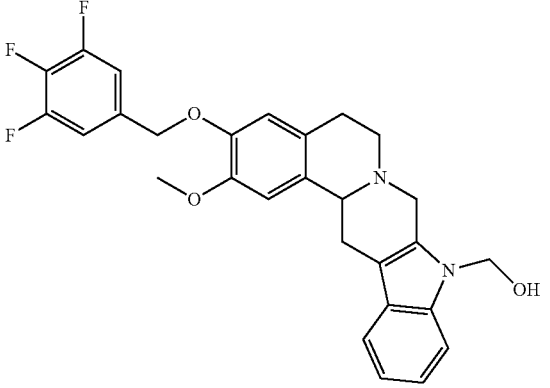 A156 |
| A157 | (2,12-dimethoxy-3-((3,4,5-trifluorobenzyl)oxy)-5,6,14,14a-tetrahydroindolo[3',2':4,5]pyridine[2,1-a]isoquinoline-9(8H)-yl)methanol | 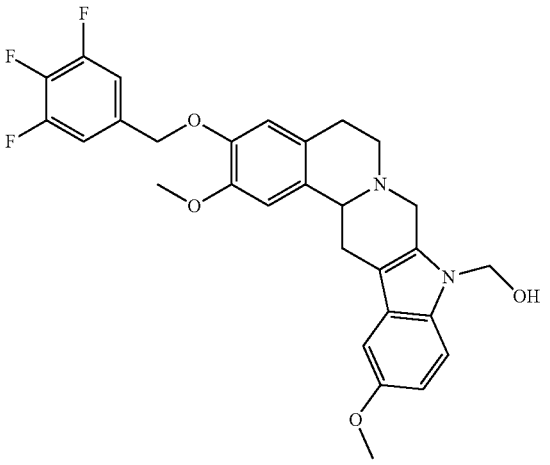 A157 |
| A158 | (3-methoxy-2-((3,4-difluorobenzyl)oxy)-5,6,14,14a-tetrahydroindolo[3',2':4,5]pyridine[2,1-a]isoquinoline-9(8H)-yl)methanol | 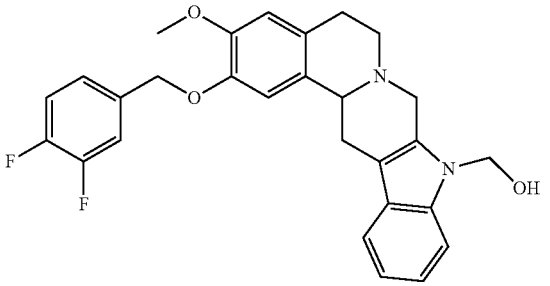 A158 |

TABLE 1-continued

| No. | Name | Structure |
|---|---|---|
| A159 | (3,12-dimethoxy-2-((3,4-difluorobenzyl)oxy)-5,6,14,14a-tetrahydroindolo[3',2':4,5]pyridine[2,1-a]isoquinoline-9(8H)-yl)methanol | 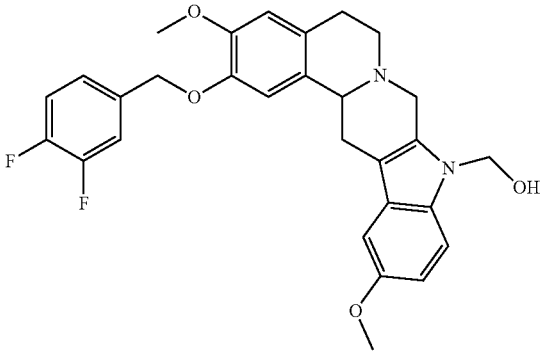 [SMILES: COc1ccc2c(c1)c1c(n2CO)CN2CCc3cc(OC)c(OCc4ccc(F)c(F)c4)cc3C2C1]<br>A159 |
| A160 | (3-methoxy-2-((3,5-difluorobenzyl)oxy)-5,6,14,14a-tetrahydroindolo[3',2':4,5]pyridine[2,1-a]isoquinoline-9(8H)-yl)methanol | 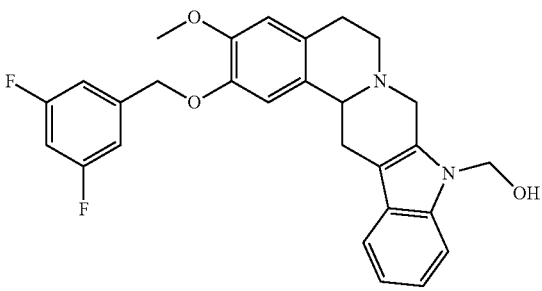 [SMILES: COc1cc2c(cc1OCc1cc(F)cc(F)c1)C1Cc3c(n(CO)c4ccccc34)CN1CC2]<br>A160 |
| A161 | (3,12-dimethoxy-2-((3,5-difluorobenzyl)oxy)-5,6,14,14a-tetrahydroindolo[3',2':4,5]pyridine[2,1-a]isoquinoline-9(8H)-yl)methanol | 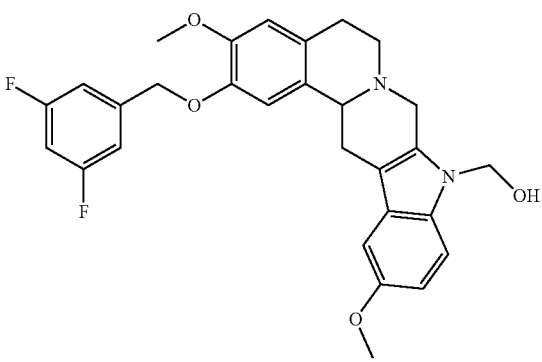 [SMILES: COc1ccc2c(c1)c1c(n2CO)CN2CCc3cc(OC)c(OCc4cc(F)cc(F)c4)cc3C2C1]<br>A161 |
| A162 | (3-methoxy-2-((3,4,5-trifluorobenzyl)oxy)-5,6,14,14a-tetrahydroindolo[3',2':4,5]pyridine[2,1-a]isoquinoline-9(8H)-yl)methanol | 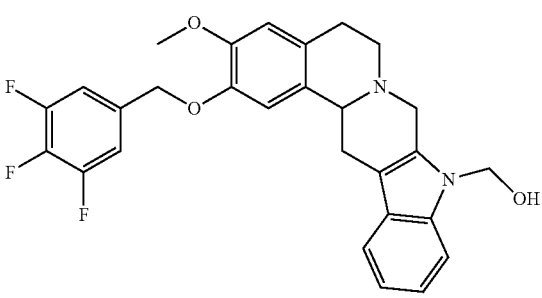 [SMILES: COc1cc2c(cc1OCc1cc(F)c(F)c(F)c1)C1Cc3c(n(CO)c4ccccc34)CN1CC2]<br>A162 |

TABLE 1-continued

| No. | Name | Structure |
|-----|------|-----------|
| A163 | (3,12-dimethoxy-2-((3,4,5-trifluorobenzyl)oxy)-5,6,14,14a-tetrahydroindolo[3',2':4,5]pyridine[2,1-a]isoquinoline-9(8H)-yl)methanol | A163 |
| B1 | 2-(benzyloxy)-8-(4-fluorophenyl)-3,12-dimethoxy-5,6,8,9,14,14a-hexahydroindolo[3',2':4,5]pyridine[2,1-a]isoquinoline | B1 |
| B2 | 2-(benzyloxy)-8-(4-fluorophenyl)-3-methoxy-5,6,8,9,14,14a-hexahydroindolo[3',2':4,5]pyridine[2,1-a]isoquinoline | B2 |
| B3 | 8-(4-fluorophenyl)-3,12-dimethoxy-2-((4-(trifluoromethyl)benzyl)oxy)-5,6,8,9,14,14a-hexahydroindolo[3',2':4,5]pyridine[2,1-a]isoquinoline | B3 |

TABLE 1-continued

| No. | Name |
|---|---|
| B4 | 8-(4-fluorophenyl)-3-methoxy-2-((4-(trifluoromethyl)benzyl)oxy)-5,6,8,9,14,14a-hexahydroindolo[3',2':4,5]pyridine[2,1-a]isoquinoline |
| B5 | 2-((4-fluorobenzyl)oxy)-8-(4-fluorophenyl)-3,12-dimethoxy-5,6,8,9,14,14a-hexahydroindolo[3',2':4,5]pyridine[2,1-a]isoquinoline |
| B6 | 2-((4-fluorobenzyl)oxy)-8-(4-fluorophenyl)-3-methoxy-5,6,8,9,14,14a-hexahydroindolo[3',2':4,5]pyridine[2,1-a]isoquinoline |
| B7 | 2-((3-fluorobenzyl)oxy)-8-(4-fluorophenyl)-3,12-dimethoxy-5,6,8,9,14,14a-hexahydroindolo[3',2':4,5]pyridine[2,1-a]isoquinoline |

TABLE 1-continued

| No. | Name | Structure |
|---|---|---|
| B8 | 2-((3-fluorobenzyl)oxy)-8-(4-fluorophenyl)-3-methoxy-5,6,8,9,14,14a-hexahydroindolo[3',2':4,5]pyridine[2,1-a]isoquinoline | 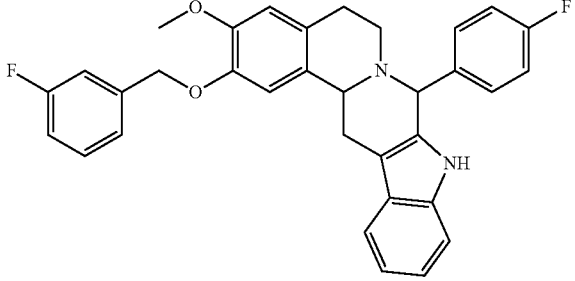 [SMILES: COc1cc2c(cc1OCc1cccc(F)c1)C1Cc3c([nH]c4ccccc34)C(c3ccc(F)cc3)N1CC2]<br>B8 |
| B9 | 2-((2-fluorobenzyl)oxy)-8-(4-fluorophenyl)-3,12-dimethoxy-5,6,8,9,14,14a-hexahydroindolo[3',2':4,5]pyridine[2,1-a]isoquinoline | 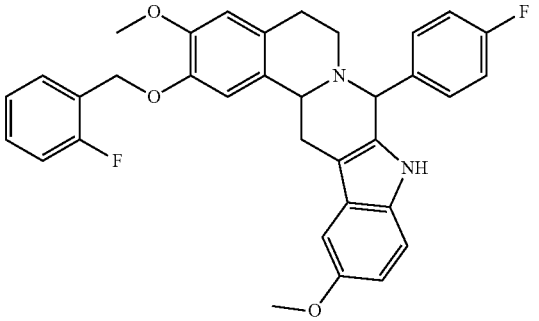 [SMILES: COc1ccc2[nH]c3c(c2c1)CC1c2cc(OCc4ccccc4F)c(OC)cc2CCN1C3c1ccc(F)cc1]<br>B9 |
| B10 | 2-((2-fluorobenzyl)oxy)-8-(4-fluorophenyl)-3-methoxy-5,6,8,9,14,14a-hexahydroindolo[3',2':4,5]pyridine[2,1-a]isoquinoline | 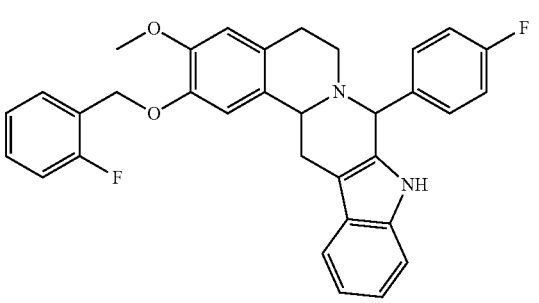 [SMILES: COc1cc2c(cc1OCc1ccccc1F)C1Cc3c([nH]c4ccccc34)C(c3ccc(F)cc3)N1CC2]<br>B10 |
| B11 | 8-(4-fluorophenyl)-3,12-dimethoxy-2-((4-methoxybenzyl)oxy)-5,6,8,9,14,14a-hexahydroindolo[3',2':4,5]pyridine[2,1-a]isoquinolin | 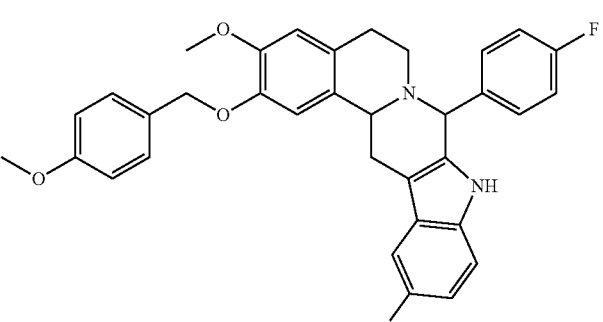<br>B11 |

TABLE 1-continued

| No. | Name | Structure |
| --- | --- | --- |
| B12 | 8-(4-fluorophenyl)-3-methoxy-2-((4-methoxybenzyl)oxy)-5,6,8,9,14,14a-hexahydroindolo[3',2':4,5]pyridine[2,1-a]isoquinoline | B12 |
| B13 | 8-(4-fluorophenyl)-3,12-dimethoxy-2-((3-methoxybenzyl)oxy)-5,6,8,9,14,14a-hexahydroindolo[3',2':4,5]pyridine[2,1-a]isoquinoline | B13 |
| B14 | 8-(4-fluorophenyl)-3-methoxy-2-((3-methoxybenzyl)oxy)-5,6,8,9,14,14a-hexahydroindolo[3',2':4,5]pyridine[2,1-a]isoquinoline | B14 |
| B15 | 8-(4-fluorophenyl)-3,12-dimethoxy-2-((4-methylbenzyl)oxy)-5,6,8,9,14,14a-hexahydroindolo[3',2':4,5]pyridine[2,1-a]isoquinoline | B15 |

TABLE 1-continued

| No. | Name |
|---|---|
| B16 | 8-(4-fluorophenyl)-3-methoxy-2-((4-methylbenzyl)oxy)-5,6,8,9,14,14a-hexahydroindolo[3',2':4,5]pyridine[2,1-a]isoquinoline |
| B17 | 2-((4-chlorobenzyl)oxy)-8-(4-fluorophenyl)-3,12-dimethoxy-5,6,8,9,14,14a-hexahydroindolo[3',2':4,5]pyridine[2,1-a]isoquinoline |
| B18 | 2-((4-chlorobenzyl)oxy)-8-(4-fluorophenyl)-3-methoxy-5,6,8,9,14,14a-hexahydroindolo[3',2':4,5]pyridine[2,1-a]isoquinoline |
| B19 | 4-(((8-(4-fluorophenyl)-3,12-dimethoxy-5,6,8,9,14,14a-hexahydroindolo[3',2':4,5]pyridine[2,1-a]isoquinoline-2-yl)oxy)methyl)benzonitrile |

TABLE 1-continued

| No. | Name | Structure |
|---|---|---|
| B20 | 4-(((8-(4-fluorophenyl)-3-methoxy-5,6,8,9,14,14a-hexahydroindolo[3',2':4,5]pyridine[2,1-a]isoquinoline-2-yl)oxy)methyl)benzontrile | 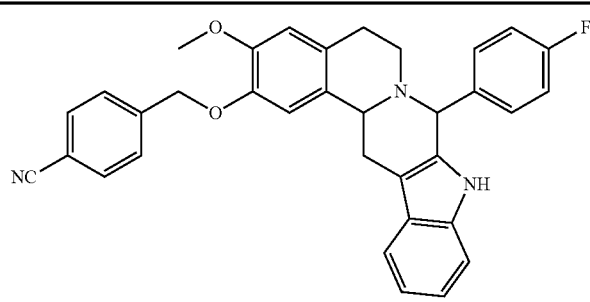 B20 |
| B21 | 2-((4-bromobenzyl)oxy)-8-(4-fluorophenyl)-3,12-dimethoxy-5,6,8,9,14,14a-hexahydroindolo[3',2':4,5]pyridine[2,1-a]isoquinoline | 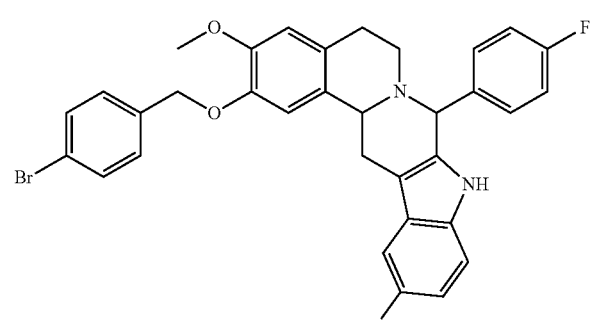 B21 |
| B22 | 2-((4-bromobenzyl)oxy)-8-(4-fluorophenyl)-3-methoxy-5,6,8,9,14,14a-hexahydroindolo[3',2':4,5]pyridine[2,1-a]isoquinoline | 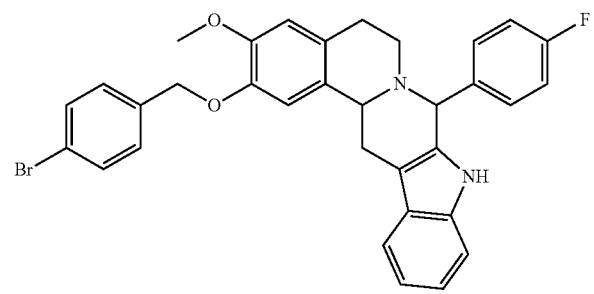 B22 |
| B23 | 2-((3-fluoro-4-(trifluoromethyl)benzyl)oxy)-8-(4-fluorophenyl)-3,12-dimethoxy-5,6,8,9,14,14a-hexahydroindolo[3',2':4,5]pyridine[2,1-a]isoquinoline | 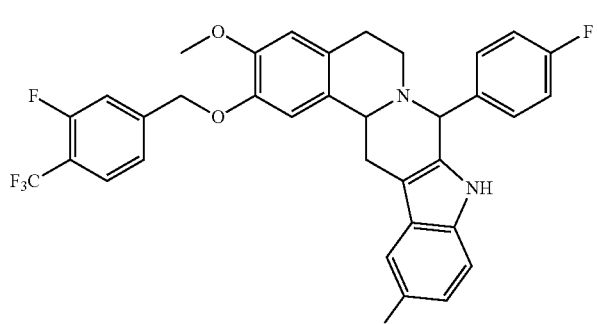 B23 |

TABLE 1-continued

| No. | Name | Structure |
|---|---|---|
| B24 | 2-((3-fluoro-4-(trifluoromethyl)benzyl)oxy)-8-(4-fluorophenyl)-3-methoxy-5,6,8,9,14,14a-hexahydroindolo[3',2':4,5]pyridine[2,1-a]isoquinoline | 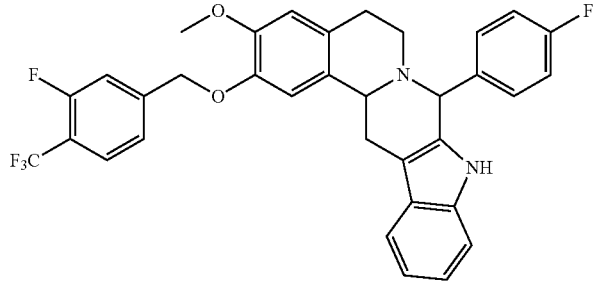 [SMILES: COc1cc2c(cc1OCc1ccc(C(F)(F)F)c(F)c1)C1Cc3c([nH]c4ccccc34)C(c3ccc(F)cc3)N1CC2]<br>B24 |
| B25 | 2-((2-fluoro-4-(trifluoromethyl)benzyl)oxy)-8-(4-fluorophenyl)-3,12-dimethoxy-5,6,8,9,14,14a-hexahydroindolo[3',2':4,5]pyridine[2,1-a]isoquinoline | 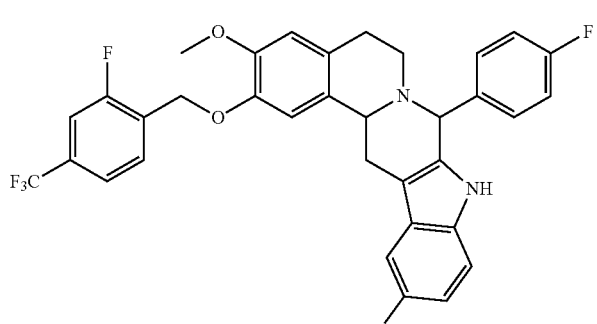<br>B25 |
| B26 | 2-((2-fluoro-4-(trifluoromethyl)benzyl)oxy)-8-(4-fluorophenyl)-3-methoxy-5,6,8,9,14,14a-hexahydroindolo[3',2':4,5]pyridine[2,1-a]isoquinoline | 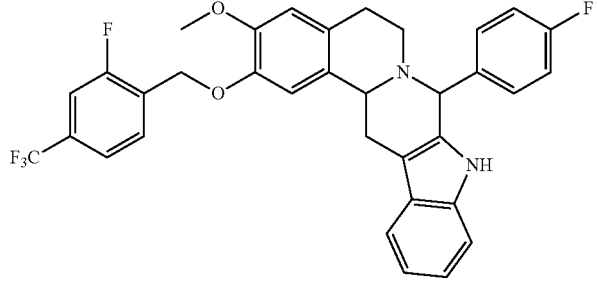 [SMILES: COc1cc2c(cc1OCc1ccc(C(F)(F)F)cc1F)C1Cc3c([nH]c4ccccc34)C(c3ccc(F)cc3)N1CC2]<br>B26 |
| B27 | 2-((4-ethylbenzyl)oxy)-8-(4-fluorophenyl)-3,12-dimethoxy-5,6,8,9,14,14a-hexahydroindolo[3',2':4,5]pyridine[2,1-a]isoquinoline | 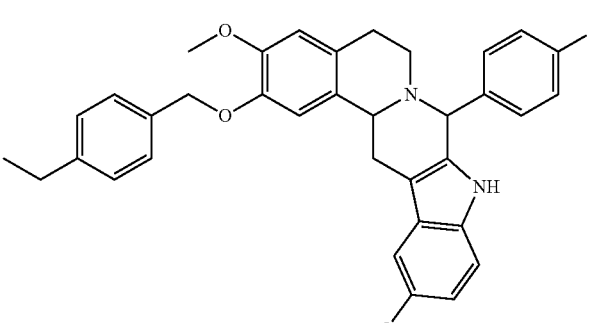<br>B27 |

TABLE 1-continued

| No. | Name |
|---|---|
| B28 | 2-((4-ethylbenzyl)oxy)-8-(4-fluorophenyl)-3-methoxy-5,6,8,9,14,14a-hexahydroindolo[3',2':4,5]pyridine[2,1-a]isoquinoline |
| B29 | 8-(4-fluorophenyl)-3,12-dimethoxy-2-(naphthalen-2-ylmethoxy)-5,6,8,9,14,14a-hexahydroindolo[3',2':4,5]pyridine[2,1-a]isoquinoline |
| B30 | 8-(4-fluorophenyl)-3-methoxy-2-(naphthalen-2-ylmethoxy)-5,6,8,9,14,14a-hexahydroindolo[3',2':4,5]pyridine[2,1-a]isoquinoline |
| B31 | 4-(((8-(4-fluorophenyl)-3,12-dimethoxy-5,6,8,9,14,14a-hexahydroindolo[3',2':4,5]pyridine[2,1-a]isoquinoline-2-yl)oxo)methyl)benzoate |

TABLE 1-continued

| No. | Name | Structure |
|---|---|---|
| B32 | 4-(((8-(4-fluorophenyl)-3-methoxy-5,6,8,9,14,14a-hexahydroindolo[3',2':4,5]pyridine[2,1-a]isoquinoline-2-yl)oxo)methyl)benzoate | B32 |
| B33 | 2-((4-(1H-pyrazol-1-yl)benzyl)oxy)-8-(4-fluorophenyl)-3,12-dimethoxy-5,6,8,9,14,14a-hexahydroindolo[3',2':4,5]pyridine[2,1-a]isoquinoline | B33 |
| B34 | 2-((4-(1H-pyrazol-1-yl)benzyl)oxy)-8-(4-fluorophenyl)-3-methoxy-5,6,8,9,14,14a-hexahydroindolo[3',2':4,5]pyridine[2,1-a]isoquinoline | B34 |
| B35 | 2-butoxy-8-(4-fluorophenyl)-3,12-dimethoxy-5,6,8,9,14,14a-hexahydroindolo[3',2':4,5]pyridine[2,1-a]isoquinoline | B35 |

TABLE 1-continued

| No. | Name | Structure |
|---|---|---|
| B36 | 2-butoxy-8-(4-fluorophenyl)-3-methoxy-5,6,8,9,14,14a-hexahydroindolo[3',2':4,5]pyridine[2,1-a]isoquinoline | 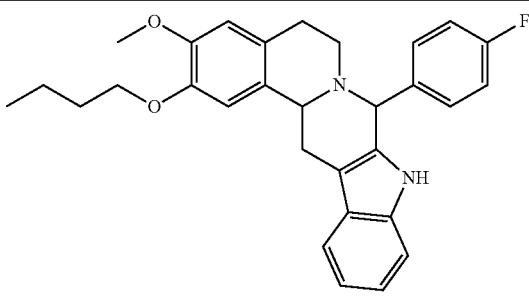<br>B36 |
| B37 | 8-(4-fluorophenyl)-12-methoxy-5,6,8,9,14,14a-hexahydroindole[3',2':4,5]pyridine[2,1-a]thiophene[3,2-g]isoquinoline | 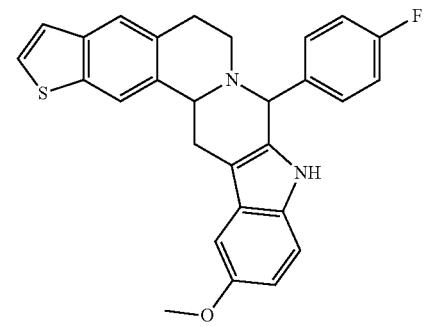 [SMILES: COc1ccc2[nH]c3c(c2c1)CC1c2cc4sccc4cc2CCN1C3c1ccc(F)cc1]<br>B37 |
| B38 | 8-(4-fluorophenyl)-5,6,8,9,14,14a-hexahydroindole[3',2':4,5]pyridine[2,1-a]thiophene[3,2-g]isoquinoline | 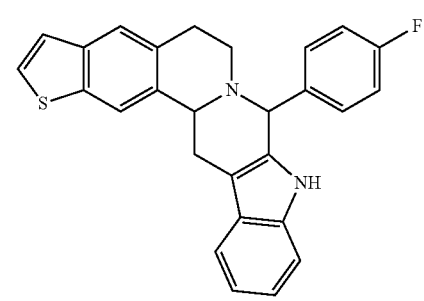 [SMILES: Fc1ccc(C2c3[nH]c4ccccc4c3CC3c4cc5sccc5cc4CCN32)cc1]<br>B38 |
| B39 | 8-(4-fluorophenyl)-3,12-dimethoxy-2-(2,2,2-trifluoroethoxy)-5,6,8,9,14,14a-hexahydroindolo[3',2':4,5]pyridine[2,1-a]isoquinoline | 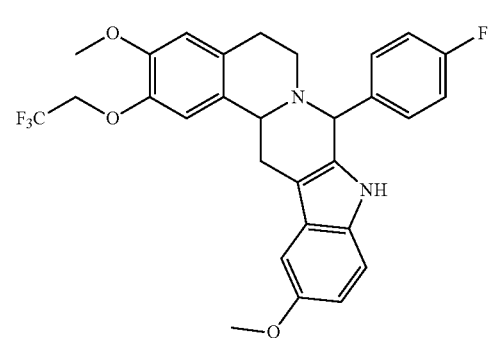 [SMILES: COc1ccc2[nH]c3c(c2c1)CC1c2cc(OCC(F)(F)F)c(OC)cc2CCN1C3c1ccc(F)cc1]<br>B39 |

TABLE 1-continued

| No. | Name |
|---|---|
| B40 | 8-(4-fluorophenyl)-3-methoxy-2-(2,2,2-trifluoroethoxy)-5,6,8,9,14,14a-hexahydroindolo[3',2':4,5]pyridine[2,1-a]isoquinoline |
| B41 | 8-(4-fluorophenyl)-3,12-dimethoxy-2-((4-(methylsulfonyl)benzyl)oxy)-5,6,8,9,14,14a-hexahydroindolo[3',2':4,5]pyridine[2,1-a]isoquinoline |
| B42 | 8-(4-fluorophenyl)-3-methoxy-2-((4-(methylsulfonyl)benzyl)oxy)-5,6,8,9,14,14a-hexahydroindolo[3',2':4,5]pyridine[2,1-a]isoquinoline |
| B43 | 2-(benzyloxy)-11-fluoro-8-(4-fluorophenyl)-3-methoxy-5,6,8,9,14,14a-hexahydroindolo[3',2':4,5]pyridine[2,1-a]isoquinoline |

TABLE 1-continued

| No. | Name | Structure |
|---|---|---|
| B44 | 2-(benzyloxy)-12-fluoro-8-(4-fluorophenyl)-3-methoxy-5,6,8,9,14,14a-hexahydroindolo[3',2':4,5]pyridine[2,1-a]isoquinoline | B44 |
| B45 | 2-(benzyloxy)-13-fluoro-8-(4-fluorophenyl)-3-methoxy-5,6,8,9,14,14a-hexahydroindolo[3',2':4,5]pyridine[2,1-a]isoquinoline | B45 |
| B46 | 2-(benzyloxy)-11-chloro-8-(4-fluorophenyl)-3-methoxy-5,6,8,9,14,14a-hexahydroindolo[3',2':4,5]pyridine[2,1-a]isoquinoline | B46 |
| B47 | 2-(benzyloxy)-12-chloro-8-(4-fluorophenyl)-3-methoxy-5,6,8,9,14,14a-hexahydroindolo[3',2':4,5]pyridine[2,1-a]isoquinoline | B47 |

TABLE 1-continued

| No. | Name | Structure |
|---|---|---|
| B48 | 2-(benzyloxy)-13-chloro-8-(4-fluorophenyl)-3-methoxy-5,6,8,9,14,14a-hexahydroindolo[3',2':4,5]pyridine[2,1-a]isoquinoline | B48 |
| B49 | 2-(benzyloxy)-11-bromo-8-(4-fluorophenyl)-3-methoxy-5,6,8,9,14,14a-hexahydroindolo[3',2':4,5]pyridine[2,1-a]isoquinoline | B49 |
| B50 | 2-(benzyloxy)-12-bromo-8-(4-fluorophenyl)-3-methoxy-5,6,8,9,14,14a-hexahydroindolo[3',2':4,5]pyridine[2,1-a]isoquinoline | B50 |
| B51 | 2-(benzyloxy)-13-bromo-8-(4-fluorophenyl)-3-methoxy-5,6,8,9,14,14a-hexahydroindolo[3',2':4,5]pyridine[2,1-a]isoquinoline | B51 |

TABLE 1-continued

| No. | Name |
|---|---|
| B52 | 2-(benzyloxy)-8-(4-fluorophenyl)-3-methoxy-5,6,8,9,14,14a-hexahydroindolo[3',2':4,5]pyridine[2,1-a]isoquinoline-12-phenol |
| B53 | 2-(benzyloxy)-8-(4-fluorophenyl)-3-methoxy-11-methyl-5,6,8,9,14,14a-hexahydroindolo[3',2':4,5]pyridine[2,1-a]isoquinoline |
| B54 | 2-(benzyloxy)-12-ethyl-8-(4-fluorophenyl)-3-methoxy-5,6,8,9,14,14a-hexahydroindolo[3',2':4,5]pyridine[2,1-a]isoquinoline |
| B55 | 3-(benzyloxy)-8-(4-fluorophenyl)-2,12-dimethoxy-5,6,8,9,14,14a-hexahydroindolo[3',2':4,5]pyridine[2,1-a]isoquinoline |

TABLE 1-continued

| No. | Name | Structure |
|---|---|---|
| B56 | 3-(benzyloxy)-8-(4-fluorophenyl)-2-methoxy-5,6,8,9,14,14a-hexahydroindolo[3',2':4,5]pyridine[2,1-a]isoquinoline | 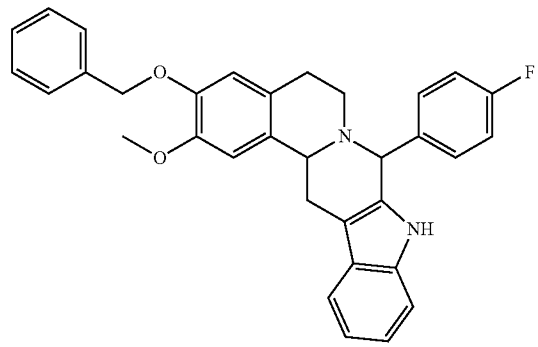 [SMILES: COc1cc2c(cc1OCc1ccccc1)CCN1C2Cc2c([nH]c3ccccc23)C1c1ccc(F)cc1] |
| B57 | 8-(4-fluorophenyl)-2,12-dimethoxy-3-((4-(trifluoromethyl)benzyl)oxy)-5,6,8,9,14,14a-hexahydroindolo[3',2':4,5]pyridine[2,1-a]isoquinoline | 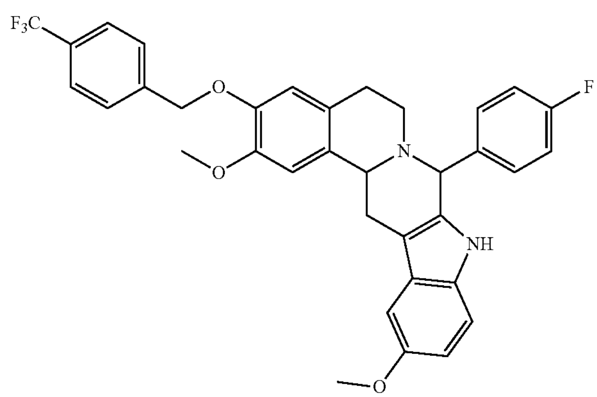 [SMILES: COc1ccc2[nH]c3c(c2c1)CC1c2cc(OC)c(OCc4ccc(C(F)(F)F)cc4)cc2CCN1C3c1ccc(F)cc1] |
| B58 | 8-(4-fluorophenyl)-2-methoxy-3-((4-(trifluoromethyl)benzyl)oxy)-5,6,8,9,14,14a-hexahydroindolo[3',2':4,5]pyridine[2,1-a]isoquinoline | 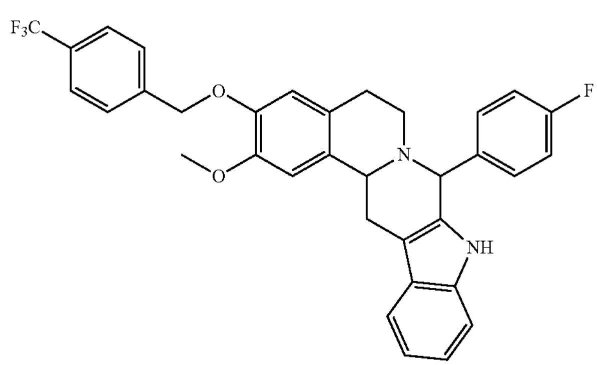 [SMILES: COc1cc2c(cc1OCc1ccc(C(F)(F)F)cc1)CCN1C2Cc2c([nH]c3ccccc23)C1c1ccc(F)cc1] |

TABLE 1-continued

| No. | Name | Structure |
|---|---|---|
| B59 | 3-((4-fluorobenzyl)oxy)-8-(4-fluorophenyl)-2,12-dimethoxy-5,6,8,9,14,14a-hexahydroindolo[3',2':4,5]pyridine[2,1-a]isoquinoline | 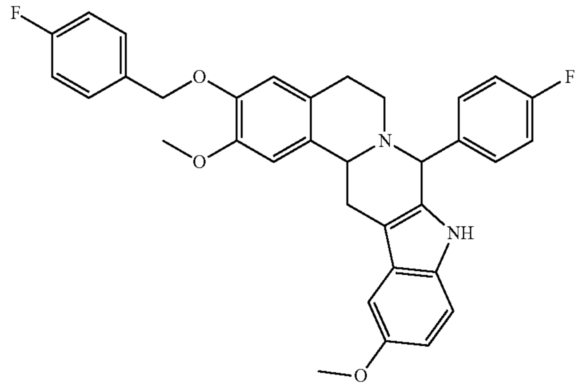 [SMILES: COc1ccc2[nH]c3c(c2c1)CC1c2cc(OC)c(OCc4ccc(F)cc4)cc2CCN1C3c1ccc(F)cc1] |
| B60 | 3-((4-fluorobenzyl)oxy)-8-(4-fluorophenyl)-2-methoxy-5,6,8,9,14,14a-hexahydroindolo[3',2':4,5]pyridine[2,1-a]isoquinoline | 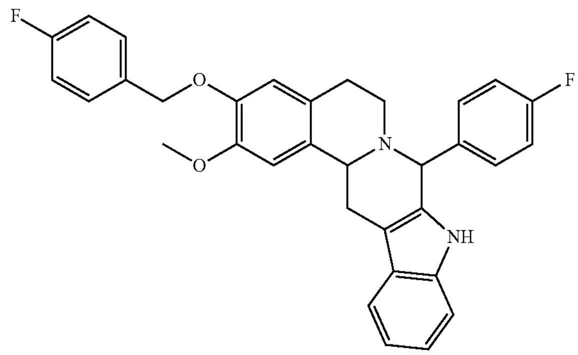 [SMILES: COc1cc2c(cc1OCc1ccc(F)cc1)CCN1C2Cc2c([nH]c3ccccc23)C1c1ccc(F)cc1] |
| B61 | 3-((3-fluorobenzyl)oxy)-8-(4-fluorophenyl)-2,12-dimethoxy-5,6,8,9,14,14a-hexahydroindolo[3',2':4,5]pyridine[2,1-a]isoquinoline | 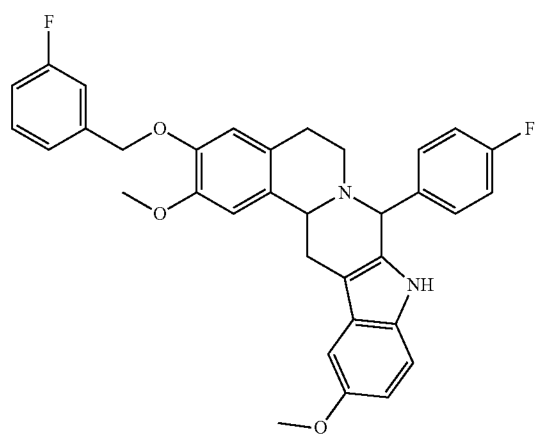 [SMILES: COc1ccc2[nH]c3c(c2c1)CC1c2cc(OC)c(OCc4cccc(F)c4)cc2CCN1C3c1ccc(F)cc1] |

TABLE 1-continued
| No. | Name | Structure |
|---|---|---|
| B62 | 3-((3-fluorobenzyl)oxy)-8-(4-fluorophenyl)-2-methoxy-5,6,8,9,14,14a-hexahydroindolo[3',2':4,5]pyridine[2,1-a]isoquinoline | 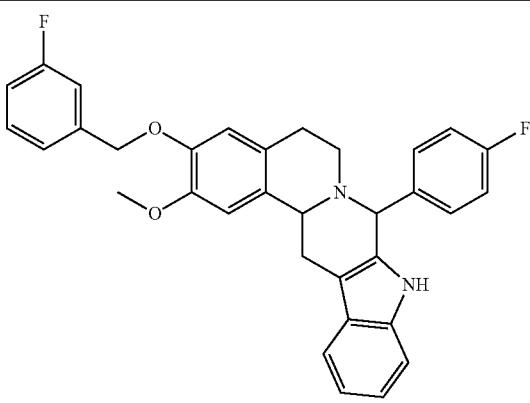<br>B62 |
| B63 | 3-((2-fluorobenzyl)oxy)-8-(4-fluorophenyl)-2,12-dimethoxy-5,6,8,9,14,14a-hexahydroindolo[3',2':4,5]pyridine[2,1-a]isoquinoline | 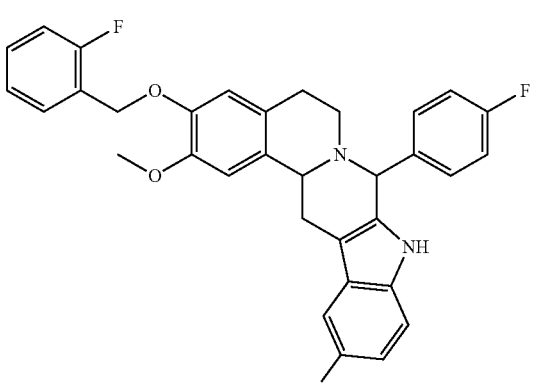<br>B63 |
| B64 | 3-((2-fluorobenzyl)oxy)-8-(4-fluorophenyl)-2-methoxy-5,6,8,9,14,14a-hexahydroindolo[3',2':4,5]pyridine[2,1-a]isoquinoline | 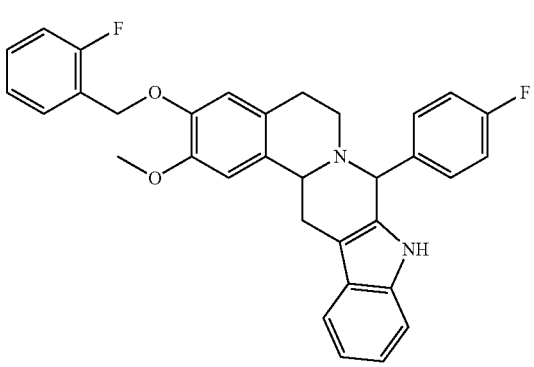 [SMILES: COc1cc2c(cc1OCc1ccccc1F)CCN1C2Cc2c([nH]c3ccccc23)C1c1ccc(F)cc1]<br>B64 |

TABLE 1-continued
| No. | Name | Structure |
|---|---|---|
| B65 | 8-(4-fluorophenyl)-2,12-dimethoxy-3-((4-methoxybenzyl)oxy)-5,6,8,9,14,14a-hexahydroindolo[3',2':4,5]pyridine[2,1-a]isoquinoline | 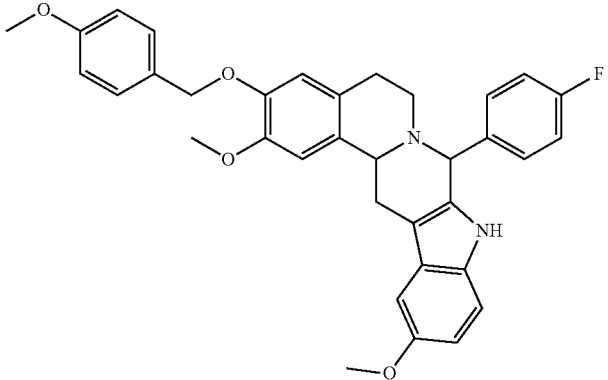 [SMILES: COc1ccc(COc2cc3c(cc2OC)C2Cc4c([nH]c5ccc(OC)cc45)C(c4ccc(F)cc4)N2CC3)cc1]<br>B65 |
| B66 | 8-(4-fluorophenyl)-2-methoxy-3-((4-methoxybenzyl)oxy)-5,6,8,9,14,14a-hexahydroindolo[3',2':4,5]pyridine[2,1-a]isoquinoline | 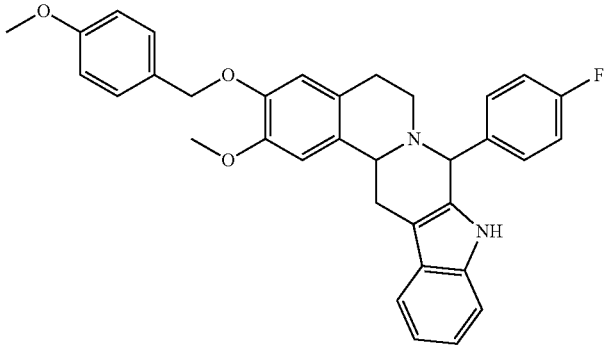 [SMILES: COc1ccc(COc2cc3c(cc2OC)C2Cc4c([nH]c5ccccc45)C(c4ccc(F)cc4)N2CC3)cc1]<br>B66 |
| B67 | 8-(4-fluorophenyl)-2,12-dimethoxy-3-((3-methoxybenzyl)oxy)-5,6,8,9,14,14a-hexahydroindolo[3',2':4,5]pyridine[2,1-a]isoquinoline | 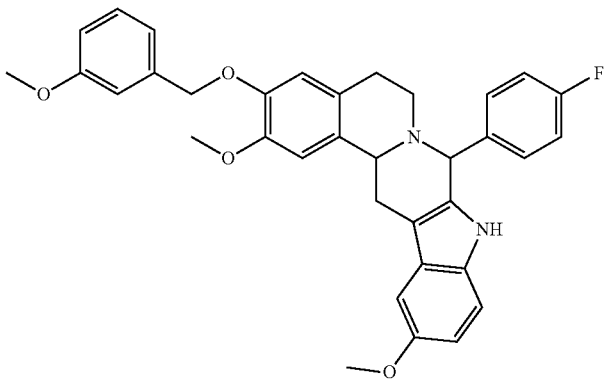 [SMILES: COc1cccc(COc2cc3c(cc2OC)C2Cc4c([nH]c5ccc(OC)cc45)C(c4ccc(F)cc4)N2CC3)c1]<br>B67 |

TABLE 1-continued

| No. | Name | Structure |
|---|---|---|
| B68 | 8-(4-fluorophenyl)-2-methoxy-3-((3-methoxybenzyl)oxy)-5,6,8,9,14,14a-hexahydroindolo[3',2':4,5]pyridine[2,1-a]isoquinoline | B68 |
| B69 | 8-(4-fluorophenyl)-2,12-dimethoxy-3-((4-methylbenzyl)oxy)-5,6,8,9,14,14a-hexahydroindolo[3',2':4,5]pyridine[2,1-a]isoquinoline | B69 |
| B70 | 8-(4-fluorophenyl)-2-methoxy-3-((4-methylbenzyl)oxy)-5,6,8,9,14,14a-hexahydroindolo[3',2':4,5]pyridine[2,1-a]isoquinoline | B70 |

TABLE 1-continued

| No. | Name |
|---|---|
| B71 | 3-((4-chlorobenzyl)oxy)-8-(4-fluorophenyl)-2,12-dimethoxy-5,6,8,9,14,14a-hexahydroindolo[3',2':4,5]pyridine[2,1-a]isoquinoline |
| B72 | 3-((4-chlorobenzyl)oxy)-8-(4-fluorophenyl)-2-methoxy-5,6,8,9,14,14a-hexahydroindolo[3',2':4,5]pyridine[2,1-a]isoquinoline |
| B73 | 4-(((8-(4-fluorophenyl)-2,12-dimethoxy-5,6,8,9,14,14a-hexahydroindolo[3',2':4,5]pyridine[2,1-a]isoquinoline-3-yl)oxy)methyl)benzonitrile |

TABLE 1-continued

| No. | Name |
|---|---|
| B74 | 4-(((8-(4-fluorophenyl)-2-methoxy-5,6,8,9,14,14a-hexahydroindolo[3',2':4,5]pyridine[2,1-a]isoquinolin-3-yl)oxy)methyl)benzonitrile |
| B75 | 3-((4-bromobenzyl)oxy)-8-(4-fluorophenyl)-2,12-dimethoxy-5,6,8,9,14,14a-hexahydroindolo[3',2':4,5]pyridine[2,1-a]isoquinoline |
| B76 | 3-((4-bromobenzyl)oxy)-8-(4-fluorophenyl)-2-methoxy-5,6,8,9,14,14a-hexahydroindolo[3',2':4,5]pyridine[2,1-a]isoquinoline |

TABLE 1-continued

| No. | Name | Structure |
|---|---|---|
| B77 | 3-((3-fluoro-4-(trifluoromethyl)benzyl)oxy)-8-(4-fluorophenyl)-2,12-dimethoxy-5,6,8,9,14,14a-hexahydroindolo[3',2':4,5]pyridine[2,1-a]isoquinoline | 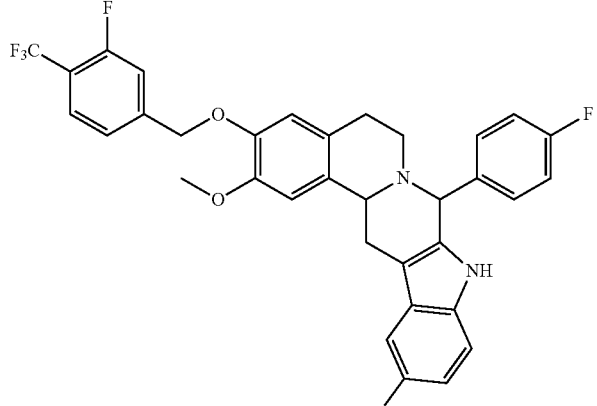<br>B77 |
| B78 | 3-((3-fluoro-4-(trifluoromethyl)benzyl)oxy)-8-(4-fluorophenyl)-2-methoxy-5,6,8,9,14,14a-hexahydroindolo[3',2':4,5]pyridine[2,1-a]isoquinoline | 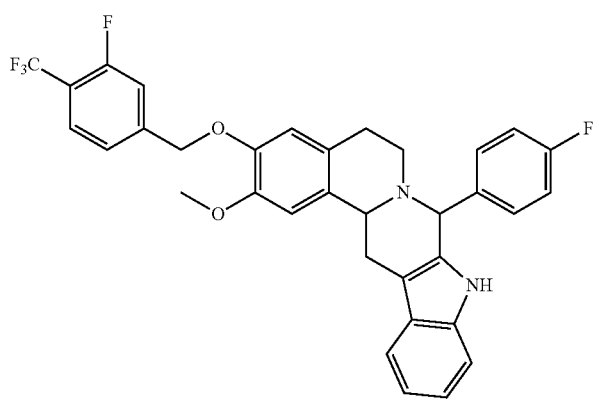 [SMILES: COc1cc2c(cc1OCc1ccc(C(F)(F)F)c(F)c1)CCN1C2Cc2c([nH]c3ccccc23)C1c1ccc(F)cc1]<br>B78 |
| B79 | 3-((2-fluoro-4-(trifluoromethyl)benzyl)oxy)-8-(4-fluorophenyl)-2,12-dimethoxy-5,6,8,9,14,14a-hexahydroindolo[3',2':4,5]pyridine[2,1-a]isoquinoline | 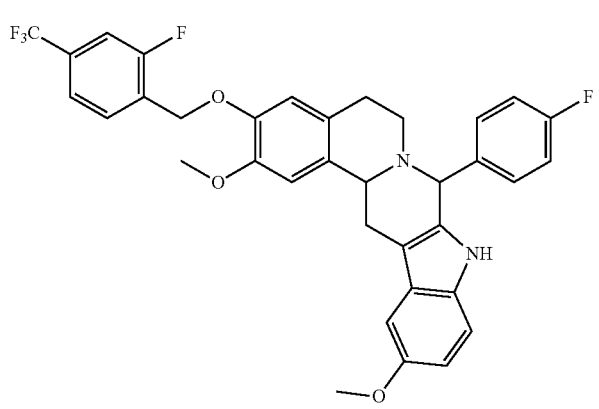 [SMILES: COc1ccc2[nH]c3c(c2c1)CC1c2cc(OC)c(OCc4ccc(C(F)(F)F)cc4F)cc2CCN1C3c1ccc(F)cc1]<br>B79 |

TABLE 1-continued
| No. | Name | Structure |
|---|---|---|
| B80 | 3-((2-fluoro-4-(trifluoromethyl)benzyl)oxy)-8-(4-fluorophenyl)-2-methoxy-5,6,8,9,14,14a-hexahydroindolo[3',2':4,5]pyridine[2,1-a]isoquinoline | 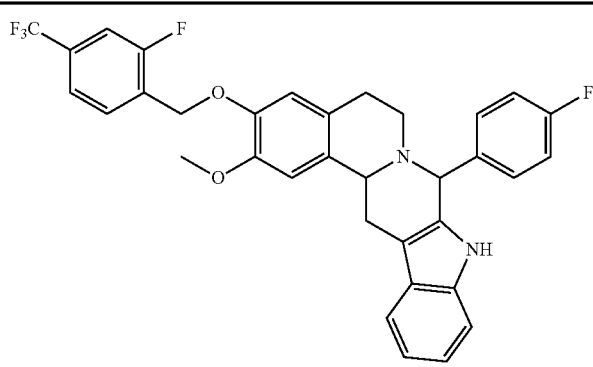<br>B80 |
| B81 | 3-((4-ethylbenzyl)oxy)-8-(4-fluorophenyl)-2,12-dimethoxy-5,6,8,9,14,14a-hexahydroindolo[3',2':4,5]pyridine[2,1-a]isoquinoline | 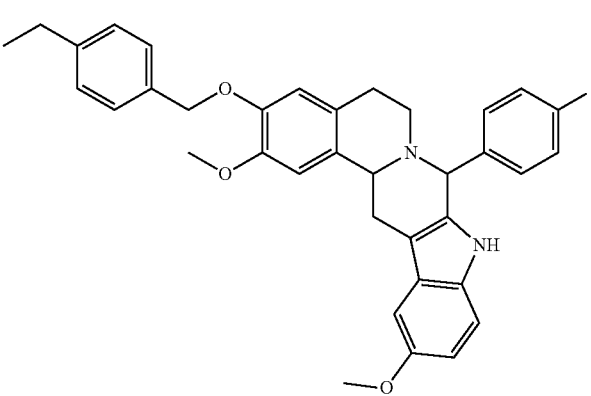<br>B81 |
| B82 | 3-((4-ethylbenzyl)oxy)-8-(4-fluorophenyl)-2-methoxy-5,6,8,9,14,14a-hexahydroindolo[3',2':4,5]pyridine[2,1-a]isoquinoline | 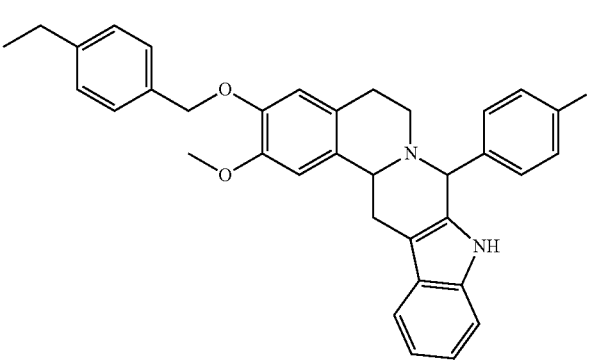<br>B82 |

TABLE 1-continued
| No. | Name | Structure |
|---|---|---|
| B83 | 8-(4-fluorophenyl)-2,12-dimethoxy-3-(naphthalen-2-ylmethoxy)-5,6,8,9,14,14a-hexahydroindolo[3',2':4,5]pyridine[2,1-a]isoquinoline | 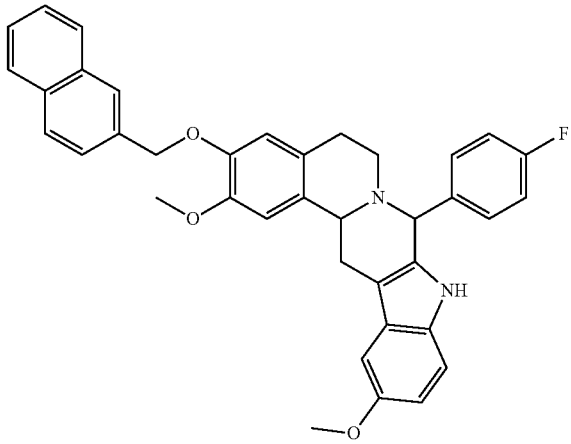 [SMILES: COc1ccc2[nH]c3c(c2c1)CC1c2cc(OC)c(OCc4ccc5ccccc5c4)cc2CCN1C3c1ccc(F)cc1]<br>B83 |
| B84 | 8-(4-fluorophenyl)-2-methoxy-3-(naphthalen-2-ylmethoxy)-5,6,8,9,14,14a-hexahydroindolo[3',2':4,5]pyridine[2,1-a]isoquinoline | 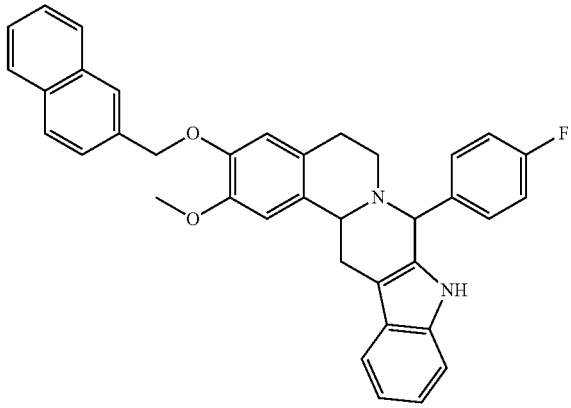 [SMILES: COc1cc2c(cc1OCc1ccc3ccccc3c1)CCN1C2Cc2c([nH]c3ccccc23)C1c1ccc(F)cc1]<br>B84 |
| B85 | 4-(((8-(4-fluorophenyl)-2,12-dimethoxy-5,6,8,9,14,14a-hexahydroindolo[3',2':4,5]pyridine[2,1-a]isoquinoline-3-yl)oxo)methyl)benzoate | 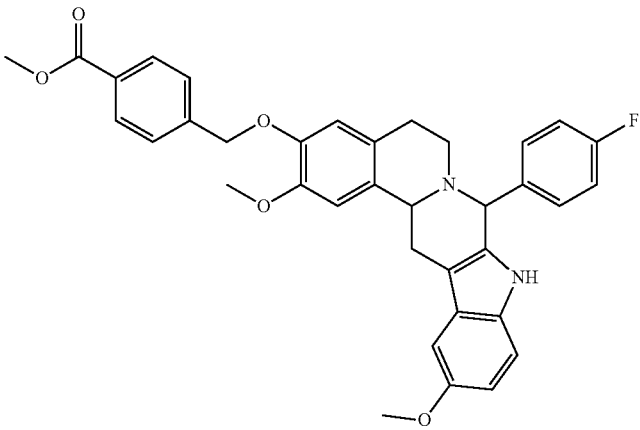 [SMILES: COC(=O)c1ccc(COc2cc3c(cc2OC)C2Cc4c([nH]c5ccc(OC)cc45)C(c4ccc(F)cc4)N2CC3)cc1]<br>B85 |

TABLE 1-continued

| No. | Name | Structure |
| --- | --- | --- |
| B86 | 4-(((8-(4-fluorophenyl)-2-methoxy-5,6,8,9,14,14a-hexahydroindolo[3',2':4,5]pyridine[2,1-a]isoquinoline-3-yl)oxo)methyl)benzoate | B86 |
| B87 | 3-((4-(1H-pyrazol-1-yl)benzyl)oxy)-8-(4-fluorophenyl)-2,12-dimethoxy-5,6,8,9,14,14a-hexahydroindolo[3',2':4,5]pyridine[2,1-a]isoquinoline | B87 |
| B88 | 3-((4-(1H-pyrazol-1-yl)benzyl)oxy)-8-(4-fluorophenyl)-2-methoxy-5,6,8,9,14,14a-hexahydroindolo[3',2':4,5]pyridine[2,1-a]isoquinoline | B88 |

TABLE 1-continued

| No. | Name |
|---|---|
| B89 | 3-butoxy-8-(4-fluorophenyl)-2,12-dimethoxy-5,6,8,9,14,14a-hexahydroindolo[3',2':4,5]pyridine[2,1-a]isoquinoline |
| B90 | 3-butoxy-8-(4-fluorophenyl)-2-methoxy-5,6,8,9,14,14a-hexahydroindolo[3',2':4,5]pyridine[2,1-a]isoquinoline |
| B91 | 3-(benzyloxy)-8-(4-fluorophenyl)-2-methoxy-11-methyl-5,6,8,9,14,14a-hexahydroindolo[3',2':4,5]pyridine[2,1-a]isoquinoline |
| B92 | 3-(benzyloxy)-8-(4-fluorophenyl)-2-methoxy-12-ethyl-5,6,8,9,14,14a-hexahydroindolo[3',2':4,5]pyridine[2,1-a]isoquinoline |

TABLE 1-continued

| No. | Name | Structure |
|---|---|---|
| B93 | 8-(4-fluorophenyl)-2,12-dimethoxy-3-(2,2,2-trifluoroethoxy)-5,6,8,9,14,14a-hexahydroindolo[3',2':4,5]pyridine[2,1-a]isoquinoline | B93 |
| B94 | 8-(4-fluorophenyl)-2-methoxy-3-(2,2,2-trifluoroethoxy)-5,6,8,9,14,14a-hexahydroindolo[3',2':4,5]pyridine[2,1-a]isoquinoline | B94 |
| B95 | 8-fluoro-2,12-dimethoxy-3-((4-(methylsulfonyl)benzyl)oxy)-5,6,8,9,14,14a-hexahydroindolo[3',2':4,5]pyridine[2,1-a]isoquinoline | B95 |
| B96 | 8-fluoro-2-methoxy-3-((4-(methylsulfonyl)benzyl)oxy)-5,6,8,9,14,14a-hexahydroindolo[3',2':4,5]pyridine[2,1-a]isoquinoline | B96 |

TABLE 1-continued

| No. | Name |
|---|---|
| B97 | 3-(benzyloxy)-11-fluoro-8-(4-fluorophenyl)-2-methoxy-5,6,8,9,14,14a-hexahydroindolo[3',2':4,5]pyridine[2,1-a]isoquinoline |
| B98 | 3-(benzyloxy)-12-fluoro-8-(4-fluorophenyl)-2-methoxy-5,6,8,9,14,14a-hexahydroindolo[3',2':4,5]pyridine[2,1-a]isoquinoline |
| B99 | 3-(benzyloxy)-13-fluoro-8-(4-fluorophenyl)-2-methoxy-5,6,8,9,14,14a-hexahydroindolo[3',2':4,5]pyridine[2,1-a]isoquinoline |

TABLE 1-continued
| No. | Name | Structure |
|---|---|---|
| B100 | 3-(benzyloxy)-11-chloro-8-(4-fluorophenyl)-2-methoxy-5,6,8,9,14,14a-hexahydroindolo[3',2':4,5]pyridine[2,1-a]isoquinoline | 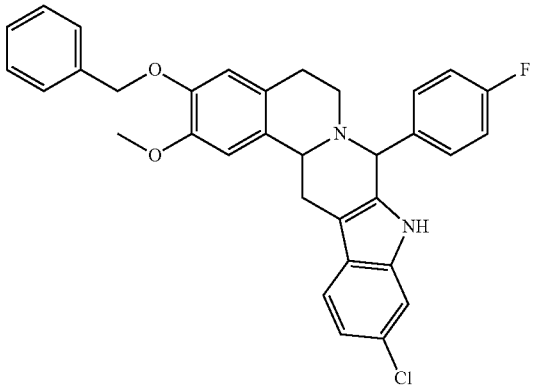<br>B100 |
| B101 | 3-(benzyloxy)-12-chloro-8-(4-fluorophenyl)-2-methoxy-5,6,8,9,14,14a-hexahydroindolo[3',2':4,5]pyridine[2,1-a]isoquinoline | 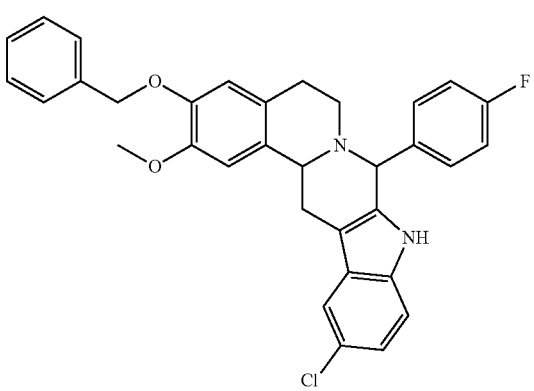 [SMILES: COc1cc2c(cc1OCc1ccccc1)CCN1C2Cc2c([nH]c3ccc(F)cc23)C1c1ccc(F)cc1]<br>B101 |
| B102 | 3-(benzyloxy)-13-chloro-8-(4-fluorophenyl)-2-methoxy-5,6,8,9,14,14a-hexahydroindolo[3',2':4,5]pyridine[2,1-a]isoquinoline | 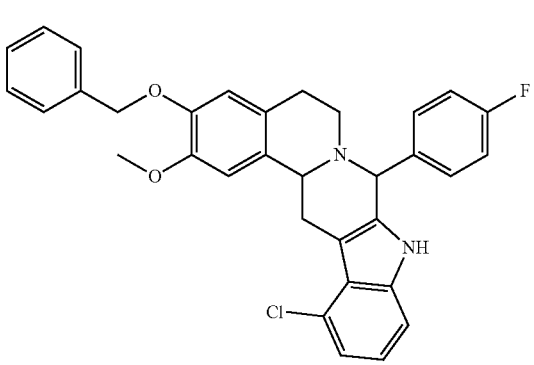 [SMILES: COc1cc2c(cc1OCc1ccccc1)CCN1C2Cc2c([nH]c3cccc(Cl)c23)C1c1ccc(F)cc1]<br>B102 |

TABLE 1-continued

| No. | Name | Structure |
|---|---|---|
| B103 | 3-(benzyloxy)-11-bromo-8-(4-fluorophenyl)-2-methoxy-5,6,8,9,14,14a-hexahydroindolo[3',2':4,5]pyridine[2,1-a]isoquinoline | B103 |
| B104 | 3-(benzyloxy)-12-bromo-8-(4-fluorophenyl)-2-methoxy-5,6,8,9,14,14a-hexahydroindolo[3',2':4,5]pyridine[2,1-a]isoquinoline | B104 |
| B105 | 3-(benzyloxy)-13-bromo-8-(4-fluorophenyl)-2-methoxy-5,6,8,9,14,14a-hexahydroindolo[3',2':4,5]pyridine[2,1-a]isoquinoline | B105 |
| B106 | 2-(benzyloxy)-8-phenyl-3,12-dimethoxy-5,6,8,9,14,14a-hexahydroindolo[3',2':4,5]pyridine[2,1-a]isoquinoline | 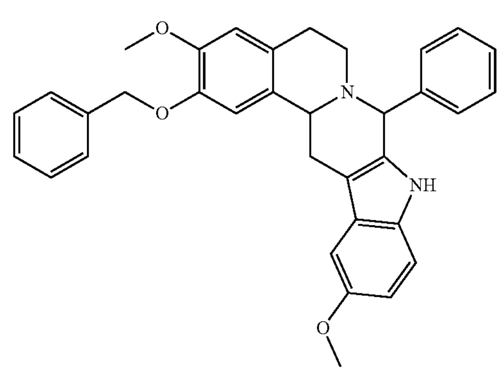 |

TABLE 1-continued

| No. | Name |
|---|---|
| B107 | 2-(benzyloxy)-8-(3-fluorophenyl)-3,12-dimethoxy-5,6,8,9,14,14a-hexahydroindolo[3',2':4,5]pyridine[2,1-a]isoquinoline |
| B108 | 2-(benzyloxy)-8-(2-fluorophenyl)-3,12-dimethoxy-5,6,8,9,14,14a-hexahydroindolo[3',2':4,5]pyridine[2,1-a]isoquinoline |
| B109 | 2-(benzyloxy)-8-benzyl-3,12-dimethoxy-5,6,8,9,14,14a-hexahydroindolo[3',2':4,5]pyridine[2,1-a]isoquinoline |
| B110 | 2-(benzyloxy)-8-thiophene-3,12-dimethoxy-5,6,8,9,14,14a-hexahydroindolo[3',2':4,5]pyridine[2,1-a]isoquinoline |

TABLE 1-continued

| No. | Name |
|---|---|
| B111 | 2-(benzyloxy)-8-furan-3,12-dimethoxy-5,6,8,9,14,14a-hexahydroindolo[3',2':4,5]pyridine[2,1-a]isoquinoline |
| B112 | 2-(benzyloxy)-8-(3-methylfuran)-3,12-dimethoxy-5,6,8,9,14,14a-hexahydroindolo[3',2':4,5]pyridine[2,1-a]isoquinoline |
| B113 | 2-(benzyloxy)-8-(5-methylfuran)-3,12-dimethoxy-5,6,8,9,14,14a-hexahydroindolo[3',2':4,5]pyridine[2,1-a]isoquinoline |
| B114 | 2-(benzyloxy)-8-(5-cyanofuran)-3,12-dimethoxy-5,6,8,9,14,14a-hexahydroindolo[3',2':4,5]pyridine[2,1-a]isoquinoline |

TABLE 1-continued

| No. | Name |
|---|---|
| B115 | 2-(benzyloxy)-8-pyrrole-3,12-dimethoxy-5,6,8,9,14,14a-hexahydroindolo[3',2':4,5]pyridine[2,1-a]isoquinoline |
| C1 | 2-((2,4-di(trifluoromethyl)benzyl)oxy)-3,12-dimethoxy-5,6,8,9,14,14a-hexahydroindolo[3',2':4,5]pyridine[2,1-a]isoquinoline |
| C2 | 2-((2,4-di(trifluoromethyl)benzyl)oxy)-3-methoxy-5,6,8,9,14,14a-hexahydroindolo[3',2':4,5]pyridine[2,1-a]isoquinoline |
| C3 | 3,12-dimethoxy-2-((4-(trifluoromethyl)benzyl)oxy)-5,6,8,9,14,14a-hexahydroindolo[3',2':4,5]pyridine[2,1-a]isoquinoline |

TABLE 1-continued

| No. | Name | Structure |
|---|---|---|
| C4 | 3-methoxy-2-((4-(trifluoromethyl)benzyl)oxy)-5,6,8,9,14,14a-hexahydroindolo[3',2':4,5]pyridine[2,1-a]isoquinoline | 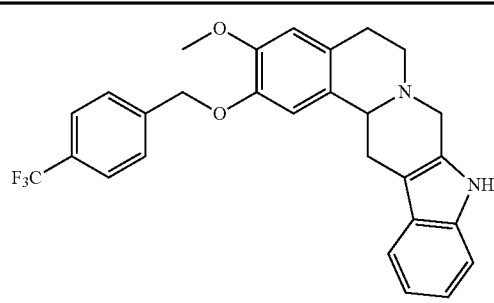<br>C4 |
| C5 | 2-((4-fluorobenzyl)oxy)-3,12-dimethoxy-5,6,8,9,14,14a-hexahydroindolo[3',2':4,5]pyridine[2,1-a]isoquinoline | 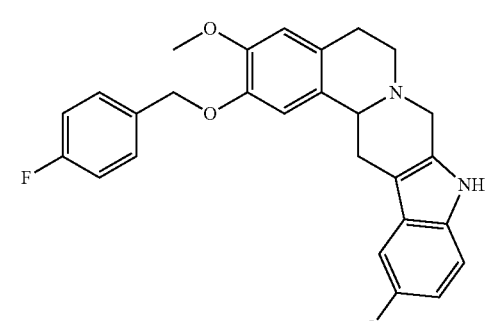<br>C5 |
| C6 | 2-((4-fluorobenzyl)oxy)-3-methoxy-5,6,8,9,14,14a-hexahydroindolo[3',2':4,5]pyridine[2,1-a]isoquinoline | 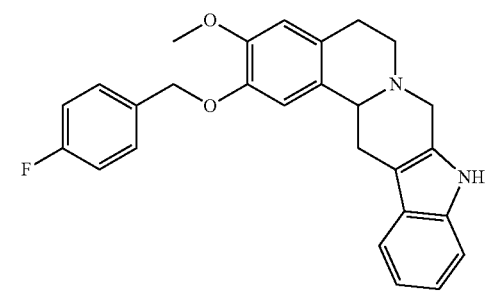 [SMILES: COc1cc2c(cc1OCc1ccc(F)cc1)C1Cc3c([nH]c4ccccc34)CN1CC2]<br>C6 |
| C7 | 2-((3-fluorobenzyl)oxy)-3,12-dimethoxy-5,6,8,9,14,14a-hexahydroindolo[3',2':4,5]pyridine[2,1-a]isoquinoline | 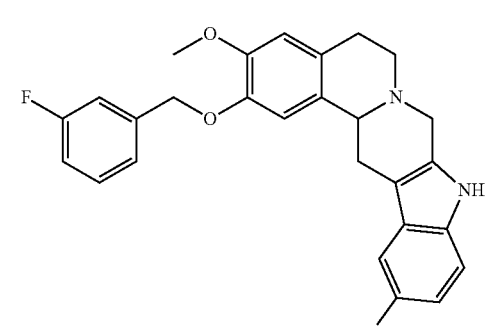<br>C7 |

TABLE 1-continued

| No. | Name |
|---|---|
| C8 | 2-((3-fluorobenzyl)oxy)-3-methoxy-5,6,8,9,14,14a-hexahydroindolo[3',2':4,5]pyridine[2,1-a]isoquinoline |
| C9 | 2-((2-fluorobenzyl)oxy)-3,12-dimethoxy-5,6,8,9,14,14a-hexahydroindolo[3',2':4,5]pyridine[2,1-a]isoquinoline |
| C10 | 2-((2-fluorobenzyl)oxy)-3-methoxy-5,6,8,9,14,14a-hexahydroindolo[3',2':4,5]pyridine[2,1-a]isoquinoline |
| C11 | 3,12-dimethoxy-2-((4-methoxybenzyl)oxy)-5,6,8,9,14,14a-hexahydroindolo[3',2':4,5]pyridine[2,1-a]isoquinoline |

TABLE 1-continued

| No. | Name |
|---|---|
| C12 | 3-methoxy-2-((4-methoxybenzyl)oxy)-5,6,8,9,14,14a-hexahydroindolo[3',2':4,5]pyridine[2,1-a]isoquinoline |
| C13 | 3,12-dimethoxy-2-((3-methoxybenzyl)oxy)-5,6,8,9,14,14a-hexahydroindolo[3',2':4,5]pyridine[2,1-a]isoquinoline |
| C14 | 3-methoxy-2-((3-methoxybenzyl)oxy)-5,6,8,9,14,14a-hexahydroindolo[3',2':4,5]pyridine[2,1-a]isoquinoline |
| C15 | 3,12-dimethoxy-2-((4-methylbenzyl)oxy)-5,6,8,9,14,14a-hexahydroindolo[3',2':4,5]pyridine[2,1-a]isoquinoline |

TABLE 1-continued
| No. | Name | Structure |
|---|---|---|
| C16 | 3-methoxy-2-((4-methylbenzyl)oxy)-5,6,8,9,14,14a-hexahydroindolo[3',2':4,5]pyridine[2,1-a]isoquinoline | 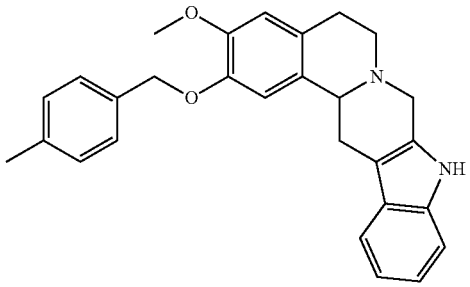 C16 |
| C17 | 2-((4-chlorobenzyl)oxy)-3,12-dimethoxy-5,6,8,9,14,14a-hexahydroindolo[3',2':4,5]pyridine[2,1-a]isoquinoline | 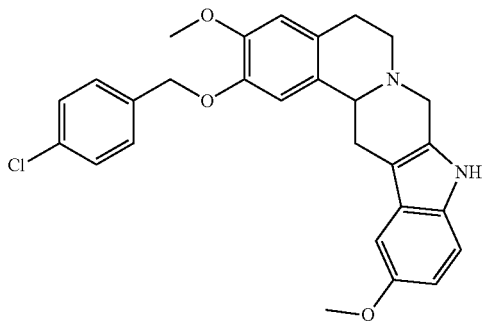 C17 |
| C18 | 2-((4-chlorobenzyl)oxy)-3-methoxy-5,6,8,9,14,14a-hexahydroindolo[3',2':4,5]pyridine[2,1-a]isoquinoline | 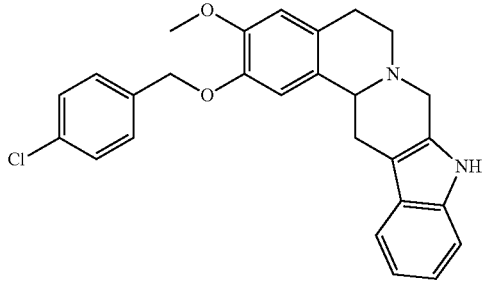 C18 |
| C19 | 4-(((3,12-dimethoxy-5,6,8,9,14,14a-hexahydroindolo[3',2':4,5]pyridine[2,1-a]isoquinoline-2-yl)oxy)methyl)benzonitrile | 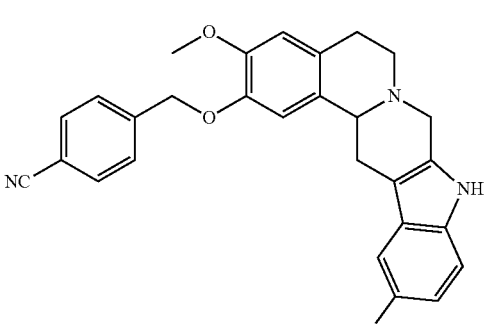 C19 |

TABLE 1-continued

| No. | Name | Structure |
|---|---|---|
| C20 | 4-(((3-methoxy-5,6,8,9,14,14a-hexahydroindolo[3',2':4,5]pyridine[2,1-a]isoquinoline-2-yl)oxy)methyl)benzonitrile | C20 |
| C21 | 2-((4-bromobenzyl)oxy)-3,12-dimethoxy-5,6,8,9,14,14a-hexahydroindolo[3',2':4,5]pyridine[2,1-a]isoquinoline | C21 |
| C22 | 2-((4-bromobenzyl)oxy)-3-methoxy-5,6,8,9,14,14a-hexahydroindolo[3',2':4,5]pyridine[2,1-a]isoquinoline | C22 |
| C23 | 2-((3-fluoro-4-(trifluoromethyl)benzyl)oxy)-3,12-dimethoxy-5,6,8,9,14,14a-hexahydroindolo[3',2':4,5]pyridine[2,1-a]isoquinoline | C23 |

TABLE 1-continued

| No. | Name | Structure |
|---|---|---|
| C24 | 2-((3-fluoro-4-(trifluoromethyl)benzyl)oxy)-3-methoxy-5,6,8,9,14,14a-hexahydroindolo[3',2':4,5]pyridine[2,1-a]isoquinoline | 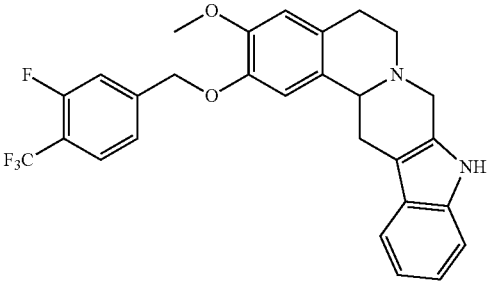 C24 |
| C25 | 2-((2-fluoro-4-(trifluoromethyl)benzyl)oxy)-3,12-dimethoxy-5,6,8,9,14,14a-hexahydroindolo[3',2':4,5]pyridine[2,1-a]isoquinoline | 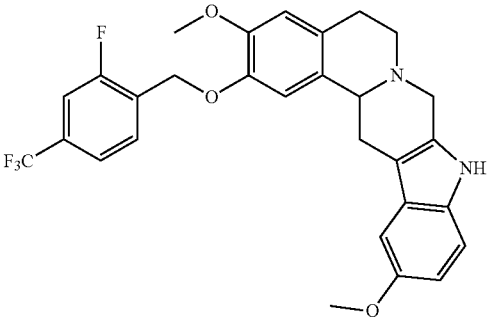 C25 |
| C26 | 2-((2-fluoro-4-(trifluoromethyl)benzyl)oxy)-3-methoxy-5,6,8,9,14,14a-hexahydroindolo[3',2':4,5]pyridine[2,1-a]isoquinoline | 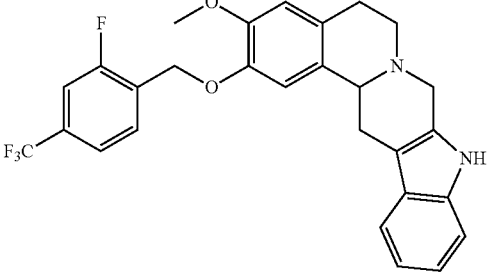 C26 |
| C27 | 2-((4-ethylbenzyl)oxy)-3,12-dimethoxy-5,6,8,9,14,14a-hexahydroindolo[3',2':4,5]pyridine[2,1-a]isoquinoline | 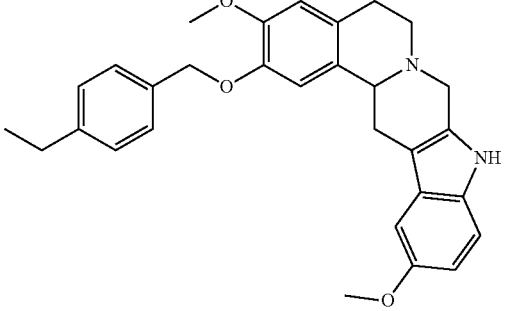 C27 |

TABLE 1-continued

| No. | Name | Structure |
|---|---|---|
| C28 | 2-((4-ethylbenzyl)oxy)-3-methoxy-5,6,8,9,14,14a-hexahydroindolo[3',2':4,5]pyridine[2,1-a]isoquinoline | C28 |
| C29 | 3,12-dimethoxy-2-(naphthalen-2-ylmethoxy)-5,6,8,9,14,14a-hexahydroindolo[3',2':4,5]pyridine[2,1-a]isoquinoline | C29 |
| C30 | 3-methoxy-2-(naphthalen-2-ylmethoxy)-5,6,8,9,14,14a-hexahydroindolo[3',2':4,5]pyridine[2,1-a]isoquinoline | C30 |
| C31 | 4-(((3,12-dimethoxy-5,6,8,9,14,14a-hexahydroindolo[3',2':4,5]pyridine[2,1-a]isoquinoline-2-yl)oxo)methyl)benzoate | C31 |

TABLE 1-continued

| No. | Name |
|---|---|
| C32 | 4-(((3-methoxy-5,6,8,9,14,14a-hexahydroindolo[3',2':4,5]pyridine[2,1-a]isoquinoline-2-yl)oxo)methyl)benzoate |
| C33 | 2-((4-(1H-pyrazol-1-yl)benzyl)oxy)-3,12-dimethoxy-5,6,8,9,14,14a-hexahydroindolo[3',2':4,5]pyridine[2,1-a]isoquinoline |
| C34 | 2-((4-(1H-pyrazol-1-yl)benzyl)oxy)-3-methoxy-5,6,8,9,14,14a-hexahydroindolo[3',2':4,5]pyridine[2,1-a]isoquinoline |
| C35 | 3-(benzyloxy)-11-fluoro-2-methoxy-5,6,8,9,14,14a-hexahydroindolo[3',2':4,5]pyridine[2,1-a]isoquinoline |

TABLE 1-continued
| No. | Name | Structure |
|---|---|---|
| C36 | 3-(benzyloxy)-12-fluoro-2-methoxy-5,6,8,9,14,14a-hexahydroindolo[3',2':4,5]pyridine[2,1-a]isoquinoline | 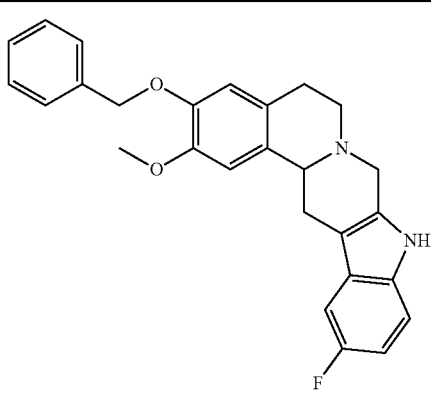 C36 |
| C37 | 3-(benzyloxy)-13-fluoro-2-methoxy-5,6,8,9,14,14a-hexahydroindolo[3',2':4,5]pyridine[2,1-a]isoquinoline | 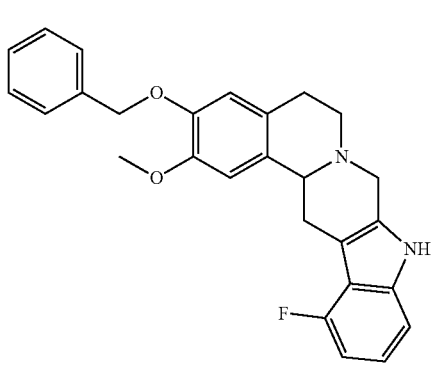 C37 |
| C38 | 3-(benzyloxy)-11-chloro-2-methoxy-5,6,8,9,14,14a-hexahydroindolo[3',2':4,5]pyridine[2,1-a]isoquinoline | 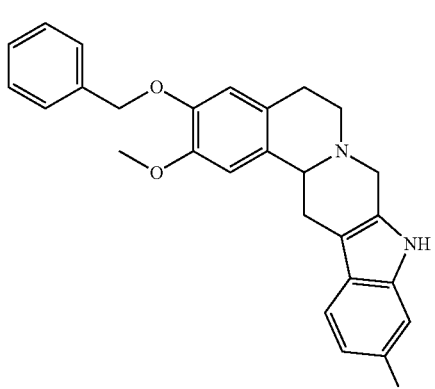 C38 |

TABLE 1-continued

| No. | Name | Structure |
|---|---|---|
| C39 | 3-(benzyloxy)-12-chloro-2-methoxy-5,6,8,9,14,14a-hexahydroindolo[3',2':4,5]pyridine[2,1-a]isoquinoline | 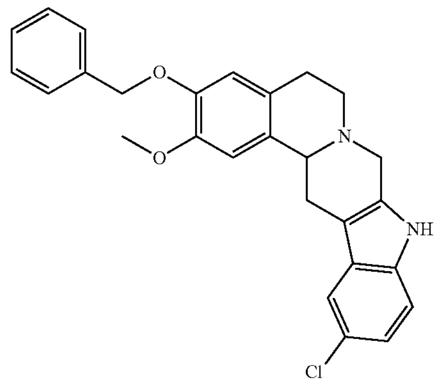 [SMILES: COc1cc2c(cc1OCc1ccccc1)CCN1Cc3[nH]c4ccc(Cl)cc4c3CC21] |
| C40 | 3-(benzyloxy)-13-chloro-2-methoxy-5,6,8,9,14,14a-hexahydroindolo[3',2':4,5]pyridine[2,1-a]isoquinoline | 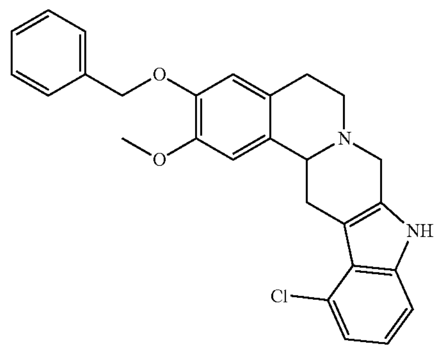 [SMILES: COc1cc2c(cc1OCc1ccccc1)CCN1Cc3[nH]c4cccc(Cl)c4c3CC21] |
| C41 | 3-(benzyloxy)-11-bromo-2-methoxy-5,6,8,9,14,14a-hexahydroindolo[3',2':4,5]pyridine[2,1-a]isoquinoline | 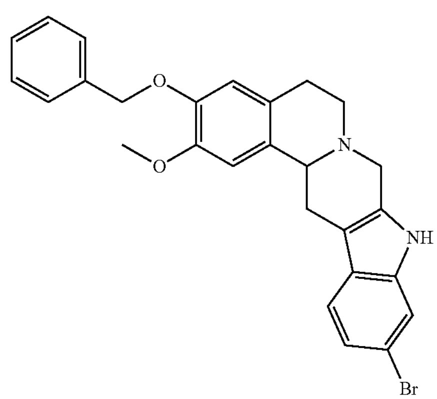 [SMILES: COc1cc2c(cc1OCc1ccccc1)CCN1Cc3[nH]c4cc(Br)ccc4c3CC21] |

TABLE 1-continued

| No. | Name | Structure |
| --- | --- | --- |
| C42 | 3-(benzyloxy)-12-bromo-2-methoxy-5,6,8,9,14,14a-hexahydroindolo[3',2':4,5]pyridine[2,1-a]isoquinoline | C42 |
| C43 | 3-(benzyloxy)-13-bromo-2-methoxy-5,6,8,9,14,14a-hexahydroindolo[3',2':4,5]pyridine[2,1-a]isoquinoline | C43 |
| C44 | 3-(benzyloxy)-2-methoxy-11-methyl-5,6,8,9,14,14a-hexahydroindolo[3',2':4,5]pyridine[2,1-a]isoquinoline | C44 |

TABLE 1-continued
| No. | Name | Structure |
|---|---|---|
| C45 | 3-(benzyloxy)-12-ethyl-2-methoxy-5,6,8,9,14,14a-hexahydroindolo[3',2':4,5]pyridine[2,1-a]isoquinoline | 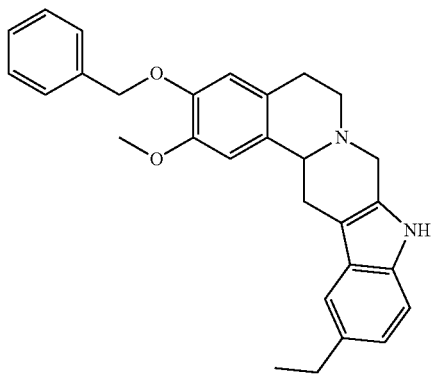 [SMILES: CCc1ccc2[nH]c3c(c2c1)CC1c2cc(OC)c(OCc4ccccc4)cc2CCN1C3]<br>C45 |
| C46 | 3-(benzyloxy)-2-methoxy-5,6,8,9,14,14a-hexahydroindolo[3',2':4,5]pyridine[2,1-a]isoquinoline-12-phenol | 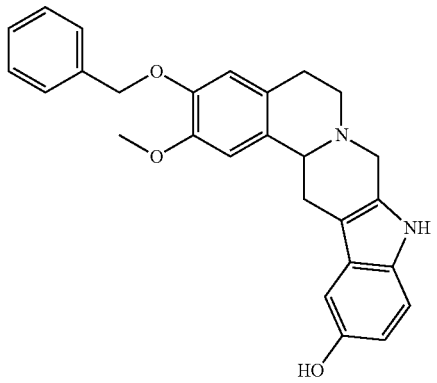 [SMILES: COc1cc2c(cc1OCc1ccccc1)CCN1Cc3[nH]c4ccc(O)cc4c3CC21]<br>C46 |
| C47 | 2,12-dimethoxy-3-((4-(trifluoromethyl)benzyl)oxy)-5,6,8,9,14,14a-hexahydroindolo[3',2':4,5]pyridine[2,1-a]isoquinoline | 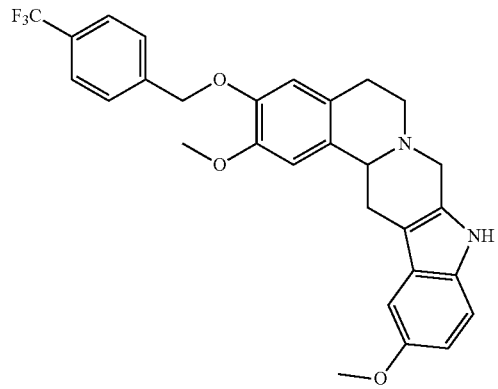<br>C47 |

TABLE 1-continued
| No. | Name | Structure |
|---|---|---|
| C48 | 2-methoxy-3-((4-(trifluoromethyl)benzyl)oxy)-5,6,8,9,14,14a-hexahydroindolo[3',2':4,5]pyridine[2,1-a]isoquinoline | 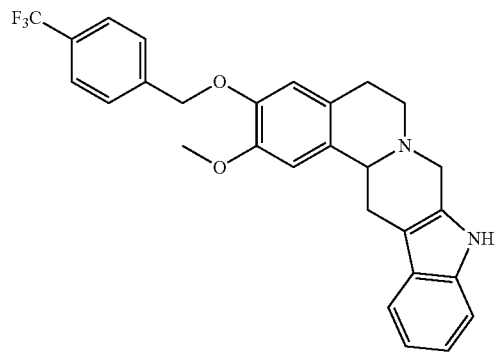 C48 |
| C49 | 3-((4-fluorobenzyl)oxy)-2,12-dimethoxy-5,6,8,9,14,14a-hexahydroindolo[3',2':4,5]pyridine[2,1-a]isoquinoline | 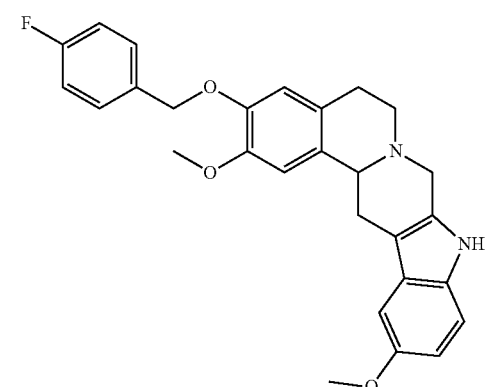 C49 |
| C50 | 3-((4-fluorobenzyl)oxy)-2-methoxy-5,6,8,9,14,14a-hexahydroindolo[3',2':4,5]pyridine[2,1-a]isoquinoline | 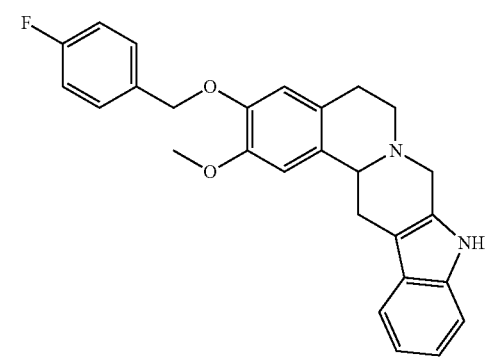 C50 |

TABLE 1-continued
| No. | Name | Structure |
|---|---|---|
| C51 | 3-((3-fluorobenzyl)oxy)-2,12-dimethoxy-5,6,8,9,14,14a-hexahydroindolo[3',2':4,5]pyridine[2,1-a]isoquinoline | 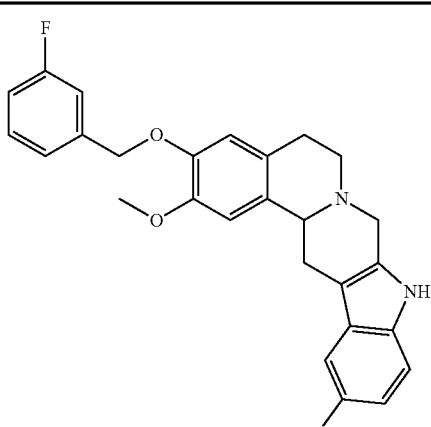<br>C51 |
| C52 | 3-((3-fluorobenzyl)oxy)-2-methoxy-5,6,8,9,14,14a-hexahydroindolo[3',2':4,5]pyridine[2,1-a]isoquinoline | 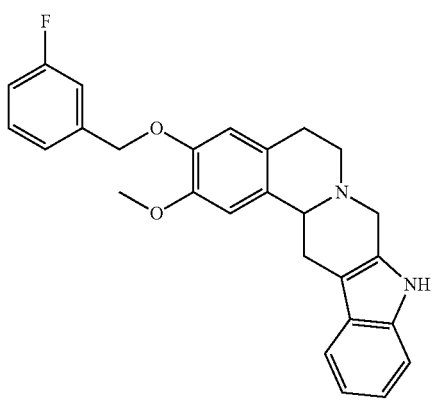 [SMILES: COc1cc2c(cc1OCc1cccc(F)c1)CCN1Cc3[nH]c4ccccc4c3CC21]<br>C52 |
| C53 | 3-((2-fluorobenzyl)oxy)-2,12-dimethoxy-5,6,8,9,14,14a-hexahydroindolo[3',2':4,5]pyridine[2,1-a]isoquinoline | 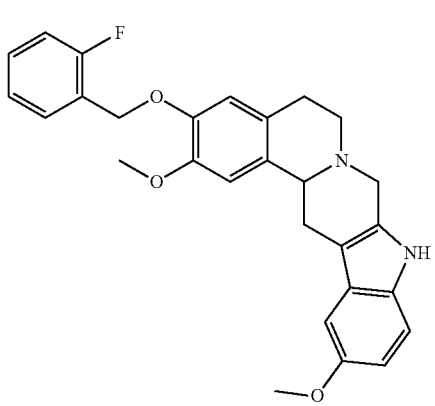 [SMILES: COc1ccc2[nH]c3c(c2c1)CC1c2cc(OC)c(OCc4ccccc4F)cc2CCN1C3]<br>C53 |

TABLE 1-continued
| No. | Name | Structure |
|---|---|---|
| C54 | 3-((2-fluorobenzyl)oxy)-2-methoxy-5,6,8,9,14,14a-hexahydroindolo[3',2':4,5]pyridine[2,1-a]isoquinoline | 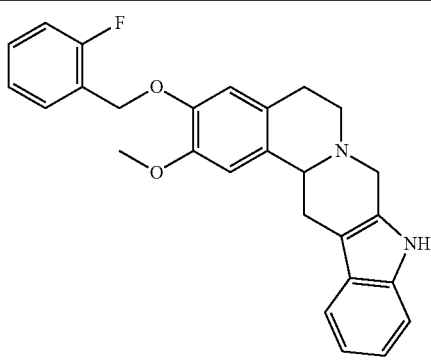 C54 |
| C55 | 2,12-dimethoxy-3-((4-methoxybenzyl)oxy)-5,6,8,9,14,14a-hexahydroindolo[3',2':4,5]pyridine[2,1-a]isoquinoline | 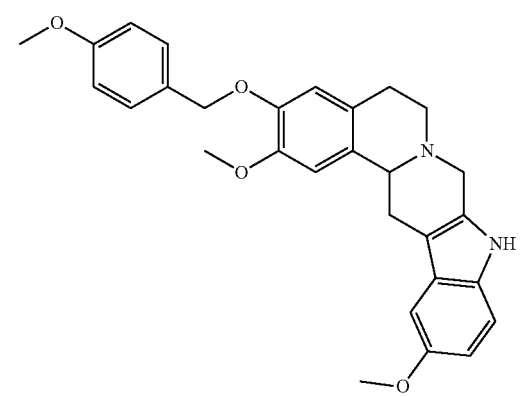 C55 |
| C56 | 2-methoxy-3-((4-methoxybenzyl)oxy)-5,6,8,9,14,14a-hexahydroindolo[3',2':4,5]pyridine[2,1-a]isoquinoline | 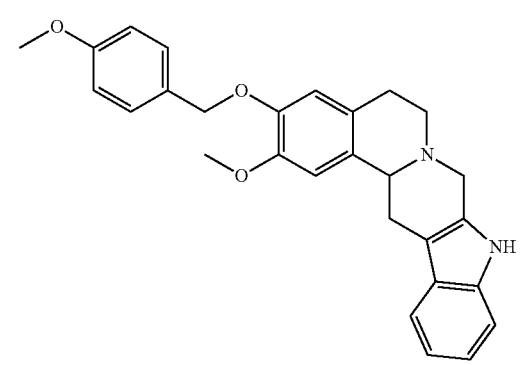 C56 |

TABLE 1-continued

| No. | Name |
|---|---|
| C57 | 2,12-dimethoxy-3-((3-methoxybenzyl)oxy)-5,6,8,9,14,14a-hexahydroindolo[3',2':4,5]pyridine[2,1-a]isoquinoline |
| C58 | 2-methoxy-3-((3-methoxybenzyl)oxy)-5,6,8,9,14,14a-hexahydroindolo[3',2':4,5]pyridine[2,1-a]isoquinoline |
| C59 | 2,12-dimethoxy-3-((4-methylbenzyl)oxy)-5,6,8,9,14,14a-hexahydroindolo[3',2':4,5]pyridine[2,1-a]isoquinoline |

TABLE 1-continued
| No. | Name | Structure |
|---|---|---|
| C60 | 2-methoxy-3-((4-methylbenzyl)oxy)-5,6,8,9,14,14a-hexahydroindolo[3',2':4,5]pyridine[2,1-a]isoquinoline | 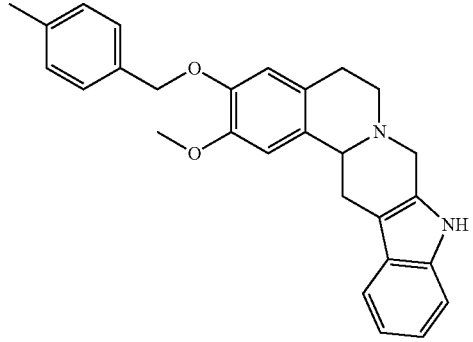 [SMILES: COc1cc2c(cc1OCc1ccc(C)cc1)CCN1Cc3[nH]c4ccccc4c3CC21]<br>C60 |
| C61 | 3-((4-chlorobenzyl)oxy)-2,12-dimethoxy-5,6,8,9,14,14a-hexahydroindolo[3',2':4,5]pyridine[2,1-a]isoquinoline | 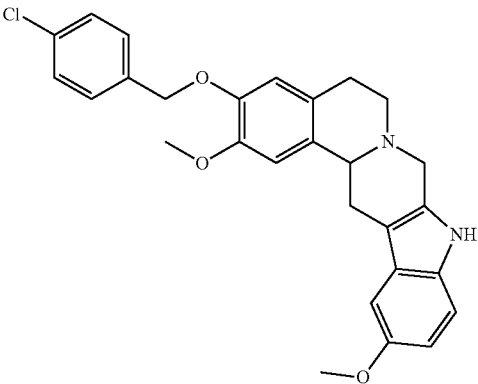<br>C61 |
| C62 | 3-((4-chlorobenzyl)oxy)-2-methoxy-5,6,8,9,14,14a-hexahydroindolo[3',2':4,5]pyridine[2,1-a]isoquinoline | 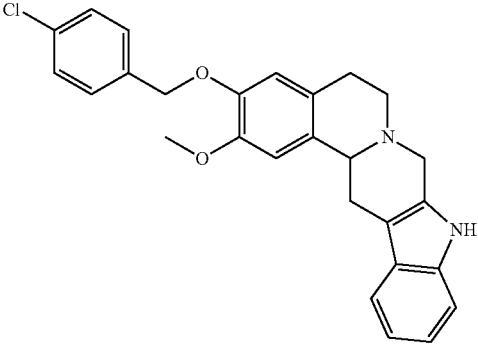<br>C62 |

TABLE 1-continued
| No. | Name | Structure |
|---|---|---|
| C63 | 4-(((2,12-dimethoxy-5,6,8,9,14,14a-hexahydroindolo[3',2':4,5]pyridine[2,1-a]isoquinoline-3-yl)oxy)methyl)benzonitrile | 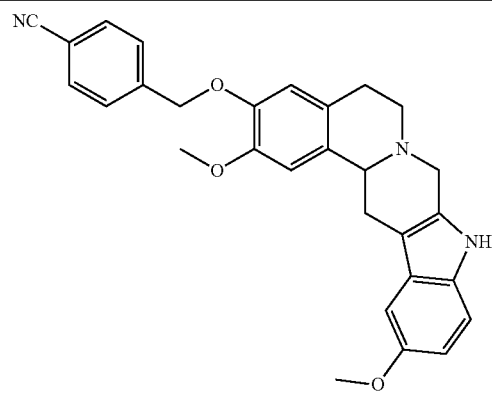 C63 |
| C64 | 4-(((2-methoxy-5,6,8,9,14,14a-hexahydroindolo[3',2':4,5]pyridine[2,1-a]isoquinoline-3-yl)oxy)methyl)benzonitrile | 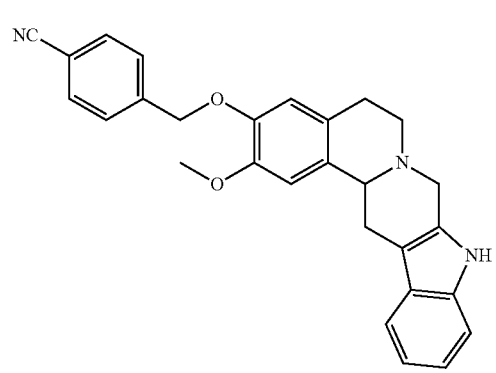 C64 |
| C65 | 3-((4-bromobenzyl)oxy)-2,12-dimethoxy-5,6,8,9,14,14a-hexahydroindolo[3',2':4,5]pyridine[2,1-a]isoquinoline | 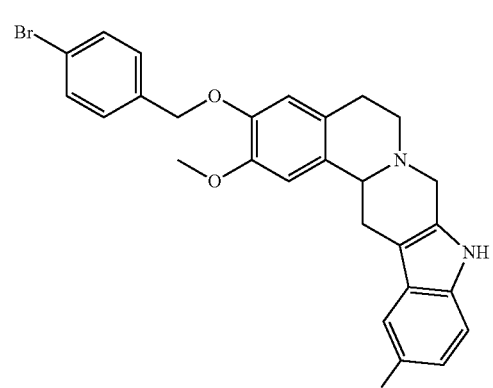 C65 |

TABLE 1-continued
| No. | Name | Structure |
|-----|------|-----------|
| C66 | 3-((4-bromobenzyl)oxy)-2-methoxy-5,6,8,9,14,14a-hexahydroindolo[3',2':4,5]pyridine[2,1-a]isoquinoline | 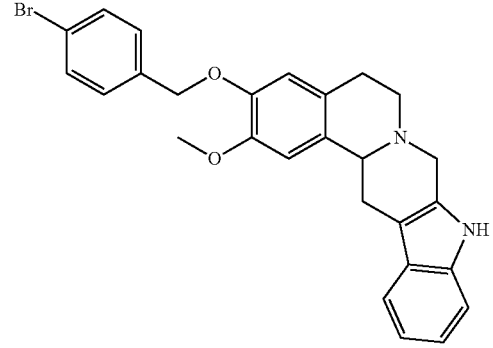 [SMILES: COc1cc2c(cc1OCc1ccc(Cl)cc1)CCN1Cc3[nH]c4ccccc4c3CC21]<br>C66 |
| C67 | 3-((3-fluoro-4-(trifluoromethyl)benzyl)oxy)-2,12-dimethoxy-5,6,8,9,14,14a-hexahydroindolo[3',2':4,5]pyridine[2,1-a]isoquinoline | 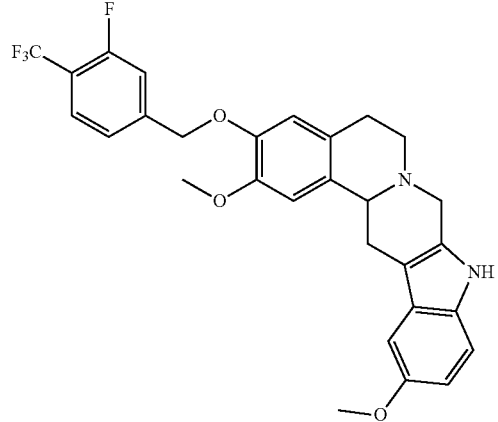 [SMILES: COc1ccc2[nH]c3c(c2c1)CC1c2cc(OC)c(OCc4ccc(C(F)(F)F)c(F)c4)cc2CCN1C3]<br>C67 |
| C68 | 3-((3-fluoro-4-(trifluoromethyl)benzyl)oxy)-2-methoxy-5,6,8,9,14,14a-hexahydroindolo[3',2':4,5]pyridine[2,1-a]isoquinoline | 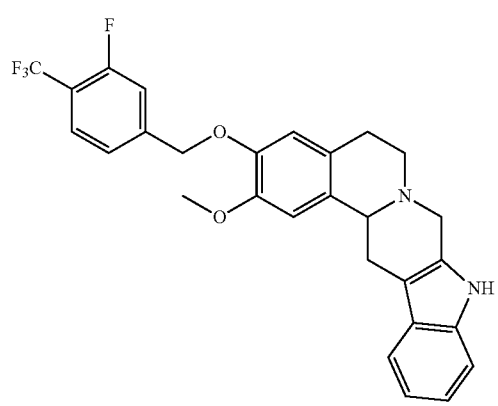 [SMILES: COc1cc2c(cc1OCc1ccc(C(F)(F)F)c(F)c1)CCN1Cc3[nH]c4ccccc4c3CC21]<br>C68 |

TABLE 1-continued
| No. | Name | Structure |
|---|---|---|
| C69 | 3-((2-fluoro-4-(trifluoromethyl)benzyl)oxy)-2,12-dimethoxy-5,6,8,9,14,14a-hexahydroindolo[3',2':4,5]pyridine[2,1-a]isoquinoline | 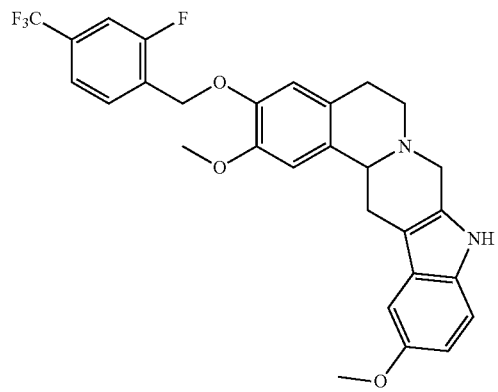 [SMILES: COc1ccc2[nH]c3c(c2c1)CC1c2cc(OC)c(OCc4ccc(C(F)(F)F)cc4F)cc2CCN1C3] |
| C70 | 3-((2-fluoro-4-(trifluoromethyl)benzyl)oxy)-2-methoxy-5,6,8,9,14,14a-hexahydroindolo[3',2':4,5]pyridine[2,1-a]isoquinoline | 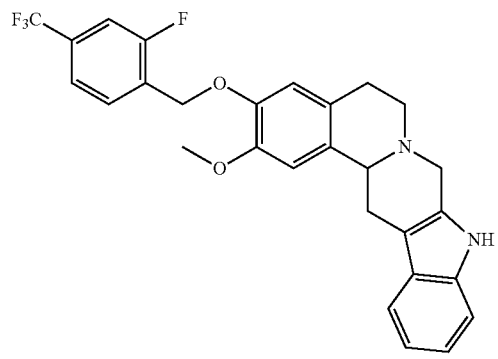 [SMILES: COc1cc2c(cc1OCc1ccc(C(F)(F)F)cc1F)CCN1Cc3[nH]c4ccccc4c3CC21] |
| C71 | 3-((4-ethylbenzyl)oxy)-2,12-dimethoxy-5,6,8,9,14,14a-hexahydroindolo[3',2':4,5]pyridine[2,1-a]isoquinoline | 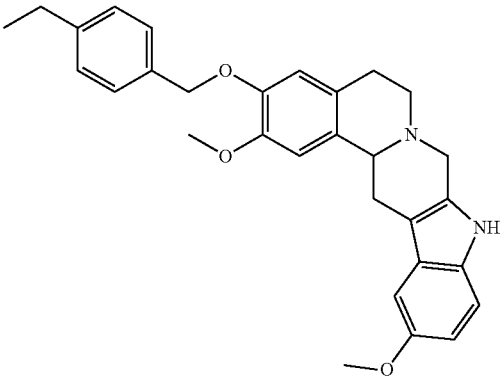 [SMILES: CCc1ccc(COc2cc3c(cc2OC)C2Cc4c([nH]c5ccc(OC)cc45)CN2CC3)cc1] |

TABLE 1-continued

| No. | Name | Structure |
| --- | --- | --- |
| C72 | 3-((4-ethylbenzyl)oxy)-2-methoxy-5,6,8,9,14,14a-hexahydroindolo[3',2':4,5]pyridine[2,1-a]isoquinoline | 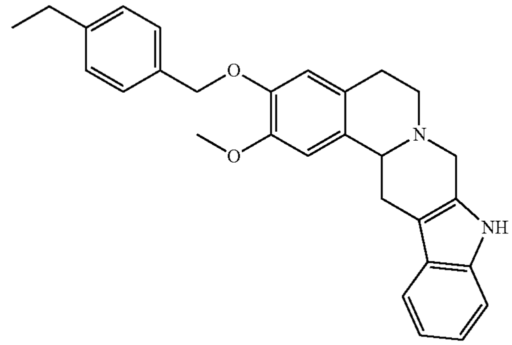 [SMILES: CCc1ccc(COc2cc3c(cc2OC)C2Cc4c([nH]c5ccccc45)CN2CC3)cc1] |
| C73 | 2,12-dimethoxy-3-(naphthalen-2-ylmethoxy)-5,6,8,9,14,14a-hexahydroindolo[3',2':4,5]pyridine[2,1-a]isoquinoline | 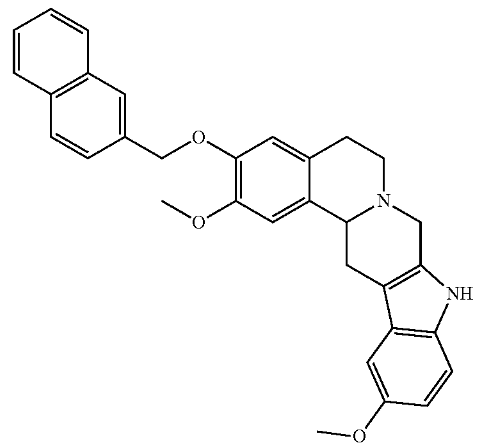 [SMILES: COc1ccc2[nH]c3c(c2c1)CC1c2cc(OC)c(OCc4ccc5ccccc5c4)cc2CCN1C3] |
| C74 | 2-methoxy-3-(naphthalen-2-ylmethoxy)-5,6,8,9,14,14a-hexahydroindolo[3',2':4,5]pyridine[2,1-a]isoquinoline | 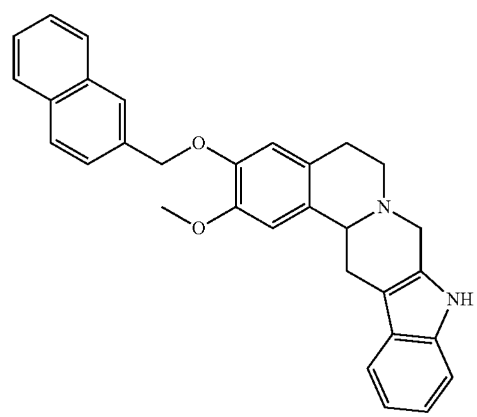 [SMILES: COc1cc2c(cc1OCc1ccc3ccccc3c1)CCN1Cc3[nH]c4ccccc4c3CC21] |

TABLE 1-continued
| No. | Name | Structure |
|---|---|---|
| C75 | 4-(((2,12-dimethoxy-5,6,8,9,14,14a-hexahydroindolo[3',2':4,5]pyridine[2,1-a]isoquinoline-3-yl)oxo)methyl)benzoate | 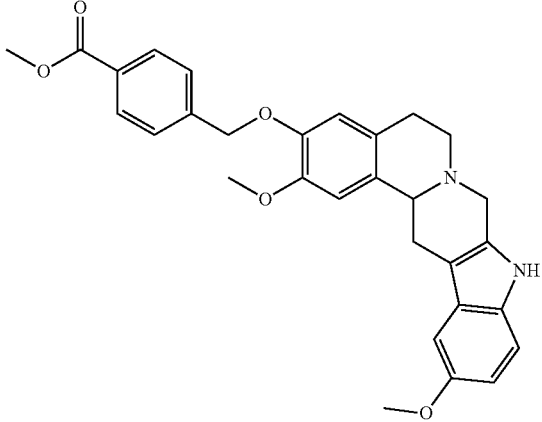 C75 |
| C76 | 4-(((2-methoxy-5,6,8,9,14,14a-hexahydroindolo[3',2':4,5]pyridine[2,1-a]isoquinoline-3-yl)oxo)methyl)benzoate | 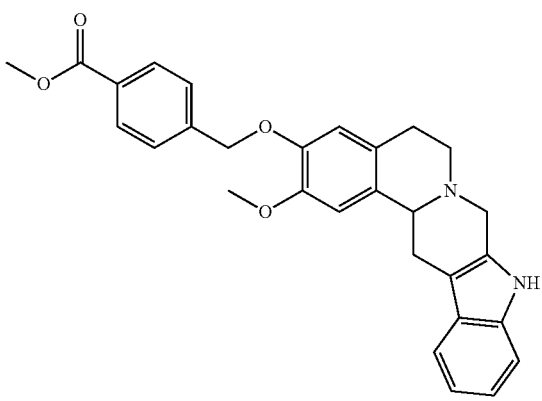 C76 |
| C77 | 3-((4-(1H-pyrazol-1-yl)benzyl)oxy)-2,12-dimethoxy-5,6,8,9,14,14a-hexahydroindolo[3',2':4,5]pyridine[2,1-a]isoquinoline | 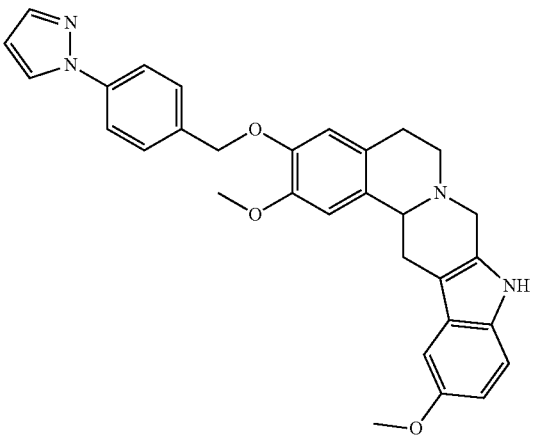 C77 |

TABLE 1-continued
| No. | Name | Structure |
|---|---|---|
| C78 | 3-((4-(1H-pyrazol-1-yl)benzyl)oxy)-2-methoxy-5,6,8,9,14,14a-hexahydroindolo[3',2':4,5]pyridine[2,1-a]isoquinoline | 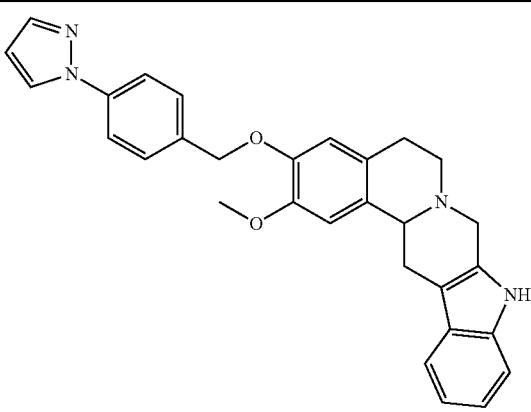 C78 |
| C79 | 2,12-dimethoxy-3-((4-(methylsulfonyl)benzyl)oxy)-5,6,8,9,14,14a-hexahydroindolo[3',2':4,5]pyridine[2,1-a]isoquinoline | 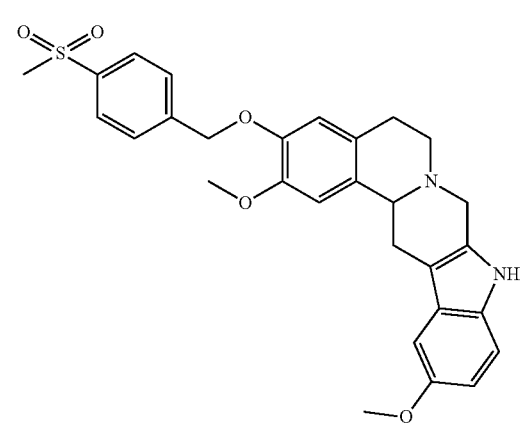 C79 |
| C80 | 2-methoxy-3-((4-(methylsulfonyl)benzyl)oxy)-5,6,8,9,14,14a-hexahydroindolo[3',2':4,5]pyridine[2,1-a]isoquinoline | 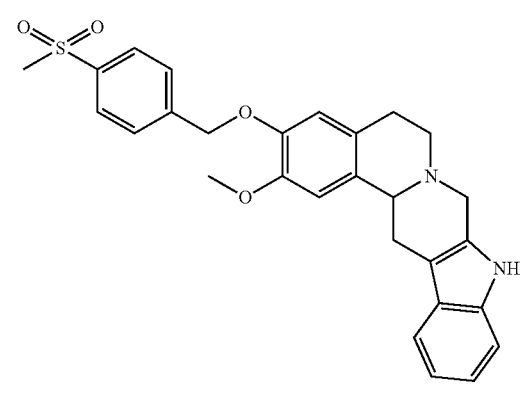 C80 |

TABLE 1-continued

| No. | Name | Structure |
|---|---|---|
| C81 | 3-(benzyloxy)-11-fluoro-2-methoxy-5,6,8,9,14,14a-hexahydroindolo[3',2':4,5]pyridine[2,1-a]isoquinoline | C81 |
| C82 | 3-(benzyloxy)-12-fluoro-2-methoxy-5,6,8,9,14,14a-hexahydroindolo[3',2':4,5]pyridine[2,1-a]isoquinoline | C82 |
| C83 | 3-(benzyloxy)-13-fluoro-2-methoxy-5,6,8,9,14,14a-hexahydroindolo[3',2':4,5]pyridine[2,1-a]isoquinoline | C83 |

TABLE 1-continued
| No. | Name | Structure |
|---|---|---|
| C84 | 3-(benzyloxy)-11-chloro-2-methoxy-5,6,8,9,14,14a-hexahydroindolo[3',2':4,5]pyridine[2,1-a]isoquinoline | 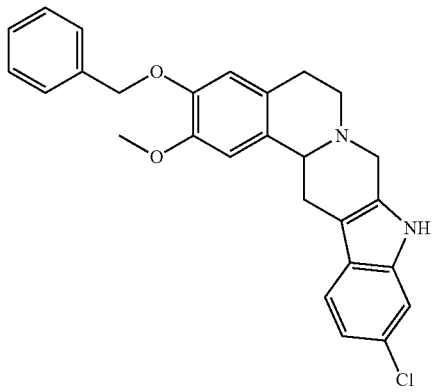<br>C84 |
| C85 | 3-(benzyloxy)-12-chloro-2-methoxy-5,6,8,9,14,14a-hexahydroindolo[3',2':4,5]pyridine[2,1-a]isoquinoline | 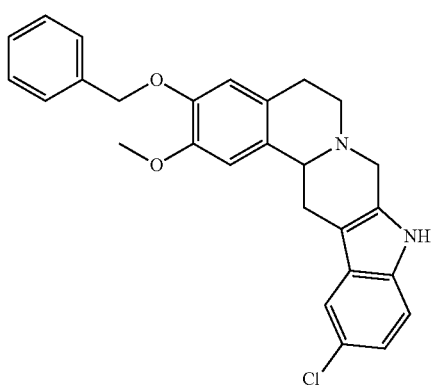<br>C85 |
| C86 | 3-(benzyloxy)-13-chloro-2-methoxy-5,6,8,9,14,14a-hexahydroindolo[3',2':4,5]pyridine[2,1-a]isoquinoline | 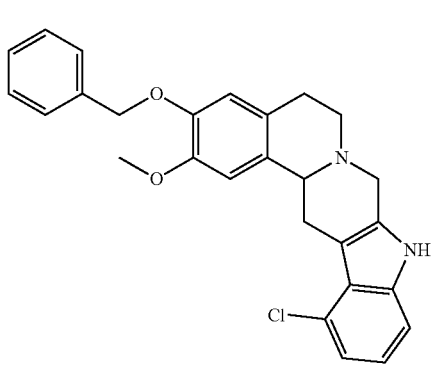 [SMILES: COc1cc2c(cc1OCc1ccccc1)CCN1Cc3[nH]c4cccc(Cl)c4c3CC21]<br>C86 |

TABLE 1-continued
| No. | Name | Structure |
|---|---|---|
| C87 | 3-(benzyloxy)-11-bromo-2-methoxy-5,6,8,9,14,14a-hexahydroindolo[3',2':4,5]pyridine[2,1-a]isoquinoline | 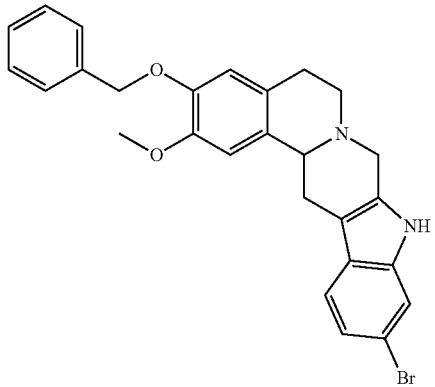<br>C87 |
| C88 | 3-(benzyloxy)-12-bromo-2-methoxy-5,6,8,9,14,14a-hexahydroindolo[3',2':4,5]pyridine[2,1-a]isoquinoline | 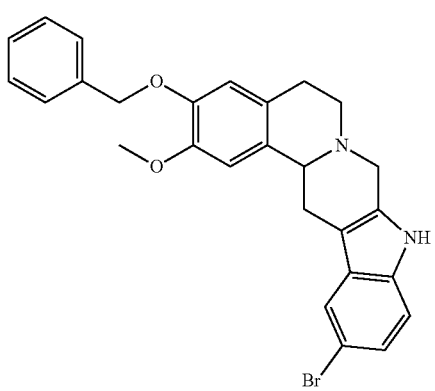<br>C88 |
| C89 | 3-(benzyloxy)-13-bromo-2-methoxy-5,6,8,9,14,14a-hexahydroindolo[3',2':4,5]pyridine[2,1-a]isoquinoline | 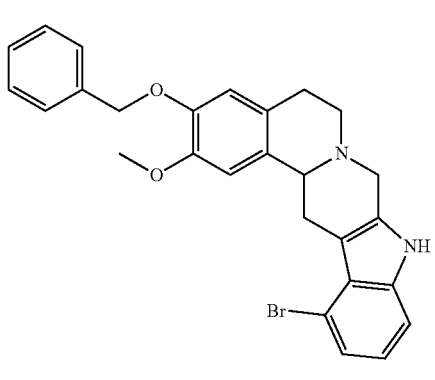<br>C89 |

TABLE 1-continued
| No. | Name | Structure |
|---|---|---|
| C90 | 3-(benzyloxy)-2-methoxy-11-methyl-5,6,8,9,14,14a-hexahydroindolo[3',2':4,5]pyridine[2,1-a]isoquinoline | 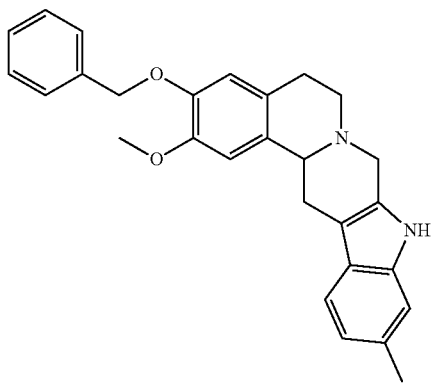 C90 |
| C91 | 3-(benzyloxy)-2-methoxy-12-ethyl-5,6,8,9,14,14a-hexahydroindolo[3',2':4,5]pyridine[2,1-a]isoquinoline | 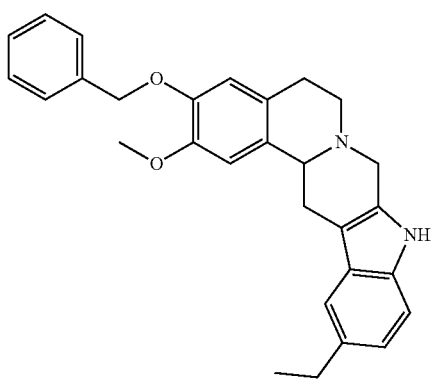 C91 |
| C92 | 2,12-dimethoxy-5,6,8,9,14,14a-hexahydroindolo[3',2':4,5]pyridine[2,1-a]isoquinoline-3-ylbenzenesulfonate | 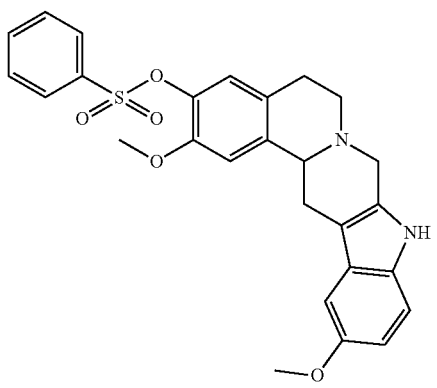 C92 |

TABLE 1-continued
| No. | Name | Structure |
|---|---|---|
| C93 | 3,12-dimethoxy-5,6,8,9,14,14a-hexahydroindolo[3',2':4,5]pyridine[2,1-a]isoquinoline-2-ylbenzenesulfonate | 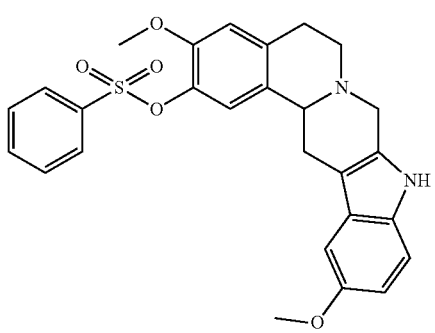 [SMILES: COc1ccc2[nH]c3c(c2c1)CC1c2cc(OS(=O)(=O)c4ccccc4)c(OC)cc2CCN1C3]<br>C93 |
| C94 | 2,11,12-trimethoxy-5,6,8,9,14,14a-hexahydroindolo[3',2':4,5]pyridine[2,1-a]isoquinoline-3-ylbenzenesulfonate | 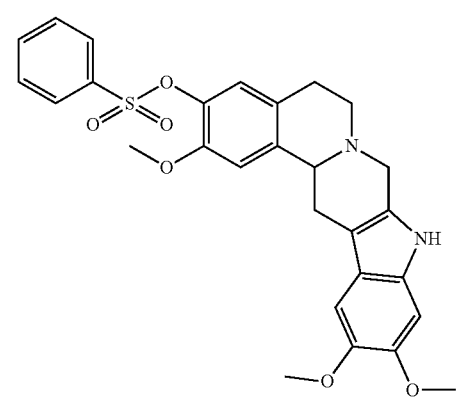<br>C94 |
| C95 | 3,11,12-trimethoxy-5,6,8,9,14,14a-hexahydroindolo[3',2':4,5]pyridine[2,1-a]isoquinoline-2-ylbenzenesulfonate | 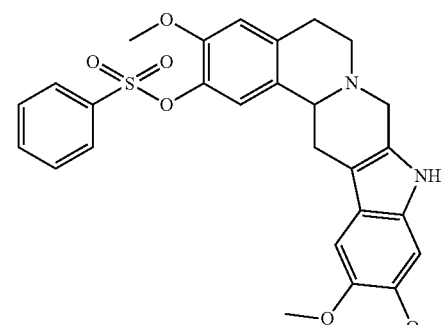<br>C95 |

TABLE 1-continued
| No. | Name | Structure |
|---|---|---|
| C96 | 2,3,11-trimethoxy-5,6,8,9,14,14a-hexahydroindolo[3',2':4,5]pyridine[2,1-a]isoquinoline-12-ylbenzenesulfonate | 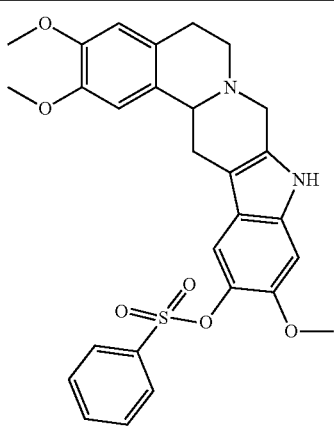 C96 |
| C97 | 2,3,12-trimethoxy-5,6,8,9,14,14a-hexahydroindolo[3',2':4,5]pyridine[2,1-a]isoquinoline-11-ylbenzenesulfonate | 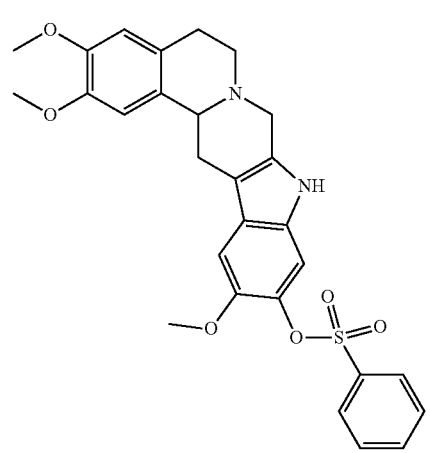 C97 |
| C98 | 4-(((2,12-dimethoxy-5,6,8,9,14,14a-hexahydroindolo[3',2':4,5]pyridine[2,1-a]isoquinoline-3-yl)oxy)methyl)benzoic acid | 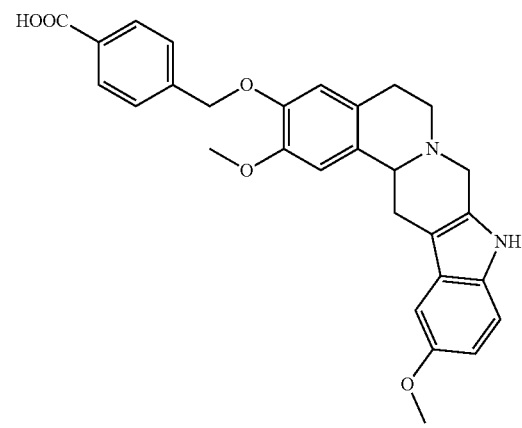 |

TABLE 1-continued
| No. | Name | Structure |
|---|---|---|
| C99 | 4-(((3,12-dimethoxy-5,6,8,9,14,14a-hexahydroindolo[3',2':4,5]pyridine[2,1-a]isoquinoline-2-yl)oxy)methyl)aniline | 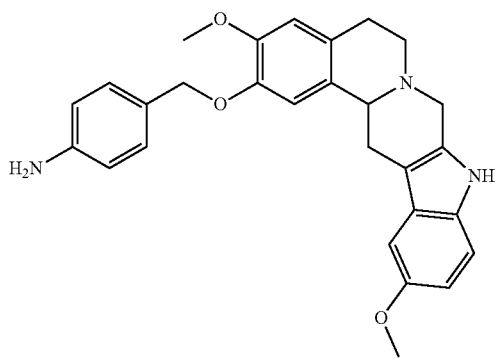 |
| C100 | 4-(((2,12-dimethoxy-5,6,8,9,14,14a-hexahydroindolo[3',2':4,5]pyridine[2,1-a]isoquinoline-3-yl)oxy)methyl)aniline | 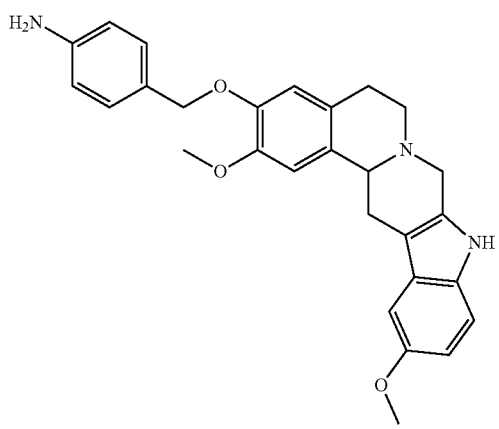 |
| C101 | 4-(((3,12-dimethoxy-5,6,8,9,14,14a-hexahydroindolo[3',2':4,5]pyridine[2,1-a]isoquinoline-2-yl)oxo)methyl)phenol | 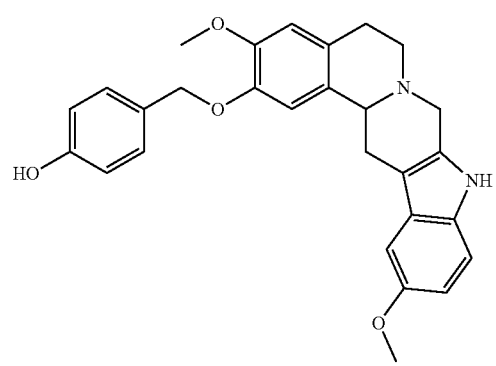 [SMILES: COc1ccc2[nH]c3c(c2c1)CC1c2cc(OCc4ccc(O)cc4)c(OC)cc2CCN1C3] |
| C102 | 4-(((2,12-dimethoxy-5,6,8,9,14,14a-hexahydroindolo[3',2':4,5]pyridine[2,1-a]isoquinoline-3-yl)oxo)methyl)phenol | 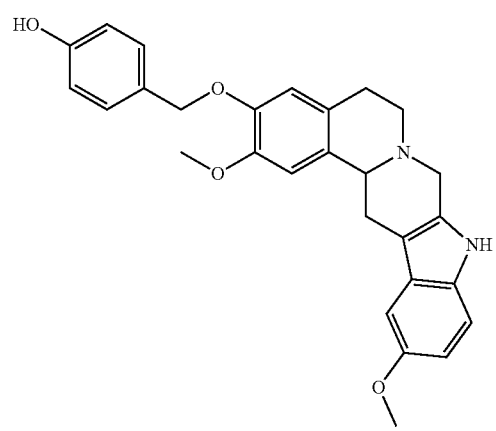 [SMILES: COc1ccc2[nH]c3c(c2c1)CC1c2cc(OC)c(OCc4ccc(O)cc4)cc2CCN1C3] |

TABLE 1-continued

| No. | Name | Structure |
|---|---|---|
| C103 | 4-(((3,12-dimethoxy-5,6,8,9,14,14a-hexahydroindolo[3',2':4,5]pyridine[2,1-a]isoquinoline-2-yl)oxy)methyl)benzoic acid | 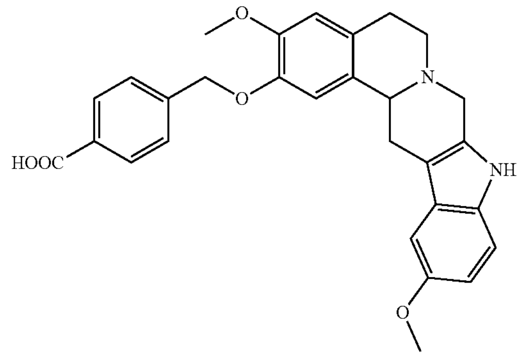 [SMILES: COc1ccc2[nH]c3c(c2c1)CC1c2cc(OCc4ccc(C(=O)O)cc4)c(OC)cc2CCN1C3] |
| (S)-C3 | S)-3,12-dimethoxy-2-((4-(trifluoromethyl)benzyl)oxy)-5,6,8,9,14,14a-hexahydroindolo[3',2':4,5]pyrido[2,1-a]isoquinoline | 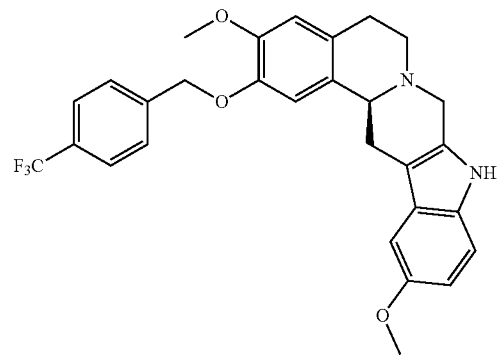 |
| (R)-C3 | R)-3,12-dimethoxy-2-((4-(trifluoromethyl)benzyl)oxy)-5,6,8,9,14,14a-hexahydroindolo[3',2':4,5]pyrido[2,1-a]isoquinoline | 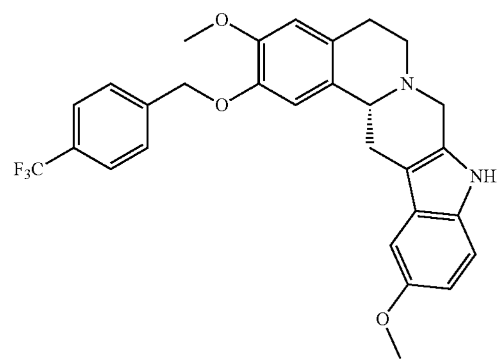 |
| (S)-C47 | S)-2,12-dimethoxy-3-((4-(trifluoromethyl)benzyl)oxy)-5,6,8,9,14,14a-hexahydroindolo[3',2':4,5]pyrido[2,1-a]isoquinoline | 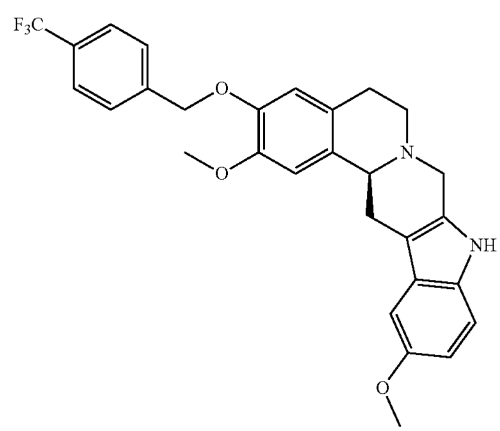 |

TABLE 1-continued

| No. | Name | Structure |
|---|---|---|
| (R)-C47 | R)-2,12-dimethoxy-3-((4-(trifluoromethyl)benzyl)oxy)-5,6,8,9,14,14a-hexahydroindolo[3',2':4,5]pyrido[2,1-a]isoquinoline | 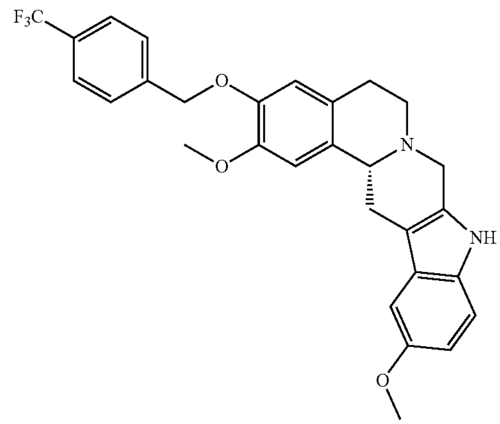 |
| C104 | 2,12-dimethoxy-3-((2-methoxybenzyl)oxy)-5,6,8,9,14,14a-hexahydroindolo[3',2':4,5]pyridine[2,1-a]isoquinoline | 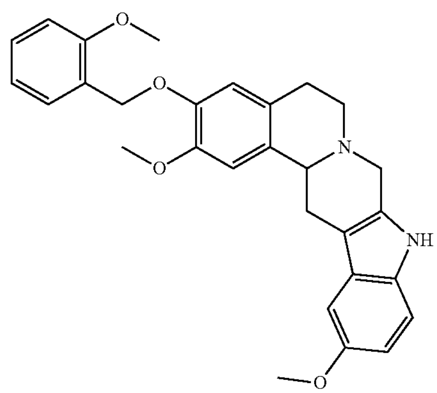 [SMILES: COc1ccc2[nH]c3c(c2c1)CC1c2cc(OC)c(OCc4ccccc4OC)cc2CCN1C3] |
| C105 | 2-methoxy-3-((2-methoxybenzyl)oxy)-5,6,8,9,14,14a-hexahydroindolo[3',2':4,5]pyridine[2,1-a]isoquinoline | 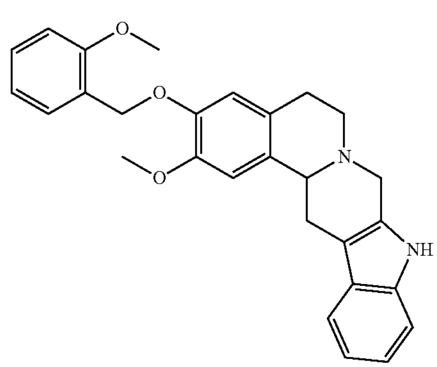 [SMILES: COc1ccccc1COc1cc2c(cc1OC)C1Cc3c([nH]c4ccccc34)CN1CC2] |

TABLE 1-continued
| No. | Name | Structure |
|---|---|---|
| C106 | 2,12-dimethoxy-3-((3-methylbenzyl)oxy)-5,6,8,9,14,14a-hexahydroindolo[3',2':4,5]pyridine[2,1-a]isoquinoline | 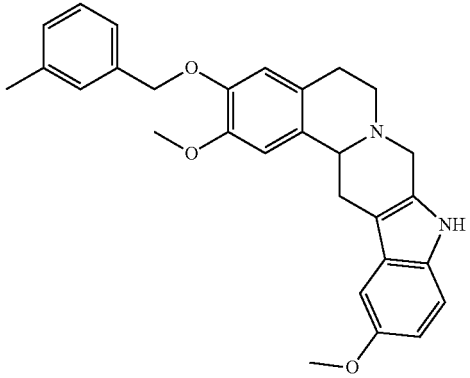 C106 |
| C107 | 2-methoxy-3-((3-methylbenzyl)oxy)-5,6,8,9,14,14a-hexahydroindolo[3',2':4,5]pyridine[2,1-a]isoquinoline | 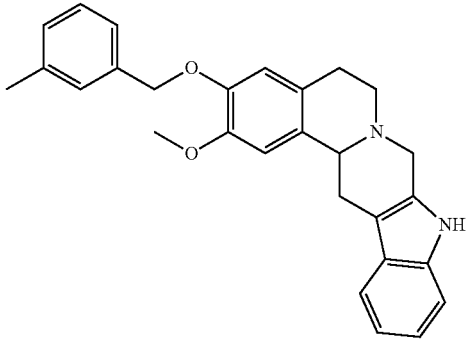 C107 |
| C108 | 2,12-dimethoxy-3-((2-methylbenzyl)oxy)-5,6,8,9,14,14a-hexahydroindolo[3',2':4,5]pyridine[2,1-a]isoquinoline | 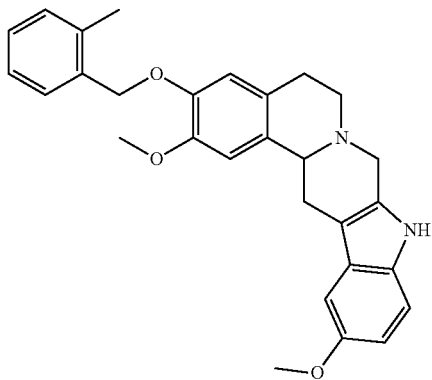 C108 |

TABLE 1-continued

| No. | Name | Structure |
|---|---|---|
| C109 | 2-methoxy-3-((2-methylbenzyl)oxy)-5,6,8,9,14,14a-hexahydroindolo[3',2':4,5]pyridine[2,1-a]isoquinoline | C109 |
| C110 | 3,12-dimethoxy-2-((2-methoxybenzyl)oxy)-5,6,8,9,14,14a-hexahydroindolo[3',2':4,5]pyridine[2,1-a]isoquinoline | C110 |
| C111 | 3-methoxy-2-((2-methoxybenzyl)oxy)-5,6,8,9,14,14a-hexahydroindolo[3',2':4,5]pyridine[2,1-a]isoquinoline | C111 |
| C112 | 3,12-dimethoxy-2-((3-methylbenzyl)oxy)-5,6,8,9,14,14a-hexahydroindolo[3',2':4,5]pyridine[2,1-a]isoquinoline | C112 |

TABLE 1-continued

| No. | Name |
|---|---|
| C113 | 3-methoxy-2-((3-methylbenzyl)oxy)-5,6,8,9,14,14a-hexahydroindolo[3',2':4,5]pyridine[2,1-a]isoquinoline |
| C114 | 3,12-dimethoxy-2-((2-methylbenzyl)oxy)-5,6,8,9,14,14a-hexahydroindolo[3',2':4,5]pyridine[2,1-a]isoquinoline |
| C115 | 3-methoxy-2-((2-methylbenzyl)oxy)-5,6,8,9,14,14a-hexahydroindolo[3',2':4,5]pyridine[2,1-a]isoquinoline |
| C116 | 2-methoxy-3-((3,4-difluorobenzyl)oxy)-5,6,8,9,14,14a-hexahydroindolo[3',2':4,5]pyridine[2,1-a]isoquinoline |

| No. | Name | Structure |
|---|---|---|
| C117 | 2,12-dimethoxy-3-((3,4-difluorobenzyl)oxy)-5,6,8,9,14,14a-hexahydroindolo[3',2':4,5]pyridine[2,1-a]isoquinoline | 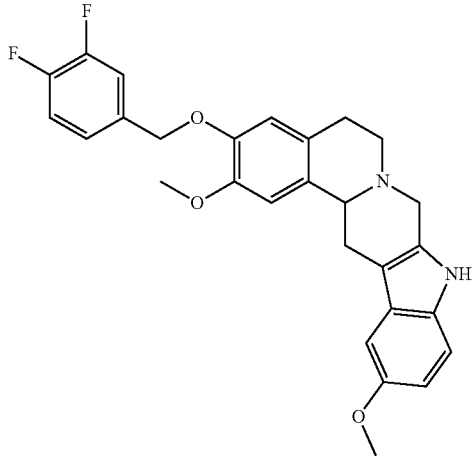 [SMILES: COc1ccc2[nH]c3c(c2c1)CC1c2cc(OC)c(OCc4ccc(F)c(F)c4)cc2CCN1C3]<br>C117 |
| C118 | 2-methoxy-3-((3,5-difluorobenzyl)oxy)-5,6,8,9,14,14a-hexahydroindolo[3',2':4,5]pyridine[2,1-a]isoquinoline | 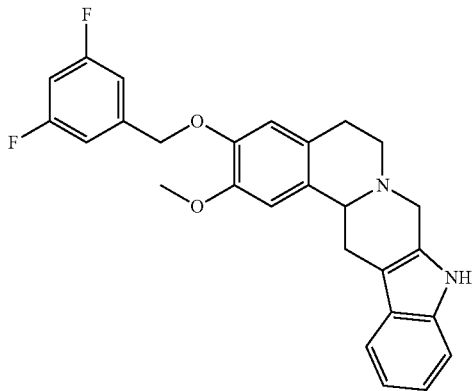 [SMILES: COc1cc2c(cc1OCc1cc(F)cc(F)c1)CCN1Cc3[nH]c4ccccc4c3CC21]<br>C118 |
| C119 | 2,12-dimethoxy-3-((3,5-difluorobenzyl)oxy)-5,6,8,9,14,14a-hexahydroindolo[3',2':4,5]pyridine[2,1-a]isoquinoline | 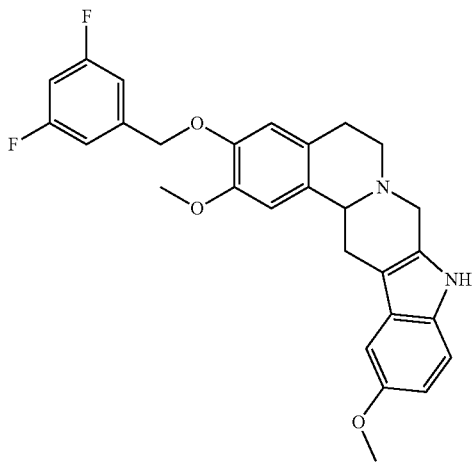 [SMILES: COc1ccc2[nH]c3c(c2c1)CC1c2cc(OC)c(OCc4cc(F)cc(F)c4)cc2CCN1C3]<br>C119 |

TABLE 1-continued
| No. | Name | Structure |
|---|---|---|
| C120 | 2-methoxy-3-((3,4,5-trifluorobenzyl)oxy)-5,6,8,9,14,14a-hexahydroindolo[3',2':4,5]pyridine[2,1-a]isoquinoline | 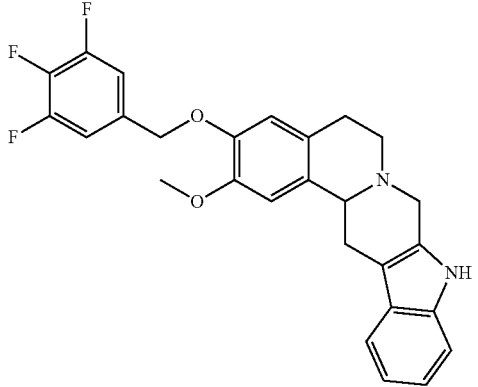 C120 |
| C121 | 2,12-dimethoxy-3-((3,4,5-trifluorobenzyl)oxy)-5,6,8,9,14,14a-hexahydroindolo[3',2':4,5]pyridine[2,1-a]isoquinoline | 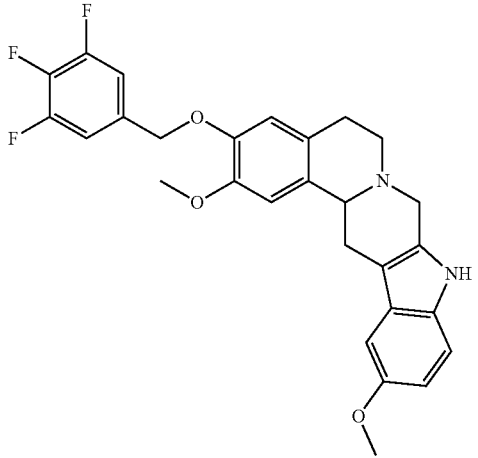 C121 |
| C122 | 3-methoxy-2-((3,4-difluorobenzyl)oxy)-5,6,8,9,14,14a-hexahydroindolo[3',2':4,5]pyridine[2,1-a]isoquinoline | 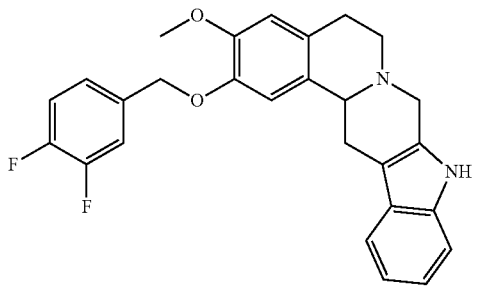 C122 |

TABLE 1-continued

| No. | Name | Structure |
|---|---|---|
| C123 | 3,12-dimethoxy-2-((3,4-difluorobenzyl)oxy)-5,6,8,9,14,14a-hexahydroindolo[3',2':4,5]pyridine[2,1-a]isoquinoline | 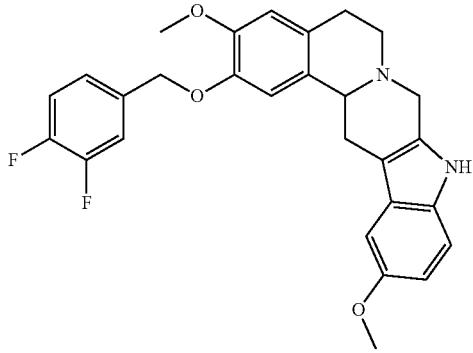 [SMILES: COc1ccc2[nH]c3c(c2c1)CC1c2cc(OCc4ccc(F)c(F)c4)c(OC)cc2CCN1C3]<br>C123 |
| C124 | 3-methoxy-2-((3,5-difluorobenzyl)oxy)-5,6,8,9,14,14a-hexahydroindolo[3',2':4,5]pyridine[2,1-a]isoquinoline | 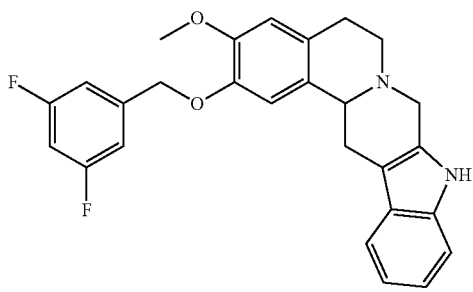 [SMILES: COc1cc2c(cc1OCc1cc(F)cc(F)c1)C1Cc3c([nH]c4ccccc34)CN1CC2]<br>C124 |
| C125 | 3,12-dimethoxy-2-((3,5-difluorobenzyl)oxy)-5,6,8,9,14,14a-hexahydroindolo[3',2':4,5]pyridine[2,1-a]isoquinoline | 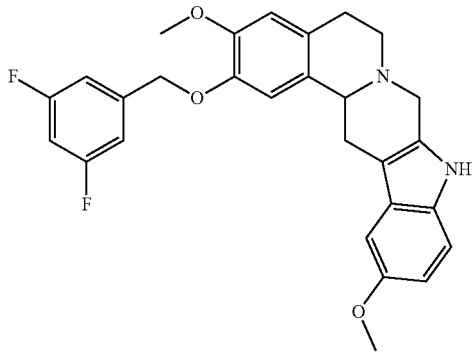 [SMILES: COc1ccc2[nH]c3c(c2c1)CC1c2cc(OCc4cc(F)cc(F)c4)c(OC)cc2CCN1C3]<br>C125 |
| C126 | 3-methoxy-2-((3,4,5-trifluorobenzyl)oxy)-5,6,8,9,14,14a-hexahydroindolo[3',2':4,5]pyridine[2,1-a]isoquinoline | 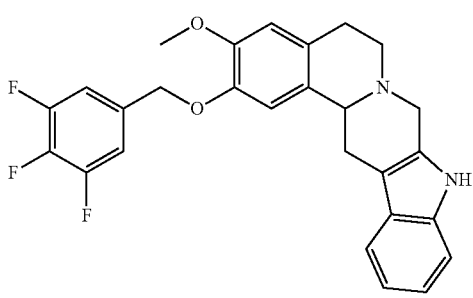 [SMILES: COc1cc2c(cc1OCc1cc(F)c(F)c(F)c1)C1Cc3c([nH]c4ccccc34)CN1CC2]<br>C126 |

| No. | Name | Structure |
|---|---|---|
| C127 | 3,12-dimethoxy-2-((3,4,5-trifluorobenzyl)oxy)-5,6,8,9,14,14a-hexahydroindolo[3',2':4,5]pyridine[2,1-a]isoquinoline | 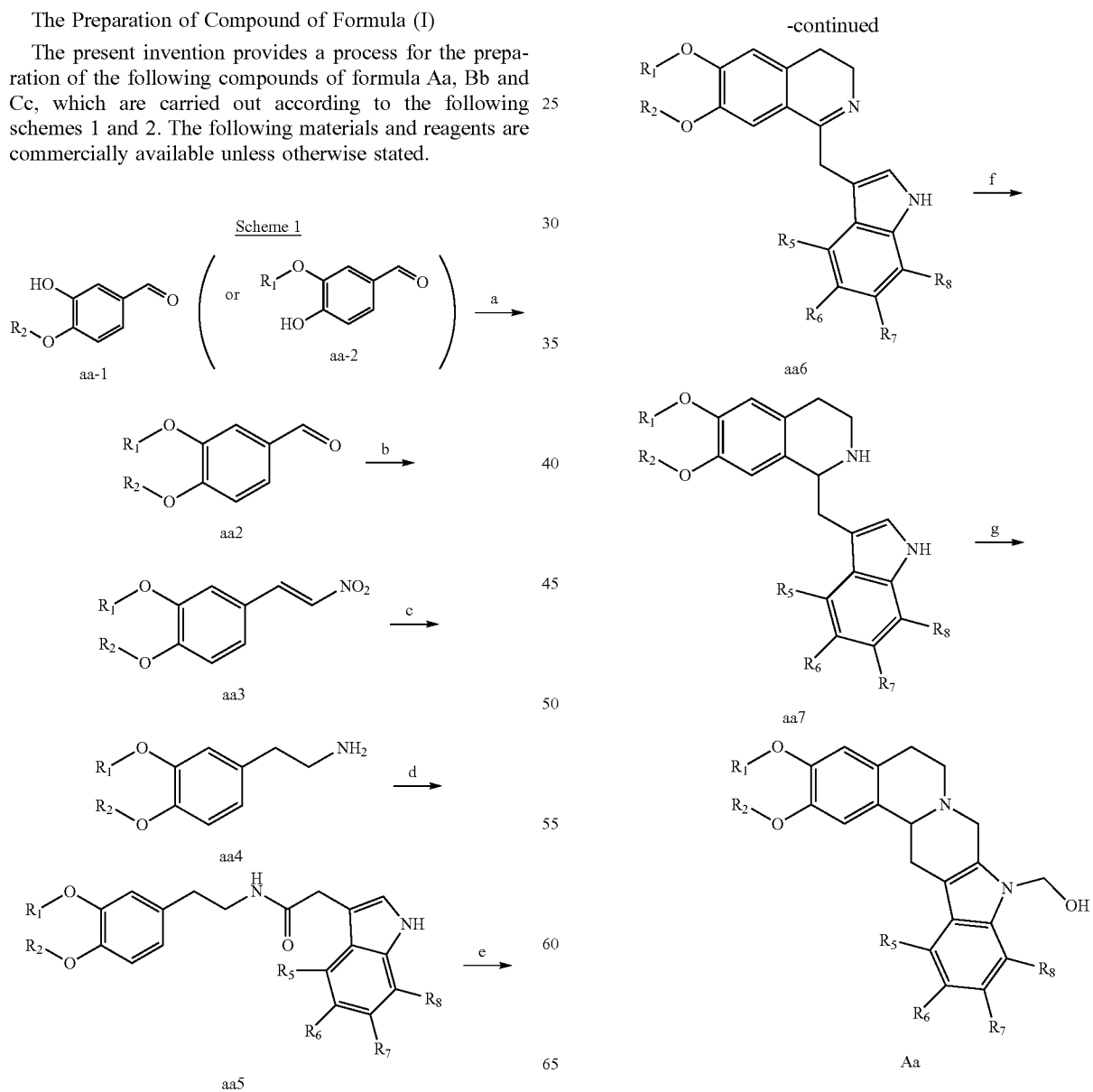 |

The Preparation of Compound of Formula (I)

The present invention provides a process for the preparation of the following compounds of formula Aa, Bb and Cc, which are carried out according to the following schemes 1 and 2. The following materials and reagents are commercially available unless otherwise stated.

Scheme 1 Step 1-a: 3-methoxy-4-hydroxy-benzaldehyde 1 and $R_1X$ ($R_1$=benzyl, alkyl, etc.) are dissolved in acetone solution, potassium carbonate is added in two portions, and the mixture is stirred at 65° C. for 4-12 hours after the addition. After the reaction is completed (TLC monitoring, UV development), the reaction solution is subjected to suction filtration, and the filtrate is collected and concentrated by distillation under reduced pressure. The crude product is purified by silica gel column chromatography (petroleum ether/ethyl acetate) to give compound aa2. The yield is 70-90%.

Step 1-b: The compound aa2 is dissolved in nitromethane, and ammonium acetate and acetic acid are added at room temperature. After the addition, the mixture is stirred at 80° C. for 2-4 hours. After the reaction is completed (TLC monitoring and UV development), the mixture is concentrated by distillation under reduced pressure, and the obtained concentrate is poured into a saturated $NaHCO_3$ solution with stirring to give a yellow solid suspension. The suspension is suction-filtered with a Buchner funnel. The obtained cake is added into isopropanol, and suction-filtered with a Buchner funnel. This operation is repeated twice to obtain a purified product aa3 in a yield of 80%-95%.

Step 1-c: $LiAlH_4$ is dissolved in anhydrous THF in an ice water bath, and then a solution of compound aa3 in tetrahydrofuran is added dropwise. After the addition is completed, the mixture is reacted in an ice water bath for 1 hour, then transferred to a 65° C. oil bath and stirred for 4-8 hours. After the reaction is completed (TLC monitoring and UV development), the reaction is cooled to room temperature, then the mixture is moved to an ice water bath to quench the reaction, and the quenched mixture is poured into a Buchner funnel and sunction-filtered under reduced pressure. The filtrate was collected, and the crude product is separated and purified by silica gel column chromatography (dichloromethane/methanol) to afford pale yellow liquid aa4, yield 30-70%.

Step 1-d: 5-methoxy-3-indolacetic acid is dissolved in anhydrous dichloromethane, and HOBT, EDC hydrochloride and triethylamine are added in one portion at room temperature. After the addition, the mixture is stirred at room temperature for 30 minutes. The solution of the compound aa4 in dichloromethane is slowly added and stirred for 10-20 hours. After the reaction is completed (TLC monitoring, UV development), an appropriate amount of water is added, and the mixture is extracted with dichloromethane, the organic layers are combined, washed twice with saturated sodium chloride solution, dried over anhydrous sodium sulfate, and concentrated. The crude product is separated and purified by silica gel column chromatography (dichloromethane/methanol) to provide compound aa5 in a yield of 60-80%.

Step 1-e: The compound aa5 was dissolved in anhydrous $CH_3CN$, and an appropriate amount of $POCl_3$ is added thereto at room temperature. After the addition, the mixture is reacted at 90° C. for 1-2 hours under argon. After the reaction is completed (TLC monitoring, UV development), the reaction solution is directly concentrated by distillation under reduced pressure, and the concentrate is quickly poured into a saturated $NaHCO_3$ ice water bath solution, rapidly stirred, and then extracted with dichloromethane. The combined organic layer is washed with saturated sodium chloride solution twice, dried over anhydrous sodium sulfate, and concentrated to give a concentrate aa6, which is directly used in the next step without purification.

Step 1-f: The concentrate aa6 is dissolved in anhydrous methanol, and sodium borohydride is added portionwise in an ice water bath. After the addition, the mixture was stirred at room temperature for 4-8 hours. After the reaction is completed (TLC monitoring, UV development), the reaction solution is concentrated, and saturated $NH_4Cl$ solution is added to the obtained concentrated liquid, and an appropriate amount of ethyl acetate is added to the mixed solution. The mixture is shaken until clear and transparent, and extracted with ethyl acetate. The combined organic layer is washed with saturated sodium chloride solution twice, dried over anhydrous sodium sulfate and concentrated to give a spumous solid aa7, yield 20-30%.

Step 1-g: The compound aa7 was dissolved in anhydrous acetonitrile, and a solution of formaldehyde and formic acid solution (or a solution of 4-fluorobenzaldehyde and formic acid solution) are added. After the addition, the mixture was stirred at 80° C. for 4-8 hours. After the reaction is completed (TLC monitoring, UV development), the reaction liquid is concentrated by distillation under reduced pressure, and a saturated sodium hydrogen carbonate solution is added to the concentrate, and the mixture is extracted with ethyl acetate. The combined organic layer is washed twice with saturated sodium chloride solution and dried over anhydrous sodium sulfate and concentrated. The crude product is purified by silica gel column chromatography (dichloromethane/methanol) to give a powdered solid Aa (yield: 60-80%).

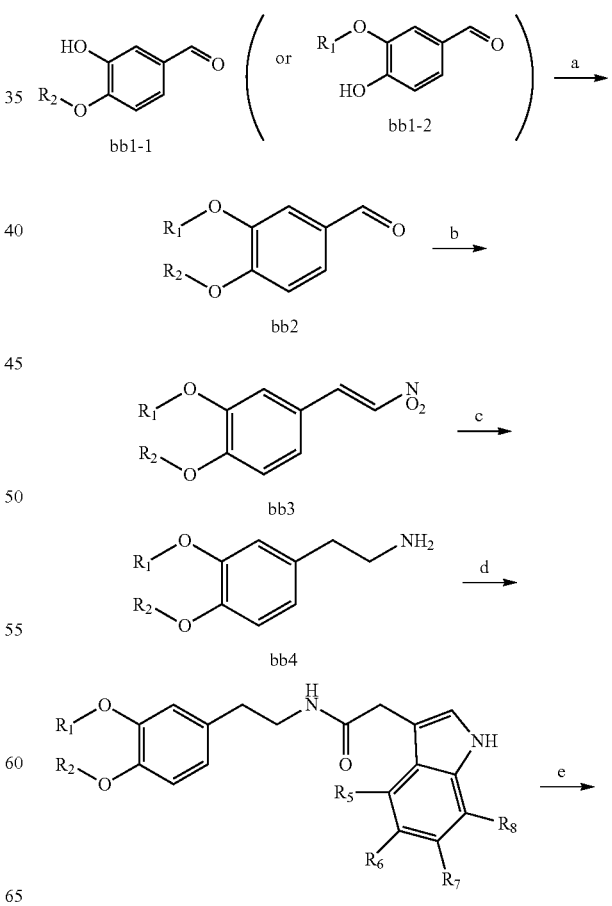

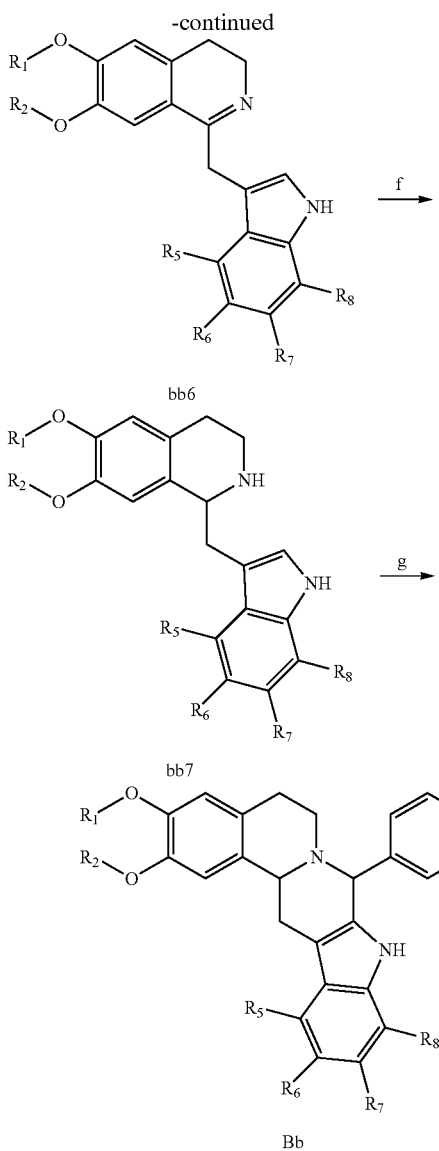

Scheme 2 Step 2-a: 3-methoxy-4-hydroxy-benzaldehyde 1 and $R_1X$ ($R_1$=benzyl, alkyl, etc.) are dissolved in acetone solution, and potassium carbonate is added in two portions, and the mixture is stirred at 65° C. for 4-12 hours after the addition. After the reaction is completed (TLC monitoring, UV development), the reaction solution is subjected to suction filtration, and the filtrate is collected and concentrated by distillation under reduced pressure. The crude product is purified by silica gel column chromatography (petroleum ether/ethyl acetate) to give compound bb2. The yield is 70-90%.

Step 2-b: The compound bb2 was dissolved in nitromethane, and ammonium acetate and acetic acid are added at room temperature. After the addition, the mixture is stirred at 80° C. for 2-4 hours. After the reaction is completed (TLC monitoring and UV development), the mixture is concentrated by distillation under reduced pressure, and the obtained concentrate is poured into a saturated $NaHCO_3$ solution with stirring to give a yellow solid suspension. The suspension is suction-filtrated with a Buchner funnel. The obtained cake is added to isopropanol, and suction-filtered with a Buchner funnel. This operation is repeated twice to obtain a purified product bb3 in a yield of 80%-95%.

Step 2-c: $LiAlH_4$ is dissolved in anhydrous THF in an ice water bath, and then a solution of compound bb3 in tetrahydrofuran is added dropwise. After the addition is completed, the mixture is reacted in an ice water bath for 1 hour, then transferred to a 65° C. oil bath and stirred for 4-8 hours. After the reaction is completed (TLC monitoring and UV development), the reaction is cooled to room temperature, then the mixture is moved to an ice water bath to quench the reaction, and the quenched mixture is poured into a Buchner funnel and sunction-filtered under reduced pressure. The filtrate was collected, and the crude product is separated and purified by silica gel column chromatography (dichloromethane/methanol) to afford pale yellow liquid bb4, yield 30-70%.

Step 2-d: 5-methoxy-3-indolacetic acid is dissolved in anhydrous dichloromethane, and HOBT, EDC hydrochloride and triethylamine are added in one portion at room temperature. After the addition, the mixture is stirred at room temperature for 30 minutes. The solution of the compound bb4 in dichloromethane is slowly added and stirred for 10-20 hours. After the reaction is completed (TLC monitoring, UV development), an appropriate amount of water is added, and the mixture is extracted with dichloromethane, the organic layers are combined, washed twice with saturated sodium chloride solution, dried over anhydrous sodium sulfate, and concentrated. The crude product is separated and purified by silica gel column chromatography (dichloromethane/methanol) to provide compound bb5 in a yield of 60-80%.

Step 2-e: The compound bb5 is dissolved in anhydrous $CH_3CN$, and an appropriate amount of $POCl_3$ is added thereto at room temperature. After the addition, the mixture is reacted at 90° C. for 1-2 hours under argon. After the reaction is completed (TLC monitoring UV development), the reaction solution is directly concentrated by distillation under reduced pressure, and the concentrate is quickly poured into a saturated $NaHCO_3$ ice water bath solution, rapidly stirred, and then extracted with dichloromethane. The combined organic layer is washed with saturated sodium chloride solution twice, dried over anhydrous sodium sulfate, and concentrated to give a concentrate bb6, which is directly used in the next step without purification.

Step 2-f: The concentrate bb6 is dissolved in anhydrous methanol, and sodium borohydride is added portionwise in an ice water bath. After the addition, the mixture was stirred at room temperature for 4-8 hours. After the reaction is completed (TLC monitoring, UV development), the reaction solution is concentrated, and saturated $NH_4Cl$ solution is added to the obtained concentrated liquid, and an appropriate amount of ethyl acetate is added to the mixed solution. The mixture is shaken until clear and transparent, and extracted with ethyl acetate. The combined organic layer is washed with saturated sodium chloride solution twice, dried over anhydrous sodium sulfate and concentrated to give a spumous solid bb7, yield 20-30%.

Step 2-g: The compound bb7 is dissolved in anhydrous acetonitrile, and a solution of 4-fluorobenzaldehyde and formic acid solution are added. After the addition, the mixture was stirred at 80° C. for 4-8 hours. After the reaction is completed (TLC monitoring, UV development), the reaction liquid is concentrated by distillation under reduced pressure, and a saturated sodium hydrogen carbonate solution is added to the concentrate, and the mixture is extracted with ethyl acetate. The combined organic layer is washed twice with saturated sodium chloride solution and dried over anhydrous sodium sulfate and concentrated. The crude product is purified by silica gel column chromatography (dichloromethane/methanol) to give a powdered solid Bb (yield: 60-80%).

Scheme 3

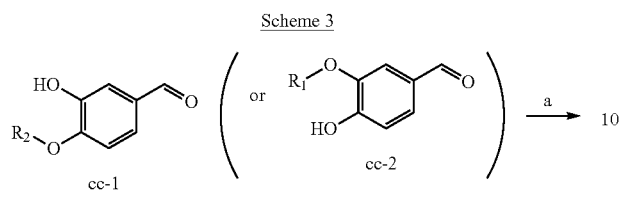

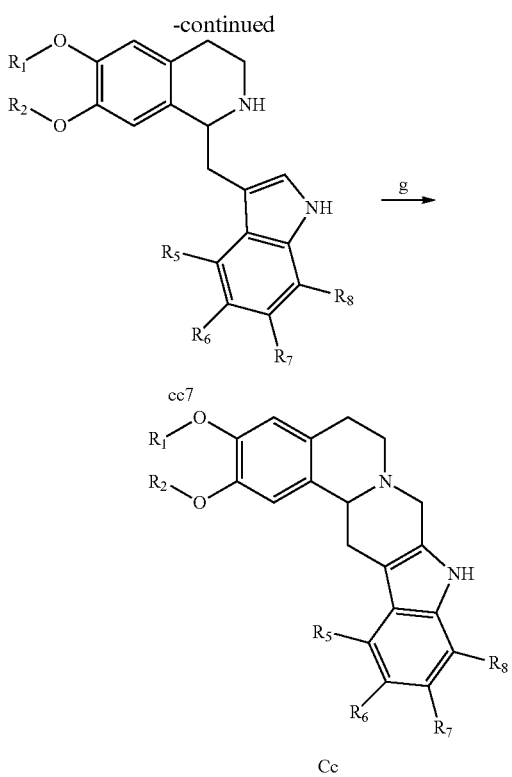

Scheme 3 Step 3-a: 3-methoxy-4-hydroxy-benzaldehyde 1 and $R_1X$ ($R_1$=benzyl, alkyl, etc.) are dissolved in acetone solution, and potassium carbonate is added in two portions, and the mixture is stirred at 65° C. for 4-12 hours after the addition. After the reaction is completed (TLC monitoring, UV development), the reaction solution is subjected to suction filtration, and the filtrate is collected and concentrated by distillation under reduced pressure. The crude product is purified by silica gel column chromatography (petroleum ether/ethyl acetate) to give compound cc2. The yield is 70-90%.

Step 3-b: The compound aa2 was dissolved in nitromethane, and ammonium acetate and acetic acid are added at room temperature. After the addition, the mixture is stirred at 80° C. for 2-4 hours. After the reaction completed (TLC monitoring and UV development), the mixture is concentrated by distillation under reduced pressure, and the obtained concentrate is poured into a saturated $NaHCO_3$ solution with stirring to give a yellow solid suspension. The suspension is suction-filtered with a Buchner funnel. The obtained cake is added to isopropanol, and suction-filtered with a Buchner funnel. This operation is repeated twice to obtain a purified product cc3 in a yield of 80%-95%.

Step 3-c: $LiAlH_4$ is dissolved in anhydrous THF in an ice water bath, and then a solution of compound cc3 in tetrahydrofuran is added dropwise. After the addition is completed, the mixture is reacted in an ice water bath for 1 hour, then transferred to a 65° C. oil bath and stirred for 4-8 hours. After the reaction is completed (TLC monitoring and UV development), the reaction is cooled to room temperature, then the mixture is moved to an ice water bath to quench the reaction, and the quenched mixture is poured into a Buchner funnel to filter under reduced pressure. The filtrate was collected, and the crude product is separated and purified by silica gel column chromatography (dichloromethane/methanol) to afford pale yellow liquid cc4, yield 30-70%.

Step 3-d: 5-methoxy-3-indolacetic acid is dissolved in anhydrous dichloromethane, and HOBT, EDC hydrochloride and triethylamine are added in one portion at room temperature. After the addition, the mixture is stirred at room temperature for 30 minutes. The solution of the compound aa4 in dichloromethane is slowly added and stirred for 10-20 hours. After the reaction is completed (TLC monitoring UV development), an appropriate amount of water is added, and the mixture is extracted with dichloromethane, the organic layers are combined, washed twice with saturated sodium chloride solution, dried over anhydrous sodium sulfate, and concentrated. The crude product is separated and purified by silica gel column chromatography (dichloromethane/methanol) to provide compound cc5 in a yield of 60-80%.

Step 3-e: The compound cc5 is dissolved in anhydrous $CH_3CN$, and an appropriate amount of $POCl_3$ is added thereto at room temperature. After the addition, the mixture is reacted at 90° C. for 1-2 hours under argon. After the reaction is completed (TLC monitoring UV development), the reaction solution is directly concentrated by distillation under reduced pressure, and the concentrate is quickly poured into a saturated $NaHCO_3$ ice water bath solution, rapidly stirred, and then extracted with dichloromethane. The combined organic layer is washed with saturated sodium chloride solution twice, dried over anhydrous sodium sulfate, and concentrated to give a concentrate cc6, which is directly used in the next step without purification.

Step 3-f: The concentrate cc6 is dissolved in anhydrous methanol, and sodium borohydride is added portionwise in an ice water bath. After the addition, the mixture was stirred at room temperature for 4-8 hours. After the reaction is completed (TLC monitoring UV development), the reaction solution is concentrated, and saturated $NH_4Cl$ solution is added to the obtained concentrated liquid, and an appropriate amount of ethyl acetate is added to the mixed solution. The mixture is shaken until clear and transparent, and extracted with ethyl acetate. The combined organic layer is washed with saturated sodium chloride solution twice, dried over anhydrous sodium sulfate and concentrated to give a spumous solid cc7, yield 20-30%.

Step 3-g: The compound cc7 was dissolved in anhydrous acetonitrile, and equimolar quantities of a solution of formaldehyde and formic acid solution (or a solution of 4-fluorobenzaldehyde and formic acid solution) are added. After the addition, the mixture was stirred at 80° C. for 4-8 hours. After the reaction is completed (TLC monitoring UV development), the reaction liquid is concentrated by distillation under reduced pressure, and a saturated sodium hydrogen carbonate solution is added to the concentrate, and the mixture is extracted with ethyl acetate. The combined organic layer is washed twice with saturated sodium chloride solution and dried over anhydrous sodium sulfate and concentrated. The crude product is purified by silica gel column chromatography (dichloromethane/methanol) to give a powdered solid Cc (yield: 60-70%).

Scheme 4

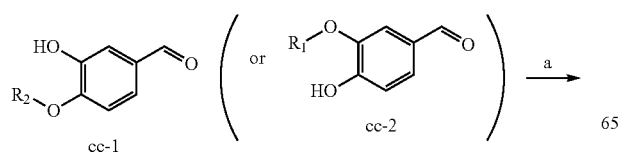

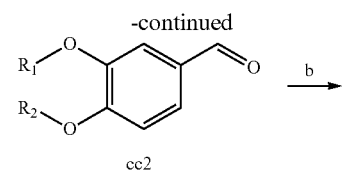

cc2

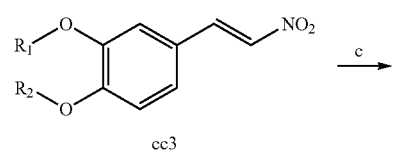

cc3

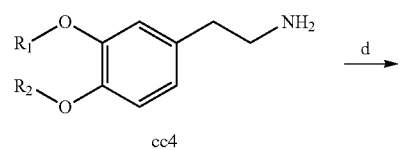

cc4

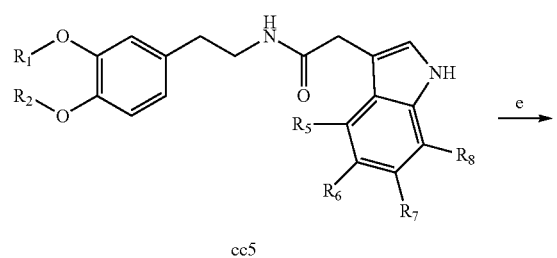

cc5

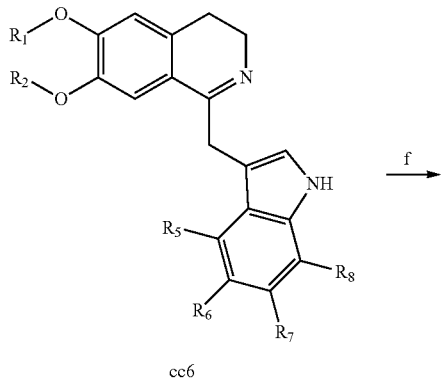

cc6

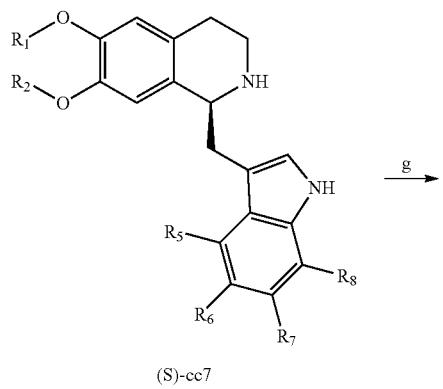

(S)-cc7

-continued

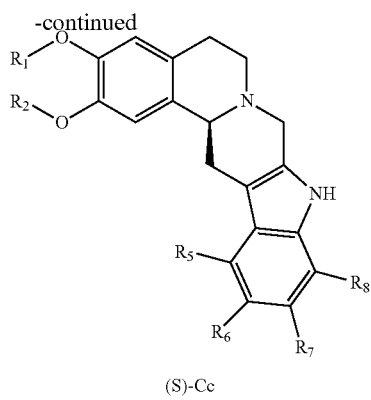

(S)-Cc

Scheme 4 Step 4-a: 3-methoxy-4-hydroxy-benzaldehyde 1 and $R_1X$ ($R_1$=benzyl, alkyl, etc.) are dissolved in acetone solution, and potassium carbonate is added in two portions, and the mixture is stirred at 65° C. for 4-12 hours after the addition. After the reaction is completed (TLC monitoring, UV development), the reaction solution is subjected to suction filtration, and the filtrate is collected and concentrated by distillation under reduced pressure. The crude product is purified by silica gel column chromatography (petroleum ether/ethyl acetate) to give compound cc2. The yield is 70-90%.

Step 4-b: The compound aa2 was dissolved in nitromethane, and ammonium acetate and acetic acid are added at room temperature. After the addition, the mixture is stirred at 80° C. for 2-4 hours. After the reaction completed (TLC monitoring and UV development), the mixture is concentrated by distillation under reduced pressure, and the obtained concentrate is poured into a saturated $NaHCO_3$ solution with stirring to give a yellow solid suspension. The suspension is suction-filtrated with a Buchner funnel. The obtained cake is added to isopropanol, and suction-filtered with a Buchner funnel. This operation is repeated twice to obtain a purified product cc3 in a yield of 80%-95%.

Step 4-c: $LiAlH_4$ is dissolved in anhydrous THF in an ice water bath, and then a solution of compound cc3 in tetrahydrofuran is added dropwise. After the addition is completed, the mixture is reacted in an ice water bath for 1 hour, then transferred to a 65° C. oil bath and stirred for 4-8 hours. After the reaction is completed (TLC monitoring and UV development), the reaction is cooled to room temperature, then the mixture is moved to an ice water bath to quench the reaction, and the quenched mixture is poured into a Buchner funnel to filter under reduced pressure. The filtrate was collected, and the crude product is separated and purified by silica gel column chromatography (dichloromethane/methanol) to afford pale yellow liquid cc4, yield 30-70%.

Step 4-d: 5-methoxy-3-indolacetic acid is dissolved in anhydrous dichloromethane, and HOBT, EDC hydrochloride and triethylamine are added in one portion at room temperature. After the addition, the mixture is stirred at room temperature for 30 minutes. The solution of the compound aa4 in dichloromethane is slowly added and stirred for 10-20 hours. After the reaction is completed (TLC monitoring UV development), an appropriate amount of water is added, and the mixture is extracted with dichloromethane, the organic layers are combined, washed twice with saturated sodium chloride solution, dried over anhydrous sodium sulfate, and concentrated. The crude product is separated and purified by silica gel column chromatography (dichloromethane/methanol) to provide compound cc5 in a yield of 60-80%.

Step 4-e: The compound cc5 is dissolved in anhydrous $CH_3CN$, and an appropriate amount of $POCl_3$ is added thereto at room temperature. After the addition, the mixture is reacted at 90° C. for 1-2 hours under argon. After the reaction is completed (TLC monitoring, UV development), the reaction solution is directly concentrated by distillation under reduced pressure, and the concentrate is quickly poured into a saturated $NaHCO_3$ ice water bath solution, rapidly stirred, and then extracted with dichloromethane. The combined organic layer is washed with saturated sodium chloride solution twice, dried over anhydrous sodium sulfate, and concentrated to give a concentrate cc6, which is directly used in the next step without purification.

Step 4-f: The concentrate cc6 is dissolved in anhydrous DMF, and a catalytic amount of (R)-type Noyori catalyst is added, and then a mixture of formic acid-triethylamine (mixed in a ratio of 9:1) is added. After the addition, the mixture is stirred at room temperature for 24 hours. After the reaction is completed (TLC monitoring, UV development), the reaction solution is concentrated, and saturated $NaHCO_3$ solution is added to the obtained concentrated liquid, the pH of solution is adjusted to >7, and an appropriate amount of ethyl acetate is added to the mixed solution. The mixture is shaken until clear and transparent, and extracted with ethyl acetate. The combined organic layer is washed with saturated sodium chloride solution twice, dried over anhydrous sodium sulfate and concentrated to give a spumous solid (S)-cc7, yield 50-60%.

Step 4-g: The compound (S)-cc7 was dissolved in anhydrous acetonitrile, and equimolar quantities of a solution of formaldehyde and formic acid solution (or a solution of 4-fluorobenzaldehyde and formic acid solution) are added. After the addition, the mixture was stirred at 80° C. for 4-8 hours. After the reaction is completed (TLC monitoring UV development), the reaction liquid is concentrated by distillation under reduced pressure, and a saturated sodium hydrogen carbonate solution is added to the concentrate, and the mixture is extracted with ethyl acetate. The combined organic layer is washed twice with saturated sodium chloride solution and dried over anhydrous sodium sulfate and concentrated. The crude product is purified by silica gel column chromatography (dichloromethane/methanol) to give a powdered solid (S)-Cc (yield: 60-70%).

Scheme 5

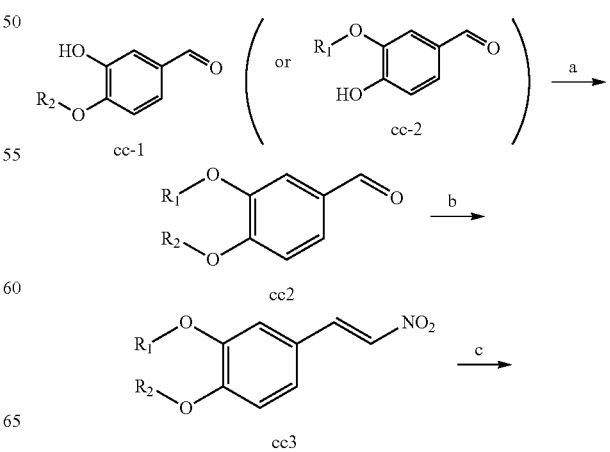

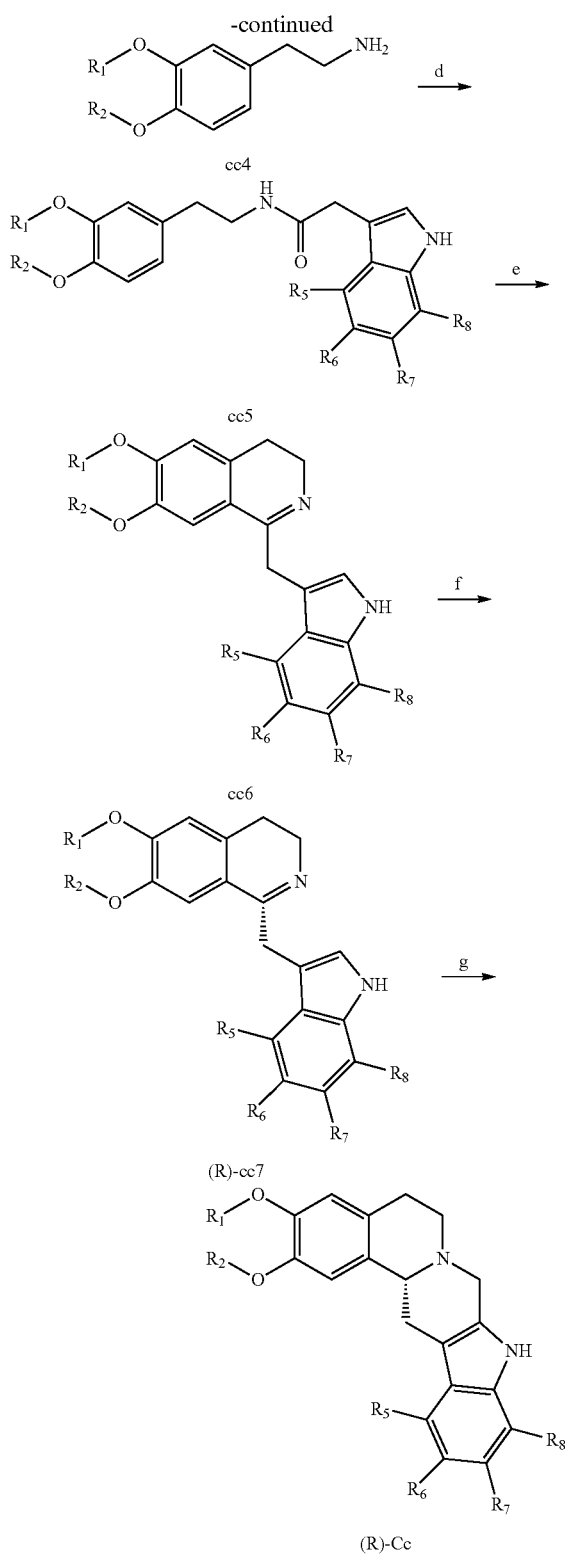

trated by distillation under reduced pressure. The crude product is purified by silica gel column chromatography (petroleum ether/ethyl acetate) to give compound cc2. The yield is 70-90%.

Step 5-b: The compound aa2 was dissolved in nitromethane, and ammonium acetate and acetic acid are added at room temperature. After the addition, the mixture is stirred at 80° C. for 2-4 hours. After the reaction completed (TLC monitoring and UV development), the mixture is concentrated by distillation under reduced pressure, and the obtained concentrate is poured into a saturated $NaHCO_3$ solution with stirring to give a yellow solid suspension. The suspension is suction-filtered with a Buchner funnel. The obtained cake is added to isopropanol, and suction-filtered with a Buchner funnel. This operation is repeated twice to obtain a purified product cc3 in a yield of 80%-95%.

Step 5-c: $LiAlH_4$ is dissolved in anhydrous THF in an ice water bath, and then a solution of compound cc3 in tetrahydrofuran is added dropwise. After the addition is completed, the mixture is reacted in an ice water bath for 1 hour, then transferred to a 65° C. oil bath and stirred for 4-8 hours. After the reaction is completed (TLC monitoring and UV development), the reaction is cooled to room temperature, then the mixture is moved to an ice water bath to quench the reaction, and the quenched mixture is poured into a Buchner funnel to filter under reduced pressure. The filtrate was collected, and the crude product is separated and purified by silica gel column chromatography (dichloromethane/methanol) to afford pale yellow liquid cc4, yield 30-70%.

Step 5-d: 5-methoxy-3-indolacetic acid is dissolved in anhydrous dichloromethane, and HOBT, EDC hydrochloride and triethylamine are added in one portion at room temperature. After the addition, the mixture is stirred at room temperature for 30 minutes. The solution of the compound aa4 in dichloromethane is slowly added and stirred for 10-20 hours. After the reaction is completed (TLC monitoring UV development), an appropriate amount of water is added, and the mixture is extracted with dichloromethane, the organic layers are combined, washed twice with saturated sodium chloride solution, dried over anhydrous sodium sulfate, and concentrated. The crude product is separated and purified by silica gel column chromatography (dichloromethane/methanol) to provide compound cc5 in a yield of 60-80%.

Step 5-e: The compound cc5 is dissolved in anhydrous $CH_3CN$, and an appropriate amount of $POCl_3$ is added thereto at room temperature. After the addition, the mixture is reacted at 90° C. for 1-2 hours under argon. After the reaction is completed (TLC monitoring UV development), the reaction solution is directly concentrated by distillation under reduced pressure, and the concentrate is quickly poured into a saturated $NaHCO_3$ ice water bath solution, rapidly stirred, and then extracted with dichloromethane. The combined organic layer is washed with saturated sodium chloride solution twice, dried over anhydrous sodium sulfate, and concentrated to give a concentrate cc6, which is directly used in the next step without purification.

Step 5-f: The concentrate cc6 is dissolved in anhydrous DMF, and a catalytic amount of (S)-type Noyori catalyst is added, and then a mixture of formic acid-triethylamine (mixed in a ratio of 9:1) is added. After the addition, the mixture is stirred at room temperature for 24 hours. After the reaction is completed (TLC monitoring UV development), the reaction solution is concentrated, and saturated $NaHCO_3$ solution is added to the obtained concentrated liquid, the pH of solution is adjusted to >7, and an appropriate amount of ethyl acetate is added to the mixed solution. The mixture is Scheme 5 Step 5-a: 3-methoxy-4-hydroxy-benzaldehyde 1 and $R_1X$ ($R_1$=benzyl, alkyl, etc.) are dissolved in acetone solution, and potassium carbonate is added in two portions, and the mixture is stirred at 65° C. for 4-12 hours after the addition. After the reaction is completed (TLC monitoring, UV development), the reaction solution is subjected to suction filtration, and the filtrate is collected and concenshaken until clear and transparent, and extracted with ethyl acetate. The combined organic layer is washed with saturated sodium chloride solution twice, dried over anhydrous sodium sulfate and concentrated to give a spumous solid (R)-cc7, yield 50-60%.

Step 5-g: The compound (R)-cc7 was dissolved in anhydrous acetonitrile, and equimolar quantities of a solution of formaldehyde and formic acid solution (or a solution of 4-fluorobenzaldehyde and formic acid solution) are added. After the addition, the mixture was stirred at 80° C. for 4-8 hours. After the reaction is completed (TLC monitoring UV development), the reaction liquid is concentrated by distillation under reduced pressure, and a saturated sodium hydrogen carbonate solution is added to the concentrate, and the mixture is extracted with ethyl acetate. The combined organic layer is washed twice with saturated sodium chloride solution and dried over anhydrous sodium sulfate and concentrated. The crude product is purified by silica gel column chromatography (dichloromethane/methanol) to give a powdered solid (R)-Cc (yield: 60-70%).

Pharmaceutical Composition and the Administration Thereof

The compounds of the present invention possess outstanding lipid-lowering activity, the compound of the present invention, and the crystal forms, pharmaceutically acceptable inorganic or organic salts, hydrates or solvates thereof, and the pharmaceutical composition comprising the compound of the present invention as a main active ingredient can be used for treating, preventing and alleviating diseases related to the proprotein convertase subtilisin Kexin-9 (PCSK9). According to the prior art, the compound of the present invention can be used in drugs for the prevention and treatment of metabolic diseases such as hyperlipemia, hypercholesterolemia, hypertriglyceridemia, fatty liver deformation, atherosclerosis, obesity and the like. The compounds disclosed herein can also reduce total cholesterol, LDL-cholesterol and triglycerides, and increase hepatic LDL receptor expression, inhibit PCSK9 expression, and activate AMP-activated protein kinases, etc.

The pharmaceutical composition of the invention comprises the compound of the present invention or the pharmaceutically acceptable salts thereof in a safe and effective dosage range and pharmaceutically acceptable excipients or carriers. Wherein the "safe and effective dosage" means that the amount of compound is sufficient to significantly ameliorate the condition without causing significant side effects. Generally, the pharmaceutical composition contains 1-2000 mg polymorphs of the invention per dose, preferably, 5-200 mg polymorphs of the invention per dose. Preferably, the "dose" is one capsule or tablet.

"Pharmaceutically acceptable carrier" means one or more compatible solid or liquid fillers, or gelatinous materials which are suitable for human use and should be of sufficient purity and sufficiently low toxicity. "Compatibility" means that each component in the composition can be admixed with the compounds of the present invention and with each other without significantly reducing the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

There is no special limitation of administration mode for the compound or pharmaceutical compositions of the present invention, and the representative administration mode includes (but is not limited to): oral, intratumoral, rectal, parenteral (intravenous, intramuscular or subcutaneous), and topical administration.

Solid dosage forms for oral administration include capsules, tablets, pills, powders and granules. In these solid dosage forms, the active compounds are mixed with at least one conventional inert excipient (or carrier), such as sodium citrate or CaHPO4, or mixed with any of the following components: (a) fillers or compatibilizer, for example, starch, lactose, sucrose, glucose, mannitol and silicic acid; (b) binders, for example, hydroxymethyl cellulose, alginates, gelatin, polyvinylpyrrolidone, sucrose and arabic gum; (c) humectant, such as, glycerol; (d) disintegrating agents such as agar, calcium carbonate, potato starch or tapioca starch, alginic acid, certain composite silicates, and sodium carbonate; (e) dissolution-retarding agents, such as paraffin; (f) absorption accelerators, for example, quaternary ammonium compounds; (g) wetting agents, such as cetyl alcohol and glyceryl monostearate; (h) adsorbents, for example, kaolin; and (i) lubricants such as talc, stearin calcium, magnesium stearate, solid polyethylene glycol, sodium lauryl sulfate, or the mixtures thereof. In capsules, tablets and pills, the dosage forms may also contain buffering agents.

The solid dosage forms such as tablets, sugar pills, capsules, pills and granules can be prepared by using coating and shell materials, such as enteric coatings and any other materials known in the art. They can contain an opaque agent. The release of the active compounds or compounds in the compositions can be released in a delayed mode in a given portion of the digestive tract. Examples of the embedding components include polymers and waxes. If necessary, the active compounds and one or more above excipients can form microcapsules.

Liquid dosage forms for oral administration include pharmaceutically acceptable emulsions, solutions, suspensions, syrups or tinctures. In addition to the active compounds, the liquid dosage forms may contain any conventional inert diluents known in the art such as water or other solvents, solubilizers and emulsifiers, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the combination thereof.

Besides these inert diluents, the composition may also contain additives such as wetting agents, emulsifiers, and suspending agent, sweetener, flavoring agents and perfume.

In addition to the active compounds, the suspension may contain suspending agent, for example, ethoxylated isooctadecanol, polyoxyethylene sorbitol and sorbitan esters, microcrystalline cellulose, methanol aluminum and agar, or the combination thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

The dosage forms for topical administration of compounds of the invention include ointments, powders, patches, aerosol, and inhalants. The active ingredients are mixed with physiologically acceptable carriers and any preservatives, buffers, or propellant if necessary, under sterile conditions.

Compounds of the present invention can be administrated alone, or in combination with any other pharmaceutically acceptable compounds.

When the pharmaceutical compositions are used, a safe and effective amount of compound of the present invention is applied to a mammal (such as human) in need of, wherein the dose of administration is a pharmaceutically effective dose. For a person weighed 60 kg, the daily dose is usually 1-2000 mg, preferably 5-500 mg. Of course, the particular dose should also depend on various factors, such as the route of administration, patient healthy status, which are well within the skills of an experienced physician.

Compared with the Prior Art, the Main Advantages of the Present Invention Include:

(1) A novel class of phenyl[a]indolo[2,3-g]quinolizine compounds and derivatives thereof are provided. The preparation method has advantages such as mild reaction conditions, abundant raw materials, easy operation and post-treatment, good corresponding selectivity, etc. The compound has a good proprotein convertase subtilisin Kexin-9 type (PCSK9) inhibitory activity.

(2) A PCSK9 inhibitor is provided, which exhibits strong in vivo lipid-lowering activity in high-fat animal model experiments, and is effective in reducing LDL-cholesterol, total cholesterol, and triglyceride levels. It is a kind of potential hypolipidemic drug, which can be used for the prevention and treatment of drugs for metabolic diseases such as hyperlipidemia, hypercholesterolemia, hypertriglyceridemia, fatty liver deformation, atherosclerosis and obesity. The compounds disclosed herein can also reduce total cholesterol, LDL-cholesterol and triglycerides, and increase hepatic LDL receptor expression, inhibit PCSK9 expression, and activate AMP-activated protein kinases.

(3) The phenyl[a]indolo[2,3-g]quinolizine compounds and derivatives of the present invention have good pharmacokinetic properties in animals.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, parts and percentage are calculated by weight.

Example 1 (2-(Benzyloxy)-3,12-dimethoxy-5,6,14,14a-tetrahydroindolo[3',2':4,5]pyridine[2,1-a]isoquinoline-9(8H)-yl)methanol (A1)

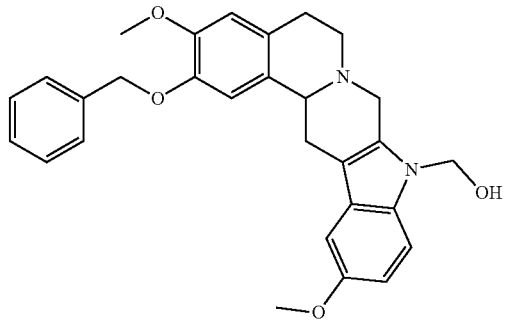

Synthetic Route:

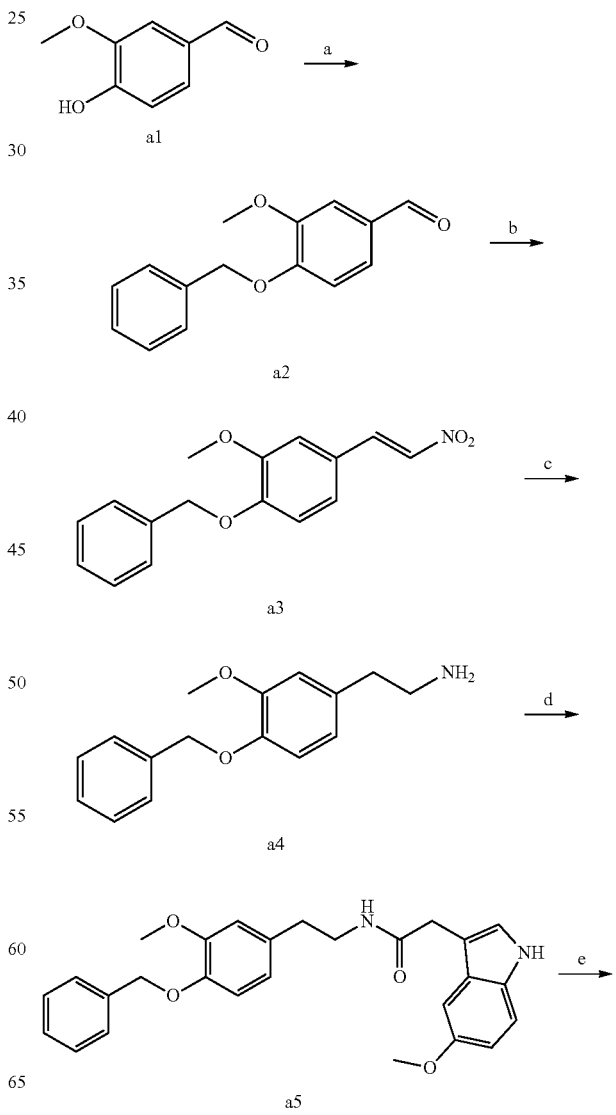

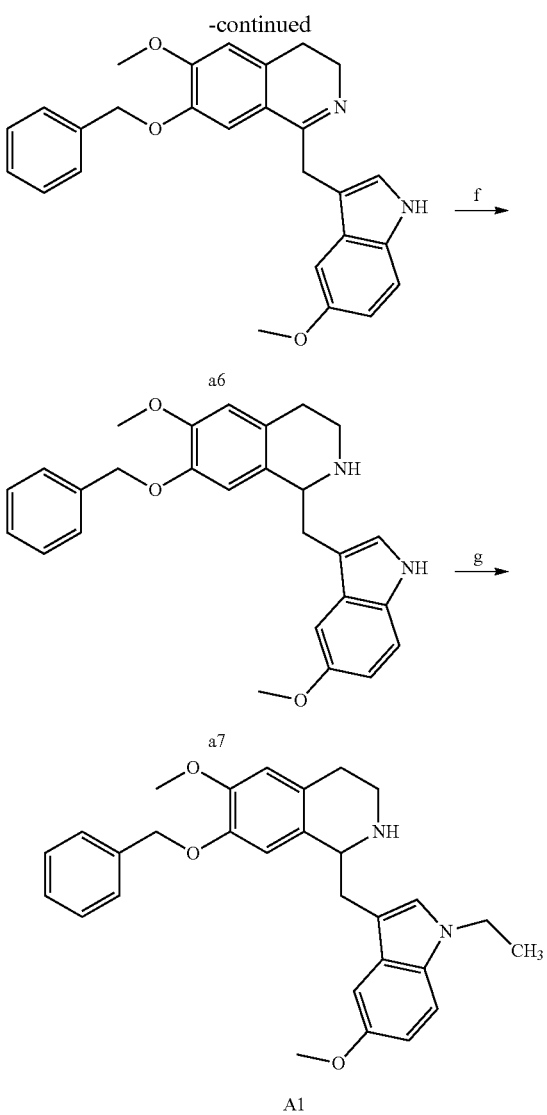

3-methoxy-4-benzyloxy-benzaldehyde (a2)

3-methoxy-4-hydroxy-benzaldehyde a1-2 (20.00 g, 131.45 mmol) and benzylbromide (26.98 g, 157.74 mmol) were dissolved in acetone solution, and potassium carbonate (36.33 g, 262.90 mmol) was added in two portions, and the mixture was stirred at 65° C. for 6 hours after the addition. After the reaction was completed (TLC monitoring, UV development), the reaction solution was suction-filtrated, and the filtrate was collected and concentrated by distillation under reduced pressure. The concentrated crude product was purified by silica gel column chromatography (petroleum ether/ethyl acetate=8/1) to give compound a2 (26.32 g, 106.47 mmol), yield 81%.

$^1$H NMR (400 MHz, Chloroform-d) δ 9.61 (s, 1H), 7.47-7.18 (m, 8H), 5.16 (s, 2H), 3.83 (s, 3H);
LRMS (ESI, m/z): 243 [M+H]$^+$.

(E)-1-(benzyloxy)-2-methoxy-4-(2-nitrovinyl)benzene (a3)

Compound a2 (26.32 g, 106.47 mmol) was dissolved in nitromethane (129.98 g, 2129.4 mmol), and ammonium acetate (16.41 g, 212.94 mmol) and acetic acid (59.86 g, 997.82 mmol) were added at room temperature, and stirred at 80° C. for 2 hours. After the reaction completed (TLC monitoring and UV development), the mixture was concentrated by distillation under reduced pressure, and the obtained concentrate was poured into a saturated NaHCO$_3$ solution with stirring to give a yellow solid suspension. The suspension was suction-filtrated under reduced pressure with a Buchner funnel. The obtained cake was added to isopropanol, and suction-filtered with a Buchner funnel. This operation was repeated twice, and the filter cake was collected and dried to obtain purified product a3 (27.34 g, 95.82 mmol), yield 90%.

$^1$H NMR (400 MHz, Chloroform-d) δ 8.16-8.14 (d, 1H), 7.98-7.96 (d, 1H), 7.47-6.94 (m, 8H), 5.16 (s, 2H), 3.83 (s, 3H);
LRMS (ESI, m/z): 286 [M+H]$^+$.

2-(4-(benzyloxy)-3-methoxyphenyl)ethylamine (a4)

LiAlH$_4$ (10.91 g, 287.46 mmol) was dissolved in anhydrous THF in an ice water bath, and then a solution of compound a3 (27.34 g, 95.82 mmol) in tetrahydrofuran was added dropwise with a separating funnel. After the addition was completed, the mixture was reacted in an ice water bath for 1 hour, then transferred to a oil bath at 65° C. and stirred for 8 hours. After the reaction was completed (TLC monitoring and UV development), the reaction was cooled to room temperature, then the mixture was moved into an ice water bath to quench the reaction, and when the stir bar was unable to stir, dichloromethane was added to the mixture. Such operation was repeated until the reaction was completely quenched. The quenched mixture was poured into a Buchner funnel and sunction-filtered under reduced pressure. The filtrate was collected, and then the crude product was separated and purified by silica gel column chromatography (dichloromethane/methanol=20/1) to give a pale yellow liquid a4 (11.10 g, 43.12 mmol), yield 45%.

$^1$H NMR (400 MHz, Chloroform-d) δ 7.47-7.38 (m, 5H), 6.83-6.74 (m, 3H), 5.16 (s, 2H), 5.11 (s, 2H), 3.83 (s, 3H); 2.98-2.84 (m, 2H), 2.80-2.74 (m, 2H);
LRMS (ESI, m/z): 258 [M+H]$^+$.

N-(4-(Benzyloxy)-3-methoxyphenethyl)-2-(5-methoxy-1H-indol-3-yl)acetamide (a5)

5-methoxy-3-indolacetic acid (9.73 g, 47.43 mmol) was added in anhydrous dichloromethane, and HOBT (10.48 g, 77.62 mmol), EDC hydrochloride (12.35 g, 64.68 mmol) and triethylamine (8.73 g, 86.24 mmol) were added in one portion at room temperature. After addition, the mixture was stirred at room temperature for 30 minutes, and compound a4 (11.10 g, 43.12 mmol) in dichloromethane was slowly added and stirred for 18 hours. After the reaction was completed (TLC monitoring, UV development), an appropriate amount of water was added, and the mixture was extracted with dichloromethane, the organic layers were combined, washed twice with saturated sodium chloride solution, dried over anhydrous sodium sulfate, and concentrated. The crude product was separated and purified by silica gel column chromatography (dichloromethane/methanol=50/1) to provide compound a5 (13.03 g, 29.32 mmol), yield 68%.

$^1$H NMR (400 MHz, Chloroform-d) δ 12.46 (s, 1H), 7.47-7.38 (m, 5H), 6.83-6.74 (m, 3H), 5.16 (s, 2H), 5.11 (s, 2H), 3.83 (s, 3H); 2.98-2.84 (m, 2H), 2.80-2.74 (m, 2H);
LRMS (ESI, m/z): 258 [M+H]$^+$.

7-(Benzyloxy)-6-methoxy-1-((5-methoxy-1H-indol-3-yl)methyl)-3,4-dihydroisoquinoline (a6)

Compound a5 (13.03 g, 29.32 mmol) was dissolved in anhydrous $CH_3CN$, and $POCl_3$ (26.97 g, 175.92 mmol) was added at room temperature. After the addition, the mixture was reacted at 90° C. for 1 hour under argon protection. After the reaction was completed (TLC monitoring, UV development), the reaction solution was directly concentrated by distillation under reduced pressure, and the concentrate was quickly poured into a saturated $NaHCO_3$ ice water bath solution, rapidly stirred, and then extracted with dichloromethane. The combined organic layers was washed with saturated sodium chloride solution twice, dried over anhydrous sodium sulfate, and concentrated to give a concentrate a6, which was very unstable imine, and was directly used in the next step without purification.

7-(Benzyloxy)-6-methoxy-1-((5-methoxy-1H-indol-3-yl)methyl)-1,2,3,4-tetrahydroisoquinoline (a7)

The concentrate a6 was dissolved in anhydrous methanol, and $NaBH_4$ (11.09 g, 293.20 mmol) was added portionwise in an ice-water bath. The mixture was stirred at room temperature for 6 hours after the addition. After the reaction was completed (TLC monitoring, UV development), the reaction solution was concentrated, and saturated $NH_4Cl$ solution was added to the obtained concentrated liquid, and an appropriate amount of ethyl acetate was added to the mixed solution. The mixture was shaken until it was clear and transparent, and extracted with ethyl acetate. The combined organic layers was washed with saturated sodium chloride solution twice, dried over anhydrous sodium sulfate and concentrated. The crude product was separated and purified by silica gel column chromatography (dichloromethane/methanol=20/1) to give a spumous solid a7 (2.51 g, 5.86 mmol), yield 20%.

$^1$H NMR (400 MHz, DMSO) δ 10.1 (s, 1H), 7.60-7.19 (m, 6H), 7.04-6.96 (m, 2H), 6.82 (s, 1H), 6.74 (dd, J=8.8, 2.3 Hz, 1H), 5.07 (s, 2H), 4.18 (d, J=15.0 Hz, 1H), 3.82 (s, 3H), 3.78 (m, 3H), 3.72-3.56 (m, 2H), 3.44 (d, J=14.2 Hz, 1H), 3.13 (m, 1H), 2.95 (m, 1H), 2.65 (d, J=13.4 Hz, 2H), 2.48-2.37 (m, 1H);

LRMS (ESI, m/z): 429 [M+H]$^+$.

(2-(Benzyloxy)-3,12-dimethoxy-5,6,14,14a-tetrahydroindolo[3',2':4,5]pyridine[2,1-a isoquinoline-9(8H)-yl)methanol (A1)

The compound a7 (2.51 g, 5.86 mmol) was dissolved in anhydrous acetonitrile, and formaldehyde (0.73 g, 23.44 mmol) and formic acid (0.035 g, 0.59 mmol) were added. After the addition, the mixture was stirred at 80° C. for 8 hours. After the reaction was completed (TLC monitoring, UV development), the reaction liquid was concentrated by distillation under reduced pressure, and a saturated sodium hydrogen carbonate solution was added to the concentrate, and the mixture was extracted with ethyl acetate. The combined organic layers was washed twice with saturated sodium chloride solution and dried over anhydrous sodium sulfate and concentrated. The crude product was purified by silica gel column chromatography (dichloromethane/methanol=20/1) to give a pale yellow powdered solid A1 (1.98 g, 4.16 mmol), yield 71%.

Example A1 (2-(Benzyloxy)-3,12-dimethoxy-5,6,14,14a-tetrahydroindolo[3',2':4,5]pyridine[2,1-a]isoquinoline-9(8H)-yl)methanol (A1)

$^1$H NMR (400 MHz, DMSO) δ 7.51-7.35 (m, 6H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 471 [M+H]$^+$.

Example A2 (2-(Benzyloxy)-3-methoxy-5,6,14,14a-tetrahydroindolo[3',2':4,5]pyridine[2,1-a]isoquinoline-9(8H)-yl)methanol (A2)

The title compound A2 was synthesized with benzyl bromide, 3-methoxy-4-hydroxybenzaldehyde and 3-indoleacetic acid according to Scheme 1.

$^1$H NMR (400 MHz, DMSO) δ 7.56-7.37 (m, 7H), 7.08 (s, 1H), 6.97 (d, J=2.1 Hz, 1H), 6.76-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 441 [M+H]$^+$.

Example A3 (3,12-Dimethoxy-2-((4-(trifluoromethyl)benzyl)oxy)-5,6,14,14a-tetrahydroindolo[3',2':4,5]pyridine[2,1-a]isoquinoline-9(8H)-yl)methanol (A3)

The title compound A3 was synthesized with (4-trifluoromethyl)benzyl bromide, 3-methoxy-4-hydroxybenzaldehyde and 5-methoxy-3-indoleacetic acid according to Scheme 1.

$^1$H NMR (400 MHz, DMSO) δ 7.71-7.53 (m, 2H), 7.50-7.35 (m, 1H), 7.31-7.15 (m, 2H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 539 [M+H]$^+$.

Example A4 (3-methoxy-2-((4-(trifluoromethyl)benzyl)oxy)-5,6,14,14a-tetrahydroindolo[3',2':4,5]pyridine[2,1-a]isoquinoline-9(8H)-yl)methanol (A4)

The title compound A4 was synthesized with (trifluoromethyl)benzyl bromide, 3-methoxy-4-hydroxybenzaldehyde and 3-indoleacetic acid according to Scheme 1.

$^1$H NMR (400 MHz, DMSO) δ 7.71-7.53 (m, 2H), 7.50-7.35 (m, 1H), 7.31-7.15 (m, 3H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 509 [M+H]$^+$.

Example A5 (2-((4-fluorobenzyl)oxy)-3,12-dimethoxy-5,6,14,14a-tetrahydroindolo[3',2':4,5]pyridine[2,1-a]isoquinoline-9(8H)-yl)methanol (A5)

The title compound A5 was synthesized with 4-fluorobenzyl bromide, 3-methoxy-4-hydroxybenzaldehyde and 5-methoxy-3-indoleacetic acid according to Scheme 1.

$^1$H NMR (400 MHz, DMSO) δ 7.57-7.47 (m, 2H), 7.36 (d, J=8.5 Hz, 1H), 7.32-7.24 (m, 2H), 7.03 (s, 1H), 6.94 (m, 1H), 6.77-6.68 (m, 2H), 6.21 (t, J=6.9 Hz, 1H), 5.37 (d, J=6.3 Hz, 2H), 5.08 (q, J=11.3 Hz, 2H), 4.16 (d, J=15.7 Hz, 1H), 3.78 (s, 3H), 3.76 (s, 3H), 3.64 (d, J=14.3 Hz, 1H), 3.55 (d, J=8.0 Hz, 1H), 3.31 (m, 1H), 3.12 (d, J=7.7 Hz, 1H), 3.03-2.88 (m, 1H), 2.66 (dd, J=12.1 Hz, 2H), 2.33 (t, J=11.5 Hz, 1H).

LRMS (ESI, m/z): 489 [M+H]$^+$.

Example A6 (2-((4-fluorobenzyl)oxy)-3-methoxy-5,6,14,14a-tetrahydroindolo[3',2':4,5]pyridine[2,1-a]isoquinoline-9(8H)-ylmethanol (A6)

The title compound A6 was synthesized with 4-fluorobenzyl bromide, 3-methoxy-4-hydroxybenzaldehyde and 3-indoleacetic acid according to Scheme 1.

$^1$H NMR (400 MHz, DMSO) δ 7.57-7.47 (m, 2H), 7.36 (d, J=8.5 Hz, 1H), 7.32-7.24 (m, 3H), 7.03 (s, 1H), 6.94 (m, 1H), 6.77-6.68 (m, 2H), 6.21 (t, J=6.9 Hz, 1H), 5.37 (d, J=6.3 Hz, 2H), 5.08 (q, J=11.3 Hz, 2H), 4.16 (d, J=15.7 Hz, 1H), 3.78 (s, 3H), 3.76 (s, 3H), 3.64 (d, J=14.3 Hz, 1H), 3.55 (d, J=8.0 Hz, 1H), 3.31 (m, 1H), 3.12 (d, J=7.7 Hz, 1H), 3.03-2.88 (m, 1H), 2.66 (dd, J=12.1 Hz, 2H), 2.33 (t, J=11.5 Hz, 1H).

LRMS (ESI, m/z): 459 [M+H]$^+$.

Example A7 (2-((3-fluorobenzyl)oxy)-3,12-dimethoxy-5,6,14,14a-tetrahydroindolo[3',2':4,5]pyridine[2,1-a]isoquinoline-9(8H)-yl)methanol (A7)

The title compound A7 was synthesized with 3-fluorobenzyl bromide, 3-methoxy-4-hydroxybenzaldehyde and 5-methoxy-3-indoleacetic acid according to Scheme 1.

$^1$H NMR (400 MHz, DMSO) δ 7.51-7.35 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 489 [M+H]$^+$.

Example A8 (2-((3-fluorobenzyl)oxy)-3-methoxy-5,6,14,14a-tetrahydroindolo[3',2':4,5]pyridine[2,1-a]isoquinoline-9(8H)-ylmethanol (A8)

The title compound A8 was synthesized with 3-fluorobenzyl bromide, 3-methoxy-4-hydroxybenzaldehyde and 3-indoleacetic acid according to Scheme 1.

$^1$H NMR (400 MHz, DMSO) δ 7.50-7.43 (m, 3H), 7.26-7.15 (m, 3H), 7.00 (s, 1H), 6.95 (d, J=2.3 Hz, 1H), 6.80 (s, 1H), 6.65 (dd, J=8.7, 2.4 Hz, 1H), 6.20 (t, J=6.1 Hz, 1H), 5.17 (s, 2H), 5.03 (s, 2H), 4.18 (d, J=15.0 Hz, 1H), 3.97 (d, J=14.6 Hz, 1H), 3.77 (s, 3H), 3.61 (dd, J=22.2, 12.4 Hz, 2H), 3.41 (d, J=14.6 Hz, 1H), 3.11 (d, J=11.1 Hz, 1H), 2.92 (d, J=10.6 Hz, 1H), 2.60 (dd, J=20.6, 13.0 Hz, 2H), 2.48-2.39 (m, 1H).

LRMS (ESI, m/z): 459 [M+H]$^+$.

Example A9 (2-((2-fluorobenzyl)oxy)-3,12-dimethoxy-5,6,14,14a-tetrahydroindolo[3',2':4,5]pyridine[2,1-a]isoquinoline-9(8H)-yl)methanol (A5)

The title compound A9 was synthesized with 2-fluorobenzyl bromide, 3-methoxy-4-hydroxybenzaldehyde and 5-methoxy-3-indoleacetic acid according to Scheme 1.

$^1$H NMR (400 MHz, DMSO) δ 7.51-7.35 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 489 [M+H]$^+$.

Example A10 (2-((2-fluorobenzyl)oxy)-3-methoxy-5,6,14,14a-tetrahydroindolo[3',2':4,5]pyridine[2,1-a]isoquinoline-9(8H)-yl)methanol (A10)

The title compound A10 was synthesized with 2-fluorobenzyl bromide, 3-methoxy-4-hydroxybenzaldehyde and 3-indoleacetic acid according to Scheme 1.

$^1$H NMR (400 MHz, DMSO) δ 7.51-7.35 (m, 5H), 7.05 (s, 1H), 6.94 (d, J=2.1 Hz, 1H), 6.79-6.69 (m, 3H), 6.22 (t, J=7.0 Hz, 1H), 5.38 (d, J=7.4 Hz, 2H), 5.08 (s, 2H), 4.18 (d, J=15.0 Hz, 1H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 459 [M+H]$^+$.

Example A11 (3,12-Dimethoxy-2-((4-methoxybenzyl)oxo)-5,6,14,14a-tetrahydroindolo[3',2':4,5]pyridine[2,1-a]isoquinoline-9(8H)-yl)methanol (A11)

The title compound A11 was synthesized with 4-methoxybenzyl bromide, 3-methoxy-4-hydroxybenzaldehyde and 5-methoxy-3-indoleacetic acid according to Scheme 1.

$^1$H NMR (400 MHz, DMSO) δ 7.40-7.28 (m, 2H), 7.10-7.03 (m, 3H), 6.98-6.87 (m, 2H), 6.79-6.68 (m, 2H), 6.22 (t, J=7.0 Hz, 1H), 5.37 (d, J=6.3 Hz, 2H), 5.09 (q, J=11.9 Hz, 2H), 4.16 (d, J=15.3 Hz, 1H), 3.79 (s, 3H), 3.78 (s, 3H), 3.76 (s, 3H), 3.64 (d, J=15.0 Hz, 1H), 3.54 (dd, J=10.6, 2.9 Hz, 1H), 3.32 (d, J=3.1 Hz, 1H), 3.17-3.08 (m, 1H), 3.03-2.85 (m, 1H), 2.73-2.56 (m, 2H), 2.33 (t, J=7.0 Hz, 1H).

LRMS (ESI, m/z): 501 [M+H]$^+$.

Example A12 (3-methoxy-2-((4-methoxybenzyl)oxo)-5,6,14,14a-tetrahydroindolo[3',2':4,5]pyridine[2,1-a]isoquinoline-9(8H)-yl)methanol (A12)

The title compound A12 was synthesized with 4-methoxybenzyl bromide, 3-methoxy-4-hydroxybenzaldehyde and 3-indoleacetic acid according to Scheme 1.

$^1$H NMR (400 MHz, DMSO) δ 7.40-7.28 (m, 2H), 7.10-7.03 (m, 4H), 6.98-6.87 (m, 2H), 6.79-6.68 (m, 2H), 6.22 (t, J=7.0 Hz, 1H), 5.37 (d, J=6.3 Hz, 2H), 5.09 (q, J=11.9 Hz, 2H), 4.16 (d, J=15.3 Hz, 1H), 3.79 (s, 3H), 3.76 (s, 3H), 3.64 (d, J=15.0 Hz, 1H), 3.54 (dd, J=10.6, 2.9 Hz, 1H), 3.32 (d, J=3.1 Hz, 1H), 3.17-3.08 (m, 1H), 3.03-2.85 (m, 1H), 2.73-2.56 (m, 2H), 2.33 (t, J=7.0 Hz, 1H).

LRMS (ESI, m/z): 471 [M+H]$^+$.

Example A13 (3,12-Dimethoxy-2-((3-methoxybenzyl)oxo)-5,6,14,14a-tetrahydroindolo[3',2':4,5]pyridine[2,1-a]isoquinoline-9(8H)-yl)methanol (A13)

The title compound A13 was synthesized with 3-methoxybenzyl bromide, 3-methoxy-4-hydroxybenzaldehyde and 5-methoxy-3-indoleacetic acid according to Scheme 1.

$^1$H NMR (400 MHz, DMSO) δ 7.40-7.28 (m, 2H), 7.10-7.03 (m, 3H), 6.98-6.87 (m, 2H), 6.79-6.68 (m, 2H), 6.22 (t, J=7.0 Hz, 1H), 5.37 (d, J=6.3 Hz, 2H), 5.09 (q, J=11.9 Hz, 2H), 4.16 (d, J=15.3 Hz, 1H), 3.79 (s, 3H), 3.78 (s, 3H), 3.76 (s, 3H), 3.64 (d, J=15.0 Hz, 1H), 3.54 (dd, J=10.6, 2.9 Hz, 1H), 3.32 (d, J=3.1 Hz, 1H), 3.17-3.08 (m, 1H), 3.03-2.85 (m, 1H), 2.73-2.56 (m, 2H), 2.33 (t, J=7.0 Hz, 1H).

LRMS (ESI, m/z): 501 [M+H]$^+$.

Example A14 (3-methoxy-2-((3-methoxybenzyl)oxo)-5,6,14,14a-tetrahydroindolo[3',2':4,5]pyridine[2,1-a]isoquinoline-9(8H)-yl)methanol (A14)

The title compound A14 was synthesized with 3-methoxybenzyl bromide, 3-methoxy-4-hydroxybenzaldehyde and 3-indoleacetic acid according to Scheme 1.

$^1$H NMR (400 MHz, DMSO) δ 7.40-7.28 (m, 2H), 7.10-7.03 (m, 4H), 6.98-6.87 (m, 2H), 6.79-6.68 (m, 2H), 6.22 (t, J=7.0 Hz, 1H), 5.37 (d, J=6.3 Hz, 2H), 5.09 (q, J=11.9 Hz, 2H), 4.16 (d, J=15.3 Hz, 1H), 3.79 (s, 3H), 3.76 (s, 3H), 3.64 (d, J=15.0 Hz, 1H), 3.54 (dd, J=10.6, 2.9 Hz, 1H), 3.32 (d, J=3.1 Hz, 1H), 3.17-3.08 (m, 1H), 3.03-2.85 (m, 1H), 2.73-2.56 (m, 2H), 2.33 (t, J=7.0 Hz, 1H).

LRMS (ESI, m/z): 471 [M+H]$^+$.

Example A15 (3,12-Dimethoxy-2-((4-methylbenzyl)oxy)-5,6,14,14a-tetrahydroindolo[3',2':4,5]pyridine[2,1-a]isoquinoline-9(8H)-yl)methanol (A15)

The title compound A15 was synthesized with 4-methylbenzyl bromide, 3-methoxy-4-hydroxybenzaldehyde and 5-methoxy-3-indoleacetic acid according to Scheme 1.

$^1$H NMR (400 MHz, DMSO) δ 7.39-7.35 (m, 3H), 7.22 (d, J=8.0 Hz, 2H), 7.06 (s, 1H), 6.96 (d, J=2.3 Hz, 1H), 6.74 (dd, J=9.7, 3.3 Hz, 2H), 6.22 (t, J=7.1 Hz, 1H), 5.38 (d, J=6.5 Hz, 2H), 5.05 (q, J=11.6 Hz, 2H), 4.17 (d, J=14.9 Hz, 1H), 3.79 (s, 3H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.03-2.86 (m, 1H), 2.74-2.57 (m, 2H), 2.37 (t, J=7.1 Hz, 2H), 2.32 (s, 3H).

LRMS (ESI, m/z): 485 [M+H]$^+$.

Example A16 (3-methoxy-2-((4-methylbenzyl)oxy)-5,6,14,14a-tetrahydroindolo[3',2':4,5]pyridine[2,1-a]isoquinoline-9(8H)-yl)methanol (A16)

The title compound A16 was synthesized with 4-methylbenzyl bromide, 3-methoxy-4-hydroxybenzaldehyde and 3-indoleacetic acid according to Scheme 1.

$^1$H NMR (400 MHz, DMSO) δ 7.39-7.35 (m, 3H), 7.28-7.21 (m, 3H), 7.06 (s, 1H), 6.96 (d, J=2.3 Hz, 1H), 6.74 (dd, J=9.7, 3.3 Hz, 2H), 6.22 (t, J=7.1 Hz, 1H), 5.38 (d, J=6.5 Hz, 2H), 5.05 (q, J=11.6 Hz, 2H), 4.17 (d, J=14.9 Hz, 1H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.03-2.86 (m, 1H), 2.74-2.57 (m, 2H), 2.37 (t, J=7.1 Hz, 2H), 2.32 (s, 3H).

LRMS (ESI, m/z): 455 [M+H]$^+$.

Example A17 (2-((4-chlorobenzyl)oxy)-3,12-dimethoxy-5,6,14,14a-tetrahydroindolo[3',2':4,5]pyridine[2,1-a]isoquinoline-9(8H)-ylmethanol (A17)

The title compound A17 was synthesized with 4-chlorobenzyl bromide, 3-methoxy-4-hydroxybenzaldehyde and 5-methoxy-3-indoleacetic acid according to Scheme 1.

$^1$H NMR (400 MHz, DMSO) δ 7.47-7.39 (m, 2H), 7.36 (d, J=8.5 Hz, 1H), 7.32-7.24 (m, 2H), 7.03 (s, 1H), 6.94 (m, 1H), 6.77-6.68 (m, 2H), 6.21 (t, J=6.9 Hz, 1H), 5.37 (d, J=6.3 Hz, 2H), 5.08 (q, J=11.3 Hz, 2H), 4.16 (d, J=15.7 Hz, 1H), 3.78 (s, 3H), 3.76 (s, 3H), 3.64 (d, J=14.3 Hz, 1H), 3.55 (d, J=8.0 Hz, 1H), 3.31 (m, 1H), 3.12 (d, J=7.7 Hz, 1H), 3.03-2.88 (m, 1H), 2.66 (dd, J=12.1 Hz, 2H), 2.33 (t, J=11.5 Hz, 1H).

LRMS (ESI, m/z): 506 [M+H]$^+$.

Example A18 (2-((4-chlorobenzyl)oxy)-3-methoxy-5,6,14,14a-tetrahydroindolo[3',2':4,5]pyridine[2,1-a]isoquinoline-9(8H)-ylmethanol (A18)

The title compound A18 was synthesized with 4-chlorobenzyl bromide, 3-methoxy-4-hydroxybenzaldehyde and 3-indoleacetic acid according to Scheme 1.

$^1$H NMR (400 MHz, DMSO) δ 7.47-7.39 (m, 2H), 7.36-7.29 (m, 2H), 7.28-7.24 (m, 3H), 7.03 (s, 1H), 6.94 (m, 1H), 6.77-6.68 (m, 2H), 6.21 (t, J=6.9 Hz, 1H), 5.37 (d, J=6.3 Hz, 2H), 5.08 (q, J=11.3 Hz, 2H), 4.16 (d, J=15.7 Hz, 1H), 3.76 (s, 3H), 3.64 (d, J=14.3 Hz, 1H), 3.55 (d, J=8.0 Hz, 1H), 3.31 (m, 1H), 3.12 (d, J=7.7 Hz, 1H), 3.03-2.88 (m, 1H), 2.66 (dd, J=12.1 Hz, 2H), 2.33 (t, J=11.5 Hz, 1H).

LRMS (ESI, m/z): 476 [M+H]$^+$.

Example A19 4-(((9-(Hydroxymethyl)-3,12-dimethoxy-5,6,8,9,14,14a-hexahydroindole[3',2':4,5]pyridine[2,1-a]isoquinolin-2-yl)oxo)methyl)benzonitrile (A19)

The title compound A19 was synthesized with 4-cyanobenzyl bromide, 3-methoxy-4-hydroxybenzaldehyde and 5-methoxy-3-indoleacetic acid according to Scheme 1.

$^1$H NMR (400 MHz, DMSO) δ 7.67-7.49 (m, 2H), 7.36 (d, J=8.5 Hz, 1H), 7.32-7.24 (m, 2H), 7.03 (s, 1H), 6.94 (m, 1H), 6.77-6.68 (m, 2H), 6.21 (t, J=6.9 Hz, 1H), 5.37 (d, J=6.3 Hz, 2H), 5.08 (q, J=11.3 Hz, 2H), 4.16 (d, J=15.7 Hz, 1H), 3.78 (s, 3H), 3.76 (s, 3H), 3.64 (d, J=14.3 Hz, 1H), 3.55 (d, J=8.0 Hz, 1H), 3.31 (m, 1H), 3.12 (d, J=7.7 Hz, 1H), 3.03-2.88 (m, 1H), 2.66 (dd, J=12.1 Hz, 2H), 2.33 (t, J=11.5 Hz, 1H).

LRMS (ESI, m/z): 496 [M+H]$^+$.

Example A20 4-(((9-(Hydroxymethyl)-3-methoxy-5,6,8,9,14,14a-hexahydroindole[3',2':4,5]pyridine[2,1-a]isoquinolin-2-yl)oxo)methyl)benzonitrile (A20)

The title compound A20 was synthesized with 4-cyanobenzyl bromide, 3-methoxy-4-hydroxybenzaldehyde and 3-indoleacetic acid according to Scheme 1.

$^1$H NMR (400 MHz, DMSO) δ 7.67-7.49 (m, 2H), 7.36-7.29 (m, 2H), 7.27-7.24 (m, 3H), 7.03 (s, 1H), 6.94 (m, 1H), 6.77-6.68 (m, 2H), 6.21 (t, J=6.9 Hz, 1H), 5.37 (d, J=6.3 Hz, 2H), 5.08 (q, J=11.3 Hz, 2H), 4.16 (d, J=15.7 Hz,

1H), 3.76 (s, 3H), 3.64 (d, J=14.3 Hz, 1H), 3.55 (d, J=8.0 Hz, 1H), 3.31 (m, 1H), 3.12 (d, J=7.7 Hz, 1H), 3.03-2.88 (m, 1H), 2.66 (dd, J=12.1 Hz, 2H), 2.33 (t, J=11.5 Hz, 1H).
LRMS (ESI, m/z): 466 [M+H]$^+$.

Example A21 (2-((4-bromobenzyl)oxy)-3,12-dimethoxy-5,6,14,14a-tetrahydroindolo[3',2':4,5]pyridine[2,1-a]isoquinoline-9(8H)-ylmethanol (A21)

The title compound A21 was synthesized with 4-bromobenzyl bromide, 3-methoxy-4-hydroxybenzaldehyde and 5-methoxy-3-indoleacetic acid according to Scheme 1.
$^1$H NMR (400 MHz, DMSO) δ 7.41-7.38 (m, 2H), 7.36 (d, J=8.5 Hz, 1H), 7.32-7.24 (m, 2H), 7.03 (s, 1H), 6.94 (m, 1H), 6.77-6.68 (m, 2H), 6.21 (t, J=6.9 Hz, 1H), 5.37 (d, J=6.3 Hz, 2H), 5.08 (q, J=11.3 Hz, 2H), 4.16 (d, J=15.7 Hz, 1H), 3.78 (s, 3H), 3.76 (s, 3H), 3.64 (d, J=14.3 Hz, 1H), 3.55 (d, J=8.0 Hz, 1H), 3.31 (m, 1H), 3.12 (d, J=7.7 Hz, 1H), 3.03-2.88 (m, 1H), 2.66 (dd, J=12.1 Hz, 2H), 2.33 (t, J=11.5 Hz, 1H).
LRMS (ESI, m/z): 549[M+H]$^+$, 551[M+H]$^+$.

Example A22 (2-((4-bromobenzyl)oxy)-3-methoxy-5,6,14,14a-tetrahydroindolo[3',2':4,5]pyridine[2,1-a]isoquinoline-9(8H)-ylmethanol (A22)

The title compound A22 was synthesized with 4-bromobenzyl bromide, 3-methoxy-4-hydroxybenzaldehyde and 3-indoleacetic acid according to Scheme 1.
$^1$H NMR (400 MHz, DMSO) δ 7.41-7.38 (m, 2H), 7.36-7.29 (m, 2H), 7.28-7.24 (m, 3H), 7.03 (s, 1H), 6.94 (m, 1H), 6.77-6.68 (m, 2H), 6.21 (t, J=6.9 Hz, 1H), 5.37 (d, J=6.3 Hz, 2H), 5.08 (q, J=11.3 Hz, 2H), 4.16 (d, J=15.7 Hz, 1H), 3.76 (s, 3H), 3.64 (d, J=14.3 Hz, 1H), 3.55 (d, J=8.0 Hz, 1H), 3.31 (m, 1H), 3.12 (d, J=7.7 Hz, 1H), 3.03-2.88 (m, 1H), 2.66 (dd, J=12.1 Hz, 2H), 2.33 (t, J=11.5 Hz, 1H).
LRMS (ESI, m/z): 519[M+H]+, 521[M+H]$^+$.

Example A23 (2-((3-Fluoro-4-(trifluoromethyl)benzyl)oxy)-3,12-dimethoxy-5,6,14,14a-tetrahydroindolo[3',2':4,5]pyridine[2,1-a]isoquinoline-9(8H)-ylmethanol (A23)

The title compound A23 was synthesized with 3-fluoro-4-(trifluoromethyl)benzyl bromide, 3-methoxy-4-hydroxybenzaldehyde and 5-methoxy-3-indoleacetic acid according to Scheme 1.
$^1$H NMR (400 MHz, DMSO) δ 7.51-7.35 (m, 4H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 557 [M+H]$^+$.

Example A24 (2-((3-Fluoro-4-(trifluoromethyl)benzyl)oxy)-3-methoxy-5,6,14,14a-tetrahydroindolo[3',2':4,5]pyridine[2,1-a]isoquinoline-9(8H)-ylmethanol (A24)

The title compound A24 was synthesized with 3-fluoro-4-(trifluoromethyl)benzyl bromide, 3-methoxy-4-hydroxybenzaldehyde and 3-indoleacetic acid according to Scheme 1.
$^1$H NMR (400 MHz, DMSO) δ 7.51-7.35 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 527 [M+H]$^+$.

Example A25 (2-((2-Fluoro-4-(trifluoromethyl)benzyl)oxy)-3,12-dimethoxy-5,6,14,14a-tetrahydroindolo[3',2':4,5]pyridine[2,1-a]isoquinoline-9(8H)-ylmethanol (A25)

The title compound A25 was synthesized with 2-fluoro-4-(trifluoromethyl)benzyl bromide, 3-methoxy-4-hydroxybenzaldehyde and 5-methoxy-3-indoleacetic acid according to Scheme 1.
$^1$H NMR (400 MHz, DMSO) δ 7.51-7.35 (m, 4H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 557 [M+H]$^+$.

Example A26 (2-((2-Fluoro-4-(trifluoromethyl)benzyl)oxy)-3-methoxy-5,6,14,14a-tetrahydroindolo[3',2':4,5]pyridine[2,1-a]isoquinoline-9(8H)-ylmethanol (A26)

The title compound A26 was synthesized with 2-fluoro-4-(trifluoromethyl)benzyl bromide, 3-methoxy-4-hydroxybenzaldehyde and 3-indoleacetic acid according to Scheme 1.
$^1$H NMR (400 MHz, DMSO) δ 7.51-7.35 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 527 [M+H]$^+$.

Example A27 (3,12-Dimethoxy-2-((4-ethylbenzyl)oxy)-5,6,14,14a-tetrahydroindolo[3',2':4,5]pyridine[2,1-a]isoquinoline-9(8H)-yl)methanol (A27)

The title compound A27 was synthesized with 4-ethylbenzyl bromide, 3-methoxy-4-hydroxybenzaldehyde and 5-methoxy-3-indoleacetic acid according to Scheme 1.
$^1$H NMR (400 MHz, DMSO) δ 7.51-7.35 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H), 2.34 (q, J=8.0 Hz, 2H), 1.01 (t, J=8.0 Hz, 3H).
LRMS (ESI, m/z): 499 [M+H]$^+$.

Example A28 (3-methoxy-2-((4-ethylbenzyl)oxy)-5,6,14,14a-tetrahydroindolo[3',2':4,5]pyridine[2,1-a]isoquinoline-9(8H)-yl)methanol (A28)

The title compound A28 was synthesized with 4-ethylbenzyl bromide, 3-methoxy-4-hydroxybenzaldehyde and 3-indoleacetic acid according to Scheme 1.

¹H NMR (400 MHz, DMSO) δ 7.51-7.35 (m, 5H), 7.21-7.05 (m, 2H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H), 2.34 (q, J=8.0 Hz, 2H), 1.01 (t, J=8.0 Hz, 3H).

LRMS (ESI, m/z): 469 [M+H]⁺.

Example A29 (3,12-Dimethoxy-2-(naphthalen-2-ylmethoxy)-5,6,14,14a-tetrahydroindolo[3',2':4,5]pyridine[2,1-a]isoquinoline-9(8H)-yl)methanol (A29)

The title compound A29 was synthesized with 2-bromomethylnaphthalene, 3-methoxy-4-hydroxybenzaldehyde and 5-methoxy-3-indoleacetic acid according to Scheme 1.

¹H NMR (400 MHz, DMSO) δ 7.67-7.32 (m, 7H), 7.25-7.12 (m, 2H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 521 [M+H]⁺.

Example A30 (3-methoxy-2-(naphthalen-2-ylmethoxy)-5,6,14,14a-tetrahydroindolo[3',2':4,5]pyridine[2,1-a]isoquinoline-9(8H)-yl)methanol (A30)

The title compound A30 was synthesized with 2-bromomethylnaphthalene, 3-methoxy-4-hydroxybenzaldehyde and 3-indoleacetic acid according to Scheme 1.

¹H NMR (400 MHz, DMSO) δ 7.67-7.32 (m, 7H), 7.25-7.12 (m, 3H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 491 [M+H]⁺.

Example A31 4-(((9-(Hydroxymethyl)-3,12-dimethoxy-5,6,8,9,14,14a-hexahydroindole[3',2':4,5]pyridine[2,1-a]isoquinolin-2-yl)oxo)methyl)benzoate (A31)

The title compound A31 was synthesized with methyl 4-bromomethylbenzoate, 3-methoxy-4-hydroxybenzaldehyde and 5-methoxy-3-indoleacetic acid according to Scheme 1.

¹H NMR (400 MHz, DMSO) δ 7.51-7.35 (m, 6H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 529 [M+H]⁺.

Example A32 4-(((9-(Hydroxymethyl)-3-methoxy-5,6,8,9,14,14a-hexahydroindole[3',2':4,5]pyridine[2,1-a]isoquinolin-2-yl)oxo)methyl)benzoate (A32)

The title compound A32 was synthesized with methyl 4-bromomethylbenzoate, 3-methoxy-4-hydroxybenzaldehyde and 3-indoleacetic acid according to Scheme 1.

¹H NMR (400 MHz, DMSO) δ 8.01-7.95 (m, 2H), 7.51-7.35 (m, 6H), 7.05-6.94 (m, 2H), 6.79-6.69 (m, 2H), 6.26 (s, 1H), 5.37 (s, 2H), 5.11 (d, J=4.8 Hz, 2H), 4.16 (d, J=15.1 Hz, 1H), 3.77 (d, J=11.4 Hz, 6H), 3.64 (d, J=15.6 Hz, 1H), 3.54 (d, J=7.2 Hz, 1H), 3.31 (s, 1H), 3.14 (s, 1H), 2.94 (d, J=11.4 Hz, 1H), 2.64 (dd, J=21.1, 13.3 Hz, 2H), 2.40-2.27 (m, 1H).

LRMS (ESI, m/z): 499 [M+H]⁺.

Example A33 (2-((4-(1H-pyrazol-1-yl)benzyl)oxy)-3,12-dimethoxy-5,6,14,14a-tetrahydroindolo[3',2':4,5]pyridine[2,1-a]isoquinoline-9(8H)-yl)methanol (A33)

The title compound A33 was synthesized with 1-4-(bromomethyl)benzene-1H-pyrazole, 3-methoxy-4-hydroxybenzaldehyde and 5-methoxy-3-indoleacetic acid according to Scheme 1.

¹H NMR (400 MHz, DMSO) δ 7.87 (d, J=8 Hz, 1H), 7.62-7.45 (m, 5H), 7.05-6.84 (m, 3H), 6.79-6.69 (m, 2H), 6.47 (q, J=8 Hz, 1H), 6.26 (s, 1H), 5.37 (s, 2H), 5.11 (d, J=4.8 Hz, 2H), 4.16 (d, J=15.1 Hz, 1H), 3.77 (d, J=11.4 Hz, 6H), 3.64 (d, J=15.6 Hz, 1H), 3.54 (d, J=7.2 Hz, 1H), 3.31 (s, 1H), 3.14 (s, 1H), 2.94 (d, J=11.4 Hz, 1H), 2.64 (dd, J=21.1, 13.3 Hz, 2H), 2.40-2.27 (m, 1H).

LRMS (ESI, m/z): 537 [M+H]⁺.

Example A34 (2-((4-(1H-pyrazol-1-yl)benzyl)oxy)-3-methoxy-5,6,14,14a-tetrahydroindolo[3',2':4,5]pyridine[2,1-a]isoquinoline-9(8H)-yl)methanol (A34)

The title compound A34 was synthesized with 1-4-(bromomethyl)benzene-1H-pyrazole, 3-methoxy-4-hydroxybenzaldehyde and 3-indoleacetic acid according to Scheme 1.

¹H NMR (400 MHz, DMSO) δ 7.87 (d, J=8 Hz, 1H), 7.62-7.45 (m, 5H), 7.05-6.84 (m, 4H), 6.79-6.69 (m, 2H), 6.47 (q, J=8 Hz, 1H), 6.26 (s, 1H), 5.37 (s, 2H), 5.11 (d, J=4.8 Hz, 2H), 4.16 (d, J=15.1 Hz, 1H), 3.77 (d, J=11.4 Hz, 6H), 3.64 (d, J=15.6 Hz, 1H), 3.54 (d, J=7.2 Hz, 1H), 3.31 (s, 1H), 3.14 (s, 1H), 2.94 (d, J=11.4 Hz, 1H), 2.64 (dd, J=21.1, 13.3 Hz, 2H), 2.40-2.27 (m, 1H).

LRMS (ESI, m/z): 507 [M+H]⁺.

Example A35 (2-Butoxy-3,12-dimethoxy-5,6,14,14a-tetrahydroindolo[3',2':4,5]pyridine[2,1-a]isoquinoline-9(8H)-yl)methanol (A35)

The title compound A35 was synthesized with bromobutane, 3-methoxy-4-hydroxybenzaldehyde and 5-methoxy-3-indoleacetic acid according to Scheme 1.

¹H NMR (400 MHz, DMSO) δ 7.36 (d, J=8.8 Hz, 1H), 6.98 (d, J=2.1 Hz, 1H), 6.96 (s, 1H), 6.73 (dd, J=8.7, 2.3 Hz, 1H), 6.69 (s, 1H), 6.23 (s, 1H), 5.37 (s, 2H), 4.16 (d, J=14.8 Hz, 1H), 3.92 (t, J=5.9 Hz, 2H), 3.79 (s, 3H), 3.77 (s, 3H), 3.65 (d, J=15.6 Hz, 1H), 3.57 (d, J=8.0 Hz, 1H), 3.44-3.40 (d, J=15.0 Hz, 1H), 3.12 (d, J=9.6 Hz, 1H), 3.03-2.86 (m, 1H), 2.63 (m, 2H), 2.47-2.37 (t, J=12.0 Hz, 1H), 1.77-1.61 (m, 2H), 1.51-1.36 (m, 2H), 0.94 (t, J=7.4 Hz, 3H).

LRMS (ESI, m/z): 437 [M+H]⁺.

Example A36 (2-Butoxy-3,12-dimethoxy-5,6,14,14a-tetrahydroindolo[3',2':4,5]pyridine[2,1-a]isoquinoline-9(8H)-yl)methanol (A36)

The title compound A36 was synthesized with bromobutane, 3-methoxy-4-hydroxybenzaldehyde and 3-indoleacetic acid according to Scheme 1.

¹H NMR (400 MHz, DMSO) δ 7.36 (d, J=8.8 Hz, 1H), 6.98 (d, J=2.1 Hz, 1H), 6.96 (s, 1H), 6.73 (dd, J=8.7, 2.3 Hz, 1H), 6.69 (s, 1H), 6.23 (s, 1H), 5.37 (s, 2H), 4.16 (d, J=14.8 Hz, 1H), 3.92 (t, J=5.9 Hz, 2H), 3.77 (s, 3H), 3.65 (d, J=15.6 Hz, 1H), 3.57 (d, J=8.0 Hz, 1H), 3.44-3.40 (d, J=15.0 Hz, 1H), 3.12 (d, J=9.6 Hz, 1H), 3.03-2.86 (m, 1H), 2.63 (m, 2H), 2.47-2.37 (t, J=12.0 Hz, 1H), 1.77-1.61 (m, 2H), 1.51-1.36 (m, 2H), 0.94 (t, J=7.4 Hz, 3H).
LRMS (ESI, m/z): 407 [M+H]⁺.

Example A37

(2,3,12-Trimethoxy-5,6,14,14a-tetrahydroindolo[3',2':4,5]pyridine[2,1-a]isoquinoline-9(8H)-yl)methanol (A37)

The title compound A37 was synthesized with 3,4-dimethoxybenzaldehyde and 5-methoxy-3-indoleacetic acid according to Scheme 1.
¹H NMR (300 MHz, DMSO) δ 7.27-7.16 (m, 1H), 6.91 (d, J=2.1 Hz, 1H), 6.80 (d, J=2.2 Hz, 1H), 6.77 (s, 1H), 6.63 (s, 1H), 5.61 (s, 1H), 5.26 (dd, J=31.9, 10.9 Hz, 2H), 3.91 (s, 3H), 3.87 (s, 3H), 3.85 (s, 3H), 3.64 (d, J=14.9 Hz, 1H), 3.54 (d, J=7.4 Hz, 1H), 3.48-3.35 (m, 1H), 3.16 (m, 2H), 2.86 (d, J=11.0 Hz, 1H), 2.72-2.49 (m, 3H).
LRMS (ESI, m/z): 395 [M+H]⁺.

Example A38

(2,3-dimethoxy-5,6,14,14a-tetrahydroindolo[3',2':4,5]pyridine[2,1-a]isoquinoline-9(8H)-yl)methanol (A38)

The title compound A38 was synthesized with 3,4-dimethoxybenzaldehyde and 3-indoleacetic acid according to Scheme 1.
¹H NMR (300 MHz, DMSO) δ 7.27-7.16 (m, 2H), 6.91 (d, J=2.1 Hz, 1H), 6.80 (d, J=2.2 Hz, 1H), 6.77 (s, 1H), 6.63 (s, 1H), 5.61 (s, 1H), 5.26 (dd, J=31.9, 10.9 Hz, 2H), 3.91 (s, 3H), 3.85 (s, 3H), 3.64 (d, J=14.9 Hz, 1H), 3.54 (d, J=7.4 Hz, 1H), 3.48-3.35 (m, 1H), 3.16 (m, 2H), 2.86 (d, J=11.0 Hz, 1H), 2.72-2.49 (m, 3H).
LRMS (ESI, m/z): 365 [M+H]⁺.

Example A39 (3,12-Dimethoxy-2-(2,2,2-trifluoroethoxy)-5,6,14,14a-tetrahydroindolo[3',2':4,5]pyridine[2,1-a]isoquinoline-9(8H)-yl)methanol (A39)

The title compound A39 was synthesized with 2,2,2-trifluoroethyl-p-toluenesulfonate and 5-methoxy-3-indoleacetic acid according to Scheme 1.
¹H NMR (400 MHz, DMSO) δ 7.37 (d, J=8.8 Hz, 1H), 7.13 (s, 1H), 6.96 (d, J=2.4 Hz, 1H), 6.79 (s, 1H), 6.74 (dd, J=8.8, 2.5 Hz, 1H), 6.24 (s, 1H), 5.37 (s, 2H), 4.76-4.65 (m, 2H), 4.17 (d, J=15.0 Hz, 1H), 3.78 (s, 3H), 3.77 (s, 3H), 3.65 (d, J=14.8 Hz, 1H), 3.60-3.54 (m, 1H), 3.48-3.42 (m, 1H), 3.14 (dd, J=8.5, 2.6 Hz, 1H), 2.98 (dd, J=18.7, 8.2 Hz, 1H), 2.74-2.60 (m, 2H), 2.46-2.35 (m, 1H).
LRMS (ESI, m/z): 463 [M+H]⁺.

Example A40 (3-methoxy-2-(2,2,2-trifluoroethoxy)-5,6,14,14a-tetrahydroindolo[3',2':4,5]pyridine[2,1-a]isoquinoline-9(8H)-yl)methanol (A40)

The title compound A40 was synthesized with 2,2,2-trifluoroethyl-p-toluenesulfonate and 3-indoleacetic acid according to Scheme 1.
¹H NMR (400 MHz, DMSO) δ 7.37 (d, J=8.8 Hz, 1H), 7.30-7.23 (m, 2H), 6.96 (d, J=2.4 Hz, 1H), 6.79 (s, 1H), 6.74 (dd, J=8.8, 2.5 Hz, 1H), 6.24 (s, 1H), 5.37 (s, 2H), 4.76-4.65 (m, 2H), 4.17 (d, J=15.0 Hz, 1H), 3.77 (s, 3H), 3.65 (d, J=14.8 Hz, 1H), 3.60-3.54 (m, 1H), 3.48-3.42 (m, 1H), 3.14 (dd, J=8.5, 2.6 Hz, 1H), 2.98 (dd, J=18.7, 8.2 Hz, 1H), 2.74-2.60 (m, 2H), 2.46-2.35 (m, 1H).
LRMS (ESI, m/z): 433 [M+H]⁺.

Example A41 (3,12-Dimethoxy-2-((4-(methylsulfonyl)benzyl)oxy)-5,6,14,14a-tetrahydroindolo[3',2':4,5]pyridine[2,1-a]isoquinoline-9(8H)-yl)methanol (A41)

The title compound A41 was synthesized with 4-methanesulfonylbenzyl bromide, 3-methoxy-4-hydroxybenzaldehyde and 5-methoxy-3-indoleacetic acid according to Scheme 1.
¹H NMR (400 MHz, DMSO) δ 7.39-7.35 (m, 3H), 7.22 (d, J=8.0 Hz, 2H), 7.06 (s, 1H), 6.96 (d, J=2.3 Hz, 1H), 6.74 (dd, J=9.7, 3.3 Hz, 2H), 6.22 (t, J=7.1 Hz, 1H), 5.38 (d, J=6.5 Hz, 1H), 5.05 (q, J=11.6 Hz, 1H), 4.17 (d, J=14.9 Hz, 1H), 3.79 (s, 3H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.05 (s, 3H), 3.03-2.86 (m, 1H), 2.74-2.57 (m, 2H), 2.37 (t, J=7.1 Hz, 2H).
LRMS (ESI, m/z): 549 [M+H]⁺.

Example A42 (3-methoxy-2-((4-methylbenzyl)oxy)-5,6,14,14a-tetrahydroindolo[3',2':4,5]pyridine[2,1-a]isoquinoline-9(8H)-yl)methanol (A42)

The title compound A42 was synthesized with 4-methanesulfonylbenzyl bromide, 3-methoxy-4-hydroxybenzaldehyde and 3-indoleacetic acid according to Scheme 1.
¹H NMR (400 MHz, DMSO) δ 7.39-7.35 (m, 4H), 7.22 (d, J=8.0 Hz, 2H), 7.06 (s, 1H), 6.96 (d, J=2.3 Hz, 1H), 6.74 (dd, J=9.7, 3.3 Hz, 2H), 6.22 (t, J=7.1 Hz, 1H), 5.38 (d, J=6.5 Hz, 1H), 5.05 (q, J=11.6 Hz, 1H), 4.17 (d, J=14.9 Hz, 1H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.05 (s, 3H), 3.03-2.86 (m, 1H), 2.74-2.57 (m, 2H), 2.37 (t, J=7.1 Hz, 2H).
LRMS (ESI, m/z): 519 [M+H]⁺.

Example A43 (2-(Benzyloxy)-11-fluoro-3-methoxy-5,6,14,14a-tetrahydroindolo[3',2':4,5]pyridine[2,1-a]isoquinoline-9(8H)-yl)methanol (A43)

The title compound A42 was synthesized with 6-fluoro-3-indolacetic acid, 3-methoxy-4-hydroxybenzaldehyde and benzyl bromide according to Scheme 1.
¹H NMR (400 MHz, DMSO) δ 7.51-7.35 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 459 [M+H]⁺.

Example A44 (2-(Benzyloxy)-12-fluoro-3-methoxy-5,6,14,14a-tetrahydroindolo[3',2':4,5]pyridine[2,1-a]isoquinoline-9(8H)-yl)methanol (A44)

The title compound A44 was synthesized with 5-fluoro-3-indolacetic acid, 3-methoxy-4-hydroxybenzaldehyde and benzyl bromide according to Scheme 1.

¹H NMR (400 MHz, DMSO) δ 7.51-7.35 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 459 [M+H]⁺.

Example A45 (2-(Benzyloxy)-13-fluoro-3-methoxy-5,6,14,14a-tetrahydroindolo[3',2':4,5]pyridine[2,1-a]isoquinoline-9(8H)-yl)methanol (A45)

The title compound A45 was synthesized with 4-fluoro-3-indolacetic acid, 3-methoxy-4-hydroxybenzaldehyde and benzyl bromide according to Scheme 1.
¹H NMR (400 MHz, DMSO) δ 7.51-7.35 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 459 [M+H]⁺.

Example A46 (2-(Benzyloxy)-11-chloro-3-methoxy-5,6,14,14a-tetrahydroindolo[3',2':4,5]pyridine[2,1-a]isoquinoline-9(8H)-yl)methanol (A46)

The title compound A46 was synthesized with 6-chloro-3-indolacetic acid, 3-methoxy-4-hydroxybenzaldehyde and benzyl bromide according to Scheme 1.
¹H NMR (400 MHz, DMSO) δ 7.51-7.35 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 475 [M+H]⁺.

Example A47 (2-(Benzyloxy)-12-chloro-3-methoxy-5,6,14,14a-tetrahydroindolo[3',2':4,5]pyridine[2,1-a]isoquinoline-9(8H)-yl)methanol (A47)

The title compound A47 was synthesized with 5-chloro-3-indolacetic acid, 3-methoxy-4-hydroxybenzaldehyde and benzyl bromide according to Scheme 1.
¹H NMR (400 MHz, DMSO) δ 7.51-7.35 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 475 [M+H]⁺.

Example A48 (2-(Benzyloxy)-13-chloro-3-methoxy-5,6,14,14a-tetrahydroindolo[3',2':4,5]pyridine[2,1-a]isoquinoline-9(8H)-yl)methanol (A48)

The title compound A48 was synthesized with 4-chloro-3-indolacetic acid, 3-methoxy-4-hydroxybenzaldehyde and benzyl bromide according to Scheme 1.
¹H NMR (400 MHz, DMSO) δ 7.51-7.35 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 475 [M+H]⁺.

Example A49 (2-(Benzyloxy)-11-bromo-3-methoxy-5,6,14,14a-tetrahydroindolo[3',2':4,5]pyridine[2,1-a]isoquinoline-9(8H)-yl)methanol (A49)

The title compound A49 was synthesized with 6-bromo-3-indolacetic acid, 3-methoxy-4-hydroxybenzaldehyde and benzyl bromide according to Scheme 1.
¹H NMR (400 MHz, DMSO) δ 7.51-7.35 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 519 [M+H]⁺, 521 [M+H]⁺.

Example A50 (2-(Benzyloxy)-12-bromo-3-methoxy-5,6,14,14a-tetrahydroindolo[3',2':4,5]pyridine[2,1-a]isoquinoline-9(8H)-yl)methanol (A50)

The title compound A50 was synthesized with 5-bromo-3-indolacetic acid, 3-methoxy-4-hydroxybenzaldehyde and benzyl bromide according to Scheme 1.
¹H NMR (400 MHz, DMSO) δ 7.51-7.35 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 519 [M+H]⁺, 521 [M+H]⁺.

Example A51 (2-(Benzyloxy)-13-bromo-3-methoxy-5,6,14,14a-tetrahydroindolo[3',2':4,5]pyridine[2,1-a]isoquinoline-9(8H)-yl)methanol (A51)

The title compound A51 was synthesized with 4-bromo-3-indolacetic acid, 3-methoxy-4-hydroxybenzaldehyde and benzyl bromide according to Scheme 1.
¹H NMR (400 MHz, DMSO) δ 7.51-7.35 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 519 [M+H]⁺, 521 [M+H]⁺.

Example A52 2-(Benzyloxy)-9-(hydroxymethyl)-3-methoxy-5,6,8,9,14,14a-hexahydroindole[3',2':4,5]pyridine[2,1-a]isoquinolin-12-phenol (A52)

The title compound A52 was synthesized with 5-hydroxy-3-indolacetic acid, 3-methoxy-4-hydroxybenzaldehyde and benzyl bromide according to Scheme 1.
¹H NMR (400 MHz, DMSO) δ 7.51-7.35 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.35 (s, 1H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2

Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 457 [M+H]$^+$.

Example A53 (2-(Benzyloxy)-3-methoxy-11-methyl-5,6,14,14a-tetrahydroindolo[3',2':4,5]pyridine[2,1-a]isoquinoline-9(8H)-yl)methanol (A53)

The title compound A53 was synthesized with 6-methyl-3-indolacetic acid, 3-methoxy-4-hydroxybenzaldehyde and benzyl bromide according to Scheme 1.
$^1$H NMR (400 MHz, DMSO) δ 7.39-7.35 (m, 3H), 7.28-7.21 (m, 3H), 7.06 (s, 1H), 6.96 (d, J=2.3 Hz, 1H), 6.74 (dd, J=9.7, 3.3 Hz, 2H), 6.22 (t, J=7.1 Hz, 1H), 5.38 (d, J=6.5 Hz, 1H), 5.05 (q, J=11.6 Hz, 1H), 4.17 (d, J=14.9 Hz, 1H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.03-2.86 (m, 1H), 2.74-2.57 (m, 2H), 2.37 (t, J=7.1 Hz, 2H), 2.32 (s, 3H).
LRMS (ESI, m/z): 455 [M+H]$^+$.

Example A54 (2-(Benzyloxy)-12-ethyl-3-methoxy-5,6,14,14a-tetrahydroindolo[3',2':4,5]pyridine[2,1-a]isoquinoline-9(8H)-yl)methanol (A54)

The title compound A54 was synthesized with 5-ethyl-3-indolacetic acid, 3-methoxy-4-hydroxybenzaldehyde and benzyl bromide according to Scheme 1.
$^1$H NMR (400 MHz, DMSO) δ 7.39-7.35 (m, 3H), 7.28-7.21 (m, 3H), 7.06 (s, 1H), 6.96 (d, J=2.3 Hz, 1H), 6.74 (dd, J=9.7, 3.3 Hz, 2H), 6.22 (t, J=7.1 Hz, 1H), 5.38 (d, J=6.5 Hz, 1H), 5.05 (q, J=11.6 Hz, 1H), 4.17 (d, J=14.9 Hz, 1H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.03-2.86 (m, 1H), 2.74-2.57 (m, 2H), 2.37 (t, J=7.1 Hz, 2H), 2.34 (q, J=8.0 Hz, 2H), 1.01 (t, J=8.0 Hz, 3H).
LRMS (ESI, m/z): 469 [M+H]$^+$.

Example A55 (3-(Benzyloxy)-2,12-dimethoxy-5,6,14,14a-tetrahydroindolo[3',2':4,5]pyridine[2,1-a]isoquinoline-9(8H)-yl)methanol (A55)

The title compound A55 was synthesized with bromobenzyl, 3-hydroxy-4methoxybenzaldehyde and 5-methoxy-3-indoleacetic acid according to Scheme 1.
$^1$H NMR (400 MHz, DMSO) δ 7.51-7.35 (m, 6H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 471 [M+H]$^+$.

Example A56 (3-(Benzyloxy)-2-methoxy-5,6,14,14a-tetrahydroindolo[3',2':4,5]pyridine[2,1-a]isoquinoline-9(8H)-yl)methanol (A56)

The title compound A56 was synthesized with benzyl bromide, 3-hydroxy-4methoxybenzaldehyde and 3-indoleacetic acid according to Scheme 1.
$^1$H NMR (400 MHz, DMSO) δ 7.56-7.37 (m, 7H), 7.08 (s, 1H), 6.97 (d, J=2.1 Hz, 1H), 6.76-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 441 [M+H]$^+$.

Example A57 (2,12-Dimethoxy-3-((4-(trifluoromethyl)benzyl)oxy)-5,6,14,14a-tetrahydroindolo[3',2':4,5]pyridine[2,1-a]isoquinoline-9(8H)-yl)methanol (A57)

The title compound A57 was synthesized with 4-trifluoromethylbenzyl bromide, 3-hydroxy-4methoxybenzaldehyde and 5-methoxy-3-indoleacetic acid according to Scheme 1.
$^1$H NMR (400 MHz, DMSO) δ 7.71-7.53 (m, 2H), 7.50-7.35 (m, 1H), 7.31-7.15 (m, 2H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 539 [M+H]$^+$.

Example A58 (2-methoxy-3-((4-(trifluoromethyl)benzyl)oxy)-5,6,14,14a-tetrahydroindolo[3',2':4,5]pyridine[2,1-a]isoquinoline-9(8H)-yl)methanol (A58)

The title compound A58 was synthesized with 4-trifluoromethylbenzyl bromide, 3-hydroxy-4methoxybenzaldehyde and 3-indoleacetic acid according to Scheme 1.
$^1$H NMR (400 MHz, DMSO) δ 7.71-7.53 (m, 2H), 7.50-7.35 (m, 1H), 7.31-7.15 (m, 3H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 509 [M+H]$^+$.

Example A59 (3-((4-fluorobenzyl)oxy)-2,12-dimethoxy-5,6,14,14a-tetrahydroindolo[3',2':4,5]pyridine[2,1-a]isoquinoline-9(8H)-yl)methanol (A59)

The title compound A59 was synthesized with 4-fluorobenzyl bromide, 3-hydroxy-4methoxybenzaldehyde and 5-methoxy-3-indoleacetic acid according to Scheme 1.
$^1$H NMR (400 MHz, DMSO) δ 7.57-7.47 (m, 2H), 7.36 (d, J=8.5 Hz, 1H), 7.32-7.24 (m, 2H), 7.03 (s, 1H), 6.94 (m, 1H), 6.77-6.68 (m, 2H), 6.21 (t, J=6.9 Hz, 1H), 5.37 (d, J=6.3 Hz, 2H), 5.08 (q, J=11.3 Hz, 2H), 4.16 (d, J=15.7 Hz, 1H), 3.78 (s, 3H), 3.76 (s, 3H), 3.64 (d, J=14.3 Hz, 1H), 3.55 (d, J=8.0 Hz, 1H), 3.31 (m, 1H), 3.12 (d, J=7.7 Hz, 1H), 3.03-2.88 (m, 1H), 2.66 (dd, J=12.1 Hz, 2H), 2.33 (t, J=11.5 Hz, 1H).
LRMS (ESI, m/z): 489 [M+H]$^+$.

Example A60 (3-((4-fluorobenzyl)oxy)-2-methoxy-5,6,14,14a-tetrahydroindolo[3',2':4,5]pyridine[2,1-a]isoquinoline-9(8H)-ylmethanol (A60)

The title compound A60 was synthesized with 4-fluorobenzyl bromide, 3-hydroxy-4methoxybenzaldehyde and 3-indoleacetic acid according to Scheme 1.

¹H NMR (400 MHz, DMSO) δ 7.57-7.47 (m, 2H), 7.36 (d, J=8.5 Hz, 1H), 7.32-7.24 (m, 3H), 7.03 (s, 1H), 6.94 (m, 1H), 6.77-6.68 (m, 2H), 6.21 (t, J=6.9 Hz, 1H), 5.37 (d, J=6.3 Hz, 2H), 5.08 (q, J=11.3 Hz, 2H), 4.16 (d, J=15.7 Hz, 1H), 3.78 (s, 3H), 3.76 (s, 3H), 3.64 (d, J=14.3 Hz, 1H), 3.55 (d, J=8.0 Hz, 1H), 3.31 (m, 1H), 3.12 (d, J=7.7 Hz, 1H), 3.03-2.88 (m, 1H), 2.66 (dd, J=12.1 Hz, 2H), 2.33 (t, J=11.5 Hz, 1H).
LRMS (ESI, m/z): 459 [M+H]⁺.

Example A61 (3-((3-fluorobenzyl)oxy)-2,12-dimethoxy-5,6,14,14a-tetrahydroindolo[3',2':4,5]pyridine[2,1-a]isoquinoline-9(8H)-yl)methanol (A61)

The title compound A61 was synthesized with 3-fluorobenzyl bromide, 3-hydroxy-4methoxybenzaldehyde and 5-methoxy-3-indoleacetic acid according to Scheme 1.
¹H NMR (400 MHz, DMSO) δ 7.51-7.35 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 489 [M+H]⁺.

Example A62 (3-((3-fluorobenzyl)oxy)-2-methoxy-5,6,14,14a-tetrahydroindolo[3',2':4,5]pyridine[2,1-a]isoquinoline-9(8H)-yl)methanol (A62)

The title compound A62 was synthesized with 3-fluorobenzyl bromide, 3-hydroxy-4methoxybenzaldehyde and 3-indoleacetic acid according to Scheme 1.
¹H NMR (400 MHz, DMSO) δ 7.50-7.43 (m, 3H), 7.26-7.15 (m, 3H), 7.00 (s, 1H), 6.95 (d, J=2.3 Hz, 1H), 6.80 (s, 1H), 6.65 (dd, J=8.7, 2.4 Hz, 1H), 6.20 (t, 1H), 5.17 (s, 2H), 5.03 (s, 2H), 4.18 (d, J=15.0 Hz, 1H), 3.97 (d, J=14.6 Hz, 1H), 3.77 (s, 3H), 3.61 (dd, J=22.2, 12.4 Hz, 2H), 3.41 (d, J=14.6 Hz, 1H), 3.11 (d, J=11.1 Hz, 1H), 2.92 (d, J=10.6 Hz, 1H), 2.60 (dd, J=20.6, 13.0 Hz, 2H), 2.48-2.39 (m, 1H).
LRMS (ESI, m/z): 459 [M+H]⁺.

Example A63 (3-((2-fluorobenzyl)oxy)-2,12-dimethoxy-5,6,14,14a-tetrahydroindolo[3',2':4,5]pyridine[2,1-a]isoquinoline-9(8H)-yl)methanol (A63)

The title compound A63 was synthesized with 2-fluorobenzyl bromide, 3-hydroxy-4methoxybenzaldehyde and 5-methoxy-3-indoleacetic acid according to Scheme 1.
¹H NMR (400 MHz, DMSO) δ 7.51-7.35 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 489 [M+H]⁺.

Example A64 (3-((2-fluorobenzyl)oxy)-2-methoxy-5,6,14,14a-tetrahydroindolo[3',2':4,5]pyridine[2,1-a]isoquinoline-9(8H)-yl)methanol (A64)

The title compound A64 was synthesized with 2-fluorobenzyl bromide, 3-hydroxy-4methoxybenzaldehyde and 3-indoleacetic acid according to Scheme 1.
¹H NMR (400 MHz, DMSO) δ 7.51-7.35 (m, 5H), 7.05 (s, 1H), 6.94 (d, J=2.1 Hz, 1H), 6.79-6.69 (m, 3H), 6.22 (t, J=7.0 Hz, 1H), 5.38 (d, J=7.4 Hz, 2H), 5.08 (s, 2H), 4.18 (d, J=15.0 Hz, 1H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 459 [M+H]⁺.

Example A65 (2,12-Dimethoxy-3-((4-methoxybenzyl)oxo)-5,6,14,14a-tetrahydroindolo[3',2':4,5]pyridine[2,1-a]isoquinoline-9(8H)-yl)methanol (A65)

The title compound A65 was synthesized with 4-methoxybenzyl bromide, 3-hydroxy-4methoxybenzaldehyde and 5-methoxy-3-indoleacetic acid according to Scheme 1.
¹H NMR (400 MHz, DMSO) δ 7.40-7.28 (m, 2H), 7.10-7.03 (m, 3H), 6.98-6.87 (m, 2H), 6.79-6.68 (m, 2H), 6.22 (t, J=7.0 Hz, 1H), 5.37 (d, J=6.3 Hz, 2H), 5.09 (q, J=11.9 Hz, 2H), 4.16 (d, J=15.3 Hz, 1H), 3.79 (s, 3H), 3.78 (s, 3H), 3.76 (s, 3H), 3.64 (d, J=15.0 Hz, 1H), 3.54 (dd, J=10.6, 2.9 Hz, 1H), 3.32 (d, J=3.1 Hz, 1H), 3.17-3.08 (m, 1H), 3.03-2.85 (m, 1H), 2.73-2.56 (m, 2H), 2.33 (t, J=7.0 Hz, 1H).
LRMS (ESI, m/z): 501 [M+H]⁺.

Example A66 (2-methoxy-3-((4-methoxybenzyl)oxo)-5,6,14,14a-tetrahydroindolo[3',2':4,5]pyridine[2,1-a]isoquinoline-9(8H)-yl)methanol (A66)

The title compound A66 was synthesized with 4-methoxybenzyl bromide, 3-hydroxy-4methoxybenzaldehyde and 3-indoleacetic acid according to Scheme 1.
¹H NMR (400 MHz, DMSO) δ 7.40-7.28 (m, 2H), 7.10-7.03 (m, 4H), 6.98-6.87 (m, 2H), 6.79-6.68 (m, 2H), 6.22 (t, J=7.0 Hz, 1H), 5.37 (d, J=6.3 Hz, 2H), 5.09 (q, J=11.9 Hz, 2H), 4.16 (d, J=15.3 Hz, 1H), 3.79 (s, 3H), 3.76 (s, 3H), 3.64 (d, J=15.0 Hz, 1H), 3.54 (dd, J=10.6, 2.9 Hz, 1H), 3.32 (d, J=3.1 Hz, 1H), 3.17-3.08 (m, 1H), 3.03-2.85 (m, 1H), 2.73-2.56 (m, 2H), 2.33 (t, J=7.0 Hz, 1H).
LRMS (ESI, m/z): 471 [M+H]⁺.

Example A67 (2,12-Dimethoxy-3-((3-methoxybenzyl)oxo)-5,6,14,14a-tetrahydroindolo[3',2':4,5]pyridine[2,1-a]isoquinoline-9(8H)-yl)methanol (A67)

The title compound A67 was synthesized with 3-methoxybenzyl bromide, 3-hydroxy-4methoxybenzaldehyde and 5-methoxy-3-indoleacetic acid according to Scheme 1.
¹H NMR (400 MHz, DMSO) δ 7.40-7.28 (m, 2H), 7.10-7.03 (m, 3H), 6.98-6.87 (m, 2H), 6.79-6.68 (m, 2H), 6.22 (t, J=7.0 Hz, 1H), 5.37 (d, J=6.3 Hz, 2H), 5.09 (q, J=11.9 Hz, 2H), 4.16 (d, J=15.3 Hz, 1H), 3.79 (s, 3H), 3.78 (s, 3H), 3.76 (s, 3H), 3.64 (d, J=15.0 Hz, 1H), 3.54 (dd, J=10.6, 2.9 Hz, 1H), 3.32 (d, J=3.1 Hz, 1H), 3.17-3.08 (m, 1H), 3.03-2.85 (m, 1H), 2.73-2.56 (m, 2H), 2.33 (t, J=7.0 Hz, 1H).
LRMS (ESI, m/z): 501 [M+H]⁺.

Example A68 (2-methoxy-3-((3-methoxybenzyl)oxo)-5,6,14,14a-tetrahydroindolo[3',2':4,5]pyridine[2,1-a]isoquinoline-9(8H)-yl)methanol (A68)

The title compound A68 was synthesized with 3-methoxybenzyl bromide, 3-hydroxy-4methoxybenzaldehyde and 3-indoleacetic acid according to Scheme 1.

¹H NMR (400 MHz, DMSO) δ 7.40-7.28 (m, 2H), 7.10-7.03 (m, 4H), 6.98-6.87 (m, 2H), 6.79-6.68 (m, 2H), 6.22 (t, J=7.0 Hz, 1H), 5.37 (d, J=6.3 Hz, 2H), 5.09 (q, J=11.9 Hz, 2H), 4.16 (d, J=15.3 Hz, 1H), 3.79 (s, 3H), 3.76 (s, 3H), 3.64 (d, J=15.0 Hz, 1H), 3.54 (dd, J=10.6, 2.9 Hz, 1H), 3.32 (d, J=3.1 Hz, 1H), 3.17-3.08 (m, 1H), 3.03-2.85 (m, 1H), 2.73-2.56 (m, 2H), 2.33 (t, J=7.0 Hz, 1H).
LRMS (ESI, m/z): 471 [M+H]⁺.

Example A69 (2,12-Dimethoxy-3-((4-methylbenzyl)oxy)-5,6,14,14a-tetrahydroindolo[3',2':4,5]pyridine[2,1-a]isoquinoline-9(8H)-yl)methanol (A69)

The title compound A69 was synthesized with 4-methylbenzyl bromide, 3-hydroxy-4methoxybenzaldehyde and 5-methoxy-3-indoleacetic acid according to Scheme 1.
¹H NMR (400 MHz, DMSO) δ 7.39-7.35 (m, 3H), 7.22 (d, J=8.0 Hz, 2H), 7.06 (s, 1H), 6.96 (d, J=2.3 Hz, 1H), 6.74 (dd, J=9.7, 3.3 Hz, 2H), 6.22 (t, J=7.1 Hz, 1H), 5.38 (d, J=6.5 Hz, 2H), 5.05 (q, J=11.6 Hz, 2H), 4.17 (d, J=14.9 Hz, 1H), 3.79 (s, 3H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.03-2.86 (m, 1H), 2.74-2.57 (m, 2H), 2.37 (t, J=7.1 Hz, 2H), 2.32 (s, 3H).
LRMS (ESI, m/z): 485 [M+H]⁺.

Example A70 (2-methoxy-3-((4-methylbenzyl)oxy)-5,6,14,14a-tetrahydroindolo[3',2':4,5]pyridine[2,1-a]isoquinoline-9(8H)-yl)methanol (A70)

The title compound A70 was synthesized with 4-methylbenzyl bromide, 3-hydroxy-4methoxybenzaldehyde and 3-indoleacetic acid according to Scheme 1.
¹H NMR (400 MHz, DMSO) δ 7.39-7.35 (m, 3H), 7.28-7.21 (m, 3H), 7.06 (s, 1H), 6.96 (d, J=2.3 Hz, 1H), 6.74 (dd, J=9.7, 3.3 Hz, 2H), 6.22 (t, J=7.1 Hz, 1H), 5.38 (d, J=6.5 Hz, 2H), 5.05 (q, J=11.6 Hz, 2H), 4.17 (d, J=14.9 Hz, 1H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.03-2.86 (m, 1H), 2.74-2.57 (m, 2H), 2.37 (t, J=7.1 Hz, 2H), 2.32 (s, 3H).
LRMS (ESI, m/z): 455 [M+H]⁺.

Example A71 (3-((4-chlorobenzyl)oxy)-2,12-dimethoxy-5,6,14,14a-tetrahydroindolo[3',2':4,5]pyridine[2,1-a]isoquinoline-9(8H)-ylmethanol (A71)

The title compound A71 was synthesized with 4-chlorobenzyl bromide, 3-hydroxy-4methoxybenzaldehyde and 5-methoxy-3-indoleacetic acid according to Scheme 1.
¹H NMR (400 MHz, DMSO) δ 7.47-7.39 (m, 2H), 7.36 (d, J=8.5 Hz, 1H), 7.32-7.24 (m, 2H), 7.03 (s, 1H), 6.94 (m, 1H), 6.77-6.68 (m, 2H), 6.21 (t, J=6.9 Hz, 1H), 5.37 (d, J=6.3 Hz, 2H), 5.08 (q, J=11.3 Hz, 2H), 4.16 (d, J=15.7 Hz, 1H), 3.78 (s, 3H), 3.76 (s, 3H), 3.64 (d, J=14.3 Hz, 1H), 3.55 (d, J=8.0 Hz, 1H), 3.31 (m, 1H), 3.12 (d, J=7.7 Hz, 1H), 3.03-2.88 (m, 1H), 2.66 (dd, J=12.1 Hz, 2H), 2.33 (t, J=11.5 Hz, 1H).
LRMS (ESI, m/z): 506 [M+H]⁺.

Example A72 (3-((4-chlorobenzyl)oxy)-2-methoxy-5,6,14,14a-tetrahydroindolo[3',2':4,5]pyridine[2,1-a]isoquinoline-9(8H)-ylmethanol (A72)

The title compound A72 was synthesized with 4-methylbenzyl bromide, 3-hydroxy-4methoxybenzaldehyde and 3-indoleacetic acid according to Scheme 1.
¹H NMR (400 MHz, DMSO) δ 7.47-7.39 (m, 2H), 7.36-7.29 (m, 2H), 7.28-7.24 (m, 3H), 7.03 (s, 1H), 6.94 (m, 1H), 6.77-6.68 (m, 2H), 6.21 (t, J=6.9 Hz, 1H), 5.37 (d, J=6.3 Hz, 2H), 5.08 (q, J=11.3 Hz, 2H), 4.16 (d, J=15.7 Hz, 1H), 3.76 (s, 3H), 3.64 (d, J=14.3 Hz, 1H), 3.55 (d, J=8.0 Hz, 1H), 3.31 (m, 1H), 3.12 (d, J=7.7 Hz, 1H), 3.03-2.88 (m, 1H), 2.66 (dd, J=12.1 Hz, 2H), 2.33 (t, J=11.5 Hz, 1H).
LRMS (ESI, m/z): 476 [M+H]⁺.

Example A73 4-(((9-(Hydroxymethyl)-2,12-dimethoxy-5,6,8,9,14,14a-hexahydroindole[3',2':4,5]pyridine[2,1-a]isoquinolin-3-yl)oxo)methyl)benzonitrile (A73)

The title compound A73 was synthesized with 4-cyanobenzyl bromide, 3-hydroxy-4methoxybenzaldehyde and 5-methoxy-3-indoleacetic acid according to Scheme 1.
¹H NMR (400 MHz, DMSO) δ 7.67-7.49 (m, 2H), 7.36 (d, J=8.5 Hz, 1H), 7.32-7.24 (m, 2H), 7.03 (s, 1H), 6.94 (m, 1H), 6.77-6.68 (m, 2H), 6.21 (t, J=6.9 Hz, 1H), 5.37 (d, J=6.3 Hz, 2H), 5.08 (q, J=11.3 Hz, 2H), 4.16 (d, J=15.7 Hz, 1H), 3.78 (s, 3H), 3.76 (s, 3H), 3.64 (d, J=14.3 Hz, 1H), 3.55 (d, J=8.0 Hz, 1H), 3.31 (m, 1H), 3.12 (d, J=7.7 Hz, 1H), 3.03-2.88 (m, 1H), 2.66 (dd, J=12.1 Hz, 2H), 2.33 (t, J=11.5 Hz, 1H).
LRMS (ESI, m/z): 496 [M+H]⁺.

Example A74 4-(((9-(Hydroxymethyl)-2-methoxy-5,6,8,9,14,14a-hexahydroindole[3',2':4,5]pyridine[2,1-a]isoquinolin-3-yl)oxo)methyl)benzonitrile (A74)

The title compound A74 was synthesized with 4-cyanobenzyl bromide, 3-hydroxy-4methoxybenzaldehyde and 3-indoleacetic acid according to Scheme 1.
¹H NMR (400 MHz, DMSO) δ 7.67-7.49 (m, 2H), 7.36-7.29 (m, 2H), 7.27-7.24 (m, 3H), 7.03 (s, 1H), 6.94 (m, 1H), 6.77-6.68 (m, 2H), 6.21 (t, J=6.9 Hz, 1H), 5.37 (d, J=6.3 Hz, 2H), 5.08 (q, J=11.3 Hz, 2H), 4.16 (d, J=15.7 Hz, 1H), 3.76 (s, 3H), 3.64 (d, J=14.3 Hz, 1H), 3.55 (d, J=8.0 Hz, 1H), 3.31 (m, 1H), 3.12 (d, J=7.7 Hz, 1H), 3.03-2.88 (m, 1H), 2.66 (dd, J=12.1 Hz, 2H), 2.33 (t, J=11.5 Hz, 1H).
LRMS (ESI, m/z): 466 [M+H]⁺.

Example A75 (3-((4-bromobenzyl)oxy)-2,12-dimethoxy-5,6,14,14a-tetrahydroindolo[3',2':4,5]pyridine[2,1-a]isoquinoline-9(8H)-ylmethanol (A75)

The title compound A75 was synthesized with 4-bromobenzyl bromide, 3-hydroxy-4methoxybenzaldehyde and 5-methoxy-3-indoleacetic acid according to Scheme 1.
¹H NMR (400 MHz, DMSO) δ 7.41-7.38 (m, 2H), 7.36 (d, J=8.5 Hz, 1H), 7.32-7.24 (m, 2H), 7.03 (s, 1H), 6.94 (m, 1H), 6.77-6.68 (m, 2H), 6.21 (t, J=6.9 Hz, 1H), 5.37 (d, J=6.3 Hz, 2H), 5.08 (q, J=11.3 Hz, 2H), 4.16 (d, J=15.7 Hz, 1H), 3.78 (s, 3H), 3.76 (s, 3H), 3.64 (d, J=14.3 Hz, 1H), 3.55 (d, J=8.0 Hz, 1H), 3.31 (m, 1H), 3.12 (d, J=7.7 Hz, 1H), 3.03-2.88 (m, 1H), 2.66 (dd, J=12.1 Hz, 2H), 2.33 (t, J=11.5 Hz, 1H).
LRMS (ESI, m/z): 549[M+H]⁺, 551[M+H]⁺.

Example A76 (3-((4-bromobenzyl)oxy)-2-methoxy-5,6,14,14a-tetrahydroindolo[3',2':4,5]pyridine[2,1-a]isoquinoline-9(8H)-ylmethanol (A76)

The title compound A76 was synthesized with 4-bromobenzyl bromide, 3-hydroxy-4methoxybenzaldehyde and 3-indoleacetic acid according to Scheme 1.

¹H NMR (400 MHz, DMSO) δ 7.41-7.38 (m, 2H), 7.36-7.29 (m, 2H), 7.28-7.24 (m, 3H), 7.03 (s, 1H), 6.94 (m, 1H), 6.77-6.68 (m, 2H), 6.21 (t, J=6.9 Hz, 1H), 5.37 (d, J=6.3 Hz, 2H), 5.08 (q, J=11.3 Hz, 2H), 4.16 (d, J=15.7 Hz, 1H), 3.76 (s, 3H), 3.64 (d, J=14.3 Hz, 1H), 3.55 (d, J=8.0 Hz, 1H), 3.31 (m, 1H), 3.12 (d, J=7.7 Hz, 1H), 3.03-2.88 (m, 1H), 2.66 (dd, J=12.1 Hz, 2H), 2.33 (t, J=11.5 Hz, 1H).
LRMS (ESI, m/z): 519[M+H]+, 521[M+H]⁺.

Example A77 (3-((3-Fluoro-4-(trifluoromethyl)benzyl)oxy)-2,12-dimethoxy-5,6,14,14a-tetrahydroindolo[3',2':4,5]pyridine[2,1-a]isoquinoline-9(8H)-ylmethanol (A77)

The title compound A77 was synthesized with 3-fluoro-4-trifluoromethylbenzyl bromide, 3-hydroxy-4methoxybenzaldehyde and 5-methoxy-3-indoleacetic acid according to Scheme 1.
¹H NMR (400 MHz, DMSO) δ 7.51-7.35 (m, 4H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 557 [M+H]⁺.

Example A78 (3-((3-Fluoro-4-(trifluoromethyl)benzyl)oxy)-2-methoxy-5,6,14,14a-tetrahydroindolo[3',2':4,5]pyridine[2,1-a]isoquinoline-9(8H)-ylmethanol (A78)

The title compound A78 was synthesized with 3-fluoro-4-trifluoromethylbenzyl bromide, 3-hydroxy-4methoxybenzaldehyde and 3-indoleacetic acid according to Scheme 1.
¹H NMR (400 MHz, DMSO) δ 7.51-7.35 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 527 [M+H]⁺.

Example A79 (3-((2-Fluoro-4-(trifluoromethyl)benzyl)oxy)-2,12-dimethoxy-5,6,14,14a-tetrahydroindolo[3',2':4,5]pyridine[2,1-a]isoquinoline-9(8H)-ylmethanol (A79)

The title compound A79 was synthesized with 2-fluoro-4-trifluoromethylbenzyl bromide, 3-hydroxy-4methoxybenzaldehyde and 5-methoxy-3-indoleacetic acid according to Scheme 1.
¹H NMR (400 MHz, DMSO) δ 7.51-7.35 (m, 4H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 557 [M+H]⁺.

Example A80 (3-((2-Fluoro-4-(trifluoromethyl)benzyl)oxy)-2-methoxy-5,6,14,14a-tetrahydroindolo[3',2':4,5]pyridine[2,1-a]isoquinoline-9(8H)-ylmethanol (A80)

The title compound A80 was synthesized with 2-fluoro-4-trifluoromethylbenzyl bromide, 3-hydroxy-4methoxybenzaldehyde and 3-indoleacetic acid according to Scheme 1.
¹H NMR (400 MHz, DMSO) δ 7.51-7.35 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 527 [M+H]⁺.

Example A81 (2,12-Dimethoxy-3-((4-ethylbenzyl)oxy)-5,6,14,14a-tetrahydroindolo[3',2':4,5]pyridine[2,1-a]isoquinoline-9(8H)-yl)methanol (A81)

The title compound A81 was synthesized with 4-ethylbenzyl bromide, 3-hydroxy-4methoxybenzaldehyde and 5-methoxy-3-indoleacetic acid according to Scheme 1.
¹H NMR (400 MHz, DMSO) δ 7.51-7.35 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H), 2.34 (q, J=8.0 Hz, 2H), 1.01 (t, J=8.0 Hz, 3H).
LRMS (ESI, m/z): 499 [M+H]⁺.

Example A82 (2-methoxy-3-((4-ethylbenzyl)oxy)-5,6,14,14a-tetrahydroindolo[3',2':4,5]pyridine[2,1-a]isoquinoline-9(8H)-yl)methanol (A82)

The title compound A82 was synthesized with 4-ethylbenzyl bromide, 3-hydroxy-4methoxybenzaldehyde and 3-indoleacetic acid according to Scheme 1.
¹H NMR (400 MHz, DMSO) δ 7.51-7.35 (m, 5H), 7.21-7.05 (m, 2H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H), 2.34 (q, J=8.0 Hz, 2H), 1.01 (t, J=8.0 Hz, 3H).
LRMS (ESI, m/z): 469 [M+H]⁺.

Example A83 (2,12-Dimethoxy-3-(naphthalen-2-ylmethoxy)-5,6,14,14a-tetrahydroindolo[3',2':4,5]pyridine[2,1-a]isoquinoline-9(8H)-yl)methanol (A83)

The title compound A83 was synthesized with 2-bromomethylnaphthalene, 3-hydroxy-4-methoxybenzaldehyde and 5-methoxy-3-indoleacetic acid according to Scheme 1.
¹H NMR (400 MHz, DMSO) δ 7.67-7.32 (m, 7H), 7.25-7.12 (m, 2H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 521 [M+H]⁺.

Example A84 (2-methoxy-3-(naphthalen-2-ylmethoxy)-5,6,14,14a-tetrahydroindolo[3',2':4,5]pyridine[2,1-a]isoquinoline-9(8H)-yl)methanol (A84)

The title compound A84 was synthesized with 2-bromomethylnaphthalene, 3-hydroxy-4-methoxybenzaldehyde and 3-indoleacetic acid according to Scheme 1.

¹H NMR (400 MHz, DMSO) δ 7.67-7.32 (m, 7H), 7.25-7.12 (m, 3H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 491 [M+H]⁺.

Example A85 4-(((9-(Hydroxymethyl)-2,12-dimethoxy-5,6,8,9,14,14a-hexahydroindole[3',2':4,5]pyridine[2,1-a]isoquinolin-3-yl)oxo)methyl)benzoate (A85)

The title compound A85 was synthesized with methyl 4-bromomethylbenzoate, 3-hydroxy-4-methoxybenzaldehyde and 5-methoxy-3-indoleacetic acid according to Scheme 1.
¹H NMR (400 MHz, DMSO) δ 7.51-7.35 (m, 6H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 529 [M+H]⁺.

Example A86 4-(((9-(Hydroxymethyl)-2-methoxy-5,6,8,9,14,14a-hexahydroindole[3',2':4,5]pyridine[2,1-a]isoquinolin-3-yl)oxo)methyl)benzoate (A86)

The title compound A86 was synthesized with methyl 4-bromomethylbenzoate, 3-hydroxy-4-methoxybenzaldehyde and 3-indoleacetic acid according to Scheme 1.
¹H NMR (400 MHz, DMSO) δ 8.01-7.95 (m, 2H), 7.51-7.35 (m, 6H), 7.05-6.94 (m, 2H), 6.79-6.69 (m, 2H), 6.26 (s, 1H), 5.37 (s, 2H), 5.11 (d, J=4.8 Hz, 2H), 4.16 (d, J=15.1 Hz, 1H), 3.77 (d, J=11.4 Hz, 6H), 3.64 (d, J=15.6 Hz, 1H), 3.54 (d, J=7.2 Hz, 1H), 3.31 (s, 1H), 3.14 (s, 1H), 2.94 (d, J=11.4 Hz, 1H), 2.64 (dd, J=21.1, 13.3 Hz, 2H), 2.40-2.27 (m, 1H).
LRMS (ESI, m/z): 499 [M+H]⁺.

Example A87 (3-((4-(1H-pyrazol-1-yl)benzyl)oxy)-2,12-dimethoxy-5,6,14,14a-tetrahydroindolo[3',2':4,5]pyridine[2,1-a]isoquinoline-9(8H)-yl)methanol (A87)

The title compound A87 was synthesized with 1-4-(bromomethyl)benzene-1H-pyrazole, 3-hydroxy-4methoxybenzaldehyde and 5-methoxy-3-indoleacetic acid according to Scheme 1.
¹H NMR (400 MHz, DMSO) δ 7.87 (d, J=8 Hz, 1H), 7.62-7.45 (m, 5H), 7.05-6.84 (m, 3H), 6.79-6.69 (m, 2H), 6.47 (q, J=8 Hz, 1H), 6.26 (s, 1H), 5.37 (s, 2H), 5.11 (d, J=4.8 Hz, 2H), 4.16 (d, J=15.1 Hz, 1H), 3.77 (d, J=11.4 Hz, 6H), 3.64 (d, J=15.6 Hz, 1H), 3.54 (d, J=7.2 Hz, 1H), 3.31 (s, 1H), 3.14 (s, 1H), 2.94 (d, J=11.4 Hz, 1H), 2.64 (dd, J=21.1, 13.3 Hz, 2H), 2.40-2.27 (m, 1H).
LRMS (ESI, m/z): 537 [M+H]⁺.

Example A88 (3-((4-(1H-pyrazol-1-yl)benzyl)oxy)-2-methoxy-5,6,14,14a-tetrahydroindolo[3',2':4,5]pyridine[2,1-a]isoquinoline-9(8H)-yl)methanol (A88)

The title compound A88 was synthesized with 1-4-(bromomethyl)benzene-1H-pyrazole, 3-hydroxy-4-methoxybenzaldehyde and 3-indoleacetic acid according to Scheme 1.
¹H NMR (400 MHz, DMSO) δ 7.87 (d, J=8 Hz, 1H), 7.62-7.45 (m, 5H), 7.05-6.84 (m, 4H), 6.79-6.69 (m, 2H), 6.47 (q, J=8 Hz, 1H), 6.26 (s, 1H), 5.37 (s, 2H), 5.11 (d, J=4.8 Hz, 2H), 4.16 (d, J=15.1 Hz, 1H), 3.77 (d, J=11.4 Hz, 6H), 3.64 (d, J=15.6 Hz, 1H), 3.54 (d, J=7.2 Hz, 1H), 3.31 (s, 1H), 3.14 (s, 1H), 2.94 (d, J=11.4 Hz, 1H), 2.64 (dd, J=21.1, 13.3 Hz, 2H), 2.40-2.27 (m, 1H).
LRMS (ESI, m/z): 507 [M+H]⁺.

Example A89 (3-Butoxy-2,12-dimethoxy-5,6,14,14a-tetrahydroindolo[3',2':4,5]pyridine[2,1-a]isoquinoline-9(8H)-yl)methanol (A89)

The title compound A89 was synthesized with bromobutane, 3-hydroxy-4-methoxybenzaldehyde and 5-methoxy-3-indoleacetic acid according to Scheme 1.
¹H NMR (400 MHz, DMSO) δ 7.36 (d, J=8.8 Hz, 1H), 6.98 (d, J=2.1 Hz, 1H), 6.96 (s, 1H), 6.73 (dd, J=8.7, 2.3 Hz, 1H), 6.69 (s, 1H), 6.23 (s, 1H), 5.37 (s, 2H), 4.16 (d, J=14.8 Hz, 1H), 3.92 (t, J=5.9 Hz, 2H), 3.79 (s, 3H), 3.77 (s, 3H), 3.65 (d, J=15.6 Hz, 1H), 3.57 (d, J=8.0 Hz, 1H), 3.44-3.40 (d, J=15.0 Hz, 1H), 3.12 (d, J=9.6 Hz, 1H), 3.03-2.86 (m, 1H), 2.63 (m, 2H), 2.47-2.37 (t, J=12.0 Hz, 1H), 1.77-1.61 (m, 2H), 1.51-1.36 (m, 2H), 0.94 (t, J=7.4 Hz, 3H).
LRMS (ESI, m/z): 437 [M+H]⁺.

Example A90 (3-Butoxy-2,12-dimethoxy-5,6,14,14a-tetrahydroindolo[3',2':4,5]pyridine[2,1-a]isoquinoline-9(8H)-yl)methanol (A90)

The title compound A90 was synthesized with bromobutane, 3-hydroxy-4methoxybenzaldehyde and 3-indoleacetic acid according to Scheme 1.
¹H NMR (400 MHz, DMSO) δ 7.36 (d, J=8.8 Hz, 1H), 6.98 (d, J=2.1 Hz, 1H), 6.96 (s, 1H), 6.73 (dd, J=8.7, 2.3 Hz, 1H), 6.69 (s, 1H), 6.23 (s, 1H), 5.37 (s, 2H), 4.16 (d, J=14.8 Hz, 1H), 3.92 (t, J=5.9 Hz, 2H), 3.77 (s, 3H), 3.65 (d, J=15.6 Hz, 1H), 3.57 (d, J=8.0 Hz, 1H), 3.44-3.40 (d, J=15.0 Hz, 1H), 3.12 (d, J=9.6 Hz, 1H), 3.03-2.86 (m, 1H), 2.63 (m, 2H), 2.47-2.37 (t, J=12.0 Hz, 1H), 1.77-1.61 (m, 2H), 1.51-1.36 (m, 2H), 0.94 (t, J=7.4 Hz, 3H).
LRMS (ESI, m/z): 407 [M+H]⁺.

Example A91 (12-fluoro-2,3-dimethoxy-5,6,14,14a-tetrahydroindolo[3',2':4,5]pyridine[2,1-a]isoquinoline-9(8H)-yl)methanol (A91)

The title compound A91 was synthesized with 5-fluoro-3-indolacetic acid and 3,4-dimethoxybenzaldehyde according to Scheme 1.
¹H NMR (300 MHz, DMSO) δ 7.27-7.16 (m, 1H), 6.91 (d, J=2.1 Hz, 1H), 6.80 (d, J=2.2 Hz, 1H), 6.77 (s, 1H), 6.63 (s, 1H), 5.61 (s, 1H), 5.26 (dd, J=31.9, 10.9 Hz, 2H), 3.87 (s, 3H), 3.85 (s, 3H), 3.64 (d, J=14.9 Hz, 1H), 3.54 (d, J=7.4 Hz, 1H), 3.48-3.35 (m, 1H), 3.16 (m, 2H), 2.86 (d, J=11.0 Hz, 1H), 2.72-2.49 (m, 3H).
LRMS (ESI, m/z): 383 [M+H]⁺.

Example A92 (12-methyl-2,3-dimethoxy-5,6,14,14a-tetrahydroindolo[3',2':4,5]pyridine[2,1-a]isoquinoline-9(8H)-yl)methanol (A92)

The title compound A91 was synthesized with 5-methyl-3-indolacetic acid and 3,4-dimethoxybenzaldehyde according to Scheme 1.
¹H NMR (300 MHz, DMSO) δ 7.27-7.16 (m, 2H), 6.91 (d, J=2.1 Hz, 1H), 6.80 (d, J=2.2 Hz, 1H), 6.77 (s, 1H), 6.63

(s, 1H), 5.61 (s, 1H), 5.26 (dd, J=31.9, 10.9 Hz, 2H), 3.91 (s, 3H), 3.85 (s, 3H), 3.64 (d, J=14.9 Hz, 1H), 3.54 (d, J=7.4 Hz, 1H), 3.48-3.35 (m, 1H), 3.16 (m, 2H), 2.86 (d, J=11.0 Hz, 1H), 2.72-2.49 (m, 3H), 2.34 (s, 3H).
LRMS (ESI, m/z): 379 [M+H]$^+$.

Example A93 (2,12-Dimethoxy-3-(2,2,2-trifluoroethoxy)-5,6,14,14a-tetrahydroindolo[3',2':4,5]pyridine[2,1-a]isoquinoline-9(8H)-yl)methanol (A93)

The title compound A93 was synthesized with 2,2,2-trifluoroethyl-p-toluenesulfonate, 3-hydroxy-4-methoxybenzaldehyde and 5-methoxy-3-indoleacetic acid according to Scheme 1.
$^1$H NMR (400 MHz, DMSO) δ 7.37 (d, J=8.8 Hz, 1H), 7.13 (s, 1H), 6.96 (d, J=2.4 Hz, 1H), 6.79 (s, 1H), 6.74 (dd, J=8.8, 2.5 Hz, 1H), 6.24 (s, 1H), 5.37 (s, 2H), 4.76-4.65 (m, 2H), 4.17 (d, J=15.0 Hz, 1H), 3.78 (s, 3H), 3.77 (s, 3H), 3.65 (d, J=14.8 Hz, 1H), 3.60-3.54 (m, 1H), 3.48-3.42 (m, 1H), 3.14 (dd, J=8.5, 2.6 Hz, 1H), 2.98 (dd, J=18.7, 8.2 Hz, 1H), 2.74-2.60 (m, 2H), 2.46-2.35 (m, 1H).
LRMS (ESI, m/z): 463 [M+H]$^+$.

Example A94 (2-methoxy-3-(2,2,2-trifluoroethoxy)-5,6,14,14a-tetrahydroindolo[3',2':4,5]pyridine[2,1-a]isoquinoline-9(8H)-yl)methanol (A94)

The title compound A94 was synthesized with 2,2,2-trifluoroethyl-p-toluenesulfonate, 3-hydroxy-4-methoxybenzaldehyde and 3-indoleacetic acid according to Scheme 1.
$^1$H NMR (400 MHz, DMSO) δ 7.37 (d, J=8.8 Hz, 1H), 7.30-7.23 (m, 2H), 6.96 (d, J=2.4 Hz, 1H), 6.79 (s, 1H), 6.74 (dd, J=8.8, 2.5 Hz, 1H), 6.24 (s, 1H), 5.37 (s, 2H), 4.76-4.65 (m, 2H), 4.17 (d, J=15.0 Hz, 1H), 3.77 (s, 3H), 3.65 (d, J=14.8 Hz, 1H), 3.60-3.54 (m, 1H), 3.48-3.42 (m, 1H), 3.14 (dd, J=8.5, 2.6 Hz, 1H), 2.98 (dd, J=18.7, 8.2 Hz, 1H), 2.74-2.60 (m, 2H), 2.46-2.35 (m, 1H).
LRMS (ESI, m/z): 433 [M+H]$^+$.

Example A95 (2,12-Dimethoxy-3-((4-(methylsulfonyl)benzyl)oxy)-5,6,14,14a-tetrahydroindolo[3',2':4,5]pyridine[2,1-a]isoquinoline-9(8H)-yl)methanol (A95)

The title compound A95 was synthesized with 4-methanesulfonylbenzyl bromide, 3-hydroxy-4-methoxybenzaldehyde and 5-methoxy-3-indoleacetic acid according to Scheme 1.
$^1$H NMR (400 MHz, DMSO) δ 7.39-7.35 (m, 3H), 7.22 (d, J=8.0 Hz, 2H), 7.06 (s, 1H), 6.96 (d, J=2.3 Hz, 1H), 6.74 (dd, J=9.7, 3.3 Hz, 2H), 6.22 (t, J=7.1 Hz, 1H), 5.38 (d, J=6.5 Hz, 2H), 5.05 (q, J=11.6 Hz, 2H), 4.17 (d, J=14.9 Hz, 1H), 3.79 (s, 3H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.05 (s, 3H), 3.03-2.86 (m, 1H), 2.74-2.57 (m, 2H), 2.37 (m, 1H).
LRMS (ESI, m/z): 549 [M+H]$^+$.

Example A96 (2-methoxy-3-((4-methylbenzyl)oxy)-5,6,14,14a-tetrahydroindolo[3',2':4,5]pyridine[2,1-a]isoquinoline-9(8H)-yl)methanol (A96)

The title compound A96 was synthesized with 4-methanesulfonylbenzyl bromide, 3-hydroxy-4methoxybenzaldehyde and 3-indoleacetic acid according to Scheme 1.
$^1$H NMR (400 MHz, DMSO) δ 7.39-7.35 (m, 3H), 7.22 (d, J=8.0 Hz, 2H), 7.09-7.06 (m, 2H), 6.96 (d, J=2.3 Hz, 1H), 6.74 (dd, J=9.7, 3.3 Hz, 2H), 6.22 (t, J=7.1 Hz, 1H), 5.38 (d, J=6.5 Hz, 2H), 5.05 (q, J=11.6 Hz, 2H), 4.17 (d, J=14.9 Hz, 1H), 3.79 (s, 3H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.05 (s, 3H), 3.03-2.86 (m, 1H), 2.74-2.57 (m, 2H), 2.37 (m, 1H).
LRMS (ESI, m/z): 519 [M+H]$^+$.

Example A97 (3-(Benzyloxy)-11-fluoro-2-methoxy-5,6,14,14a-tetrahydroindolo[3',2':4,5]pyridine[2,1-a]isoquinoline-9(8H)-yl)methanol (A97)

The title compound A97 was synthesized with 6-fluoro-3-indolacetic acid, 3-hydroxy-4-methoxybenzaldehyde and benzyl bromide according to Scheme 1.
$^1$H NMR (400 MHz, DMSO) δ 7.51-7.35 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 459 [M+H]$^+$.

Example A98 3-(Benzyloxy)-12-fluoro-2-methoxy-5,6,14,14a-tetrahydroindolo[3',2':4,5]pyridine[2,1-a]isoquinoline-9(8H)-yl)methanol (A98)

The title compound A98 was synthesized with 5-fluoro-3-indolacetic acid, 3-hydroxy-4-methoxybenzaldehyde and benzyl bromide according to Scheme 1.
$^1$H NMR (400 MHz, DMSO) δ 7.51-7.35 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 459 [M+H]$^+$.

Example A99 (3-(Benzyloxy)-13-fluoro-2-methoxy-5,6,14,14a-tetrahydroindolo[3',2':4,5]pyridine[2,1-a]isoquinoline-9(8H)-yl)methanol (A99)

The title compound A45 was synthesized with 4-fluoro-3-indolacetic acid, 3-hydroxy-4-methoxybenzaldehyde and benzyl bromide according to Scheme 1.
$^1$H NMR (400 MHz, DMSO) δ 7.51-7.35 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 459 [M+H]$^+$.

Example A100 (3-(Benzyloxy)-11-chloro-2-methoxy-5,6,14,14a-tetrahydroindolo[3',2':4,5]pyridine[2,1-a]isoquinoline-9(8H)-yl)methanol (A100)

The title compound A100 was synthesized with 6-chloro-3-indolacetic acid, 3-hydroxy-4-methoxybenzaldehyde and benzyl bromide according to Scheme 1.
$^1$H NMR (400 MHz, DMSO) δ 7.51-7.35 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 475 [M+H]⁺.

Example A101 (3-(Benzyloxy)-12-chloro-2-methoxy-5,6,14,14a-tetrahydroindolo[3',2':4,5]pyridine[2,1-a]isoquinoline-9(8H)-yl)methanol (A101)

The title compound A101 was synthesized with 5-chloro-3-indolacetic acid, 3-hydroxy-4-methoxybenzaldehyde and benzyl bromide according to Scheme 1.
¹H NMR (400 MHz, DMSO) δ 7.51-7.35 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 475 [M+H]⁺.

Example A102 (3-(Benzyloxy)-13-chloro-2-methoxy-5,6,14,14a-tetrahydroindolo[3',2':4,5]pyridine[2,1-a]isoquinoline-9(8H)-yl)methanol (A102)

The title compound A102 was synthesized with 4-chloro-3-indolacetic acid, 3-hydroxy-4-methoxybenzaldehyde and benzyl bromide according to Scheme 1.
¹H NMR (400 MHz, DMSO) δ 7.51-7.35 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 475 [M+H]⁺.

Example A103 (3-(Benzyloxy)-11-bromo-2-methoxy-5,6,14,14a-tetrahydroindolo[3',2':4,5]pyridine[2,1-a]isoquinoline-9(8H)-yl)methanol (A103)

The title compound A103 was synthesized with 6-bromo-3-indolacetic acid, 3-hydroxy-4-methoxybenzaldehyde and benzyl bromide according to Scheme 1.
¹H NMR (400 MHz, DMSO) δ 7.51-7.35 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 519 [M+H]⁺, 521 [M+H]⁺.

Example A104 (3-(Benzyloxy)-12-bromo-2-methoxy-5,6,14,14a-tetrahydroindolo[3',2':4,5]pyridine[2,1-a]isoquinoline-9(8H)-yl)methanol (A104)

The title compound A104 was synthesized with 5-bromo-3-indolacetic acid, 3-hydroxy-4-methoxybenzaldehyde and benzyl bromide according to Scheme 1.
¹H NMR (400 MHz, DMSO) δ 7.51-7.35 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 519 [M+H]⁺, 521 [M+H]⁺.

Example A105 (3-(Benzyloxy)-13-bromo-2-methoxy-5,6,14,14a-tetrahydroindolo[3',2':4,5]pyridine[2,1-a]isoquinoline-9(8H)-yl)methanol (A105)

The title compound A105 was synthesized with 4-bromo-3-indolacetic acid, 3-hydroxy-4-methoxybenzaldehyde and benzyl bromide according to Scheme 1.
¹H NMR (400 MHz, DMSO) δ 7.51-7.35 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 519 [M+H]⁺, 521 [M+H]⁺.

Example A106 (3-(Benzyloxy)-11-methyl-5,6,14,14a-tetrahydroindolo[3',2':4,5]pyridine[2,1-a]isoquinoline-9(8H)-yl)methanol (A106)

The title compound A106 was synthesized with 6-methyl-3-indolacetic acid, 3-hydroxy-4-methoxybenzaldehyde and benzyl bromide according to Scheme 1.
¹H NMR (400 MHz, DMSO) δ 7.39-7.35 (m, 3H), 7.28-7.21 (m, 3H), 7.06 (s, 1H), 6.96 (d, J=2.3 Hz, 1H), 6.74 (dd, J=9.7, 3.3 Hz, 2H), 6.22 (t, J=7.1 Hz, 1H), 5.38 (d, J=6.5 Hz, 2H), 5.05 (q, J=11.6 Hz, 2H), 4.17 (d, J=14.9 Hz, 1H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.03-2.86 (m, 1H), 2.74-2.57 (m, 2H), 2.37 (t, J=7.1 Hz, 2H), 2.32 (s, 3H).
LRMS (ESI, m/z): 455 [M+H]⁺.

Example A107 (3-(Benzyloxy)-12-ethyl-5,6,14,14a-tetrahydroindolo[3',2':4,5]pyridine[2,1-a]isoquinoline-9(8H)-yl)methanol (A107)

The title compound A107 was synthesized with 5-ethyl-3-indolacetic acid, 3-hydroxy-4-methoxybenzaldehyde and benzyl bromide according to Scheme 1.
¹H NMR (400 MHz, DMSO) δ 7.39-7.35 (m, 3H), 7.28-7.21 (m, 3H), 7.06 (s, 1H), 6.96 (d, J=2.3 Hz, 1H), 6.74 (dd, J=9.7, 3.3 Hz, 2H), 6.22 (t, J=7.1 Hz, 1H), 5.38 (d, J=6.5 Hz, 2H), 5.05 (q, J=11.6 Hz, 2H), 4.17 (d, J=14.9 Hz, 1H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.03-2.86 (m, 1H), 2.74-2.57 (m, 2H), 2.37 (t, J=7.1 Hz, 2H), 2.34 (q, J=8.0 Hz, 2H), 1.01 (t, J=8.0 Hz, 3H).
LRMS (ESI, m/z): 469 [M+H]⁺.

Example A108 (12-methoxy-5,6,14,14a-tetrahydro-[1,3]dioxazo[4,5-g]indolo[3',2':4,5]pyridine[2,1-a]isoquinoline-9(8H)-yl)methanol (A108)

The title compound A108 was synthesized with piperonal and 5-methoxy-3-indoleacetic acid according to Scheme 1.
¹H NMR (400 MHz, DMSO) δ 7.46 (d, 7.9 Hz, 1H), 7.18-7.07 (m, 1H), 7.03 (dd, J=13.1, 5.7 Hz, 2H), 6.69 (s, 1H), 6.28 (s, 1H), 5.97 (d, J=4.4 Hz, 2H), 5.41 (s, 2H), 4.18 (d, J=15.1 Hz, 1H), 3.75 (s, 3H), 3.68 (d, J=15.2 Hz, 1H), 3.58 (d, J=10.4, 3.1 Hz, 1H), 3.35 (d, J=3.2 Hz, 1H), 3.16-3.06 (m, 1H), 2.93 (m, 1H), 2.64 (dd, J=18.2, 10.6 Hz, 2H), 2.44 (d, J=12.5 Hz, 1H).
LRMS (ESI, m/z): 379 [M+H]⁺.

Example A109 (5,6,14,14a-tetrahydro-[1,3]dioxazo[4,5-g]indolo[3',2':4,5]pyridine[2,1-a]isoquinoline-9(8H)-yl)methanol (A109)

The title compound A109 was synthesized with piperonal and 3-indoleacetic acid according to Scheme 1.

¹H NMR (400 MHz, DMSO) δ 7.46 (dd, J=14.0, 7.9 Hz, 2H), 7.18-7.07 (m, 1H), 7.03 (dd, J=13.1, 5.7 Hz, 2H), 6.69 (s, 1H), 6.28 (s, 1H), 5.97 (d, J=4.4 Hz, 2H), 5.41 (s, 2H), 4.18 (d, J=15.1 Hz, 1H), 3.68 (d, J=15.2 Hz, 1H), 3.58 (dd, J=10.4, 3.1 Hz, 1H), 3.35 (d, J=3.2 Hz, 1H), 3.16-3.06 (m, 1H), 2.93 (m, 1H), 2.64 (dd, J=18.2, 10.6 Hz, 2H), 2.44 (d, J=12.5 Hz, 1H).

LRMS (ESI, m/z): 349 [M+H]⁺.

Example A110 (12-methoxy-5,6,14,14a-tetrahydro-[1,3]dioxazo[4,5-g]indolo[3',2':4,5]pyridine[2,1-a]isoquinoline-9(8H)-yl)methanol (A110)

The title compound A110 was synthesized with 1-benzothiophene-5-carboxaldehyde and 5-methoxy-3-indoleacetic acid according to Scheme 1.

¹H NMR (400 MHz, DMSO) δ 7.78-7.37 (m, 4H), 7.21-7.17 (m, 1H), 7.03-6.87 (m, 2H), 6.28 (s, 1H), 5.97 (d, J=4.4 Hz, 2H), 4.18 (d, J=15.1 Hz, 1H), 3.75 (s, 3H), 3.68 (d, J=15.2 Hz, 1H), 3.58 (dd, J=10.4, 3.1 Hz, 1H), 3.35 (d, J=3.2 Hz, 1H), 3.16-3.06 (m, 1H), 2.93 (m, 1H), 2.64 (dd, J=18.2, 10.6 Hz, 2H), 2.44 (d, J=12.5 Hz, 1H).

LRMS (ESI, m/z): 391 [M+H]⁺.

Example A1111 (5,6,14,14a-tetrahydro-[1,3]dioxazo[4,5-g]indolo[3',2':4,5]pyridine[2,1-a]isoquinoline-9(8H)-yl)methanol (A111)

The title compound A111 was synthesized with 1-benzothiophene-5-carboxaldehyde and 3-indoleacetic acid according to Scheme 1.

¹H NMR (400 MHz, DMSO) δ 7.78-7.37 (m, 4H), 7.21-7.17 (m, 2H), 7.03-6.87 (m, 2H), 6.28 (s, 1H), 5.97 (d, J=4.4 Hz, 2H), 4.18 (d, J=15.1 Hz, 1H), 3.68 (d, J=15.2 Hz, 1H), 3.58 (dd, J=10.4, 3.1 Hz, 1H), 3.35 (d, J=3.2 Hz, 1H), 3.16-3.06 (m, 1H), 2.93 (m, 1H), 2.64 (dd, J=18.2, 10.6 Hz, 2H), 2.44 (d, J=12.5 Hz, 1H).

LRMS (ESI, m/z): 361 [M+H]⁺.

Example A112 methyl (2-(benzyloxy)-3,12-dimethoxy-5,6,14,14a-tetrahydroindolo[3',2':4,5]pyridine[2,1-a]isoquinoline-9(8H)-yl)acetate (A112)

The target compound A112 was synthesized with acetic acid and A1.

¹H NMR (400 MHz, DMSO) δ 7.51-7.35 (m, 6H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H), 2.21 (s, 3H).

LRMS (ESI, m/z): 513 [M+H]⁺.

Example A113 methyl (2-(benzyloxy)-3,12-dimethoxy-5,6,14,14a-tetrahydroindolo[3',2':4,5]pyridine[2,1-a]isoquinoline-9(8H)-yl)cyclohexylsulfonate (A113)

The target compound A113 was synthesized with cyclohexylsulfonic acid and A1.

¹H NMR (400 MHz, DMSO) δ 7.51-7.35 (m, 6H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.94 (m, 1H), 2.65 (d, J=13.4 Hz, 2H), 2.44 (t, J=12.0 Hz, 1H), 2.09-1.84 (m, 4H), 1.53-1.43 (m, 4H), 1.49-1.47 (m, 2H).

LRMS (ESI, m/z): 617 [M+H]⁺.

Example A114 methyl (2-(benzyloxy)-3,12-dimethoxy-5,6,14,14a-tetrahydroindolo[3',2':4,5]pyridine[2,1-a]isoquinoline-9(8H)-yl)benzenesulfonate (A114)

The target compound A114 was synthesized with benzenesulfonic acid and A1.

¹H NMR (400 MHz, DMSO) δ 8.07-7.68 (m, 5H), 7.51-7.35 (m, 6H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.94 (m, 1H), 2.65 (d, J=13.4 Hz, 2H), 2.44 (t, J=12.0 Hz, 1H).

LRMS (ESI, m/z): 611 [M+H]⁺.

Example A115 methyl (2-(benzyloxy)-3,12-dimethoxy-5,6,14,14a-tetrahydroindolo[3',2':4,5]pyridine[2,1-a]isoquinoline-9(8H)-yl)4-fluorobenzenesulfonate (A115)

The target compound A115 was synthesized with 4-fluorobenzenesulfonic acid and A1.

¹H NMR (400 MHz, DMSO) δ 7.85-7.46 (m, 4H), 7.51-7.35 (m, 6H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.94 (m, 1H), 2.65 (d, J=13.4 Hz, 2H), 2.44 (t, J=12.0 Hz, 1H).

LRMS (ESI, m/z): 629 [M+H]⁺.

Example A116 methyl (2-(benzyloxy)-3,12-dimethoxy-5,6,14,14a-tetrahydroindolo[3',2':4,5]pyridine[2,1-a]isoquinoline-9(8H)-yl)3-fluorobenzenesulfonate (A116)

The target compound A116 was synthesized with 3-fluorobenzenesulfonic acid and A1.

¹HNMR (400 MHz, DMSO) δ 7.90-7.60 (m, 4H), 7.51-7.35 (m, 6H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.94 (m, 1H), 2.65 (d, J=13.4 Hz, 2H), 2.44 (t, J=12.0 Hz, 1H).

LRMS (ESI, m/z): 629 [M+H]⁺.

Example A117 methyl (2-(benzyloxy)-3,12-dimethoxy-5,6,14,14a-tetrahydroindolo[3',2':4,5]pyridine[2,1-a]isoquinoline-9(8H)-yl)2-fluorobenzenesulfonate (A117)

The target compound A117 was synthesized with 2-fluorobenzenesulfonic acid and A1.

$^1$HNMR (400 MHz, DMSO) δ 8.11-7.45 (m, 4H), 7.85-7.46 (m, 4H), 7.51-7.35 (m, 6H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.94 (m, 1H), 2.65 (d, J=13.4 Hz, 2H), 2.44 (t, J=12.0 Hz, 1H).

LRMS (ESI, m/z): 629 [M+H]$^+$.

Example A118 methyl (2-(benzyloxy)-3,12-dimethoxy-5,6,14,14a-tetrahydroindolo[3',2':4,5]pyridine[2,1-a]isoquinoline-9(8H)-yl)benzylbenzenesulfonate (A118)

The target compound A118 was synthesized with benzylbenzenesulfonic acid and A1.

$^1$HNMR (400 MHz, DMSO) δ 7.90-7.60 (m, 4H), 7.85-7.46 (m, 4H), 7.51-7.35 (m, 6H), 7.39-7.26 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.67 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.94 (m, 1H), 2.65 (d, J=13.4 Hz, 2H), 2.44 (t, J=12.0 Hz, 1H).

LRMS (ESI, m/z): 625 [M+H]$^+$.

Example A119 methyl (2-(benzyloxy)-3,12-dimethoxy-5,6,14,14a-tetrahydroindolo[3',2':4,5]pyridine[2,1-a]isoquinoline-9(8H)-yl)benzoic acid (A119)

The target compound A119 was synthesized with benzoic acid and A1.

$^1$HNMR (400 MHz, DMSO) δ 8.05-7.56 (m, 5H), 7.90-7.60 (m, 4H), 7.85-7.46 (m, 4H), 7.51-7.35 (m, 6H), 7.39-7.26 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.67 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.94 (m, 1H), 2.65 (d, J=13.4 Hz, 2H), 2.44 (t, J=12.0 Hz, 1H).

LRMS (ESI, m/z): 575 [M+H]$^+$.

Example A120 methyl (2-(benzyloxy)-3,12-dimethoxy-5,6,14,14a-tetrahydroindolo[3',2':4,5]pyridine[2,1-a]isoquinoline-9(8H)-yl)N,N-dimethylformate (A120)

The target compound A120 was synthesized with N,N-dimethylformic acid and A1.

$^1$HNMR (400 MHz, DMSO) δ 7.90-7.60 (m, 4H), 7.85-7.46 (m, 4H), 7.51-7.35 (m, 6H), 7.39-7.26 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.67 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.47 (s, 6H), 3.44 (d, J=14.2 Hz, 1H), 3.14 (d, J=8.3 Hz, 1H), 2.95 (t, J=12.0 Hz, 1H), 2.94 (m, 1H), 2.65 (d, J=13.4 Hz, 2H), 2.44 (t, J=12.0 Hz, 1H).

LRMS (ESI, m/z): 542 [M+H]$^+$.

Example A121 methyl (2-(benzyloxy)-3,12-dimethoxy-5,6,14,14a-tetrahydroindolo[3',2':4,5]pyridine[2,1-a]isoquinoline-9(8H)-yl)4-fluorobenzoate (A121)

The target compound A121 was synthesized with 4-fluorobenzoic acid and A1.

$^1$HNMR (400 MHz, DMSO) δ 8.03-7.35 (m, 4H), 7.90-7.60 (m, 4H), 7.85-7.46 (m, 4H), 7.51-7.35 (m, 6H), 7.39-7.26 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.67 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.94 (m, 1H), 2.65 (d, J=13.4 Hz, 2H), 2.44 (t, J=12.0 Hz, 1H).

LRMS (ESI, m/z): 593 [M+H]$^+$.

Example A122 methyl (2-(benzyloxy)-3,12-dimethoxy-5,6,14,14a-tetrahydroindolo[3',2':4,5]pyridine[2,1-a]isoquinoline-9(8H)-yl)3-fluorobenzoate (A122)

The target compound A122 was synthesized by 3-fluorobenzoic acid and A1.

$^1$HNMR (400 MHz, DMSO) δ 7.90-7.60 (m, 4H), 7.85-7.46 (m, 4H), 7.82-7.42 (m, 4H), 7.51-7.35 (m, 6H), 7.39-7.26 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.67 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.94 (m, 1H), 2.65 (d, J=13.4 Hz, 2H), 2.44 (t, J=12.0 Hz, 1H).

LRMS (ESI, m/z): 593 [M+H]$^+$.

Example A123 methyl (2-(benzyloxy)-3,12-dimethoxy-5,6,14,14a-tetrahydroindolo[3',2':4,5]pyridine[2,1-a]isoquinoline-9(8H)-yl)2-fluorobenzoate (A123)

The target compound A123 was synthesized by 2-fluorobenzoic acid and A1.

$^1$HNMR (400 MHz, DMSO) δ 8.03-7.33 (m, 4H), 7.90-7.60 (m, 4H), 7.85-7.46 (m, 4H), 7.51-7.35 (m, 6H), 7.39-7.26 (m, 5H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.67 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.94 (m, 1H), 2.65 (d, J=13.4 Hz, 2H), 2.44 (t, J=12.0 Hz, 1H).

LRMS (ESI, m/z): 593 [M+H]$^+$.

Example A124 9-(hydroxymethyl)-2,12-dimethoxy-5,6,8,9,14,14a-hexahydroindolo[3',2':4,5]pyridine[2,1-a]isoquinolin-3-ylbenzenesulfonate The title compound A124 was synthesized with benzenesulfonyl chloride, 3-hydroxy-4methoxybenzaldehyde and 5-methoxy-3-indoleacetic acid according to Scheme 1.

¹H NMR (400 MHz, DMSO) δ 7.86-7.35 (m, 4H), 7.22 (d, J=8.0 Hz, 2H), 7.06 (s, 1H), 6.96 (d, J=2.3 Hz, 1H), 6.74 (dd, J=9.7, 3.3 Hz, 2H), 6.22 (t, J=7.1 Hz, 1H), 5.38 (d, J=6.5 Hz, 2H), 4.17 (d, J=14.9 Hz, 1H), 3.79 (s, 3H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.03-2.86 (m, 1H), 2.74-2.57 (m, 2H), 2.37 (m, 1H).
LRMS (ESI, m/z): 521 [M+H]⁺.

Example A125 9-(hydroxymethyl)-3,12-dimethoxy-5,6,8,9,14,14a-hexahydroindolo[3',2':4,5]pyridine[2,1-a]isoquinolin-3-ylbenzenesulfonate The title compound A125 was synthesized with benzenesulfonyl chloride, 4-hydroxy-3-methoxybenzaldehyde and 5-methoxy-3-indoleacetic acid according to Scheme 1.
¹H NMR (400 MHz, DMSO) δ 7.86-7.35 (m, 4H), 7.22-7.06 (m, 3H), 6.96 (d, J=2.3 Hz, 1H), 6.74 (dd, J=9.7, 3.3 Hz, 2H), 6.22 (t, J=7.1 Hz, 1H), 5.38 (d, J=6.5 Hz, 2H), 4.17 (d, J=14.9 Hz, 1H), 3.79 (s, 3H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.03-2.86 (m, 1H), 2.74-2.57 (m, 2H), 2.37 (m, 1H).
LRMS (ESI, m/z): 521 [M+H]⁺.

Example A126 (S)-(2-(Benzyloxy)-3,12-dimethoxy-5,6,14,14a-tetrahydroindolo[3',2':4,5]pyridine[2,1-a]isoquinoline-9(8H)-yl)methanol (A126)

The title compound A126 was synthesized with benzyl bromide, 4-hydroxy-3-methoxybenzaldehyde and 5-methoxy-3-indoleacetic acid according to Scheme 1.
¹H NMR (400 MHz, DMSO) δ 7.51-7.35 (m, 6H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 471 [M+H]⁺.

Example A127 (R)-(2-(Benzyloxy)-3,12-dimethoxy-5,6,14,14a-tetrahydroindolo[3',2':4,5]pyridine[2,1-a]isoquinoline-9(8H)-yl)methanol (A127)

The title compound A127 was synthesized with benzyl bromide, 4-hydroxy-3-methoxybenzaldehyde and 5-methoxy-3-indoleacetic acid according to Scheme 1.
¹H NMR (400 MHz, DMSO) δ 7.51-7.35 (m, 6H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 471 [M+H]⁺.

Example A128 (S)-(2-(Benzyloxy)-2,12-dimethoxy-5,6,14,14a-tetrahydroindolo[3',2':4,5]pyridine[2,1-a]isoquinoline-9(8H)-yl)methanol (A128)

The title compound A128 was synthesized with benzyl bromide, 3-hydroxy-4-methoxybenzaldehyde and 5-methoxy-3-indoleacetic acid according to Scheme 1.
¹H NMR (400 MHz, DMSO) δ 7.51-7.35 (m, 6H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 471 [M+H]⁺.

Example A129 (R)-(2-(Benzyloxy)-2,12-dimethoxy-5,6,14,14a-tetrahydroindolo[3',2':4,5]pyridine[2,1-a]isoquinoline-9(8H)-yl)methanol (A129)

The title compound A129 was synthesized with benzyl bromide, 3-hydroxy-4-methoxybenzaldehyde and 5-methoxy-3-indoleacetic acid according to Scheme 1.
¹H NMR (400 MHz, DMSO) δ 7.51-7.35 (m, 6H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 471 [M+H]⁺.

Example A130 (3-(Benzyloxy)-8-isopropyl-2,12-dimethoxy-5,6,14,14a-tetrahydroindolo[3',2':4,5]pyridine[2,1-a]isoquinoline-9(8H)-yl)methanol (A130)

The title compound A130 was synthesized with benzyl bromide, 3-hydroxy-4-methoxybenzaldehyde and 5-methoxy-3-indoleacetic acid according to Scheme 1.
¹H NMR (400 MHz, DMSO) δ 7.51-7.35 (m, 6H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.89 (d, J=7.0 Hz, 1H), 3.80 (s, 3H), 3.77 (s, 3H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (m, 1H), 2.44 (t, J=12.0 Hz, 1H), 0.91 (d, J=7.2 Hz, 6H).
LRMS (ESI, m/z): 513 [M+H]⁺.

Example A131 (2-(Benzyloxy)-8-isopropyl-3,12-dimethoxy-5,6,14,14a-tetrahydroindolo[3',2':4,5]pyridine[2,1-a]isoquinoline-9(8H)-yl)methanol (A131)

The title compound A131 was synthesized with benzyl bromide, 4-hydroxy-3-methoxybenzaldehyde and 5-methoxy-3-indoleacetic acid according to Scheme 1.
¹H NMR (400 MHz, DMSO) δ 7.51-7.35 (m, 6H), 7.05-6.94 (m, 2H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.89 (d, J=7.0 Hz, 1H), 3.80 (s, 3H), 3.77 (s, 3H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (m, 1H), 2.44 (t, J=12.0 Hz, 1H), 0.91 (d, J=7.2 Hz, 6H).
LRMS (ESI, m/z): 513 [M+H]⁺.

Example A132 2-(benzyloxy)-3,12-dimethoxy-9-(benzenesulfonyl)-5,6,8,9,14,14a-hexahydroindole[3',2':4,5]pyridine[2,1-a]isoquinoline (A132)

The title compound A132 was synthesized with benzyl bromide, 4-hydroxy-3-methoxybenzaldehyde and 5-methoxy-3-indoleacetic acid according to Scheme 1.
¹H NMR (400 MHz, DMSO) δ 7.51-7.35 (m, 5H), 7.51-7.35 (m, 6H), 7.05-6.94 (m, 2H), 6.79-6.69 (m, 2H), 5.08 (s, 2H), 4.18 (d, J=15.0 Hz, 1H), 3.89 (d, J=7.0 Hz, 1H), 3.80 (s, 3H), 3.77 (s, 3H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (m, 1H), 2.44 (t, J=12.0 Hz, 1H).
LRMS (ESI, m/z): 581 [M+H]$^+$.

Example A133 3-(benzyloxy)-2,12-dimethoxy-9-(benzenesulfonyl)-5,6,8,9,14,14a-hexahydroindole[3',2':4,5]pyridine[2,1-a]isoquinoline (A133)

The title compound A133 was synthesized with benzyl bromide, 3-hydroxy-4-methoxybenzaldehyde and 5-methoxy-3-indoleacetic acid according to Scheme 1.
$^1$H NMR (400 MHz, DMSO) δ 7.51-7.35 (m, 5H), 7.51-7.35 (m, 6H), 7.05-6.94 (m, 2H), 6.79-6.69 (m, 2H), 5.08 (s, 2H), 4.18 (d, J=15.0 Hz, 1H), 3.89 (d, J=7.0 Hz, 1H), 3.80 (s, 3H), 3.77 (s, 3H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (m, 1H), 2.44 (t, J=12.0 Hz, 1H).
LRMS (ESI, m/z): 581 [M+H]$^+$.

Example A134 (2-((4-aminobenzyl)oxy)-3,12-dimethoxy-5,6,14,14a-tetrahydroindolo[3',2':4,5]pyridine[2,1-a]isoquinoline-9(8H)-yl)methanol (A134)

The title compound A134 was synthesized with p-aminobenzyl bromide, 4-hydroxy-3-methoxybenzaldehyde and 5-methoxy-3-indoleacetic acid according to Scheme 1.
$^1$H NMR (400 MHz, DMSO) δ 7.51-7.35 (m, 4H), 7.05 (s, 1H), 6.94 (d, J=2.1 Hz, 1H), 6.79-6.69 (m, 2H), 6.27 (s, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 486 [M+H]$^+$.

Example A135 (3-((4-aminobenzyl)oxy)-2,12-dimethoxy-5,6,14,14a-tetrahydroindolo[3',2':4,5]pyridine[2,1-a]isoquinoline-9(8H)-yl)methanol (A135)

The title compound A135 was synthesized with p-aminobenzyl bromide, 3-hydroxy-4-methoxybenzaldehyde and 5-methoxy-3-indoleacetic acid according to Scheme 1.
$^1$H NMR (400 MHz, DMSO) δ 7.51-7.35 (m, 4H), 7.05 (s, 1H), 6.94 (d, J=2.1 Hz, 1H), 6.79-6.69 (m, 2H), 6.27 (s, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 486 [M+H]$^+$.

Example A136 4-(((9-(Hydroxymethyl)-3,12-dimethoxy-5,6,8,9,14,14a-hexahydroindole[3',2':4,5]pyridine[2,1-a]isoquinolin-2-yl)oxo)methyl)phenol (A136)

The title compound A136 was synthesized with p-hydroxybenzyl bromide, 4-hydroxy-3-methoxybenzaldehyde and 5-methoxy-3-indoleacetic acid according to Scheme 1.
$^1$H NMR (400 MHz, DMSO) δ 7.51-7.35 (m, 4H), 7.05 (s, 1H), 6.94 (d, J=2.1 Hz, 1H), 6.79-6.69 (m, 2H), 6.27 (s, 2H), 6.22 (t, J=7.0 Hz, 1H), 5.38 (d, J=7.4 Hz, 2H), 5.31 (s, 1H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 487 [M+H]$^+$.

Example A137 4-(((9-(Hydroxymethyl)-2,12-dimethoxy-5,6,8,9,14,14a-hexahydroindole[3',2':4,5]pyridine[2,1-a]isoquinolin-3-yl)oxo)methyl)phenol (A137)

The title compound A137 was synthesized with p-hydroxybenzyl bromide, 3-hydroxy-4-methoxybenzaldehyde and 5-methoxy-3-indoleacetic acid according to Scheme 1.
$^1$H NMR (400 MHz, DMSO) δ 7.51-7.35 (m, 4H), 7.05 (s, 1H), 6.94 (d, J=2.1 Hz, 1H), 6.79-6.69 (m, 2H), 6.27 (s, 2H), 6.22 (t, J=7.0 Hz, 1H), 5.38 (d, J=7.4 Hz, 2H), 5.31 (s, 1H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 487 [M+H]$^+$.

Example A138 4-(((9-(Hydroxymethyl)-3,12-dimethoxy-5,6,8,9,14,14a-hexahydroindole[3',2':4,5]pyridine[2,1-a]isoquinolin-2-yl)oxo)methyl)benzoic acid (A138)

The title compound A138 was synthesized with p-carboxybenzyl bromide, 4-hydroxy-3-methoxybenzaldehyde and 5-methoxy-3-indoleacetic acid according to Scheme 1.
$^1$H NMR (400 MHz, DMSO) δ 11.01 (s, 1H), 7.51-7.35 (m, 4H), 7.05 (s, 1H), 6.94 (d, J=2.1 Hz, 1H), 6.79-6.69 (m, 2H), 6.27 (s, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 515 [M+H]$^+$.

Example A139 4-(((9-(Hydroxymethyl)-2,12-dimethoxy-5,6,8,9,14,14a-hexahydroindole[3',2':4,5]pyridine[2,1-a]isoquinolin-3-yl)oxo)methyl)benzoic acid (A139)

The title compound A139 was synthesized with p-carboxybenzyl bromide, 3-hydroxy-4-methoxybenzaldehyde and 5-methoxy-3-indoleacetic acid according to Scheme 1.
$^1$H NMR (400 MHz, DMSO) δ 11.01 (s, 1H), 7.51-7.35 (m, 4H), 7.05 (s, 1H), 6.94 (d, J=2.1 Hz, 1H), 6.79-6.69 (m, 2H), 6.27 (s, 2H), 6.22 (t, J=7.0 Hz, 1H), 5.38 (d, J=7.4 Hz, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 515 [M+H]$^+$.

Example (S)-A55 S)-(3-(Benzyloxy)-2,12-dimethoxy-5,6,14,14a-tetrahydroindole[3',2':4,5]pyridine[2,1-a]isoquinoline-9(8H)-yl)methanol ((S)-A55)

The title compound (S)-A55 was synthesized with benzyl bromide, 3-hydroxy-4methoxybenzaldehyde and 5-methoxy-3-indoleacetic acid according to Scheme 1.
$^1$H NMR (400 MHz, DMSO) δ 7.51-7.35 (m, 6H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.16 (s, 2H), 4.29 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 471 [M+H]$^+$

Example (R)-A55 R)-(3-(Benzyloxy)-2,12-dimethoxy-5,6,14,14a-tetrahydroindole[3',2':4,5]pyridine[2,1-a]isoquinoline-9(8H)-yl)methanol ((R)-A55)

The title compound (R)-A55 was synthesized with benzyl bromide, 3-hydroxy-4methoxybenzaldehyde and 5-methoxy-3-indoleacetic acid according to Scheme 1.

$^1$H NMR (400 MHz, DMSO) δ 7.51-7.35 (m, 6H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.16 (s, 2H), 4.29 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 471 [M+H]$^+$

Example (S)-A1 S)-(2-(Benzyloxy)-3,12-dimethoxy-5,6,14,14a-tetrahydroindole[3',2':4,5]pyridine[2,1-a]isoquinoline-9(8H)-yl)methanol (S)-A1)

$^1$H NMR (400 MHz, DMSO) δ 7.51-7.35 (m, 6H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.16 (s, 2H), 4.29 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 471 [M+H]$^+$

Example (R)-A1 R)-(2-(Benzyloxy)-3,12-dimethoxy-5,6,14,14a-tetrahydroindole[3',2':4,5]pyridine[2,1-a]isoquinoline-9(8H)-yl)methanol (R)-A1)

$^1$H NMR (400 MHz, DMSO) δ 7.51-7.35 (m, 6H), 7.05 (s, 1H), 6.94 (d, J=2.1 Hz, 1H), 6.79-6.69 (m, 2H), 6.22 (t, J=7.0 Hz, 1H), 5.38 (d, J=7.4 Hz, 2H), 5.16 (s, 2H), 4.29 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 471 [M+H]$^+$

Example A140 (2,12-Dimethoxy-3-((2-methoxybenzyl)oxo)-5,6,14,14a-tetrahydroindolo[3',2':4,5]pyridine[2,1-a]isoquinoline-9(8H)-yl)methanol (A140)

The title compound A140 was synthesized with 2-methoxybenzyl bromide, 3-hydroxy-4methoxybenzaldehyde and 5-methoxy-3-indoleacetic acid according to Scheme 1.

$^1$H NMR (500 MHz, Chloroform) δ 7.26 (s, 1H), 7.18 (s, 1H), 6.96-6.84 (m, 5H), 6.81 (s, 1H), 6.32 (s, 1H), 6.11-6.07 (m, 2H), 5.23-5.19 (m, 2H), 4.49 (s, 1H), 3.86-3.84 (m, 3H), 3.84-3.73 (m, 8H), 3.67 (s, 1H), 3.18 (s, 1H), 3.07 (s, 1H), 3.02 (s, 1H), 2.77 (d, J=0.8 Hz, 2H), 2.60 (s, 1H), 1.00 (s, 1H).

LRMS (ESI, m/z): 501 [M+H]$^+$.

Example A141 (2-methoxy-3-((2-methoxybenzyl)oxo)-5,6,14,14a-tetrahydroindolo[3',2':4,5]pyridine[2,1-a]isoquinoline-9(8H)-yl)methanol (A141)

The title compound A141 was synthesized with 2-methoxybenzyl bromide, 3-hydroxy-4methoxybenzaldehyde and 3-indoleacetic acid according to Scheme 1.

$^1$H NMR (500 MHz, Chloroform) δ 7.33 (s, 1H), 7.25-7.14 (m, 3H), 7.04 (s, 1H), 6.94-6.81 (m, 4H), 6.62 (s, 1H), 6.11-6.07 (m, 2H), 5.22-5.18 (m, 2H), 4.29 (s, 1H), 3.83 (s, 1H), 3.83-3.74 (m, 3H), 3.74-3.70 (m, 3H), 3.54 (s, 1H), 3.09 (s, 1H), 2.84 (s, 1H), 2.79 (d, J=0.8 Hz, 2H), 2.73 (s, 1H), 2.66 (s, 1H), 1.08 (s, 1H).

LRMS (ESI, m/z): 471 [M+H]$^+$.

Example A142 (2,12-Dimethoxy-3-((3-methylbenzyl)oxo)-5,6,14,14a-tetrahydroindolo[3',2':4,5]pyridine[2,1-a]isoquinoline-9(8H)-yl)methanol (A142)

The title compound A142 was synthesized with 3-methylbenzyl bromide, 3-hydroxy-4methoxybenzaldehyde and 5-methoxy-3-indoleacetic acid according to Scheme 1.

$^1$H NMR (500 MHz, Chloroform) δ 7.08-6.93 (m, 17H), 6.91 (s, 1H), 6.84 (s, 3H), 6.64 (s, 3H), 6.26 (s, 3H), 6.11-6.07 (m, 6H), 5.01-4.97 (m, 6H), 4.29 (s, 3H), 3.87-3.83 (m, 9H), 3.82-3.78 (m, 9H), 3.75 (s, 3H), 3.37 (s, 3H), 3.08 (s, 2H), 2.82 (d, J=0.8 Hz, 6H), 2.63 (s, 3H), 2.37-2.33 (m, 9H), 2.27 (s, 2H), 2.00 (s, 2H), 1.51 (s, 3H).

LRMS (ESI, m/z): 485 [M+H]$^+$.

Example A143 (2-methoxy-3-((3-methylbenzyl)oxo)-5,6,14,14a-tetrahydroindolo[3',2':4,5]pyridine[2,1-a]isoquinoline-9(8H)-yl)methanol (A143)

The title compound A143 was synthesized with 3-methylbenzyl bromide, 3-hydroxy-4methoxybenzaldehyde and 3-indoleacetic acid according to Scheme 1.

$^1$H NMR (500 MHz, Chloroform) δ 7.34 (s, 1H), 7.22 (d, J=4.6 Hz, 2H), 7.15 (dd, J=14.7, 5.2 Hz, 4H), 7.08 (s, 1H), 6.89 (s, 1H), 6.63 (s, 1H), 6.11-6.07 (m, 2H), 5.17-5.13 (m, 2H), 4.29 (s, 1H), 3.85-3.64 (m, 4H), 3.53 (s, 1H), 3.11 (s, 1H), 2.91 (d, J=0.8 Hz, 2H), 2.78 (s, 1H), 2.71 (s, 1H), 2.64 (s, 1H), 2.38-2.34 (m, 3H), 1.20 (s, 1H).

LRMS (ESI, m/z): 455 [M+H]$^+$.

Example A144 (2,12-Dimethoxy-3-((2-methylbenzyl)oxo)-5,6,14,14a-tetrahydroindolo[3',2':4,5]pyridine[2,1-a]isoquinoline-9(8H)-yl)methanol (A144)

The title compound A144 was synthesized with 2-methylbenzyl bromide, 3-hydroxy-4methoxybenzaldehyde and 5-methoxy-3-indoleacetic acid according to Scheme 1.

$^1$H NMR (500 MHz, Chloroform) δ 7.15 (d, J=3.5 Hz, 53H), 7.10 (s, 25H), 7.00 (s, 2H), 7.00-6.84 (m, 105H), 6.77 (s, 26H), 6.50 (s, 26H), 6.11-6.07 (m, 52H), 5.22-5.18 (m, 52H), 4.29 (s, 25H), 3.96-3.80 (m, 107H), 3.80-3.76 (m, 79H), 3.52 (s, 27H), 3.12 (s, 26H), 2.95 (d, J=0.8 Hz, 52H), 2.76 (s, 21H), 2.72 (s, 29H), 2.60 (s, 20H), 2.34-2.30 (m, 78H), 1.11 (s, 26H).

LRMS (ESI, m/z): 485 [M+H]$^+$.

Example A145 (2-methoxy-3-((2-methylbenzyl)oxo)-5,6,14,14a-tetrahydroindolo[3',2':4,5]pyridine[2,1-a]isoquinoline-9(8H)-yl)methanol (A145)

The title compound A145 was synthesized with 2-methylbenzyl bromide, 3-hydroxy-4methoxybenzaldehyde and 3-indoleacetic acid according to Scheme 1.

$^1$H NMR (500 MHz, Chloroform) δ 7.34 (s, 2H), 7.21 (d, J=13.7 Hz, 5H), 7.13 (dd, J=18.1, 14.5 Hz, 7H), 7.03 (s, 2H), 6.89 (s, 2H), 6.62 (s, 2H), 6.11-6.07 (m, 4H), 5.23-5.19 (m, 4H), 4.29 (s, 2H), 3.85-3.64 (m, 8H), 3.53 (s, 2H), 3.12 (s, 2H), 2.94 (d, J=0.8 Hz, 4H), 2.78 (s, 1H), 2.73 (s, 2H), 2.66 (s, 2H), 2.39-2.35 (m, 6H), 1.20 (s, 2H).

LRMS (ESI, m/z): 455 [M+H]$^+$.

Example A146 (3,12-Dimethoxy-2-((2-methoxybenzyl)oxo)-5,6,14,14a-tetrahydroindolo[3',2':4,5]pyridine[2,1-a]isoquinoline-9(8H)-yl)methanol (A146)

The title compound A146 was synthesized with 2-methoxybenzyl bromide, vanillin and 5-methoxy-3-indoleacetic acid according to Scheme 1.

$^1$H NMR (500 MHz, Chloroform) δ 7.22 (d, J=18.6 Hz, 2H), 7.07 (s, 1H), 6.95 (d, J=1.8 Hz, 2H), 6.89-6.84 (m, 3H), 6.31 (s, 1H), 6.11-6.07 (m, 2H), 5.24-5.20 (m, 2H), 4.29 (s, 1H), 3.88-3.84 (m, 6H), 3.83-3.60 (m, 4H), 3.54 (s, 1H), 3.10 (s, 1H), 2.94 (s, 1H), 2.78 (d, J=0.8 Hz, 2H), 2.72 (s, 1H), 2.46 (s, 1H), 1.18 (s, 1H).

LRMS (ESI, m/z): 501 [M+H]$^+$.

Example A147 (3-methoxy-2-((2-methoxybenzyl)oxo)-5,6,14,14a-tetrahydroindolo[3',2':4,5]pyridine[2,1-a]isoquinoline-9(8H)-yl)methanol (A147)

The title compound A147 was synthesized with 2-methoxybenzyl bromide, vanillin and 3-indoleacetic acid according to Scheme 1.

$^1$H NMR (500 MHz, Chloroform) δ 7.36 (s, 3H), 7.29-7.18 (m, 9H), 6.96-6.82 (m, 12H), 6.75 (s, 3H), 6.64 (s, 3H), 6.11-6.07 (m, 6H), 5.24-5.20 (m, 6H), 4.29 (s, 3H), 3.87-3.73 (m, 21H), 3.55 (s, 3H), 3.12 (s, 3H), 2.79 (d, J=0.8 Hz, 6H), 2.70 (d, J=5.0 Hz, 5H), 2.48 (s, 2H), 0.93 (s, 3H).

LRMS (ESI, m/z): 471 [M+H]$^+$.

Example A148 (3,12-Dimethoxy-2-((3-methylbenzyl)oxo)-5,6,14,14a-tetrahydroindolo[3',2':4,5]pyridine[2,1-a]isoquinoline-9(8H)-yl)methanol (A148)

The title compound A148 was synthesized with 3-methylbenzyl bromide, vanillin and 5-methoxy-3-indoleacetic acid according to Scheme 1.

$^1$H NMR (500 MHz, Chloroform) δ 7.20 (d, J=5.7 Hz, 2H), 7.13 (d, J=4.2 Hz, 2H), 7.06 (s, 1H), 6.94 (d, J=19.6 Hz, 2H), 6.87 (s, 1H), 6.28 (s, 1H), 6.11-6.07 (m, 2H), 5.20-5.16 (m, 2H), 4.29 (s, 1H), 3.90-3.62 (m, 7H), 3.53 (s, 1H), 3.14 (s, 1H), 2.95 (d, J=0.8 Hz, 2H), 2.73 (d, J=2.5 Hz, 2H), 2.56 (s, 1H), 2.37-2.33 (m, 3H), 1.20 (s, 1H).

LRMS (ESI, m/z): 485 [M+H]$^+$.

Example A149 (3-methoxy-2-((3-methylbenzyl)oxo)-5,6,14,14a-tetrahydroindolo[3',2':4,5]pyridine[2,1-a]isoquinoline-9(8H)-yl)methanol (A149)

The title compound A149 was synthesized with 3-methylbenzyl bromide, vanillin and 3-indoleacetic acid according to Scheme 1.

$^1$H NMR (500 MHz, Chloroform) δ 7.34 (s, 1H), 7.22 (d, J=6.1 Hz, 2H), 7.16 (d, J=1.9 Hz, 2H), 7.12 (s, 1H), 7.07 (s, 1H), 7.00 (s, 1H), 6.89 (s, 1H), 6.63 (s, 1H), 6.11-6.07 (m, 2H), 5.23-5.19 (m, 2H), 4.29 (s, 1H), 3.86-3.64 (m, 4H), 3.53 (s, 1H), 3.12 (s, 1H), 2.94 (d, J=0.8 Hz, 2H), 2.80 (s, 1H), 2.72 (s, 1H), 2.68 (s, 1H), 2.37-2.33 (m, 3H), 1.20 (s, 1H).

LRMS (ESI, m/z): 455 [M+H]$^+$.

Example A150 (3,12-Dimethoxy-2-((2-methylbenzyl)oxo)-5,6,14,14a-tetrahydroindolo[3',2':4,5]pyridine[2,1-a]isoquinoline-9(8H)-yl)methanol (A150)

The title compound A150 was synthesized with 2-methylbenzyl bromide, vanillin and 5-methoxy-3-indoleacetic acid according to Scheme 1.

$^1$H NMR (500 MHz, Chloroform) δ 7.23 (s, 1H), 7.19-7.08 (m, 4H), 6.86 (d, J=1.9 Hz, 2H), 6.78 (s, 1H), 6.29 (s, 1H), 6.11-6.07 (m, 2H), 5.22-5.18 (m, 2H), 4.29 (s, 1H), 3.86-3.82 (m, 3H), 3.82-3.75 (m, 4H), 3.53 (s, 1H), 3.10 (s, 1H), 2.91 (s, 1H), 2.76 (t, J=7.4 Hz, 3H), 2.66 (s, 1H), 2.33-2.29 (m, 3H), 1.20 (s, 1H).

LRMS (ESI, m/z): 485 [M+H]$^+$.

Example A151 (3-methoxy-2-((2-methoxybenzyl)oxo)-5,6,14,14a-tetrahydroindolo[3',2':4,5]pyridine[2,1-a]isoquinoline-9(8H)-yl)methanol (A151)

The title compound A151 was synthesized with 2-methylbenzyl bromide, vanillin and 3-indoleacetic acid according to Scheme 1.

$^1$H NMR (500 MHz, Chloroform) δ 7.35 (s, 1H), 7.22 (d, J=17.4 Hz, 2H), 7.15 (dd, J=11.3, 8.2 Hz, 4H), 6.92 (d, J=14.7 Hz, 2H), 6.66 (s, 1H), 6.11-6.07 (m, 2H), 5.22-5.18 (m, 2H), 4.29 (s, 1H), 3.86-3.65 (m, 4H), 3.56 (s, 1H), 3.14 (s, 1H), 2.94 (d, J=0.8 Hz, 2H), 2.80 (s, 1H), 2.73 (s, 1H), 2.69 (s, 1H), 2.40-2.36 (m, 3H), 1.17 (s, 1H).

LRMS (ESI, m/z): 455 [M+H]$^+$.

Example A152 (2-methoxy-3-((3,4-difluorobenzyl)oxo)-5,6,14,14a-tetrahydroindolo[3',2':4,5]pyridine[2,1-a]isoquinoline-9(8H)-yl)methanol (A152)

The title compound A152 was synthesized with 3,4-difluorobenzyl bromide, 3-hydroxy-4methoxybenzaldehyde and 3-indoleacetic acid according to Scheme 1.

$^1$H NMR (500 MHz, Chloroform) δ 7.34 (s, 1H), 7.23 (s, 1H), 7.10 (s, 1H), 7.01 (q, J=8.0 Hz, 4H), 6.89 (s, 1H), 6.62 (s, 1H), 6.11-6.07 (m, 2H), 5.22-5.18 (m, 2H), 4.29 (s, 1H), 3.87-3.64 (m, 4H), 3.53 (s, 1H), 3.12 (s, 1H), 2.95 (d, J=0.8 Hz, 2H), 2.78 (s, 1H), 2.73 (s, 1H), 2.66 (s, 1H), 1.20 (s, 1H).

LRMS (ESI, m/z): 477 [M+H]$^+$.

Example A153 (2,12-dimethoxy-3-((3,4-difluorobenzyl)oxo)-5,6,14,14a-tetrahydroindolo[3',2':4,5]pyridine[2,1-a]isoquinoline-9(8H)-yl)methanol (A153)

The title compound A153 was synthesized with 3,4-difluorobenzyl bromide, 3-hydroxy-4methoxybenzaldehyde and 5-methoxy-3-indoleacetic acid according to Scheme 1.

$^1$H NMR (500 MHz, Chloroform) δ 7.04-6.84 (m, 7H), 6.44 (s, 1H), 6.11-6.07 (m, 2H), 5.23-5.19 (m, 2H), 4.29 (s, 1H), 3.84-3.62 (m, 7H), 3.54 (s, 1H), 3.12 (s, 1H), 2.90 (d, J=0.8 Hz, 2H), 2.78 (s, 1H), 2.67 (s, 1H), 2.56 (s, 1H), 1.14 (s, 1H).

LRMS (ESI, m/z): 507 [M+H]$^+$.

Example A154 (2-methoxy-3-((3,5-difluorobenzyl)oxo)-5,6,14,14a-tetrahydroindolo[3',2':4,5]pyridine[2,1-a]isoquinoline-9(8H)-yl)methanol (A154)

The title compound A154 was synthesized with 3,5-difluorobenzyl bromide, 3-hydroxy-4methoxybenzaldehyde and 3-indoleacetic acid according to Scheme 1.

$^1$H NMR (500 MHz, Chloroform) δ 7.34 (s, 1H), 7.23 (s, 1H), 7.13 (s, 1H), 7.05 (s, 1H), 6.96-6.80 (m, 2H), 6.77 (d, J=20.3 Hz, 1H), 6.73 (s, 1H), 6.63 (s, 1H), 6.11-6.07 (m, 2H), 5.20-5.16 (m, 2H), 4.29 (s, 1H), 3.86-3.64 (m, 4H), 3.53 (s, 1H), 3.11 (s, 1H), 2.91 (d, J=0.8 Hz, 2H), 2.78 (s, 1H), 2.71 (s, 1H), 2.64 (s, 1H), 1.20 (s, 1H).

LRMS (ESI, m/z): 477 [M+H]$^+$.

Example A155 (2,12-dimethoxy-3-((3,5-difluorobenzyl)oxo)-5,6,14,14a-tetrahydroindolo[3',2':4,5]pyridine[2,1-a]isoquinoline-9(8H)-yl)methanol (A155)

The title compound A155 was synthesized with 3,5-difluorobenzyl bromide, 3-hydroxy-4methoxybenzaldehyde and 5-methoxy-3-indoleacetic acid according to Scheme 1.

$^1$H NMR (500 MHz, Chloroform) δ 7.04-6.87 (m, 3H), 6.85 (s, 1H), 6.81-6.66 (m, 2H), 6.57 (s, 1H), 6.46 (s, 1H), 6.11-6.07 (m, 2H), 5.25-5.21 (m, 2H), 4.29 (s, 1H), 3.85-3.64 (m, 7H), 3.54 (s, 1H), 3.12 (s, 1H), 2.95 (d, J=0.8 Hz, 2H), 2.76 (d, J=15.8 Hz, 2H), 2.57 (s, 1H), 1.20 (s, 1H).

LRMS (ESI, m/z): 507 [M+H]$^+$.

Example A156 (2-Methoxy-3-((3,4,5-trifluorobenzyl)oxy)-5,6,14,14a-tetrahydroindolo[3',2':4,5]pyridine[2,1-a]isoquinoline-9(8H)-yl)methanol (A156)

The title compound A156 was synthesized with 3,4,5-trifluorobenzyl bromide, 3-hydroxy-4methoxybenzaldehyde and 3-indoleacetic acid according to Scheme 1.

$^1$H NMR (500 MHz, Chloroform) δ 7.34 (s, 1H), 7.23 (s, 1H), 7.04 (s, 1H), 6.99 (s, 1H), 6.89 (s, 1H), 6.85-6.81 (m, 2H), 6.63 (s, 1H), 6.11-6.07 (m, 2H), 5.21-5.17 (m, 2H), 4.29 (s, 1H), 3.85-3.66 (m, 4H), 3.53 (s, 1H), 3.12 (s, 1H), 2.92 (d, J=0.8 Hz, 2H), 2.80 (s, 1H), 2.72 (s, 1H), 2.66 (s, 1H), 1.19 (s, 1H).

LRMS (ESI, m/z): 495 [M+H]$^+$.

Example A157 (2,12-dimethoxy-3-((3,4,5-trifluorobenzyl)oxy)-5,6,14,14a-tetrahydroindolo[3',2':4,5]pyridine[2,1-a]isoquinoline-9(8H)-yl)methanol (A157)

The title compound A157 was synthesized with 3,4,5-trifluorobenzyl bromide, 3-hydroxy-4methoxybenzaldehyde and 5-methoxy-3-indoleacetic acid according to Scheme 1.

$^1$H NMR (500 MHz, Chloroform) δ 6.95 (d, J=13.7 Hz, 6H), 6.89 (s, 3H), 6.83 (s, 3H), 6.75-6.71 (m, 6H), 6.48 (s, 3H), 6.11-6.07 (m, 6H), 5.24-5.20 (m, 6H), 4.29 (s, 3H), 3.92-3.78 (m, 21H), 3.49 (s, 3H), 3.10 (s, 2H), 3.04 (d, J=0.8 Hz, 6H), 2.91 (s, 2H), 2.68 (s, 2H), 2.58 (s, 3H), 1.13 (s, 3H).

LRMS (ESI, m/z): 525 [M+H]$^+$.

Example A158 (3-methoxy-2-((3,4-difluorobenzyl)oxo)-5,6,14,14a-tetrahydroindolo[3',2':4,5]pyridine[2,1-a]isoquinoline-9(8H)-yl)methanol (A158)

The title compound A158 was synthesized with 3,4-difluorobenzyl bromide, vanillin and 3-indoleacetic acid according to Scheme 1.

$^1$H NMR (500 MHz, Chloroform) δ 7.34 (s, 4H), 7.23 (s, 4H), 7.12 (s, 4H), 7.07-6.97 (m, 16H), 6.89 (s, 5H), 6.63 (s, 4H), 6.11-6.07 (m, 8H), 5.22-5.18 (m, 8H), 4.29 (s, 4H), 3.85-3.65 (m, 16H), 3.53 (s, 4H), 3.12 (s, 4H), 2.94 (d, J=0.8 Hz, 8H), 2.80 (s, 3H), 2.72 (s, 5H), 2.68 (s, 2H), 1.20 (s, 4H).

LRMS (ESI, m/z): 477 [M+H]$^+$.

Example A159 (3,12-dimethoxy-2-((3,4-difluorobenzyl)oxo)-5,6,14,14a-tetrahydroindolo[3',2':4,5]pyridine[2,1-a]isoquinoline-9(8H)-yl)methanol (A159)

The title compound A159 was synthesized with 3,4-difluorobenzyl bromide, vanillin and 5-methoxy-3-indoleacetic acid according to Scheme 1.

$^1$H NMR (500 MHz, Chloroform) δ 7.15 (s, 1H), 7.06 (s, 1H), 7.03-6.94 (m, 3H), 6.84 (d, J=5.8 Hz, 2H), 6.32 (s, 1H), 6.11-6.07 (m, 2H), 5.23-5.19 (m, 2H), 4.29 (s, 1H), 3.86-3.76 (m, 7H), 3.61 (s, 1H), 3.12 (s, 1H), 3.04-2.93 (m, 3H), 2.76 (s, 1H), 2.58 (s, 1H), 1.13 (s, 1H).

LRMS (ESI, m/z): 507 [M+H]$^+$.

Example A160 (3-methoxy-2-((3,5-difluorobenzyl)oxo)-5,6,14,14a-tetrahydroindolo[3',2':4,5]pyridine[2,1-a]isoquinoline-9(8H)-yl)methanol (A160)

The title compound A160 was synthesized with 3,5-difluorobenzyl bromide, vanillin and 3-indoleacetic acid according to Scheme 1.

$^1$H NMR (500 MHz, Chloroform) δ 7.35 (s, 36H), 7.23 (s, 36H), 7.13 (s, 36H), 6.89 (s, 65H), 6.79 (dd, J=4.7, 1.6 Hz, 120H), 6.65 (s, 38H), 6.11-6.07 (m, 72H), 5.23-5.19 (m, 72H), 4.29 (s, 35H), 3.95-3.62 (m, 150H), 3.74-3.62 (m, 2H), 3.52 (s, 38H), 3.10 (s, 36H), 2.92 (s, 27H), 2.79 (s, 29H), 2.75 (d, J=0.8 Hz, 76H), 2.66 (s, 37H), 1.19 (s, 36H).

LRMS (ESI, m/z): 477 [M+H]$^+$.

Example A161 (3,12-dimethoxy-2-((3,5-difluorobenzyl)oxo)-5,6,14,14a-tetrahydroindolo[3',2':4,5]pyridine[2,1-a]isoquinoline-9(8H)-yl)methanol (A161)

The title compound A161 was synthesized with 3,5-difluorobenzyl bromide, vanillin and 5-methoxy-3-indoleacetic acid according to Scheme 1.

$^1$H NMR (500 MHz, Chloroform) δ 7.14 (s, 90H), 6.96 (s, 91H), 6.88 (d, J=8.6 Hz, 184H), 6.85-6.76 (m, 189H), 6.74 (s, 88H), 6.32 (s, 90H), 6.11-6.07 (m, 180H), 5.25-5.21 (m, 180H), 4.29 (s, 87H), 3.86 (s, 9H), 4.10-3.67 (m, 654H), 3.60 (s, 94H), 3.22 (s, 78H), 2.89 (dd, J=15.0, 3.5 Hz, 355H), 2.75 (s, 71H), 1.17 (s, 90H).

LRMS (ESI, m/z): 507 [M+H]$^+$.

Example A162 (3-Methoxy-2-((3,4,5-trifluorobenzyl)oxy)-5,6,14,14a-tetrahydroindolo[3',2':4,5]pyridine[2,1-a]isoquinoline-9(8H)-yl)methanol (A162)

The title compound A162 was synthesized with 3,4,5-trifluorobenzyl bromide, vanillin and 3-indoleacetic acid according to Scheme 1.

$^1$H NMR (500 MHz, Chloroform) δ 7.34 (s, 1H), 7.24 (s, 1H), 7.03 (s, 1H), 6.91 (s, 1H), 6.83-6.78 (m, 3H), 6.66 (s, 1H), 6.11-6.07 (m, 2H), 5.22-5.18 (m, 2H), 4.29 (s, 1H), 3.86-3.82 (m, 4H), 3.56 (s, 1H), 3.15 (s, 1H), 2.94 (d, J=0.8 Hz, 2H), 2.80 (s, 1H), 2.73 (s, 1H), 2.68 (s, 1H), 0.95 (s, 1H).

LRMS (ESI, m/z): 495 [M+H]$^+$.

Example A163 (3,12-dimethoxy-2-((3,4,5-trifluorobenzyl)oxy)-5,6,14,14a-tetrahydroindolo[3',2':4,5]pyridine[2,1-a]isoquinoline-9(8H)-yl)methanol (A163)

The title compound A163 was synthesized with 3,4,5-trifluorobenzyl bromide, vanillin and 5-methoxy-3-indoleacetic acid according to Scheme 1.

$^1$H NMR (500 MHz, Chloroform) δ 7.07 (s, 1H), 6.91-6.84 (m, 3H), 6.84-6.80 (m, 2H), 6.27 (s, 1H), 6.11-6.07 (m, 2H), 5.23-5.19 (m, 2H), 4.29 (s, 1H), 3.86-3.67 (m, 7H), 3.54 (s, 1H), 3.12 (s, 1H), 2.94 (d, J=0.8 Hz, 2H), 2.78 (s, 1H), 2.74 (s, 1H), 2.68 (s, 1H), 1.20 (s, 1H).

LRMS (ESI, m/z): 525 [M+H]$^+$.

Example B1 2-(benzyloxy)-8-(4-fluorophenyl)-3,12-dimethoxy-5,6,8,9,14,14a-hexahydroindole[3',2':4,5]pyridine[2,1-a]isoquinoline (B1)

The target compound B1 was synthesized by repeating A1 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 8H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.72 (s, 3H), 3.16 (dd, J=15.5, 4.7 Hz, 2H), 2.87-2.72 (m, 2H), 2.69-2.51 (m, 2H).

LRMS (ESI, m/z): 535 [M+H]$^+$.

Example B2 2-(benzyloxy)-8-(4-fluorophenyl)-3-methoxy-5,6,8,9,14,14a-hexahydroindole[3',2':4,5]pyridine[2,1-a]isoquinoline (B2)

The target compound B2 was synthesized by repeating A2 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 9H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.16 (dd, J=15.5, 4.7 Hz, 2H), 2.87-2.72 (m, 2H), 2.69-2.51 (m, 2H).

LRMS (ESI, m/z): 505 [M+H]$^+$.

Example B3 8-(4-Fluorophenyl)-3,12-dimethoxy-2-((4-(trifluoromethyl)benzyl)oxy)-5,6,8,9,14,14a-hexahydroindolo[3',2':4,5]pyridine[2,1-a]isoquinoline (B3)

The target compound B3 was synthesized by repeating A3 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.72 (s, 3H), 3.16 (dd, J=15.5, 4.7 Hz, 2H), 2.87-2.72 (m, 2H), 2.69-2.51 (m, 2H).

LRMS (ESI, m/z): 603 [M+H]$^+$.

Example B4 8-(4-Fluorophenyl)-3-methoxy-2-((4-(trifluoromethyl)benzyl)oxy)-5,6,8,9,14,14a-hexahydroindolo[3',2':4,5]pyridine[2,1-a]isoquinoline (B4)

The target compound B4 was synthesized by repeating A4 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 8H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.16 (dd, J=15.5, 4.7 Hz, 2H), 2.87-2.72 (m, 2H), 2.69-2.51 (m, 2H).

LRMS (ESI, m/z): 573 [M+H]$^+$.

Example B5 2-((4-fluorobenzyl)oxo)-8-(4-fluorophenyl)-3,12-dimethoxy-5,6,8,9,14,14a-hexahydroindole[3',2':4,5]pyridine[2,1-a]isoquinoline (B5)

The target compound B5 was synthesized by repeating A5 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.72 (s, 3H), 3.16 (dd, J=15.5, 4.7 Hz, 2H), 2.87-2.72 (m, 2H), 2.69-2.51 (m, 2H).

LRMS (ESI, m/z): 553 [M+H]$^+$.

Example B6 2-((4-fluorobenzyl)oxo)-8-(4-fluorophenyl)-3-methoxy-5,6,8,9,14,14a-hexahydroindole[3',2': 4,5]pyridine[2,1-a]isoquinoline (B6)

The target compound B6 was synthesized by repeating A6 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 9H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.16 (dd, J=15.5, 4.7 Hz, 2H), 2.87-2.72 (m, 2H), 2.69-2.51 (m, 2H).

LRMS (ESI, m/z): 523 [M+H]$^+$.

Example B7 2-((3-fluorobenzyl)oxo)-8-(4-fluorophenyl)-3,12-dimethoxy-5,6,8,9,14,14a-hexahydroindole[3',2':4,5]pyridine[2,1-a]isoquinoline (B7)

The target compound B7 was synthesized by repeating A7 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.72 (s, 3H), 3.16 (dd, J=15.5, 4.7 Hz, 2H), 2.87-2.72 (m, 2H), 2.69-2.51 (m, 2H).

LRMS (ESI, m/z): 553 [M+H]$^+$.

Example B8 2-((3-fluorobenzyl)oxo)-8-(4-fluorophenyl)-3-methoxy-5,6,8,9,14,14a-hexahydroindole[3',2': 4,5]pyridine[2,1-a]isoquinoline (B8)

The target compound B8 was synthesized by repeating A8 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 9H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.16 (dd, J=15.5, 4.7 Hz, 2H), 2.87-2.72 (m, 2H), 2.69-2.51 (m, 2H).

LRMS (ESI, m/z): 523 [M+H]$^+$.

Example B9 2-((2-fluorobenzyl)oxo)-8-(4-fluorophenyl)-3,12-dimethoxy-5,6,8,9,14,14a-hexahydroindole[3',2':4,5]pyridine[2,1-a]isoquinoline (B9)

The target compound B9 was synthesized by repeating A9 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.72 (s, 3H), 3.16 (dd, J=15.5, 4.7 Hz, 2H), 2.87-2.72 (m, 2H), 2.69-2.51 (m, 2H).

LRMS (ESI, m/z): 553 [M+H]$^+$.

Example B10 2-((2-fluorobenzyl)oxo)-8-(4-fluorophenyl)-3-methoxy-5,6,8,9,14,14a-hexahydroindole[3',2': 4,5]pyridine[2,1-a]isoquinoline (B10)

The target compound B10 was synthesized by repeating A10 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 9H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.16 (dd, J=15.5, 4.7 Hz, 2H), 2.87-2.72 (m, 2H), 2.69-2.51 (m, 2H).

LRMS (ESI, m/z): 523 [M+H]$^+$.

Example B11 8-(4-Fluorophenyl)-3,12-dimethoxy-2-((4-methoxybenzyl)oxo)-5,6,8,9,14,14a-hexahydroindolo[3',2':4,5]pyridine[2,1-a]isoquinoline (B11)

The target compound B11 was synthesized by repeating A11 with 4-fluorobenzaldehyde.

$^1$H NMR (400 MHz, DMSO) δ 10.64 (s, 1H), 8.03-7.97 (m, 3H), 7.38-7.27 (m, 3H), 7.23-7.09 (m, 3H), 7.02 (d, J=2.4 Hz, 1H), 6.95 (d, J=2.3 Hz, 1H), 6.89 (dd, J=8.4, 2.7 Hz, 1H), 6.68 (d, J=3.3 Hz, 1H), 5.14 (s, 1H), 5.01 (q, J=12.2 Hz, 2H), 3.96-3.89 (m, 1H), 3.77 (s, 3H), 3.76 (s, 3H), 3.72 (s, 3H), 3.21-3.05 (m, 2H), 2.84-2.75 (m, 2H), 2.70-2.60 (m, 1H), 2.56 (d, J=12.7 Hz, 1H).

LRMS (ESI, m/z): 565 [M+H]$^+$.

Example B12 8-(4-Fluorophenyl)-3-methoxy-2-((4-methoxybenzyl)oxo)-5,6,8,9,14,14a-hexahydroindolo[3',2':4,5]pyridine[2,1-a]isoquinoline (B12)

The target compound B12 was synthesized by repeating A12 with 4-fluorobenzaldehyde.

$^1$H NMR (400 MHz, DMSO) δ 10.64 (s, 1H), 8.03-7.97 (m, 3H), 7.38-7.27 (m, 3H), 7.23-7.09 (m, 4H), 7.02 (d, J=2.4 Hz, 1H), 6.95 (d, J=2.3 Hz, 1H), 6.89 (dd, J=8.4, 2.7 Hz, 1H), 6.68 (d, J=3.3 Hz, 1H), 5.14 (s, 1H), 5.01 (q, J=12.2 Hz, 2H), 3.96-3.89 (m, 1H), 3.77 (s, 3H), 3.72 (s, 3H), 3.21-3.05 (m, 2H), 2.84-2.75 (m, 2H), 2.70-2.60 (m, 1H), 2.56 (d, J=12.7 Hz, 1H).

LRMS (ESI, m/z): 535 [M+H]$^+$.

Example B13 8-(4-Fluorophenyl)-3,12-dimethoxy-2-((3-methoxybenzyl)oxo)-5,6,8,9,14,14a-hexahydroindolo[3',2':4,5]pyridine[2,1-a]isoquinoline (B13)

The target compound B13 was synthesized by repeating A13 with 4-fluorobenzaldehyde.

$^1$H NMR (400 MHz, DMSO) δ 10.64 (s, 1H), 8.03-7.97 (m, 3H), 7.38-7.27 (m, 3H), 7.23-7.09 (m, 3H), 7.02 (d, J=2.4 Hz, 1H), 6.95 (d, J=2.3 Hz, 1H), 6.89 (dd, J=8.4, 2.7 Hz, 1H), 6.68 (d, J=3.3 Hz, 1H), 5.14 (s, 1H), 5.01 (q, J=12.2 Hz, 2H), 3.96-3.89 (m, 1H), 3.77 (s, 3H), 3.76 (s, 3H), 3.72 (s, 3H), 3.21-3.05 (m, 2H), 2.84-2.75 (m, 2H), 2.70-2.60 (m, 1H), 2.56 (d, J=12.7 Hz, 1H).

LRMS (ESI, m/z): 565 [M+H]$^+$.

Example B14 8-(4-Fluorophenyl)-3-methoxy-2-((3-methoxybenzyl)oxo)-5,6,8,9,14,14a-hexahydroindolo[3',2':4,5]pyridine[2,1-a]isoquinoline (B13)

The target compound B14 was synthesized by repeating A14 with 4-fluorobenzaldehyde.

$^1$H NMR (400 MHz, DMSO) δ 10.64 (s, 1H), 8.03-7.97 (m, 3H), 7.38-7.27 (m, 3H), 7.23-7.09 (m, 4H), 7.02 (d, J=2.4 Hz, 1H), 6.95 (d, J=2.3 Hz, 1H), 6.89 (dd, J=8.4, 2.7 Hz, 1H), 6.68 (d, J=3.3 Hz, 1H), 5.14 (s, 1H), 5.01 (q, J=12.2 Hz, 2H), 3.96-3.89 (m, 1H), 3.77 (s, 3H), 3.72 (s, 3H), 3.21-3.05 (m, 2H), 2.84-2.75 (m, 2H), 2.70-2.60 (m, 1H), 2.56 (d, J=12.7 Hz, 1H).

LRMS (ESI, m/z): 535 [M+H]$^+$.

Example B15 8-(4-Fluorophenyl)-3,12-dimethoxy-2-((4-methylbenzyl)oxo)-5,6,8,9,14,14a-hexahydroindolo[3',2':4,5]pyridine[2,1-a]isoquinoline (B13)

The target compound B15 was synthesized by repeating A15 with 4-fluorobenzaldehyde.

$^1$H NMR (400 MHz, DMSO) δ 10.64 (s, 1H), 8.03-7.97 (m, 3H), 7.38-7.27 (m, 3H), 7.23-7.09 (m, 3H), 7.02 (d, J=2.4 Hz, 1H), 6.95 (d, J=2.3 Hz, 1H), 6.89 (dd, J=8.4, 2.7 Hz, 1H), 6.68 (d, J=3.3 Hz, 1H), 5.14 (s, 1H), 5.01 (q, J=12.2 Hz, 2H), 3.96-3.89 (m, 1H), 3.77 (s, 3H), 3.72 (s, 3H), 3.21-3.05 (m, 2H), 2.84-2.75 (m, 2H), 2.70-2.60 (m, 1H), 2.56 (d, J=12.7 Hz, 1H), 2.36 (s, 3H).

LRMS (ESI, m/z): 549 [M+H]$^+$.

Example B16 8-(4-Fluorophenyl)-3-methoxy-2-((4-methylbenzyl)oxo)-5,6,8,9,14,14a-hexahydroindolo[3',2':4,5]pyridine[2,1-a]isoquinoline (B13)

The target compound B16 was synthesized by repeating A16 with 4-fluorobenzaldehyde.

$^1$H NMR (400 MHz, DMSO) δ 10.64 (s, 1H), 8.03-7.97 (m, 3H), 7.38-7.27 (m, 3H), 7.23-7.09 (m, 4H), 7.02 (d, J=2.4 Hz, 1H), 6.95 (d, J=2.3 Hz, 1H), 6.89 (dd, J=8.4, 2.7 Hz, 1H), 6.68 (d, J=3.3 Hz, 1H), 5.14 (s, 1H), 5.01 (q, J=12.2 Hz, 2H), 3.96-3.89 (m, 1H), 3.77 (s, 3H), 3.21-3.05 (m, 2H), 2.84-2.75 (m, 2H), 2.70-2.60 (m, 1H), 2.56 (d, J=12.7 Hz, 1H), 2.36 (s, 3H).

LRMS (ESI, m/z): 519 [M+H]$^+$.

Example B17 2-((4-chlorobenzyl)oxo)-8-(4-fluorophenyl)-3,12-dimethoxy-5,6,8,9,14,14a-hexahydroindole[3',2':4,5]pyridine[2,1-a]isoquinoline (B17)

The target compound B17 was synthesized by repeating A17 with 4-fluorobenzaldehyde.

$^1$H NMR (400 MHz, DMSO) δ 10.70 (s, 1H), 7.39 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.72 (s, 3H), 3.16 (dd, J=15.5, 4.7 Hz, 2H), 2.87-2.72 (m, 2H), 2.69-2.51 (m, 2H).

LRMS (ESI, m/z): 570 [M+H]$^+$.

Example B18 2-((4-chlorobenzyl)oxo)-8-(4-fluorophenyl)-3-methoxy-5,6,8,9,14,14a-hexahydroindole[3,2':4,5]pyridine[2,1-a]isoquinoline (B18)

The target compound B18 was synthesized by repeating A18 with 4-fluorobenzaldehyde.

$^1$H NMR (400 MHz, DMSO) δ 10.70 (s, 1H), 7.39 (dd, J=8.6, 5.7 Hz, 2H), 7.26-7.09 (m, 9H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.16 (dd, J=15.5, 4.7 Hz, 2H), 2.87-2.72 (m, 2H), 2.69-2.51 (m, 2H).

LRMS (ESI, m/z): 540 [M+H]$^+$.

Example B19 4-(((8-(4-Fluorophenyl)-3,12-dimethoxy-5,6,8,9,14,14a-hexahydroindole[3',2':4,5]pyridine[2,1-a]isoquinolin-2-yl)oxo)methyl)benzonitrile (B19)

The target compound B19 was synthesized by repeating A19 with 4-fluorobenzaldehyde.

$^1$H NMR (400 MHz, DMSO) δ 10.70 (s, 1H), 7.43 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.72 (s, 3H), 3.16 (dd, J=15.5, 4.7 Hz, 2H), 2.87-2.72 (m, 2H), 2.69-2.51 (m, 2H).

LRMS (ESI, m/z): 560 [M+H]$^+$.

Example B20 4-(((8-(4-Fluorophenyl)-3-methoxy-5,6,8,9,14,14a-hexahydroindole[3',2':4,5]pyridine[2,1-a]isoquinolin-2-yl)oxo)methyl)benzonitrile (B20)

The target compound B20 was synthesized by repeating A20 with 4-fluorobenzaldehyde.

$^1$H NMR (400 MHz, DMSO) δ 10.70 (s, 1H), 7.43 (dd, J=8.6, 5.7 Hz, 2H), 7.26-7.09 (m, 9H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.16 (dd, J=15.5, 4.7 Hz, 2H), 2.87-2.72 (m, 2H), 2.69-2.51 (m, 2H).

LRMS (ESI, m/z): 530 [M+H]$^+$.

Example B21 2-((4-bromobenzyl)oxo)-8-(4-fluorophenyl)-3,12-dimethoxy-5,6,8,9,14,14a-hexahydroindole[3',2':4,5]pyridine[2,1-a]isoquinoline (B21)

The target compound B21 was synthesized by repeating A21 with 4-fluorobenzaldehyde.

$^1$H NMR (400 MHz, DMSO) δ 10.70 (s, 1H), 7.35 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.72 (s, 3H), 3.16 (dd, J=15.5, 4.7 Hz, 2H), 2.87-2.72 (m, 2H), 2.69-2.51 (m, 2H).

LRMS (ESI, m/z): 613 [M+H]$^+$, 615 [M+H]$^+$

Example B22 2-((4-bromobenzyl)oxo)-8-(4-fluorophenyl)-3-methoxy-5,6,8,9,14,14a-hexahydroindole[3',2': 4,5]pyridine[2,1-a]isoquinoline (B22)

The target compound B22 was synthesized by repeating A22 with 4-fluorobenzaldehyde.

$^1$H NMR (400 MHz, DMSO) δ 10.70 (s, 1H), 7.35 (dd, J=8.6, 5.7 Hz, 2H), 7.26-7.09 (m, 9H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.16 (dd, J=15.5, 4.7 Hz, 2H), 2.87-2.72 (m, 2H), 2.69-2.51 (m, 2H).

LRMS (ESI, m/z): 583 [M+H]$^+$, 585 [M+H]$^+$

Example B23 2-((3-fluoro-4-(trifluoromethyl)benzyl)oxo)-8-(4-fluorophenyl)-3,12-dimethoxy-5,6,8,9,14,14a-hexahydroindole[3',2':4,5]pyridine[2,1-a]isoquinoline (B23)

The target compound B23 was synthesized by repeating A23 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.72 (s, 3H), 3.16 (dd, J=15.5, 4.7 Hz, 2H), 2.87-2.72 (m, 2H), 2.69-2.51 (m, 2H).

LRMS (ESI, m/z): 621 [M+H]$^+$.

Example B24 2-((3-fluoro-4-(trifluoromethyl)benzyl)oxo)-8-(4-fluorophenyl)-3-methoxy-5,6,8,9,14,14a-hexahydroindole[3',2':4,5]pyridine[2,1-a]isoquinoline (B24)

The target compound B24 was synthesized by repeating A24 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 9H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.16 (dd, J=15.5, 4.7 Hz, 2H), 2.87-2.72 (m, 2H), 2.69-2.51 (m, 2H).

LRMS (ESI, m/z): 591 [M+H]$^+$.

Example B25 2-((2-fluoro-4-(trifluoromethyl)benzyl)oxo)-8-(4-fluorophenyl)-3,12-dimethoxy-5,6,8,9,14,14a-hexahydroindole[3',2':4,5]pyridine[2,1-a]isoquinoline (B25)

The target compound B25 was synthesized by repeating A25 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.72 (s, 3H), 3.16 (dd, J=15.5, 4.7 Hz, 2H), 2.87-2.72 (m, 2H), 2.69-2.51 (m, 2H).

LRMS (ESI, m/z): 621 [M+H]$^+$.

Example B26 2-((2-fluoro-4-(trifluoromethyl)benzyl)oxo)-8-(4-fluorophenyl)-3-methoxy-5,6,8,9,14,14a-hexahydroindole[3',2':4,5]pyridine[2,1-a]isoquinoline (B26)

The target compound B26 was synthesized by repeating A26 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 9H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.16 (dd, J=15.5, 4.7 Hz, 2H), 2.87-2.72 (m, 2H), 2.69-2.51 (m, 2H).

LRMS (ESI, m/z): 591 [M+H]$^+$.

Example B27 2-((4-ethylbenzyl)oxo)-8-(4-fluorophenyl)-3,12-dimethoxy-5,6,8,9,14,14a-hexahydroindole[3',2':4,5]pyridine[2,1-a]isoquinoline (B27)

The target compound B27 was synthesized by repeating A27 with 4-fluorobenzaldehyde.

$^1$H NMR (400 MHz, DMSO) δ 10.64 (s, 1H), 8.03-7.97 (m, 3H), 7.38-7.27 (m, 3H), 7.23-7.09 (m, 3H), 7.02 (d, J=2.4 Hz, 1H), 6.95 (d, J=2.3 Hz, 1H), 6.89 (dd, J=8.4, 2.7 Hz, 1H), 6.68 (d, J=3.3 Hz, 1H), 5.14 (s, 1H), 5.01 (q, J=12.2 Hz, 2H), 3.96-3.89 (m, 1H), 3.77 (s, 3H), 3.72 (s, 3H), 3.21-3.05 (m, 2H), 2.84-2.75 (m, 2H), 2.70-2.60 (m, 1H), 2.56 (d, J=12.7 Hz, 1H), 2.36 (q, J=8.0 Hz, 2H), 1.06 (t, J=8.0 Hz, 3H).

LRMS (ESI, m/z): 563 [M+H]$^+$.

Example B28 2-((4-ethylbenzyl)oxo)-8-(4-fluorophenyl)-3-methoxy-5,6,8,9,14,14a-hexahydroindole[3',2':4,5]pyridine[2,1-a]isoquinoline (B28)

The target compound B28 was synthesized by repeating A28 with 4-fluorobenzaldehyde.

$^1$H NMR (400 MHz, DMSO) δ 10.64 (s, 1H), 8.03-7.97 (m, 3H), 7.38-7.27 (m, 3H), 7.23-7.09 (m, 4H), 7.02 (d, J=2.4 Hz, 1H), 6.95 (d, J=2.3 Hz, 1H), 6.89 (dd, J=8.4, 2.7 Hz, 1H), 6.68 (d, J=3.3 Hz, 1H), 5.14 (s, 1H), 5.01 (q, J=12.2 Hz, 2H), 3.96-3.89 (m, 1H), 3.77 (s, 3H), 3.21-3.05 (m, 2H), 2.84-2.75 (m, 2H), 2.70-2.60 (m, 1H), 2.56 (d, J=12.7 Hz, 1H), 2.36 (q, J=8.0 Hz, 2H), 1.06 (t, J=8.0 Hz, 3H).

LRMS (ESI, m/z): 533 [M+H]$^+$.

Example B29 8-(4-Fluorophenyl)-3,12-dimethoxy-2-(naphthalen-2-ylmethoxy)-5,6,8,9,14,14a-hexahydroindolo[3',2':4,5]pyridine[2,1-a]isoquinoline (B29)

The target compound B29 was synthesized by repeating A29 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 10H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.72 (s, 3H), 3.16 (dd, J=15.5, 4.7 Hz, 2H), 2.87-2.72 (m, 2H), 2.69-2.51 (m, 2H).

LRMS (ESI, m/z): 585 [M+H]$^+$.

Example B30 8-(4-Fluorophenyl)-3-methoxy-2-(naphthalen-2-ylmethoxy)-5,6,8,9,14,14a-hexahydroindolo[3',2':4,5]pyridine[2,1-a]isoquinoline (B30)

The target compound B30 was synthesized by repeating A30 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 11H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.16 (dd, J=15.5, 4.7 Hz, 2H), 2.87-2.72 (m, 2H), 2.69-2.51 (m, 2H).

LRMS (ESI, m/z): 555 [M+H]$^+$.

Example B31 4-(((8-(4-Fluorophenyl)-3,12-dimethoxy-5,6,8,9,14,14a-hexahydroindole[3',2':4,5]pyridine[2,1-a]isoquinolin-2-yl)oxo)methyl)benzoate (B31)

The target compound B31 was synthesized by repeating A31 with 4-fluorobenzaldehyde.

$^1$H NMR (400 MHz, DMSO) δ 10.64 (s, 1H), 8.03-7.97 (m, 3H), 7.38-7.27 (m, 3H), 7.23-7.09 (m, 3H), 7.02 (d, J=2.4 Hz, 1H), 6.95 (d, J=2.3 Hz, 1H), 6.89 (dd, J=8.4, 2.7 Hz, 1H), 6.68 (d, J=3.3 Hz, 1H), 5.14 (s, 1H), 5.01 (q, J=12.2 Hz, 2H), 3.96-3.89 (m, 1H), 3.77 (s, 3H), 3.76 (s, 3H), 3.72 (s, 3H), 3.21-3.05 (m, 2H), 2.84-2.75 (m, 2H), 2.70-2.60 (m, 1H), 2.56 (d, J=12.7 Hz, 1H).

LRMS (ESI, m/z): 593 [M+H]$^+$.

Example B32 4-(((8-(4-Fluorophenyl)-3-methoxy-5,6,8,9,14,14a-hexahydroindole[3',2':4,5]pyridine[2,1-a]isoquinolin-2-yl)oxo)methyl)benzoate (B31)

The target compound B32 was synthesized by repeating A32 with 4-fluorobenzaldehyde.

$^1$H NMR (400 MHz, DMSO) δ 10.64 (s, 1H), 8.03-7.97 (m, 3H), 7.38-7.27 (m, 3H), 7.23-7.09 (m, 4H), 7.02 (d, J=2.4 Hz, 1H), 6.95 (d, J=2.3 Hz, 1H), 6.89 (dd, J=8.4, 2.7 Hz, 1H), 6.68 (d, J=3.3 Hz, 1H), 5.14 (s, 1H), 5.01 (q, J=12.2 Hz, 2H), 3.96-3.89 (m, 1H), 3.77 (s, 3H), 3.72 (s, 3H), 3.21-3.05 (m, 2H), 2.84-2.75 (m, 2H), 2.70-2.60 (m, 1H), 2.56 (d, J=12.7 Hz, 1H).

LRMS (ESI, m/z): 563 [M+H]$^+$.

Example B33 2-((4-(1H-pyrazol-1-yl)benzyl)oxo)-8-(4-fluorophenyl)-3,12-dimethoxy-5,6,8,9,14,14a-hexahydroindole[3',2':4,5]pyridine[2,1-a]isoquinoline (B33)

The target compound B33 was synthesized by repeating A33 with 4-fluorobenzaldehyde.

$^1$H NMR (400 MHz, DMSO) δ 10.70 (s, 1H), 7.87 (d, J=8 Hz, 1H), 7.62-7.45 (m, 5H), 7.26-7.09 (m, 4H), 7.05-6.84 (m, 3H), 6.79-6.69 (m, 2H), 6.47 (q, J=8 Hz, 1H), 5.11 (s, 1H), 4.16 (d, J=15.1 Hz, 1H), 3.77 (d, J=11.4 Hz, 6H), 3.64 (d, J=15.6 Hz, 1H), 3.54 (d, J=7.2 Hz, 1H), 3.31 (s, 1H), 3.14 (s, 1H), 2.94 (d, J=11.4 Hz, 1H), 2.64 (dd, J=21.1, 13.3 Hz, 2H), 2.40-2.27 (m, 1H).

LRMS (ESI, m/z): 601 [M+H]$^+$.

Example B34 2-((4-(1H-pyrazol-1-yl)benzyl)oxo)-8-(4-fluorophenyl)-3-methoxy-5,6,8,9,14,14a-hexahydroindole[3',2':4,5]pyridine[2,1-a]isoquinoline (B34)

The target compound B34 was synthesized by repeating A34 with 4-fluorobenzaldehyde.

$^1$H NMR (400 MHz, DMSO) δ 10.70 (s, 1H), 7.87 (d, J=8 Hz, 1H), 7.62-7.45 (m, 5H), 7.26-7.09 (m, 5H), 7.05-6.84 (m, 3H), 6.79-6.69 (m, 2H), 6.47 (q, J=8 Hz, 1H), 5.11 (s, 1H), 4.16 (d, J=15.1 Hz, 1H), 3.77 (s, 3H), 3.64 (d, J=15.6 Hz, 1H), 3.54 (d, J=7.2 Hz, 1H), 3.31 (s, 1H), 3.14 (s, 1H), 2.94 (d, J=11.4 Hz, 1H), 2.64 (dd, J=21.1, 13.3 Hz, 2H), 2.40-2.27 (m, 1H).

LRMS (ESI, m/z): 571 [M+H]$^+$.

Example B35 2-butoxy-8-(4-fluorophenyl)-3,12-dimethoxy-5,6,8,9,14,14a-hexahydroindole[3',2':4,5]pyridine[2,1-a]isoquinoline (B35)

The target compound B35 was synthesized by repeating A35 with 4-fluorobenzaldehyde.

$^1$H NMR (400 MHz, DMSO) δ 10.66 (s, 1H), 7.36 (d, J=8.8 Hz, 1H), 7.26-7.09 (m, 4H), 6.98 (d, J=2.1 Hz, 1H), 6.96 (s, 1H), 6.73 (dd, J=8.7, 2.3 Hz, 1H), 6.69 (s, 1H), 5.37 (t, J=12.0 Hz, 2H), 4.16 (s, 1H), 3.92 (t, J=5.9 Hz, 2H), 3.77 (s, 3H), 3.65 (s, 1H), 3.44-3.40 (d, J=15.0 Hz, 1H), 3.12 (d, J=9.6 Hz, 1H), 2.47-2.37 (t, J=5.9 Hz, 2H), 1.77-1.61 (m, 2H), 1.51-1.36 (m, 2H), 0.94 (t, J=7.4 Hz, 3H).

LRMS (ESI, m/z): 501 [M+H]$^+$.

Example B36 2-butoxy-8-(4-fluorophenyl)-3-methoxy-5,6,8,9,14,14a-hexahydroindole[3',2':4,5]pyridine[2,1-a]isoquinoline (B36)

The target compound B36 was synthesized by repeating A36 with 4-fluorobenzaldehyde.

$^1$H NMR (400 MHz, DMSO) δ 10.66 (s, 1H), 7.36 (d, J=8.8 Hz, 1H), 7.26-7.09 (m, 5H), 6.98 (d, J=2.1 Hz, 1H), 6.96 (s, 1H), 6.73 (dd, J=8.7, 2.3 Hz, 1H), 6.69 (s, 1H), 5.37 (t, J=12.0 Hz, 2H), 4.16 (s, 1H), 3.92 (t, J=5.9 Hz, 2H), 3.77 (s, 3H), 3.72 (s, 3H), 3.65 (s, 1H), 3.44-3.40 (d, J=15.0 Hz, 1H), 3.12 (d, J=9.6 Hz, 1H), 2.47-2.37 (t, J=5.9 Hz, 2H), 1.77-1.61 (m, 2H), 1.51-1.36 (m, 2H), 0.94 (t, J=7.4 Hz, 3H).

LRMS (ESI, m/z): 471 [M+H]$^+$.

Example B37 8-(4-Fluorophenyl)-12-methoxy-5,6,8,9,14,14a-hexahydroindole[3',2':4,5]pyridine[2,1-a]thiophene[3,2-g]isoquinoline (B37)

The target compound B37 was synthesized by repeating A37 with 4-fluorobenzaldehyde.

$^1$H NMR (400 MHz, DMSO) δ 10.63 (s, 1H), 7.78-7.37 (m, 4H), 7.29-7.07 (m, 5H), 7.03-6.87 (m, 2H), 4.18 (d, J=15.1 Hz, 1H), 3.75 (s, 3H), 3.68 (d, J=15.2 Hz, 1H), 3.58 (dd, J=10.4, 3.1 Hz, 1H), 3.35 (d, J=3.2 Hz, 1H), 3.16-3.06 (m, 1H), 2.64 (dd, J=18.2, 10.6 Hz, 2H), 2.44 (d, J=12.5 Hz, 1H).

LRMS (ESI, m/z): 455 [M+H]$^+$.

Example B38 8-(4-Fluorophenyl)-5,6,8,9,14,14a-hexahydroindole[3',2':4,5]pyridine[2,1-a]thiophene[3,2-g]isoquinoline (B38)

The target compound B38 was synthesized by repeating A38 with 4-fluorobenzaldehyde.

$^1$H NMR (400 MHz, DMSO) δ 10.63 (s, 1H), 7.78-7.37 (m, 4H), 7.29-7.07 (m, 5H), 7.03-6.87 (m, 2H), 4.18 (d, J=15.1 Hz, 1H), 3.75 (s, 3H), 3.68 (d, J=15.2 Hz, 1H), 3.58 (dd, J=10.4, 3.1 Hz, 1H), 3.35 (d, J=3.2 Hz, 1H), 3.16-3.06 (m, 1H), 2.64 (dd, J=18.2, 10.6 Hz, 2H), 2.44 (d, J=12.5 Hz, 1H).

LRMS (ESI, m/z): 425 [M+H]$^+$.

Example B39 8-(4-Fluorophenyl)-3,12-dimethoxy-2-(2,2,2-trifluoroethoxy)-5,6,8,9,14,14a-hexahydroindolo[3',2':4,5]pyridine[2,1-a]isoquinoline (B39)

The target compound B39 was synthesized by repeating A39 with 4-fluorobenzaldehyde.

$^1$H NMR (400 MHz, DMSO) δ 10.71 (s, 1H), 7.37 (d, J=8.8 Hz, 1H), 7.29-7.07 (m, 5H), 6.96 (d, J=2.4 Hz, 1H), 6.79 (s, 1H), 6.74 (dd, J=8.8, 2.5 Hz, 1H), 5.37 (s, 2H), 4.76-4.65 (m, 2H), 4.17 (d, J=15.0 Hz, 1H), 3.78 (s, 3H), 3.77 (s, 3H), 3.65 (d, J=14.8 Hz, 1H), 3.14 (dd, J=8.5, 2.6 Hz, 1H), 2.98 (dd, J=18.7, 8.2 Hz, 1H), 2.74-2.60 (m, 1H), 2.46-2.35 (m, 1H).

LRMS (ESI, m/z): 527 [M+H]$^+$.

Example B40 8-(4-Fluorophenyl)-3-methoxy-2-(2,2,2-trifluoroethoxy)-5,6,8,9,14,14a-hexahydroindolo[3',2':4,5]pyridine[2,1-a]isoquinoline (B40)

The target compound B40 was synthesized by repeating A40 with 4-fluorobenzaldehyde.

$^1$H NMR (400 MHz, DMSO) δ 10.71 (s, 1H), 7.37 (d, J=8.8 Hz, 1H), 7.29-7.07 (m, 6H), 6.96 (d, J=2.4 Hz, 1H), 6.79 (s, 1H), 6.74 (dd, J=8.8, 2.5 Hz, 1H), 5.37 (s, 2H), 4.76-4.65 (m, 2H), 4.17 (d, J=15.0 Hz, 1H), 3.77 (s, 3H), 3.65 (d, J=14.8 Hz, 1H), 3.14 (dd, J=8.5, 2.6 Hz, 1H), 2.98 (dd, J=18.7, 8.2 Hz, 1H), 2.74-2.60 (m, 1H), 2.46-2.35 (m, 1H).

LRMS (ESI, m/z): 497 [M+H]$^+$.

Example B41 8-(4-Fluorophenyl)-3,12-dimethoxy-2-((4-(methylsulfonyl)benzyl)oxy)-5,6,8,9,14,14a-hexahydroindolo[3',2':4,5]pyridine[2,1-a]isoquinoline (B41)

The target compound B41 was synthesized by repeating A41 with 4-fluorobenzaldehyde.

$^1$H NMR (400 MHz, DMSO) δ 10.67 (s, 1H), 7.39-7.35 (m, 3H), 7.29-7.07 (m, 6H), 7.06 (s, 1H), 6.96 (d, J=2.3 Hz, 2H), 6.74 (dd, J=9.7, 3.3 Hz, 2H), 5.05 (q, J=11.6 Hz, 2H), 4.17 (d, J=14.9 Hz, 1H), 3.79 (s, 3H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.05 (s, 3H), 3.03-2.86 (m, 1H), 2.74-2.57 (m, 1H), 2.37 (m, 1H).

LRMS (ESI, m/z): 613 [M+H]$^+$.

Example B42 8-(4-Fluorophenyl)-3-methoxy-2-((4-(methylsulfonyl)benzyl)oxy)-5,6,8,9,14,14a-hexahydroindolo[3',2':4,5]pyridine[2,1-a]isoquinoline (B42)

The target compound B42 was synthesized by repeating A42 with 4-fluorobenzaldehyde.

$^1$H NMR (400 MHz, DMSO) δ 10.67 (s, 1H), 7.39-7.35 (m, 3H), 7.29-7.07 (m, 7H), 7.06 (s, 1H), 6.96 (d, J=2.3 Hz, 2H), 6.74 (dd, J=9.7, 3.3 Hz, 2H), 5.05 (q, J=11.6 Hz, 2H), 4.17 (d, J=14.9 Hz, 1H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.05 (s, 3H), 3.03-2.86 (m, 1H), 2.74-2.57 (m, 1H), 2.37 (m, 1H).

LRMS (ESI, m/z): 583 [M+H]$^+$.

Example B43 2-(benzyloxy)-11-fluoro-8-(4-fluorophenyl)-3-methoxy-5,6,8,9,14,14a-hexahydroindole[3',2':4,5]pyridine[2,1-a]isoquinoline (B43)

The target compound B43 was synthesized by repeating A43 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.72 (s, 3H), 3.16 (dd, J=15.5, 4.7 Hz, 2H), 2.87-2.72 (m, 2H), 2.69-2.51 (m, 2H).

LRMS (ESI, m/z): 523 [M+H]$^+$.

Example B44 2-(benzyloxy)-12-fluoro-8-(4-fluorophenyl)-3-methoxy-5,6,8,9,14,14a-hexahydroindole[3 2':4,5]pyridine[2,1-a]isoquinoline (B44)

The target compound B44 was synthesized by repeating A44 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.72 (s, 3H), 3.16 (dd, J=15.5, 4.7 Hz, 2H), 2.87-2.72 (m, 2H), 2.69-2.51 (m, 2H).

LRMS (ESI, m/z): 523 [M+H]$^+$.

Example B45 2-(benzyloxy)-13-fluoro-8-(4-fluorophenyl)-3-methoxy-5,6,8,9,14,14a-hexahydroindole[3 2':4,5]pyridine[2,1-a]isoquinoline (B45)

The target compound B45 was synthesized by repeating A45 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.72 (s, 3H), 3.16 (dd, J=15.5, 4.7 Hz, 2H), 2.87-2.72 (m, 2H), 2.69-2.51 (m, 2H).

LRMS (ESI, m/z): 523 [M+H]$^+$.

Example B46 2-(benzyloxy)-11-chloro-8-(4-fluorophenyl)-3-methoxy-5,6,8,9,14,14a-hexahydroindole[3',2': 4,5]pyridine[2,1-a]isoquinoline (B46)

The target compound B46 was synthesized by repeating A46 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.72 (s, 3H), 3.16 (dd, J=15.5, 4.7 Hz, 2H), 2.87-2.72 (m, 2H), 2.69-2.51 (m, 2H).

LRMS (ESI, m/z): 540 [M+H]$^+$.

Example B47 2-(benzyloxy)-12-chloro-8-(4-fluorophenyl)-3-methoxy-5,6,8,9,14,14a-hexahydroindole[3',2': 4,5]pyridine[2,1-a]isoquinoline (B47)

The target compound B47 was synthesized by repeating A47 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.72 (s, 3H), 3.16 (dd, J=15.5, 4.7 Hz, 2H), 2.87-2.72 (m, 2H), 2.69-2.51 (m, 2H).

LRMS (ESI, m/z): 540 [M+H]$^+$.

Example B48 2-(benzyloxy)-13-chloro-8-(4-fluorophenyl)-3-methoxy-5,6,8,9,14,14a-hexahydroindole[3',2': 4,5]pyridine[2,1-a]isoquinoline (B48)

The target compound B48 was synthesized by repeating A48 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.72 (s, 3H), 3.16 (dd, J=15.5, 4.7 Hz, 2H), 2.87-2.72 (m, 2H), 2.69-2.51 (m, 2H).

LRMS (ESI, m/z): 540 [M+H]$^+$.

Example B49 2-(benzyloxy)-11-bromo-8-(4-fluorophenyl)-3-methoxy-5,6,8,9,14,14a-hexahydroindole[3',2':4,5]pyridine[2,1-a]isoquinoline (B49)

The target compound B49 was synthesized by repeating A49 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.72 (s, 3H), 3.16 (dd, J=15.5, 4.7 Hz, 2H), 2.87-2.72 (m, 2H), 2.69-2.51 (m, 2H).

LRMS (ESI, m/z): 583 [M+H]$^+$, 585 [M+H]$^+$.

Example B50 2-(benzyloxy)-12-bromo-8-(4-fluorophenyl)-3-methoxy-5,6,8,9,14,14a-hexahydroindole[3',2':4,5]pyridine[2,1-a]isoquinoline (B50)

The target compound B50 was synthesized by repeating A50 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.72 (s, 3H), 3.16 (dd, J=15.5, 4.7 Hz, 2H), 2.87-2.72 (m, 2H), 2.69-2.51 (m, 2H).

LRMS (ESI, m/z): 583 [M+H]$^+$, 585 [M+H]$^+$.

Example B51 2-(benzyloxy)-13-bromo-8-(4-fluorophenyl)-3-methoxy-5,6,8,9,14,14a-hexahydroindole[3',2':4,5]pyridine[2,1-a]isoquinoline (B51)

The target compound B51 was synthesized by repeating A51 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.72 (s, 3H), 3.16 (dd, J=15.5, 4.7 Hz, 2H), 2.87-2.72 (m, 2H), 2.69-2.51 (m, 2H).

LRMS (ESI, m/z): 583 [M+H]$^+$, 585 [M+H]$^+$.

Example B52 2-(benzyloxy)-8-(4-fluorophenyl)-3-methoxy-5,6,8,9,14,14a-hexahydroindole[3',2':4,5]pyridine[2,1-a]isoquinoline-12-phenol (B52)

The target compound B52 was synthesized by repeating A52 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 9H), 6.97 (d, J=2.4 Hz, 1H), 6.85 (s, 1H), 6.76 (s, 1H), 6.68 (dd, J=8.7, 2.5 Hz, 1H), 5.32 (s, 1H), 5.12 (s, 1H), 4.99 (s, 2H), 3.94 (dd, J=10.4, 4.7 Hz, 1H), 3.75 (s, 3H), 3.16 (dd, J=15.5, 4.7 Hz, 2H), 2.87-2.72 (m, 2H), 2.69-2.51 (m, 2H).

LRMS (ESI, m/z): 521 [M+H]$^+$.

Example B53 2-(benzyloxy)-8-(4-fluorophenyl)-3-methoxy-11-methyl-5,6,8,9,14,14a-hexahydroindole[3',2':4,5]pyridine[2,1-a]isoquinoline (B53)

The target compound B53 was synthesized by repeating A53 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 9H), 6.97 (d, J=2.4 Hz, 1H), 6.76 (s, 1H), 6.68 (dd, J=8.7, 2.5 Hz, 1H), 5.32 (s, 1H), 5.12 (s, 1H), 4.99 (s, 2H), 3.94 (dd, J=10.4, 4.7 Hz, 1H), 3.75 (s, 3H), 3.16 (dd, J=15.5, 4.7 Hz, 2H), 2.87-2.72 (m, 2H), 2.69-2.51 (m, 2H), 2.35 (s, 3H).

LRMS (ESI, m/z): 519 [M+H]$^+$.

Example B54 2-(benzyloxy)-8-(4-fluorophenyl)-3-methoxy-11-methyl-5,6,8,9,14,14a-hexahydroindole[3',2':4,5]pyridine[2,1-a]isoquinoline (B54)

The target compound B54 was synthesized by repeating A54 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 9H), 6.97 (d, J=2.4 Hz, 1H), 6.76 (s, 1H), 6.68 (dd, J=8.7, 2.5 Hz, 1H), 5.32 (s, 1H), 5.12 (s, 1H), 4.99 (s, 2H), 3.94 (dd, J=10.4, 4.7 Hz, 1H), 3.75 (s, 3H), 3.16 (dd, J=15.5, 4.7 Hz, 2H), 2.87-2.72 (m, 2H), 2.69-2.51 (m, 2H), 2.35 (q, J=8.4 Hz, 2H), 1.05 (t, J=8.4 Hz, 3H).

LRMS (ESI, m/z): 533 [M+H]$^+$.

Example B55 3-(benzyloxy)-8-(4-fluorophenyl)-2,12-dimethoxy-5,6,8,9,14,14a-hexahydroindole[3',2':4,5]pyridine[2,1-a]isoquinoline (B55)

The target compound B55 was synthesized by repeating A55 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 8H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.72 (s, 3H), 3.16 (dd, J=15.5, 4.7 Hz, 2H), 2.87-2.72 (m, 2H), 2.69-2.51 (m, 2H).

LRMS (ESI, m/z): 535 [M+H]$^+$.

Example B56 3-(benzyloxy)-8-(4-fluorophenyl)-2-methoxy-5,6,8,9,14,14a-hexahydroindole[3',2':4,5]pyridine[2,1-a]isoquinoline (B56)

The target compound B56 was synthesized by repeating A56 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 9H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.16 (dd, J=15.5, 4.7 Hz, 2H), 2.87-2.72 (m, 2H), 2.69-2.51 (m, 2H).

LRMS (ESI, m/z): 505 [M+H]$^+$.

Example B57 8-(4-Fluorophenyl)-2,12-dimethoxy-3-((4-(trifluoromethyl)benzyl)oxy)-5,6,8,9,14,14a-hexahydroindolo[3',2':4,5]pyridine[2,1-a]isoquinoline (B57)

The target compound B57 was synthesized by repeating A57 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.72 (s, 3H), 3.16 (dd, J=15.5, 4.7 Hz, 2H), 2.87-2.72 (m, 2H), 2.69-2.51 (m, 2H).

LRMS (ESI, m/z): 603 [M+H]$^+$.

Example B58 8-(4-Fluorophenyl)-2-methoxy-3-((4-(trifluoromethyl)benzyl)oxy)-5,6,8,9,14,14a-hexahydroindolo[3',2':4,5]pyridine[2,1-a]isoquinoline (B58)

The target compound B58 was synthesized by repeating A58 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 8H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.16 (dd, J=15.5, 4.7 Hz, 2H), 2.87-2.72 (m, 2H), 2.69-2.51 (m, 2H).

LRMS (ESI, m/z): 573 [M+H]$^+$.

Example B59 3-((4-fluorobenzyl)oxo)-8-(4-fluorophenyl)-2,12-dimethoxy-5,6,8,9,14,14a-hexahydroindole[3',2':4,5]pyridine[2,1-a]isoquinoline (B59)

The target compound B59 was synthesized by repeating A59 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.72 (s, 3H), 3.16 (dd, J=15.5, 4.7 Hz, 2H), 2.87-2.72 (m, 2H), 2.69-2.51 (m, 2H).

LRMS (ESI, m/z): 553 [M+H]$^+$.

Example B60 3-((4-fluorobenzyl)oxo)-8-(4-fluorophenyl)-2-methoxy-5,6,8,9,14,14a-hexahydroindole[3',2': 4,5]pyridine[2,1-a]isoquinoline (B60)

The target compound B60 was synthesized by repeating A60 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 9H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.16 (dd, J=15.5, 4.7 Hz, 2H), 2.87-2.72 (m, 2H), 2.69-2.51 (m, 2H).

LRMS (ESI, m/z): 523 [M+H]$^+$.

Example B61 3-((3-fluorobenzyl)oxo)-8-(4-fluorophenyl)-2,12-dimethoxy-5,6,8,9,14,14a-hexahydroindole[3',2':4,5]pyridine[2,1-a]isoquinoline (B61)

The target compound B61 was synthesized by repeating A61 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.72 (s, 3H), 3.16 (dd, J=15.5, 4.7 Hz, 2H), 2.87-2.72 (m, 2H), 2.69-2.51 (m, 2H).

LRMS (ESI, m/z): 553 [M+H]$^+$.

Example B62 3-((3-fluorobenzyl)oxo)-8-(4-fluorophenyl)-2-methoxy-5,6,8,9,14,14a-hexahydroindole[3',2': 4,5]pyridine[2,1-a]isoquinoline (B62)

The target compound B62 was synthesized by repeating A62 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 9H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.16 (dd, J=15.5, 4.7 Hz, 2H), 2.87-2.72 (m, 2H), 2.69-2.51 (m, 2H).

LRMS (ESI, m/z): 523 [M+H]$^+$.

Example B63 3-((2-fluorobenzyl)oxo)-8-(4-fluorophenyl)-2,12-dimethoxy-5,6,8,9,14,14a-hexahydroindole[3',2':4,5]pyridine[2,1-a]isoquinoline (B63)

The target compound B63 was synthesized by repeating A63 with 4-fluorobenzaldehyde.
$^1$H NMR (400 MHz, DMSO) δ 10.70 (s, 1H), 7.48 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.72 (s, 3H), 3.16 (dd, J=15.5, 4.7 Hz, 2H), 2.87-2.72 (m, 2H), 2.69-2.51 (m, 2H).
LRMS (ESI, m/z): 553 [M+H]$^+$.

Example B64 3-((2-fluorobenzyl)oxo)-8-(4-fluorophenyl)-2-methoxy-5,6,8,9,14,14a-hexahydroindole[3',2': 4,5]pyridine[2,1-a]isoquinoline (B64)

The target compound B64 was synthesized by repeating A64 with 4-fluorobenzaldehyde.
$^1$H NMR (400 MHz, DMSO) δ 10.70 (s, 1H), 7.48 (dd, J=8.6, 5.7 Hz, 2H), 7.26-7.09 (m, 9H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.16 (dd, J=15.5, 4.7 Hz, 2H), 2.87-2.72 (m, 2H), 2.69-2.51 (m, 2H).
LRMS (ESI, m/z): 523 [M+H]$^+$.

Example B65 8-(4-Fluorophenyl)-2,12-dimethoxy-3-((4-methoxybenzyl)oxo)-5,6,8,9,14,14a-hexahydroindolo[3',2':4,5]pyridine[2,1-a]isoquinoline (B65)

The target compound B65 was synthesized by repeating A65 with 4-fluorobenzaldehyde.
$^1$H NMR (400 MHz, DMSO) δ 10.64 (s, 1H), 8.03-7.97 (m, 3H), 7.38-7.27 (m, 3H), 7.23-7.09 (m, 3H), 7.02 (d, J=2.4 Hz, 1H), 6.95 (d, J=2.3 Hz, 1H), 6.89 (dd, J=8.4, 2.7 Hz, 1H), 6.68 (d, J=3.3 Hz, 1H), 5.14 (s, 1H), 5.01 (q, J=12.2 Hz, 2H), 3.96-3.89 (m, 1H), 3.77 (s, 3H), 3.76 (s, 3H), 3.72 (s, 3H), 3.21-3.05 (m, 2H), 2.84-2.75 (m, 2H), 2.70-2.60 (m, 1H), 2.56 (d, J=12.7 Hz, 1H).
LRMS (ESI, m/z): 565 [M+H]$^+$.

Example B66 8-(4-Fluorophenyl)-2-methoxy-2-((4-methoxybenzyl)oxo)-5,6,8,9,14,14a-hexahydroindolo[3',2':4,5]pyridine[2,1-a]isoquinoline (B66)

The target compound B66 was synthesized by repeating A66 with 4-fluorobenzaldehyde.
$^1$H NMR (400 MHz, DMSO) δ 10.64 (s, 1H), 8.03-7.97 (m, 3H), 7.38-7.27 (m, 3H), 7.23-7.09 (m, 4H), 7.02 (d, J=2.4 Hz, 1H), 6.95 (d, J=2.3 Hz, 1H), 6.89 (dd, J=8.4, 2.7 Hz, 1H), 6.68 (d, J=3.3 Hz, 1H), 5.14 (s, 1H), 5.01 (q, J=12.2 Hz, 2H), 3.96-3.89 (m, 1H), 3.77 (s, 3H), 3.72 (s, 3H), 3.21-3.05 (m, 2H), 2.84-2.75 (m, 2H), 2.70-2.60 (m, 1H), 2.56 (d, J=12.7 Hz, 1H).
LRMS (ESI, m/z): 535 [M+H]$^+$.

Example B67 8-(4-Fluorophenyl)-2,12-dimethoxy-3-((3-methoxybenzyl)oxo)-5,6,8,9,14,14a-hexahydroindolo[3',2':4,5]pyridine[2,1-a]isoquinoline (B67)

The target compound B67 was synthesized by repeating A67 with 4-fluorobenzaldehyde.
$^1$H NMR (400 MHz, DMSO) δ 10.64 (s, 1H), 8.03-7.97 (m, 3H), 7.38-7.27 (m, 3H), 7.23-7.09 (m, 3H), 7.02 (d, J=2.4 Hz, 1H), 6.95 (d, J=2.3 Hz, 1H), 6.89 (dd, J=8.4, 2.7 Hz, 1H), 6.68 (d, J=3.3 Hz, 1H), 5.14 (s, 1H), 5.01 (q, J=12.2 Hz, 2H), 3.96-3.89 (m, 1H), 3.77 (s, 3H), 3.76 (s, 3H), 3.72 (s, 3H), 3.21-3.05 (m, 2H), 2.84-2.75 (m, 2H), 2.70-2.60 (m, 1H), 2.56 (d, J=12.7 Hz, 1H).
LRMS (ESI, m/z): 565 [M+H]$^+$.

Example B68 8-(4-Fluorophenyl)-2-methoxy-3-((3-methoxybenzyl)oxo)-5,6,8,9,14,14a-hexahydroindolo[3',2':4,5]pyridine[2,1-a]isoquinoline (B68)

The target compound B68 was synthesized by repeating A68 with 4-fluorobenzaldehyde.
$^1$H NMR (400 MHz, DMSO) δ 10.64 (s, 1H), 8.03-7.97 (m, 3H), 7.38-7.27 (m, 3H), 7.23-7.09 (m, 4H), 7.02 (d, J=2.4 Hz, 1H), 6.95 (d, J=2.3 Hz, 1H), 6.89 (dd, J=8.4, 2.7 Hz, 1H), 6.68 (d, J=3.3 Hz, 1H), 5.14 (s, 1H), 5.01 (q, J=12.2 Hz, 2H), 3.96-3.89 (m, 1H), 3.77 (s, 3H), 3.72 (s, 3H), 3.21-3.05 (m, 2H), 2.84-2.75 (m, 2H), 2.70-2.60 (m, 1H), 2.56 (d, J=12.7 Hz, 1H).
LRMS (ESI, m/z): 535 [M+H]$^+$.

Example B69 8-(4-Fluorophenyl)-2,12-dimethoxy-3-((4-methylbenzyl)oxo)-5,6,8,9,14,14a-hexahydroindolo[3',2':4,5]pyridine[2,1-a]isoquinoline (B69)

The target compound B69 was synthesized by repeating A69 with 4-fluorobenzaldehyde.
$^1$H NMR (400 MHz, DMSO) δ 10.64 (s, 1H), 8.03-7.97 (m, 3H), 7.38-7.27 (m, 3H), 7.23-7.09 (m, 3H), 7.02 (d, J=2.4 Hz, 1H), 6.95 (d, J=2.3 Hz, 1H), 6.89 (dd, J=8.4, 2.7 Hz, 1H), 6.68 (d, J=3.3 Hz, 1H), 5.14 (s, 1H), 5.01 (q, J=12.2 Hz, 2H), 3.96-3.89 (m, 1H), 3.77 (s, 3H), 3.72 (s, 3H), 3.21-3.05 (m, 2H), 2.84-2.75 (m, 2H), 2.70-2.60 (m, 1H), 2.56 (d, J=12.7 Hz, 1H), 2.36 (s, 3H).
LRMS (ESI, m/z): 549 [M+H]$^+$.

Example B70 8-(4-Fluorophenyl)-2-methoxy-3-((4-methylbenzyl)oxo)-5,6,8,9,14,14a-hexahydroindolo[3',2':4,5]pyridine[2,1-a]isoquinoline (B70)

The target compound B70 was synthesized by repeating A70 with 4-fluorobenzaldehyde.
$^1$H NMR (400 MHz, DMSO) δ 10.64 (s, 1H), 8.03-7.97 (m, 3H), 7.38-7.27 (m, 3H), 7.23-7.09 (m, 4H), 7.02 (d, J=2.4 Hz, 1H), 6.95 (d, J=2.3 Hz, 1H), 6.89 (dd, J=8.4, 2.7 Hz, 1H), 6.68 (d, J=3.3 Hz, 1H), 5.14 (s, 1H), 5.01 (q, J=12.2 Hz, 2H), 3.96-3.89 (m, 1H), 3.77 (s, 3H), 3.21-3.05 (m, 2H), 2.84-2.75 (m, 2H), 2.70-2.60 (m, 1H), 2.56 (d, J=12.7 Hz, 1H), 2.36 (s, 3H).
LRMS (ESI, m/z): 519 [M+H]$^+$.

Example B71 3-((4-chlorobenzyl)oxo)-8-(4-fluorophenyl)-2,12-dimethoxy-5,6,8,9,14,14a-hexahydroindole[3',2':4,5]pyridine[2,1-a]isoquinoline (B71)

The target compound B71 was synthesized by repeating A71 with 4-fluorobenzaldehyde.
$^1$H NMR (400 MHz, DMSO) δ 10.70 (s, 1H), 7.39 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.72 (s, 3H), 3.16 (dd, J=15.5, 4.7 Hz, 2H), 2.87-2.72 (m, 2H), 2.69-2.51 (m, 2H).
LRMS (ESI, m/z): 570 [M+H]$^+$.

Example B72 3-((4-chlorobenzyl)oxo)-8-(4-fluorophenyl)-2-methoxy-5,6,8,9,14,14a-hexahydroindole[3,2': 4,5]pyridine[2,1-a]isoquinoline (B72)

The target compound B72 was synthesized by repeating A72 with 4-fluorobenzaldehyde.
$^{1}$H NMR (400 MHz, DMSO) δ 10.70 (s, 1H), 7.39 (dd, J=8.6, 5.7 Hz, 2H), 7.26-7.09 (m, 9H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.16 (dd, J=15.5, 4.7 Hz, 2H), 2.87-2.72 (m, 2H), 2.69-2.51 (m, 2H).
LRMS (ESI, m/z): 540 [M+H]$^{+}$.

Example B73 4-(((8-(4-Fluorophenyl)-2,12-dimethoxy-5,6,8,9,14,14a-hexahydroindole[3',2':4,5]pyridine[2,1-a]isoquinolin-3-yl)oxo)methyl)benzonitrile (B73)

The target compound B73 was synthesized by repeating A73 with 4-fluorobenzaldehyde.
$^{1}$H NMR (400 MHz, DMSO) δ 10.70 (s, 1H), 7.43 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.72 (s, 3H), 3.16 (dd, J=15.5, 4.7 Hz, 2H), 2.87-2.72 (m, 2H), 2.69-2.51 (m, 2H).
LRMS (ESI, m/z): 560 [M+H]$^{+}$.

Example B74 4-(((8-(4-Fluorophenyl)-2-methoxy-5,6,8,9,14,14a-hexahydroindole[3',2':4,5]pyridine[2,1-a]isoquinolin-3-yl)oxo)methyl)benzonitrile (B74)

The target compound B74 was synthesized by repeating A74 with 4-fluorobenzaldehyde.
$^{1}$H NMR (400 MHz, DMSO) δ 10.70 (s, 1H), 7.43 (dd, J=8.6, 5.7 Hz, 2H), 7.26-7.09 (m, 9H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.16 (dd, J=15.5, 4.7 Hz, 2H), 2.87-2.72 (m, 2H), 2.69-2.51 (m, 2H).
LRMS (ESI, m/z): 530 [M+H]$^{+}$.

Example B75 3-((4-bromobenzyl)oxo)-8-(4-fluorophenyl)-2,12-dimethoxy-5,6,8,9,14,14a-hexahydroindole[3',2':4,5]pyridine[2,1-a]isoquinoline (B75)

The target compound B75 was synthesized by repeating A75 with 4-fluorobenzaldehyde.
$^{1}$H NMR (400 MHz, DMSO) δ 10.70 (s, 1H), 7.35 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.72 (s, 3H), 3.16 (dd, J=15.5, 4.7 Hz, 2H), 2.87-2.72 (m, 2H), 2.69-2.51 (m, 2H).
LRMS (ESI, m/z): 613 [M+H]$^{+}$, 615 [M+H]$^{+}$.

Example B76 3-((4-bromobenzyl)oxo)-8-(4-fluorophenyl)-2-methoxy-5,6,8,9,14,14a-hexahydroindole[3,2': 4,5]pyridine[2,1-a]isoquinoline (B76)

The target compound B76 was synthesized by repeating A76 with 4-fluorobenzaldehyde.
$^{1}$H NMR (400 MHz, DMSO) δ 10.70 (s, 1H), 7.35 (dd, J=8.6, 5.7 Hz, 2H), 7.26-7.09 (m, 9H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.16 (dd, J=15.5, 4.7 Hz, 2H), 2.87-2.72 (m, 2H), 2.69-2.51 (m, 2H).
LRMS (ESI, m/z): 583 [M+H]$^{+}$, 585 [M+H]$^{+}$.

Example B77 3-((3-fluoro-4-(trifluoromethyl)benzyl)oxo)-8-(4-fluorophenyl)-2,12-dimethoxy-5,6,8,9,14,14a-hexahydroindole[3',2':4,5]pyridine[2,1-a]isoquinoline (B77)

The target compound B77 was synthesized by repeating A77 with 4-fluorobenzaldehyde.
$^{1}$H NMR (400 MHz, DMSO) δ 10.70 (s, 1H), 7.48 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.72 (s, 3H), 3.16 (dd, J=15.5, 4.7 Hz, 2H), 2.87-2.72 (m, 2H), 2.69-2.51 (m, 2H).
LRMS (ESI, m/z): 621 [M+H]$^{+}$.

Example B78 3-((3-fluoro-4-(trifluoromethyl)benzyl)oxo)-8-(4-fluorophenyl)-2-methoxy-5,6,8,9,14,14a-hexahydroindole[3',2':4,5]pyridine[2,1-a]isoquinoline (B78)

The target compound B78 was synthesized by repeating A78 with 4-fluorobenzaldehyde.
$^{1}$H NMR (400 MHz, DMSO) δ 10.70 (s, 1H), 7.48 (dd, J=8.6, 5.7 Hz, 2H), 7.26-7.09 (m, 9H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.16 (dd, J=15.5, 4.7 Hz, 2H), 2.87-2.72 (m, 2H), 2.69-2.51 (m, 2H).
LRMS (ESI, m/z): 591 [M+H]$^{+}$.

Example B79 3-((2-fluoro-4-(trifluoromethyl)benzyl)oxo)-8-(4-fluorophenyl)-2,12-dimethoxy-5,6,8,9,14,14a-hexahydroindole[3',2':4,5]pyridine[2,1-a]isoquinoline (B79)

The target compound B79 was synthesized by repeating A79 with 4-fluorobenzaldehyde.
$^{1}$H NMR (400 MHz, DMSO) δ 10.70 (s, 1H), 7.48 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.72 (s, 3H), 3.16 (dd, J=15.5, 4.7 Hz, 2H), 2.87-2.72 (m, 2H), 2.69-2.51 (m, 2H).
LRMS (ESI, m/z): 621 [M+H]$^{+}$.

Example B80 3-((2-fluoro-4-(trifluoromethyl)benzyl)oxo)-8-(4-fluorophenyl)-2-methoxy-5,6,8,9,14,14a-hexahydroindole[3',2':4,5]pyridine[2,1-a]isoquinoline (B80)

The target compound B80 was synthesized by repeating A80 with 4-fluorobenzaldehyde.
$^{1}$H NMR (400 MHz, DMSO) δ 10.70 (s, 1H), 7.48 (dd, J=8.6, 5.7 Hz, 2H), 7.26-7.09 (m, 9H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.16 (dd, J=15.5, 4.7 Hz, 2H), 2.87-2.72 (m, 2H), 2.69-2.51 (m, 2H).
LRMS (ESI, m/z): 591 [M+H]$^{+}$.

Example B81 3-((4-ethylbenzyl)oxo)-8-(4-fluorophenyl)-2,12-dimethoxy-5,6,8,9,14,14a-hexahydroindol e[3',2':4,5]pyridine[2,1-a]isoquinoline (B81)

The target compound B81 was synthesized by repeating A81 with 4-fluorobenzaldehyde.

$^1$H NMR (400 MHz, DMSO) δ 10.64 (s, 1H), 8.03-7.97 (m, 3H), 7.38-7.27 (m, 3H), 7.23-7.09 (m, 3H), 7.02 (d, J=2.4 Hz, 1H), 6.95 (d, J=2.3 Hz, 1H), 6.89 (dd, J=8.4, 2.7 Hz, 1H), 6.68 (d, J=3.3 Hz, 1H), 5.14 (s, 1H), 5.01 (q, J=12.2 Hz, 2H), 3.96-3.89 (m, 1H), 3.77 (s, 3H), 3.72 (s, 3H), 3.21-3.05 (m, 2H), 2.84-2.75 (m, 2H), 2.70-2.60 (m, 1H), 2.56 (d, J=12.7 Hz, 1H), 2.36 (q, J=8.0 Hz, 2H), 1.06 (t, J=8.0 Hz, 3H).

LRMS (ESI, m/z): 563 [M+H]$^+$.

Example B82 3-((4-ethylbenzyl)oxo)-8-(4-fluorophenyl)-2-methoxy-5,6,8,9,14,14a-hexahydroindole[3',2':4,5]pyridine[2,1-a]isoquinoline (B82)

The target compound B82 was synthesized by repeating A82 with 4-fluorobenzaldehyde.

$^1$H NMR (400 MHz, DMSO) δ 10.64 (s, 1H), 8.03-7.97 (m, 3H), 7.38-7.27 (m, 3H), 7.23-7.09 (m, 4H), 7.02 (d, J=2.4 Hz, 1H), 6.95 (d, J=2.3 Hz, 1H), 6.89 (dd, J=8.4, 2.7 Hz, 1H), 6.68 (d, J=3.3 Hz, 1H), 5.14 (s, 1H), 5.01 (q, J=12.2 Hz, 2H), 3.96-3.89 (m, 1H), 3.77 (s, 3H), 3.21-3.05 (m, 2H), 2.84-2.75 (m, 2H), 2.70-2.60 (m, 1H), 2.56 (d, J=12.7 Hz, 1H), 2.36 (q, J=8.0 Hz, 2H), 1.06 (t, J=8.0 Hz, 3H).

LRMS (ESI, m/z): 533 [M+H]$^+$.

Example B83 8-(4-Fluorophenyl)-2,12-dimethoxy-3-(naphthalen-2-ylmethoxy)-5,6,8,9,14,14a-hexahydroindolo[3',2':4,5]pyridine[2,1-a]isoquinoline (B83)

The target compound B83 was synthesized by repeating A83 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 10H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.72 (s, 3H), 3.16 (dd, J=15.5, 4.7 Hz, 2H), 2.87-2.72 (m, 2H), 2.69-2.51 (m, 2H).

LRMS (ESI, m/z): 585 [M+H]$^+$.

Example B84 8-(4-Fluorophenyl)-2-methoxy-3-(naphthalen-2-ylmethoxy)-5,6,8,9,14,14a-hexahydroindolo[3',2':4,5]pyridine[2,1-a]isoquinoline (B84)

The target compound B84 was synthesized by repeating A84 with 4-fluorobenzaldehyde.

$^1$H NMR (400 MHz, DMSO) δ 10.70 (s, 1H), 7.48 (dd, J=8.6, 5.7 Hz, 2H), 7.26-7.09 (m, 11H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.75 (s, 3H), 3.16 (dd, J=15.5, 4.7 Hz, 2H), 2.87-2.72 (m, 2H), 2.69-2.51 (m, 2H).

LRMS (ESI, m/z): 555 [M+H]$^+$.

Example B85 4-(((8-(4-Fluorophenyl)-2,12-dimethoxy-5,6,8,9,14,14a-hexahydroindole[3',2':4,5]pyridine[2,1-a]isoquinolin-3-yl)oxo)methyl)benzoate (B85)

The target compound B85 was synthesized by repeating A85 with 4-fluorobenzaldehyde.

$^1$H NMR (400 MHz, DMSO) δ 10.64 (s, 1H), 8.03-7.97 (m, 3H), 7.38-7.27 (m, 3H), 7.23-7.09 (m, 3H), 7.02 (d, J=2.4 Hz, 1H), 6.95 (d, J=2.3 Hz, 1H), 6.89 (dd, J=8.4, 2.7 Hz, 1H), 6.68 (d, J=3.3 Hz, 1H), 5.14 (s, 1H), 5.01 (q, J=12.2 Hz, 2H), 3.96-3.89 (m, 1H), 3.77 (s, 3H), 3.76 (s, 3H), 3.72 (s, 3H), 3.21-3.05 (m, 2H), 2.84-2.75 (m, 2H), 2.70-2.60 (m, 1H), 2.56 (d, J=12.7 Hz, 1H).

LRMS (ESI, m/z): 593 [M+H]$^+$.

Example B86 4-(((8-(4-Fluorophenyl)-2-methoxy-5,6,8,9,14,14a-hexahydroindole[3',2':4,5]pyridine[2,1-a]isoquinolin-3-yl)oxo)methyl)benzoate (B85)

The target compound B86 was synthesized by repeating A86 with 4-fluorobenzaldehyde.

$^1$H NMR (400 MHz, DMSO) δ 10.64 (s, 1H), 8.03-7.97 (m, 3H), 7.38-7.27 (m, 3H), 7.23-7.09 (m, 4H), 7.02 (d, J=2.4 Hz, 1H), 6.95 (d, J=2.3 Hz, 1H), 6.89 (dd, J=8.4, 2.7 Hz, 1H), 6.68 (d, J=3.3 Hz, 1H), 5.14 (s, 1H), 5.01 (q, J=12.2 Hz, 2H), 3.96-3.89 (m, 1H), 3.77 (s, 3H), 3.72 (s, 3H), 3.21-3.05 (m, 2H), 2.84-2.75 (m, 2H), 2.70-2.60 (m, 1H), 2.56 (d, J=12.7 Hz, 1H).

LRMS (ESI, m/z): 563 [M+H]$^+$.

Example B87 3-((4-(1H-pyrazol-1-yl)benzyl)oxo)-8-(4-fluorophenyl)-2,12-dimethoxy-5,6,8,9,14,14a-hexahydroindole[3',2':4,5]pyridine[2,1-a]isoquinoline (B87)

The target compound B87 was synthesized by repeating A87 with 4-fluorobenzaldehyde.

$^1$H NMR (400 MHz, DMSO) δ 10.70 (s, 1H), 7.87 (d, J=8 Hz, 1H), 7.62-7.45 (m, 5H), 7.26-7.09 (m, 4H), 7.05-6.84 (m, 3H), 6.79-6.69 (m, 2H), 6.47 (q, J=8 Hz, 1H), 5.11 (s, 1H), 4.16 (d, J=15.1 Hz, 1H), 3.77 (d, J=11.4 Hz, 6H), 3.64 (d, J=15.6 Hz, 1H), 3.54 (d, J=7.2 Hz, 1H), 3.31 (s, 1H), 3.14 (s, 1H), 2.94 (d, J=11.4 Hz, 1H), 2.64 (dd, J=21.1, 13.3 Hz, 2H), 2.40-2.27 (m, 1H).

LRMS (ESI, m/z): 601 [M+H]$^+$.

Example B88 3-((4-(1H-pyrazol-1-yl)benzyl)oxo)-8-(4-fluorophenyl)-2-methoxy-5,6,8,9,14,14a-hexahydroindole[3',2':4,5]pyridine[2,1-a]isoquinoline (B88)

The target compound B88 was synthesized by repeating A88 with 4-fluorobenzaldehyde.

$^1$H NMR (400 MHz, DMSO) δ 10.70 (s, 1H), 7.87 (d, J=8 Hz, 1H), 7.62-7.45 (m, 5H), 7.26-7.09 (m, 5H), 7.05-6.84 (m, 3H), 6.79-6.69 (m, 2H), 6.47 (q, J=8 Hz, 1H), 5.11 (s, 1H), 4.16 (d, J=15.1 Hz, 1H), 3.77 (s, 3H), 3.64 (d, J=15.6 Hz, 1H), 3.54 (d, J=7.2 Hz, 1H), 3.31 (s, 1H), 3.14 (s, 1H), 2.94 (d, J=11.4 Hz, 1H), 2.64 (dd, J=21.1, 13.3 Hz, 2H), 2.40-2.27 (m, 1H).

LRMS (ESI, m/z): 571 [M+H]$^+$.

Example B89 3-butoxy-8-(4-fluorophenyl)-2,12-dimethoxy-5,6,8,9,14,14a-hexahydroindole[3',2':4,5]pyridine[2,1-a]isoquinoline (B89)

The target compound B89 was synthesized by repeating A89 with 4-fluorobenzaldehyde.

$^1$H NMR (400 MHz, DMSO) δ 10.66 (s, 1H), 7.36 (d, J=8.8 Hz, 1H), 7.26-7.09 (m, 4H), 6.98 (d, J=2.1 Hz, 1H), 6.96 (s, 1H), 6.73 (dd, J=8.7, 2.3 Hz, 1H), 6.69 (s, 1H), 5.37 (t, J=12.0 Hz, 2H), 4.16 (s, 1H), 3.92 (t, J=5.9 Hz, 2H), 3.77 (s, 3H), 3.65 (s, 1H), 3.44-3.40 (d, J=15.0 Hz, 1H), 3.12 (d, J=9.6 Hz, 1H), 2.47-2.37 (t, J=5.9 Hz, 2H), 1.77-1.61 (m, 2H), 1.51-1.36 (m, 2H), 0.94 (t, J=7.4 Hz, 3H).

LRMS (ESI, m/z): 501 [M+H]$^+$.

Example B90 3-butoxy-8-(4-fluorophenyl)-2-methoxy-5,6,8,9,14,14a-hexahydroindole[3',2':4,5]pyridine[2,1-a]isoquinoline (B90)

The target compound B90 was synthesized by repeating A90 with 4-fluorobenzaldehyde.

$^1$H NMR (400 MHz, DMSO) δ 10.66 (s, 1H), 7.36 (d, J=8.8 Hz, 1H), 7.26-7.09 (m, 5H), 6.98 (d, J=2.1 Hz, 1H), 6.96 (s, 1H), 6.73 (dd, J=8.7, 2.3 Hz, 1H), 6.69 (s, 1H), 5.37 (t, J=12.0 Hz, 2H), 4.16 (s, 1H), 3.92 (t, J=5.9 Hz, 2H), 3.77 (s, 3H), 3.72 (s, 3H), 3.65 (s, 1H), 3.44-3.40 (d, J=15.0 Hz, 1H), 3.12 (d, J=9.6 Hz, 1H), 2.47-2.37 (t, J=5.9 Hz, 2H), 1.77-1.61 (m, 2H), 1.51-1.36 (m, 2H), 0.94 (t, J=7.4 Hz, 3H).

LRMS (ESI, m/z): 471 [M+H]$^+$.

Example B91 3-(benzyloxy)-8-(4-fluorophenyl)-2-methoxy-11-methyl-5,6,8,9,14,14a-hexahydroindole[3',2':4,5]pyridine[2,1-a]isoquinoline (B91)

The target compound B91 was synthesized by repeating A91 with 4-fluorobenzaldehyde.

$^1$H NMR (400 MHz, DMSO) δ 10.64 (s, 1H), 8.03-7.97 (m, 3H), 7.38-7.27 (m, 3H), 7.23-7.09 (m, 4H), 7.02 (d, J=2.4 Hz, 1H), 6.95 (d, J=2.3 Hz, 1H), 6.89 (dd, J=8.4, 2.7 Hz, 1H), 6.68 (d, J=3.3 Hz, 1H), 5.14 (s, 1H), 5.01 (q, J=12.2 Hz, 2H), 3.96-3.89 (m, 1H), 3.77 (s, 3H), 3.21-3.05 (m, 2H), 2.84-2.75 (m, 2H), 2.70-2.60 (m, 1H), 2.56 (d, J=12.7 Hz, 1H), 2.36 (s, 3H).

LRMS (ESI, m/z): 519 [M+H]$^+$.

Example B92 3-(Benzyloxy)-8-(4-fluorophenyl)-2-methoxy-12-ethyl-5,6,8,9,14,14a-hexahydroindole[3',2':4,5]pyridine[2,1-a]isoquinoline (B92)

The target compound B92 was synthesized by repeating A92 with 4-fluorobenzaldehyde.

$^1$H NMR (400 MHz, DMSO) δ 10.64 (s, 1H), 8.03-7.97 (m, 3H), 7.38-7.27 (m, 3H), 7.23-7.09 (m, 4H), 7.02 (d, J=2.4 Hz, 1H), 6.95 (d, J=2.3 Hz, 1H), 6.89 (dd, J=8.4, 2.7 Hz, 1H), 6.68 (d, J=3.3 Hz, 1H), 5.14 (s, 1H), 5.01 (q, J=12.2 Hz, 2H), 3.96-3.89 (m, 1H), 3.77 (s, 3H), 3.21-3.05 (m, 2H), 2.84-2.75 (m, 2H), 2.70-2.60 (m, 1H), 2.56 (d, J=12.7 Hz, 1H), 2.36 (q, J=8.0 Hz, 2H), 1.06 (t, J=8.0 Hz, 3H).

LRMS (ESI, m/z): 533 [M+H]$^+$.

Example B93 8-(4-Fluorophenyl)-2,12-dimethoxy-3-(2,2,2-trifluoroethoxy)-5,6,8,9,14,14a-hexahydroindolo[3',2':4,5]pyridine[2,1-a]isoquinoline (B93)

The target compound B93 was synthesized by repeating A93 with 4-fluorobenzaldehyde.

$^1$H NMR (400 MHz, DMSO) δ 10.71 (s, 1H), 7.37 (d, J=8.8 Hz, 1H), 7.29-7.07 (m, 5H), 6.96 (d, J=2.4 Hz, 1H), 6.79 (s, 1H), 6.74 (dd, J=8.8, 2.5 Hz, 1H), 5.37 (s, 2H), 4.76-4.65 (m, 2H), 4.17 (d, J=15.0 Hz, 1H), 3.78 (s, 3H), 3.77 (s, 3H), 3.65 (d, J=14.8 Hz, 1H), 3.14 (dd, J=8.5, 2.6 Hz, 1H), 2.98 (dd, J=18.7, 8.2 Hz, 1H), 2.74-2.60 (m, 1H), 2.46-2.35 (m, 1H).

LRMS (ESI, m/z): 527 [M+H]$^+$.

Example B94 8-(4-Fluorophenyl)-2-methoxy-3-(2,2,2-trifluoroethoxy)-5,6,8,9,14,14a-hexahydroindolo[3',2':4,5]pyridine[2,1-a]isoquinoline (B94)

The target compound B94 was synthesized by repeating A94 with 4-fluorobenzaldehyde.

$^1$H NMR (400 MHz, DMSO) δ 10.71 (s, 1H), 7.37 (d, J=8.8 Hz, 1H), 7.29-7.07 (m, 6H), 6.96 (d, J=2.4 Hz, 1H), 6.79 (s, 1H), 6.74 (dd, J=8.8, 2.5 Hz, 1H), 5.37 (s, 2H), 4.76-4.65 (m, 2H), 4.17 (d, J=15.0 Hz, 1H), 3.77 (s, 3H), 3.65 (d, J=14.8 Hz, 1H), 3.14 (dd, J=8.5, 2.6 Hz, 1H), 2.98 (dd, J=18.7, 8.2 Hz, 1H), 2.74-2.60 (m, 1H), 2.46-2.35 (m, 1H).

LRMS (ESI, m/z): 497 [M+H]$^+$.

Example B95 8-(4-Fluorophenyl)-2,12-dimethoxy-3-((4-(methylsulfonyl)benzyl)oxy)-5,6,8,9,14,14a-hexahydroindolo[3',2':4,5]pyridine[2,1-a]isoquinoline (B95)

The target compound B95 was synthesized by repeating A95 with 4-fluorobenzaldehyde.

$^1$H NMR (400 MHz, DMSO) δ 10.67 (s, 1H), 7.39-7.35 (m, 3H), 7.29-7.07 (m, 6H), 7.06 (s, 1H), 6.96 (d, J=2.3 Hz, 2H), 6.74 (dd, J=9.7, 3.3 Hz, 2H), 5.05 (q, J=11.6 Hz, 2H), 4.17 (d, J=14.9 Hz, 1H), 3.79 (s, 3H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.05 (s, 3H), 3.03-2.86 (m, 1H), 2.74-2.57 (m, 1H), 2.37 (m, 1H).

LRMS (ESI, m/z): 613 [M+H]$^+$.

Example B96 8-(4-Fluorophenyl)-2-methoxy-3-((4-(methylsulfonyl)benzyl)oxy)-5,6,8,9,14,14a-hexahydroindolo[3',2':4,5]pyridine[2,1-a]isoquinoline (B96)

The target compound B96 was synthesized by repeating A96 with 4-fluorobenzaldehyde.

$^1$H NMR (400 MHz, DMSO) δ 10.67 (s, 1H), 7.39-7.35 (m, 3H), 7.29-7.07 (m, 7H), 7.06 (s, 1H), 6.96 (d, J=2.3 Hz, 2H), 6.74 (dd, J=9.7, 3.3 Hz, 2H), 5.05 (q, J=11.6 Hz, 2H), 4.17 (d, J=14.9 Hz, 1H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.05 (s, 3H), 3.03-2.86 (m, 1H), 2.74-2.57 (m, 1H), 2.37 (m, 1H).

LRMS (ESI, m/z): 583 [M+H]$^+$.

Example B97 3-(benzyloxy)-11-fluoro-8-(4-fluorophenyl)-2-methoxy-5,6,8,9,14,14a-hexahydroindole[3',2': 4,5]pyridine[2,1-a]isoquinoline (B97)

The target compound B97 was synthesized by repeating A97 with 4-fluorobenzaldehyde.
$^1$H NMR (400 MHz, DMSO) δ 10.70 (s, 1H), 7.48 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.72 (s, 3H), 3.16 (dd, J=15.5, 4.7 Hz, 2H), 2.87-2.72 (m, 2H), 2.69-2.51 (m, 2H).
LRMS (ESI, m/z): 523 [M+H]$^+$.

Example B98 3-(benzyloxy)-12-fluoro-8-(4-fluorophenyl)-2-methoxy-5,6,8,9,14,14a-hexahydroindole[3 2':4,5]pyridine[2,1-a]isoquinoline (B98)

The target compound B98 was synthesized by repeating A98 with 4-fluorobenzaldehyde.
$^1$H NMR (400 MHz, DMSO) δ 10.70 (s, 1H), 7.48 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.72 (s, 3H), 3.16 (dd, J=15.5, 4.7 Hz, 2H), 2.87-2.72 (m, 2H), 2.69-2.51 (m, 2H).
LRMS (ESI, m/z): 523 [M+H]$^+$.

Example B99 3-(benzyloxy)-13-fluoro-8-(4-fluorophenyl)-2-methoxy-5,6,8,9,14,14a-hexahydroindole[3 2':4,5]pyridine[2,1-a]isoquinoline (B99)

The target compound B99 was synthesized by repeating A99 with 4-fluorobenzaldehyde.
$^1$H NMR (400 MHz, DMSO) δ 10.70 (s, 1H), 7.48 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.72 (s, 3H), 3.16 (dd, J=15.5, 4.7 Hz, 2H), 2.87-2.72 (m, 2H), 2.69-2.51 (m, 2H).
LRMS (ESI, m/z): 523 [M+H]$^+$.

Example B100 3-(benzyloxy)-11-chloro-8-(4-fluorophenyl)-2-methoxy-5,6,8,9,14,14a-hexahydroindole[3 2':4,5]pyridine[2,1-a]isoquinoline (B100)

The target compound B100 was synthesized by repeating A100 with 4-fluorobenzaldehyde.
$^1$H NMR (400 MHz, DMSO) δ 10.70 (s, 1H), 7.48 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.72 (s, 3H), 3.16 (dd, J=15.5, 4.7 Hz, 2H), 2.87-2.72 (m, 2H), 2.69-2.51 (m, 2H).
LRMS (ESI, m/z): 540 [M+H]$^+$.

Example B101 3-(benzyloxy)-12-chloro-8-(4-fluorophenyl)-2-methoxy-5,6,8,9,14,14a-hexahydroindole[3 2':4,5]pyridine[2,1-a]isoquinoline (B101)

The target compound B101 was synthesized by repeating A101 with 4-fluorobenzaldehyde.
$^1$H NMR (400 MHz, DMSO) δ 10.70 (s, 1H), 7.48 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.72 (s, 3H), 3.16 (dd, J=15.5, 4.7 Hz, 2H), 2.87-2.72 (m, 2H), 2.69-2.51 (m, 2H).
LRMS (ESI, m/z): 540 [M+H]$^+$.

Example B102 3-(benzyloxy)-13-chloro-8-(4-fluorophenyl)-2-methoxy-5,6,8,9,14,14a-hexahydroindole[3',2': 4,5]pyridine[2,1-a]isoquinoline (B102)

The target compound B102 was synthesized by repeating A102 with 4-fluorobenzaldehyde.
$^1$H NMR (400 MHz, DMSO) δ 10.70 (s, 1H), 7.48 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.72 (s, 3H), 3.16 (dd, J=15.5, 4.7 Hz, 2H), 2.87-2.72 (m, 2H), 2.69-2.51 (m, 2H).
LRMS (ESI, m/z): 540 [M+H]$^+$.

Example B103 3-(benzyloxy)-11-bromo-8-(4-fluorophenyl)-2-methoxy-5,6,8,9,14,14a-hexahydroindole[3',2':4,5]pyridine[2,1-a]isoquinoline (B103)

The target compound B103 was synthesized by repeating A103 with 4-fluorobenzaldehyde.
$^1$H NMR (400 MHz, DMSO) δ 10.70 (s, 1H), 7.48 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.72 (s, 3H), 3.16 (dd, J=15.5, 4.7 Hz, 2H), 2.87-2.72 (m, 2H), 2.69-2.51 (m, 2H).
LRMS (ESI, m/z): 583 [M+H]$^+$, 585 [M+H]$^+$.

Example B104 3-(benzyloxy)-12-bromo-8-(4-fluorophenyl)-2-methoxy-5,6,8,9,14,14a-hexahydroindole[3',2':4,5]pyridine[2,1-a]isoquinoline (B104)

The target compound B104 was synthesized by repeating A104 with 4-fluorobenzaldehyde.
$^1$H NMR (400 MHz, DMSO) δ 10.70 (s, 1H), 7.48 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.72 (s, 3H), 3.16 (dd, J=15.5, 4.7 Hz, 2H), 2.87-2.72 (m, 2H), 2.69-2.51 (m, 2H).
LRMS (ESI, m/z): 583 [M+H]$^+$, 585 [M+H]$^+$.

Example B105 3-(benzyloxy)-13-bromo-8-(4-fluorophenyl)-2-methoxy-5,6,8,9,14,14a-hexahydroindole[3',2':4,5]pyridine[2,1-a]isoquinoline (B105)

The target compound B105 was synthesized by repeating A105 with 4-fluorobenzaldehyde.
$^1$H NMR (400 MHz, DMSO) δ 10.70 (s, 1H), 7.48 (dd, J=8.6, 5.7 Hz, 2H), 7.26-7.09 (m, 7H), 6.97 (d, J=2.4 Hz, 1H), 6.85 (s, 1H), 6.76 (s, 1H), 6.68 (dd, J=8.7, 2.5 Hz, 1H), 5.12 (s, 1H), 4.99 (s, 2H), 3.94 (dd, J=10.4, 4.7 Hz, 1H), 3.72 (s, 3H), 3.16 (dd, J=15.5, 4.7 Hz, 2H), 2.87-2.72 (m, 2H), 2.69-2.51 (m, 2H).
LRMS (ESI, m/z): 583 [M+H]$^+$, 585 [M+H]$^+$.

Example B106 2-(benzyloxy)-8-phenyl-3,12-dimethoxy-5,6,8,9,14,14a-hexahydroindole[3',2':4,5]pyridine[2,1-a]isoquinoline (B106)

The target compound B106 was synthesized by repeating B1 with benzaldehyde.

$^1$H NMR (400 MHz, DMSO) δ 10.70 (s, 1H), 7.61-7.35 (m, 4H), 7.37-7.26 (m, 5H), 7.05 (s, 1H), 6.94 (d, J=2.1 Hz, 1H), 6.79-6.69 (m, 2H), 5.08 (s, 1H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 517 [M+H]$^+$.

Example B107 2-(benzyloxy)-8-(3-fluorophenyl)-3,12-dimethoxy-5,6,8,9,14,14a-hexahydroindole[3',2':4,5]pyridine[2,1-a]isoquinoline (B107)

The target compound B107 was synthesized by repeating B1 with 3-fluorobenzaldehyde.

$^1$H NMR (400 MHz, DMSO) δ 10.70 (s, 1H), 7.61-7.35 (m, 4H), 7.14-7.05 (m, 4H), 7.05 (s, 1H), 6.94 (d, J=2.1 Hz, 1H), 6.79-6.69 (m, 2H), 5.08 (s, 1H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 535 [M+H]$^+$.

Example B108 2-(benzyloxy)-8-(2-fluorophenyl)-3,12-dimethoxy-5,6,8,9,14,14a-hexahydroindole[3',2':4,5]pyridine[2,1-a]isoquinoline (B108)

The target compound B108 was synthesized by repeating B1 with 2-fluorobenzaldehyde.

$^1$H NMR (400 MHz, DMSO) δ 10.70 (s, 1H), 7.61-7.35 (m, 4H), 7.48-7.10 (m, 4H), 7.05 (s, 1H), 6.94 (d, J=2.1 Hz, 1H), 6.79-6.69 (m, 2H), 5.08 (s, 1H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 535 [M+H]$^+$.

Example B109 2-(benzyloxy)-8-benzyl-3,12-dimethoxy-5,6,8,9,14,14a-hexahydroindole[3',2':4,5]pyridine[2,1-a]isoquinoline (B109)

The target compound B109 was synthesized by repeating B1 with phenylacetaldehyde.

$^1$H NMR (400 MHz, DMSO) δ 10.70 (s, 1H), 7.61-7.35 (m, 4H), 7.40-7.27 (m, 5H), 7.05 (s, 1H), 6.94 (d, J=2.1 Hz, 1H), 6.79-6.69 (m, 2H), 5.08 (t, 1H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 3.00-2.75 (d, 2H), 2.95 (t, J=12.0 Hz, 1H), 2.65 (d, J=13.4 Hz, 2H), 2.44 (t, J=12.0 Hz, 1H).

LRMS (ESI, m/z): 531 [M+H]$^+$.

Example B110 2-(benzyloxy)-8-thiophene-3,12-dimethoxy-5,6,8,9,14,14a-hexahydroindole[3',2':4,5]pyridine[2,1-a]isoquinoline (B110)

The target compound B110 was synthesized by repeating B1 with thiophenecarboxaldehyde.

$^1$H NMR (400 MHz, DMSO) δ 10.70 (s, 1H), 7.61-7.35 (m, 4H), 7.40-6.83 (m, 3H), 7.05 (s, 1H), 6.94 (d, J=2.1 Hz, 1H), 6.79-6.69 (m, 2H), 5.08 (s, 1H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 523 [M+H]$^+$.

Example B111 2-(benzyloxy)-8-furan-3,12-dimethoxy-5,6,8,9,14,14a-hexahydroindole[3',2':4,5]pyridine[2,1-a]isoquinoline (B111)

The target compound B111 was synthesized by repeating B1 with furaldehyde.

$^1$H NMR (400 MHz, DMSO) δ 10.70 (s, 1H), 7.65-6.26 (m, 3H), 7.61-7.35 (m, 4H), 7.05 (s, 1H), 6.94 (d, J=2.1 Hz, 1H), 6.79-6.69 (m, 2H), 5.08 (s, 1H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 507 [M+H]$^+$.

Example B112 2-(benzyloxy)-8-(3-methylfuran)-3,12-dimethoxy-5,6,8,9,14,14a-hexahydroindole[3',2':4,5]pyridine[2,1-a]isoquinoline (B112)

The target compound B112 was synthesized by repeating B1 with 3-methyl furaldehyde.

$^1$H NMR (400 MHz, DMSO) δ 10.70 (s, 1H), 7.61-7.35 (m, 4H), 7.50-6.24 (m, 2H), 7.05 (s, 1H), 6.94 (d, J=2.1 Hz, 1H), 6.79-6.69 (m, 2H), 5.08 (s, 1H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H), 1.93 (s, 3H).

LRMS (ESI, m/z): 521 [M+H]$^+$.

Example B113 2-(benzyloxy)-8-(5-methylfuran)-3,12-dimethoxy-5,6,8,9,14,14a-hexahydroindole[3',2':4,5]pyridine[2,1-a]isoquinoline (B113)

The target compound B113 was synthesized by repeating B1 with 5-methyl furaldehyde.

$^1$H NMR (400 MHz, DMSO) δ 10.70 (s, 1H), 7.61-7.35 (m, 4H), 7.05 (s, 1H), 6.94 (d, J=2.1 Hz, 1H), 6.79-6.69 (m, 2H), 6.14-6.02 (m, 2H), 5.08 (s, 1H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H), 2.30 (s, 3H).

LRMS (ESI, m/z): 521 [M+H]$^+$.

Example B114 2-(benzyloxy)-8-(5-cyanofuran)-3, 12-dimethoxy-5,6,8,9,14,14a-hexahydroindole[3',2':4,5]pyridine[2,1-a]isoquinoline (B114)

The target compound B114 was synthesized by repeating B1 with 5-cyano furaldehyde.

$^1$H NMR (400 MHz, DMSO) δ 10.70 (s, 1H), 7.61-7.35 (m, 4H), 7.09-6.58 (m, 2H), 7.05 (s, 1H), 6.94 (d, J=2.1 Hz, 1H), 6.79-6.69 (m, 2H), 5.08 (s, 1H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 532 [M+H]$^+$.

Example B115 2-(benzyloxy)-8-pyrrole-3,12-dimethoxy-5,6,8,9,14,14a-hexahydroindole[3',2':4,5]pyridine[2,1-a]isoquinoline (B115)

The target compound B115 was synthesized by repeating B1 with pyrrole formaldehyde.

$^1$H NMR (400 MHz, DMSO) δ 10.70 (s, 1H), 7.61-7.35 (m, 4H), 7.05 (s, 1H), 6.94 (d, J=2.1 Hz, 1H), 6.79-6.69 (m, 2H), 6.69-5.72 (m, 3H), 5.08 (s, 1H), 5.00 (s, 1H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 506 [M+H]$^+$.

Example C1 2-((2,4-bis(trifluoromethyl)benzyl)oxy)-3,12-dimethoxy-5,6,8,9,14,14a-hexahydroindole[3',2':4,5]pyridine[2,1-a]isoquinoline (C1)

The title compound C1 was synthesized with benzyl bromide and 3-methoxy-4-hydroxybenzaldehyde according to Scheme 3.

$^1$H NMR (400 MHz, DMSO) δ 10.70 (s, 1H), 7.61-7.35 (m, 4H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 577 [M+H]$^+$.

Example C2 2-((2,4-bis(trifluoromethyl)benzyl)oxy)-3-methoxy-5,6,8,9,14,14a-hexahydroindole[3',2':4,5]pyridine[2,1-a]isoquinoline (C2)

The title compound C2 was synthesized with benzyl bromide and 3-methoxy-4-hydroxybenzaldehyde according to Scheme 3.

$^1$H NMR (400 MHz, DMSO) δ 10.70 (s, 1H), 7.56-7.37 (m, 7H), 7.08 (s, 1H), 6.97 (d, J=2.1 Hz, 1H), 6.76-6.69 (m, 2H), 5.08 (s, 2H), 4.18 (d, J=15.0 Hz, 1H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 547 [M+H]$^+$.

Example C3 3,12-dimethoxy-2-((4-(trifluoromethyl)benzyl)oxy)-5,6,8,9,14,14a-hexahydroindolo[3',2':4,5]pyridine[2,1-a]isoquinoline (C3)

The title compound C3 was synthesized according to Scheme 3, while benzyl bromide was substituted with 4-trifluoromethylbenzyl bromide.

$^1$H NMR (400 MHz, DMSO) δ 10.70 (s, 1H), 7.71-7.53 (m, 2H), 7.50-7.35 (m, 1H), 7.31-7.15 (m, 2H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 509 [M+H]$^+$.

Example C4 3-methoxy-2-((4-(trifluoromethyl)benzyl)oxy)-5,6,8,9,14,14a-hexahydroindolo[3',2':4,5]pyridine[2,1-a]isoquinoline (C4)

The title compound C4 was synthesized according to Scheme 3, while benzyl bromide was substituted with 4-trifluoromethylbenzyl bromide.

$^1$H NMR (400 MHz, DMSO) δ 10.70 (s, 1H), 7.71-7.53 (m, 2H), 7.50-7.35 (m, 1H), 7.31-7.15 (m, 3H), 7.05 (s, 1H), 6.94 (d, J=2.1 Hz, 1H), 6.79-6.69 (m, 2H), 5.08 (s, 2H), 4.18 (d, J=15.0 Hz, 1H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 479 [M+H]$^+$.

Example C5 2-((4-Fluorobenzyl)oxo)-3,12-dimethoxy-5,6,8,9,14,14a-hexahydroindole[3',2':4,5]pyridine[2,1-a]isoquinoline (C5)

The title compound C5 was synthesized according to Scheme 3, while benzyl bromide was substituted with 4-fluorobenzyl bromide.

$^1$H NMR (400 MHz, DMSO) δ 10.68 (s, 1H), 7.57-7.47 (m, 2H), 7.36 (d, J=8.5 Hz, 1H), 7.32-7.24 (m, 2H), 7.03 (s, 1H), 6.94 (m, 1H), 6.77-6.68 (m, 2H), 5.08 (q, J=11.3 Hz, 2H), 4.16 (d, J=15.7 Hz, 1H), 3.78 (s, 3H), 3.76 (s, 3H), 3.64 (d, J=14.3 Hz, 1H), 3.55 (d, J=8.0 Hz, 1H), 3.31 (m, 1H), 3.12 (d, J=7.7 Hz, 1H), 3.03-2.88 (m, 1H), 2.66 (dd, J=12.1 Hz, 2H), 2.33 (t, J=11.5 Hz, 1H).

LRMS (ESI, m/z): 459 [M+H]$^+$.

Example C6 2-((4-Fluorobenzyl)oxo)-3-methoxy-5,6,8,9,14,14a-hexahydroindole[3',2':4,5]pyridine[2,1-a]isoquinoline (C6)

The title compound C6 was synthesized according to Scheme 3, while benzyl bromide was substituted with 4-fluorobenzyl bromide.

$^1$H NMR (400 MHz, DMSO) δ 10.68 (s, 1H), 7.57-7.47 (m, 2H), 7.36 (d, J=8.5 Hz, 1H), 7.32-7.24 (m, 3H), 7.03 (s, 1H), 6.94 (m, 1H), 6.77-6.68 (m, 2H), 5.08 (q, J=11.3 Hz, 2H), 4.16 (d, J=15.7 Hz, 1H), 3.78 (s, 3H), 3.76 (s, 3H), 3.64 (d, J=14.3 Hz, 1H), 3.55 (d, J=8.0 Hz, 1H), 3.31 (m, 1H), 3.12 (d, J=7.7 Hz, 1H), 3.03-2.88 (m, 1H), 2.66 (dd, J=12.1 Hz, 2H), 2.33 (t, J=11.5 Hz, 1H).

LRMS (ESI, m/z): 429 [M+H]$^+$.

Example C7 2-((3-Fluorobenzyl)oxo)-3,12-dimethoxy-5,6,8,9,14,14a-hexahydroindole[3',2':4,5]pyridine[2,1-a]isoquinoline (C7)

The title compound C7 was synthesized according to Scheme 1, while benzyl bromide was substituted with 3-fluorobenzyl bromide.

$^1$H NMR (400 MHz, DMSO) δ 10.68 (s, 1H), 7.51-7.35 (m, 5H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77

(s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 459 [M+H]$^+$.

Example C8 2-((3-Fluorobenzyl)oxo)-3-methoxy-5,6,8,9,14,14a-hexahydroindole[3',2':4,5]pyridine[2,1-a]isoquinoline (C8)

The title compound C8 was synthesized according to Scheme 1, while benzyl bromide was substituted with 3-fluorobenzyl bromide.
$^1$H NMR (400 MHz, DMSO) δ 10.68 (s, 1H), 7.50-7.43 (m, 3H), 7.26-7.15 (m, 3H), 7.00 (s, 1H), 6.95 (d, J=2.3 Hz, 1H), 6.80 (s, 1H), 6.65 (dd, J=8.7, 2.4 Hz, 1H), 5.08 (s, 2H), 4.18 (d, J=15.0 Hz, 1H), 3.97 (d, J=14.6 Hz, 1H), 3.77 (s, 3H), 3.61 (dd, J=22.2, 12.4 Hz, 2H), 3.41 (d, J=14.6 Hz, 1H), 3.11 (d, J=11.1 Hz, 1H), 2.92 (d, J=10.6 Hz, 1H), 2.60 (dd, J=20.6, 13.0 Hz, 2H), 2.48-2.39 (m, 1H).
LRMS (ESI, m/z): 429 [M+H]$^+$.

Example C9 2-((2-Fluorobenzyl)oxo)-3,12-dimethoxy-5,6,8,9,14,14a-hexahydroindole[3',2':4,5]pyridine[2,1-a]isoquinoline (C9)

The title compound C9 was synthesized according to Scheme 3, while benzyl bromide was substituted with 2-fluorobenzyl bromide.
$^1$H NMR (400 MHz, DMSO) δ 10.68 (s, 1H), 7.51-7.35 (m, 5H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 459 [M+H]$^+$.

Example C10 2-((2-Fluorobenzyl)oxo)-3-methoxy-5,6,8,9,14,14a-hexahydroindole[3',2':4,5]pyridine[2,1-a]isoquinoline (C10)

The title compound C10 was synthesized according to Scheme 3, while benzyl bromide was substituted with 2-fluorobenzyl bromide.
$^1$H NMR (400 MHz, DMSO) δ 10.68 (s, 1H), 7.51-7.35 (m, 5H), 7.05 (s, 1H), 6.94 (d, J=2.1 Hz, 1H), 6.79-6.69 (m, 3H), 5.08 (s, 2H), 4.18 (d, J=15.0 Hz, 1H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 429 [M+H]$^+$.

Example C11 3,12-dimethoxy-2-((4-methoxybenzyl)oxo)-5,6,8,9,14,14a-hexahydroindolo[3',2':4,5]pyridine[2,1-a]isoquinoline (C1)

The title compound C11 was synthesized according to Scheme 3, while benzyl bromide was substituted with 4-methoxybenzyl bromide.
$^1$H NMR (400 MHz, DMSO) δ 10.65 (s, 1H), 7.40-7.28 (m, 2H), 7.10-7.03 (m, 3H), 6.98-6.87 (m, 2H), 6.79-6.68 (m, 2H), 5.09 (q, J=11.9 Hz, 2H), 4.16 (d, J=15.3 Hz, 1H), 3.79 (s, 3H), 3.78 (s, 3H), 3.76 (s, 3H), 3.64 (d, J=15.0 Hz, 1H), 3.54 (dd, J=10.6, 2.9 Hz, 1H), 3.32 (d, J=3.1 Hz, 1H), 3.17-3.08 (m, 1H), 3.03-2.85 (m, 1H), 2.73-2.56 (m, 2H), 2.33 (t, J=7.0 Hz, 1H).
LRMS (ESI, m/z): 471 [M+H]$^+$.

Example C12 3-methoxy-2-((4-methoxybenzyl)oxo)-5,6,8,9,14,14a-hexahydroindolo[3',2':4,5]pyridine[2,1-a]isoquinoline (C12)

The title compound C12 was synthesized according to Scheme 3, while benzyl bromide was substituted with 4-methoxybenzyl bromide.
$^1$H NMR (400 MHz, DMSO) δ 10.65 (s, 1H), 7.40-7.28 (m, 2H), 7.10-7.03 (m, 4H), 6.98-6.87 (m, 2H), 6.79-6.68 (m, 2H), 5.09 (q, J=11.9 Hz, 2H), 4.16 (d, J=15.3 Hz, 1H), 3.79 (s, 3H), 3.76 (s, 3H), 3.64 (d, J=15.0 Hz, 1H), 3.54 (dd, J=10.6, 2.9 Hz, 1H), 3.32 (d, J=3.1 Hz, 1H), 3.17-3.08 (m, 1H), 3.03-2.85 (m, 1H), 2.73-2.56 (m, 2H), 2.33 (t, J=7.0 Hz, 1H).
LRMS (ESI, m/z): 441 [M+H]$^+$.

Example C13 3,12-dimethoxy-2-((3-methoxybenzyl)oxo)-5,6,8,9,14,14a-hexahydroindolo[3',2':4,5]pyridine[2,1-a]isoquinoline (C13)

The title compound C13 was synthesized according to Scheme 3, while benzyl bromide was substituted with 3-methoxybenzyl bromide.
$^1$H NMR (400 MHz, DMSO) δ 10.65 (s, 1H), 7.40-7.28 (m, 2H), 7.10-7.03 (m, 3H), 6.98-6.87 (m, 2H), 6.79-6.68 (m, 2H), 5.09 (q, J=11.9 Hz, 2H), 4.16 (d, J=15.3 Hz, 1H), 3.79 (s, 3H), 3.78 (s, 3H), 3.76 (s, 3H), 3.64 (d, J=15.0 Hz, 1H), 3.54 (dd, J=10.6, 2.9 Hz, 1H), 3.32 (d, J=3.1 Hz, 1H), 3.17-3.08 (m, 1H), 3.03-2.85 (m, 1H), 2.73-2.56 (m, 2H), 2.33 (t, J=7.0 Hz, 1H).
LRMS (ESI, m/z): 471 [M+H]$^+$.

Example C14 (3-methoxy-2-((3-methoxybenzyl)oxo)-5,6,14,14a-tetrahydroindolo[3',2':4,5]pyridine[2,1-a]isoquinoline-9(8H)-yl)methanol (C14)

The title compound C14 was synthesized according to Scheme 3, while benzyl bromide was substituted with 3-methoxybenzyl bromide.
$^1$H NMR (400 MHz, DMSO) δ 10.65 (s, 1H), 7.40-7.28 (m, 2H), 7.10-7.03 (m, 4H), 6.98-6.87 (m, 2H), 6.79-6.68 (m, 2H), 5.09 (q, J=11.9 Hz, 2H), 4.16 (d, J=15.3 Hz, 1H), 3.79 (s, 3H), 3.76 (s, 3H), 3.64 (d, J=15.0 Hz, 1H), 3.54 (dd, J=10.6, 2.9 Hz, 1H), 3.32 (d, J=3.1 Hz, 1H), 3.17-3.08 (m, 1H), 3.03-2.85 (m, 1H), 2.73-2.56 (m, 2H), 2.33 (t, J=7.0 Hz, 1H).
LRMS (ESI, m/z): 441 [M+H]$^+$.

Example C15 3,12-dimethoxy-2-((4-methylbenzyl)oxy)-5,6,8,9,14,14a-hexahydroindolo[3',2':4,5]pyridine[2,1-a]isoquinoline (C15)

The title compound C15 was synthesized according to Scheme 3, while benzyl bromide was substituted with 4-methylbenzyl bromide.
$^1$H NMR (400 MHz, DMSO) δ 10.65 (s, 1H), 7.39-7.35 (m, 3H), 7.22 (d, J=8.0 Hz, 2H), 7.06 (s, 1H), 6.96 (d, J=2.3 Hz, 1H), 6.74 (dd, J=9.7, 3.3 Hz, 2H), 5.05 (q, J=11.6 Hz, 1H), 4.17 (d, J=14.9 Hz, 2H), 3.79 (s, 3H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.03-2.86 (m, 1H), 2.74-2.57 (m, 2H), 2.37 (t, J=7.1 Hz, 2H), 2.32 (s, 3H).
LRMS (ESI, m/z): 455 [M+H]$^+$.

Example C16 3-methoxy-2-((4-methylbenzyl)oxy)-5,6,8,9,14,14a-hexahydroindolo[3',2':4,5]pyridine[2,1-a]isoquinoline (C16)

The title compound C16 was synthesized according to Scheme 3, while benzyl bromide was substituted with 4-methylbenzyl bromide.

$^1$H NMR (400 MHz, DMSO) δ 10.65 (s, 1H), 7.39-7.35 (m, 3H), 7.28-7.21 (m, 3H), 7.06 (s, 1H), 6.96 (d, J=2.3 Hz, 1H), 6.74 (dd, J=9.7, 3.3 Hz, 2H), 5.05 (q, J=11.6 Hz, 1H), 4.17 (d, J=14.9 Hz, 1H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.03-2.86 (m, 1H), 2.74-2.57 (m, 2H), 2.37 (t, J=7.1 Hz, 2H), 2.32 (s, 3H).

LRMS (ESI, m/z): 425 [M+H]$^+$.

Example C17 2-((4-chlorobenzyl)oxo)-3,12-dimethoxy-5,6,8,9,14,14a-hexahydroindole[3',2':4,5]pyridine[2,1-a]isoquinoline (C17)

The title compound C17 was synthesized according to Scheme 3, while benzyl bromide was substituted with 4-chlorobenzyl bromide.

$^1$H NMR (400 MHz, DMSO) δ 10.65 (s, 1H), 7.47-7.39 (m, 2H), 7.36 (d, J=8.5 Hz, 1H), 7.32-7.24 (m, 2H), 7.03 (s, 1H), 6.94 (m, 1H), 6.77-6.68 (m, 2H), 5.08 (q, J=11.3 Hz, 2H), 4.16 (d, J=15.7 Hz, 1H), 3.78 (s, 3H), 3.76 (s, 3H), 3.64 (d, J=14.3 Hz, 1H), 3.55 (d, J=8.0 Hz, 1H), 3.31 (m, 1H), 3.12 (d, J=7.7 Hz, 1H), 3.03-2.88 (m, 1H), 2.66 (dd, J=12.1 Hz, 2H), 2.33 (t, J=11.5 Hz, 1H).

LRMS (ESI, m/z): 476 [M+H]$^+$.

Example C18 2-((4-chlorobenzyl)oxo)-3-methoxy-5,6,8,9,14,14a-hexahydroindole[3',2':4,5]pyridine[2,1-a]isoquinoline (C18)

The title compound C18 was synthesized according to Scheme 3, while benzyl bromide was substituted with 4-chlorobenzyl bromide.

$^1$H NMR (400 MHz, DMSO) δ 10.65 (s, 1H), 7.47-7.39 (m, 2H), 7.36-7.29 (m, 2H), 7.28-7.24 (m, 3H), 7.03 (s, 1H), 6.94 (m, 1H), 6.77-6.68 (m, 2H), 5.08 (q, J=11.3 Hz, 2H), 4.16 (d, J=15.7 Hz, 1H), 3.76 (s, 3H), 3.64 (d, J=14.3 Hz, 1H), 3.55 (d, J=8.0 Hz, 1H), 3.31 (m, 1H), 3.12 (d, J=7.7 Hz, 1H), 3.03-2.88 (m, 1H), 2.66 (dd, J=12.1 Hz, 2H), 2.33 (t, J=11.5 Hz, 1H).

LRMS (ESI, m/z): 446 [M+H]$^+$.

Example C19 4-(((3,12-dimethoxy-5,6,8,9,14,14a-hexahydroindolo[3',2':4,5]pyridine[2,1-a]isoquinolin-2-yl)oxo)methyl)benzonitrile (C19)

The title compound C19 was synthesized according to Scheme 3, while benzyl bromide was substituted with 4-cyanobenzyl bromide.

$^1$H NMR (400 MHz, DMSO) δ 10.65 (s, 1H), 7.67-7.49 (m, 2H), 7.36 (d, J=8.5 Hz, 1H), 7.32-7.24 (m, 2H), 7.03 (s, 1H), 6.94 (m, 1H), 6.77-6.68 (m, 2H), 5.08 (q, J=11.3 Hz, 2H), 4.16 (d, J=15.7 Hz, 1H), 3.78 (s, 3H), 3.76 (s, 3H), 3.64 (d, J=14.3 Hz, 1H), 3.55 (d, J=8.0 Hz, 1H), 3.31 (m, 1H), 3.12 (d, J=7.7 Hz, 1H), 3.03-2.88 (m, 1H), 2.66 (dd, J=12.1 Hz, 2H), 2.33 (t, J=11.5 Hz, 1H).

LRMS (ESI, m/z): 466 [M+H]$^+$.

Example C20 4-(((3-methoxy-5,6,8,9,14,14a-hexahydroindolo[3',2':4,5]pyridine[2,1-a]isoquinolin-2-yl)oxo)methyl)benzonitrile (C20)

The title compound C20 was synthesized according to Scheme 3, while benzyl bromide was substituted with 4-cyanobenzyl bromide.

$^1$H NMR (400 MHz, DMSO) δ 10.65 (s, 1H), 7.67-7.49 (m, 2H), 7.36-7.29 (m, 2H), 7.27-7.24 (m, 3H), 7.03 (s, 1H), 6.94 (m, 1H), 6.77-6.68 (m, 2H), 5.08 (q, J=11.3 Hz, 2H), 4.16 (d, J=15.7 Hz, 1H), 3.76 (s, 3H), 3.64 (d, J=14.3 Hz, 1H), 3.55 (d, J=8.0 Hz, 1H), 3.31 (m, 1H), 3.12 (d, J=7.7 Hz, 1H), 3.03-2.88 (m, 1H), 2.66 (dd, J=12.1 Hz, 2H), 2.33 (t, J=11.5 Hz, 1H).

LRMS (ESI, m/z): 436 [M+H]$^+$.

Example C21 2-((4-bromobenzyl)oxo)-3,12-dimethoxy-5,6,8,9,14,14a-hexahydroindole[3',2':4,5]pyridine[2,1-a]isoquinoline (C21)

The title compound C21 was synthesized according to Scheme 3, while benzyl bromide was substituted with 4-bromobenzyl bromide.

$^1$H NMR (400 MHz, DMSO) δ 10.65 (s, 1H), 7.41-7.38 (m, 2H), 7.36 (d, J=8.5 Hz, 1H), 7.32-7.24 (m, 2H), 7.03 (s, 1H), 6.94 (m, 1H), 6.77-6.68 (m, 2H), 5.08 (q, J=11.3 Hz, 2H), 4.16 (d, J=15.7 Hz, 1H), 3.78 (s, 3H), 3.76 (s, 3H), 3.64 (d, J=14.3 Hz, 1H), 3.55 (d, J=8.0 Hz, 1H), 3.31 (m, 1H), 3.12 (d, J=7.7 Hz, 1H), 3.03-2.88 (m, 1H), 2.66 (dd, J=12.1 Hz, 2H), 2.33 (t, J=11.5 Hz, 1H).

LRMS (ESI, m/z): 519[M+H]+, 521[M+H]$^+$.

Example C22 2-((4-bromobenzyl)oxo)-3-methoxy-5,6,8,9,14,14a-hexahydroindole[3',2':4,5]pyridine[2,1-a]isoquinoline (C22)

The title compound C22 was synthesized according to Scheme 3, while benzyl bromide was substituted with 4-bromobenzyl bromide.

$^1$H NMR (400 MHz, DMSO) δ 10.65 (s, 1H), 7.41-7.38 (m, 2H), 7.36-7.29 (m, 2H), 7.28-7.24 (m, 3H), 7.03 (s, 1H), 6.94 (m, 1H), 6.77-6.68 (m, 2H), 5.08 (q, J=11.3 Hz, 2H), 4.16 (d, J=15.7 Hz, 1H), 3.76 (s, 3H), 3.64 (d, J=14.3 Hz, 1H), 3.55 (d, J=8.0 Hz, 1H), 3.31 (m, 1H), 3.12 (d, J=7.7 Hz, 1H), 3.03-2.88 (m, 1H), 2.66 (dd, J=12.1 Hz, 2H), 2.33 (t, J=11.5 Hz, 1H).

LRMS (ESI, m/z): 489[M+H]$^+$, 491[M+H]$^+$.

Example C23 2-((3-fluoro-4-(trifluoromethyl)benzyl)oxy)-3,12-dimethoxy-5,6,8,9,14,14a-hexahydroindole[3',2':4,5]pyridine[2,1-a]isoquinoline (C23)

The title compound C23 was synthesized according to Scheme 3, while benzyl bromide was substituted with 3-fluoro-4-(trifluoromethyl)benzyl bromide.

$^1$H NMR (400 MHz, DMSO) δ 10.75 (s, 1H), 7.51-7.35 (m, 4H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 527 [M+H]$^+$.

Example C24 2-((3-fluoro-4-(trifluoromethyl)benzyl)oxy)-3-methoxy-5,6,8,9,14,14a-hexahydroindole[3',2': 4,5]pyridine[2,1-a]isoquinoline (C24)

The title compound C24 was synthesized according to Scheme 3, while benzyl bromide was substituted with 3-fluoro-4-(trifluoromethyl)benzyl bromide.

¹H NMR (400 MHz, DMSO) δ 10.75 (s, 1H), 7.51-7.35 (m, 5H), 7.05 (s, 1H), 6.94 (d, J=2.1 Hz, 1H), 6.79-6.69 (m, 2H), 5.08 (s, 2H), 4.18 (d, J=15.0 Hz, 1H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 497 [M+H]⁺.

Example C25 2-((2-fluoro-4-(trifluoromethyl)benzyl)oxy)-3,12-dimethoxy-5,6,8,9,14,14a-hexahydroindole[3',2':4,5]pyridine[2,1-a]isoquinoline (C25)

The title compound C25 was synthesized according to Scheme 2, while benzyl bromide was substituted with 3-fluoro-4-(trifluoromethyl)benzyl bromide.
¹H NMR (400 MHz, DMSO) δ 10.75 (s, 1H), 7.51-7.35 (m, 4H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 527 [M+H]⁺.

Example C26 2-((2-fluoro-4-(trifluoromethyl)benzyl)oxy)-3-methoxy-5,6,8,9,14,14a-hexahydroindole[3',2':4,5]pyridine[2,1-a]isoquinoline (C26)

The title compound C26 was synthesized according to Scheme 2, while benzyl bromide was substituted with 3-fluoro-4-(trifluoromethyl)benzyl bromide.
¹H NMR (400 MHz, DMSO) δ 10.75 (s, 1H), 7.51-7.35 (m, 5H), 7.05 (s, 1H), 6.94 (d, J=2.1 Hz, 1H), 6.79-6.69 (m, 2H), 5.08 (s, 2H), 4.18 (d, J=15.0 Hz, 1H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 497 [M+H]⁺.

Example C27 2-((4-ethylbenzyl)oxo)-3,12-dimethoxy-5,6,8,9,14,14a-hexahydroindole[3',2':4,5]pyridine[2,1-a]isoquinoline (C27)

The title compound C27 was synthesized according to Scheme 3, while benzyl bromide was substituted with 4-ethylbenzyl bromide.
¹H NMR (400 MHz, DMSO) δ 10.75 (s, 1H), 7.51-7.35 (m, 5H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H), 2.34 (q, J=8.0 Hz, 2H), 1.01 (t, J=8.0 Hz, 3H).
LRMS (ESI, m/z): 469 [M+H]⁺.

Example C28 2-((4-ethylbenzyl)oxo)-3-methoxy-5,6,8,9,14,14a-hexahydroindole[3',2':4,5]pyridine[2,1-a]isoquinoline (C28)

The title compound C28 was synthesized according to Scheme 3, while benzyl bromide was substituted with 4-ethylbenzyl bromide.
¹H NMR (400 MHz, DMSO) δ 10.75 (s, 1H), 7.51-7.35 (m, 5H), 7.21-7.05 (m, 2H), 6.94 (d, J=2.1 Hz, 1H), 6.79-6.69 (m, 2H), 5.08 (s, 2H), 4.18 (d, J=15.0 Hz, 1H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H), 2.34 (q, J=8.0 Hz, 2H), 1.01 (t, J=8.0 Hz, 3H).
LRMS (ESI, m/z): 439 [M+H]⁺.

Example C29 3,12-dimethoxy-2-(naphthalen-2-ylmethoxy)-5,6,8,9,14,14a-hexahydroindolo[3',2':4,5]pyridine[2,1-a]isoquinoline (C29)

The title compound C29 was synthesized according to Scheme 3, while benzyl bromide was substituted with 2-bromomethylnaphthalene.
¹H NMR (400 MHz, DMSO) δ 10.70 (s, 1H), 7.67-7.32 (m, 7H), 7.25-7.12 (m, 2H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 491 [M+H]⁺.

Example C30 3-methoxy-2-(naphthalen-2-ylmethoxy)-5,6,8,9,14,14a-hexahydroindolo[3',2':4,5]pyridine[2,1-a]isoquinoline (C30)

The title compound C30 was synthesized according to Scheme 3, while benzyl bromide was substituted with 2-bromomethylnaphthalene.
¹H NMR (400 MHz, DMSO) δ 10.70 (s, 1H), 7.67-7.32 (m, 7H), 7.25-7.12 (m, 3H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 461 [M+H]⁺.

Example C31 4-(((9-(Hydroxymethyl)-3,12-dimethoxy-5,6,8,9,14,14a-hexahydroindole[3',2':4,5]pyridine[2,1-a]isoquinolin-2-yl)oxo)methyl)benzoate (C31)

The title compound C31 was synthesized according to Scheme 3, while benzyl bromide was substituted with methyl 4-bromomethyl benzoate.
¹H NMR (400 MHz, DMSO) δ 10.70 (s, 1H), 7.51-7.35 (m, 6H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 499 [M+H]⁺.

Example C32 4-(((9-(Hydroxymethyl)-3-methoxy-5,6,8,9,14,14a-hexahydroindole[3',2':4,5]pyridine[2,1-a]isoquinolin-2-yl)oxo)methyl)benzoate (C32)

The title compound C32 was synthesized according to Scheme 3, while benzyl bromide was substituted with methyl 4-bromomethylbenzoate.
¹H NMR (400 MHz, DMSO) δ 10.70 (s, 1H), 8.01-7.95 (m, 2H), 7.51-7.35 (m, 6H), 7.05-6.94 (m, 2H), 6.79-6.69 (m, 2H), 5.11 (d, J=4.8 Hz, 2H), 4.16 (d, J=15.1 Hz, 1H), 3.77 (d, J=11.4 Hz, 6H), 3.64 (d, J=15.6 Hz, 1H), 3.54 (d, J=7.2 Hz, 1H), 3.31 (s, 1H), 3.14 (s, 1H), 2.94 (d, J=11.4 Hz, 1H), 2.64 (dd, J=21.1, 13.3 Hz, 2H), 2.40-2.27 (m, 1H).
LRMS (ESI, m/z): 469 [M+H]⁺.

Example C33 2-((4-(1H-pyrazol-1-yl)benzyl)oxo)-3,12-dimethoxy-5,6,8,9,14,14a-hexahydroindole[3',2':4,5]pyridine[2,1-a]isoquinoline (C33)

The title compound C33 was synthesized according to Scheme 3, while benzyl bromide was substituted with 1-ó4-(bromomethyl)benzene-1H-pyrazole.

$^1$H NMR (400 MHz, DMSO) δ 10.70 (s, 1H), 7.87 (d, J=8 Hz, 1H), 7.62-7.45 (m, 5H), 7.05-6.84 (m, 3H), 6.79-6.69 (m, 2H), 6.47 (q, J=8 Hz, 1H), 5.11 (d, J=4.8 Hz, 2H), 4.16 (d, J=15.1 Hz, 1H), 3.77 (d, J=11.4 Hz, 6H), 3.64 (d, J=15.6 Hz, 1H), 3.54 (d, J=7.2 Hz, 1H), 3.31 (s, 1H), 3.14 (s, 1H), 2.94 (d, J=11.4 Hz, 1H), 2.64 (dd, J=21.1, 13.3 Hz, 2H), 2.40-2.27 (m, 1H).

LRMS (ESI, m/z): 507 [M+H]$^+$.

Example C34 2-((4-(1H-pyrazol-1-yl)benzyl)oxo)-3-methoxy-5,6,8,9,14,14a-hexahydroindole[3',2':4,5]pyridine[2,1-a]isoquinoline (C34)

The title compound C34 was synthesized according to Scheme 3, while benzyl bromide was substituted with 1-ó4-(bromomethyl)benzene-1H-pyrazole.

$^1$H NMR (400 MHz, DMSO) δ 10.70 (s, 1H), 7.87 (d, J=8 Hz, 1H), 7.62-7.45 (m, 5H), 7.05-6.84 (m, 4H), 6.79-6.69 (m, 2H), 6.47 (q, J=8 Hz, 1H), 5.11 (d, J=4.8 Hz, 2H), 4.16 (d, J=15.1 Hz, 1H), 3.77 (d, J=11.4 Hz, 6H), 3.64 (d, J=15.6 Hz, 1H), 3.54 (d, J=7.2 Hz, 1H), 3.31 (s, 1H), 3.14 (s, 1H), 2.94 (d, J=11.4 Hz, 1H), 2.64 (dd, J=21.1, 13.3 Hz, 2H), 2.40-2.27 (m, 1H).

LRMS (ESI, m/z): 477 [M+H]$^+$.

Example C35 3-(benzyloxy)-11-fluoro-2-methoxy-5,6,8,9,14,14a-hexahydroindole[3',2':4,5]pyridine[2,1-a]isoquinoline (C35)

The title compound C35 was synthesized according to Scheme 3, while 5-methoxy-3-indoleacetic acid was replaced with 6-fluoro-3-indoleacetic acid.

$^1$H NMR (400 MHz, DMSO) δ 10.72 (s, 1H), 7.51-7.35 (m, 5H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 429 [M+H]$^+$.

Example C36 3-(benzyloxy)-12-fluoro-2-methoxy-5,6,8,9,14,14a-hexahydroindole[3',2':4,5]pyridine[2,1-a]isoquinoline (C36)

The title compound C36 was synthesized according to Scheme 3, while 5-methoxy-3-indoleacetic acid was replaced with 5-fluoro-3-indoleacetic acid.

$^1$H NMR (400 MHz, DMSO) δ 10.70 (s, 1H), 7.51-7.35 (m, 5H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 429 [M+H]$^+$.

Example C37 3-(benzyloxy)-11-fluoro-2-methoxy-5,6,8,9,14,14a-hexahydroindole[3',2':4,5]pyridine[2,1-a]isoquinoline (C37)

The title compound C37 was synthesized according to Scheme 3, while 5-methoxy-3-indoleacetic acid was replaced with 4-fluoro-3-indoleacetic acid.

$^1$H NMR (400 MHz, DMSO) δ 10.70 (s, 1H), 7.51-7.35 (m, 5H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 429 [M+H]$^+$.

Example C38 3-(benzyloxy)-11-chloro-2-methoxy-5,6,8,9,14,14a-hexahydroindole[3' 2':4,5]pyridine[2,1-a]isoquinoline (C38)

The title compound C38 was synthesized according to Scheme 3, while 5-methoxy-3-indoleacetic acid was replaced with 6-chloro-3-indoleacetic acid.

$^1$H NMR (400 MHz, DMSO) δ 10.70 (s, 1H), 7.51-7.35 (m, 5H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 445 [M+H]$^+$.

Example C39 3-(benzyloxy)-12-chloro-2-methoxy-5,6,8,9,14,14a-hexahydroindole[3' 2':4,5]pyridine[2,1-a]isoquinoline (C39)

The title compound C39 was synthesized according to Scheme 3, while 5-methoxy-3-indoleacetic acid was replaced with 5-chloro-3-indoleacetic acid.

$^1$H NMR (400 MHz, DMSO) δ 10.70 (s, 1H), 7.51-7.35 (m, 5H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 445 [M+H]$^+$.

Example C40 (3-(Benzyloxy)-13-chloro-2-methoxy-5,6,14,14a-tetrahydroindolo[3',2':4,5]pyridine[2,1-a]isoquinoline-9(8H)-yl)methanol (C40)

The title compound C40 was synthesized according to Scheme 3, while 5-methoxy-3-indoleacetic acid was replaced with 4-chloro-3-indoleacetic acid. 1H NMR (400 MHz, DMSO) δ 10.70 (s, 1H), 7.51-7.35 (m, 5H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 445 [M+H]$^+$.

Example C41 3-(benzyloxy)-11-bromo-2-methoxy-5,6,8,9,14,14a-hexahydroindole[3',2':4,5]pyridine[2,1-a]isoquinoline (C41)

The title compound C41 was synthesized according to Scheme 3, while 5-methoxy-3-indoleacetic acid was replaced with 6-bromo-3-indoleacetic acid. 1H NMR (400 MHz, DMSO) δ 10.70 (s, 1H), 7.51-7.35 (m, 5H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 489 [M+H]$^+$, 491 [M+H]$^+$.

Example C42 3-(benzyloxy)-12-bromo-2-methoxy-5,6,8,9,14,14a-hexahydroindole[3',2':4,5]pyridine[2,1-a]isoquinoline (C42)

The title compound C42 was synthesized according to Scheme 3, while 5-methoxy-3-indoleacetic acid was replaced with 5-bromo-3-indoleacetic acid.

$^1$H NMR (400 MHz, DMSO) δ 10.70 (s, 1H), 7.51-7.35 (m, 5H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 489 [M+H]$^+$, 491 [M+H]$^+$.

Example C43 3-(benzyloxy)-13-bromo-2-methoxy-5,6,8,9,14,14a-hexahydroindole[3',2':4,5]pyridine[2,1-a]isoquinoline (C43)

The title compound C43 was synthesized according to Scheme 3, while 5-methoxy-3-indoleacetic acid was replaced with 4-bromo-3-indoleacetic acid.

$^1$H NMR (400 MHz, DMSO) δ 10.70 (s, 1H), 7.51-7.35 (m, 5H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 489 [M+H]$^+$, 491 [M+H]$^+$.

Example C44 3-(benzyloxy)-2-methoxy-11-methyl-5,6,8,9,14,14a-hexahydroindole[3',2':4,5]pyridine[2,1-a]isoquinoline (C44)

The title compound C44 was synthesized according to Scheme 3, while 5-methoxyindoleacetic acid was replaced with 6-methyl-3-indoleacetic acid.

$^1$H NMR (400 MHz, DMSO) δ 10.70 (s, 1H), 7.39-7.35 (m, 3H), 7.28-7.21 (m, 3H), 7.06 (s, 1H), 6.96 (d, J=2.3 Hz, 1H), 6.74 (dd, J=9.7, 3.3 Hz, 2H), 5.05 (q, J=11.6 Hz, 2H), 4.17 (d, J=14.9 Hz, 1H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.03-2.86 (m, 1H), 2.74-2.57 (m, 2H), 2.37 (t, J=7.1 Hz, 2H), 2.32 (s, 3H).

LRMS (ESI, m/z): 425 [M+H]$^+$.

Example C45 3-(benzyloxy)-12-ethyl-2-methoxy-5,6,8,9,14,14a-hexahydroindole[3',2':4,5]pyridine[2,1-a]isoquinoline (C45)

The title compound C45 was synthesized according to Scheme 1, while 5-methoxyindoleacetic acid was replaced with 5-ethyl-3-indoleacetic acid.

$^1$H NMR (400 MHz, DMSO) δ 10.70 (s, 1H), 7.39-7.35 (m, 3H), 7.28-7.21 (m, 3H), 7.06 (s, 1H), 6.96 (d, J=2.3 Hz, 1H), 6.74 (dd, J=9.7, 3.3 Hz, 2H), 5.05 (q, J=11.6 Hz, 2H), 4.17 (d, J=14.9 Hz, 1H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.03-2.86 (m, 1H), 2.74-2.57 (m, 2H), 2.37 (t, J=7.1 Hz, 2H), 2.34 (q, J=8.0 Hz, 2H), 1.01 (t, J=8.0 Hz, 3H).

LRMS (ESI, m/z): 439 [M+H]$^+$.

Example C46 3-(benzyloxy)-2-methoxy-5,6,8,9,14,14a-hexahydroindolo[3',2':4,5]pyridine[2,1-a]isoquinolin-12-phenol (C46)

The title compound C46 was synthesized according to Scheme-3, while 5-methoxyindoleacetic acid was replaced with 5-hydroxy-3-indoleacetic acid.

$^1$H NMR (400 MHz, DMSO) δ 10.70 (s, 1H), 7.39-7.35 (m, 3H), 7.28-7.21 (m, 3H), 7.06 (s, 1H), 6.96 (d, J=2.3 Hz, 1H), 6.74 (dd, J=9.7, 3.3 Hz, 2H), 5.26 (s, 1H), 5.05 (q, J=11.6 Hz, 2H), 4.17 (d, J=14.9 Hz, 1H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.03-2.86 (m, 1H), 2.74-2.57 (m, 2H), 2.37 (t, J=7.1 Hz, 2H).

LRMS (ESI, m/z): 427 [M+H]$^+$.

Example C47 2,12-dimethoxy-3-((4-(trifluoromethyl)benzyl)oxy)-5,6,8,9,14,14a-hexahydroindolo[3',2':4,5]pyridine[2,1-a]isoquinoline (C47)

The title compound C47 was synthesized according to Scheme 3, while benzyl bromide was substituted with 4-trifluoromethylbenzyl bromide.

$^1$H NMR (400 MHz, DMSO) δ 10.70 (s, 1H), 7.71-7.53 (m, 2H), 7.50-7.35 (m, 1H), 7.31-7.15 (m, 2H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 509 [M+H]$^+$.

Example C48 2-methoxy-3-((4-(trifluoromethyl)benzyl)oxy)-5,6,8,9,14,14a-hexahydroindolo[3',2':4,5]pyridine[2,1-a]isoquinoline (C48)

The title compound C48 was synthesized according to Scheme 3, while benzyl bromide was substituted with 4-trifluoromethylbenzyl bromide.

$^1$H NMR (400 MHz, DMSO) δ 10.70 (s, 1H), 7.71-7.53 (m, 2H), 7.50-7.35 (m, 1H), 7.31-7.15 (m, 3H), 7.05 (s, 1H), 6.94 (d, J=2.1 Hz, 1H), 6.79-6.69 (m, 2H), 5.08 (s, 2H), 4.18 (d, J=15.0 Hz, 1H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 479 [M+H]$^+$.

Example C49 3-((4-Fluorobenzyl)oxo)-2,12-dimethoxy-5,6,8,9,14,14a-hexahydroindole[3',2':4,5]pyridine[2,1-a]isoquinoline (C49)

The title compound C49 was synthesized according to Scheme 3, while benzyl bromide was substituted with 4-fluorobenzyl bromide.

$^1$H NMR (400 MHz, DMSO) δ 10.70 (s, 1H), 7.57-7.47 (m, 2H), 7.36 (d, J=8.5 Hz, 1H), 7.32-7.24 (m, 2H), 7.03 (s,

1H), 6.94 (m, 1H), 6.77-6.68 (m, 2H), 5.08 (q, J=11.3 Hz, 2H), 4.16 (d, J=15.7 Hz, 1H), 3.78 (s, 3H), 3.76 (s, 3H), 3.64 (d, J=14.3 Hz, 1H), 3.55 (d, J=8.0 Hz, 1H), 3.31 (m, 1H), 3.12 (d, J=7.7 Hz, 1H), 3.03-2.88 (m, 1H), 2.66 (dd, J=12.1 Hz, 2H), 2.33 (t, J=11.5 Hz, 1H).
LRMS (ESI, m/z): 459 [M+H]$^+$.

Example C50 3-((4-fluorobenzyl)oxo)-2-methoxy-5,6,8,9,14,14a-hexahydroindole[3',2':4,5]pyridine[2,1-a]isoquinoline (C50)

The title compound C50 was synthesized according to Scheme 3, while benzyl bromide was substituted with 4-fluorobenzyl bromide.
$^1$H NMR (400 MHz, DMSO) δ 10.70 (s, 1H), 7.57-7.47 (m, 2H), 7.36 (d, J=8.5 Hz, 1H), 7.32-7.24 (m, 3H), 7.03 (s, 1H), 6.94 (m, 1H), 6.77-6.68 (m, 2H), 5.08 (q, J=11.3 Hz, 2H), 4.16 (d, J=15.7 Hz, 1H), 3.78 (s, 3H), 3.76 (s, 3H), 3.64 (d, J=14.3 Hz, 1H), 3.55 (d, J=8.0 Hz, 1H), 3.31 (m, 1H), 3.12 (d, J=7.7 Hz, 1H), 3.03-2.88 (m, 1H), 2.66 (dd, J=12.1 Hz, 2H), 2.33 (t, J=11.5 Hz, 1H).
LRMS (ESI, m/z): 429 [M+H]$^+$.

Example C51 3-((3-Fluorobenzyl)oxo)-2,12-dimethoxy-5,6,8,9,14,14a-hexahydroindole[3',2':4,5]pyridine[2,1-a]isoquinoline (C51)

The title compound C51 was synthesized according to Scheme 3, while benzyl bromide was substituted with 3-fluorobenzyl bromide.
$^1$H NMR (400 MHz, DMSO) δ 10.70 (s, 1H), 7.51-7.35 (m, 5H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 459 [M+H]$^+$.

Example C52 3-((3-fluorobenzyl)oxo)-2-methoxy-5,6,8,9,14,14a-hexahydroindole[3',2':4,5]pyridine[2,1-a]isoquinoline (C52)

The title compound C52 was synthesized according to Scheme 3, while benzyl bromide was substituted with 3-fluorobenzyl bromide.
$^1$H NMR (400 MHz, DMSO) δ 10.70 (s, 1H), 7.50-7.43 (m, 3H), 7.26-7.15 (m, 3H), 7.00 (s, 1H), 6.95 (d, J=2.3 Hz, 1H), 6.80 (s, 1H), 6.65 (dd, J=8.7, 2.4 Hz, 1H), 5.03 (s, 2H), 4.18 (d, J=15.0 Hz, 1H), 3.97 (d, J=14.6 Hz, 1H), 3.77 (s, 3H), 3.61 (dd, J=22.2, 12.4 Hz, 2H), 3.41 (d, J=14.6 Hz, 1H), 3.11 (d, J=11.1 Hz, 1H), 2.92 (d, J=10.6 Hz, 1H), 2.60 (dd, J=20.6, 13.0 Hz, 2H), 2.48-2.39 (m, 1H).
LRMS (ESI, m/z): 429 [M+H]$^+$.

Example C53 3-((2-Fluorobenzyl)oxo)-2,12-dimethoxy-5,6,8,9,14,14a-hexahydroindole[3',2':4,5]pyridine[2,1-a]isoquinoline (C53)

The title compound C53 was synthesized according to Scheme 2, while benzyl bromide was substituted with 2-fluorobenzyl bromide.
$^1$H NMR (400 MHz, DMSO) δ 10.70 (s, 1H), 7.51-7.35 (m, 5H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 459 [M+H]$^+$.

Example C54 3-((2-fluorobenzyl)oxo)-2-methoxy-5,6,8,9,14,14a-hexahydroindole[3',2':4,5]pyridine[2,1-a]isoquinoline (C54)

The title compound C54 was synthesized according to Scheme 2, while benzyl bromide was substituted with 2-fluorobenzyl bromide.
$^1$H NMR (400 MHz, DMSO) δ 10.70 (s, 1H), 7.51-7.35 (m, 5H), 7.05 (s, 1H), 6.94 (d, J=2.1 Hz, 1H), 6.79-6.69 (m, 3H), 5.08 (s, 2H), 4.18 (d, J=15.0 Hz, 1H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 429 [M+H]$^+$.

Example C55 (2,12-dimethoxy-3-((4-methoxybenzyl)oxo)-5,6,8,9,14,14a-hexahydroindolo[3',2':4,5]pyridine[2,1-a]isoquinoline (C55)

The title compound C55 was synthesized according to Scheme 4, while benzyl bromide was substituted with 4-methoxybenzyl bromide.
$^1$H NMR (400 MHz, DMSO) δ 10.70 (s, 1H), 7.40-7.28 (m, 2H), 7.10-7.03 (m, 3H), 6.98-6.87 (m, 2H), 6.79-6.68 (m, 2H), 5.09 (q, J=11.9 Hz, 2H), 4.16 (d, J=15.3 Hz, 1H), 3.79 (s, 3H), 3.78 (s, 3H), 3.76 (s, 3H), 3.64 (d, J=15.0 Hz, 1H), 3.54 (dd, J=10.6, 2.9 Hz, 1H), 3.32 (d, J=3.1 Hz, 1H), 3.17-3.08 (m, 1H), 3.03-2.85 (m, 1H), 2.73-2.56 (m, 2H), 2.33 (t, J=7.0 Hz, 1H).
LRMS (ESI, m/z): 471 [M+H]$^+$.

Example C56 (2-methoxy-3-((4-methoxybenzyl)oxo)-5,6,8,9,14,14a-hexahydroindolo[3',2':4,5]pyridine[2,1-a]isoquinoline (C56)

The title compound C56 was synthesized according to Scheme 4, while benzyl bromide was substituted with 4-methoxybenzyl bromide.
$^1$H NMR (400 MHz, DMSO) δ 10.70 (s, 1H), 7.40-7.28 (m, 2H), 7.10-7.03 (m, 4H), 6.98-6.87 (m, 2H), 6.79-6.68 (m, 2H), 5.09 (q, J=11.9 Hz, 2H), 4.16 (d, J=15.3 Hz, 1H), 3.79 (s, 3H), 3.76 (s, 3H), 3.64 (d, J=15.0 Hz, 1H), 3.54 (dd, J=10.6, 2.9 Hz, 1H), 3.32 (d, J=3.1 Hz, 1H), 3.17-3.08 (m, 1H), 3.03-2.85 (m, 1H), 2.73-2.56 (m, 2H), 2.33 (t, J=7.0 Hz, 1H).
LRMS (ESI, m/z): 441 [M+H]$^+$.

Example C57 2,12-dimethoxy-3-((3-methoxybenzyl)oxo)-5,6,8,9,14,14a-hexahydroindolo[3',2':4,5]pyridine[2,1-a]isoquinoline (C57)

The title compound C57 was synthesized according to Scheme 3, while benzyl bromide was substituted with 3-methoxybenzyl bromide.
$^1$H NMR (400 MHz, DMSO) δ 10.70 (s, 1H), 7.40-7.28 (m, 2H), 7.10-7.03 (m, 3H), 6.98-6.87 (m, 2H), 6.79-6.68 (m, 2H), 5.09 (q, J=11.9 Hz, 2H), 4.16 (d, J=15.3 Hz, 1H), 3.79 (s, 3H), 3.78 (s, 3H), 3.76 (s, 3H), 3.64 (d, J=15.0 Hz, 1H), 3.54 (dd, J=10.6, 2.9 Hz, 1H), 3.32 (d, J=3.1 Hz, 1H), 3.17-3.08 (m, 1H), 3.03-2.85 (m, 1H), 2.73-2.56 (m, 2H), 2.33 (t, J=7.0 Hz, 1H).
LRMS (ESI, m/z): 471 [M+H]$^+$.

Example C58 (2-methoxy-3-((3-methoxybenzyl)oxo)-5,6,8,9,14,14a-hexahydroindolo[3',2':4,5]pyridine[2,1-a]isoquinoline (C58)

The title compound C58 was synthesized according to Scheme 3, while benzyl bromide was substituted with 3-methoxybenzyl bromide.

$^1$H NMR (400 MHz, DMSO) δ 10.70 (s, 1H), 7.40-7.28 (m, 2H), 7.10-7.03 (m, 4H), 6.98-6.87 (m, 2H), 6.79-6.68 (m, 2H), 5.09 (q, J=11.9 Hz, 2H), 4.16 (d, J=15.3 Hz, 1H), 3.79 (s, 3H), 3.76 (s, 3H), 3.64 (d, J=15.0 Hz, 1H), 3.54 (dd, J=10.6, 2.9 Hz, 1H), 3.32 (d, J=3.1 Hz, 1H), 3.17-3.08 (m, 1H), 3.03-2.85 (m, 1H), 2.73-2.56 (m, 2H), 2.33 (t, J=7.0 Hz, 1H).

LRMS (ESI, m/z): 441 [M+H]$^+$.

Example C59 (2,12-dimethoxy-3-((4-methylbenzyl)oxy)-5,6,8,9,14,14a-hexahydroindolo[3',2':4,5]pyridine[2,1-a]isoquinoline (C59)

The title compound C59 was synthesized according to Scheme 3, while benzyl bromide was substituted with 4-methylbenzyl bromide.

$^1$H NMR (400 MHz, DMSO) δ 10.70 (s, 1H), 7.39-7.35 (m, 3H), 7.22 (d, J=8.0 Hz, 2H), 7.06 (s, 1H), 6.96 (d, J=2.3 Hz, 1H), 6.74 (dd, J=9.7, 3.3 Hz, 2H), 5.05 (q, J=11.6 Hz, 1H), 4.17 (d, J=14.9 Hz, 1H), 3.79 (s, 3H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.03-2.86 (m, 1H), 2.74-2.57 (m, 2H), 2.37 (t, J=7.1 Hz, 2H), 2.32 (s, 3H).

LRMS (ESI, m/z): 455 [M+H]$^+$.

Example C60 (2-methoxy-3-((4-methylbenzyl)oxy)-5,6,8,9,14,14a-hexahydroindolo[3',2':4,5]pyridine[2,1-a]isoquinoline (C60)

The title compound C60 was synthesized according to Scheme 3, while benzyl bromide was substituted with 4-methylbenzyl bromide.

$^1$H NMR (400 MHz, DMSO) δ 10.70 (s, 1H), 7.39-7.35 (m, 3H), 7.28-7.21 (m, 3H), 7.06 (s, 1H), 6.96 (d, J=2.3 Hz, 1H), 6.74 (dd, J=9.7, 3.3 Hz, 2H), 5.05 (q, J=11.6 Hz, 2H), 4.17 (d, J=14.9 Hz, 1H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.03-2.86 (m, 1H), 2.74-2.57 (m, 2H), 2.37 (t, J=7.1 Hz, 2H), 2.32 (s, 3H).

LRMS (ESI, m/z): 425 [M+H]$^+$.

Example C61 (3-((4-chlorobenzyl)oxo)-2,12-dimethoxy-5,6,8,9,14,14a-hexahydroindole[3',2':4,5]pyridine[2,1-a]isoquinoline (C61)

The title compound C61 was synthesized according to Scheme 3, while benzyl bromide was substituted with 4-chlorobenzyl bromide.

$^1$H NMR (400 MHz, DMSO) δ 10.70 (s, 1H), 7.47-7.39 (m, 2H), 7.36 (d, J=8.5 Hz, 1H), 7.32-7.24 (m, 2H), 7.03 (s, 1H), 6.94 (m, 1H), 6.77-6.68 (m, 2H), 5.08 (q, J=11.3 Hz, 2H), 4.16 (d, J=15.7 Hz, 1H), 3.78 (s, 3H), 3.76 (s, 3H), 3.64 (d, J=14.3 Hz, 1H), 3.55 (d, J=8.0 Hz, 1H), 3.31 (m, 1H), 3.12 (d, J=7.7 Hz, 1H), 3.03-2.88 (m, 1H), 2.66 (dd, J=12.1 Hz, 2H), 2.33 (t, J=11.5 Hz, 1H).

LRMS (ESI, m/z): 476 [M+H]$^+$.

Example C62 (3-((4-chlorobenzyl)oxo)-2-methoxy-5,6,8,9,14,14a-hexahydroindole[3',2':4,5]pyridine[2,1-a]isoquinoline (C62)

The title compound C62 was synthesized according to Scheme 3, while benzyl bromide was substituted with 4-chlorobenzyl bromide.

$^1$H NMR (400 MHz, DMSO) δ 10.70 (s, 1H), 7.47-7.39 (m, 2H), 7.36-7.29 (m, 2H), 7.28-7.24 (m, 3H), 7.03 (s, 1H), 6.94 (m, 1H), 6.77-6.68 (m, 2H), 5.08 (q, J=11.3 Hz, 2H), 4.16 (d, J=15.7 Hz, 1H), 3.76 (s, 3H), 3.64 (d, J=14.3 Hz, 1H), 3.55 (d, J=8.0 Hz, 1H), 3.31 (m, 1H), 3.12 (d, J=7.7 Hz, 1H), 3.03-2.88 (m, 1H), 2.66 (dd, J=12.1 Hz, 2H), 2.33 (t, J=11.5 Hz, 1H).

LRMS (ESI, m/z): 446 [M+H]$^+$.

Example C63 3-((4-chlorobenzyl)oxo)-2-methoxy-5,6,8,9,14,14a-hexahydroindole[3',2':4,5]pyridine[2,1-a]isoquinoline (C63)

The title compound C63 was synthesized according to Scheme 3, while benzyl bromide was substituted with 4-cyanobenzyl bromide.

$^1$H NMR (400 MHz, DMSO) δ 10.70 (s, 1H), 7.67-7.49 (m, 2H), 7.36 (d, J=8.5 Hz, 1H), 7.32-7.24 (m, 2H), 7.03 (s, 1H), 6.94 (m, 1H), 6.77-6.68 (m, 2H), 5.08 (q, J=11.3 Hz, 2H), 4.16 (d, J=15.7 Hz, 1H), 3.78 (s, 3H), 3.76 (s, 3H), 3.64 (d, J=14.3 Hz, 1H), 3.55 (d, J=8.0 Hz, 1H), 3.31 (m, 1H), 3.12 (d, J=7.7 Hz, 1H), 3.03-2.88 (m, 1H), 2.66 (dd, J=12.1 Hz, 2H), 2.33 (t, J=11.5 Hz, 1H).

LRMS (ESI, m/z): 466 [M+H]$^+$.

Example C64

4-(((2-methoxy-5,6,8,9,14,14a-hexahydroindolo[3',2':4,5]pyridine[2,1-a]isoquinolin-3-yl)oxo)methyl)benzonitrile (C64)

The title compound C64 was synthesized according to Scheme 3, while benzyl bromide was substituted with 4-cyanobenzyl bromide.

$^1$H NMR (400 MHz, DMSO) δ 10.70 (s, 1H), 7.67-7.49 (m, 2H), 7.36-7.29 (m, 2H), 7.27-7.24 (m, 3H), 7.03 (s, 1H), 6.94 (m, 1H), 6.77-6.68 (m, 2H), 5.08 (q, J=11.3 Hz, 2H), 4.16 (d, J=15.7 Hz, 1H), 3.76 (s, 3H), 3.64 (d, J=14.3 Hz, 1H), 3.55 (d, J=8.0 Hz, 1H), 3.31 (m, 1H), 3.12 (d, J=7.7 Hz, 1H), 3.03-2.88 (m, 1H), 2.66 (dd, J=12.1 Hz, 2H), 2.33 (t, J=11.5 Hz, 1H).

LRMS (ESI, m/z): 436 [M+H]$^+$.

Example C65 (3-((4-bromobenzyl)oxo)-2,12-dimethoxy-5,6,8,9,14,14a-hexahydroindole[3',2':4,5]pyridine[2,1-a]isoquinoline (C65)

The title compound C65 was synthesized according to Scheme 3, while benzyl bromide was substituted with 4-bromobenzyl bromide.

$^1$H NMR (400 MHz, DMSO) δ 10.70 (s, 1H), 7.41-7.38 (m, 2H), 7.36 (d, J=8.5 Hz, 1H), 7.32-7.24 (m, 2H), 7.03 (s, 1H), 6.94 (m, 1H), 6.77-6.68 (m, 2H), 5.08 (q, J=11.3 Hz, 2H), 4.16 (d, J=15.7 Hz, 1H), 3.78 (s, 3H), 3.76 (s, 3H), 3.64 (d, J=14.3 Hz, 1H), 3.55 (d, J=8.0 Hz, 1H), 3.31 (m, 1H), 3.12 (d, J=7.7 Hz, 1H), 3.03-2.88 (m, 1H), 2.66 (dd, J=12.1 Hz, 2H), 2.33 (t, J=11.5 Hz, 1H).

LRMS (ESI, m/z): 519[M+H]+, 521[M+H]$^+$.

Example C66 (3-((4-bromobenzyl)oxo)-2-methoxy-5,6,8,9,14,14a-hexahydroindole[3',2':4,5]pyridine[2,1-a]isoquinoline (C66)

The title compound C66 was synthesized according to Scheme 3, while benzyl bromide was substituted with 4-bromobenzyl bromide.

$^1$H NMR (400 MHz, DMSO) δ 10.70 (s, 1H), 7.41-7.38 (m, 2H), 7.36-7.29 (m, 2H), 7.28-7.24 (m, 3H), 7.03 (s, 1H), 6.94 (m, 1H), 6.77-6.68 (m, 2H), 5.08 (q, J=11.3 Hz, 2H), 4.16 (d, J=15.7 Hz, 1H), 3.76 (s, 3H), 3.64 (d, J=14.3 Hz, 1H), 3.55 (d, J=8.0 Hz, 1H), 3.31 (m, 1H), 3.12 (d, J=7.7 Hz, 1H), 3.03-2.88 (m, 1H), 2.66 (dd, J=12.1 Hz, 2H), 2.33 (t, J=11.5 Hz, 1H).

LRMS (ESI, m/z): 489[M+H]$^+$, 491[M+H]$^+$.

Example C67 3-((3-fluoro-4-(trifluoromethyl)benzyl)oxy)-2,12-dimethoxy-5,6,8,9,14,14a-hexahydroindole[3',2':4,5]pyridine[2,1-a]isoquinoline (C67)

The title compound C67 was synthesized according to Scheme 3, while benzyl bromide was substituted with 3-fluoro-4-(trifluoromethyl)benzyl bromide.

$^1$H NMR (400 MHz, DMSO) δ 10.70 (s, 1H), 7.51-7.35 (m, 4H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 527 [M+H]$^+$.

Example C68 3-((3-fluoro-4-(trifluoromethyl)benzyl)oxy)-2-methoxy-5,6,8,9,14,14a-hexahydroindole[3',2': 4,5]pyridine[2,1-a]isoquinoline (C68)

The title compound C68 was synthesized according to Scheme 3, while benzyl bromide was substituted with 3-fluoro-4-(trifluoromethyl)benzyl bromide.

$^1$H NMR (400 MHz, DMSO) δ 10.70 (s, 1H), 7.51-7.35 (m, 5H), 7.05 (s, 1H), 6.94 (d, J=2.1 Hz, 1H), 6.79-6.69 (m, 2H), 5.08 (s, 2H), 4.18 (d, J=15.0 Hz, 1H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 497 [M+H]$^+$.

Example C69 3-((2-fluoro-4-(trifluoromethyl)benzyl)oxy)-2,12-dimethoxy-5,6,8,9,14,14a-hexahydroindole[3',2':4,5]pyridine[2,1-a]isoquinoline (C69)

The title compound C69 was synthesized according to Scheme 2, while benzyl bromide was substituted with 2-fluoro-4-(trifluoromethyl)benzyl bromide.

$^1$H NMR (400 MHz, DMSO) δ 10.70 (s, 1H), 7.51-7.35 (m, 4H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 527 [M+H]$^+$.

Example C70 3-((2-fluoro-4-(trifluoromethyl)benzyl)oxy)-2-methoxy-5,6,8,9,14,14a-hexahydroindole[3',2': 4,5]pyridine[2,1-a]isoquinoline (C70)

The title compound C70 was synthesized according to Scheme 2, while benzyl bromide was substituted with 3-fluoro-4-(trifluoromethyl)benzyl bromide.

$^1$H NMR (400 MHz, DMSO) δ 10.70 (s, 1H), 7.51-7.35 (m, 5H), 7.05 (s, 1H), 6.94 (d, J=2.1 Hz, 1H), 6.79-6.69 (m, 2H), 5.08 (s, 2H), 4.18 (d, J=15.0 Hz, 1H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 497 [M+H]$^+$.

Example C71 (2,12-dimethoxy-3-((4-ethylbenzyl)oxy)-5,6,8,9,14,14a-hexahydroindolo[3',2':4,5]pyridine[2,1-a]isoquinoline (C71)

The title compound C71 was synthesized according to Scheme 3, while benzyl bromide was substituted with 4-ethylbenzyl bromide.

$^1$H NMR (400 MHz, DMSO) δ 10.70 (s, 1H), 7.51-7.35 (m, 5H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H), 2.34 (q, J=8.0 Hz, 2H), 1.01 (t, J=8.0 Hz, 3H).

LRMS (ESI, m/z): 469 [M+H]$^+$.

Example C72 (2-methoxy-3-((4-ethylbenzyl)oxy)-5,6,8,9,14,14a-hexahydroindolo[3',2':4,5]pyridine[2,1-a]isoquinoline (C72)

The title compound C72 was synthesized according to Scheme 3, while benzyl bromide was substituted with 4-ethylbenzyl bromide.

$^1$H NMR (400 MHz, DMSO) δ 10.70 (s, 1H), 7.51-7.35 (m, 5H), 7.21-7.05 (m, 2H), 6.94 (d, J=2.1 Hz, 1H), 6.79-6.69 (m, 2H), 6.22 (t, J=7.0 Hz, 1H), 5.38 (d, J=7.4 Hz, 2H), 5.08 (s, 2H), 4.18 (d, J=15.0 Hz, 1H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H), 2.34 (q, J=8.0 Hz, 2H), 1.01 (t, J=8.0 Hz, 3H).

LRMS (ESI, m/z): 439 [M+H]$^+$.

Example C73 (2,12-dimethoxy-3-(naphthalen-2-ylmethoxy)-5,6,14,14a-hexahydroindolo[3',2':4,5]pyridine[2,1-a]isoquinoline (C73)

The title compound C73 was synthesized according to Scheme 3, while benzyl bromide was substituted with 2-bromomethylnaphthalene.

$^1$H NMR (400 MHz, DMSO) δ 10.70 (s, 1H), 7.67-7.32 (m, 7H), 7.25-7.12 (m, 2H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 491 [M+H]$^+$.

Example C74 (2-methoxy-3-(naphthalen-2-ylmethoxy)-5,6,8,9,14,14a-hexahydroindolo[3',2':4,5]pyridine[2,1-a]isoquinoline (C74)

The title compound C74 was synthesized according to Scheme 3, while benzyl bromide was substituted with 2-bromomethylnaphthalene.

¹H NMR (400 MHz, DMSO) δ 10.70 (s, 1H), 7.67-7.32 (m, 7H), 7.25-7.12 (m, 3H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 461 [M+H]⁺.

Example C75 4-(((2,12-dimethoxy-5,6,8,9,14,14a-hexahydroindolo[3',2':4,5]pyridine[2,1-a]isoquinolin-3-yl)oxo)methyl)benzoate (C75)

The title compound C75 was synthesized according to Scheme 3, while benzyl bromide was substituted with methyl 4-bromomethyl benzoate.
¹H NMR (400 MHz, DMSO) δ 10.70 (s, 1H), 7.51-7.35 (m, 6H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 499 [M+H]⁺.

Example C76

4-(((2-methoxy-5,6,8,9,14,14a-hexahydroindolo[3',2':4,5]pyridine[2,1-a]isoquinolin-3-yl)oxo)methyl)benzoate (C76)

The title compound C76 was synthesized according to Scheme 3, while benzyl bromide was substituted with methyl 4-bromomethyl benzoate.
¹H NMR (400 MHz, DMSO) δ 10.70 (s, 1H), 8.01-7.95 (m, 2H), 7.51-7.35 (m, 6H), 7.05-6.94 (m, 2H), 6.79-6.69 (m, 2H), 5.11 (d, J=4.8 Hz, 2H), 4.16 (d, J=15.1 Hz, 1H), 3.77 (d, J=11.4 Hz, 6H), 3.64 (d, J=15.6 Hz, 1H), 3.54 (d, J=7.2 Hz, 1H), 3.31 (s, 1H), 3.14 (s, 1H), 2.94 (d, J=11.4 Hz, 1H), 2.64 (dd, J=21.1, 13.3 Hz, 2H), 2.40-2.27 (m, 1H).
LRMS (ESI, m/z): 469 [M+H]⁺.

Example C77 (3-((4-(1H-pyrazol-1-yl)benzyl)oxo)-2,12-dimethoxy-5,6,8,9,14,14a-hexahydroindole[3',2':4,5]pyridine[2,1-a]isoquinoline (C77)

The title compound C77 was synthesized according to Scheme 3, while benzyl bromide was substituted with 1-ó4-(bromomethyl)benzene-1H-pyrazole.
¹H NMR (400 MHz, DMSO) δ 10.70 (s, 1H), 7.87 (d, J=8 Hz, 1H), 7.62-7.45 (m, 5H), 7.05-6.84 (m, 3H), 6.79-6.69 (m, 2H), 6.47 (q, J=8 Hz, 1H), 5.11 (d, J=4.8 Hz, 2H), 4.16 (d, J=15.1 Hz, 1H), 3.77 (d, J=11.4 Hz, 6H), 3.64 (d, J=15.6 Hz, 1H), 3.54 (d, J=7.2 Hz, 1H), 3.31 (s, 1H), 3.14 (s, 1H), 2.94 (d, J=11.4 Hz, 1H), 2.64 (dd, J=21.1, 13.3 Hz, 2H), 2.40-2.27 (m, 1H).
LRMS (ESI, m/z): 507 [M+H]⁺.

Example C78 (3-((4-(1H-pyrazol-1-yl)benzyl)oxo)-2-methoxy-5,6,8,9,14,14a-hexahydroindole[3',2':4,5]pyridine[2,1-a]isoquinoline (C78)

The title compound C78 was synthesized according to Scheme 3, while benzyl bromide was substituted with 1-ó4-(bromomethyl)benzene-1H-pyrazole.
¹H NMR (400 MHz, DMSO) δ 10.70 (s, 1H), 7.87 (d, J=8 Hz, 1H), 7.62-7.45 (m, 5H), 7.05-6.84 (m, 4H), 6.79-6.69 (m, 2H), 6.47 (q, J=8 Hz, 1H), 5.11 (d, J=4.8 Hz, 2H), 4.16 (d, J=15.1 Hz, 1H), 3.77 (d, J=11.4 Hz, 6H), 3.64 (d, J=15.6 Hz, 1H), 3.54 (d, J=7.2 Hz, 1H), 3.31 (s, 1H), 3.14 (s, 1H), 2.94 (d, J=11.4 Hz, 1H), 2.64 (dd, J=21.1, 13.3 Hz, 2H), 2.40-2.27 (m, 1H).
LRMS (ESI, m/z): 477 [M+H]⁺.

Example C79 2,12-dimethoxy-3-((4-(methylsulfonyl)benzyl)oxy)-5,6,8,9,14,14a-hexahydroindolo[3',2':4,5]pyridine[2,1-a]isoquinoline (C79)

The title compound C79 was synthesized according to Scheme 3, while benzyl bromide was substituted with 4-(methylsulfonyl)benzyl bromide.
¹H NMR (400 MHz, DMSO) δ 10.70 (s, 1H), 7.39-7.35 (m, 3H), 7.22 (d, J=8.0 Hz, 2H), 7.06 (s, 1H), 6.96 (d, J=2.3 Hz, 1H), 6.74 (dd, J=9.7, 3.3 Hz, 2H), 5.05 (q, J=11.6 Hz, 2H), 4.17 (d, J=14.9 Hz, 1H), 3.79 (s, 3H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.05 (s, 3H), 3.03-2.86 (m, 1H), 2.74-2.57 (m, 2H), 2.37 (t, J=7.1 Hz, 2H).
LRMS (ESI, m/z): 519 [M+H]⁺.

Example C80 2-methoxy-3-((4-methylbenzyl)oxy)-5,6,8,9,14,14a-hexahydroindolo[3',2':4,5]pyridine[2,1-a]isoquinoline (C80)

The title compound C80 was synthesized according to Scheme 3, while benzyl bromide was substituted with 4-(methylsulfonyl)benzyl bromide.
¹H NMR (400 MHz, DMSO) δ 10.70 (s, 1H), 7.39-7.35 (m, 4H), 7.22 (d, J=8.0 Hz, 2H), 7.06 (s, 1H), 6.96 (d, J=2.3 Hz, 1H), 6.74 (dd, J=9.7, 3.3 Hz, 2H), 5.05 (q, J=11.6 Hz, 2H), 4.17 (d, J=14.9 Hz, 1H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.05 (s, 3H), 3.03-2.86 (m, 1H), 2.74-2.57 (m, 2H), 2.37 (t, J=7.1 Hz, 2H).
LRMS (ESI, m/z): 489 [M+H]⁺.

Example C81 (3-(benzyloxy)-11-fluoro-2-methoxy-5,6,8,9,14,14a-hexahydroindole[3',2':4,5]pyridine[2,1-a]isoquinoline (C81)

The title compound C81 was synthesized according to Scheme 3, while 5-methoxy-3-indoleacetic acid was replaced with 6-fluoro-3-indoleacetic acid.
¹H NMR (400 MHz, DMSO) δ 10.70 (s, 1H), 7.51-7.35 (m, 5H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 429 [M+H]⁺.

Example C82

3-(benzyloxy)-12-fluoro-2-methoxy-5,6,14,14a-hexahydroindole[3',2':4,5]pyridine[2,1-a]isoquinoline (C82)

The title compound C82 was synthesized according to Scheme 3, while 5-methoxy-3-indoleacetic acid was replaced with 5-fluoro-3-indoleacetic acid. ¹H NMR (400 MHz, DMSO) δ 10.70 (s, 1H), 7.51-7.35 (m, 5H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 429 [M+H]$^+$.

Example C83 (3-(benzyloxy)-13-fluoro-2-methoxy-5,6,8,9,14,14a-hexahydroindole[3',2':4,5]pyridine[2,1-a]isoquinoline (C83)

The title compound C82 was synthesized according to Scheme 3, while 5-methoxy-3-indoleacetic acid was replaced with 4-fluoro-3-indoleacetic acid. $^1$H NMR (400 MHz, DMSO) δ 10.70 (s, 1H), 7.51-7.35 (m, 5H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 429 [M+H]$^+$.

Example C84

3-(benzyloxy)-11-chloro-2-methoxy-5,6,8,9,14,14a-hexahydroindole[3',2':4,5]pyridine[2,1-a]isoquinoline (C84)

The title compound C84 was synthesized according to Scheme 3, while 5-methoxy-3-indoleacetic acid was replaced with 6-chloro-3-indoleacetic acid.
$^1$H NMR (400 MHz, DMSO) δ 10.70 (s, 1H), 7.51-7.35 (m, 5H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 445 [M+H]$^+$.

Example C85

3-(benzyloxy)-12-chloro-2-methoxy-5,6,8,9,14,14a-hexahydroindole[3' 2':4,5]pyridine[2,1-a]isoquinoline (C85)

The title compound C85 was synthesized according to Scheme 3, while 5-methoxy-3-indoleacetic acid was replaced with 5-chloro-3-indoleacetic acid.
$^1$H NMR (400 MHz, DMSO) δ 10.70 (s, 1H), 7.51-7.35 (m, 5H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 445 [M+H]$^+$.

Example C86 3-(Benzyloxy)-13-chloro-2-methoxy-5,6,8,9,14,14a-hexahydroindolo[3',2':4,5]pyridine[2,1-a]isoquinoline (C86)

The title compound C86 was synthesized according to Scheme 3, while 5-methoxy-3-indoleacetic acid was replaced with 4-chloro-3-indoleacetic acid.
$^1$H NMR (400 MHz, DMSO) δ 10.70 (s, 1H), 7.51-7.35 (m, 5H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 445 [M+H]$^+$.

Example C87 3-(benzyloxy)-11-bromo-2-methoxy-5,6,8,9,14,14a-hexahydroindole[3',2':4,5]pyridine[2,1-a]isoquinoline (C87)

The title compound C87 was synthesized according to Scheme 3, while 5-methoxy-3-indoleacetic acid was replaced with 6-bromo-3-indoleacetic acid.
$^1$H NMR (400 MHz, DMSO) δ 10.70 (s, 1H), 7.51-7.35 (m, 5H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 489 [M+H]$^+$, 491 [M+H]$^+$.

Example C88 3-(benzyloxy)-12-bromo-2-methoxy-5,6,8,9,14,14a-hexahydroindole[3',2':4,5]pyridine[2,1-a]isoquinoline (C88)

The title compound C88 was synthesized according to Scheme 3, while 5-methoxy-3-indoleacetic acid was replaced with 5-bromo-3-indoleacetic acid.
$^1$H NMR (400 MHz, DMSO) δ 10.70 (s, 1H), 7.51-7.35 (m, 5H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 489 [M+H]$^+$, 491 [M+H]$^+$.

Example C89 3-(benzyloxy)-13-bromo-2-methoxy-5,6,8,9,14,14a-hexahydroindole[3',2':4,5]pyridine[2,1-a]isoquinoline (C89)

The title compound C89 was synthesized according to Scheme 3, while 5-methoxy-3-indoleacetic acid was replaced with 4-bromo-3-indoleacetic acid.
$^1$H NMR (400 MHz, DMSO) δ 10.70 (s, 1H), 7.51-7.35 (m, 5H), 7.05 (s, 1H), 6.94 (d, J=2.1 Hz, 1H), 6.79-6.69 (m, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 489 [M+H]$^+$, 491 [M+H]$^+$.

Example C90 3-(benzyloxy)-2-methoxy-11-methyl-5,6,8,9,14,14a-hexahydroindole[3',2':4,5]pyridine[2,1-a]isoquinoline (C90)

The title compound C90 was synthesized according to Scheme-3, while 5-methoxy-3-indoleacetic acid was replaced with 6-methyl-3-indoleacetic acid.
$^1$H NMR (400 MHz, DMSO) δ 10.65 (s, 1H), 7.39-7.35 (m, 3H), 7.28-7.21 (m, 3H), 7.06 (s, 1H), 6.96 (d, J=2.3 Hz, 1H), 6.74 (dd, J=9.7, 3.3 Hz, 2H), 5.05 (q, J=11.6 Hz, 1H), 4.17 (d, J=14.9 Hz, 1H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.03-2.86 (m, 1H), 2.74-2.57 (m, 2H), 2.37 (t, J=7.1 Hz, 2H), 2.32 (s, 3H).
LRMS (ESI, m/z): 425 [M+H]$^+$.

Example C91 3-(benzyloxy)-2-methoxy-12-ethyl-5,6,8,9,14,14a-hexahydroindole[3',2':4,5]pyridine[2,1-a]isoquinoline (C91)

The title compound C91 was synthesized according to Scheme 3, while benzyl bromide was substituted with 4-ethylbenzyl bromide.

¹H NMR (400 MHz, DMSO) δ 10.75 (s, 1H), 7.51-7.35 (m, 5H), 7.21-7.05 (m, 2H), 6.94 (d, J=2.1 Hz, 1H), 6.79-6.69 (m, 2H), 5.08 (s, 2H), 4.18 (d, J=15.0 Hz, 1H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H), 2.34 (q, J=8.0 Hz, 2H), 1.01 (t, J=8.0 Hz, 3H).
LRMS (ESI, m/z): 439 [M+H]⁺.

Example C92 2,12-dimethoxy-5,6,8,9,14,14a-hexahydroindolo[3',2':4,5]pyridine[2,1-a]isoquinolin-3-yl benzenesulfonate The title compound C92 was synthesized with benzenesulfonyl chloride, 3-hydroxy-4-methoxybenzaldehyde and 5-methoxy-3-indoleacetic acid according to Scheme 3.
¹H NMR (400 MHz, DMSO) δ 10.70 (s, 1H), 7.86-7.35 (m, 4H), 7.22 (d, J=8.0 Hz, 2H), 7.06 (s, 1H), 6.96 (d, J=2.3 Hz, 1H), 6.74 (dd, J=9.7, 3.3 Hz, 2H), 4.17 (d, J=14.9 Hz, 1H), 3.79 (s, 3H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.03-2.86 (m, 1H), 2.74-2.57 (m, 2H), 2.37 (m, 1H).
LRMS (ESI, m/z): 491 [M+H]⁺.

Example C93 3,12-dimethoxy-5,6,8,9,14,14a-hexahydroindolo[3',2':4,5]pyridine[2,1-a]isoquinolin-2-yl benzenesulfonate The title compound C93 was synthesized with benzenesulfonyl chloride, 4-hydroxy-3-methoxybenzaldehyde and 5-methoxy-3-indoleacetic acid according to Scheme 3.
¹H NMR (400 MHz, DMSO) δ 10.70 (s, 1H), 7.86-7.35 (m, 4H), 7.22 (d, J=8.0 Hz, 2H), 7.06 (s, 1H), 6.96 (d, J=2.3 Hz, 1H), 6.74 (dd, J=9.7, 3.3 Hz, 2H), 4.17 (d, J=14.9 Hz, 1H), 3.79 (s, 3H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.03-2.86 (m, 1H), 2.74-2.57 (m, 2H), 2.37 (m, 1H).
LRMS (ESI, m/z): 491 [M+H]⁺.

Example C94 2,11,12-trimethoxy-5,6,8,9,14,14a-hexahydroindolo[3',2':4,5]pyridine[2,1-a]isoquinolin-3-ylbenzenesulfonate The title compound C94 was synthesized with benzenesulfonyl chloride, 3-hydroxy-4-methoxybenzaldehyde and 5,6-dimethoxy-3-indoleacetic acid according to Scheme 3.
¹H NMR (400 MHz, DMSO) δ 10.70 (s, 1H), 7.86-7.35 (m, 4H), 7.22 (s, 1H), 7.06 (s, 1H), 6.96 (d, J=2.3 Hz, 1H), 6.94 (s, 1H), 6.74 (s, 1H), 4.17 (d, J=14.9 Hz, 1H), 3.79 (s, 3H), 3.77 (s, 3H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.03-2.86 (m, 1H), 2.74-2.57 (m, 2H), 2.37 (m, 1H).
LRMS (ESI, m/z): 521 [M+H]⁺.

Example C95 3,11,12-trimethoxy-5,6,8,9,14,14a-hexahydroindolo[3',2':4,5]pyridine[2,1-a]isoquinolin-2-ylbenzenesulfonate The title compound C95 was synthesized with benzenesulfonyl chloride, 4-hydroxy-3-methoxybenzaldehyde and 5,6-dimethoxy-3-indoleacetic acid according to Scheme 3.
¹H NMR (400 MHz, DMSO) δ 10.70 (s, 1H), 7.86-7.35 (m, 4H), 7.22 (s, 1H), 7.06 (s, 1H), 6.96 (d, J=2.3 Hz, 1H), 6.94 (s, 1H), 6.74 (s, 1H), 4.17 (d, J=14.9 Hz, 1H), 3.79 (s, 3H), 3.77 (s, 3H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.03-2.86 (m, 1H), 2.74-2.57 (m, 2H), 2.37 (m, 1H).
LRMS (ESI, m/z): 521 [M+H]⁺.

Example C96 2,3,11-trimethoxy-5,6,8,9,14,14a-hexahydroindolo[3',2':4,5]pyridine[2,1-a]isoquinolin-12-ylbenzenesulfonate The title compound C96 was synthesized with 3,4-dimethoxybenzaldehyde and 5-hydroxy-6-methoxy-3-indoleacetic acid according to Scheme 3.
¹H NMR (400 MHz, DMSO) δ 10.70 (s, 1H), 7.86-7.35 (m, 4H), 7.22 (s, 1H), 7.06 (s, 1H), 6.96 (d, J=2.3 Hz, 1H), 6.94 (s, 1H), 6.74 (s, 1H), 4.17 (d, J=14.9 Hz, 1H), 3.79 (s, 3H), 3.77 (s, 3H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.03-2.86 (m, 1H), 2.74-2.57 (m, 2H), 2.37 (m, 1H).
LRMS (ESI, m/z): 521 [M+H]⁺.

Example C97 2,11,12-trimethoxy-5,6,8,9,14,14a-hexahydroindolo[3',2':4,5]pyridine[2,1-a]isoquinolin-11-ylbenzenesulfonate The title compound C97 was synthesized with 3,4-dimethoxybenzaldehyde and 5-methoxy-6-hydroxy-3-indoleacetic acid according to Scheme 3.
¹H NMR (400 MHz, DMSO) δ 10.70 (s, 1H), 7.86-7.35 (m, 4H), 7.22 (s, 1H), 7.06 (s, 1H), 6.96 (d, J=2.3 Hz, 1H), 6.94 (s, 1H), 6.74 (s, 1H), 4.17 (d, J=14.9 Hz, 1H), 3.79 (s, 3H), 3.77 (s, 3H), 3.75 (s, 3H), 3.65 (d, J=15.1 Hz, 1H), 3.55 (dd, J=10.7, 3.0 Hz, 1H), 3.39 (d, J=3.7 Hz, 1H), 3.13 (d, J=11.2 Hz, 1H), 3.03-2.86 (m, 1H), 2.74-2.57 (m, 2H), 2.37 (m, 1H).
LRMS (ESI, m/z): 521 [M+H]⁺.

Example C98 4-(((9-(Hydroxymethyl)-2,12-dimethoxy-5,6,8,9,14,14a-hexahydroindole[3',2':4,5]pyridine[2,1-a]isoquinolin-3-yl)oxo)methyl)benzoic acid (C98)

The title compound C98 was synthesized with p-carboxybenzyl bromide, 3-hydroxy-4-methoxybenzaldehyde and 5-methoxy-3-indoleacetic acid according to Scheme 3.
¹H NMR (400 MHz, DMSO) δ 11.01 (s, 1H), 10.71 (s, 1H), 7.51-7.35 (m, 4H), 7.05 (s, 1H), 6.94 (d, J=2.1 Hz, 1H), 6.79-6.69 (m, 3H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 485 [M+H]⁺.

Example C99 4-(((3,12-dimethoxy-5,6,8,9,14,14a-hexahydroindolo[3',2':4,5]pyridine[2,1-a]isoquinolin-2-yl)oxo)methyl)aniline (C99)

The title compound C99 was synthesized with p-aminobenzyl bromide, 4-hydroxy-3-methoxybenzaldehyde and 5-methoxy-3-indoleacetic acid according to Scheme 3.
¹H NMR (400 MHz, DMSO) δ 10.70 (s, 1H), 7.51-7.35 (m, 4H), 7.05 (s, 1H), 6.94 (d, J=2.1 Hz, 1H), 6.79-6.69 (m, 2H), 6.27 (s, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6

Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 456 [M+H]⁺.

Example C100 4-(((3,12-dimethoxy-5,6,8,9,14,14a-hexahydroindolo[3',2':4,5]pyridine[2,1-a]isoquinolin-2-yl)oxo)methyl)aniline (C100)

The title compound C100 was synthesized with p-aminobenzyl bromide, 4-hydroxy-3-methoxybenzaldehyde and 5-methoxy-3-indoleacetic acid according to Scheme 3.

¹H NMR (400 MHz, DMSO) δ 10.70 (s, 1H), 7.51-7.35 (m, 4H), 7.05 (s, 1H), 6.94 (d, J=2.1 Hz, 1H), 6.79-6.69 (m, 2H), 6.27 (s, 2H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 456 [M+H]⁺.

Example C101 4-(((3,12-dimethoxy-5,6,8,9,14,14a-hexahydroindolo[3',2':4,5]pyridine[2,1-a]isoquinolin-2-yl)oxo)methyl)phenol (C101)

The title compound C101 was synthesized with p-hydroxybenzyl bromide, 4-hydroxy-3-methoxybenzaldehyde and 5-methoxy-3-indoleacetic acid according to Scheme 3.

¹H NMR (400 MHz, DMSO) δ 10.70 (s, 1H), 7.51-7.35 (m, 4H), 7.05 (s, 1H), 6.94 (d, J=2.1 Hz, 1H), 6.79-6.69 (m, 2H), 6.27 (s, 1H), 5.31 (s, 1H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 457 [M+H]⁺.

Example C102 4-(((3,12-dimethoxy-5,6,8,9,14,14a-hexahydroindolo[3',2':4,5]pyridine[2,1-a]isoquinolin-2-yl)oxo)methyl)phenol (C101)

The title compound C102 was synthesized with p-hydroxybenzyl bromide, 3-hydroxy-4-methoxybenzaldehyde and 5-methoxy-3-indoleacetic acid according to Scheme 3.

¹H NMR (400 MHz, DMSO) δ 10.70 (s, 1H), 7.51-7.35 (m, 4H), 7.05 (s, 1H), 6.94 (d, J=2.1 Hz, 1H), 6.79-6.69 (m, 2H), 6.27 (s, 1H), 5.31 (s, 1H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 457 [M+H]⁺.

Example C103 4-(((9-(Hydroxymethyl)-3,12-dimethoxy-5,6,8,9,14,14a-hexahydroindole[3',2':4,5]pyridine[2,1-a]isoquinolin-2-yl)oxo)methyl)benzoic acid (C103)

The title compound C103 was synthesized with p-carboxybenzyl bromide, 4-hydroxy-3-methoxybenzaldehyde and 5-methoxy-3-indoleacetic acid according to Scheme 3.

¹H NMR (400 MHz, DMSO) δ 11.01 (s, 1H), 10.71 (s, 1H), 7.51-7.35 (m, 4H), 7.05 (s, 1H), 6.94 (d, J=2.1 Hz, 1H), 6.79-6.69 (m, 3H), 5.08 (s, 2H), 4.18 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 485 [M+H]⁺.

Example (S)—C3

S)-3,12-Dimethoxy-2-((4-(trifluoromethyl)benzyl)oxy)-5,6,8,9,14,14a-hexahydroindolo[3',2':4,5]pyrido[2,1-a]isoquinoline ((S)—C3)

The title compound (S)—C3 was synthesized according to Scheme 4, while benzyl bromide was substituted with 4-trifluoromethylbenzyl bromide.

¹H NMR (400 MHz, DMSO) δ 10.70 (s, 1H), 7.71-7.53 (m, 2H), 7.50-7.35 (m, 1H), 7.31-7.15 (m, 2H), 7.05 (s, 1H), 6.94 (d, J=2.1 Hz, 1H), 6.79-6.69 (m, 2H), 5.16 (s, 2H), 4.29 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 509 [M+H]⁺.

Example (R)—C3 R)-3,12-Dimethoxy-2-((4-(trifluoromethyl)benzyl)oxy)-5,6,8,9,14,14a-hexahydroindolo[3',2':4,5]pyrido[2,1-a]isoquinoline ((R)—C3)

The title compound (R)—C3 was synthesized according to Scheme 4, while benzyl bromide was substituted with 4-trifluoromethylbenzyl bromide. 1H NMR (400 MHz, DMSO) δ 10.70 (s, 1H), 7.71-7.53 (m, 2H), 7.50-7.35 (m, 1H), 7.31-7.15 (m, 2H), 7.05 (s, 1H), 6.94 (d, J=2.1 Hz, 1H), 6.79-6.69 (m, 2H), 5.16 (s, 2H), 4.29 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 509 [M+H]⁺.

Example (S)—C47 (S)-2,12-Dimethoxy-3-((4-(trifluoromethyl)benzyl)oxo)-5,6,8,9,14,14a-hexahydroindolo[3',2':4,5]pyrido[2,1-a]isoquinoline ((S)—C47)

The title compound (S)—C47 was synthesized according to Scheme 4, while benzyl bromide was substituted with 4-trifluoromethylbenzyl bromide.

¹H NMR (400 MHz, DMSO) δ 10.70 (s, 1H), 7.71-7.53 (m, 2H), 7.50-7.35 (m, 1H), 7.31-7.15 (m, 2H), 7.05 (s, 1H), 6.94 (d, J=2.1 Hz, 1H), 6.79-6.69 (m, 2H), 5.16 (s, 2H), 4.29 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).

LRMS (ESI, m/z): 509 [M+H]⁺

Example (R)—C47 (R)-2,12-Dimethoxy-3-((4-(trifluoromethyl)benzyl)oxy)-5,6,8,9,14,14a-hexahydroindolo[3',2':4,5]pyrido[2,1-a]isoquinoline ((R)—C47)

The title compound (R)—C47 was synthesized according to Scheme 4, while benzyl bromide was substituted with 4-trifluoromethylbenzyl bromide.

¹H NMR (400 MHz, DMSO) δ 10.70 (s, 1H), 7.71-7.53 (m, 2H), 7.50-7.35 (m, 1H), 7.31-7.15 (m, 2H), 7.05 (s, 1H), 6.94 (d, J=2.1 Hz, 1H), 6.79-6.69 (m, 2H), 5.18 (s, 2H), 4.29 (d, J=15.0 Hz, 1H), 3.80 (s, 3H), 3.77 (s, 3H), 3.67 (d, J=14.2 Hz, 1H), 3.60 (d, J=9.6 Hz, 1H), 3.44 (d, J=14.2 Hz, 1H), 3.14 (d, J=8.3 Hz, 1H), 2.95 (t, J=12.0 Hz, 1H), 2.65 (d, J=13.4 Hz, 2H), 2.44 (t, J=12.0 Hz, 1H).
LRMS (ESI, m/z): 509 [M+H]$^+$

Example C104 2,12-dimethoxy-3-((2-methoxybenzyl)oxo)-5,6,8,9,14,14a-hexahydroindolo[3',2':4,5]pyridine[2,1-a]isoquinoline (C104)

The title compound C104 was synthesized with 2-methoxybenzyl bromide, 3-hydroxy-4-methoxybenzaldehyde and 5-methoxy-3-indoleacetic acid according to Scheme 3.
$^1$H NMR (500 MHz, Chloroform) δ 7.21 (s, 1H), 7.04 (d, J=3.9 Hz, 2H), 6.91 (dd, J=9.8, 5.4 Hz, 4H), 6.78 (s, 1H), 6.73 (d, J=5.6 Hz, 2H), 5.22-5.18 (m, 2H), 4.29 (s, 1H), 3.92-3.66 (m, 10H), 3.52 (s, 1H), 3.10 (s, 1H), 2.88 (d, J=0.8 Hz, 2H), 2.80 (s, 1H), 2.69 (s, 1H), 2.58 (s, 1H).
LRMS (ESI, m/z): 471 [M+H]$^+$

Example C105 2-methoxy-3-((2-methoxybenzyl)oxo)-5,6,8,9,14,14a-hexahydroindolo[3',2':4,5]pyridine[2,1-a]isoquinoline (C104)

The title compound C105 was synthesized with 2-methoxybenzyl bromide, 3-hydroxy-4-methoxybenzaldehyde and 3-indoleacetic acid according to Scheme 3.
$^1$H NMR (500 MHz, Chloroform) δ 7.23 (d, J=5.0 Hz, 8H), 7.17 (d, J=3.2 Hz, 8H), 7.03 (d, J=13.5 Hz, 8H), 7.00-6.93 (m, 11H), 6.86 (d, J=6.4 Hz, 9H), 5.21-5.17 (m, 8H), 4.29 (s, 4H), 3.79 (s, 4H), 3.73-3.69 (m, 12H), 3.64-3.60 (m, 12H), 3.54 (s, 4H), 3.12 (s, 3H), 2.95 (d, J=0.8 Hz, 8H), 2.82 (s, 3H), 2.71 (s, 4H), 2.63 (s, 3H).
LRMS (ESI, m/z): 441 [M+H]$^+$

Example C106 2,12-dimethoxy-3-((3-methylbenzyl)oxo)-5,6,8,9,14,14a-hexahydroindolo[3',2':4,5]pyridine[2,1-a]isoquinoline (C106)

The title compound C106 was synthesized with 3-methylbenzyl bromide, 3-hydroxy-4-methoxybenzaldehyde and 5-methoxy-3-indoleacetic acid according to Scheme 3.
$^1$H NMR (500 MHz, Chloroform) δ 7.34 (s, 1H), 7.22 (s, 1H), 7.14-7.04 (m, 4H), 7.02 (s, 1H), 6.91 (s, 1H), 6.76 (d, J=19.9 Hz, 2H), 4.78-4.74 (m, 2H), 4.29 (s, 1H), 3.83-3.69 (m, 4H), 3.69-3.40 (m, 4H), 3.12 (s, 1H), 2.94 (t, J=6.1 Hz, 3H), 2.79 (s, 1H), 2.60 (s, 1H), 2.37-2.33 (m, 3H).
LRMS (ESI, m/z): 455 [M+H]$^+$

Example C107 2-methoxy-3-((3-methylbenzyl)oxo)-5,6,8,9,14,14a-hexahydroindolo[3',2':4,5]pyridine[2,1-a]isoquinoline (C107)

The title compound C107 was synthesized with 3-methylbenzyl bromide, 3-hydroxy-4-methoxybenzaldehyde and 3-indoleacetic acid according to Scheme 3.
$^1$H NMR (500 MHz, Chloroform) δ 7.21 (dd, J=18.1, 12.8 Hz, 12H), 7.11-6.99 (m, 15H), 6.91 (s, 4H), 6.83 (s, 2H), 5.23-5.19 (m, 6H), 4.29 (s, 3H), 3.86-3.84 (m, 7H), 3.77 (s, 5H), 3.57 (s, 3H), 3.21 (s, 3H), 2.86 (d, J=4.0 Hz, 6H), 2.74 (t, J=2.0 Hz, 9H), 2.37-2.33 (m, 9H).
LRMS (ESI, m/z): 425 [M+H]$^+$

Example C108 2,12-dimethoxy-3-((2-methylbenzyl)oxo)-5,6,8,9,14,14a-hexahydroindolo[3',2':4,5]pyridine[2,1-a]isoquinoline (C108)

The title compound C108 was synthesized with 2-methylbenzyl bromide, 3-hydroxy-4-methoxybenzaldehyde and 5-methoxy-3-indoleacetic acid according to Scheme 3.
$^1$H NMR (500 MHz, Chloroform) δ 7.12 (s, 1H), 7.09-7.00 (m, 5H), 6.99-6.78 (m, 3H), 6.70 (s, 1H), 5.21-5.17 (m, 2H), 4.29 (s, 1H), 3.83-3.69 (m, 7H), 3.54 (s, 1H), 3.12 (s, 1H), 2.90 (d, J=0.8 Hz, 2H), 2.69 (d, J=7.6 Hz, 2H), 2.56 (s, 1H), 2.37-2.33 (m, 3H).
LRMS (ESI, m/z): 455 [M+H]$^+$

Example C109 2-methoxy-3-((2-methylbenzyl)oxo)-5,6,8,9,14,14a-hexahydroindolo[3',2':4,5]pyridine[2,1-a]isoquinoline (C109)

The title compound C109 was synthesized with 2-methylbenzyl bromide, 3-hydroxy-4-methoxybenzaldehyde and 3-indoleacetic acid according to Scheme 3.
$^1$H NMR (500 MHz, Chloroform) δ 7.23 (s, 1H), 7.20-7.12 (m, 5H), 7.04 (dd, J=19.3, 8.0 Hz, 4H), 6.87 (s, 1H), 5.20-5.16 (m, 2H), 4.29 (s, 1H), 3.84-3.64 (m, 4H), 3.55 (s, 1H), 3.13 (s, 1H), 2.95 (d, J=0.8 Hz, 2H), 2.81 (s, 1H), 2.72 (s, 1H), 2.66 (s, 1H), 2.40-2.36 (m, 3H).
LRMS (ESI, m/z): 425 [M+H]$^+$

Example C110 3,12-dimethoxy-2-((2-methoxybenzyl)oxo)-5,6,8,9,14,14a-hexahydroindolo[3',2':4,5]pyridine[2,1-a]isoquinoline (C110)

The title compound C110 was synthesized with 2-methoxybenzyl bromide, vanillin and 5-methoxy-3-indoleacetic acid according to Scheme 3.
$^1$H NMR (500 MHz, Chloroform) δ 7.19 (d, J=18.2 Hz, 8H), 7.11 (s, 4H), 7.09-6.90 (m, 16H), 6.88 (s, 1H), 6.84 (d, J=39.4 Hz, 7H), 6.53 (s, 4H), 5.21-5.17 (m, 8H), 4.29 (s, 4H), 3.85-3.61 (m, 40H), 3.55 (s, 4H), 3.12 (s, 4H), 2.93 (d, J=0.8 Hz, 8H), 2.83 (s, 3H), 2.70 (d, J=19.5 Hz, 7H).
LRMS (ESI, m/z): 471 [M+H]$^+$

Example C111 3-methoxy-2-((2-methoxybenzyl)oxo)-5,6,8,9,14,14a-hexahydroindolo[3',2':4,5]pyridine[2,1-a]isoquinoline (C111)

The title compound C111 was synthesized with 2-methoxybenzyl bromide, vanillin and 3-indoleacetic acid according to Scheme 3.
$^1$H NMR (500 MHz, Chloroform) δ 7.25 (d, J=16.4 Hz, 2H), 7.18 (d, J=4.0 Hz, 2H), 7.10 (s, 1H), 7.05 (d, J=9.0 Hz, 2H), 6.97-6.82 (m, 4H), 5.24-5.20 (m, 2H), 4.29 (s, 1H), 3.86-3.66 (m, 7H), 3.55 (s, 1H), 3.14 (s, 1H), 2.94 (d, J=0.8 Hz, 2H), 2.80 (s, 1H), 2.71 (d, J=14.1 Hz, 2H).
LRMS (ESI, m/z): 441 [M+H]$^+$

Example C112 3,12-dimethoxy-2-((3-methylbenzyl)oxo)-5,6,8,9,14,14a-hexahydroindolo[3',2':4,5]pyridine[2,1-a]isoquinoline (C112)

The title compound C112 was synthesized with 3-methylbenzyl bromide, vanillin and 5-methoxy-3-indoleacetic acid according to Scheme 3.
$^1$H NMR (500 MHz, Chloroform) δ 7.20 (d, J=5.4 Hz, 8H), 7.14 (d, J=5.8 Hz, 8H), 7.09-6.95 (m, 12H), 6.92 (s, 4H), 6.79 (s, 4H), 6.52 (s, 4H), 5.20-5.16 (m, 8H), 4.29 (s, 4H), 3.85-3.61 (m, 28H), 3.55 (s, 4H), 3.13 (s, 3H), 2.94 (d, J=0.8 Hz, 8H), 2.81 (s, 3H), 2.72 (s, 5H), 2.67 (s, 2H), 2.37-2.33 (m, 12H).

LRMS (ESI, m/z): 455 [M+H]+

Example C113 3-methoxy-2-((3-methylbenzyl)oxo)-5,6,8,9,14,14a-hexahydroindolo[3',2':4,5]pyridine[2,1-a]isoquinoline (C113)

The title compound C113 was synthesized with 3-methylbenzyl bromide, vanillin and 3-indoleacetic acid according to Scheme 3.

$^1$H NMR (500 MHz, Chloroform) δ 7.18 (dt, J=19.8, 10.6 Hz, 6H), 7.05 (t, J=15.5 Hz, 3H), 6.92 (s, 1H), 6.87 (s, 1H), 5.20-5.16 (m, 2H), 4.29 (s, 1H), 3.85-3.63 (m, 4H), 3.55 (s, 1H), 3.12 (s, 1H), 2.93 (d, J=0.8 Hz, 2H), 2.78 (s, 1H), 2.74 (s, 1H), 2.68 (s, 1H), 2.37-2.33 (m, 3H).

LRMS (ESI, m/z): 425 [M+H]+

Example C114 3,12-dimethoxy-2-((2-methylbenzyl)oxo)-5,6,8,9,14,14a-hexahydroindolo[3',2':4,5]pyridine[2,1-a]isoquinoline (C114)

The title compound C114 was synthesized with 2-methylbenzyl bromide, vanillin and 5-methoxy-3-indoleacetic acid according to Scheme 3.

$^1$H NMR (500 MHz, Chloroform) δ 7.23 (s, 1H), 7.18-7.08 (m, 4H), 6.99 (d, J=5.0 Hz, 2H), 6.79 (d, J=8.2 Hz, 2H), 6.54 (s, 1H), 5.22-5.18 (m, 2H), 4.29 (s, 1H), 3.86-3.82 (m, 3H), 3.82-3.75 (m, 4H), 3.54 (s, 1H), 3.10 (s, 1H), 2.91 (s, 1H), 2.76 (t, J=8.7 Hz, 3H), 2.66 (s, 1H), 2.33-2.29 (m, 3H).

LRMS (ESI, m/z): 455 [M+H]+

Example C115 3-methoxy-2-((2-methylbenzyl)oxo)-5,6,8,9,14,14a-hexahydroindolo[3',2':4,5]pyridine[2,1-a]isoquinoline (C115)

The title compound C115 was synthesized with 2-methylbenzyl bromide, vanillin and 3-indoleacetic acid according to Scheme 3.

$^1$H NMR (500 MHz, Chloroform) δ 7.27-7.10 (m, 21H), 7.06 (d, J=11.4 Hz, 6H), 6.92 (d, J=17.8 Hz, 6H), 5.22-5.18 (m, 6H), 4.29 (s, 3H), 3.98-3.64 (m, 12H), 3.55 (s, 3H), 3.14 (s, 3H), 2.94 (d, J=0.8 Hz, 6H), 2.80 (s, 2H), 2.73 (s, 4H), 2.69 (s, 2H), 2.40-2.36 (m, 9H).

LRMS (ESI, m/z): 425 [M+H]+

Example C116 2-methoxy-3-((3,4-difluorobenzyl)oxo)-5,6,8,9,14,14a-hexahydroindolo[3',2':4,5]pyridine[2,1-a]isoquinoline (C116)

$^1$H NMR (500 MHz, Chloroform) δ 7.23 (s, 130H), 7.15 (d, J=13.8 Hz, 265H), 7.07-6.97 (m, 787H), 6.87 (s, 137H), 5.19-5.15 (m, 258H), 4.29 (s, 125H), 3.85 (s, 8H), 4.06-3.64 (m, 537H), 3.55 (s, 134H), 3.12 (s, 127H), 2.90 (d, J=0.8 Hz, 258H), 2.78 (s, 98H), 2.71 (s, 132H), 2.65 (s, 101H).

LRMS (ESI, m/z): 525 [M+H]+

Example C117 2,12-dimethoxy-3-((3,4-difluorobenzyl)oxo)-5,6,8,9,14,14a-hexahydroindolo[3',2':4,5]pyridine[2,1-a]isoquinoline (C117)

$^1$H NMR (500 MHz, Chloroform) δ 7.09-6.94 (m, 76H), 6.93 (s, 2H), 6.93-6.79 (m, 125H), 6.71 (s, 25H), 5.23-5.19 (m, 49H), 4.29 (s, 24H), 3.88-3.69 (m, 178H), 3.55 (s, 26H), 3.13 (s, 19H), 2.95 (d, J=0.8 Hz, 49H), 2.72 (d, J=3.9 Hz, 47H), 2.60 (s, 19H).

LRMS (ESI, m/z): 477 [M+H]+

Example C118 2-methoxy-3-((3,5-difluorobenzyl)oxo)-5,6,8,9,14,14a-hexahydroindolo[3',2':4,5]pyridine[2,1-a]isoquinoline (C118)

$^1$H NMR (500 MHz, Chloroform) δ 7.23 (s, 4H), 7.17 (s, 4H), 7.13 (s, 4H), 7.03 (d, J=11.6 Hz, 8H), 6.92-6.79 (m, 14H), 6.73 (s, 5H), 6.71 (d, J=1.5 Hz, 1H), 5.24-5.20 (m, 8H), 4.29 (s, 4H), 3.84-3.64 (m, 16H), 3.53 (s, 4H), 3.11 (s, 4H), 2.90 (s, 3H), 2.82 (d, J=0.8 Hz, 8H), 2.77 (s, 3H), 2.66 (s, 4H).

LRMS (ESI, m/z): 447 [M+H]+

Example C119 2,12-dimethoxy-3-((3,5-difluorobenzyl)oxo)-5,6,8,9,14,14a-hexahydroindolo[3',2':4,5]pyridine[2,1-a]isoquinoline (C119)

$^1$H NMR (500 MHz, Chloroform) δ 7.08-6.99 (m, 12H), 6.87 (d, J=33.0 Hz, 8H), 6.78-6.66 (m, 12H), 6.44 (s, 4H), 5.25-5.21 (m, 8H), 4.29 (s, 4H), 3.84-3.64 (m, 28H), 3.53 (s, 4H), 3.12 (s, 3H), 2.97 (d, J=0.8 Hz, 8H), 2.81 (s, 3H), 2.67 (d, J=0.6 Hz, 6H).

LRMS (ESI, m/z): 477 [M+H]+

Example C120 2-methoxy-3-((3,4,5-trifluorobenzyl)oxo)-5,6,8,9,14,14a-hexahydroindolo[3',2':4,5]pyridine[2,1-a]isoquinoline (C120)

$^1$H NMR (500 MHz, Chloroform) δ 7.23 (s, 1H), 7.17 (s, 1H), 7.05 (dd, J=21.8, 6.8 Hz, 4H), 6.86 (s, 1H), 6.84-6.80 (m, 2H), 5.22-5.18 (m, 2H), 4.29 (s, 1H), 3.87-3.68 (m, 4H), 3.55 (s, 1H), 3.13 (s, 1H), 2.95 (d, J=0.8 Hz, 2H), 2.80 (s, 1H), 2.73 (s, 1H), 2.66 (s, 1H).

LRMS (ESI, m/z): 465 [M+H]+

Example C121 2,12-dimethoxy-3-((3,4,5-trifluorobenzyl)oxo)-5,6,8,9,14,14a-hexahydroindolo[3',2':4,5]pyridine[2,1-a]isoquinoline (C121)

$^1$H NMR (500 MHz, Chloroform) δ 7.08 (s, 1H), 7.03 (d, J=3.5 Hz, 2H), 6.89 (d, J=12.6 Hz, 2H), 6.74-6.66 (m, 3H), 5.10-5.06 (m, 2H), 4.29 (s, 1H), 3.83-3.77 (m, 7H), 3.56 (s, 1H), 3.13 (s, 1H), 3.03 (d, J=0.8 Hz, 2H), 2.79 (d, J=4.8 Hz, 2H), 2.67 (s, 1H).

LRMS (ESI, m/z): 495 [M+H]+

Example C122 3-methoxy-2-((3,4-difluorobenzyl)oxo)-5,6,8,9,14,14a-hexahydroindolo[3',2':4,5]pyridine[2,1-a]isoquinoline (C122)

$^1$H NMR (500 MHz, Chloroform) δ 7.23 (s, 9H), 7.17 (s, 9H), 7.08-6.96 (m, 65H), 6.88 (s, 10H), 5.24-5.20 (m, 18H), 4.29 (s, 9H), 3.85 (s, 1H), 3.85-3.64 (m, 36H), 3.55 (s, 9H), 3.14 (s, 9H), 2.89 (d, J=0.8 Hz, 18H), 2.75 (d, J=17.3 Hz, 17H), 2.66 (s, 7H).

LRMS (ESI, m/z): 447 [M+H]+

Example C123 3,12-dimethoxy-2-((3,4-difluorobenzyl)oxo)-5,6,8,9,14,14a-hexahydroindolo[3',2':4,5]pyridine[2,1-a]isoquinoline (C123)

$^1$H NMR (500 MHz, Chloroform) δ 7.07-6.96 (m, 7H), 6.81 (s, 1H), 6.56 (s, 1H), 5.24-5.20 (m, 2H), 4.29 (s, 1H), 3.86-3.82 (m, 6H), 3.80 (s, 1H), 3.55 (s, 1H), 3.15 (s, 1H), 2.91 (d, J=0.8 Hz, 2H), 2.82 (s, 1H), 2.70 (d, J=11.2 Hz, 2H).
LRMS (ESI, m/z): 477 [M+H]$^+$ Example C124 3-methoxy-2-((3,5-difluorobenzyl) oxo)-5,6,8,9,14,14a-hexahydroindolo[3',2':4,5]pyridine[2,1-a]isoquinoline (C124)

$^1$H NMR (500 MHz, Chloroform) δ 7.24 (s, 1H), 7.17 (s, 1H), 7.13 (s, 1H), 7.04 (d, J=15.6 Hz, 2H), 6.89 (s, 1H), 6.80 (dd, J=4.1, 0.9 Hz, 4H), 5.23-5.19 (m, 2H), 4.29 (s, 1H), 3.94-3.73 (m, 4H), 3.54 (s, 1H), 3.10 (s, 1H), 2.92 (s, 1H), 2.77 (t, J=10.1 Hz, 3H), 2.66 (s, 1H).
LRMS (ESI, m/z): 447 [M+H]$^+$ Example C125 3,12-dimethoxy-2-((3,5-difluorobenzyl)oxo)-5,6,8,9,14,14a-hexahydroindolo[3',2':4,5]pyridine[2,1-a]isoquinoline (C125)

$^1$H NMR (500 MHz, Chloroform) δ 7.15 (s, 1H), 6.99 (d, J=13.0 Hz, 2H), 6.84-6.75 (m, 4H), 6.73 (s, 1H), 6.54 (s, 1H), 5.24-5.20 (m, 2H), 4.29 (s, 1H), 3.85-3.71 (m, 7H), 3.54 (s, 1H), 3.10 (s, 1H), 2.91 (s, 1H), 2.78 (t, J=7.4 Hz, 3H), 2.66 (s, 1H).
LRMS (ESI, m/z): 477 [M+H]$^+$ Example C126 3-methoxy-2-((3,4,5-trifluorobenzyl) oxo)-5,6,8,9,14,14a-hexahydroindolo[3',2':4,5]pyridine[2,1-a]isoquinoline (C126)

$^1$H NMR (500 MHz, Chloroform) δ 7.24 (s, 1H), 7.16 (d, J=11.8 Hz, 2H), 7.04 (d, J=14.7 Hz, 2H), 6.88 (s, 1H), 6.84-6.79 (m, 3H), 5.23-5.19 (m, 2H), 4.29 (s, 1H), 3.86-3.75 (m, 4H), 3.54 (s, 1H), 3.10 (s, 1H), 2.91 (s, 1H), 2.78 (t, J=4.2 Hz, 3H), 2.66 (s, 1H).
LRMS (ESI, m/z): 465 [M+H]$^+$ Example C127 3,12-dimethoxy-2-((3,4,5-trifluorobenzyl)oxo)-5,6,8,9,14,14a-hexahydroindolo[3',2':4,5]pyridine[2,1-a]isoquinoline (C127)

$^1$H NMR (500 MHz, Chloroform) δ 7.15 (s, 1H), 6.99 (d, J=11.9 Hz, 2H), 6.84-6.74 (m, 4H), 6.53 (s, 1H), 5.23-5.19 (m, 2H), 4.29 (s, 1H), 3.85-3.75 (m, 7H), 3.54 (s, 1H), 3.10 (s, 1H), 2.91 (s, 1H), 2.78 (t, J=6.2 Hz, 3H), 2.66 (s, 1H).
LRMS (ESI, m/z): 495 [M+H]$^+$

Examples of Biological Experiments

Example 1. In Vitro Study of Lipid-Lowering Activity (1) Experimental Method HepG2 cells were inoculated in 24-well plates, cultured in DMEM containing 10% FBS for 24 h or 48 h, and then transferred to DMEM containing 2% defatted serum and cultivated for 24 h. The old culture solution was discarded and replaced with new 2% defatted serum DMEM, and a test compound (the working concentration of which is 5 uM, triplicate for each sample) was added and incubated for 24 h. The old culture solution was abandoned and DMEM containing DiI-LDL (20 ug/ml) was added (300 ul/per 24 wells), incubated for 3 h. DMEM containing DiI-LDL was discarded, and cells were rinsed twice with PBS containing 0.4% BSA, and 3 times with PBS to remove excess DiI-LDL. Isopropanol was added (500 ul/per well of a 24-well plate), and was kept in darkness. After shaken for 20 minutes, 200 ul of supernatant was sucked to a black fluorescent plate, and fluorescence intensity (FLU) was detected at excitation light 520 nm and emission light 578 nm.

The experimental results were calculated: LDL uptake rate=(FLU value of sample group to be tested/FLU value of blank group)×100%.

(2) Experimental Results

TABLE 1

| | in vitro lipid-lowering activity | |
|---|---|---|
| Serial No. | No. | LDL uptake rate |
| 1 | A1 | 148.46% |
| 2 | A5 | 155.94% |
| 3 | A9 | 113.39% |
| 4 | A10 | 108.39% |
| 5 | A13 | 107.39% |
| 6 | A15 | 115.47% |
| 7 | A37 | 99.08% |
| 8 | A38 | 123.30% |
| 9 | A39 | 146.93% |
| 10 | A55 | 194.41% |
| 11 | A57 | 112.04% |
| 12 | A60 | 108.39% |
| 13 | A61 | 165.45% |
| 13 | A63 | 137.64% |
| 14 | A69 | 139.91% |
| 15 | A70 | 80.61% |
| 16 | A109 | 100.49% |
| 17 | (S)-A55 | 120.49% |
| 18 | (R)-A55 | 199.94% |
| 19 | (S)-A1 | 115.86% |
| 20 | (R)-A1 | 185.15% |
| 21 | A142 | 108.21% |
| 22 | A143 | 91.08% |
| 23 | B5 | 133.74% |
| 24 | B6 | 107.85% |
| 25 | B9 | 94.26% |
| 26 | B10 | 107.85% |
| 27 | B13 | 104.62% |
| 28 | B15 | 110.80% |
| 29 | B16 | 107.13% |
| 30 | B55 | 125.41% |
| 31 | B59 | 108.82% |
| 32 | B60 | 114.18% |
| 33 | B61 | 116.33% |
| 34 | C47 | 149.82% |
| 35 | C49 | 194.03% |
| 36 | C51 | 191.73% |
| 37 | C53 | 111.61% |
| 38 | C54 | 110.08% |
| 39 | C59 | 147.46% |
| 35 | C60 | 84.31% |
| 36 | (S)-C3 | 111.02% |
| 37 | (R)-C3 | 218.44% |
| 38 | (S)-C47 | 272.92% |
| 39 | (R)-C47 | 292.48% |
| 40 | C106 | 110.95% |
| 41 | C107 | 69.51% |
| 42 | CVI-LM001 | 79.31% |
| 43 | Positive control | 137.93% |

Example 2 Test of Cell Biological Activity (1) Experimental Method

HEK293 cells stably expressing α1A-adrenergic receptor (α1A-AR) and G protein Gμ16 were seeded in 96-well plates. After 24 hours of culture, the medium was removed, and 40 μL of Hank's balanced salt solution (HBSS: containing 5.4 mM KCl, 0.3 mM Na$_2$HPO$_4$, 0.4 mM KH$_2$PO$_4$, 4.2 mM NaHCO$_3$, 1.3 mM CaCl$_2$, 0.5 mM MgCl$_2$, 0.6 mM MgSO$_4$, 137 mM NaCl, 5.6 mM D-glucose and 250 μM sulfinpyridone, pH 7.4) containing 2 μM of MFluo-4AM was added to each well, and incubated for 45 minutes in an incubator. The dye was aspirated and 50 μL of HBSS containing a test compound or 1% DMSO (negative control) was added and incubated for 10 minutes at room temperature, and then read with Flex Station 3 microplate reader. At the specified time point, 25 μL of agonist phenylephrine (final concentration 30 nM) will be automatically added by the detector into the reaction system, and simultaneously stimulated with 485 nm light, and the change in intensity of fluorescence caused by the change in the intracellular calcium ion concentration was detected at 525 nm. After incubated with different drugs, the response rate of cells to α1A-AR agonist phenylephrine is calculated by the following formula: % reaction rate=(DB)/(SB)*100%; where D is phenylephrine-induced signal peak after incubated with the drug to be tested; B is phenylephrine-induced signal peak after incubated with 10 μM positive control drug Tamsulosin; S is phenylephrine-induced signal peak after incubated with negative control 1% DMSO. The response rate of different doses of the same drug was analyzed by GraphPad Prism software to obtain a dose-response curve and the $IC_{50}$ value was measured. Each experiment was performed in ex vivo tissues of 3 Beagle dogs.

(2) Experimental Results

TABLE 2

Antagonistic activity of compounds on α1A-AR

| Serial No. | No. | α1A-AR/$IC50_{(nM)}$ |
|---|---|---|
| 1 | A61 | 4531 |
| 2 | A63 | 57730 |
| 3 | A69 | >>100000 |
| 4 | B5 | >>100000 |
| 5 | B55 | >>100000 |
| 6 | C47 | >>100000 |
| 7 | C49 | 6583 |
| 8 | C53 | 17540 |
| 9 | C59 | >>100000 |
| 10 | Positive control | 2.141 |

In vitro antagonistic activities of the compounds to α1A-AR were studied. The antagonistic activity of each compound to α1A-AR was weak, and the antagonistic activity of most compounds to α1A-AR was less than 10000 nM (such as A63, A69, B5, B55, C47, C49, C53, C59), and these compounds have a strong activity-regulating effect on PCSK9 (as known from Table 1). Meanwhile, such compounds are inactive against $D_1$, $D_2$ and 5-HT.

Example 3 In Vivo Study of Lipid-Lowering Activity (1) Experimental Method

After adaptively feeding Syrian golden hamsters (male, 80-100 g) for a week, all hamsters were fed with high-fat diet. Two weeks later, blood was collected from the orbital venous plexus, serum was separated, and levels of total cholesterol (TC), triglyceride (TG), high-density lipoprotein (HDL-C) and low-density lipoprotein (LDL-C) in serum were measured. They were evenly grouped according to blood lipid levels into 7 groups: model control group, A1 intragastric administration group, A1 intraperitoneal administration group, A5 intragastric administration group, A5 intraperitoneal administration group, A55 intragastric administration group, A55 intraperitoneal administration group, B5 intragastric administration group, B5 intraperitoneal administration group, and the animals in each group were continued to be administered with high fat diet. The compound was formulated with 0.5% CMC-Na (7.5 mg/ml), and the intragastric administration group was intragastrically administered once a day (administered dose: 30 mg/kg) for three weeks. The compound was formulated with physiological saline containing 5% DMSO, 10% hydrogenated castor oil (7.5 mg/ml), and the intraperitoneal administration group was intraperitoneally administered once a day (administered dose: 30 mg/kg) for three weeks. Blood lipid levels and body weights were measured every 10 days. After three weeks, the animals were sacrificed and the liver was stored in a −80° C. refrigerator.

(2) Experimental Results

TABLE 3

Study of lipid-lowering activity in golden hamsters

| Compound | Administration pathway | CHOL mmol/L | TG mmol/L | HDL-C mmol/L | LDL-C mmol/L | body weight (g) |
|---|---|---|---|---|---|---|
| A1 | oral | 27.93 | 28.61 | 2.56 | 13.64 | 169.67 |
|  | abdominal | 9.75 | 8.16 | 1.63 | 5.25 | 148.17 |
| A5 | oral | 15.32 | 15.46 | 4.01 | 7.44 | 148.43 |
|  | abdominal | 11.36 | 13.26 | 1.77 | 6.16 | 150.57 |
| A55 | oral | 11.81 | 6.74 | 3.88 | 5.56 | 138.86 |
|  | abdominal | 17.86 | 19.77 | 2.98 | 9.39 | 144.57 |
| B5 | oral | 14.79 | 11.94 | 3.99 | 7.66 | 147.86 |
|  | abdominal | 14.92 | 16.14 | 2.90 | 7.89 | 142.71 |
| Model group |  | 22.99 | 24.42 | 3.92 | 12.22 | 166.00 |

The results showed that in the hyperlipidemia model, compounds A1, A5, A55 and B5 significantly reduced the contents of cholesterol (CHOL), triglyceride (TG) and low density lipoprotein (LDL-C) in the blood of golden hamsters.

TABLE 4

Study of lipid-lowering activity in golden hamsters

| Compound | Dose | Administration pathway | TC mmol/L | TG mmol/L | LDL-C mmol/L |
|---|---|---|---|---|---|
| A61 | 30 | oral | 37.11 ± 11.19 | 30.29 ± 12.36 | 21.45 ± 6.27 |
| A61 | 100 | oral | 22.57 ± 6.37 | 10.32 ± 5.41 | 13.76 ± 4.15 |
| C3 | 30 | oral | 25.08 ± 16.98 | 13.66 ± 15.87 | 14.33 ± 8.74 |
| C3 | 100 | oral | 21.17 ± 3.89 | 4.56 ± 1.16 | 13.31 ± 3.01 |
| CVI-LM001 | 30 | oral | 30.78 ± 11.5 | 23.2 ± 13.2 | 18.44 ± 6.25 |
| CVI-LM001 | 100 | oral | 20.14 ± 5.41 | 9.61 ± 5.11 | 12.39 ± 4 |
| C9 | 30 | oral | 36.87 ± 23.13 | 33.6 ± 34 | 20.52 ± 11.15 |
| C47 | 30 | oral | 19.73 ± 6.44 | 8.7 ± 4.72 | 11.73 ± 4.16 |
| Model group |  |  | 37.32 ± 13.12 | 30.27 ± 17.04 | 22.66 ± 7.94 |

Example 4: Pharmacokinetics (1) Experimental Method

A1 10 μL of a plasma sample was taken in a centrifuge tube and 100 μL of methanol:acetonitrile (1:1, v/v) was added, vortexed for 1 min, centrifugated (14000 rpm) for 5 min, and 50 μL supernatant was taken, mixed with equal volume of water, and analysised after vortex mixing. The linear range of A1 is: 0.1-300 ng/mL for oral administration and 1-3000 ng/mL for intravenous injection.

A55 10 μL of a plasma sample was taken in a centrifuge tube and 100 μL of methanol:acetonitrile (1:1, v/v) was added, vortexed for 1 min, centrifugated (14000 rpm) for 5 min, and 50 μL supernatant was taken, mixed with equal volume of water, and analysised after vortex mixing. The linear range of A55 is: 0.1-300 ng/mL for oral administration and 0.3-3000 ng/mL for intravenous injection.

(1) Experimental Results

TABLE 5

Rat pharmacokinetic parameters of compounds A1 and A55

| Compound | | $T_{1/2}$ (h) | $T_{max}$ (h) | $C_{max}$ (ng/mL) | $AUC_{last}$ (h*ng/mL) | $AUC_{INF\_obs}$ (h*ng/mL) | $CL_{\_obs}$ (mL/min/kg) | $MRT_{INF\_obs}$ (h) | $Vss_{\_obs}$ (mL/kg) | F % |
|---|---|---|---|---|---|---|---|---|---|---|
| A1 | p.o. | * | 6.00 | 159 | 776 | — | — | — | — | 20.3 |
|  | i.v. | 2.58 | 0.083 | 1109 | 1910 | 1980 | 5051 | 3.3 | 16582 |  |
| A55 | p.o. | 0.71 | 4.00 | 62 | 334 | 335 | — | 4.8 | — | 6.2 |
|  | i.v. | 1.88 | 0.083 | 2741 | 2716 | 2731 | 3662 | 1.7 | 6407 |  |
| C3 | i.g | 6.53 | 4 | 296.8 | 3963.9 | 4337.9 | \ | 7.74 | \ | 57.2 |
|  | i.p | 18.5 | \ | \ | 3465.2 | 9362.4 | 1.07 | 15.3 | 28.6 |  |
| C47 | i.g | 38.2 | 4 | 251 | 9245 | 563535 | \ | 56.1 | \ | 31.0 |
|  | i.p | 51.2 | 24 | 276 | 14914 | 1120348 | \ | 66.4 | \ |  |

It can be found from the experimental results that the phenyl[a]indolo[2,3-g]quinolizine compounds and derivatives of the present invention have low toxicity and good solubility.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A phenyl [a] indole [2,3-g] quinazine compound of formula (I), or an enantiomer, diastereomer, racemate, and mixture thereof, a pharmaceutically acceptable salt, crystalline hydrate and solvate thereof,

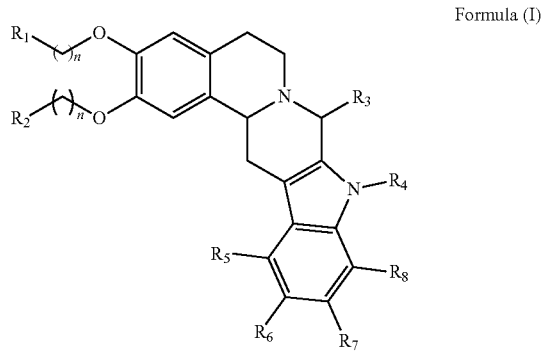

Formula (I)

wherein $R_1$ and $R_2$ are each independently selected from the group consisting of hydrogen, deuterium, tritium, halogen, a substituted or unsubstituted C1-C6 alkyl, substituted or unsubstituted C1-C6 alkoxy, substituted or unsubstituted C6-C10 aryl, substituted or unsubstituted 5-7 membered heterocyclic ring, substituted or unsubstituted C1-C6 alkylphenyl, substituted or unsubstituted C1-C6 alkyl (5-7 membered heteroaryl), substituted or unsubstituted C3-C12 cycloalkyl, substituted or unsubstituted C2-C10 acyl, substituted or unsubstituted C2-C10 ester group, amino group, substituted or unsubstituted C1-C6 amide group, $—SO_2R_9$, $—OSO_2R_9$, $—OCOR_9$; and $R_1$ and $R_2$ are not both hydrogen;

or the $R_1$ and $R_2$ and the adjacent $—(CH2)n-O$ and $C=C$ together form a substituted or unsubstituted 5-7 membered heterocyclic ring, wherein the heterocyclic ring is an aromatic heterocyclic ring;

$R_3$ and $R_4$ are each independently selected from the group consisting of hydrogen, deuterium, tritium, halogen, amine, hydroxy, a substituted or unsubstituted C1-C6 alkyl, substituted or unsubstituted C1-C6 alkoxy, substituted or unsubstituted C6-C10 aryl, substituted or unsubstituted 5-7 membered heterocyclic ring, substituted or unsubstituted C1-C6 alkylphenyl, substituted or unsubstituted C3-C12 cycloalkyl, substituted or unsubstituted C2-C10 acyl, substituted or unsubstituted C2-C10 ester group, amino, C1-C6 alkylamino, substituted or unsubstituted C1-C6 amide group, $—SO_2R_9$, $—OSO_2R_9$, $—OCOR_9$;

$R_5$, $R_6$, $R_7$ and $R_8$ are each independently selected from the group consisting of hydrogen, deuterium, tritium, halogen, hydroxy, a substituted or unsubstituted C1-C6 alkyl, substituted or unsubstituted C1-C6 alkoxy, substituted or unsubstituted C1-C6 alkylphenyl, substituted or unsubstituted C1-C6 alkyl-(5-7 membered heteroaryl), substituted or unsubstituted C3-C12 cycloalkyl, cyano, nitro, carboxyl, sulfydryl, $—NR_9R_{10}$, $—NCOR_9R_{10}$, $—SO_2R_9$, $—SO_2NR_9R_{10}$, $—OSO_2R_9$, or $—OCOR_9$;

$R_9$ and $R_{10}$ are independently hydrogen, deuterium, tritium, halogen, an unsubstituted or 1-3 halogen substituted C1-C6 alkyl, or C3-C6 cycloalkane unsubstituted or substituted by 1-3 halogens, C6-C10 aryl unsubstituted or substituted by 1 to 3 halogens, C1-C3 alkyl-(C6-C10 aryl) unsubstituted or substituted by 1-3 halogens, 5-7 membered heteroaryl unsubstituted or substituted by 1-3 halogens;

and when both of $R_3$ and $R_4$ are hydrogen, at least one of $R_1$, $R_2$, $R_6$, or $R_7$ is selected from the group consisting of an unsubstituted or substituted C6-C10 aryl, substituted 5-7-membered heterocyclic ring, and —SO₂R₉;
when both of R₃ and R₄ are hydrogen and R₁ or R₂ is
an unsubstituted phenyl, then R₆ and R₇ are not hydrogen or methoxy (—OCH₃); or when both of R₃ and R₄
are hydrogen and R₁ or R₂ is an unsubstituted phenyl
and R₆ and R₇ are hydrogen or methoxy (—OCH₃),
then R₅ is halogen;

wherein the "substituted" refers to one or more hydrogen
atoms on the group being substituted with a substituent
selected from the group consisting of halogen, a C1-C6
alkyl unsubstituted or substituted by halogen or C3-C6
(preferably C1-C4) cycloalkyl, C1-C4 alkoxy, C3-C6
cycloalkyl, C1-C4 linear or branched alkyl substituted
amine group, hydroxy, cyano, nitro, oxygen atom
(=O), hydroxy-C1-C6 alkyl, carboxyl, sulfydryl,
C6-C10 aryl unsubstituted or substituted by 1 to 3
halogens or hydroxy groups, unsubstituted or halogenated 5-7 membered heterocyclic ring, unsubstituted or
halogenated C2-C6 acyl, C1-C6 hydroxyalkyl,
—NR₉R₁₀, —NCOR₉R₁₀, —SO₂R₉, —OSO₂R₉,
—SO₂NR₉R₁₀, —COOR₉ and —OCOR₉;

n is 0 or 1;

and when

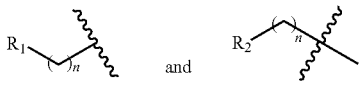

are both methyl, then R₄ is selected from the group consisting of halogen, amine, hydroxy, a substituted or unsubstituted C1-C6 alkyl, substituted or unsubstituted C1-C6
alkoxy, substituted or unsubstituted C6-C10 aryl, substituted
or unsubstituted 5-7 membered heterocyclic ring, substituted
or unsubstituted C1-C6 alkylphenyl, substituted or unsubstituted C3-C12 cycloalkyl, substituted or unsubstituted
C2-C10 acyl, substituted or unsubstituted C2-C10 ester
group, amino, C1-C6 alkylamino, substituted or unsubstituted C1-C6 amide group, —SO₂R₉, —OSO₂R₉, and
—OCOR₉.

2. The compound of claim 1, or enantiomer, diastereomer,
racemate, or mixture thereof, and pharmaceutically acceptable salt, crystalline hydrate and solvate thereof, wherein the
phenyl [a] fluorene [2,3-g] quinazine compound has the
following formula R-(I) or the formula S-(I):

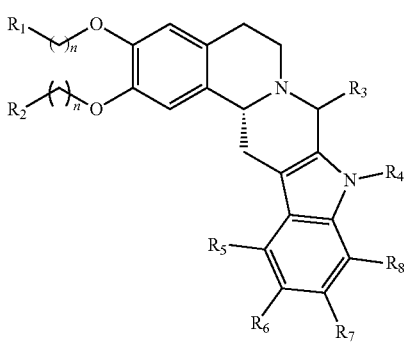

Formula R-(I)

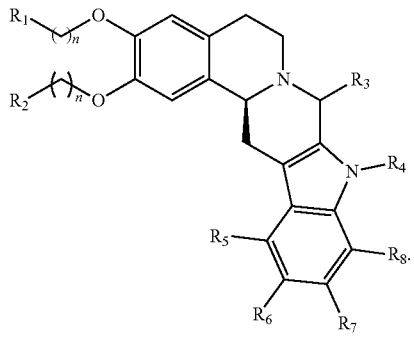

Formula S-(I)

3. The compound of claim 1, or enantiomer, diastereomer,
racemate, or mixture thereof, and pharmaceutically acceptable salt, crystalline hydrate and solvate thereof, wherein R₃
is hydrogen or a substituted or unsubstituted C1-C6 alkyl,
and R₄ is selected from the group consisting of a substituted
or unsubstituted C1-C6 alkyl, substituted or unsubstituted
C1-C6 alkoxy, substituted or unsubstituted C1-C6 alkylphenyl, substituted or unsubstituted 5-7-membered heterocyclic
ring, substituted or unsubstituted C3-C12 cycloalkyl, substituted or unsubstituted C2-C10 acyl, substituted or unsubstituted C2-C10 ester group, and —OSO₂R₉.

4. The compound of claim 1, or enantiomer, diastereomer,
racemate, or mixture thereof, and pharmaceutically acceptable salt, crystalline hydrate and solvate thereof, wherein R₄
is hydrogen, and R₃ is selected from the group consisting of
a substituted or unsubstituted C6-C10 aryl, substituted or
unsubstituted 5-7 membered heterocyclic ring, substituted or
unsubstituted C1-C6 alkylphenyl, and substituted or unsubstituted C3-C12 cycloalkyl.

5. The compound of claim 1, or enantiomer, diastereomer,
racemate, or mixture thereof, and pharmaceutically acceptable salt, crystalline hydrate and solvate thereof, wherein R₃
and R₄ are hydrogen; and
at least one of R₁ and R₂ is a group selected from the
group consisting of a substituted or unsubstituted
C6-C10 aryl, substituted or unsubstituted 5-7 membered heterocyclic ring, substituted or unsubstituted
C1-C6 alkylphenyl group, substituted or unsubstituted
C1-C6 alkyl-(5-7 membered heteroaryl), substituted or
unsubstituted C3-C12 cycloalkyl, and —SO₂R₉; or
at least one of R₅, R₆, R₇, and R₈ is a group selected from
the group consisting of a substituted or unsubstituted
C1-C6 alkylphenyl, substituted or unsubstituted C1-C6
alkyl-(5-7 membered heteroaryl), substituted or unsubstituted C3-C12 cycloalkyl, and —SO₂R₉.

6. The compound of claim 1, or enantiomer, diastereomer,
racemate, or mixture thereof, and pharmaceutically acceptable salt, crystalline hydrate and solvate thereof, wherein:
R₁ and R₂ are each independently selected from the group
consisting of hydrogen, hydrazine, hydrazine deuterium, tritium, halogen, substituted or unsubstituted
C1-C6 alkyl, and substituted or unsubstituted C6-C10
aryl;
or the R₁ and R₂ are taken together form a substituted or
unsubstituted 5-7 membered heterocyclic ring, wherein
the heterocyclic ring is an aromatic heterocyclic ring;
R₃ is selected from the group consisting of hydrogen,
deuterium, tritium, halogen, a substituted or unsubstituted C6-C10 aryl, and substituted or unsubstituted 5-7
membered heterocyclic ring;

369

R$_4$ is hydrogen, deuterium, tritium, halogen, a substituted or unsubstituted hydroxy-C1-C6 alkyl, C1-C6 alkylene-OCOR$_9$, or C1-C6 alkylene-OCOR$_9$; and R$_5$, R$_6$, R$_7$ and R$_8$ are each independently hydrogen, deuterium, tritium, halogen, a substituted or unsubstituted C1-C6 alkyl, substituted or unsubstituted C1-C6 alkoxy, substituted or unsubstituted C3-C6 cycloalkyl, hydroxyl, cyano, nitro, carboxyl, sulfydryl, —NR$_9$R$_{10}$, —NCOR$_9$R$_{10}$, —SO$_2$R$_9$, —SO$_2$NR$_9$R$_{10}$, or —OCOR$_9$.

7. The compound of claim 1, wherein the compound is selected from the following group:

| No. | Name | Structure |
|---|---|---|
| A1 | (2-(benzyloxy)-3,12-dimethoxy-5,6,14,14a-tetrahydroindolo[3',2':4,5]pyridine[2,1-a]isoquinoline-9(8H)-yl)methanol | 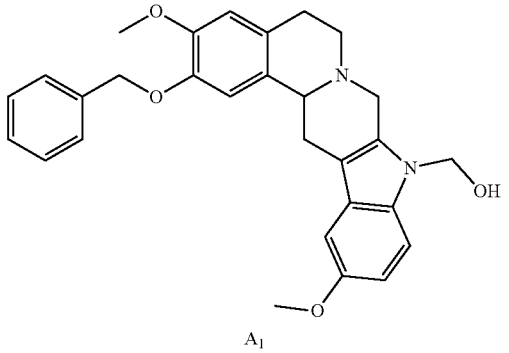 |
| A2 | (2-(benzyloxy)-3-methoxy-5,6,14,14a-tetrahydroindolo[3',2':4,5]pyridine[2,1-a]isoquinoline-9(8H)-yl)methanol | 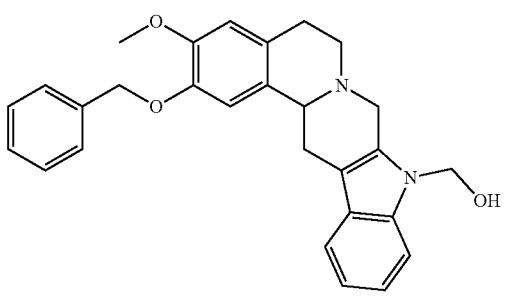 |
| A3 | (3,12-dimethoxy-2-((4-(trifluoromethyl)benzyl)oxy)-5,6,14,14a-tetrahydroindolo[3',2':4,5]pyridine[2,1-a]isoquinoline-9(8H)-yl)methanol | 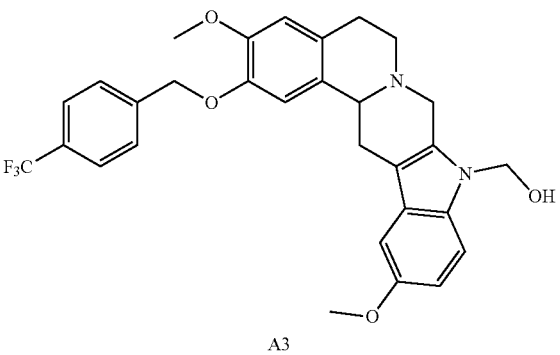 [SMILES: COc1ccc2c(c1)c1c(n2CO)CN2CCc3cc(OC)c(OCc4ccc(C(F)(F)F)cc4)cc3C2C1 ; "A3"] |
| A4 | (3-methoxy-2((4-(trifluoromethyl)benzyl)oxy)-5,6,14,14a-tetrahydroindolo[3',2':4,5]pyridine[2,1-a]isoquinoline-9(8H)-yl)methanol | 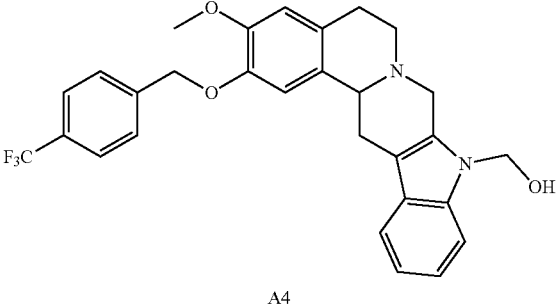 [SMILES: COc1cc2c(cc1OCc1ccc(C(F)(F)F)cc1)C1Cc3c(n(CO)c4ccccc34)CN1CC2 ; "A4"] |

-continued

| No. | Name | Structure |
|---|---|---|
| A5 | (2-((4-fluorobenzyl)oxy)-3,12-dimethoxy-5,6,14,14a-tetrahydroindolo[3',2':4,5]pyridine[2,1-a]isoquinoline-9(8H)-yl)methanol | 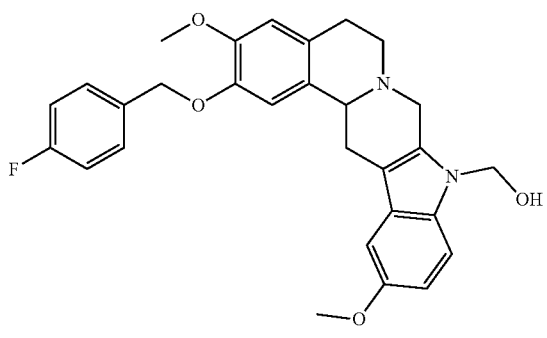<br>A5 |
| A6 | (2-((4-fluorobenzyl)oxy)-3-methoxy-5,6,14,14a-tetrahydroindolo[3',2':4,5]pyridine[2,1-a]isoquinoline-9(8H)-yl)methanol | 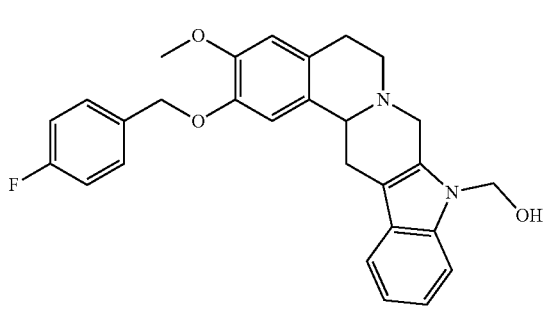<br>A6 |
| A7 | (2-((3-fluorobenzyl)oxy)-3,12-dimethoxy-5,6,14,14a-tetrahydroindolo[3',2':4,5]pyridine[2,1-a]isoquinoline-9(8H)-yl)methanol | 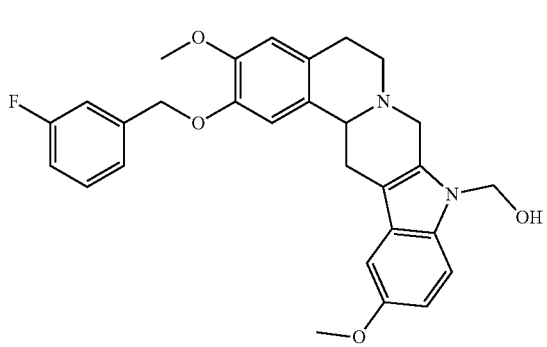<br>A7 |
| A8 | (2-((3-fluorobenzyl)oxy)-3-methoxy-5,6,14,14a-tetrahydroindolo[3',2':4,5]pyridine[2,1-a]isoquinoline-9(8H)-yl)methanol | 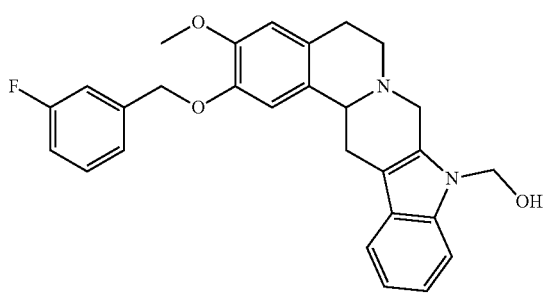<br>A8 |

-continued

| No. | Name | Structure |
|---|---|---|
| A9 | (2-((2-fluorobenzyl)oxy)-3,12-dimethoxy-5,6,14,14a-tetrahydroindolo[3',2':4,5]pyridine[2,1-a]isoquinoline-9(8H)-yl)methanol | 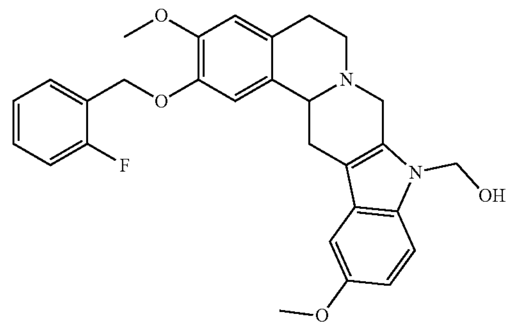 |
| A10 | (2-((2-fluorobenzyl)oxy)-3-methoxy-5,6,14,14a-tetrahydroindolo[3',2':4,5]pyridine[2,1-a]isoquinoline-9(8H)-yl)methanol | 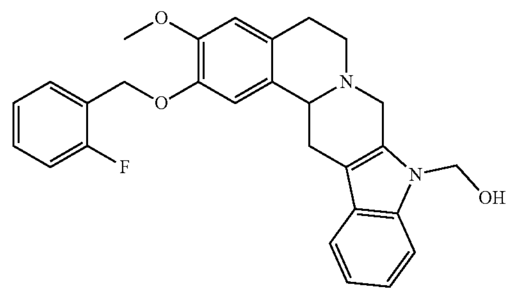 |
| A11 | (3,12-dimethoxy-2-((4-methoxybenzyl)oxy)-5,6,14,14a-tetrahydroindolo[3',2':4,5]pyridine[2,1-a]isoquinoline-9(8H)-yl)methanol | 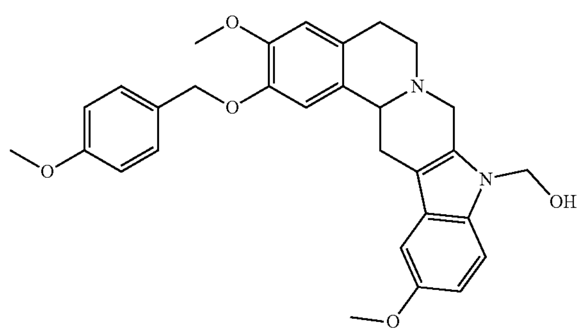 |
| A12 | (3-methoxy-2-((4-methoxybenzyl)oxy)-5,6,14,14a-tetrahydroindolo[3',2':4,5]pyridine[2,1-a]isoquinoline-9(8H)-yl)methanol | 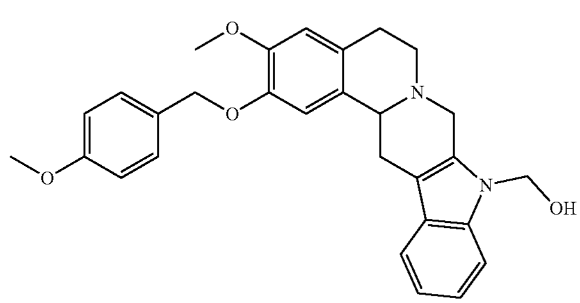 |

-continued

| No. | Name | Structure |
|---|---|---|
| A13 | (3,12-dimethoxy-2-((3-methoxybenzyl)oxy)-5,6,14,14a-tetrahydroindolo[3',2':4,5]pyridine[2,1-a]isoquinoline-9(8H)-yl)methanol | 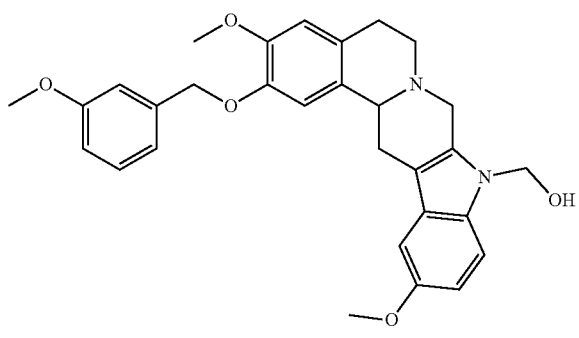<br>A13 |
| A14 | (3-methoxy-2-((3-methoxybenzyl)oxy)-5,6,14,14a-tetrahydroindolo[3',2':4,5]pyridine[2,1-a]isoquinoline-9(8H)-yl)methanol | 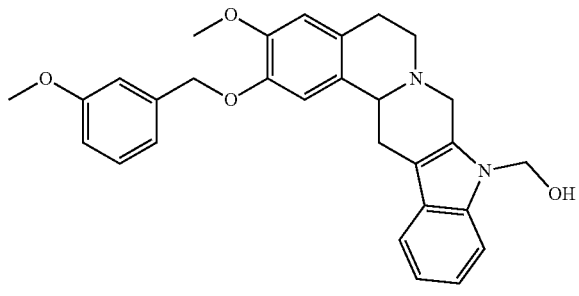<br>A14 |
| A15 | (3,12-dimethoxy-2-((4-methylbenzyl)oxy)-5,6,14,14a-tetrahydroindolo[3',2':4,5]pyridine[2,1-a]isoquinoline-9(8H)-yl)methanol | 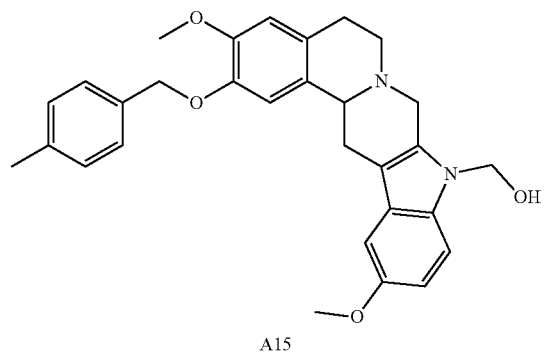<br>A15 |
| A16 | (3-methoxy-2-((4-methylbenzyl)oxy)-5,6,14,14a-tetrahydroindolo[3',2':4,5]pyridine[2,1-a]isoquinoline-9(8H)-yl)methanol | 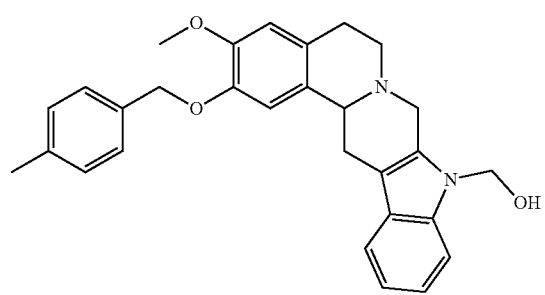<br>A16 |

-continued

| No. | Name | Structure |
|---|---|---|
| A17 | (2-((4-chlorobenzyl)oxy)-3,12-dimethoxy-5,6,14,14a-tetrahydroindolo[3',2':4,5]pyridine[2,1-a]isoquinoline-9(8H)-yl)methanol | 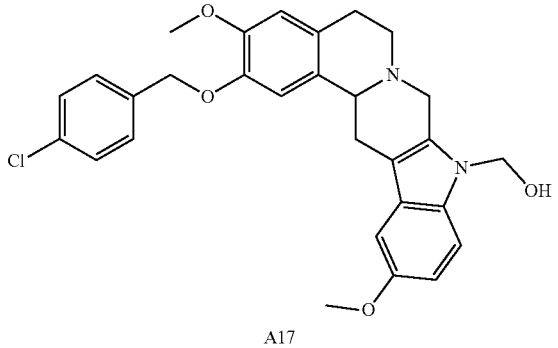 [SMILES: COc1ccc2c(c1)c1c(n2CO)CN2CCc3cc(OC)c(OCc4ccc(Cl)cc4)cc3C2C1 ; "A17"]<br>A17 |
| A18 | (2-((4-chlorobenzyl)oxy)-3-methoxy-5,6,14,14a-tetrahydroindolo[3',2':4,5]pyridine[2,1-a]isoquinoline-9(8H)-yl)methanol | 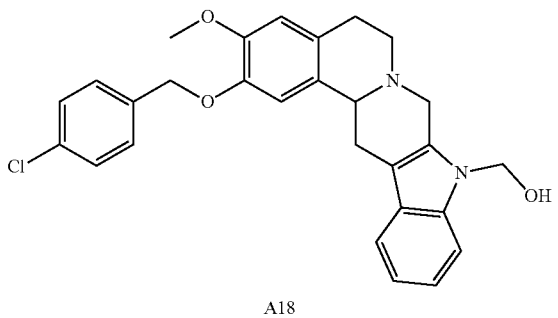 [SMILES: COc1cc2c(cc1OCc1ccc(Cl)cc1)C1Cc3c(n(CO)c4ccccc34)CN1CC2 ; "A18"]<br>A18 |
| A19 | 4-(((9-(hydroxymethyl)-3,12-dimethoxy-5,6,8,9,14,14a-hexahydroindolo[3',2':4,5]pyridine[2,1-a]isoquinoline-2-yl)oxy)methyl)benzonitrile | 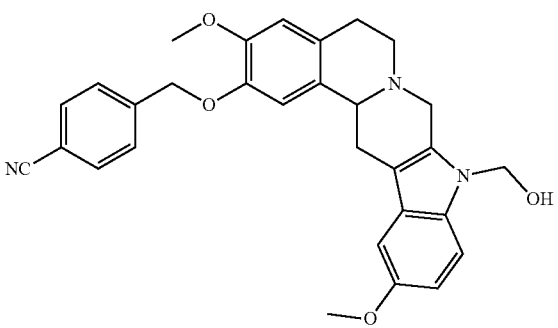<br>A19 |
| A20 | 4-(((9-(hydroxymethyl)-3-methoxy-5,6,8,9,14,14a-hexahydroindolo[3',2':4,5]pyridine[2,1-a]isoquinoline-2-yl)oxy)methyl)benzonitrile | 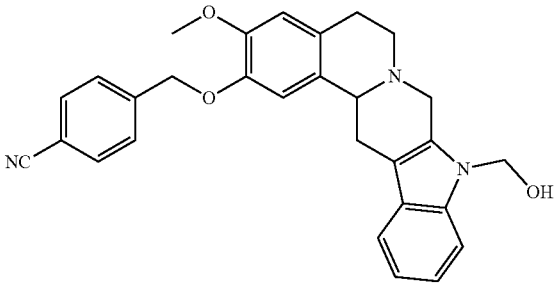<br>A20 |

-continued

| No. | Name | Structure |
|---|---|---|
| A21 | (2-((4-bromobenzyl)oxy)-3,12-dimethoxy-5,6,14,14a-tetrahydroindolo[3',2':4,5]pyridine[2,1-a]isoquinoline-9(8H)-yl)methanol | 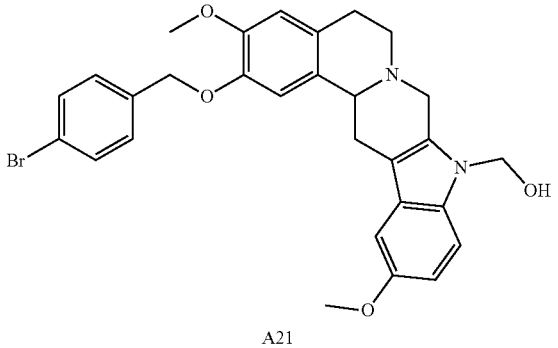<br>A21 |
| A22 | (2-((4-bromobenzyl)oxy)-3-methoxy-5,6,14,14a-tetrahydroindolo[3',2':4,5]pyridine[2,1-a]isoquinoline-9(8H)-yl)methanol | 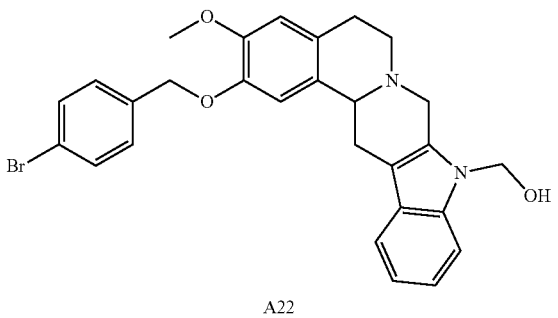<br>A22 |
| A23 | (2-((3-fluoro-4-(trifluoromethyl)benzyl)oxy)-3,12-dimethoxy-5,6,14,14a-tetrahydroindolo[3',2':4,5]pyridine[2,1-a]isoquinoline-9(8H)-yl)methanol | 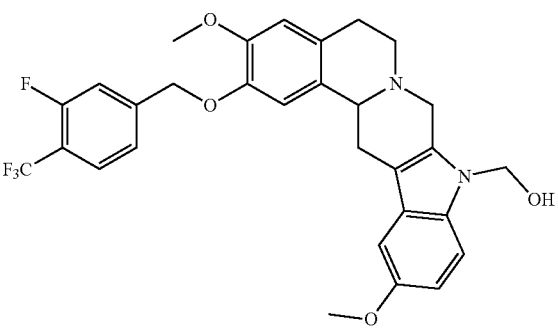<br>A23 |
| A24 | (2-((3-fluoro-4-(trifluoromethyl)benzyl)oxy)-3-methoxy-5,6,14,14a-tetrahydroindolo[3',2':4,5]pyridine[2,1-a]isoquinoline-9(8H)-yl)methanol | 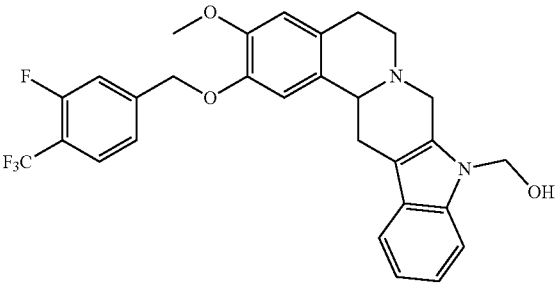<br>A24 |

-continued

| No. | Name | Structure |
|---|---|---|
| A25 | (2-((2-fluoro-4-(trifluoromethyl)benzyl)oxy)-3,12-dimethoxy-5,6,14,14a-tetrahydroindolo[3',2':4,5]pyridine[2,1-a]isoquinoline-9(8H)-yl)methanol | 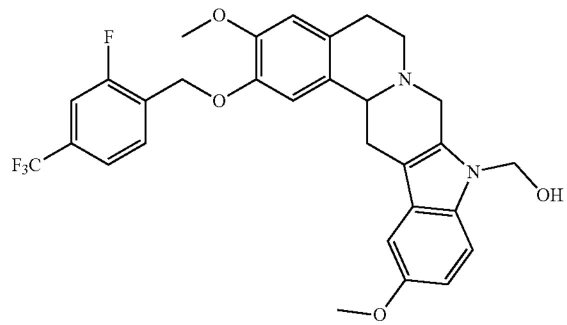 |
| A26 | (2-((2-fluoro-4-(trifluoromethyl)benzyl)oxy)-3-methoxy-5,6,14,14a-tetrahydroindolo[3',2':4,5]pyridine[2,1-a]isoquinoline-9(8H)-yl)methanol | 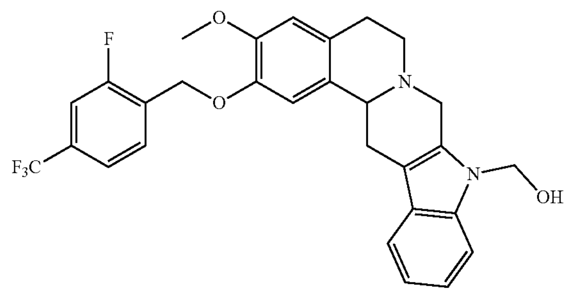 |
| A27 | (3,12-dimethoxy-2-((4-ethylbenzyl)oxy)-5,6,14,14a-tetrahydroindolo[3',2':4,5]pyridine[2,1-a]isoquinoline-9(8H)-yl)methanol | 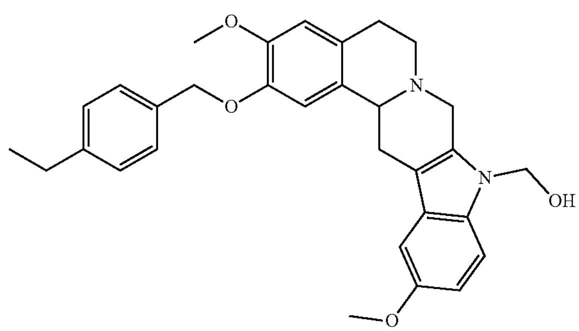 |
| A28 | (3-methoxy-2-((4-ethylbenzyl)oxy)-5,6,14,14a-tetrahydroindolo[3',2':4,5]pyridine[2,1-a]isoquinoline-9(8H)-yl)methanol | 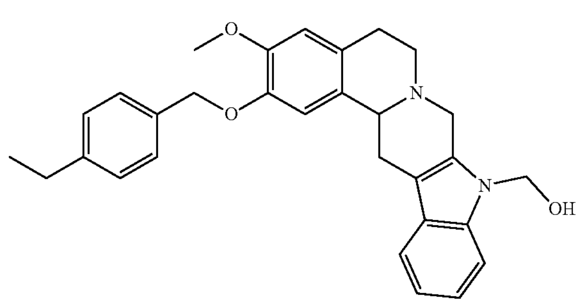 |

-continued

| No. | Name | Structure |
|---|---|---|
| A29 | (3,12-dimethoxy-2-(naphthalen-2-ylmethoxy)-5,6,14,14a-tetrahydroindolo[3',2':4,5]pyridine[2,1-a]isoquinoline-9(8H)-yl)methanol | 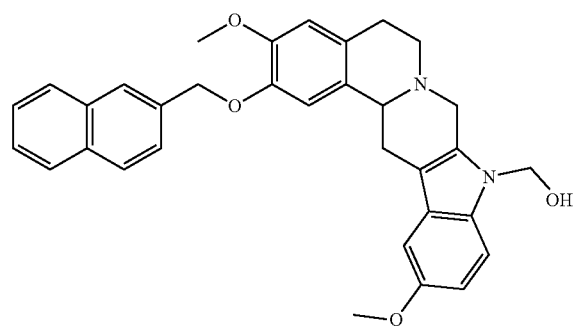<br>A29 |
| A30 | (3-methoxy-2-(naphthalen-2-ylmethoxy)-5,6,14,14a-tetrahydroindolo[3',2':4,5]pyridine[2,1-a]isoquinoline-9(8H)-yl)methanol | 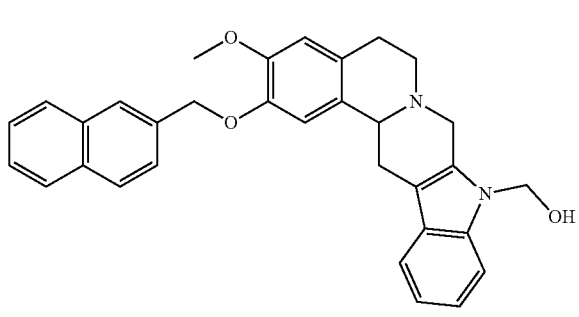<br>A30 |
| A31 | 4-(((9-(hydroxymethyl)-3,12-dimethoxy-5,6,8,9,14,14a-hexahydroindolo[3',2':4,5]pyridine[2,1-a]isoquinoline-2-yl)oxo)methyl)benzoate | 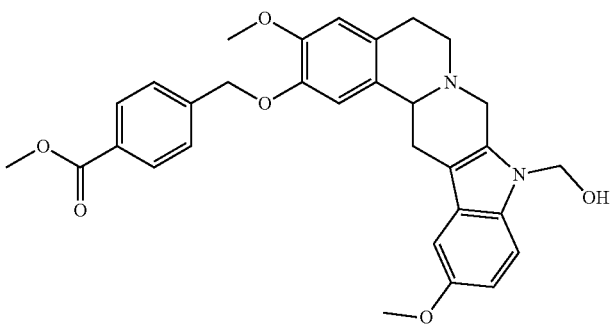<br>A31 |
| A32 | 4-(((9-(hydroxymethyl)-3-methoxy-5,6,8,9,14,14a-hexahydroindolo[3',2':4,5]pyridine[2,1-a]isoquinoline-2-yl)oxo)methyl)benzoate | 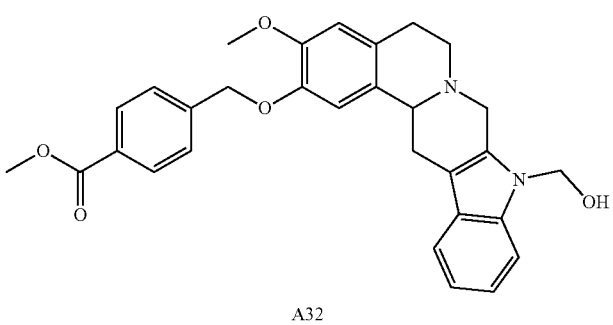 [SMILES: COC(=O)c1ccc(COc2cc3c(cc2OC)CCN2Cc4c(c5ccccc5n4CO)CC32)cc1 ; "A32"]<br>A32 |

-continued

| No. | Name | Structure |
|---|---|---|
| A33 | (2-((4-(1H-pyrazol-1-yl)benzyl)oxy)-3,12-dimethoxy-5,6,14,14a-tetrahydroindolo[3',2':4,5]pyridine[2,1-a]isoquinoline-9(8H)-yl)methanol | 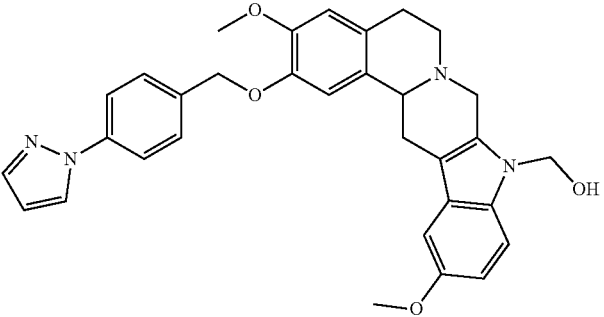<br>A33 |
| A34 | (2-((4-(1H-pyrazol-1-yl)benzyl)oxy)-3-methoxy-5,6,14,14a-tetrahydroindolo[3',2':4,5]pyridine[2,1-a]isoquinoline-9(8H)-yl)methanol | 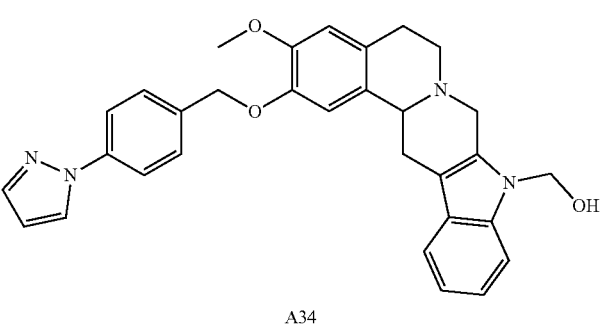 [SMILES: COc1cc2c(cc1OCc1ccc(-n3cccn3)cc1)C1Cc3c(n(CO)c4ccccc34)CN1CC2 ; "A34"]<br>A34 |
| A35 | (2-butoxy-3,12-dimethoxy-5,6,14,14a-tetrahydroindolo[3',2':4,5]pyridine[2,1-a]isoquinoline-9(8H)-yl)methanol | 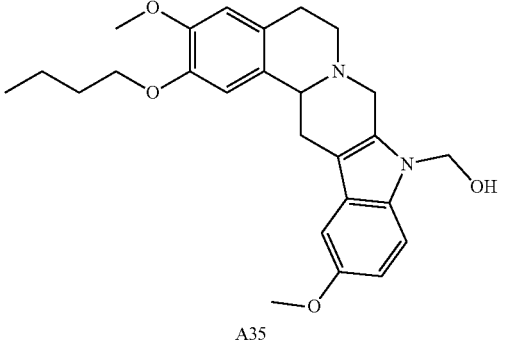<br>A35 |
| A36 | (2-butoxy-3-methoxy-5,6,14,14a-tetrahydroindolo[3',2':4,5]pyridine[2,1-a]isoquinoline-9(8H)-yl)methanol | 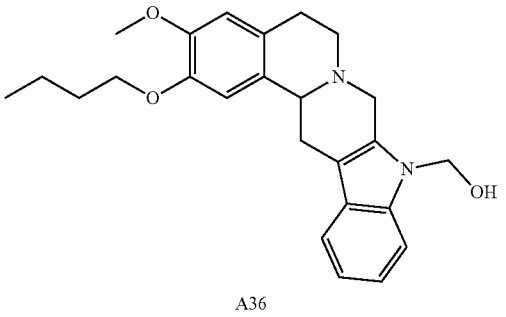 [SMILES: CCCCOc1cc2c(cc1OC)CCN1Cc3c(c4ccccc4n3CO)CC21 ; "A36"]<br>A36 |

-continued

| No. | Name | Structure |
|---|---|---|
| A37 | (2,3,12-trimethoxy-5,6,14,14a-tetrahydroindolo[3',2':4,5]pyridine[2,1-a]isoquinoline-9(8H)-yl)methanol | 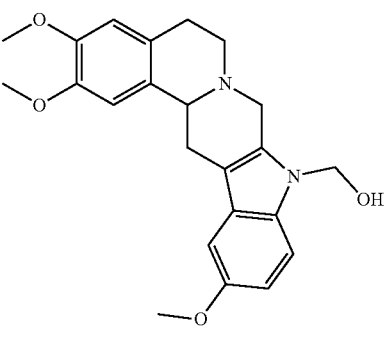<br>A37 |
| A38 | (2,3-dimethoxy-5,6,14,14a-tetrahydroindolo[3',2':4,5]pyridine[2,1-a]isoquinoline-9(8H)-yl)methanol | 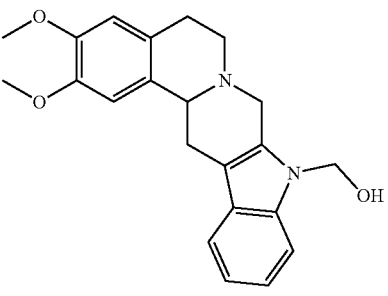<br>A38 |
| A39 | (3,12-dimethoxy-2-(2,2,2-trifluoroethoxy)-5,6,14,14a-tetrahydroindolo[3',2':4,5]pyridine[2,1-a]isoquinoline-9(8H)-yl)methanol | 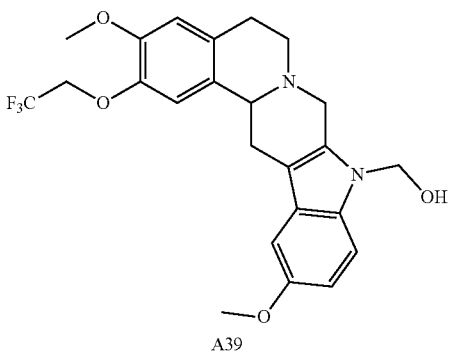<br>A39 |
| A40 | (3-methoxy-2-(2,2,2-trifluoroethoxy)-5,6,14,14a-tetrahydroindolo[3',2':4,5]pyridine[2,1-a]isoquinoline-9(8H)-yl)methanol | 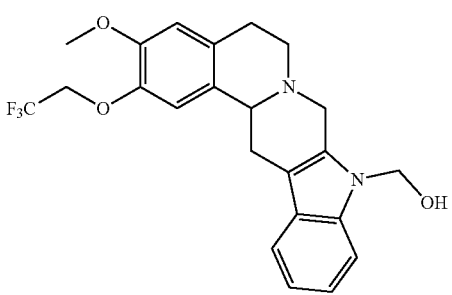<br>A40 |

-continued

| No. | Name | Structure |
|---|---|---|
| A41 | (3,12-dimethoxy-2-((4-(methylsulfonyl)benzyl)oxy)-5,6,14,14a-tetrahydroindolo[3',2':4,5]pyridine[2,1-a]isoquinoline-9(8H)-yl)methanol | 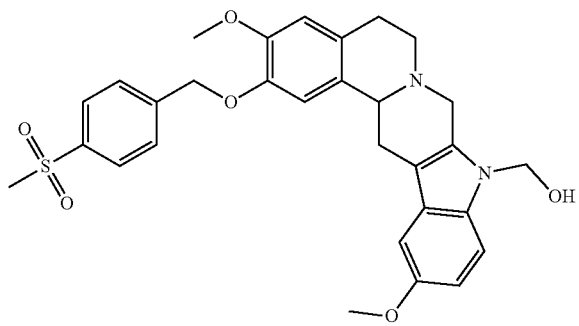<br>A41 |
| A42 | (3-methoxy-2-((4-(methylsulfonyl)benzyl)oxy)-5,6,14,14a-tetrahydroindolo[3',2':4,5]pyridine[2,1-a]isoquinoline-9(8H)-yl)methanol | 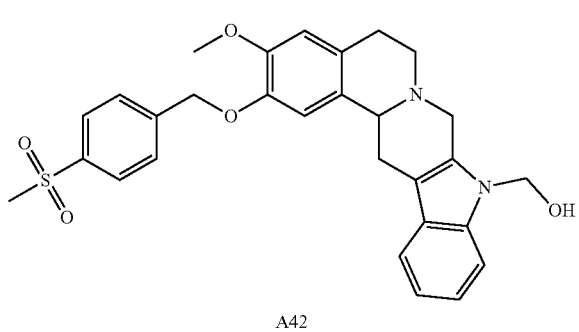 [SMILES: COc1cc2c(cc1OCc1ccc(S(C)(=O)=O)cc1)C1Cc3c(n(CO)c4ccccc34)CN1CC2 ; "A42"]<br>A42 |
| A43 | (2-(benzyloxy)-11-fluoro-3-methoxy-5,6,14,14a-tetrahydroindolo[3',2':4,5]pyridine[2,1-a]isoquinoline-9(8H)-yl)methanol | 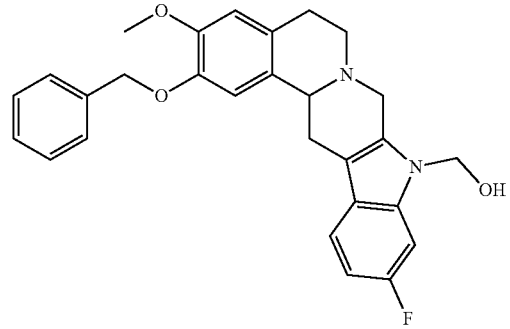<br>A43 |
| A44 | (2-(benzyloxy)-12-fluoro-3-methoxy-5,6,14,14a-tetrahydroindolo[3',2':4,5]pyridine[2,1-a]isoquinoline-9(8H)-yl)methanol | 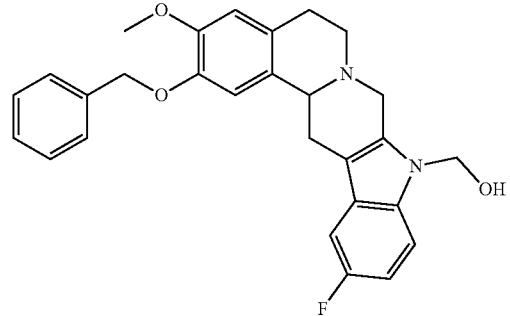<br>A44 |

-continued

| No. | Name | Structure |
|---|---|---|
| A45 | (2-(benzyloxy)-13-fluoro-3-methoxy-5,6,14,14a-tetrahydroindolo[3',2':4,5]pyridine[2,1-a]isoquinoline-9(8H)-yl)methanol | 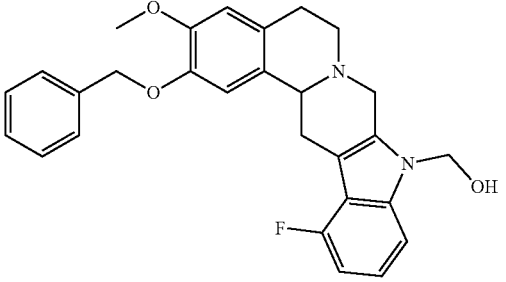<br>A45 |
| A46 | (2-(benzyloxy)-11-chloro-3-methoxy-5,6,14,14a-tetrahydroindolo[3',2':4,5]pyridine[2,1-a]isoquinoline-9(8H)-yl)methanol | 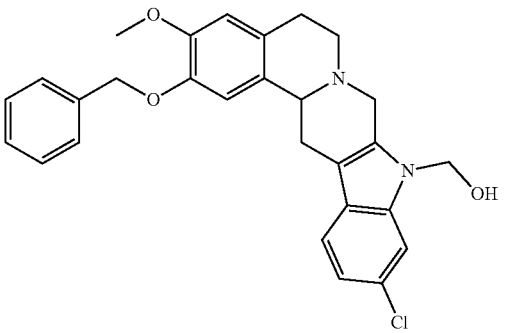<br>A46 |
| A47 | (2-(benzyloxy)-12-chloro-3-methoxy-5,6,14,14a-tetrahydroindolo[3',2':4,5]pyridine[2,1-a]isoquinoline-9(8H)-yl)methanol | 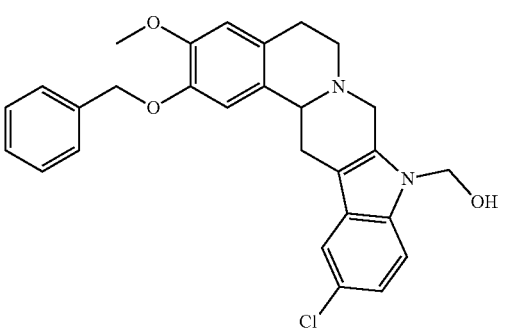<br>A47 |
| A48 | (2-(benzyloxy)-13-chloro-3-methoxy-5,6,14,14a-tetrahydroindolo[3',2':4,5]pyridine[2,1-a]isoquinoline-9(8H)-yl)methanol | 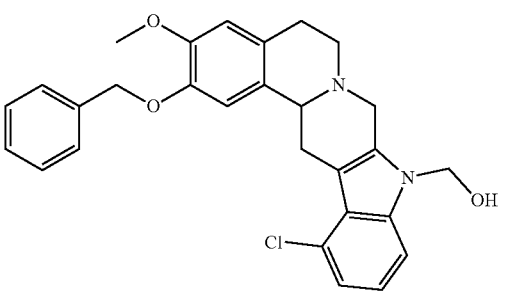<br>A48 |

-continued

| No. | Name | Structure |
|---|---|---|
| A49 | (2-(benzyloxy)-11-bromo-3-methoxy-5,6,14,14a-tetrahydroindolo[3',2':4,5]pyridine[2,1-a]isoquinoline-9(8H)-yl)methanol | A49 |
| A50 | (2-(benzyloxy)-12-bromo-3-methoxy-5,6,14,14a-tetrahydroindolo[3',2':4,5]pyridine[2,1-a]isoquinoline-9(8H)-yl)methanol | A50 |
| A51 | (2-(benzyloxy)-13-bromo-3-methoxy-5,6,14,14a-tetrahydroindolo[3',2':4,5]pyridine[2,1-a]isoquinoline-9(8H)-yl)methanol | A51 |
| A52 | 2-(benzyloxy)-9-(hydroxymethyl)-3-methoxy-5,6,8,9,14,14a-hexahydroindolo[3',2':4,5]pyridine[2,1-a]isoquinoline-12-phenol | A52 |

-continued

| No. | Name | Structure |
|---|---|---|
| A53 | (2-(benzyloxy)-3-methoxy-11-methyl-5,6,14,14a-tetrahydroindolo[3',2':4,5]pyridine[2,1-a]isoquinoline-9(8H)-yl)methanol | 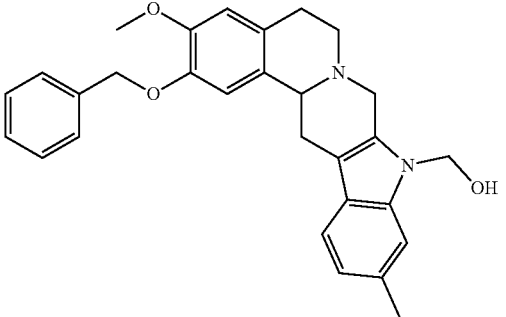<br>A53 |
| A54 | (2-(benzyloxy)-12-ethyl-3-methoxy-5,6,14,14a-tetrahydroindolo[3',2':4,5]pyridine[2,1-a]isoquinoline-9(8H)-yl)methanol | 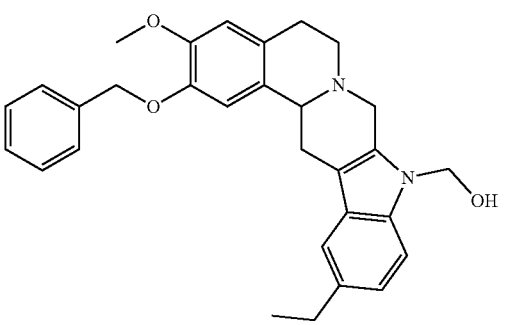<br>A54 |
| A55 | (3-(benzyloxy)-2,12-dimethoxy-5,6,14,14a-tetrahydroindolo[3',2':4,5]pyridine[2,1-a]isoquinoline-9(8H)-yl)methanol | 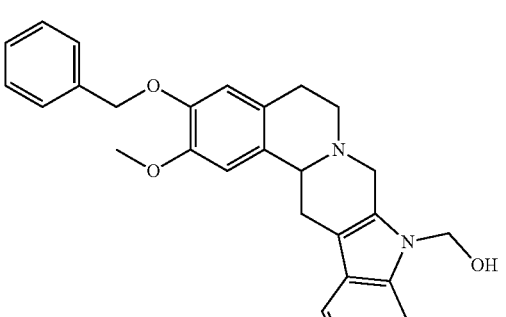<br>A55 |
| A56 | (3-(benzyloxy)-2-methoxy-5,6,14,14a-tetrahydroindolo[3',2':4,5]pyridine[2,1-a]isoquinoline-9(8H)-yl)methanol | 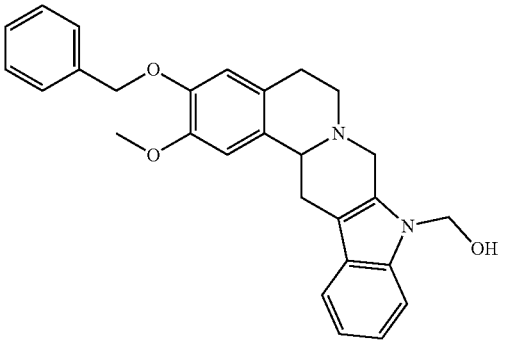<br>A56 |

| No. | Name | Structure |
|---|---|---|
| A57 | (2,12-dimethoxy-3-((4-(trifluoromethyl)benzyl)oxy)-5,6,14,14a-tetrahydroindolo[3',2':4,5]pyridine[2,1-a]isoquinoline-9(8H)-yl)methanol | A57 |
| A58 | (2-methoxy-3-((4-(trifluoromethyl)benzyl)oxy)-5,6,14,14a-tetrahydroindolo[3',2':4,5]pyridine[2,1-a]isoquinoline-9(8H)-yl)methanol | A58 |
| A59 | (3-((4-fluorobenzyl)oxy)-2,12-dimethoxy-5,6,14,14a-tetrahydroindolo[3',2':4,5]pyridine[2,1-a]isoquinoline-9(8H)-yl)methanol | A59 |
| A60 | (3-((4-fluorobenzyl)oxy)-2-methoxy-5,6,14,14a-tetrahydroindolo[3',2':4,5]pyridine[2,1-a]isoquinoline-9(8H)-yl)methanol | A60 |

-continued
| No. | Name | Structure |
|---|---|---|
| A61 | (3-((3-fluorobenzyl)oxy)-2,12-dimethoxy-5,6,14,14a-tetrahydroindolo[3',2':4,5]pyridine[2,1-a]isoquinoline-9(8H)-yl)methanol | 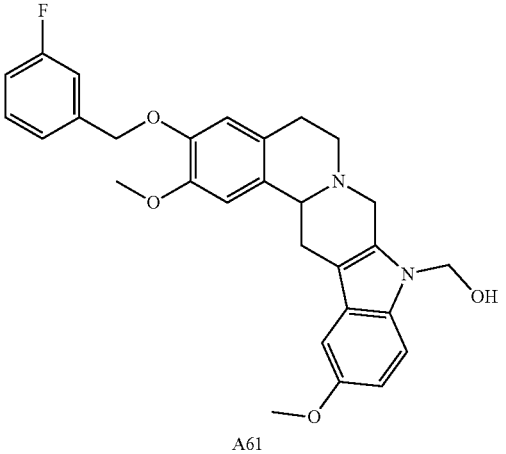<br>A61 |
| A62 | (3-((3-fluorobenzyl)oxy)-2-methoxy-5,6,14,14a-tetrahydroindolo[3',2':4,5]pyridine[2,1-a]isoquinoline-9(8H)-yl)methanol | 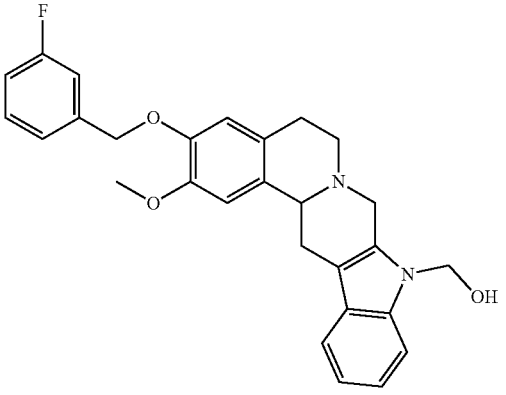<br>A62 |
| A63 | (3-((2-fluorobenzyl)oxy)-2,12-dimethoxy-5,6,14,14a-tetrahydroindolo[3',2':4,5]pyridine[2,1-a]isoquinoline-9(8H)-yl)methanol | 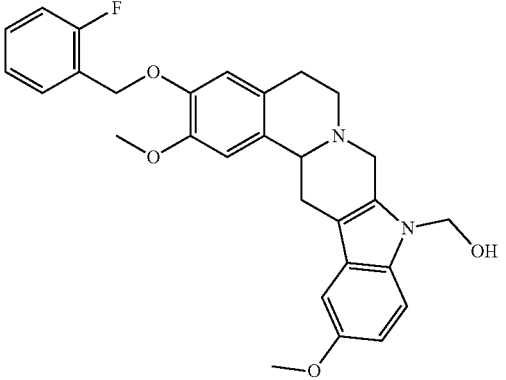<br>A63 |

-continued

| No. | Name | Structure |
|---|---|---|
| A64 | (3-((2-fluorobenzyl)oxy)-2-dimethoxy-5,6,14,14a-tetrahydroindolo[3',2':4,5]pyridine[2,1-a]isoquinoline-9(8H)-yl)methanol | 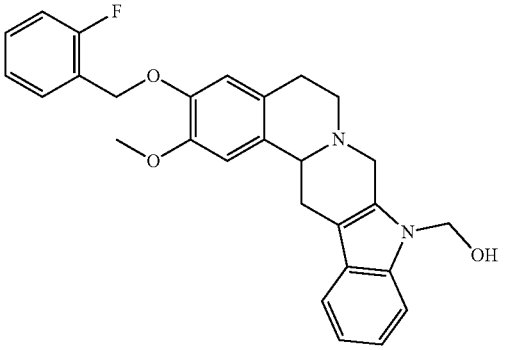<br>A64 |
| A65 | (2,12-dimethoxy-3-((4-methoxybenzyl)oxy)-5,6,14,14a-tetrahydroindolo[3',2':4,5]pyridine[2,1-a]isoquinoline-9(8H)-yl)methanol | 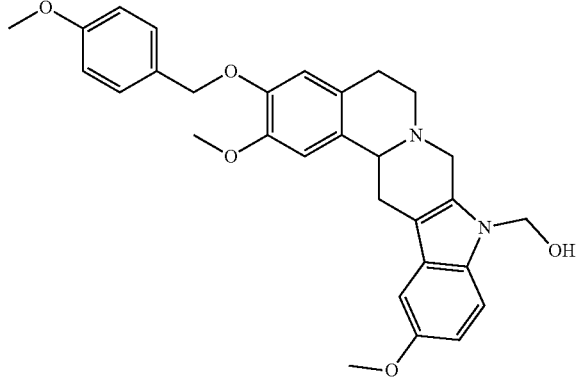<br>A65 |
| A66 | (2-methoxy-3-((4-methoxybenzyl)oxy)-5,6,14,14a-tetrahydroindolo[3',2':4,5]pyridine[2,1-a]isoquinoline-9(8H)-yl)methanol | 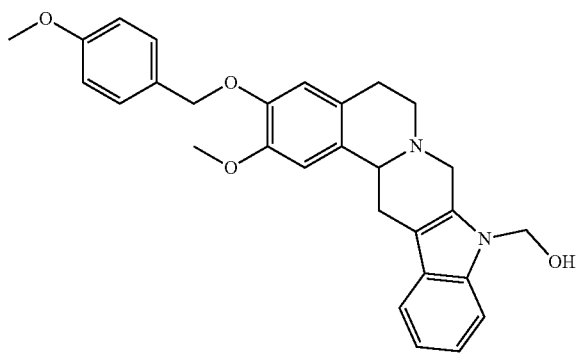<br>A66 |
| A67 | (2,12-dimethoxy-3-((3-methoxybenzyl)oxy)-5,6,14,14a-tetrahydroindolo[3',2':4,5]pyridine[2,1-a]isoquinoline-9(8H)-yl)methanol | 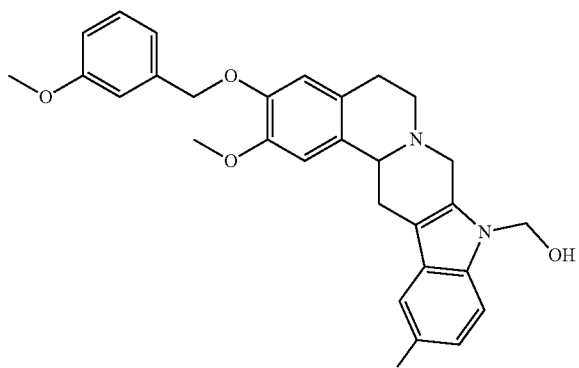<br>A67 |

-continued

| No. | Name | Structure |
|---|---|---|
| A68 | (2-methoxy-3-((3-methoxybenzyl)oxy)-5,6,14,14a-tetrahydroindolo[3',2':4,5]pyridine[2,1-a]isoquinoline-9(8H)-yl)methanol | 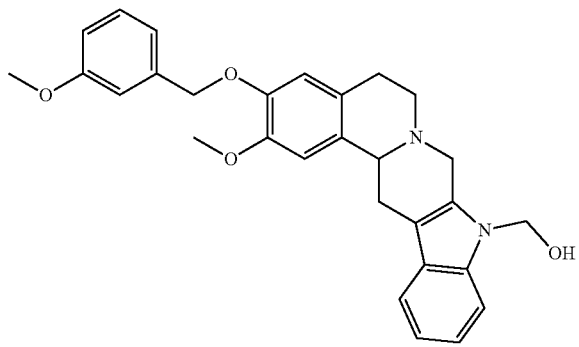<br>A68 |
| A69 | (2,12-dimethoxy-3-((4-methylbenzyl)oxy)-5,6,14,14a-tetrahydroindolo[3',2':4,5]pyridine[2,1-a]isoquinoline-9(8H)-yl)methanol | 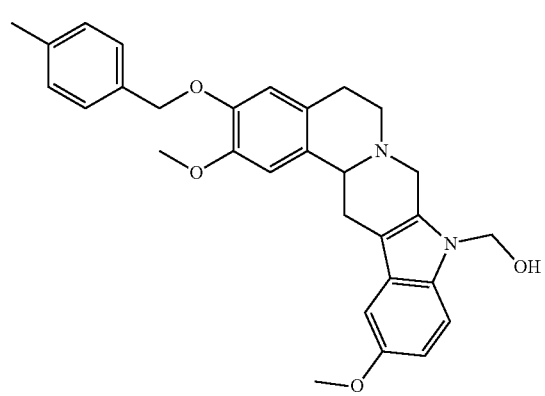<br>A69 |
| A70 | (2-methoxy-3-((4-methylbenzyl)oxy)-5,6,14,14a-tetrahydroindolo[3',2':4,5]pyridine[2,1-a]isoquinoline-9(8H)-yl)methanol | 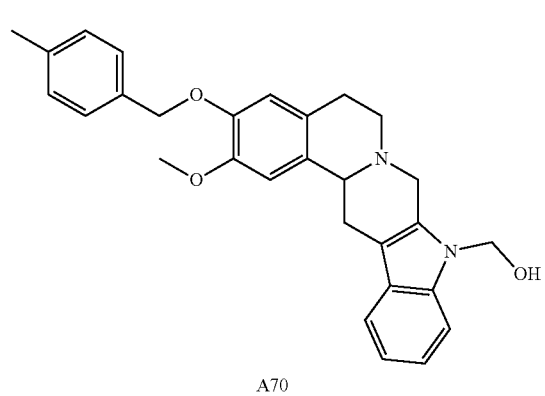 [SMILES: COc1cc2c(cc1OCc1ccc(C)cc1)CCN1Cc3c(c4ccccc4n3CO)CC21 ; "A70"]<br>A70 |
| A71 | (3-((4-chlorobenzyl)oxy)-2,12-dimethoxy-5,6,14,14a-tetrahydroindolo[3',2':4,5]pyridine[2,1-a]isoquinoline-9(8H)-yl)methanol | 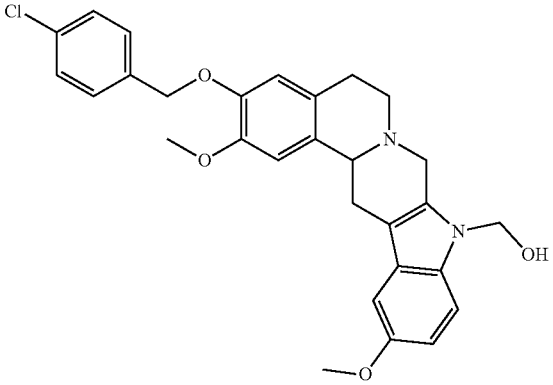<br>A71 |

| No. | Name | Structure |
|---|---|---|
| A72 | (3-((4-chlorobenzyl)oxy)-2-methoxy-5,6,14,14a-tetrahydroindolo[3',2':4,5]pyridine[2,1-a]isoquinoline-9(8H)-yl)methanol | 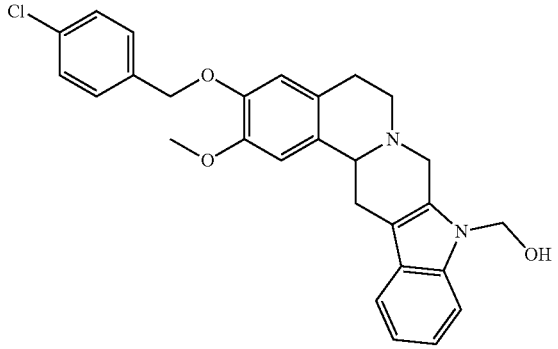 A72 |
| A73 | 4-(((9-(hydroxymethyl)-2,12-dimethoxy-5,6,8,9,14,14a-hexahydroindolo[3',2':4,5]pyridine[2,1-a]isoquinoline-3-yl)oxy)methyl)benzonitrile | 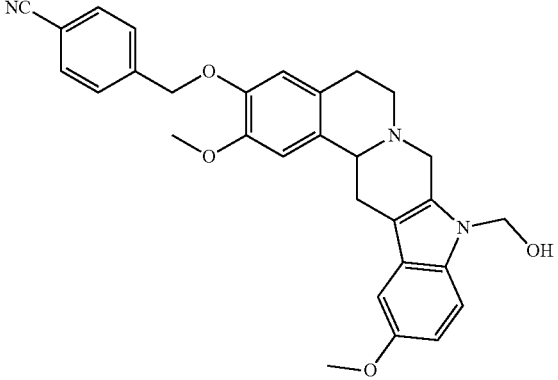 A73 |
| A74 | 4-(((9-(hydroxymethyl)-2-methoxy-5,6,8,9,14,14a-hexahydroindolo[3',2':4,5]pyridine[2,1-a]isoquinoline-3-yl)oxy)methyl)benzonitrile | 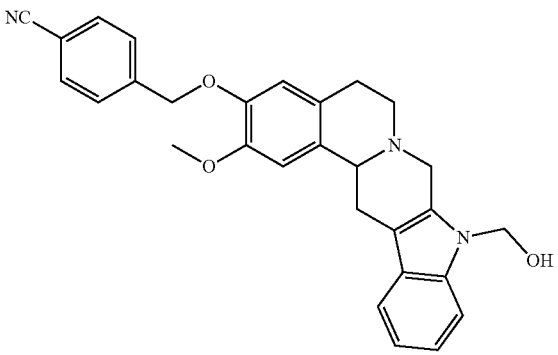 A74 |
| A75 | (3-((4-bromobenzyl)oxy)-2,12-dimethoxy-5,6,14,14a-tetrahydroindolo[3',2':4,5]pyridine[2,1-a]isoquinoline-9(8H)-yl)methanol | 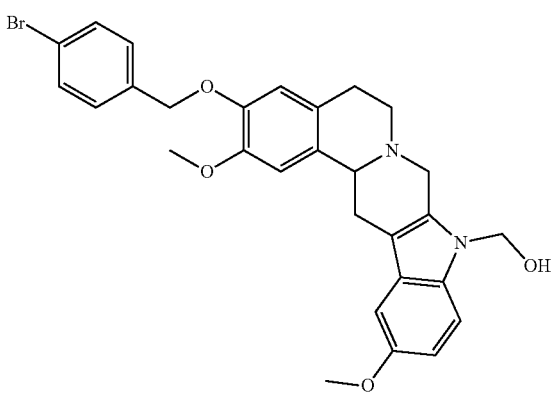 A75 |

| No. | Name | Structure |
|---|---|---|
| A76 | (3-((4-iodobenzyl)oxy)-2-methoxy-5,6,14,14a-tetrahydroindolo[3',2':4,5]pyridine[2,1-a]isoquinoline-9(8H)-yl)methanol | 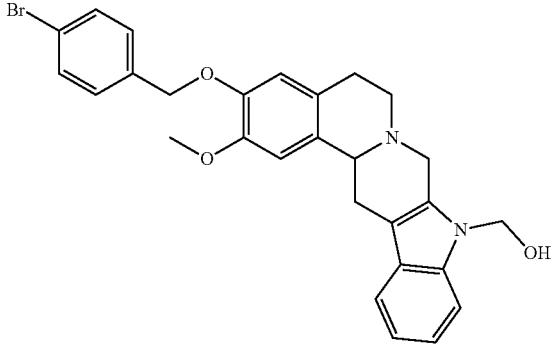 A76 |
| A77 | (3-((3-fluoro-4-(trifluoromethyl)benzyl)oxy)-2,12-dimethoxy-5,6,14,14a-tetrahydroindolo[3',2':4,5]pyridine[2,1-a]isoquinoline-9(8H)-yl)methanol | 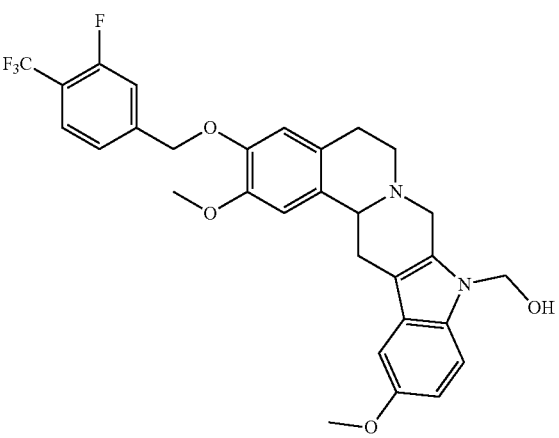 A77 |
| A78 | (3-((3-fluoro-4-(trifluoromethyl)benzyl)oxy)-2-methoxy-5,6,14,14a-tetrahydroindolo[3',2':4,5]pyridine[2,1-a]isoquinoline-9(8H)-yl)methanol | 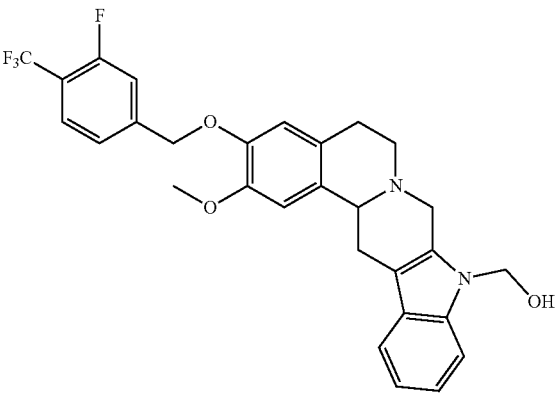 A78 |

-continued

| No. | Name | Structure |
|---|---|---|
| A79 | (3-((2-fluoro-4-(trifluoromethyl)benzyl)oxy)-2,12-dimethoxy-5,6,14,14a-tetrahydroindolo[3',2':4,5]pyridine[2,1-a]isoquinoline-9(8H)-yl)methanol | 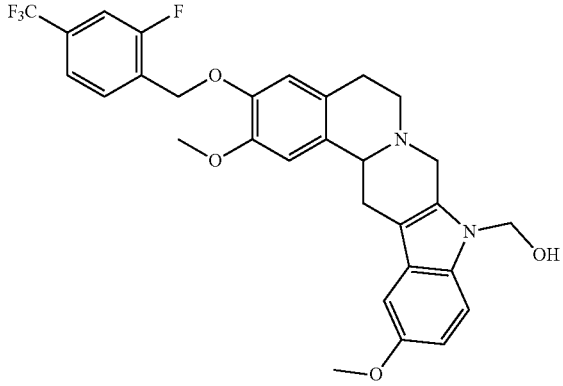<br>A79 |
| A80 | (3-(((2-fluoro-4-(trifluoromethyl)benzyl)oxy)-2-methoxy-5,6,14,14a-tetrahydroindolo[3',2':4,5]pyridine[2,1-a]isoquinoline-9(8H)-yl)methanol | 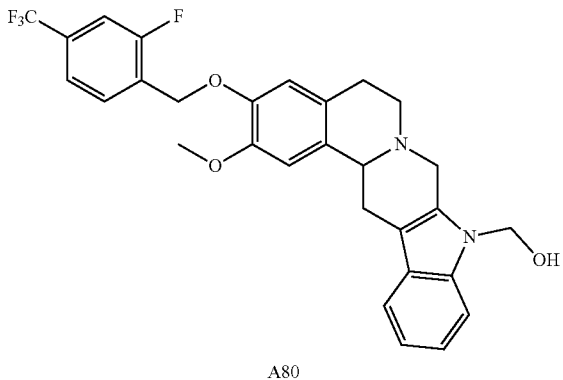 [SMILES: COc1cc2c(cc1OCc1ccc(C(F)(F)F)cc1F)CCN1Cc3c(c4ccccc4n3CO)CC21 ; "A80"]<br>A80 |
| A81 | (2,12-dimethoxy-3-((4-ethylbenzyl)oxy)-5,6,14,14a-tetrahydroindolo[3',2':4,5]pyridine[2,1-a]isoquinoline-9(8H)-yl)methanol | 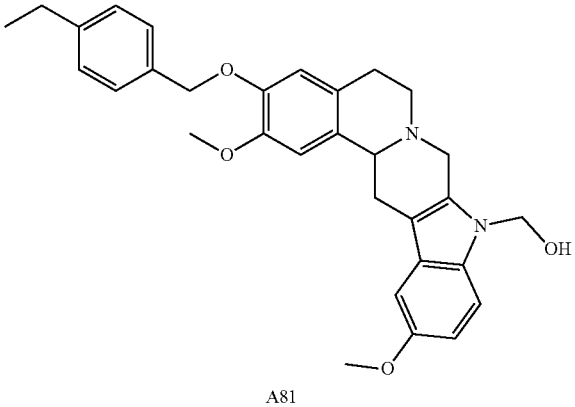 [SMILES: CCc1ccc(COc2cc3c(cc2OC)C2Cc4c(n(CO)c5ccc(OC)cc45)CN2CC3)cc1 ; "A81"]<br>A81 |
| A82 | (2-methoxy-3-((4-ethylbenzyl)oxy)-5,6,14,14a-tetrahydroindolo[3',2':4,5]pyridine[2,1-a]isoquinoline-9(8H)-yl)methanol | 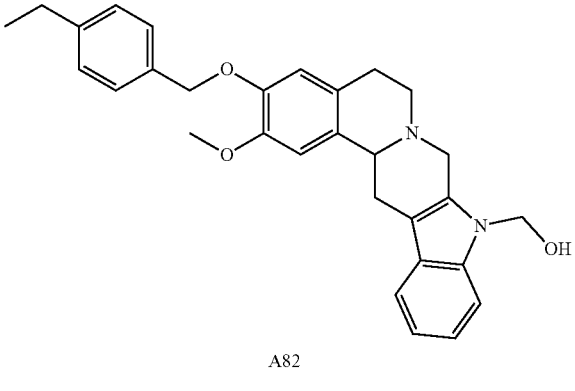 [SMILES: CCc1ccc(COc2cc3c(cc2OC)C2Cc4c(n(CO)c5ccccc45)CN2CC3)cc1 ; "A82"]<br>A82 |

-continued
| No. | Name | Structure |
|---|---|---|
| A83 | (2,12-dimethoxy-3-(naphthalen-2-ylmethoxy)-5,6,14,14a-tetrahydroindolo[3',2':4,5]pyridine[2,1-a]isoquinoline-9(8H)-yl)methanol | 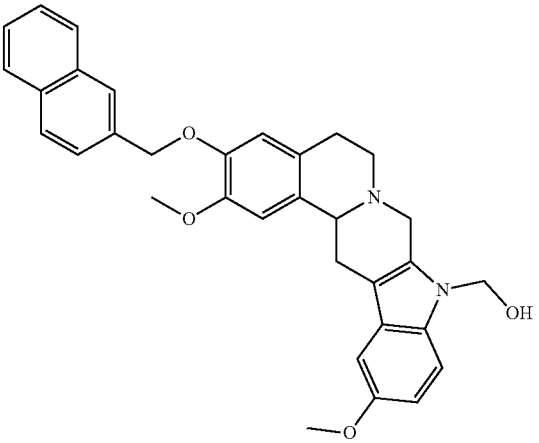 |
| A84 | (2-methoxy-3-(naphthalen-2-ylmethoxy)-5,6,14,14a-tetrahydroindolo[3',2':4,5]pyridine[2,1-a]isoquinoline-9(8H)-yl)methanol | 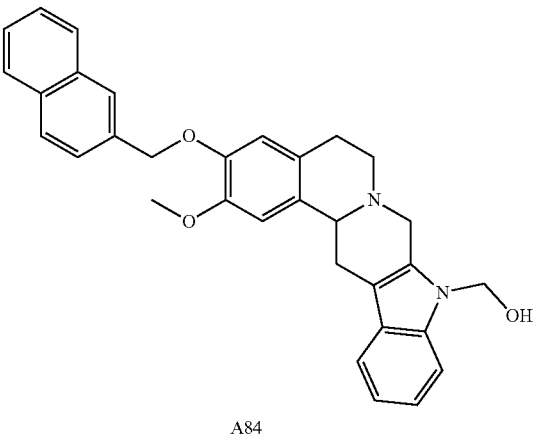 [SMILES: COc1cc2c(cc1OCc1ccc3ccccc3c1)CCN1Cc3c(c4ccccc4n3CO)CC21 ; "A84"] |
| A85 | 4-(((9-(hydroxymethyl)-2,12-dimethoxy-5,6,8,9,14,14a-hexahydroindolo[3',2':4,5]pyridine[2,1-a]isoquinoline-3-yl)oxo)methyl)benzoate | 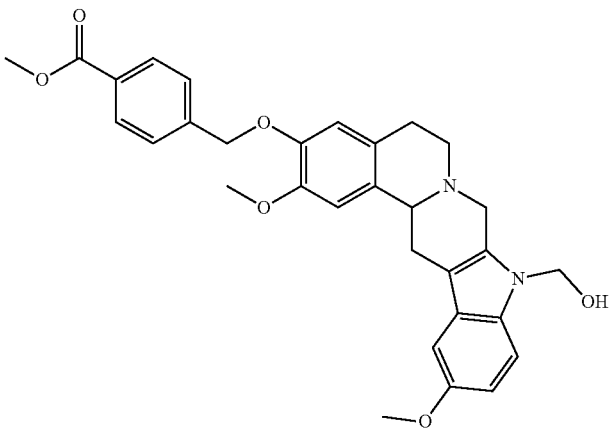 |

-continued

| No. | Name | Structure |
|---|---|---|
| A86 | 4-(((9-(hydroxymethyl)-2-methoxy-5,6,8,9,14,14a-hexahydroindolo[3',2':4,5]pyridine[2,1-a]isoquinoline-3-yl)oxo)methyl)benzoate | A86 |
| A87 | (3-((4-(1H-pyrazol-1-yl)benzyl)oxy)-2,12-dimethoxy-5,6,14,14a-tetrahydroindolo[3',2':4,5]pyridine[2,1-a]isoquinoline-9(8H)-yl)methanol | A87 |
| A88 | (3-((4-(1H-pyrazol-1-yl)benzyl)oxy)-2-methoxy-5,6,14,14a-tetrahydroindolo[3',2':4,5]pyridine[2,1-a]isoquinoline-9(8H)-yl)methanol | A88 |

-continued

| No. | Name | Structure |
|---|---|---|
| A89 | (3-butoxy-2,12-dimethoxy-5,6,14,14a-tetrahydroindolo[3',2':4,5]pyridine[2,1-a]isoquinoline-9(8H)-yl)methanol | 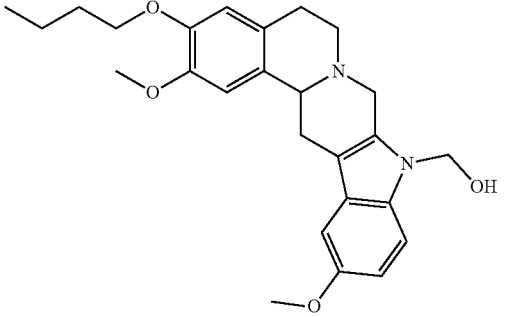<br>A89 |
| A90 | (3-butoxy-2-methoxy-5,6,14,14a-tetrahydroindolo[3',2':4,5]pyridine[2,1-a]isoquinoline-9(8H)-yl)methanol | 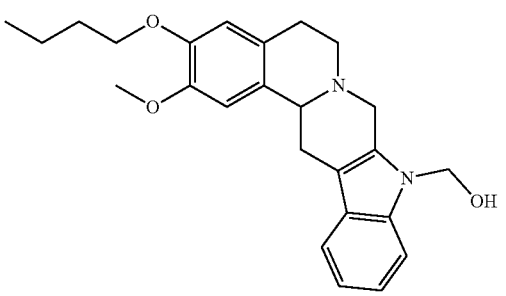<br>A90 |
| A91 | (12-fluoro-2,3-dimethoxy-5,6,14,14a-tetrahydroindolo[3',2':4,5]pyridine[2,1-a]isoquinoline-9(8H)-yl)methanol | 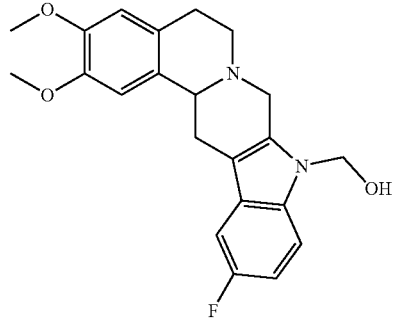<br>A91 |
| A92 | (12-methyl-2,3-dimethoxy-5,6,14,14a-tetrahydroindolo[3',2':4,5]pyridine[2,1-a]isoquinoline-9(8H)-yl)methanol | 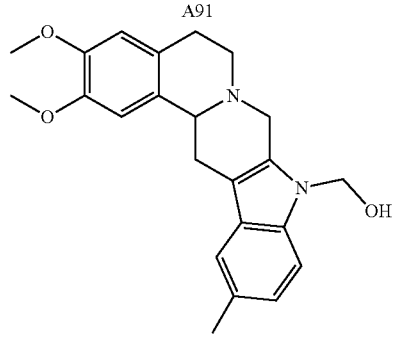<br>A92 |

-continued

| No. | Name | Structure |
|---|---|---|
| A93 | (2,12-dimethoxy-3-(2,2,2-trifluoroethoxy)-5,6,14,14a-tetrahydroindolo[3',2':4,5]pyridine[2,1-a]isoquinoline-9(8H)-yl)methanol | A93 |
| A94 | (2-methoxy-3-(2,2,2-trifluoroethoxy)-5,6,14,14a-tetrahydroindolo[3',2':4,5]pyridine[2,1-a]isoquinoline-9(8H)-yl)methanol | A94 |
| A95 | (2,12-dimethoxy-3-((4-(methylsulfonyl)benzyl)oxy)-5,6,14,14a-tetrahydroindolo[3',2':4,5]pyridine[2,1-a]isoquinoline-9(8H)-yl)methanol | A95 |
| A96 | (2-methoxy-3-((4-(methylsulfonyl)benzyl)oxy)-5,6,14,14a-tetrahydroindolo[3',2':4,5]pyridine[2,1-a]isoquinoline-9(8H)-yl)methanol | A96 |

-continued
| No. | Name | Structure |
|---|---|---|
| A97 | (3-(benzyloxy)-11-fluoro-2-methoxy-5,6,14,14a-tetrahydroindolo[3',2':4,5]pyridine[2,1-a]isoquinoline-9(8H)-yl)methanol | 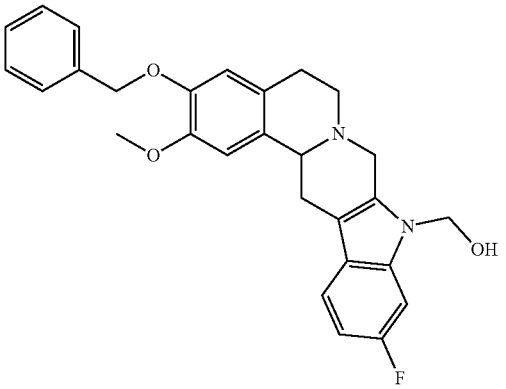<br>A97 |
| A98 | (3-(benzyloxy)-12-fluoro-2-methoxy-5,6,14,14a-tetrahydroindolo[3',2':4,5]pyridine[2,1-a]isoquinoline-9(8H)-yl)methanol | 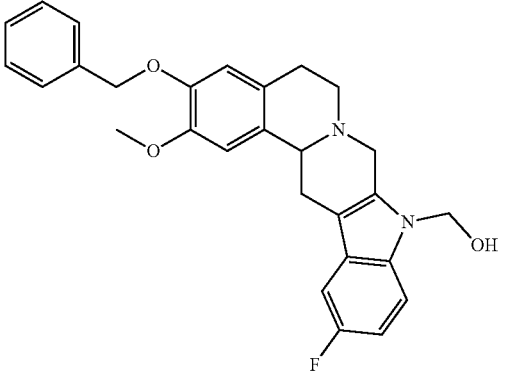<br>A98 |
| A99 | (3-(benzyloxy)-13-fluoro-2-methoxy-5,6,14,14a-tetrahydroindolo[3',2':4,5]pyridine[2,1-a]isoquinoline-9(8H)-yl)methanol | 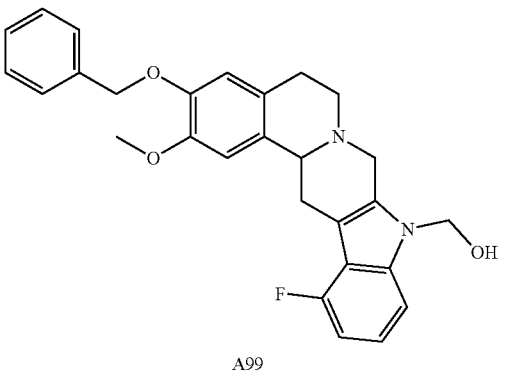 [SMILES: COc1cc2c(cc1OCc1ccccc1)CCN1Cc3c(c4c(F)cccc4n3CO)CC21 ; "A99"]<br>A99 |

-continued

| No. | Name | Structure |
|---|---|---|
| A100 | (3-(benzyloxy)-11-chloro-2-methoxy-5,6,14,14a-tetrahydroindolo[3',2':4,5]pyridine[2,1-a]isoquinoline-9(8H)-yl)methanol | A100 |
| A101 | (3-(benzyloxy)-12-chloro-2-methoxy-5,6,14,14a-tetrahydroindolo[3',2':4,5]pyridine[2,1-a]isoquinoline-9(8H)-yl)methanol | A101 |
| A102 | (3-(benzyloxy)-13-chloro-2-methoxy-5,6,14,14a-tetrahydroindolo[3',2':4,5]pyridine[2,1-a]isoquinoline-9(8H)-yl)methanol | A102 |

-continued

| No. | Name | Structure |
|---|---|---|
| A103 | (3-(benzyloxy)-11-bromo-2-methoxy-5,6,14,14a-tetrahydroindolo[3',2':4,5]pyridine[2,1-a]isoquinoline-9(8H)-yl)methanol | A103 |
| A104 | (3-(benzyloxy)-12-bromo-2-methoxy-5,6,14,14a-tetrahydroindolo[3',2':4,5]pyridine[2,1-a]isoquinoline-9(8H)-yl)methanol | A104 |
| A105 | (3-(benzyloxy)-13-bromo-2-methoxy-5,6,14 14a-tetrahydroindolo[3',2':4,5]pyridine[2,1-a]isoquinoline-9(8H)-yl)methanol | A105 |
| A106 | (3-(benzyloxy)-11-methyl-5,6,14,14a-tetrahydroindolo[3',2':4,5]pyridine[2,1-a]isoquinoline-9(8H)-yl)methanol | A106 |

-continued

| No. | Name | Structure |
|---|---|---|
| A107 | (3-(benzyloxy)-12-ethyl-5,6,14,14a-tetrahydroindolo[3',2':4,5]pyridine[2,1-a]isoquinoline-9(8H)-yl)methanol | 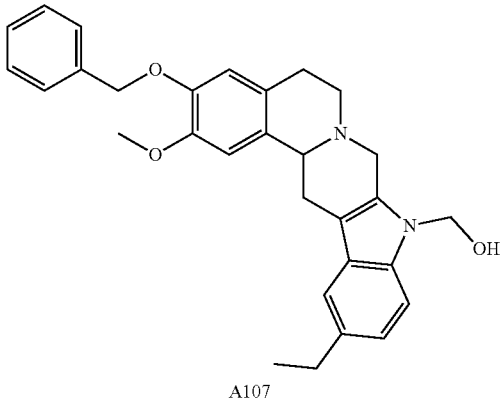<br>A107 |
| A108 | (12-methoxy-5,6,14,14a-tetrahydro-[1,3]dioxazo[4,5-g]indolo[3',2':4,5]pyridine[2,1-a]isoquinoline-9(8H)-yl)methanol | 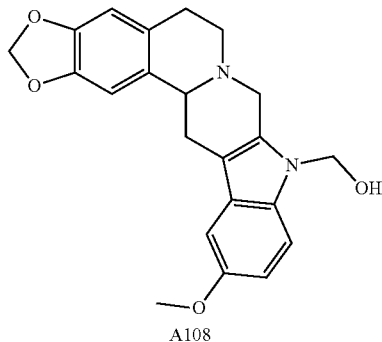<br>A108 |
| A109 | (5,6,14,14a-tetrahydro-[1,3]dioxazo[4,5-g]indolo[3',2':4,5]pyridine[2,1-a]isoquinoline-9(8H)-yl)methanol | 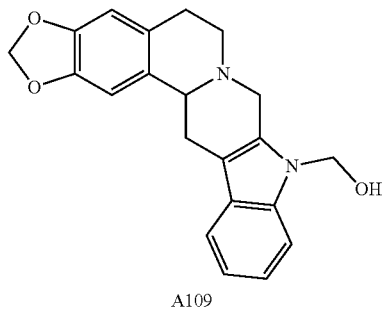<br>A109 |
| A112 | methyl (2-(benzyloxy)-3,12-dimethoxy-5,6,14,14a-tetrahydroindolo[3',2':4,5]pyridine[2,1-a]isoquinoline-9(8H)-yl)acetate | 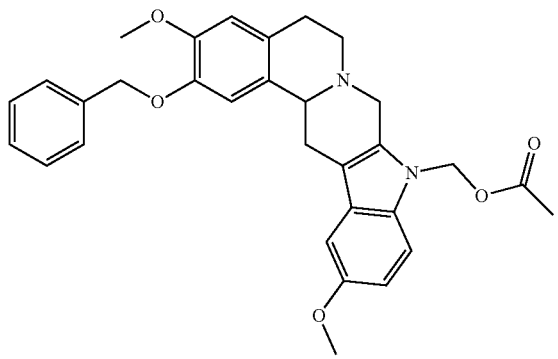 [SMILES: COc1ccc2c(c1)c1c(n2COC(C)=O)CN2CCc3cc(OC)c(OCc4ccccc4)cc3C2C1] |

-continued

| No. | Name | Structure |
| --- | --- | --- |
| A113 | methyl (2-(benzyloxy)-3,12-dimethoxy-5,6,14,14a-tetrahydroindolo[3',2':4,5]pyridine[2,1-a]isoquinoline-9(8H)-yl) cyclohexylsulfonate | 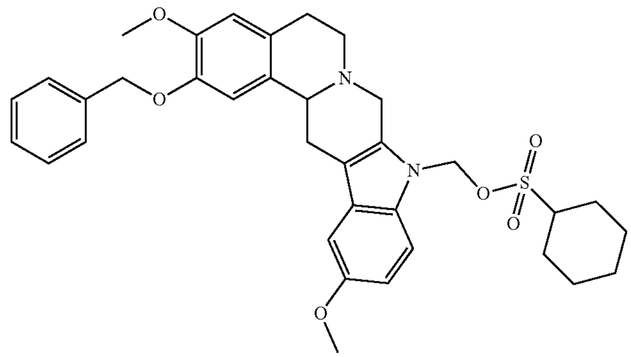 [SMILES: COc1ccc2c(c1)c1c(n2COS(=O)(=O)C2CCCCC2)CN2CCc3cc(OC)c(OCc4ccccc4)cc3C2C1] |
| A114 | methyl (2-(benzyloxy)-3,12-dimethoxy-5,6,14,14a-tetrahydroindolo[3',2':4,5]pyridine[2,1-a]isoquinoline-9(8H)-yl) benzenesulfonate | 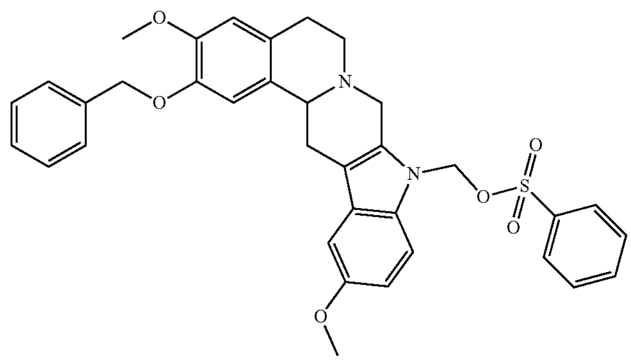 [SMILES: COc1ccc2c(c1)c1c(n2COS(=O)(=O)c2ccccc2)CN2CCc3cc(OC)c(OCc4ccccc4)cc3C2C1] |
| A115 | methyl (2-(benzyloxy)-3,12-dimethoxy-5,6,14,14a-tetrahydroindolo[3',2':4,5]pyridine[2,1-a]isoquinoline-9(8H)-yl)4-fluorobenzenesulfonate | 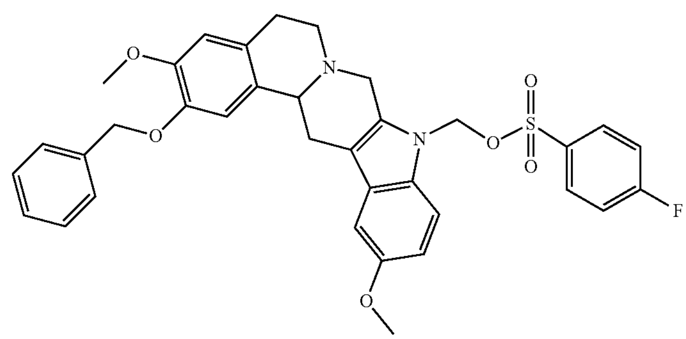 [SMILES: COc1ccc2c(c1)c1c(n2COS(=O)(=O)c2ccc(F)cc2)CN2CCc3cc(OC)c(OCc4ccccc4)cc3C2C1] |
| A116 | methyl (2-(benzyloxy)-3,12-dimethoxy-5,6,14,14a-tetrahydroindolo[3',2':4,5]pyridine[2,1-a]isoquinoline-9(8H)-yl)3-fluorobenzenesulfonate | 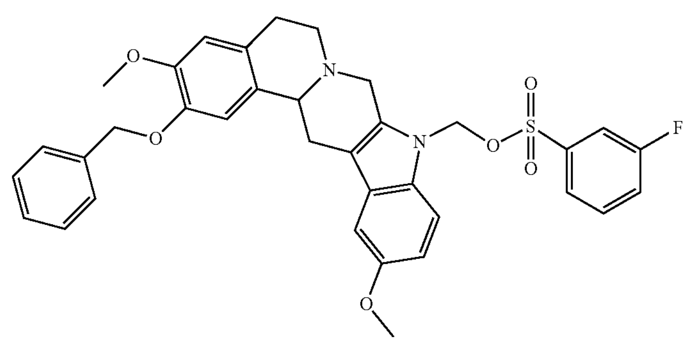 [SMILES: COc1ccc2c(c1)c1c(n2COS(=O)(=O)c2cccc(F)c2)CN2CCc3cc(OC)c(OCc4ccccc4)cc3C2C1] |

-continued

| No. | Name | Structure |
|---|---|---|
| A117 | methyl (2-(benzyloxy)-3,12-dimethoxy-5,6,14,14a-tetrahydroindolo[3',2':4,5]pyridine[2,1-a]isoquinoline-9(8H)-yl)2-fluorobenzenesulfonate | 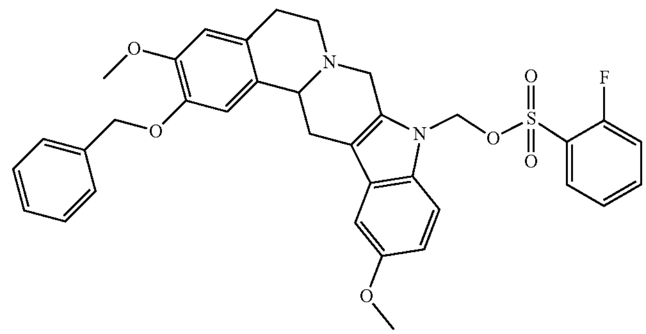 [SMILES: COc1ccc2c(c1)c1c(n2COS(=O)(=O)c2ccccc2F)CN2CCc3cc(OC)c(OCc4ccccc4)cc3C2C1] |
| A118 | methyl (2-(benzyloxy)-3,12-dimethoxy-5,6,14,14a-tetrahydroindolo[3',2':4,5]pyridine[2,1-a]isoquinoline-9(8H)-yl)benzylbenzenesulfonate | 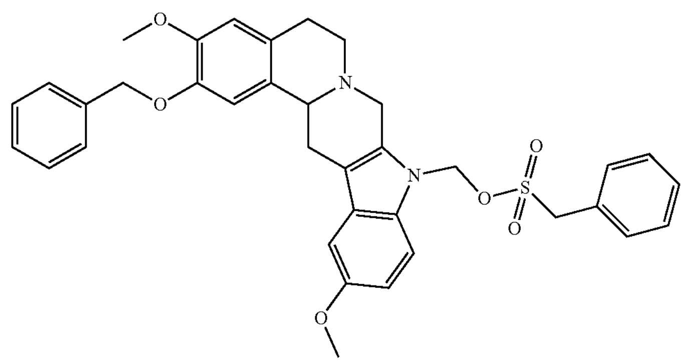 [SMILES: COc1ccc2c(c1)c1c(n2COS(=O)(=O)Cc2ccccc2)CN2CCc3cc(OC)c(OCc4ccccc4)cc3C2C1] |
| A119 | methyl (2-(benzyloxy)-3,12-dimethoxy-5,6,14,14a-tetrahydroindolo[3',2':4,5]pyridine[2,1-a]isoquinoline-9(8H)-yl)benzoate | 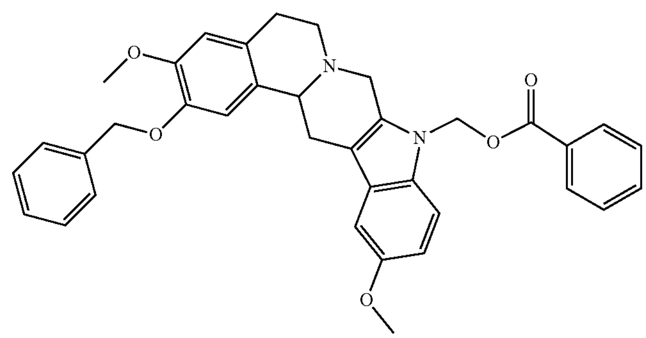 [SMILES: COc1ccc2c(c1)c1c(n2COC(=O)c2ccccc2)CN2CCc3cc(OC)c(OCc4ccccc4)cc3C2C1] |
| A120 | methyl (2-(benzyloxy)-3,12-dimethoxy-5,6,14,14a-tetrahydroindolo[3',2':4,5]pyridine[2,1-a]isoquinoline-9(8H)-yl)N,N-dimethylformate | 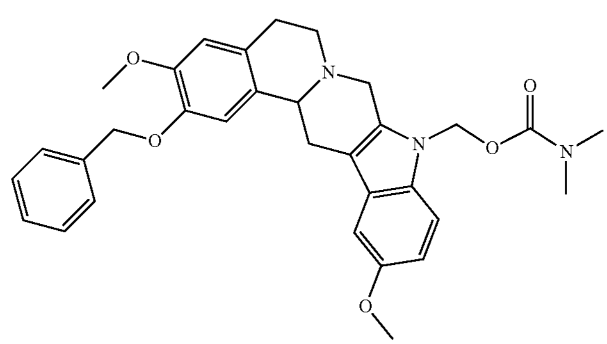 [SMILES: COc1ccc2c(c1)c1c(n2COC(=O)N(C)C)CN2CCc3cc(OC)c(OCc4ccccc4)cc3C2C1] |

| No. | Name | Structure |
|---|---|---|
| A121 | methyl (2-(benzyloxy)-3,12-dimethoxy-5,6,14,14a-tetrahydroindolo[3',2':4,5]pyridine[2,1-a]isoquinoline-9(8H)-yl) 4-fluorobenzoate | 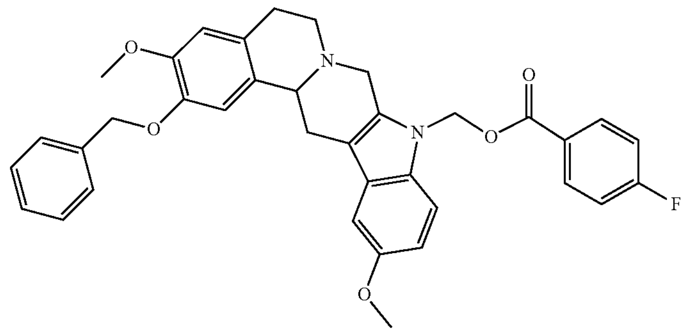 [SMILES: COc1ccc2c(c1)c1c(n2COC(=O)c2ccc(F)cc2)CN2CCc3cc(OC)c(OCc4ccccc4)cc3C2C1] |
| A122 | methyl (2-(benzyloxy)-3,12-dimethoxy-5,6,14,14a-tetrahydroindolo[3',2':4,5]pyridine[2,1-a]isoquinoline-9(8H)-yl) 3-fluorobenzoate | 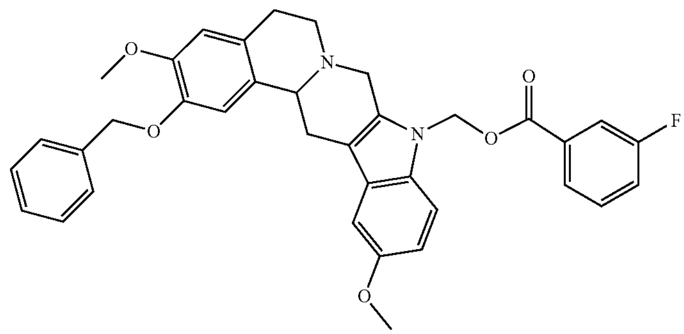 [SMILES: COc1ccc2c(c1)c1c(n2COC(=O)c2cccc(F)c2)CN2CCc3cc(OC)c(OCc4ccccc4)cc3C2C1] |
| A123 | methyl (2-(benzyloxy)-3,12-dimethoxy-5,6,14,14a-tetrahydroindolo[3',2':4,5]pyridine[2,1-a]isoquinoline-9(8H)-yl) 2-fluorobenzoate | 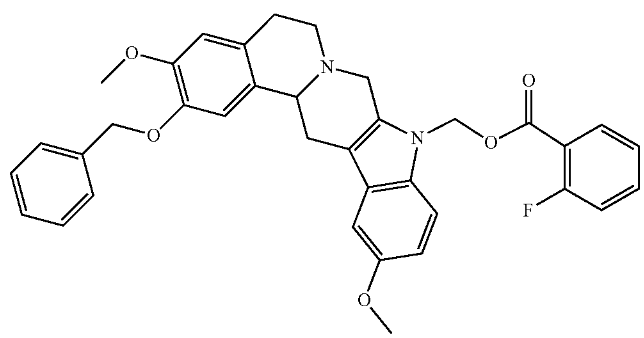 [SMILES: COc1ccc2c(c1)c1c(n2COC(=O)c2ccccc2F)CN2CCc3cc(OC)c(OCc4ccccc4)cc3C2C1] |
| A124 | 9-(hydroxymethyl)-2,12-dimethoxy-5,6,8,9,14,14a-hexahydroindolo[3',2':4,5]pyridine[2,1-a]isoquinoline-3-ylbenzenesulfonate | 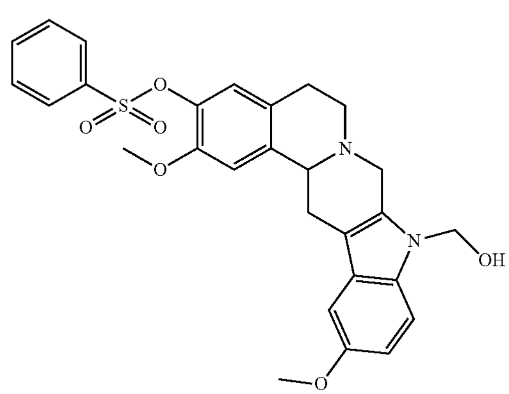 [SMILES: COc1ccc2c(c1)c1c(n2CO)CN2CCc3cc(OS(=O)(=O)c4ccccc4)c(OC)cc3C2C1] |

| No. | Name | Structure |
|---|---|---|
| A125 | 9-(hydroxymethyl)-3,12-dimethoxy-5,6,8,9,14,14a-hexahydroindolo[3',2':4,5]pyridine[2,1-a]isoquinoline-2-ylbenzenesulfonate | 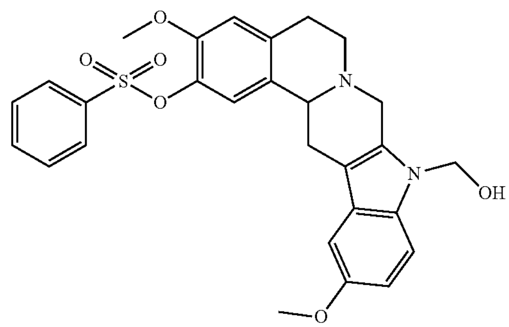 [SMILES: COc1ccc2c(c1)c1c(n2CO)CN2CCc3cc(OC)c(OS(=O)(=O)c4ccccc4)cc3C2C1] |
| A130 | (3-(benzyloxy)-8-isopropyl-2,12-dimethoxy-5,6,14,14a-tetrahydroindolo[3',2':4,5]pyridine[2,1-a]isoquinoline-9(8H)-yl)methanol | 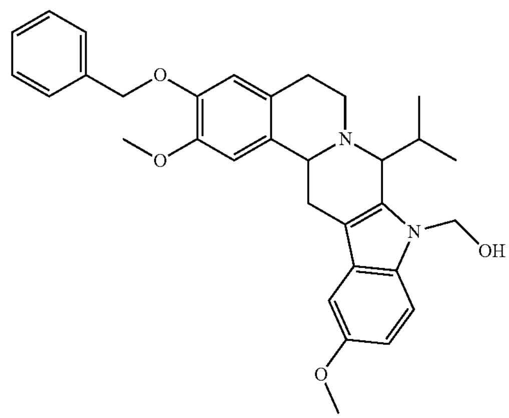 [SMILES: COc1ccc2c(c1)c1c(n2CO)C(C(C)C)N2CCc3cc(OCc4ccccc4)c(OC)cc3C2C1] |
| A131 | (2-(benzyloxy)-8-isopropyl-3,12-dimethoxy-5,6,14,14a-tetrahydroindolo[3',2':4,5]pyridine[2,1-a]isoquinoline-9(8H)-yl)methanol | 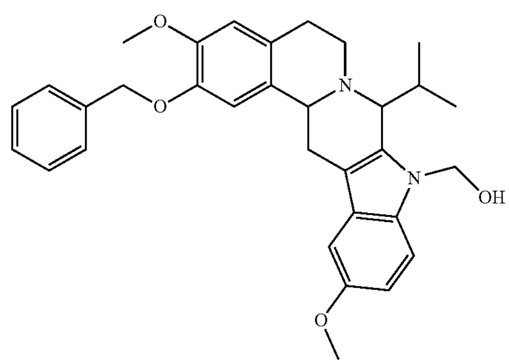 [SMILES: COc1ccc2c(c1)c1c(n2CO)C(C(C)C)N2CCc3cc(OC)c(OCc4ccccc4)cc3C2C1] |
| A132 | 2-(benzyloxy)-3,12-dimethoxy-9-(benzenesulfonyl)-5,6,8,9,14,14a-hexahydroindolo[3',2':4,5]pyridine[2,1-a]isoquinoline | 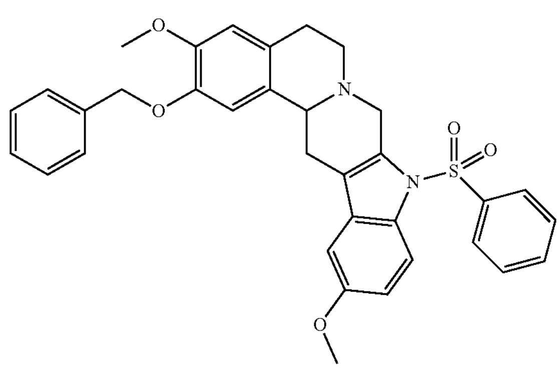 [SMILES: COc1ccc2c(c1)c1c(n2S(=O)(=O)c2ccccc2)CN2CCc3cc(OC)c(OCc4ccccc4)cc3C2C1] |

| No. | Name | Structure |
|---|---|---|
| A133 | 3-(benzyloxy)-2,12-dimethoxy-9-(benzene-sulfonyl)-5,6,8,9,14,14a-hexahydroindolo[3',2':4,5]pyridine[2,1-a]isoquinoline | 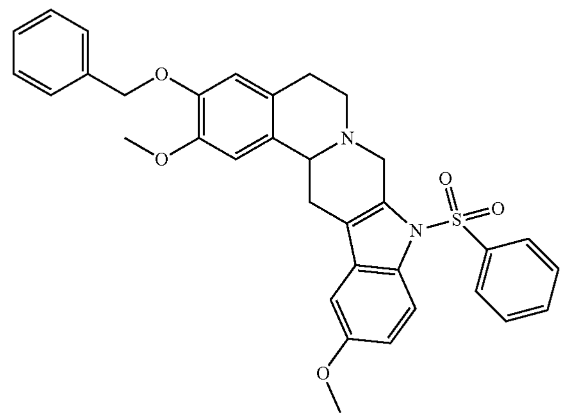 [SMILES: COc1ccc2c(c1)c1c(n2S(=O)(=O)c2ccccc2)CN2CCc3cc(OCc4ccccc4)c(OC)cc3C2C1] |
| A134 | (2-((4-aminobenzyl)oxy)-3,12-dimethoxy-5,6,14,14a-tetrahydroindolo[3',2':4,5]pyridine[2,1-a]isoquinoline-9(8H)-yl)methanol | 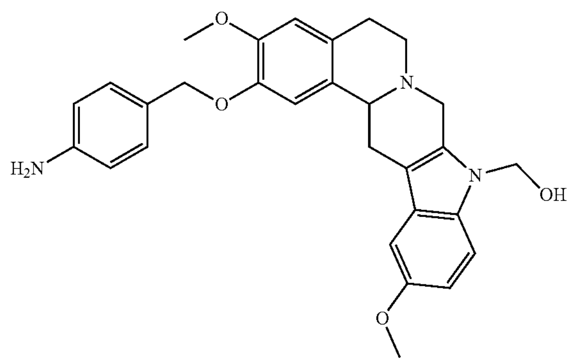 [SMILES: COc1ccc2c(c1)c1c(n2CO)CN2CCc3cc(OC)c(OCc4ccc(N)cc4)cc3C2C1] |
| A135 | (3-((4-aminobenzyl)oxy)-2,12-dimethoxy-5,6,14,14a-tetrahydroindolo[3',2':4,5]pyridine[2,1-a]isoquinoline-9(8H)-yl)methanol | 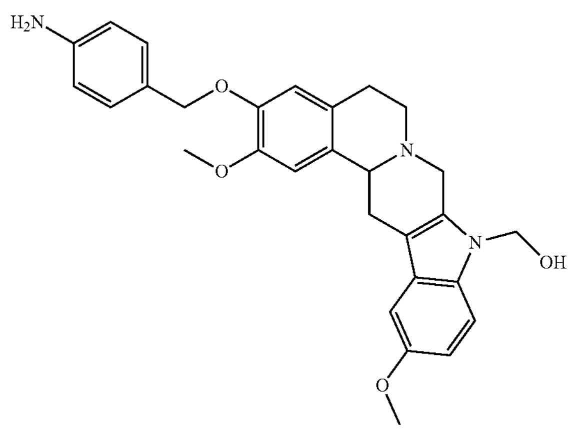 [SMILES: COc1ccc2c(c1)c1c(n2CO)CN2CCc3cc(OCc4ccc(N)cc4)c(OC)cc3C2C1] |
| A136 | 4-(((9-(hydroxymethyl)-3,12-dimethoxy-5,6,8,9,14,14a-hexahydroindolo[3',2':4,5]pyridine[2,1-a]isoquinoline-2-yl)oxo)methyl)phenol | 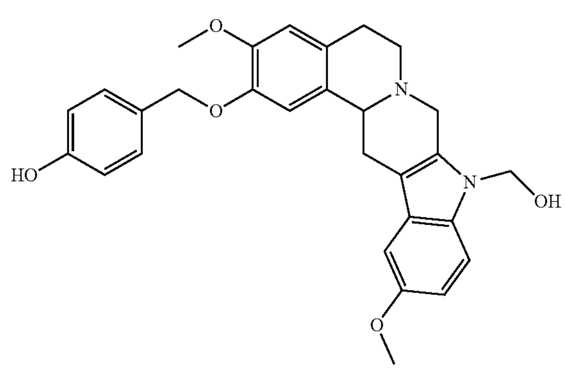 [SMILES: COc1ccc2c(c1)c1c(n2CO)CN2CCc3cc(OC)c(OCc4ccc(O)cc4)cc3C2C1] |

-continued

| No. | Name | Structure |
| --- | --- | --- |
| A137 | 4-(((9-(hydroxymethyl)-2,12-dimethoxy-5,6,8,9,14,14a-hexahydroindolo[3',2':4,5]pyridine[2,1-a]isoquinoline-3-yl)oxo)methyl)phenol | 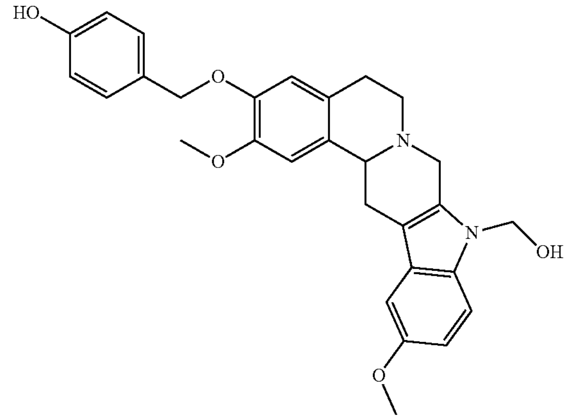 [SMILES: COc1ccc2c(c1)c1c(n2CO)CN2CCc3cc(OCc4ccc(O)cc4)c(OC)cc3C2C1] |
| A138 | 4-(((9-(Hydroxymethyl)-3,12-dimethoxy-5,6,8,9,14,14a-hexahydroindole1[3',2':4,5]pyridine[2,1-a]isoquinolin-2-yl)oxo)methyl)benzoic acid | 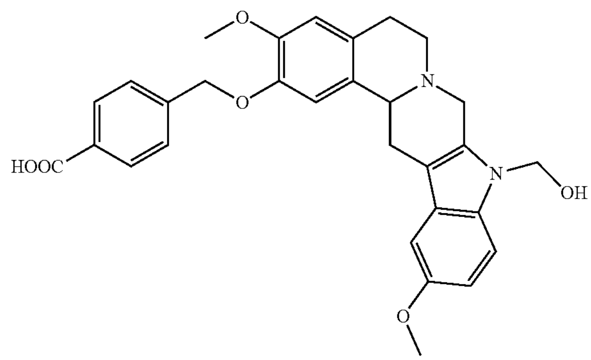 [SMILES: COc1ccc2c(c1)c1c(n2CO)CN2CCc3cc(OC)c(OCc4ccc(C(=O)O)cc4)cc3C2C1] |
| A139 | 4-(((9-(Hydroxymethyl)-2,12-dimethoxy-5,6,8,9,14,14a-hexahydroindole1[3',2':4,5]pyridine[2,1-a]isoquinolin-3-yl)oxo)methyl)benzoic acid | 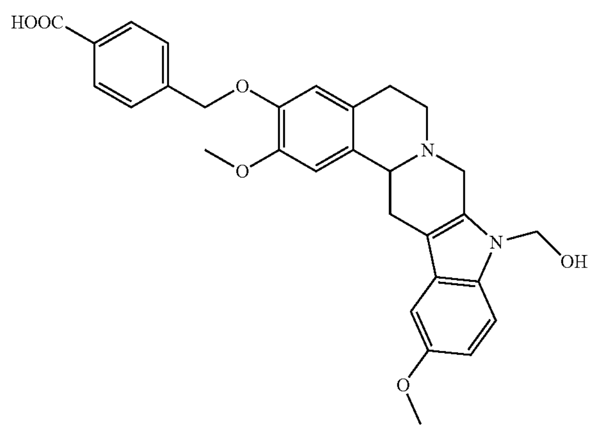 [SMILES: COc1ccc2c(c1)c1c(n2CO)CN2CCc3cc(OCc4ccc(C(=O)O)cc4)c(OC)cc3C2C1] |
| (S)-A55 | S)-(3-(Benzyloxy)-2,12-dimethoxy-5,6,14,14a-tetrahydroindole[3',2':4,5]pyridine[2,1-a]isoquinoline-9(8H)-yl)methanol | 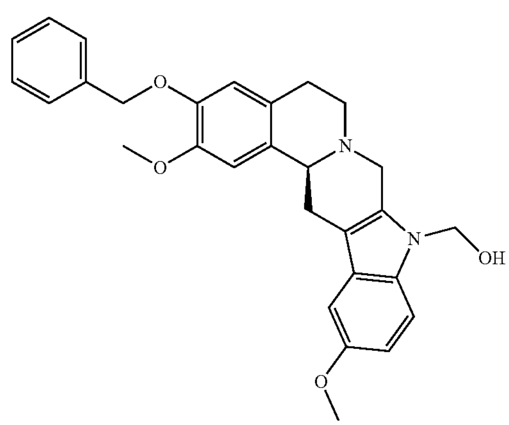 [SMILES: COc1ccc2c(c1)c1c(n2CO)CN2CCc3cc(OCc4ccccc4)c(OC)cc3[C@@H]2C1] |

-continued

| No. | Name | Structure |
| --- | --- | --- |
| (R)-A55 | R)-(3-(Benzyloxy)-2,12-dimethoxy-5,6,14,14a-tetrahydroindole1[3',2':4,5]pyridine[2,1-a]isoquinoline-9(8H)-yl)methanol | 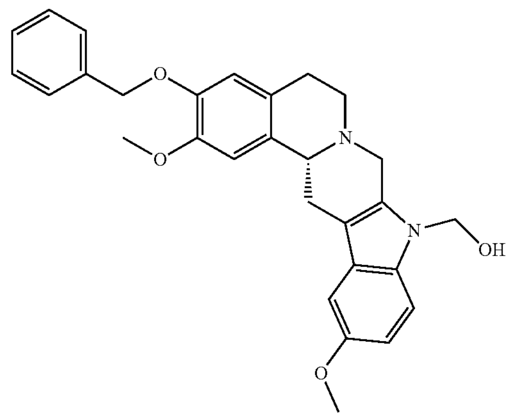 [SMILES: COc1ccc2c(c1)c1c(n2CO)CN2CCc3cc(OCc4ccccc4)c(OC)cc3[C@H]2C1] |
| (S)-A1 | S)-(2-(benzyloxy)-3,12-dimethoxy-5,8,14,14a-tetrahydroindole[3',2':4,5]pyridine[2,1-a]isoquinoline-9(6H)-yl)methanol | 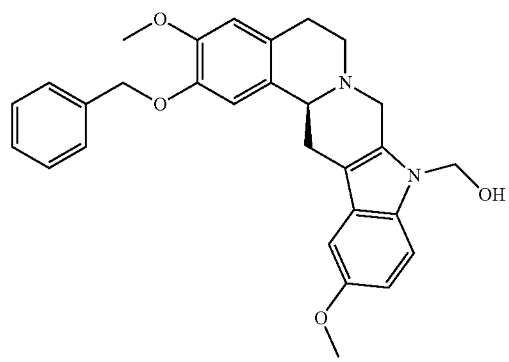 [SMILES: COc1ccc2c(c1)c1c(n2CO)CN2CCc3cc(OC)c(OCc4ccccc4)cc3[C@@H]2C1] |
| (R)-A1 | R)-(2-(benzyloxy)-3,12-dimethoxy-5,8,14,14a-tetrahydroindole[3',2':4,5]pyridine[2,1-a]isoquinoline-9(6H)-yl)methanol | 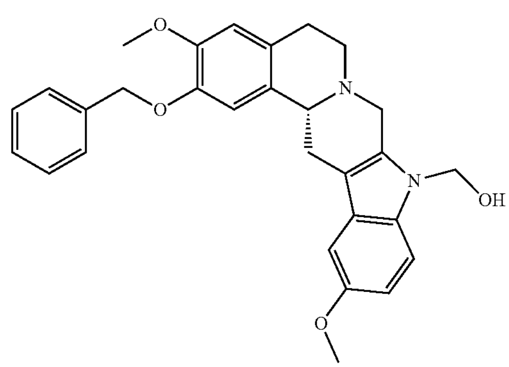 [SMILES: COc1ccc2c(c1)c1c(n2CO)CN2CCc3cc(OC)c(OCc4ccccc4)cc3[C@H]2C1] |
| A140 | (2,12-dimethoxy-3-((2-methoxybenzyl)oxy)-5,6,14,14a-tetrahydroindolo[3',2':4,5]pyridine[2,1-a]isoquinoline-9(8H)-yl)methanol | 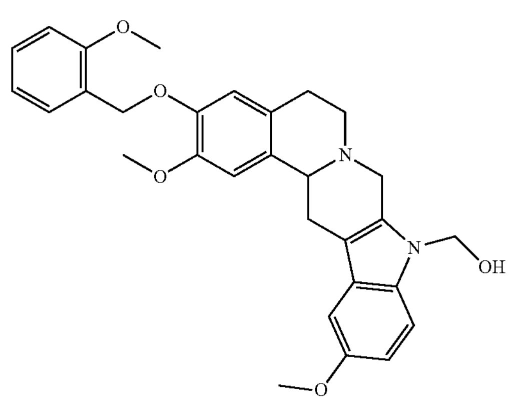 |

-continued

| No. | Name | Structure |
|---|---|---|
| A141 | (2-methoxy-3-((2-methoxybenzyl)oxy)-5,6,14,14a-tetrahydroindolo[3',2':4,5]pyridine[2,1-a]isoquinoline-9(8H)-yl)methanol | 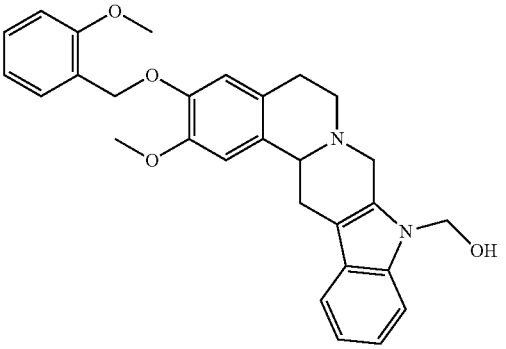<br>A141 |
| A142 | (2,12-dimethoxy-3-((3-methylbenzyl)oxy)-5,6,14,14a-tetrahydroindolo[3',2':4,5]pyridine[2,1-a]isoquinoline-9(8H)-yl)methanol | 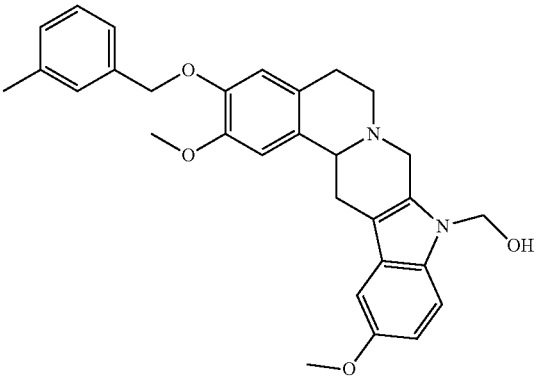<br>A142 |
| A143 | (2-methoxy-3-((3-methylbenzyl)oxy)-5,6,14,14a-tetrahydroindolo[3',2':4,5]pyridine[2,1-a]isoquinoline-9(8H)-yl)methanol | 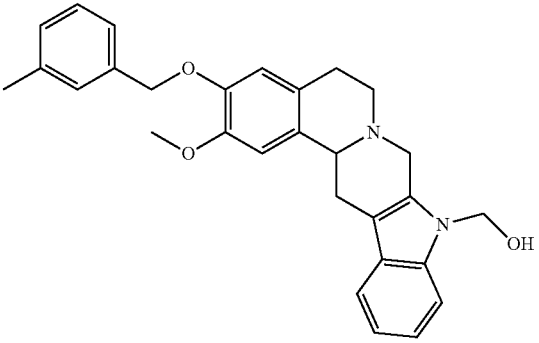<br>A143 |
| A144 | (2,12-dimethoxy-3-((2-methylbenzyl)oxy)-5,6,14,14a-tetrahydroindolo[3',2':4,5]pyridine[2,1-a]isoquinoline-9(8H)-yl)methanol | 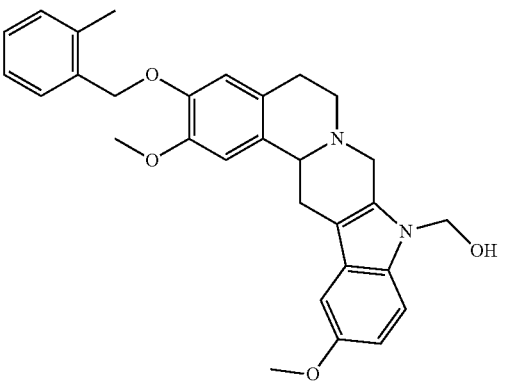<br>A144 |

| No. | Name | Structure |
|---|---|---|
| A145 | (2-methoxy-3-((2-methylbenzyl)oxy)-5,6,14,14a-tetrahydroindolo[3',2':4,5]pyridine[2,1-a]isoquinoline-9(8H)-yl)methanol | 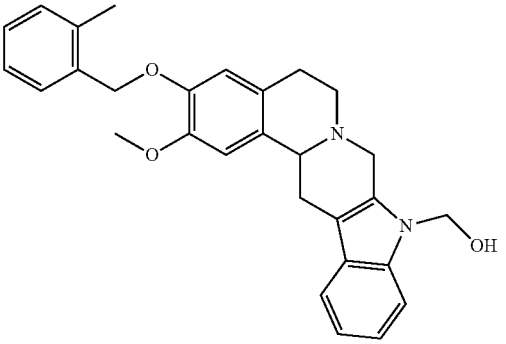 A145 |
| A146 | (3,12-dimethoxy-2-((2-methoxybenzyl)oxy)-5,6,14,14a-tetrahydroindolo[3',2':4,5]pyridine[2,1-a]isoquinoline-9(8H)-yl)methanol | 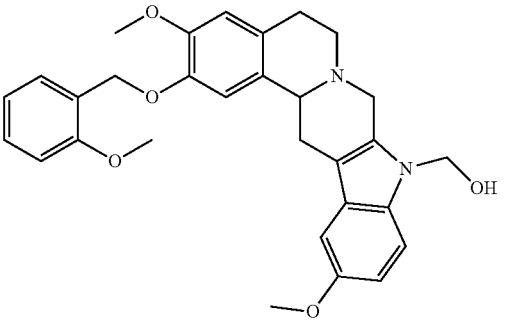 A146 |
| A147 | (3-methoxy-2-((2-methoxybenzyl)oxy)-5,6,14,14a-tetrahydroindolo[3',2':4,5]pyridine[2,1-a]isoquinoline-9(8H)-yl)methanol | 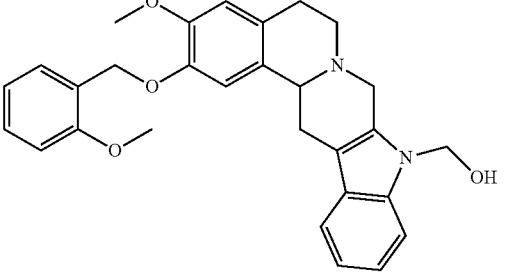 A147 |
| A148 | (3,12-dimethoxy-2-((3-methylbenzyl)oxy)-5,6,14,14a-tetrahydroindolo[3',2':4,5]pyridine[2,1-a]isoquinoline-9(8H)-yl)methanol | 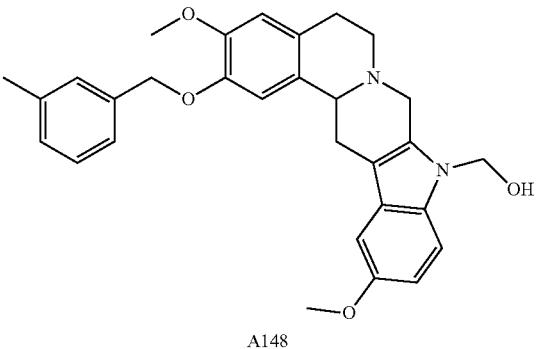 A148 |

-continued

| No. | Name | Structure |
|---|---|---|
| A149 | (3-methoxy-2-((3-methylbenzyl)oxy)-5,6,14,14a-tetrahydroindolo[3',2':4,5]pyridine[2,1-a]isoquinoline-9(8H)-yl)methanol | 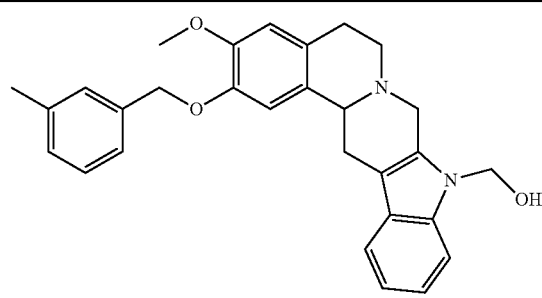<br>A149 |
| A150 | (3,12-dimethoxy-2-((2-methylbenzyl)oxy)-5,6,14,14a-tetrahydroindolo[3',2':4,5]pyridine[2,1-a]isoquinoline-9(8H)-yl)methanol | 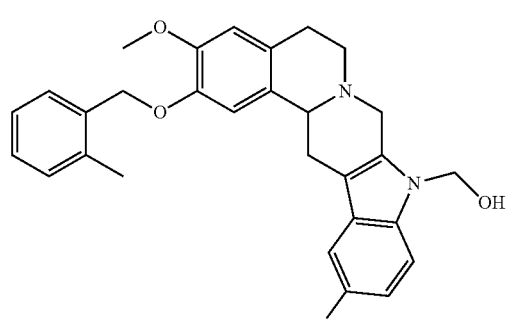<br>A150 |
| A151 | (3-methoxy-2-((2-methylbenzyl)oxy)-5,6,14,14a-tetrahydroindolo[3',2':4,5]pyridine[2,1-a]isoquinoline-9(8H)-yl)methanol | 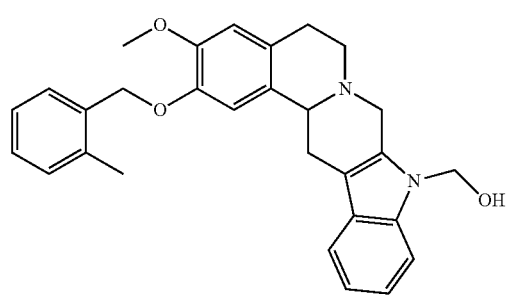<br>A151 |
| A152 | (2-methoxy-3-((3,4-difluorobenzyl)oxy)-5,6,14,14a-tetrahydroindolo[3',2':4,5]pyridine[2,1-a]isoquinoline-9(8H)-yl)methanol | 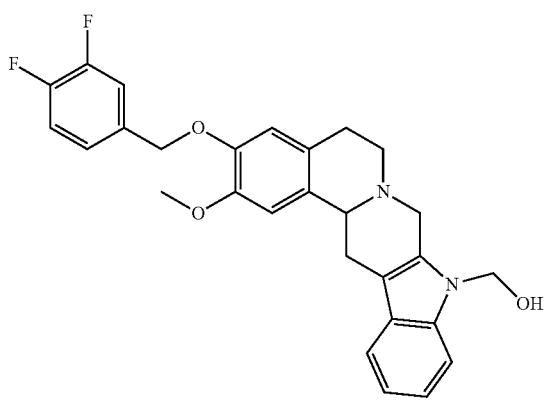<br>A152 |

-continued
| No. | Name | Structure |
|---|---|---|
| A153 | (2,12-dimethoxy-3-((3,4-difluorobenzyl)oxy)-5,6,14,14a-tetrahydroindolo[3',2':4,5]pyridine[2,1-a]isoquinoline-9(8H)-yl)methanol | 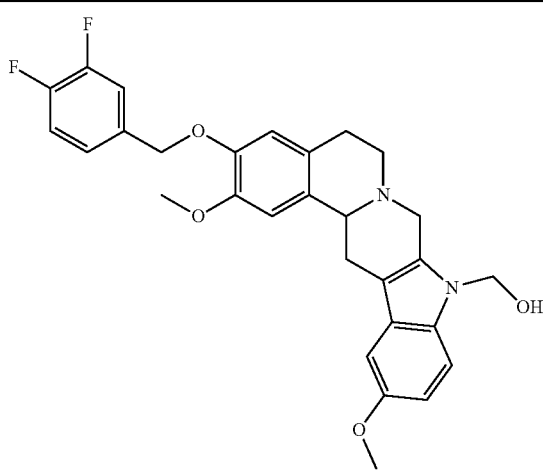<br>A153 |
| A154 | (2-methoxy-3-((3,5-difluorobenzyl)oxy)-5,6,14,14a-tetrahydroindolo[3',2':4,5]pyridine[2,1-a]isoquinoline-9(8H)-yl)methanol | 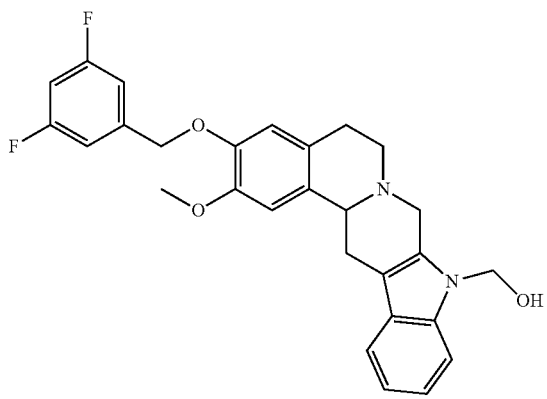<br>A154 |
| A155 | (2,12-dimethoxy-3-((3,5-difluorobenzyl)oxy)-5,6,14,14a-tetrahydroindolo[3',2':4,5]pyridine[2,1-a]isoquinoline-9(8H)-yl)methanol | 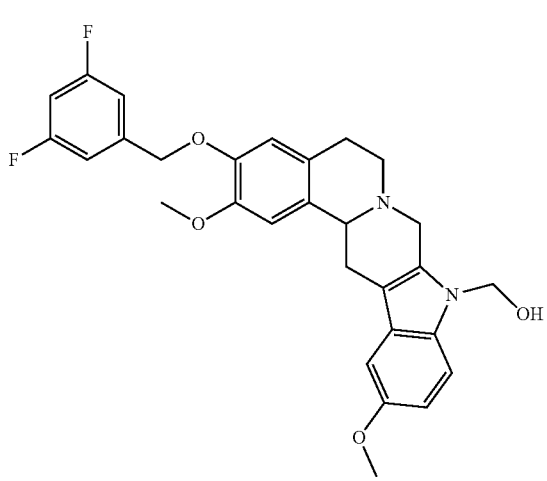<br>A155 |

-continued
| No. | Name | Structure |
|---|---|---|
| A156 | (2-methoxy-3-((3,4,5-trifluorobenzyl)oxy)-5,6,14,14a-tetrahydroindolo[3',2':4,5]pyridine[2,1-a]isoquinoline-9(8H)-yl)methanol | 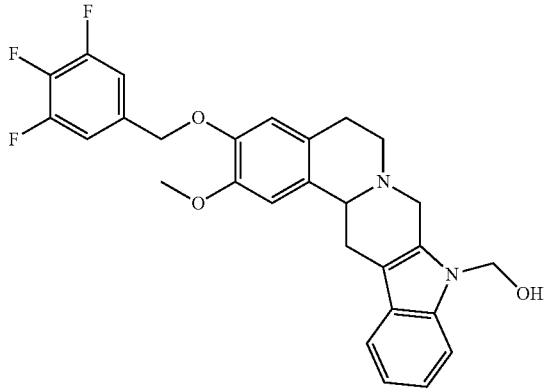<br>A156 |
| A157 | (2,12-dimethoxy-3-((3,4,5-trifluorobenzyl)oxy)-5,6,14,14a-tetrahydroindolo[3',2':4,5]pyridine[2,1-a]isoquinoline-9(8H)-yl)methanol | 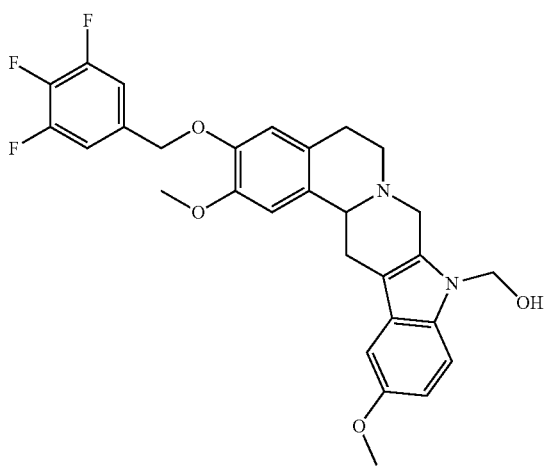<br>A157 |
| A158 | (3-methoxy-2-((3,4-difluorobenzyl)oxy)-5,6,14,14a-tetrahydroindolo[3',2':4,5]pyridine[2,1-a]isoquinoline-9(8H)-yl)methanol | 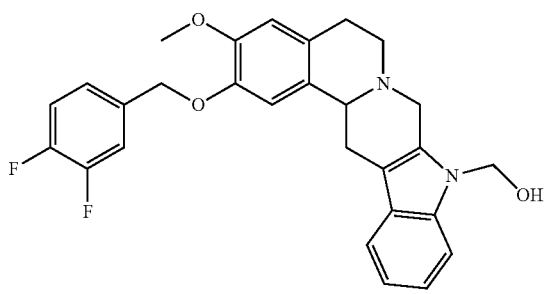<br>A158 |

-continued

| No. | Name | Structure |
|-----|------|-----------|
| A159 | (3,12-dimethoxy-2-((3,4-difluorobenzyl)oxy)-5,6,14,14a-tetrahydroindolo[3',2':4,5]pyridine[2,1-a]isoquinoline-9(8H)-yl)methanol | 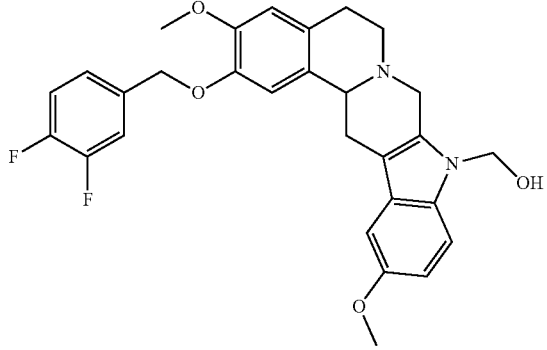<br>A159 |
| A160 | (3-methoxy-2-((3,5-difluorobenzyl)oxy)-5,6,14,14a-tetrahydroindolo[3',2':4,5]pyridine[2,1-a]isoquinoline-9(8H)-yl)methanol | 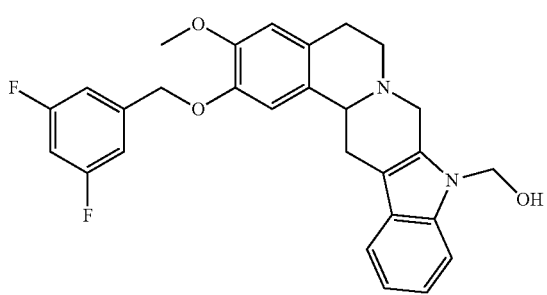<br>A160 |
| A161 | (3,12-dimethoxy-2((3,5-difluorobenzyl)oxy)-5,6,14,14a-tetrahydroindolo[3',2':4,5]pyridine[2,1-a]isoquinoline-9(8H)-yl)methanol | 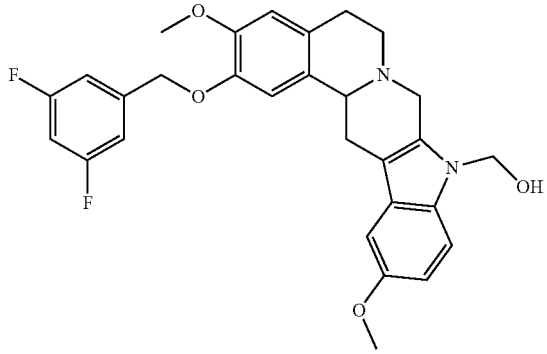<br>A161 |
| A162 | (3-methoxy-2-((3,4,5-trifluorobenzyl)oxy)-5,6,14,14a-tetrahydroindolo[3',2':4,5]pyridine[2,1-a]isoquinoline-9(8H)-yl)methanol | 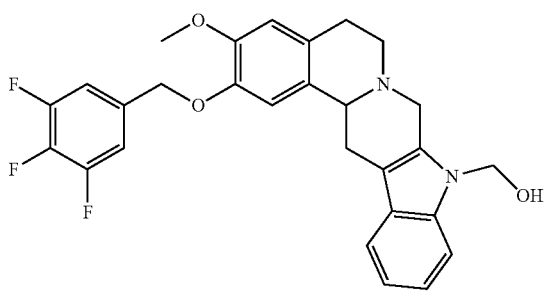<br>A162 |

-continued

| No. | Name | Structure |
|---|---|---|
| A163 | (3,12-dimethoxy-2((3,4,5-trifluorobenzyl)oxy)-5,6,14,14a-tetrahydroindolo[3',2':4,5]pyridine[2,1-a]isoquinoline-9(8H)-yl)methanol | 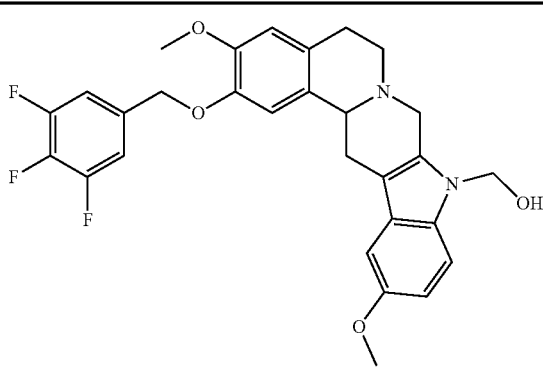<br>A163 |
| B1 | 2-(benzyloxy)-8-(4-fluorophenyl)-3,12-dimethoxy-5,6,8,9,14,14a-hexahydroindolo[3',2':4,5]pyridine[2,1-a]isoquinoline | 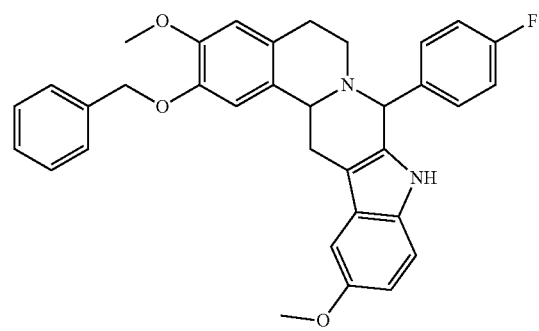 [SMILES: COc1ccc2[nH]c3c(c2c1)CC1c2cc(OCc4ccccc4)c(OC)cc2CCN1C3c1ccc(F)cc1] |
| B2 | 2-(benzyloxy)-8-(4-fluorophenyl)-3-methoxy-5,6,8,9,14,14a-hexahydroindolo[[3',2':4,5]pyridine[2,1-a]isoquinoline | 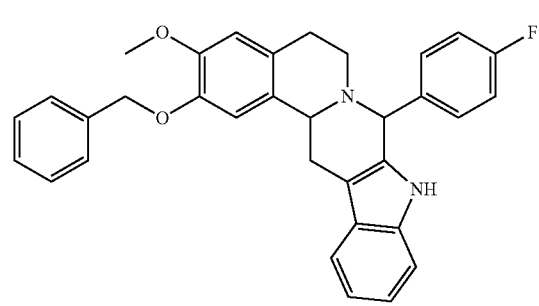<br>B2 |
| B3 | 8-(4-fluorophenyl)-3,12-dimethoxy-2-((4-(trifluoromethyl)benzyl)oxy)-5,6,8,9,14,14a-hexahydroindolo[3',2':4,5]pyridine[2,1-a]isoquinoline | 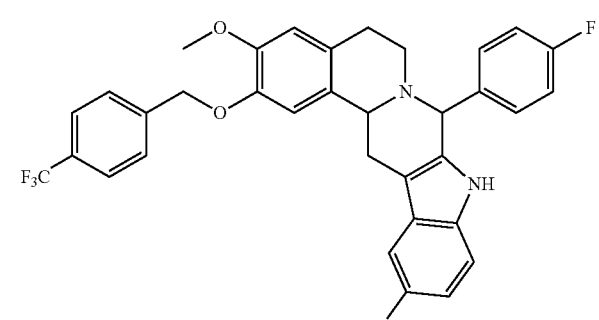<br>B3 |

| No. | Name | Structure |
|---|---|---|
| B4 | 8-(4-fluorophenyl)-3-methoxy-2-((4-(trifluoromethyl)benzyl)oxy)-5,6,8,9,14,14a-hexahydroindolo[3',2':4,5]pyridine[2,1-a]isoquinoline | B4 |
| B5 | 2-((4-fluorobenzyl)oxy)-8-(4-fluorophenyl)-3,12-dimethoxy-5,6,8,9,14,14a-hexahydroindolo[3',2':4,5]pyridine[2,1-a]isoquinoline | B5 |
| B6 | 2-((4-fluorobenzyl)oxy)-8-(4-fluorophenyl)-3-methoxy-5,6,8,9,14,14a-hexahydroindolo[3',2':4,5]pyridine[2,1-a]isoquinoline | B6 |
| B7 | 2-((3-fluorobenzyl)oxy)-8-(4-fluorophenyl)-3,12-dimethoxy-5,6,8,9,14,14a-hexahydroindolo[3',2':4,5]pyridine[2,1-a]isoquinoline | B7 |

-continued

| No. | Name | Structure |
|---|---|---|
| B8 | 2-((3-fluorobenzyl)oxy)-8-(4-fluorophenyl)-3-methoxy-5,6,8,9,14,14a-hexahydroindolo[3',2':4,5]pyridine[2,1-a]isoquinoline | B8 |
| B9 | 2-((2-fluorobenzyl)oxy)-8-(4-fluorophenyl)-3,12-dimethoxy-5,6,8,9,14,14a-hexahydroindolo[3',2':4,5]pyridine[2,1-a]isoquinoline | B9 |
| B10 | 2-((2-fluorobenzyl)oxy)-8-(4-fluorophenyl)-3-methoxy-5,6,8,9,14,14a-hexahydroindolo[3',2':4,5]pyridine[2,1-a]isoquinoline | B10 |
| B11 | 8-(4-fluorophenyl)-3,12-dimethoxy-2-((4-methoxybenzyl)oxy)-5,6,8,9,14,14a-hexahydroindolo[3',2':4,5]pyridine[2,1-a]isoquinoline | B11 |

-continued

| No. | Name | Structure |
|---|---|---|
| B12 | 8-(4-fluorophenyl)-3-methoxy-2-((4-methoxybenzyl)oxy)-5,6,8,9,14,14a-hexahydroindolo[3',2':4,5]pyridine[2,1-a]isoquinoline | 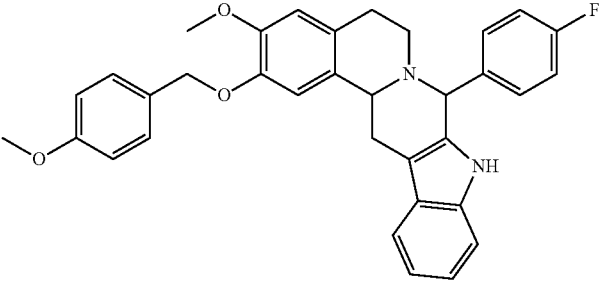 B12 |
| B13 | 8-(4-fluorophenyl)-3,12-dimethoxy-2-((3-methoxybenzyl)oxy)-5,6,8,9,14,14a-hexahydroindolo[3',2':4,5]pyridine[2,1-a]isoquinoline | 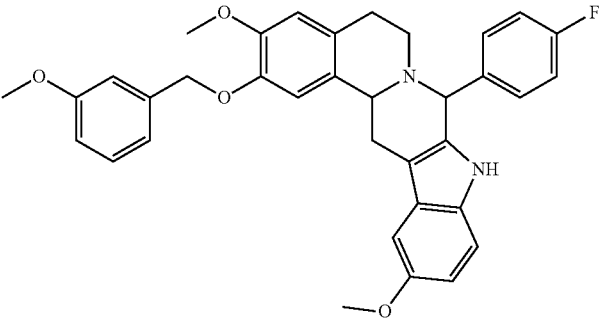 B13 |
| B14 | 8-(4-fluorophenyl)-3-methoxy-2-((3-methoxy-benzyl)oxy)-5,6,8,9,14,14a-hexahydroindolo[3',2':4,5]pyridine[2,1-a]isoquinoline | 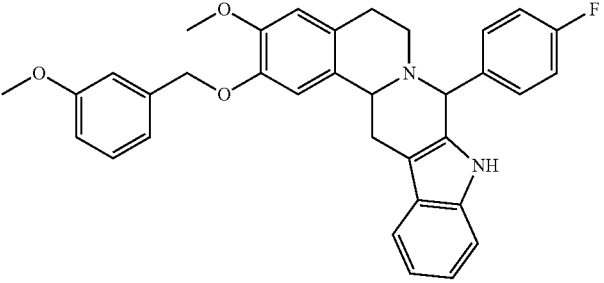 B14 |
| B15 | 8-(4-fluorophenyl)-3,12-dimethoxy-2-((4-methylbenzyl)oxy)-5,6,8,9,14,14a-hexahydroindolo[3',2':4,5]pyridine[2,1-a]isoquinoline | 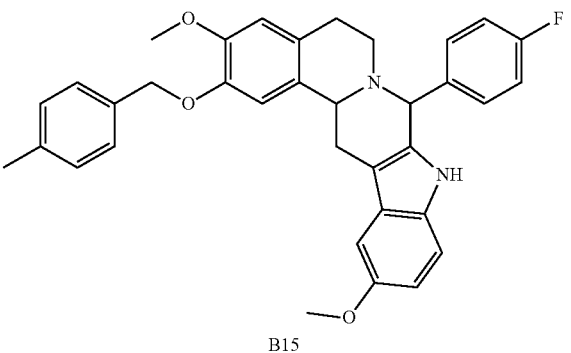 B15 |

| No. | Name | Structure |
|---|---|---|
| B16 | 8-(4-fluorophenyl)-3-methoxy-2-((4-methyl benzyl)oxy)-5,6,8,9,14,14a-hexahydroindolo[3',2':4,5]pyridine[2,1-a]isoquinoline | B16 |
| B17 | 2-((4-chlorobenzyl)oxy)-8-(4-fluorophenyl)-3,12-dimethoxy-5,6,8,9,14,14a-hexahydro-indolo[3',2':4,5]pyridine[2,1-a]isoquinoline | B17 |
| B18 | 2-((4-chlorobenzyl)oxy)-8-(4-fluorophenyl)-3-methoxy-5,6,8,9,14,14a-hexahydroindolo[3',2':4,5]pyridine[2,1-a]isoquinoline | B18 |
| B19 | 4-(((8-(4-fluorophenyl)-3,12-dimethoxy-5,6,8,9,14,14a-hexahydroindolo[3',2':4,5]pyridine[2,1-a]isoquinoline-2-yl)oxy)methyl)benzonitrile | B19 |

-continued

| No. | Name | Structure |
|---|---|---|
| B20 | 4-(((8-(4-fluorophenyl)-3-methoxy-5,6,8,9,14,14a-hexahydroindolo[3',2':4,5]pyridine[2,1-a]isoquinoline-2-yl)oxy)methyl)benzonitrile | 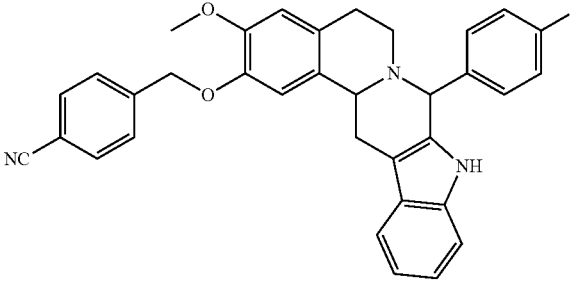<br>B20 |
| B21 | 2-((4-bromobenzyl)oxy)-8-(4-fluorophenyl)-3,12-dimethoxy-5,6,8,9,14,14a-hexahydro-indolo[3',2':4,5]pyridine[2,1-a]isoquinoline | 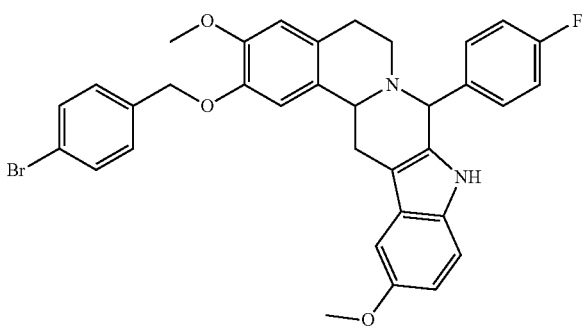<br>B21 |
| B22 | 2-((4-bromobenzyl)oxy)-8-(4-fluorophenyl)-3-methoxy-5,6,8,9,14,14a-hexahydroindolo[3',2':4,5]pyridine[2,1-a]isoquinoline | 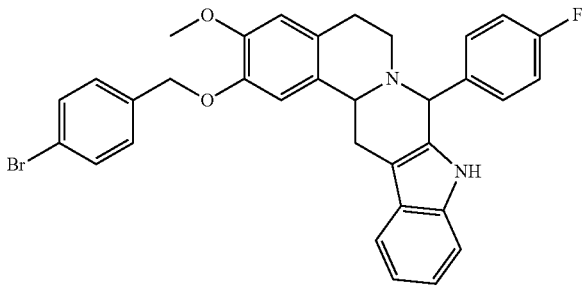<br>B22 |
| B23 | 2-((3-fluoro-4-(trifluoromethyl)benzyl)oxy)-8-(4-fluorophenyl)-3,12-dimethoxy-5,6,8,9,14,14a-hexahydroindolo[3',2':4,5]pyridine[2,1-a]isoquinoline | 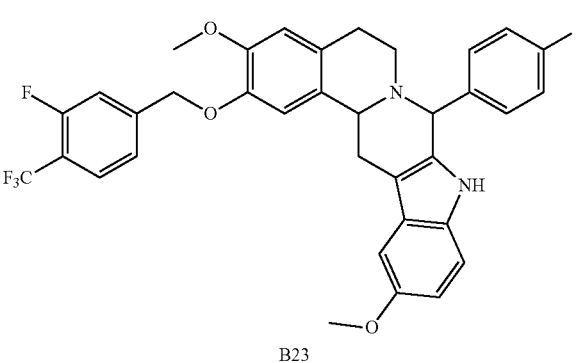<br>B23 |

| No. | Name | Structure |
|---|---|---|
| B24 | 2-((3-fluoro-4-(trifluoromethyl)benzyl)oxy)-8-(4-fluorophenyl)-3-methoxy-5,6,8,9,14,14a-hexahydroindolo[3',2':4,5]pyridine[2,1-a]isoquinoline | 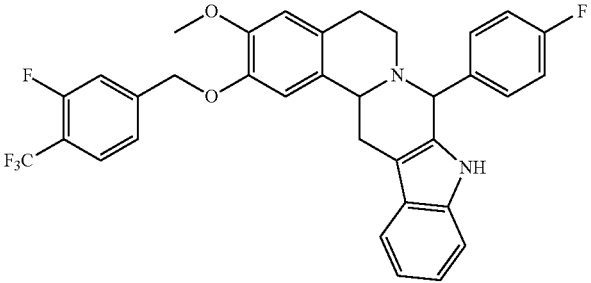 B24 |
| B25 | 2-((2-fluoro-4-(trifluoromethyl)benzyl)oxy)-8-(4-fluorophenyl)-3,12-dimethoxy-5,6,8,9,14,14a-hexahydroindolo[3',2':4,5]pyridine[2,1-a]isoquinoline | 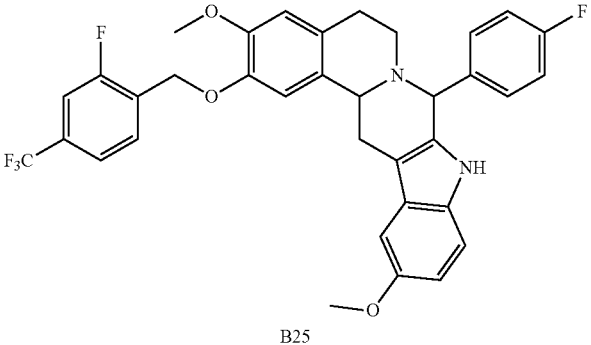 B25 |
| B26 | 2-((2-fluoro-4-(trifluoromethyl)benzyl)oxy)-8-(4-fluorophenyl)-3-methoxy-5,6,8,9,14,14a-hexahydroindolo[3',2':4,5]pyridine[2,1-a]isoquinoline | 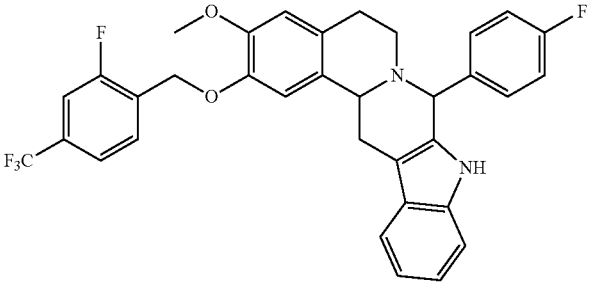 B26 |
| B27 | 2-((4-ethylbenzyl)oxy)-8-(4-fluorophenyl)-3,12-dimethoxy-5,6,8,9,14,14a-hexahydroindolo[3',2':4,5]pyridine[2,1-a]isoquinoline | 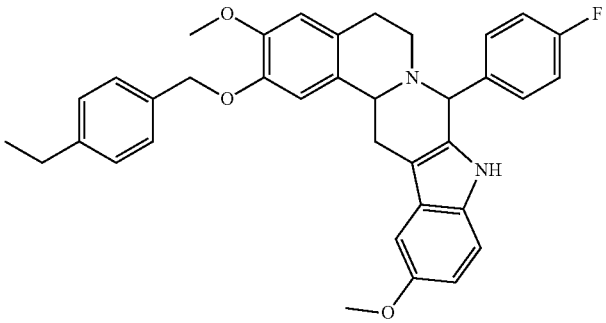 B27 |

-continued

| No. | Name | Structure |
|---|---|---|
| B28 | 2-((4-ethylbenzyl)oxy)-8-(4-fluorophenyl)-3-methoxy-5,6,8,9,14,14a-hexahydroindolo[3',2':4,5]pyridine[2,1-a]isoquinoline | B28 |
| B29 | 8-(4-fluorophenyl)-3,12-dimethoxy-2-(naphthalen-2-ylmethoxy)-5,6,8,9,14,14a-hexahydroindolo[3',2':4,5]pyridine[2,1-a]isoquinoline | B29 |
| B30 | 8-(4-fluorophenyl)-3-methoxy-2-(naphthalen-2-ylmethoxy)-5,6,8,9,14,14a-hexahydroindolo[3',2':4,5]pyridine[2,1-a]isoquinoline | B30 |
| B31 | 4-(((8-(4-fluorophenyl)-3,12-dimethoxy-5,6,8,9,14,14a-hexahydroindolo[3',2':4,5]pyridine[2,1-a]isoquinoline-2-yl)oxo)methyl)benzoate | B31 |

| No. | Name | Structure |
|---|---|---|
| B32 | 4-(((8-(4-fluorophenyl)-3-methoxy-5,6,8,9,14,14a-hexahydroindolo[3',2':4,5]pyridine[2,1-a]isoquinoline-2-yl)oxo)methyl)benzoate | 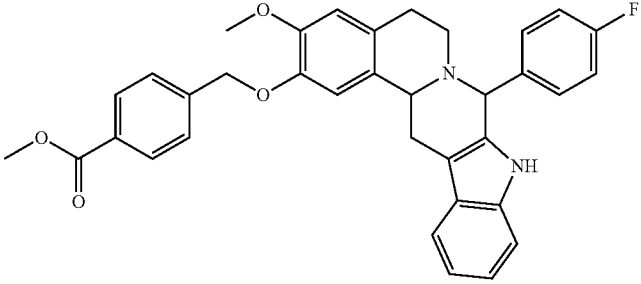<br>B32 |
| B33 | 2-((4-(1H-pyrazol-1-yl)benzyl)oxy)-8-(4-fluorophenyl)-3,12-dimethoxy-5,6,8,9,14,14a-hexahydroindolo[3',2':4,5]pyridine[2,1-a]isoquinoline | 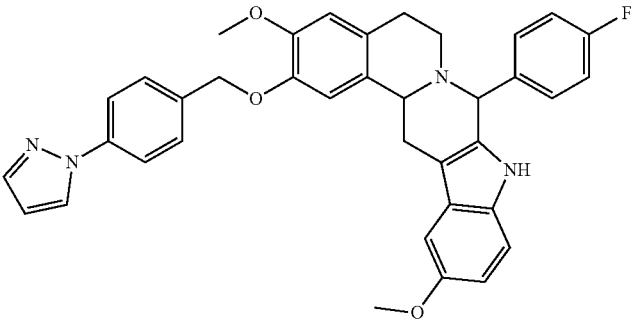<br>B33 |
| B34 | 2-((4-(1H-pyrazol-1-yl)benzyl)oxy)-8-(4-fluorophenyl)-3-methoxy-5,6,8,9,14,14a-hexahydroindolo[3',2':4,5]pyridine[2,1-a]isoquinoline | 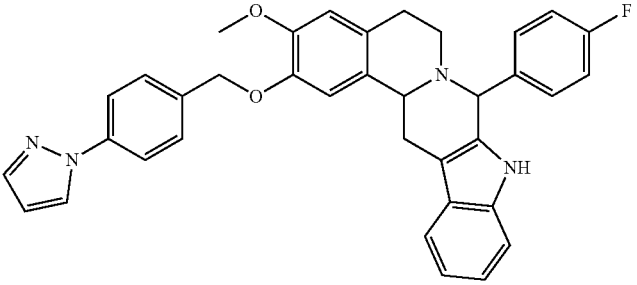<br>B34 |
| B35 | 2-butoxy-8-(4-fluorophenyl)-3,12-dimethoxy-5,6,8,9,14,14a-hexahydroindolo[3',2':4,5]pyridine[2,1-a]isoquinoline | 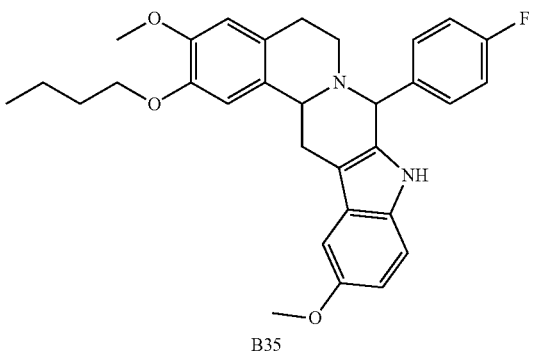 [SMILES: CCCCOc1cc2c(cc1OC)CCN1C2Cc2c([nH]c3ccc(OC)cc23)C1c1ccc(F)cc1 ; "B35"]<br>B35 |

-continued

| No. | Name | Structure |
|---|---|---|
| B36 | 2-butoxy-8-(4-fluorophenyl)-3-methoxy-5,6,8,9,14,14a-hexahydroindolo[3',2':4,5]pyridine[2,1-a]isoquinoline | 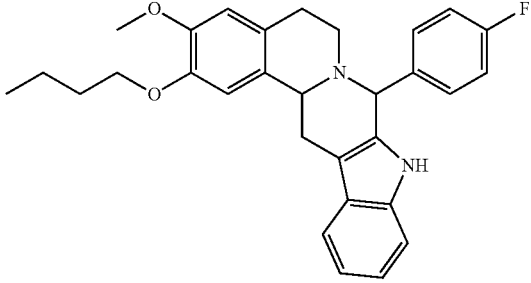<br>B36 |
| B39 | 8-(4-fluorophenyl)-3,12-dimethoxy-2-(2,2,2-trifluoroethoxy)-5,6,8,9,14,14a-hexahydroindolo[3',2':4,5]pyridine[2,1-a]isoquinoline | 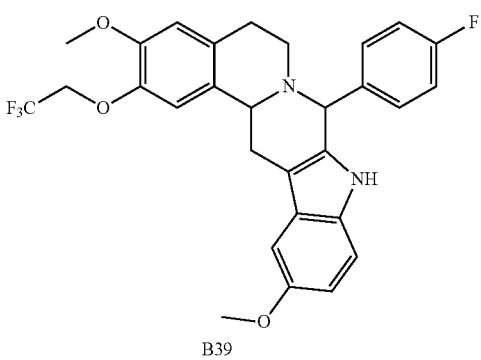 [SMILES: "B39" ; COc1ccc2[nH]c3c(c2c1)CC1c2cc(OCC(F)(F)F)c(OC)cc2CCN1C3c1ccc(F)cc1]<br>B39 |
| B40 | 8-(4-fluorophenyl)-3-methoxy-2-(2,2,2-trifluoroethoxy)-5,6,8,9,14,14a-hexahydroindolo[3',2':4,5]pyridine[2,1-a]isoquinoline | 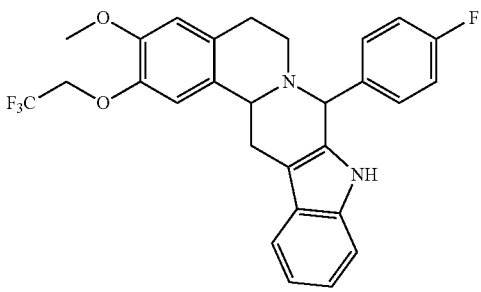<br>B40 |
| B41 | 8-(4-fluorophenyl)-3,12-dimethoxy-2-((4-(methylsulfonyl)benzyl)oxy)-5,6,8,9,14,14a-hexahydroindolo[3',2':4,5]pyridine[2,1-a]isoquinoline | 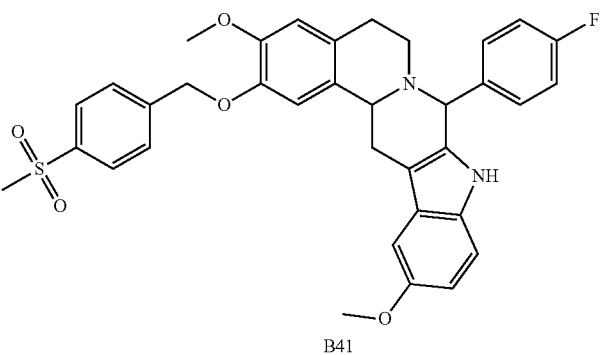<br>B41 |

-continued

| No. | Name | Structure |
|---|---|---|
| B42 | 8-(4-fluorophenyl)-3-methoxy-2-((4-(methyl-sulfonyl)benzyl)oxy)-5,6,8,9,14,14a-hexahydroindolo[3',2':4,5]pyridine[2,1-a]isoquinoline | B42 |
| B43 | 2-(benzyloxy)-11-fluoro-8-(4-fluorophenyl)-3-methoxy-5,6,8,9,14,14a-hexahydroindolo[3',2':4,5]pyridine[2,1-a]isoquinoline | B43 |
| B44 | 2-(benzyloxy)-12-fluoro-8-(4-fluorophenyl)-3-methoxy-5,6,8,9,14,14a-hexahydroindolo[3',2':4,5]pyridine[2,1-a]isoquinoline | B44 |
| B45 | 2-(benzyloxy)-13-fluoro-8-(4-fluorophenyl)-3-methoxy-5,6,8,9,14,14a-hexahydroindolo[3',2':4,5]pyridine[2,1-a]isoquinoline | B45 |

| No. | Name | Structure |
|---|---|---|
| B46 | 2-(benzyloxy)-11-chloro-8-(4-fluorophenyl)-3-methoxy-5,6,8,9,14,14a-hexahydroindolo[3',2':4,5]pyridine[2,1-a]isoquinoline | 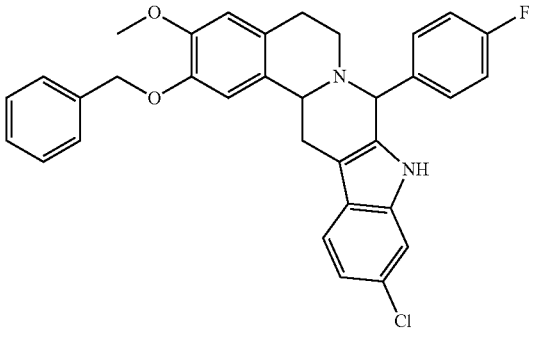<br>B46 |
| B47 | 2-(benzyloxy)-12-chloro-8-(4-fluorophenyl)-3-methoxy-5,6,8,9,14,14a-hexahydroindolo[3',2':4,5]pyridine[2,1-a]isoquinoline | 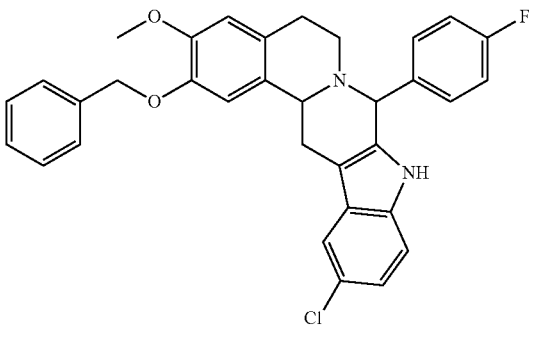<br>B47 |
| B48 | 2-(benzyloxy)-13-chloro-8-(4-fluorophenyl)-3-methoxy-5,6,8,9,14,14a-hexahydroindolo[3',2':4,5]pyridine[2,1-a]isoquinoline | 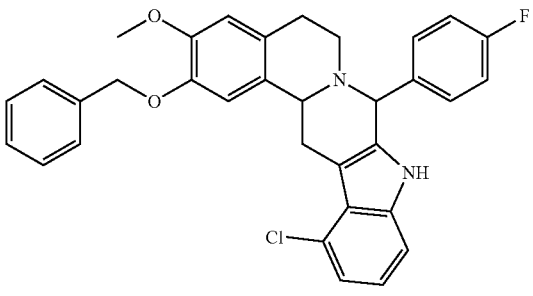<br>B48 |
| B49 | 2-(benzyloxy)-11-bromo-8-(4-fluorophenyl)-3-methoxy-5,6,8,9,14,14a-hexahydroindolo[3',2':4,5]pyridine[2,1-a]isoquinoline | 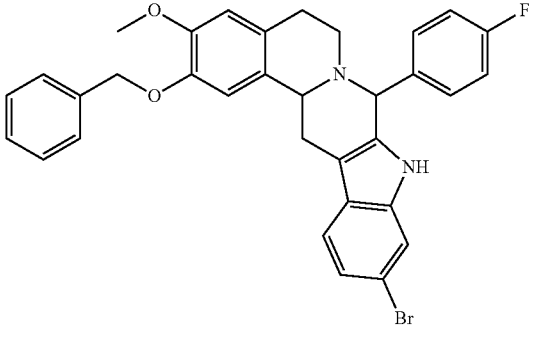<br>B49 |

-continued

| No. | Name | Structure |
|---|---|---|
| B50 | 2-(benzyloxy)-12-bromo-8-(4-fluorophenyl)-3-methoxy-5,6,8,9,14,14a-hexahydroindolo[3',2':4,5]pyridine[2,1-a]isoquinoline | 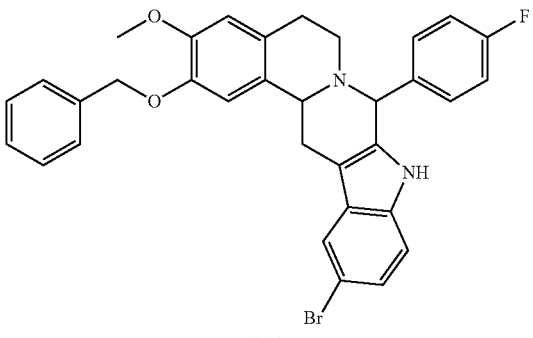<br>B50 |
| B51 | 2-(benzyloxy)-13-bromo-8-(4-fluorophenyl)-3-methoxy-5,6,8,9,14,14a-hexahydroindolo[3',2':4,5]pyridine[2,1-a]isoquinoline | 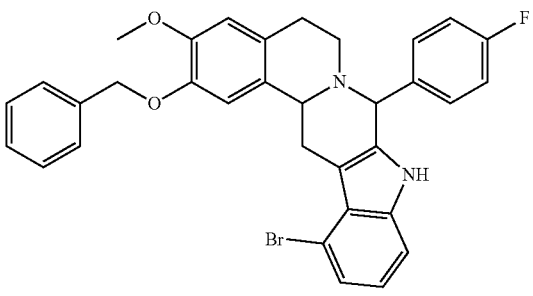<br>B51 |
| B52 | 2-(benzyloxy)-8-(4-fluorophenyl)-3-methoxy-5,6,8,9,14,14a-hexahydroindolo[3',2':4,5]pyridine[2,1-a]isoquinoline-12-phenol | 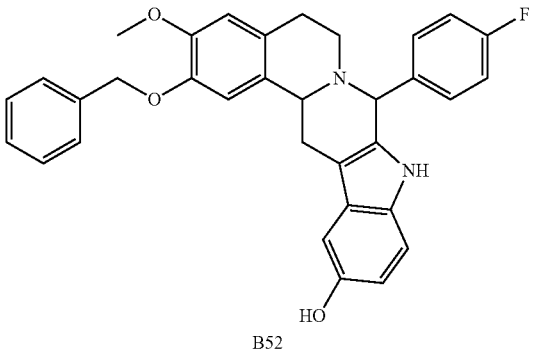<br>B52 |
| B53 | 2-(benzyloxy)-8-(4-fluorophenyl)-3-methoxy-11-methyl-5,6,8,9,14,14a-hexahydroindolo[3',2':4,5]pyridine[2,1-a]isoquinoline | 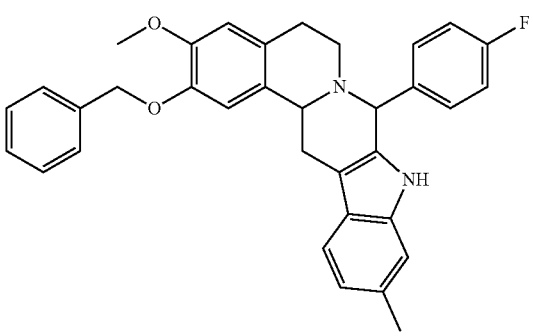<br>B53 |

| No. | Name | Structure |
|---|---|---|
| B54 | 2-(benzyloxy)-12-ethyl-8-(4-fluorophenyl)-3-methoxy-5,6,8,9,14,14a-hexahydroindolo[3',2':4,5]pyridine[2,1-a]isoquinoline | 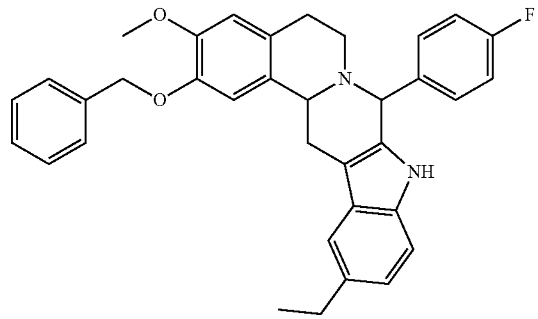 |
| B55 | 3-(benzyloxy)-8-(4-fluorophenyl)-2,12-dimethoxy-5,6,8,9,14,14a-hexahydroindolo[3',2':4,5]pyridine[2,1-a]isoquinoline | 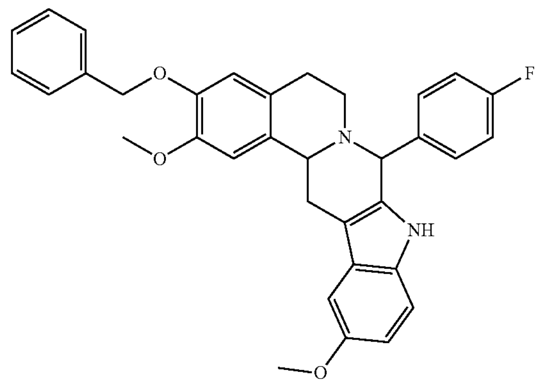 |
| B56 | 3-(benzyloxy)-8-(4-fluorophenyl)-2-methoxy-5,6,8,9,14,14a-hexahydroindolo[3',2':4,5]pyridine[2,1-a]isoquinoline | 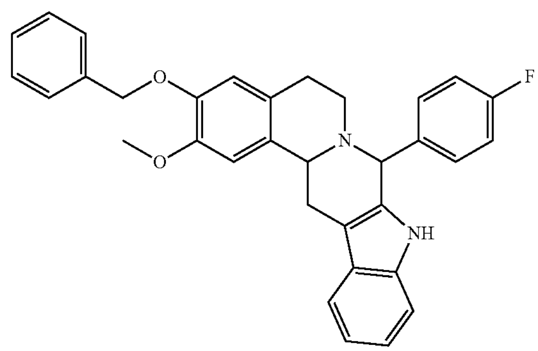 |
| B57 | 8-(4-fluorophenyl)-2,12-dimethoxy-3-((4-(trifluoromethyl)benzyl)oxy)-5,6,8,9,14,14a-hexahydroindolo[3',2':4,5]pyridine[2,1-a]isoquinoline | 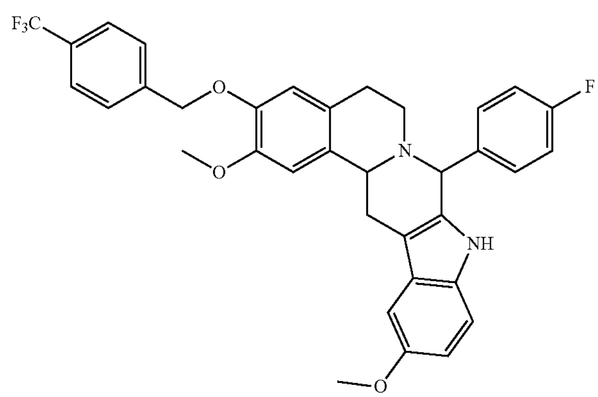 |

| No. | Name | Structure |
|---|---|---|
| B58 | 8-(4-fluorophenyl)-2-methoxy-3-((4-(trifluoromethyl)benzyl)oxy)-5,6,8,9,14,14a-hexahydroindolo[3',2':4,5]pyridine[2,1-a]isoquinoline | 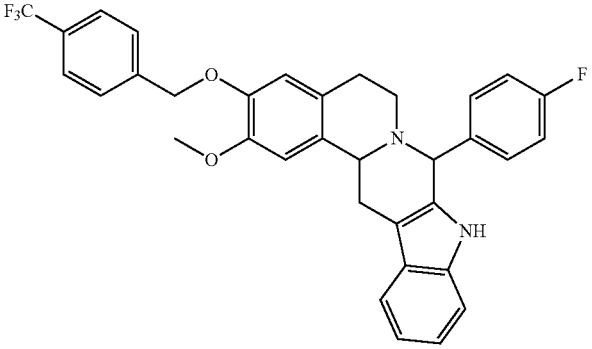 B58 |
| B59 | 3-((4-fluorobenzyl)oxy)-8-(4-fluorophenyl)-2,12-dimethoxy-5,6,8,9,14,14a-hexahydroindolo[3',2':4,5]pyridine[2,1-a]isoquinoline | 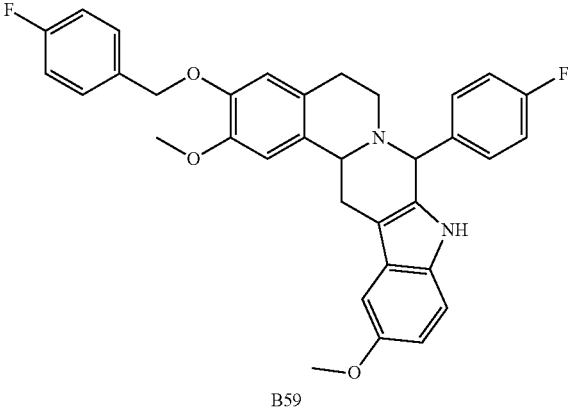 B59 |
| B60 | 3-((4-fluorobenzyl)oxy)-8-(4-fluorophenyl)-2-methoxy-5,6,8,9,14,14a-hexahydroindolo[3',2':4,5]pyridine[2,1-a]isoquinoline | 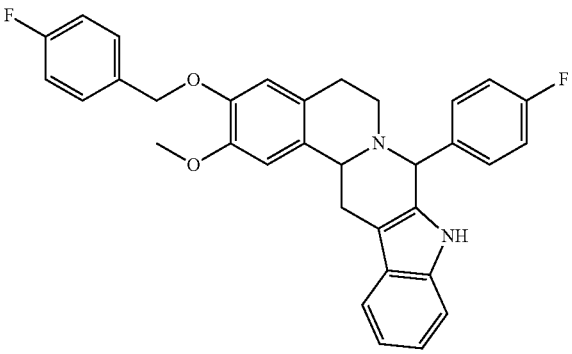 B60 |

-continued

| No. | Name | Structure |
|---|---|---|
| B61 | 3-((3-fluorobenzyl)oxy)-8-(4-fluorophenyl)-2,12-dimethoxy-5,6,8,9,14,14a-hexahydroindolo[3',2':4,5]pyridine[2,1-a]isoquinoline | B61 |
| B62 | 3-((3-fluorobenzyl)oxy)-8-(4-fluorophenyl)-2-methoxy-5,6,8,9,14,14a-hexahydroindolo[3',2':4,5]pyridine[2,1-a]isoquinoline | B62 |
| B63 | 3-((2-fluorobenzyl)oxy)-8-(4-fluorophenyl)-2,12-dimethoxy-5,6,8,9,14,14a-hexahydroindolo[3',2':4,5]pyridine[2,1-a]isoquinoline | B63 |

-continued

| No. | Name | Structure |
|---|---|---|
| B64 | 3-((2-fluorobenzyl)oxy)-8-(4-fluorophenyl)-2-methoxy-5,6,8,9,14,14a-hexahydroindolo[3',2':4,5]pyridine[2,1-a]isoquinoline | 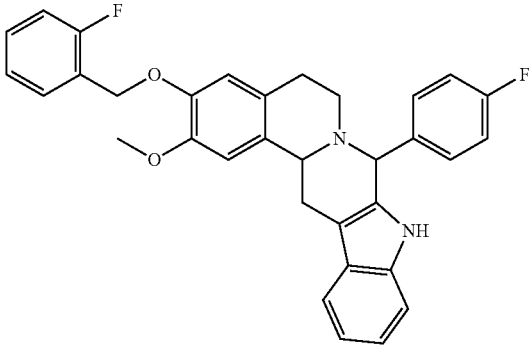<br>B64 |
| B65 | 8-(4-fluorophenyl)-2,12-dimethoxy-3-((4-methoxybenzyl)oxy)-5,6,8,9,14,14a-hexahydroindolo[3',2':4,5]pyridine[2,1-a]isoquinoline | 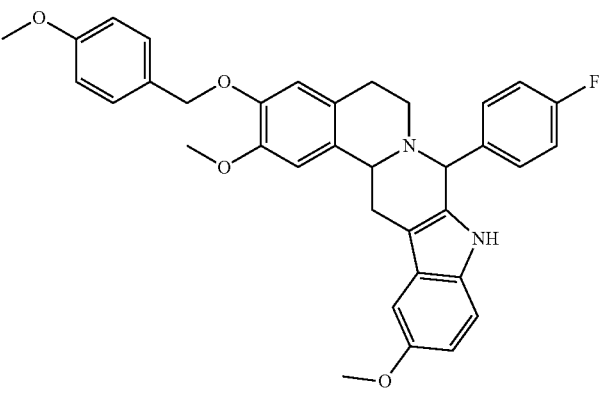<br>B65 |
| B66 | 8-(4-fluorophenyl)-2-methoxy-3-((4-methoxybenzyl)oxy)-5,6,8,9,14,14a-hexahydroindolo[3',2':4,5]pyridine[2,1-a]isoquinoline | 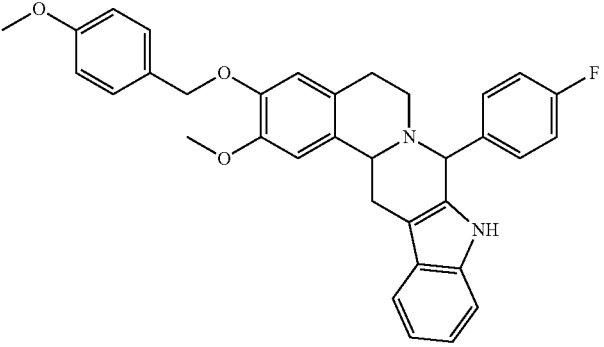<br>B66 |
| B67 | 8-(4-fluorophenyl)-2,12-dimethoxy-3-((3-methoxybenzyl)oxy)-5,6,8,9,14,14a-hexahydroindolo[3',2':4,5]pyridine[2,1-a]isoquinoline | 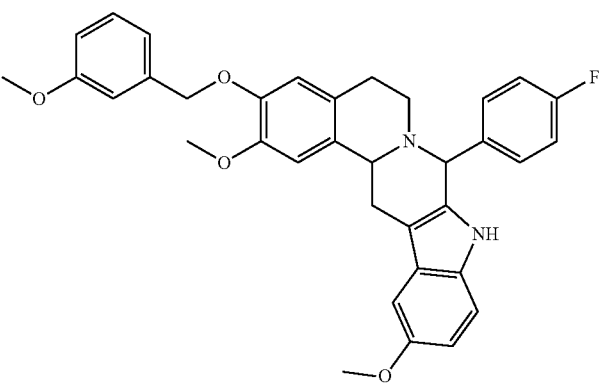<br>B67 |

| No. | Name | Structure |
| --- | --- | --- |
| B68 | 8-(4-fluorophenyl)-2-methoxy-3-((3-methoxybenzyl)oxy)-5,6,8,9,14,14a-hexahydroindolo[3',2':4,5]pyridine[2,1-a]isoquinoline | B68 |
| B69 | 8-(4-fluorophenyl)-2,12-dimethoxy-3-((4-methylbenzyl)oxy)-5,6,8,9,14,14a-hexahydroindolo[3',2':4,5]pyridine[2,1-a]isoquinoline | B69 |
| B70 | 8-(4-fluorophenyl)-2-methoxy-3-((4-methylbenzyl)oxy)-5,6,8,9,14,14a-hexahydroindolo[3',2':4,5]pyridine[2,1-a]isoquinoline | B70 |
| B71 | 3-((4-chlorobenzyl)oxy)-8-(4-fluorophenyl)-2,12-dimethoxy-5,6,8,9,14,14a-hexahydroindolo[3',2':4,5]pyridine[2,1-a]isoquinoline | B71 |

-continued

| No. | Name | Structure |
|---|---|---|
| B72 | 3-((4-chlorobenzyl)oxy)-8-(4-fluorophenyl)-2-methoxy-5,6,8,9,14,14a-hexahydroindolo[3',2':4,5]pyridine[2,1-a]isoquinoline | B72 |
| B73 | 4-(((8-(4-fluorophenyl)-2,12-dimethoxy-5,6,8,9,14,14a-hexahydroindolo[3',2':4,5]pyridine[2,1-a]isoquinoline-3-yl)oxy)methyl)benzonitrile | B73 |
| B74 | 4-(((8-(4-fluorophenyl)-2-methoxy-5,6,8,9,14,14a-hexahydroindolo[3',2':4,5]pyridine[2,1-a]isoquinoline-3-yl)oxy)methyl)benzonitrile | B74 |
| B75 | 3-((4-bromobenzyl)oxy)-8-(4-fluorophenyl)-2,12-dimethoxy-5,6,8,9,14,14a-hexahydroindolo[3',2':4,5]pyridine[2,1-a]isoquinoline | B75 |

-continued

| No. | Name | Structure |
|---|---|---|
| B76 | 3-((4-bromobenzyl)oxy)-8-(4-fluorophenyl)-2-methoxy-5,6,8,9,14,14a-hexahydroindolo[3',2':4,5]pyridine[2,1-a]isoquinoline | B76 |
| B77 | 3-((3-fluoro-4-(trifluoromethyl)benzyl)oxy)-8-(4-fluorophenyl)-2,12-dimethoxy-5,6,8,9,14,14a-hexahydroindolo[3',2':4,5]pyridine[2,1-a]isoquinoline | B77 |
| B78 | 3-((3-fluoro-4-(trifluoromethyl)benzyl)oxy)-8-(4-fluorophenyl)-2-methoxy-5,6,8,9,14,14a-hexahydroindolo[3',2':4,5]pyridine[2,1-a]isoquinoline | B78 |

-continued

| No. | Name | Structure |
|---|---|---|
| B79 | 3-((2-fluoro-4-(trifluoromethyl)benzyl)oxy)-8-(4-fluorophenyl)-2,12-dimethoxy-5,6,8,9,14,14a-hexahydroindolo[3',2':4,5]pyridine[2,1-a]isoquinoline | 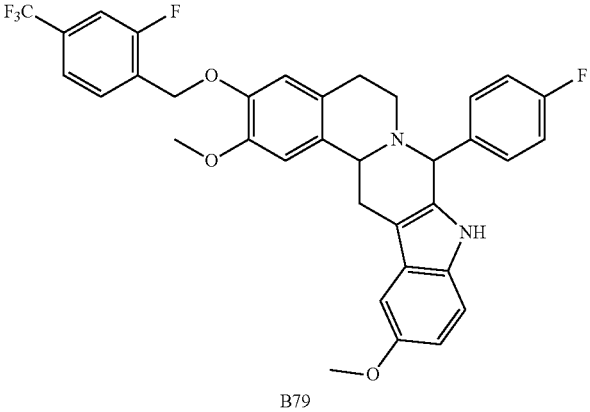 [SMILES: "B79" ; COc1ccc2[nH]c3c(c2c1)CC1c2cc(OC)c(OCc4ccc(C(F)(F)F)cc4F)cc2CCN1C3c1ccc(F)cc1]<br>B79 |
| B80 | 3-((2-fluoro-4-(trifluoromethyl)benzyl)oxy)-8-(4-fluorophenyl)-2-methoxy-5,6,8,9,14,14a-hexahydroindolo[3',2':4,5]pyridine[2,1-a]isoquinoline | 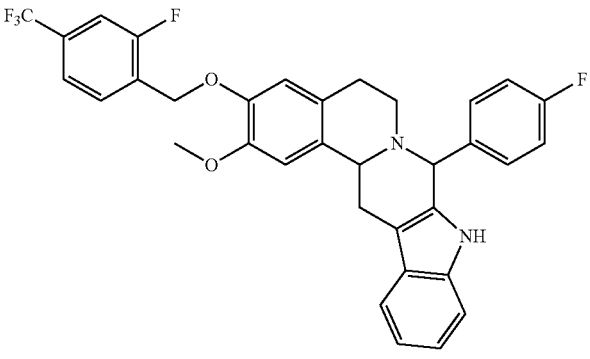<br>B80 |
| B81 | 3-((4-ethylbenzyl)oxy)-8-(4-fluorophenyl)-2,12-dimethoxy-5,6,8,9,14,14a-hexahydroindolo[3',2':4,5]pyridine[2,1-a]isoquinoline | 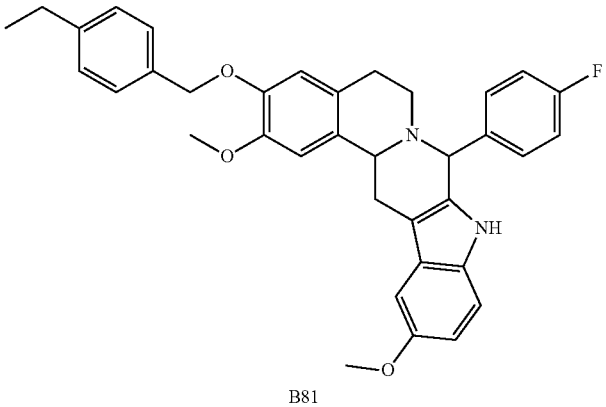 [SMILES: CCc1ccc(COc2cc3c(cc2OC)C2Cc4c([nH]c5ccc(OC)cc45)C(c4ccc(F)cc4)N2CC3)cc1 ; "B81"]<br>B81 |
| B82 | 3-((4-ethylbenzyl)oxy)-8-(4-fluorophenyl)-2-methoxy-5,6,8,9,14,14a-hexahydroindolo[3',2':4,5]pyridine[2,1-a]isoquinoline | 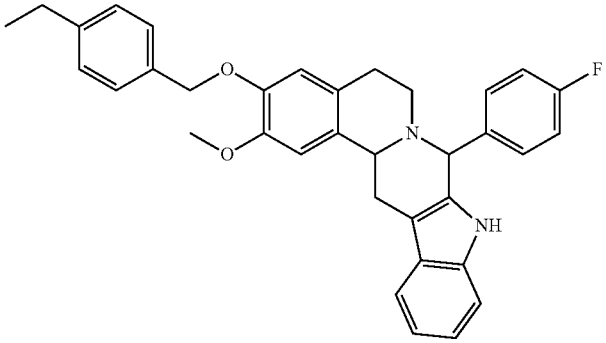<br>B82 |

-continued
| No. | Name | Structure |
|---|---|---|
| B83 | 8-(4-fluorophenyl)-2,12-dimethoxy-3-(naphthalen-2-ylmethoxy)-5,6,8,9,14,14a-hexahydroindolo[3',2':4,5]pyridine[2,1-a]isoquinoline | 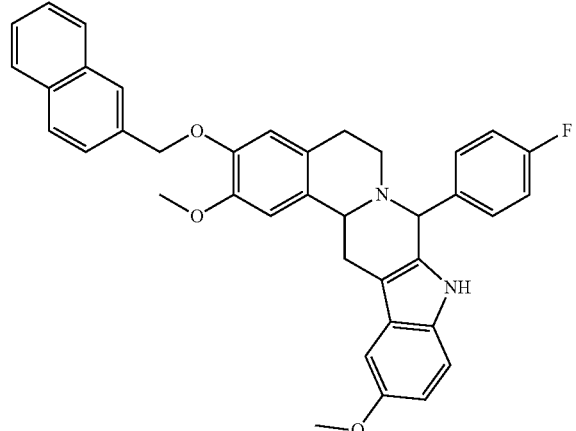 B83 |
| B84 | 8-(4-fluorophenyl)-2-methoxy-3-(naphthalen-2-ylmethoxy)-5,6,8,9,14,14a-hexahydroindolo[3',2':4,5]pyridine[2,1-a]isoquinolinee | 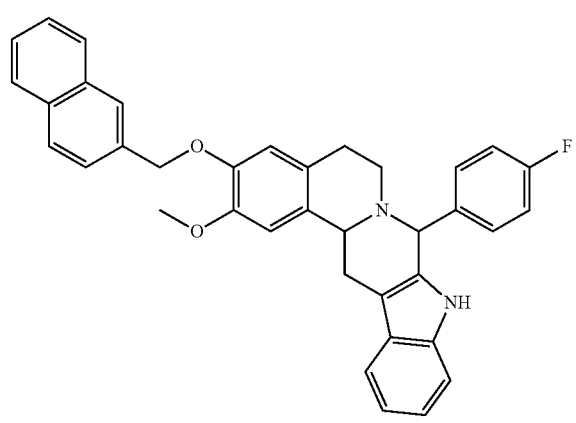 B84 |
| B85 | 4-(((8-(4-fluorophenyl)-2,12-dimethoxy-5,6,8,9,14,14a-hexahydroindolo[3',2':4,5]pyridine[2,1-a]isoquinoline-3-yl)oxo)methyl)benzoate | 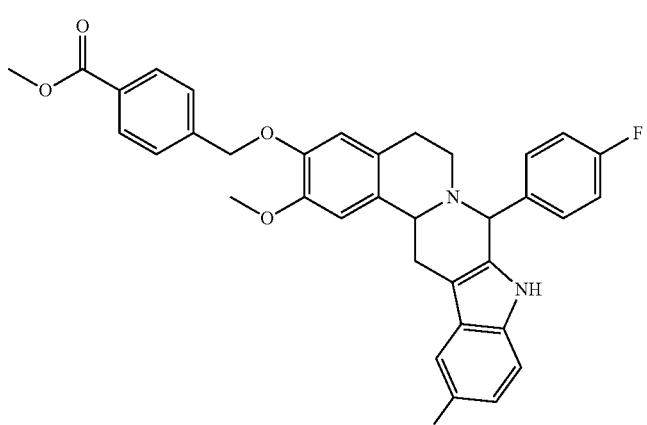 B85 |

-continued

| No. | Name | Structure |
|---|---|---|
| B86 | 4-(((8-(4-fluorophenyl)-2-methoxy-5,6,8,9,14,14a-hexahydroindolo[3',2':4,5]pyridine[2,1-a]isoquinoline-3-yl)oxo)methyl)benzoate | B86 |
| B87 | 3-((4-(1H-pyrazol-1-yl)benzyl)oxy)-8-(4-fluorophenyl)-2,12-dimethoxy-5,6,8,9,14,14a-hexahydroindolo[3',2':4,5]pyridine[2,1-a]isoquinoline | B87 |
| B88 | 3-((4-(1H-pyrazol-1-yl)benzyl)oxy)-8-(4-fluorophenyl)-2-methoxy-5,6,8,9,14,14a-hexahydroindolo[3',2':4,5]pyridine[2,1-a]isoquinoline | B88 |

-continued

| No. | Name | Structure |
|---|---|---|
| B89 | 3-butoxy-8-(4-fluorophenyl)-2,12-dimethoxy-5,6,8,9,14,14a-hexahydroindolo[3',2':4,5]pyridine[2,1-a]isoquinoline | 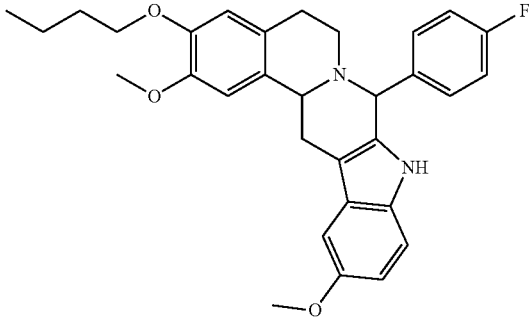<br>B89 |
| B90 | 3-butoxy-8-(4-fluorophenyl)-2-methoxy-5,6,8,9,14,14a-hexahydroindolo[3',2':4,5]pyridine[2,1-a]isoquinoline | 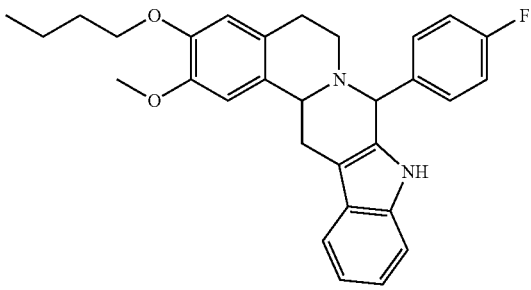<br>B90 |
| B91 | 3-(benzyloxy)-8-(4-fluorophenyl)-2-methoxy-11-methyl-5,6,8,9,14,14a-hexahydroindolo[3',2':4,5]pyridine[2,1-a]isoquinoline | 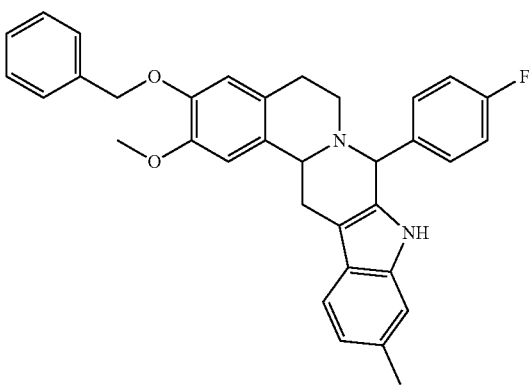<br>B91 |
| B92 | 3-(benzyloxy)-8-(4-fluorophenyl)-2-methoxy-12-ethyl-5,6,8,9,14,14a-hexahydroindolo[3',2':4,5]pyridine[2,1-a]isoquinoline | 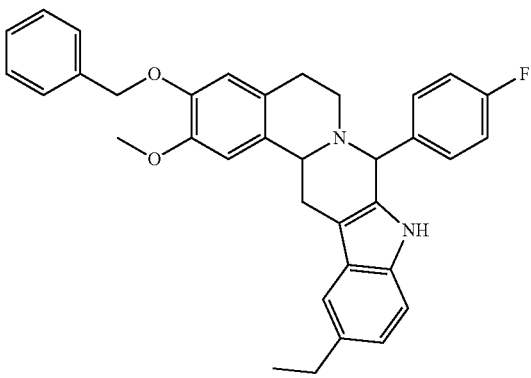<br>B92 |

-continued

| No. | Name | Structure |
|---|---|---|
| B93 | 8-(4-fluorophenyl)-2,12-dimethoxy-3-(2,2,2-trifluoroethoxy)-5,6,8,9,14,14a-hexahydroindolo[3',2':4,5]pyridine[2,1-a]isoquinoline | 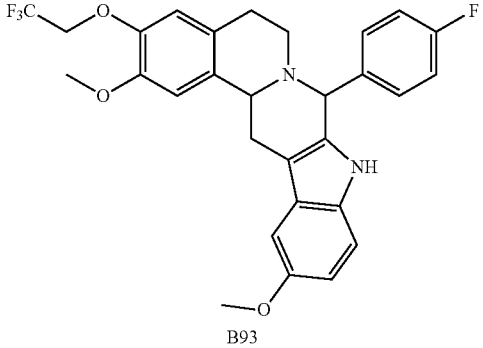<br>B93 |
| B94 | 8-(4-fluorophenyl)-2-methoxy-3-(2,2,2-trifluoroethoxy)-5,6,8,9,14,14a-hexahydroindolo[3',2':4,5]pyridine[2,1-a]isoquinoline | 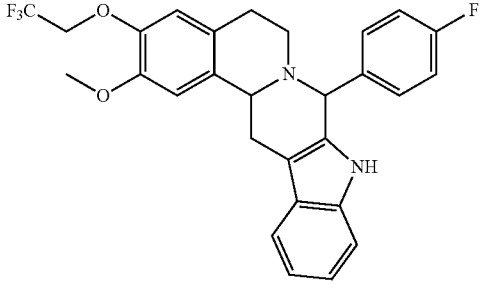<br>B94 |
| B95 | 8-fluoro-2,12-dimethoxy-3-((4-methylsulfonyl)benzyl)oxy)-5,6,8,9,14,14a-hexahydroindolo[3',2':4,5]pyridine[2,1-a]isoquinoline | 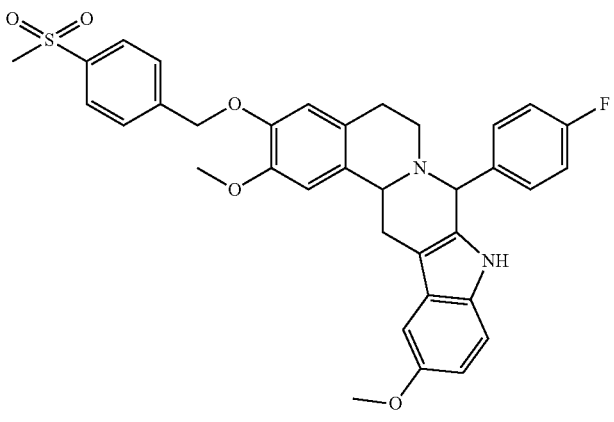<br>B95 |
| B98 | 3-(benzyloxy)-12-fluoro-8-(4-fluorophenyl)-2-methoxy-5,6,8,9,14,14a-hexahydroindolo[3',2':4,5]pyridine[2,1-a]isoquinoline | 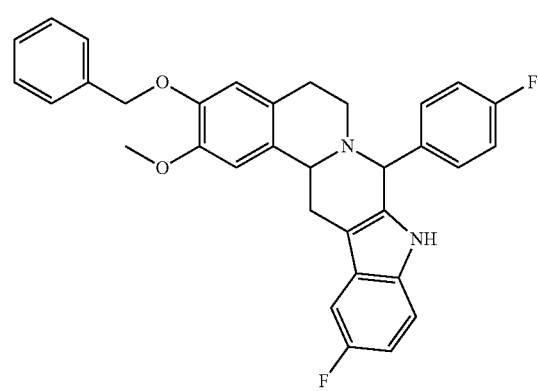<br>B98 |

-continued

| No. | Name | Structure |
|---|---|---|
| B99 | 3-(benzyloxy)-13-fluoro-8-(4-fluorophenyl)-2-methoxy-5,6,8,9,14,14a-hexahydroindolo[3',2':4,5]pyridine[2,1-a]isoquinoline | B99 |
| B100 | 3-(benzyloxy)-11-chloro-8-(4-fluorophenyl)-2-methoxy-5,6,8,9,14,14a-hexahydroindolo[3',2':4,5]pyridine[2,1-a]isoquinoline | B100 |
| B101 | 3-(benzyloxy)-12-chloro-8-(4-fluorophenyl)-2-methoxy-5,6,8,9,14,14a-hexahydroindolo[3',2':4,5]pyridine[2,1-a]isoquinoline | B101 |
| B102 | 3-(benzyloxy)-13-chloro-8-(4-fluorophenyl)-2-methoxy-5,6,8,9,14,14a-hexahydroindolo[3',2':4,5]pyridine[2,1-a]isoquinoline | B102 |

-continued

| No. | Name | Structure |
|---|---|---|
| B103 | 3-(benzyloxy)-11-bromo-8-(4-fluorophenyl)-2-methoxy-5,6,8,9,14,14a-hexahydroindolo[3',2':4,5]pyridine[2,1-a]isoquinoline | 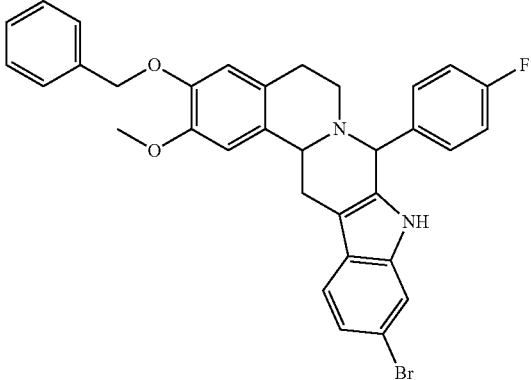<br>B103 |
| B104 | 3-(benzyloxy)-12-bromo-8-(4-fluorophenyl)-2-methoxy-5,6,8,9,14,14a-hexahydroindolo[3',2':4,5]pyridine[2,1-a]isoquinoline | 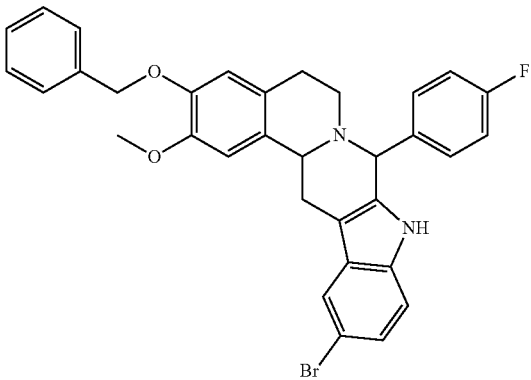<br>B104 |
| B105 | 3-(benzyloxy)-13-bromo-8-(4-fluorophenyl)-2-methoxy-5,6,8,9,14,14a-hexahydroindolo[3',2':4,5]pyridine[2,1-a]isoquinoline | 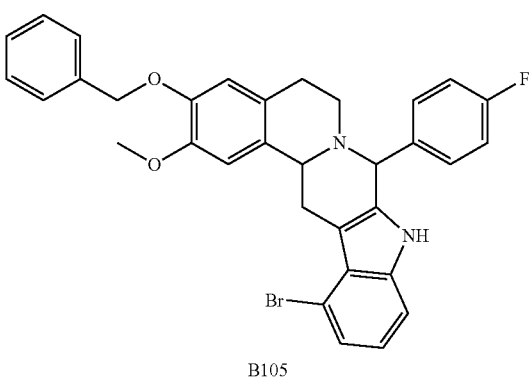<br>B105 |
| B106 | 2-(benzyloxy)-8-phenyl-3,12-dimethoxy-5,6,8,9,14,14a-hexahydroindolo[3',2':4,5]pyridine[2,1-a]isoquinoline | 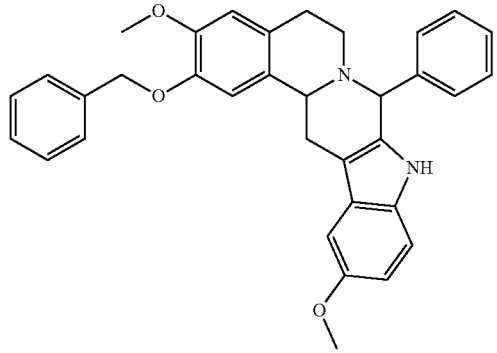 [SMILES: COc1ccc2[nH]c3c(c2c1)CC1c2cc(OCc4ccccc4)c(OC)cc2CCN1C3c1ccccc1] |

-continued

| No. | Name | Structure |
|---|---|---|
| B107 | 2-(benzyloxy)-8-(3-fluorophenyl)-3,12-dimethoxy-5,6,8,9,14,14a-hexahydroindolo[3',2':4,5]pyridine[2,1-a]isoquinoline | 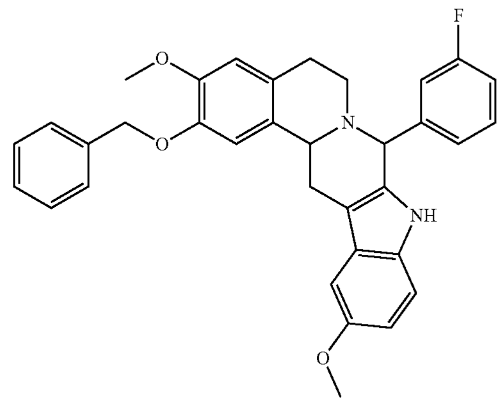 [SMILES: COc1ccc2[nH]c3c(c2c1)CC1c2cc(OCc4ccccc4)c(OC)cc2CCN1C3c1cccc(F)c1] |
| B108 | 2-(benzyloxy)-8-(2-fluorophenyl)-3,12-dimethoxy-5,6,8,9,14,14a-hexahydroindolo[3',2':4,5]pyridine[2,1-a]isoquinoline | 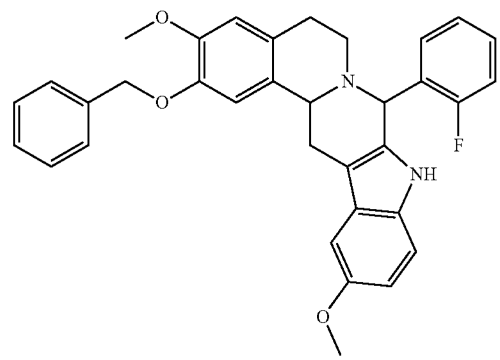 [SMILES: COc1ccc2[nH]c3c(c2c1)CC1c2cc(OCc4ccccc4)c(OC)cc2CCN1C3c1ccccc1F] |
| B109 | 2-(benzyloxy)-8-benzyl-3,12-dimethoxy-5,6,8,9,14,14a-hexahydroindolo[3',2':4,5]pyridine[2,1-a]isoquinoline | 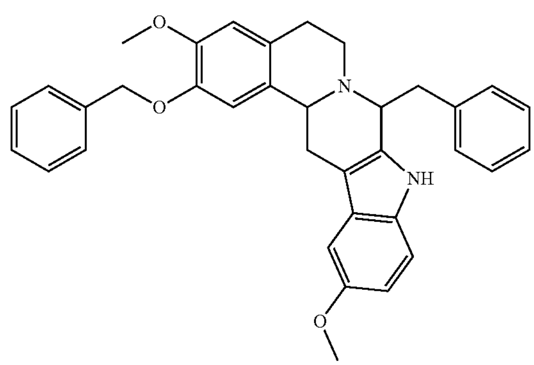 [SMILES: COc1ccc2[nH]c3c(c2c1)CC1c2cc(OCc4ccccc4)c(OC)cc2CCN1C3Cc1ccccc1] |
| B110 | 2-(benzyloxy)-8-thiophene-3,12-dimethoxy-5,6,8,9,14,14a-hexahydroindolo[3',2':4,5]pyridine[2,1-a]isoquinoline | 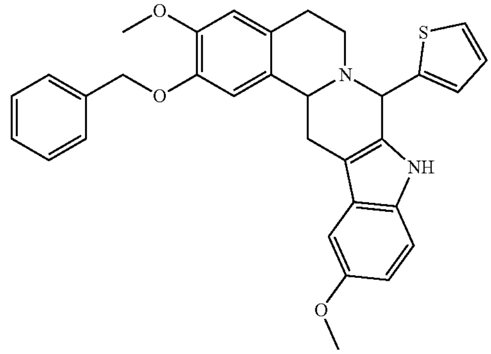 [SMILES: COc1ccc2[nH]c3c(c2c1)CC1c2cc(OCc4ccccc4)c(OC)cc2CCN1C3c1ccco1] |

-continued

| No. | Name | Structure |
|---|---|---|
| B111 | 2-(benzyloxy)-8-furan-3,12-dimethoxy-5,6,8,9,14,14a-hexahydroindolo[3',2':4,5]pyridine[2,1-a]isoquinoline | 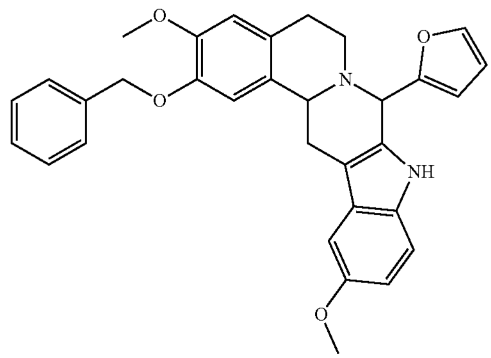 |
| B112 | 2-(benzyloxy)-8-(3-methylfuran)-3,12-dimethoxy-5,6,8,9,14,14a-hexahydroindolo[3',2':4,5]pyridine[2,1-a]isoquinoline | 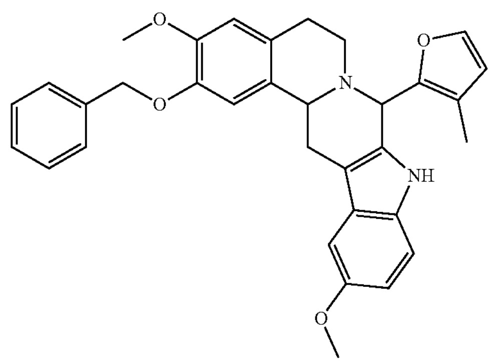 [SMILES: COc1ccc2[nH]c3c(c2c1)CC1c2cc(OCc4ccccc4)c(OC)cc2CCN1C3c1occc1C] |
| B113 | 2-(benzyloxy)-8-(5-methylfuran)-3,12-dimethoxy-5,6,8,9,14,14a-hexahydroindolo[3',2':4,5]pyridine[2,1-a]isoquinoline | 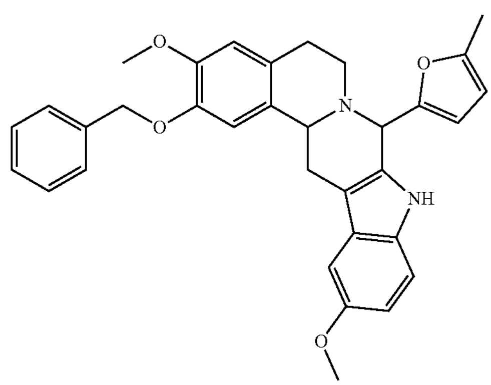 [SMILES: COc1ccc2[nH]c3c(c2c1)CC1c2cc(OCc4ccccc4)c(OC)cc2CCN1C3c1ccc(C)o1] |
| B114 | 2-(benzyloxy)-8-(5-cyanofuran)-3,12-dimethoxy-5,6,8,9,14,14a-hexahydroindolo[3',2':4,5]pyridine[2,1-a]isoquinoline | 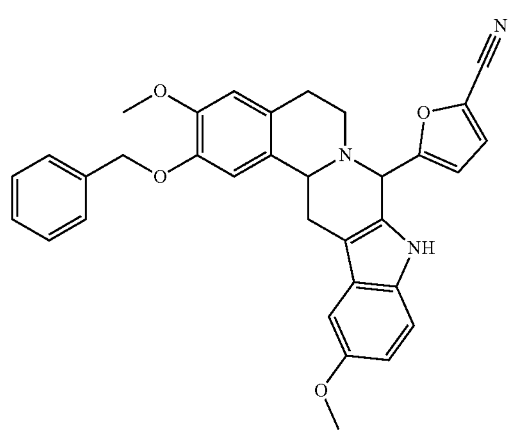 [SMILES: COc1ccc2[nH]c3c(c2c1)CC1c2cc(OCc4ccccc4)c(OC)cc2CCN1C3c1ccc(C#N)o1] |

| No. | Name | Structure |
|---|---|---|
| B115 | 2-(benzyloxy)-8-pyrrole-3,12-dimethoxy-5,6,8,9,14,14a-hexahydroindolo[3',2':4,5]pyridine[2,1-a]isoquinoline | 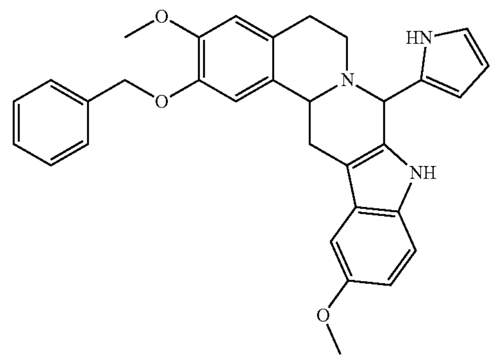 [SMILES: COc1ccc2[nH]c3c(c2c1)CC1c2cc(OCc4ccccc4)c(OC)cc2CCN1C3c1ccc[nH]1] |
| C1 | 2((2,4-di(trifluoromethyl)benzyl)oxy)-3,12-dimethoxy-5,6,8,9,14,14a-hexahydroindolo[3',2':4,5]pyridine[2,1-a]isoquinoline | 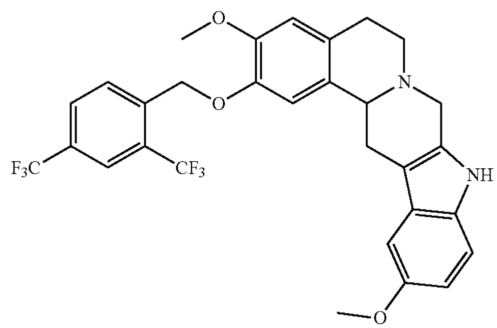 |
| C2 | 2((2,4-di(trifluoromethyl)benzyl)oxy)-3-methoxy-5,6,8,9,14,14a-hexahydroindolo[3',2':4,5]pyridine[2,1-a]isoquinoline | 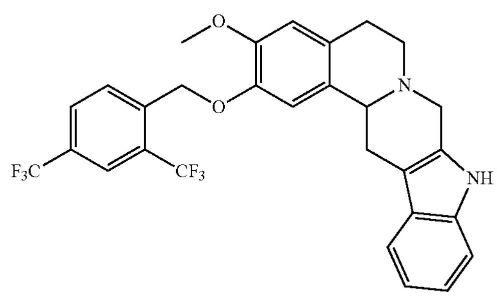 |
| C3 | 3,12-dimethoxy-2-((4-(trifluoromethyl)benzyl)oxy)-5,6,8,9,14,14a-hexahydroindolo[3',2':4,5]pyridine[2,1-a]isoquinoline | 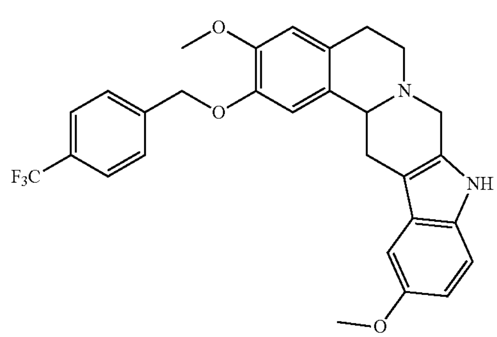 |

-continued

| No. | Name | Structure |
|---|---|---|
| C4 | 3-methoxy-2((4-(trifluoromethyl)benzyl)oxy)-5,6,8,9,14,14a-hexahydroindolo[3',2':4,5]pyridine[2,1-a]isoquinoline | C4 |
| C5 | 2-((4-fluorobenzyl)oxy)-3,12-dimethoxy-5,6,8,9,14,14a-hexahydroindolo[3',2':4,5]pyridine[2,1-a]isoquinoline | C5 |
| C6 | 2-((4-fluorobenzyl)oxy)-3-methoxy-5,6,8,9,14,14a-hexahydroindolo[3',2':4,5]pyridine[2,1-a]isoquinoline | C6 |
| C7 | 2-((3-fluorobenzyl)oxy)-3,12-dimethoxy-5,6,8,9,14,14a-hexahydroindolo[3',2':4,5]pyridine[2,1-a]isoquinoline | C7 |

-continued

| No. | Name | Structure |
|---|---|---|
| C8 | 2-((3-fluorobenzyl)oxy)-3-methoxy-5,6,8,9,14,14a-hexahydroindolo[3',2':4,5]pyridine 2,1-a]isoquinoline | C8 |
| C9 | 2-((2-fluorobenzyl)oxy)-3,12-dimethoxy-5,6,8,9,14,14a-hexahydroindolo[3',2':4,5]pyridine[2,1-a]isoquinoline | C9 |
| C10 | 2-((2-fluorobenzyl)oxy)-3-methoxy-5,6,8,9,14,14a-hexahydroindolo[3',2':4,5]pyridine[2,1-a]isoquinoline | C10 |
| C11 | 3,12-dimethoxy-2-((4-methoxybenzyl)oxy)-5,6,8,9,14,14a-hexahydroindolo[3',2':4,5]pyridine[2,1-a]isoquinoline | C11 |

-continued
| No. | Name | Structure |
|---|---|---|
| C12 | 3-methoxy-2-((4-methoxybenzyl)oxy)-5,6,8,9,14,14a-hexahydroindolo[3',2':4,5]pyridine[2,1-a]isoquinoline | 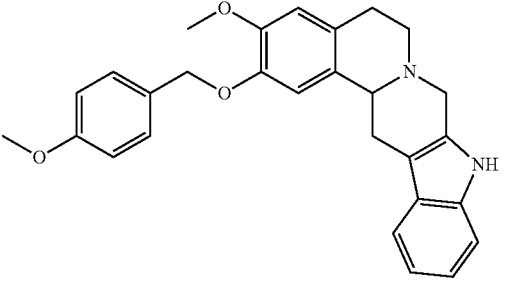<br>C12 |
| C13 | 3,12-dimethoxy-2-((3-methoxybenzyl)oxy)-5,6,8,9,14,14a-hexahydroindolo[3',2':4,5]pyridine[2,1-a]isoquinoline | 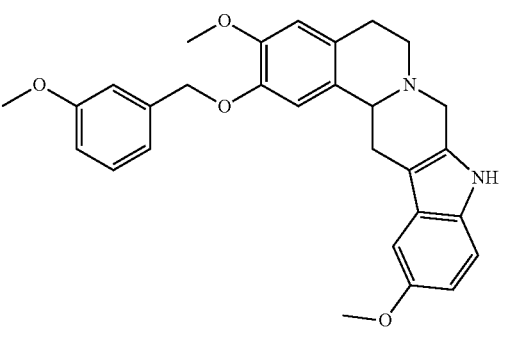<br>C13 |
| C14 | 3-methoxy-2-((3-methoxybenzyl)oxy)-5,6,8,9,14,14a-hexahydroindolo[3',2':4,5]pyridine[2,1-a]isoquinoline | 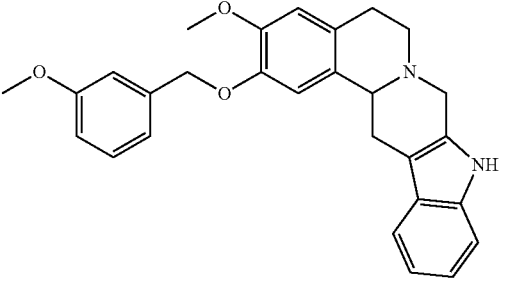<br>C14 |
| C15 | 3,12-dimethoxy-2-((4-methylbenzyl)oxy)-5,6,8,9,14,14a-hexahydroindolo[3',2':4,5]pyridine[2,1-a]isoquinoline | 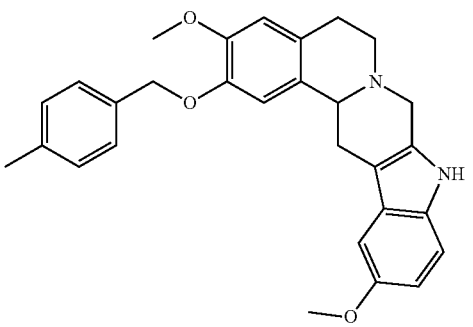<br>C15 |

| No. | Name | Structure |
|---|---|---|
| C16 | 3-methoxy-2-((4-methylbenzyl)oxy)-5,6,8,9,14,14a-hexahydroindolo[3',2':4,5]pyridine[2,1-a]isoquinoline | C16 |
| C17 | 2-((4-chlorobenzyl)oxy)-3,12-dimethoxy-5,6,8,9,14,14a-hexahydroindolo[3',2':4,5]pyridine[2,1-a]isoquinoline | C17 |
| C18 | 2-((4-chlorobenzyl)oxy)-3-methoxy-5,6,8,9,14,14a-hexahydroindolo[3',2':4,5]pyridine[2,1-a]isoquinoline | C18 |
| C19 | 4-(((3,12-dimethoxy-5,6,8,9,14,14a-hexahydroindolo[3',2':4,5]pyridine[2,1-a]isoquinoline-2-yl)oxy)methyl)benzonitrile | C19 |

-continued

| No. | Name | Structure |
|---|---|---|
| C20 | 4-(((3-methoxy-5,6,8,9,14,14a-hexahydroindolo[3',2':4,5]pyridine[2,1-a]isoquinoline-2-yl)oxy)methyl)benzonitrile | 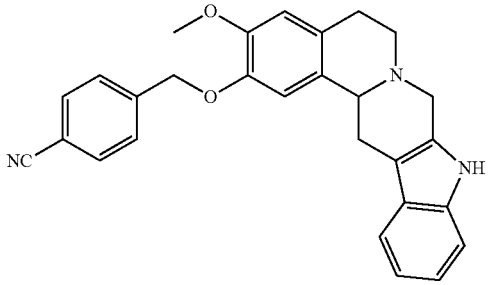 C20 |
| C21 | 2-((4-bromobenzyl)oxy)-3,12-dimethoxy-5,6,8,9,14,14a-hexahydroindolo[3',2':4,5]pyridine[2,1-a]isoquinoline | 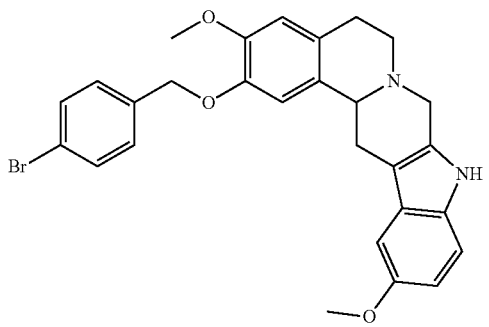 C21 |
| C22 | 2-((4-bromobenzyl)oxy)-3-methoxy-5,6,8,9,14,14a-hexahydroindolo[3',2':4,5]pyridine[2,1-a]isoquinoline | 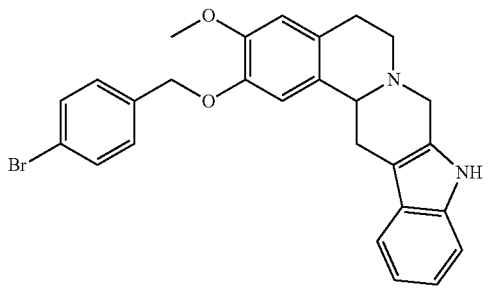 C22 |
| C23 | 2-((3-fluoro-4-(trifluoromethyl)benzyl)oxy)-3,12-dimethoxy-5,6,8,9,14,14a-hexahydroindolo[3',2':4,5]pyridine[2,1-a]isoquinoline | 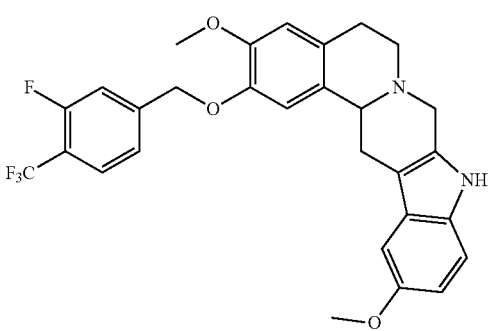 C23 |

-continued

| No. | Name | Structure |
|---|---|---|
| C24 | 2-((3-fluoro-4-(trifluoromethyl)benzyl)oxy)-3-methoxy-5,6,8,9,14,14a-hexahydroindolo[3',2':4,5]pyridine[2,1-a]isoquinoline | 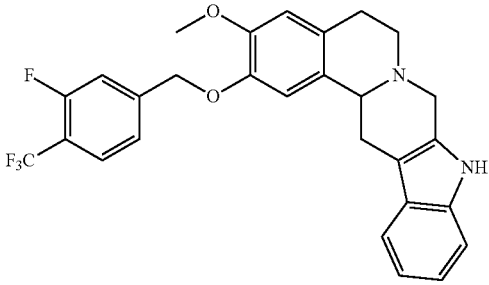<br>C24 |
| C25 | 2-((2-fluoro-4-(trifluoromethyl)benzyl)oxy)-3,12-dimethoxy-5,6,8,9,14,14a-hexahydroindolo[3',2':4,5]pyridine[2,1-a]isoquinoline | 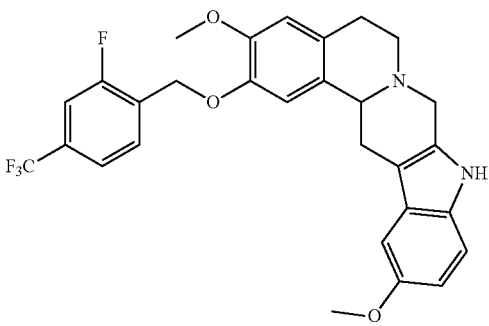<br>C25 |
| C26 | 2-((2-fluoro-4-(trifluoromethyl)benzyl)oxy)-3-methoxy-5,6,8,9,14,14a-hexahydroindolo[3',2':4,5]pyridine[2,1-a]isoquinoline | 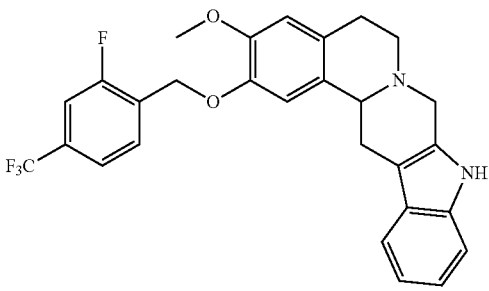<br>C26 |
| C27 | 2-((4-ethylbenzyl)oxy)-3,12-dimethoxy-5,6,8,9,14,14a-hexahydroindolo[3',2':4,5]pyridine[2,1-a]isoquinoline | 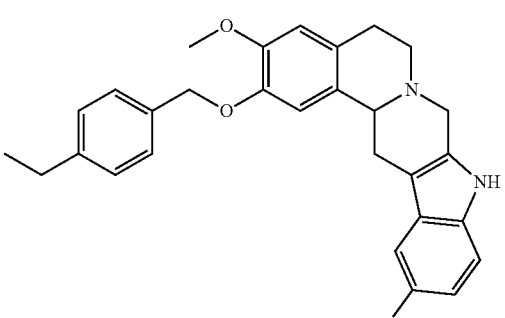<br>C27 |

-continued

| No. | Name | Structure |
|---|---|---|
| C28 | 2-((4-ethylbenzyl)oxy)-3-methoxy-5,6,8,9,14,14a-hexahydroindolo[3',2':4,5]pyridine[2,1-a]isoquinoline | 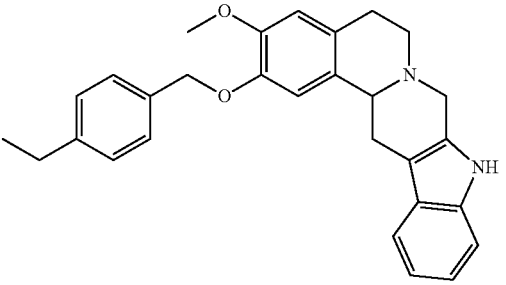<br>C28 |
| C29 | 3,12-dimethoxy-2-(naphthalen-2-ylmethoxy)-5,6,8,9,14,14a-hexahydroindolo[3',2':4,5]pyridine[2,1-a]isoquinoline | 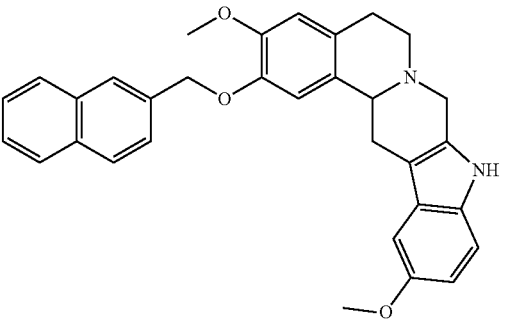<br>C29 |
| C30 | 3-methoxy-2-(naphthalen-2-ylmethoxy)-5,6,8,9,14,14a-hexahydroindolo[3',2':4,5]pyridine[2,1-a]isoquinoline | 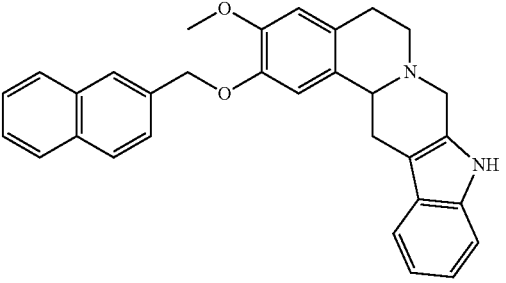<br>C30 |
| C31 | 4-(((3,12-dimethoxy-5,6,8,9,14,14a-hexahydroindolo[3',2':4,5]pyridine[2,1-a]isoquinoline-2-yl)oxo)methyl)benzoate | 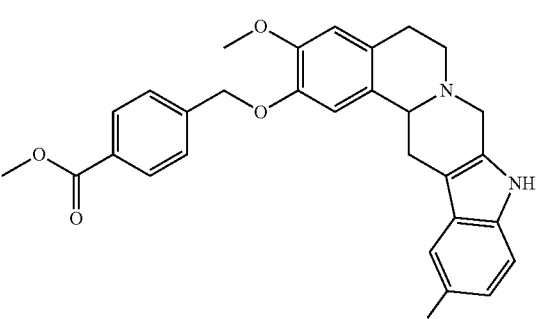<br>C31 |

-continued
| No. | Name | Structure |
|---|---|---|
| C32 | 4-(((3-methoxy-5,6,8,9,14,14a-hexahydroindolo[3',2':4,5]pyridine[2,1-a]isoquinoline-2-yl)oxo)methyl)benzoate | 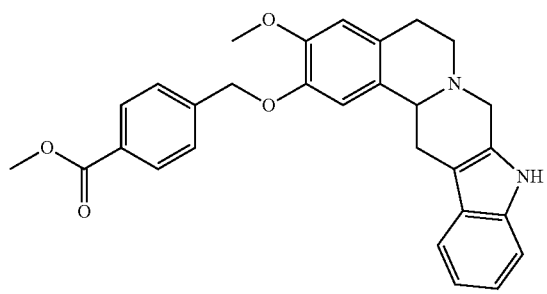 C32 |
| C33 | 2-((4-(1H-pyrazol-1-yl)benzyl)oxy)-3,12-dimethoxy-5,6,8,9,14,14a-hexahydroindolo[3',2':4,5]pyridine[2,1-a]isoquinoline | 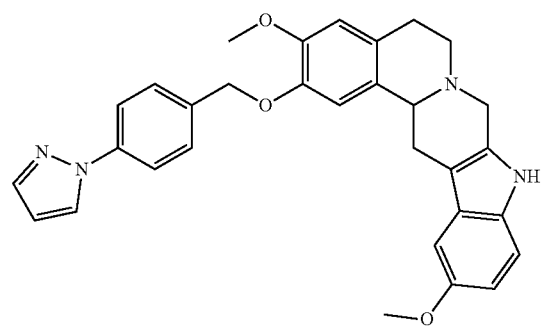 C33 |
| C34 | 2-((4-(1H-pyrazol-1-yl)benzyl)oxy)-3-methoxy-5,6,8,9,14,14a-hexahydroindolo[3',2':4,5]pyridine[2,1-a]isoquinoline | 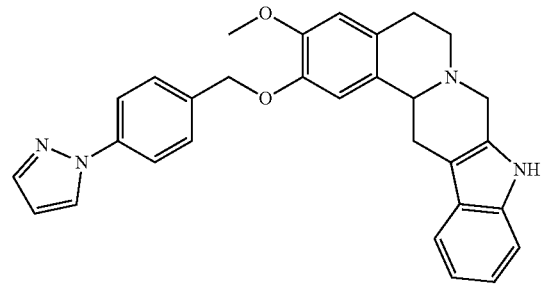 C34 |
| C35 | 3-(benzyloxy)-11-fluoro-2-methoxy-5,6,8,9,14,14a-hexahydroindolo[3',2':4,5]pyridine[2,1-a]isoquinoline | 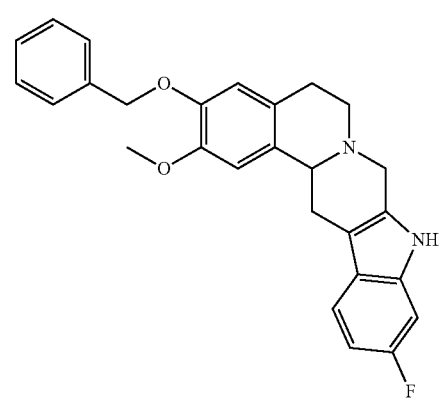 C35 |

-continued
| No. | Name | Structure |
|---|---|---|
| C36 | 3-(benzyloxy)-12-fluoro-2-methoxy-5,6,8,9,14,14a-hexahydroindolo[3',2':4,5]pyridine[2,1-a]isoquinoline | 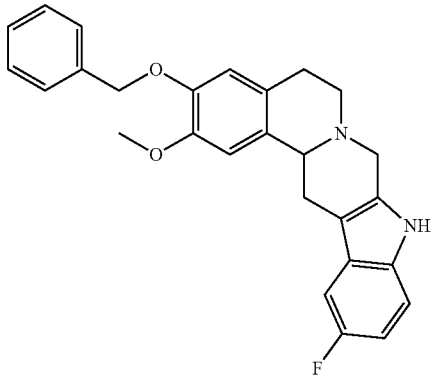<br>C36 |
| C37 | 3-(benzyloxy)-13-fluoro-2-methoxy-5,6,8,9,14,14a-hexahydroindolo[3',2':4,5]pyridine[2,1-a]isoquinoline | 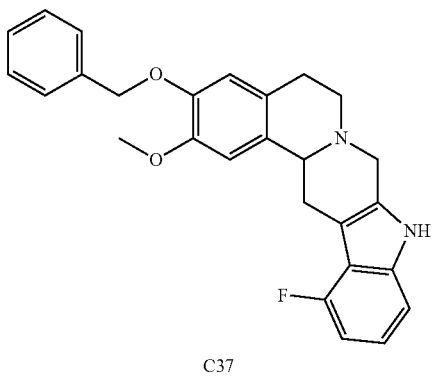 [SMILES: COc1cc2c(cc1OCc1ccccc1)CCN1Cc3[nH]c4cccc(F)c4c3CC21 ; "C37"]<br>C37 |
| C38 | 3-(benzyloxy)-11-chloro-2-methoxy-5,6,8,9,14,14a-hexahydroindolo[3',2':4,5]pyridine[2,1-a]isoquinoline | 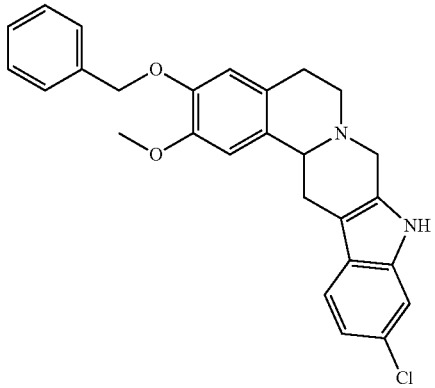<br>C38 |
| C39 | 3-(benzyloxy)-12-chloro-2-methoxy-5,6,8,9,14,14a-hexahydroindolo[3',2':4,5]pyridine[2,1-a]isoquinoline | 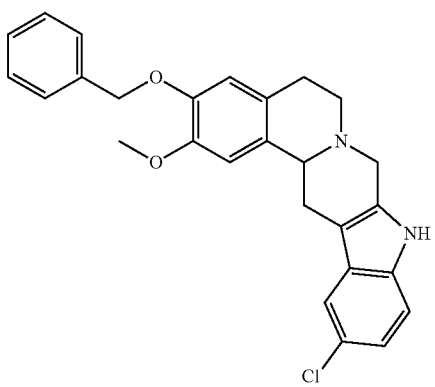<br>C39 |

-continued

| No. | Name | Structure |
|---|---|---|
| C40 | 3-(benzyloxy)-13-chloro-2-methoxy-5,6,8,9,14,14a-hexahydroindolo[3',2':4,5]pyridine[2,1-a]isoquinoline | C40 |
| C41 | 3-(benzyloxy)-11-bromo-2-methoxy-5,6,8,9,14,14a-hexahydroindolo[3',2':4,5]pyridine[2,1-a]isoquinoline | C41 |
| C42 | 3-(benzyloxy)-12-bromo-2-methoxy-5,6,8,9,14,14a-hexahydroindolo[3',2':4,5]pyridine[2,1-a]isoquinoline | C42 |
| C43 | 3-(benzyloxy)-13-bromo-2-methoxy-5,6,8,9,14,14a-hexahydroindolo[3',2':4,5]pyridine[2,1-a]isoquinoline | C43 |

-continued
| No. | Name | Structure |
|---|---|---|
| C44 | 3-(benzyloxy)-2-methoxy-11-methyl-5,6,8,9,14,14a-hexahydroindolo[3',2':4,5]pyridine[2,1-a]isoquinoline | 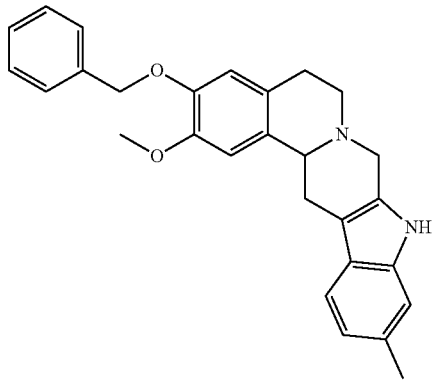<br>C44 |
| C45 | 3-(benzyloxy)-12-ethyl-2-methoxy-5,6,8,9,14,14a-hexahydroindolo[3',2':4,5]pyridine[2,1-a]isoquinoline | 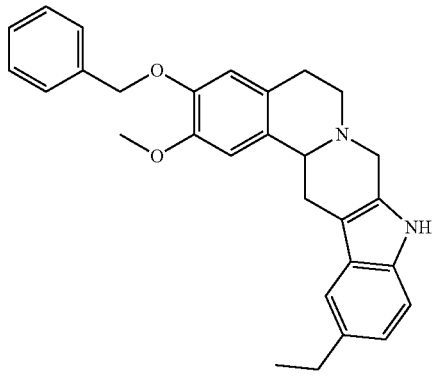<br>C45 |
| C46 | 3-(benzyloxy)-2-methoxy-5,6,8,9,14,14a-hexahydroindolo[3',2':4,5]pyridine[2,1-a]isoquinoline-12-phenol | 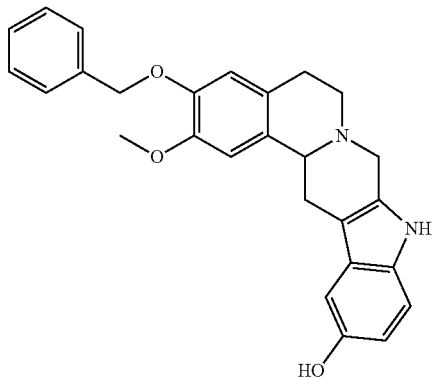<br>C46 |

-continued

| No. | Name | Structure |
|---|---|---|
| C47 | 2,12-dimethoxy-3-((4-(trifluoromethyl)benzyl)oxy)-5,6,8,9,14,14a-hexahydro-indolo[3',2':4,5]pyridine[2,1-a]isoquinoline | 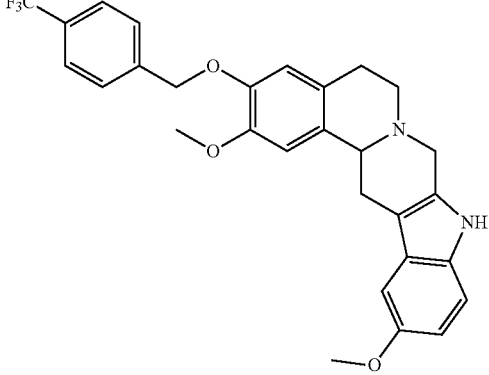<br>C47 |
| C48 | 2-methoxy-3-((4-(trifluoromethyl)benzyl)oxy)-5,6,8,9,14,14a-hexahydroindolo[3',2':4,5]pyridine[2,1-a]isoquinoline | 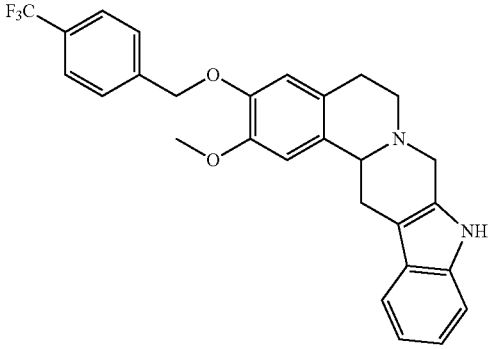<br>C48 |
| C49 | 3-((4-fluorobenzyl)oxy)-2,12-dimethoxy-5,6,8,9,14,14a-hexahydroindolo[3',2':4,5]pyridine[2,1-a]isoquinoline | 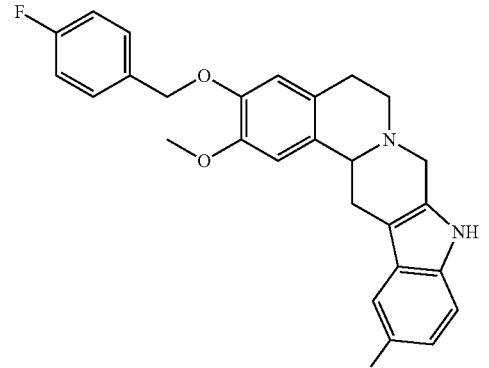<br>C49 |
| C50 | 3-((4-fluorobenzyl)oxy)-2-methoxy-5,6,8,9,14,14a-hexahydroindolo[3',2':4,5]pyridine[2,1-a]isoquinoline | 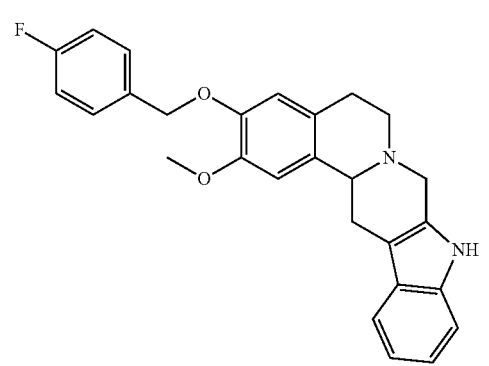<br>C50 |

| No. | Name | Structure |
|---|---|---|
| C51 | 3-((3-fluorobenzyl)oxy)-2,12-dimethoxy-5,6,8,9,14,14a-hexahydroindolo[3',2':4,5]pyridine[2,1-a]isoquinoline | 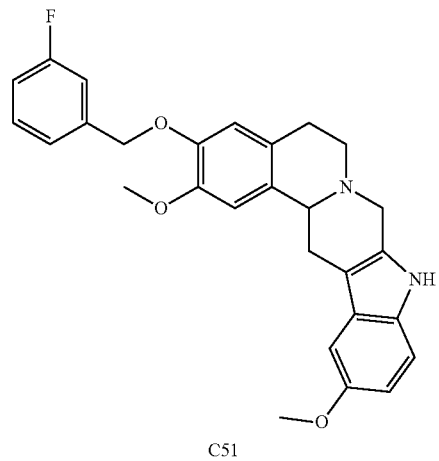 [SMILES: COc1ccc2[nH]c3c(c2c1)CC1c2cc(OC)c(OCc4cccc(F)c4)cc2CCN1C3 ; "C51"]<br>C51 |
| C52 | 3-((3-fluorobenzyl)oxy)-2-methoxy-5,6,8,9,14,14a-hexahydroindolo[3',2':4,5]pyridine[2,1-a]isoquinoline | 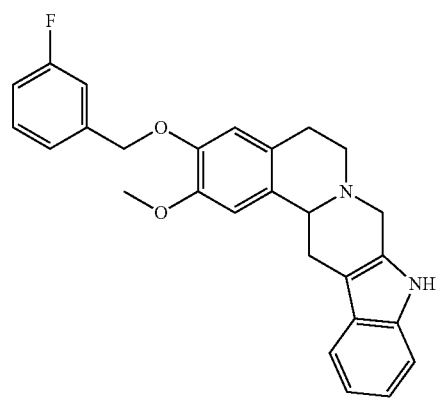<br>C52 |
| C53 | 3-((2-fluorobenzyl)oxy)-2,12-dimethoxy-5,6,8,9,14,14a-hexahydroindolo[3',2':4,5]pyridine[2,1-a]isoquinoline | 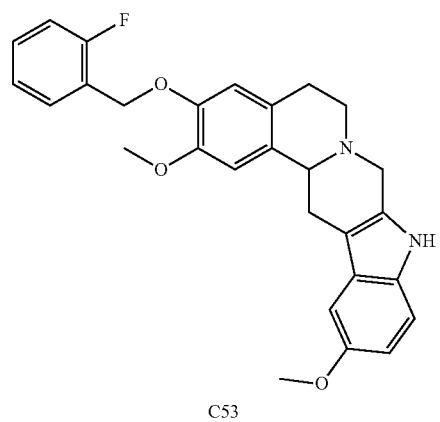 [SMILES: COc1ccc2[nH]c3c(c2c1)CC1c2cc(OC)c(OCc4ccccc4F)cc2CCN1C3 ; "C53"]<br>C53 |

-continued
| No. | Name | Structure |
|---|---|---|
| C54 | 3-((2-fluorobenzyl)oxy)-2-methoxy-5,6,8,9,14,14a-hexahydroindolo[3',2':4,5]pyridine[2,1-a]isoquinoline | 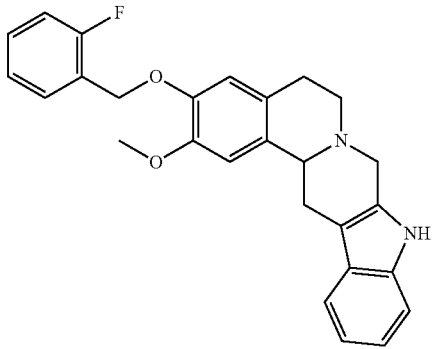<br>C54 |
| C55 | 2,12-dimethoxy-3-((4-methoxybenzyl)oxy)-5,6,8,9,14,14a-hexahydroindolo[3',2':4,5]pyridine[2,1-a]isoquinoline | 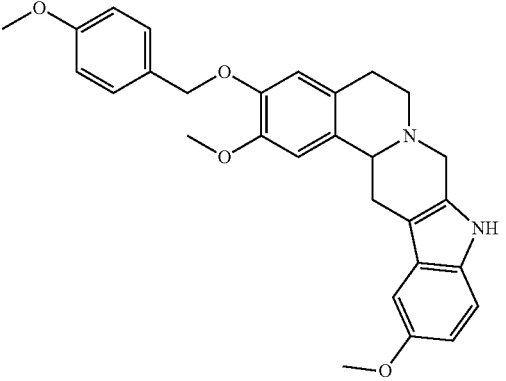<br>C55 |
| C56 | 2-methoxy-3-((4-methoxybenzyl)oxy)-5,6,8,9,14,14a-hexahydroindolo[3',2':4,5]pyridine[2,1-a]isoquinoline | 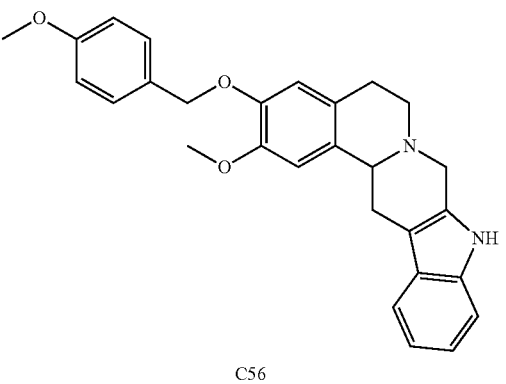 [SMILES: COc1ccc(COc2cc3c(cc2OC)C2Cc4c([nH]c5ccccc45)CN2CC3)cc1 ; "C56"]<br>C56 |
| C57 | 2,12-dimethoxy-3-((3-methoxybenzyl)oxy)-5,6,8,9,14,14a-hexahydroindolo[3',2':4,5]pyridine[2,1-a]isoquinoline | 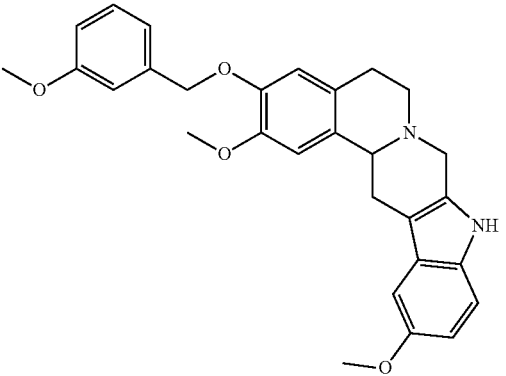<br>C57 |

-continued
| No. | Name | Structure |
|---|---|---|
| C58 | 2-methoxy-3-((3-methoxybenzyl)oxy)-5,6,8,9,14,14a-hexahydroindolo[3',2':4,5]pyridine[2,1-a]isoquinoline | 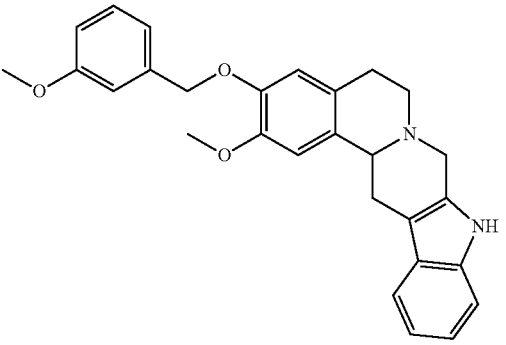<br>C58 |
| C59 | 2,12-dimethoxy-3-((4-methylbenzyl)oxy)-5,6,8,9,14,14a-hexahydroindolo[3',2':4,5]pyridine[2,1-a]isoquinoline | 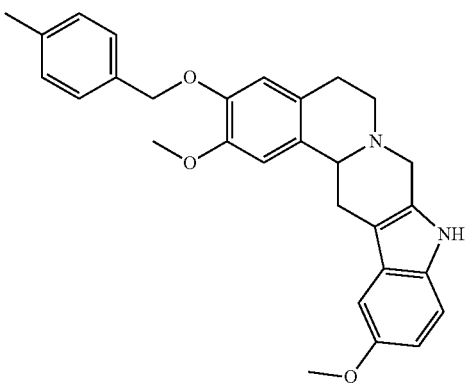<br>C59 |
| C60 | 2-methoxy-3-((4-methylbenzyl)oxy)-5,6,8,9,14,14a-hexahydroindolo[3',2':4,5]pyridine[2,1-a]isoquinoline | 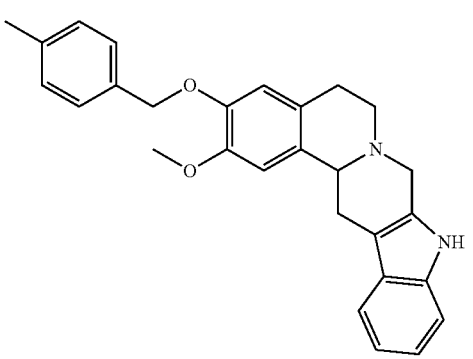<br>C60 |
| C61 | 3-((4-chlorobenzyl)oxy)-2,12-dimethoxy-5,6,8,9,14,14a-hexahydroindolo[3',2':4,5]pyridine[2,1-a]isoquinoline | 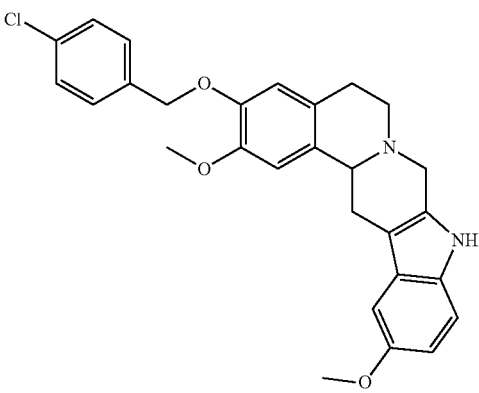<br>C61 |

-continued

| No. | Name | Structure |
|-----|------|-----------|
| C62 | 3-((4-chlorobenzyl)oxy)-2-methoxy-5,6,8,9,14,14a-hexahydroindolo[3',2':4,5]pyridine[2,1-a]isoquinoline | 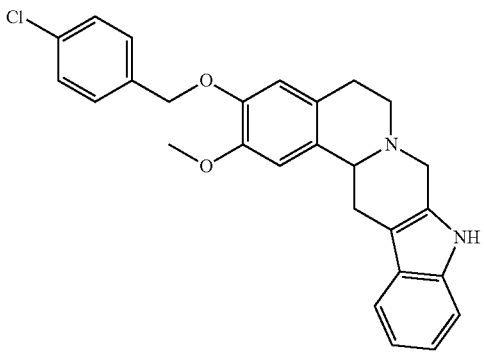<br>C62 |
| C63 | 4-(((2,12-dimethoxy-5,6,8,9,14,14a-hexahydroindolo[3',2':4,5]pyridine[2,1-a]isoquinoline-3-yl)oxy)methyl)benzonitrile | 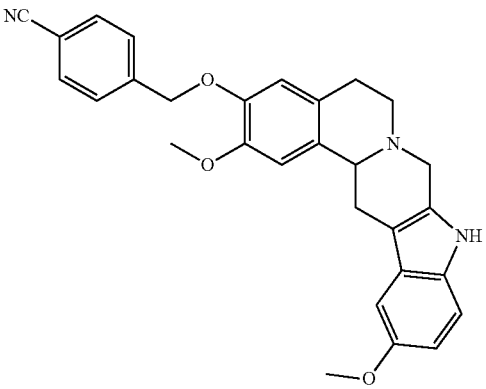<br>C63 |
| C64 | 4-(((2-methoxy-5,6,8,9,14,14a-hexahydroindolo[3',2':4,5]pyridine[2,1-a]isoquinoline-3-yl)oxy)methyl)benzonitrile | 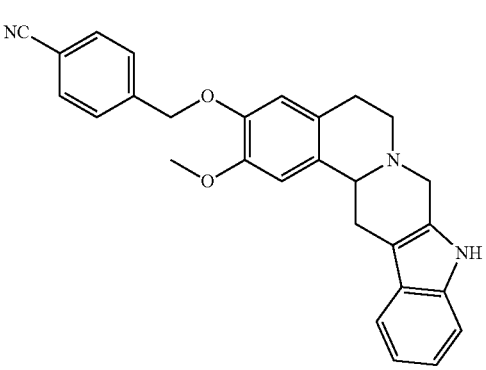<br>C64 |
| C65 | 3-((4-bromobenzyl)oxy)-2,12-dimethoxy-5,6,8,9,14,14a-hexahydroindolo[3',2':4,5]pyridine[2,1-a]isoquinoline | 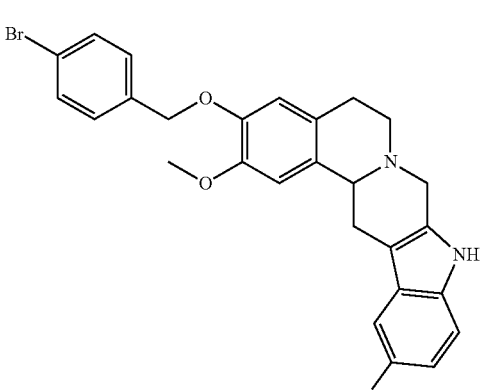<br>C65 |

-continued
| No. | Name | Structure |
|---|---|---|
| C66 | 3-((4-bromobenzyl)oxy)-2-methoxy-5,6,8,9,14,14a-hexahydroindolo[3',2':4,5]pyridine 2,1-a]isoquinoline | 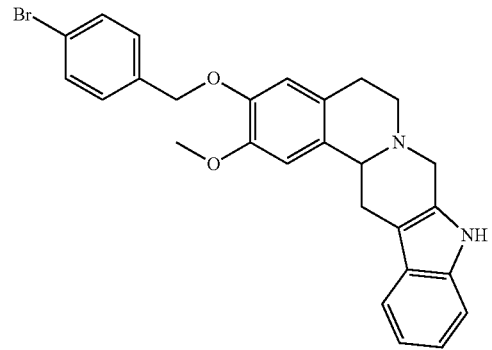<br>C66 |
| C67 | 3-((3-fluoro-4-(trifluoromethyl)benzyl)oxy)-2,12-dimethoxy-5,6,8,9,14,14a-hexahydroindolo[3',2':4,5]pyridine[2,1-a]isoquinoline | 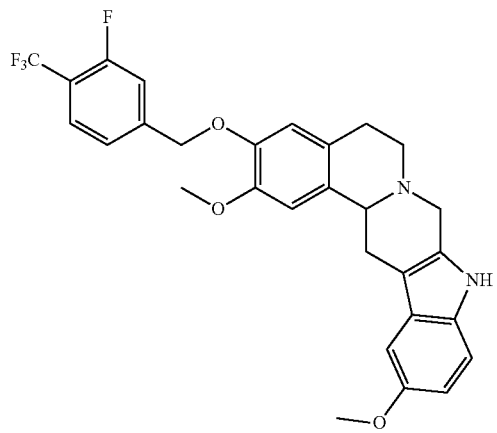<br>C67 |
| C68 | 3-((3-fluoro-4-(trifluoromethyl)benzyl)oxy)-2-methoxy-5,6,8,9,14,14a-hexahydroindolo[3',2':4,5]pyridine[2,1-a]isoquinoline | 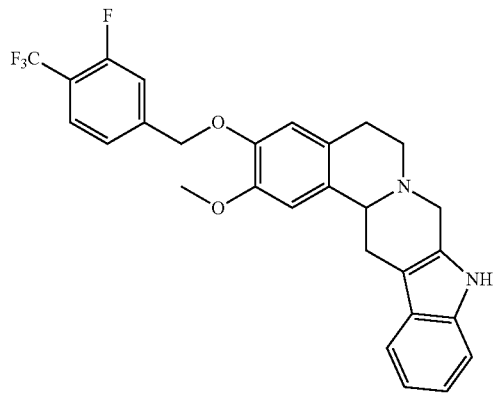<br>C68 |

-continued

| No. | Name | Structure |
|---|---|---|
| C69 | 3-((2-fluoro-4-(trifluoromethyl)benzyl)oxy)-2,12-dimethoxy-5,6,8,9,14,14a-hexahydroindolo[3',2':4,5]pyridine[2,1-a]isoquinoline | C69 |
| C70 | 3-((2-fluoro-4-(trifluoromethyl)benzyl)oxy)-2-methoxy-5,6,8,9,14,14a-hexahydroindolo[3',2':4,5]pyridine[2,1-a]isoquinoline | C70 |
| C71 | 3-((4-ethylbenzyl)oxy)-2,12-dimethoxy-5,6,8,9,14,14a-hexahydroindolo[3',2':4,5]pyridine[2,1-a]isoquinoline | C71 |
| C72 | 3-((4-ethylbenzyl)oxy)-2-methoxy-5,6,8,9,14,14a-hexahydroindolo[3',2':4,5]pyridine[2,1-a]isoquinoline | C72 |

-continued
| No. | Name | Structure |
|---|---|---|
| C73 | 2,12-dimethoxy-3-(naphthalen-2-ylmethoxy)-5,6,8,9,14,14a-hexahydroindolo[3',2':4,5]pyridine[2,1-a]isoquinoline | 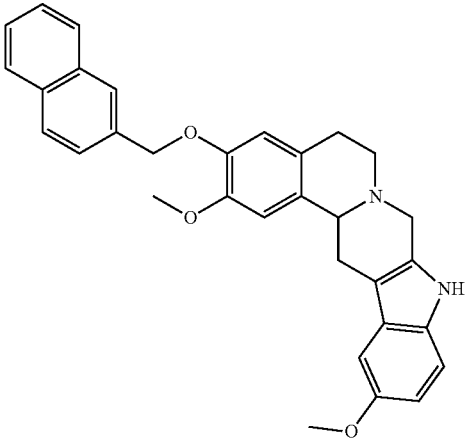 C73 |
| C74 | 2-methoxy-3-(naphthalen-2-ylmethoxy)-5,6,8,9,14,14a-hexahydroindolo[3',2':4,5]pyridine[2,1-a]isoquinoline | 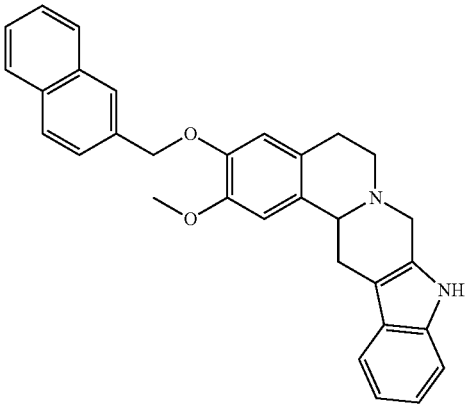 C74 |
| C75 | 4-(((2,12-dimethoxy-5,6,8,9,14,14a-hexahydroindolo[3',2':4,5]pyridine[2,1-a]isoquinoline-3-yl)oxo)methyl)benzoate | 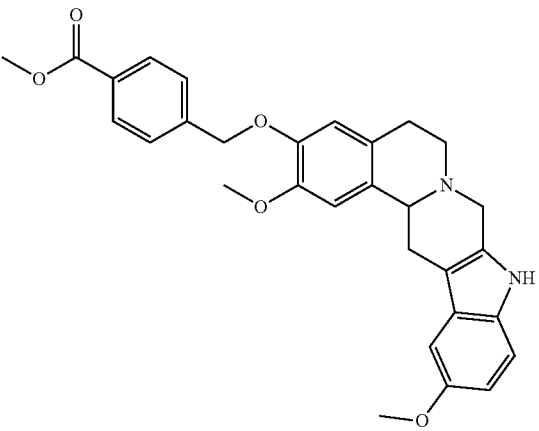 C75 |

| No. | Name | Structure |
|---|---|---|
| C76 | 4-(((2-methoxy-5,6,8,9,14,14a-hexahydroindolo[3',2':4,5]pyridine[2,1-a]isoquinoline-3-yl)oxo)methyl)benzoate | 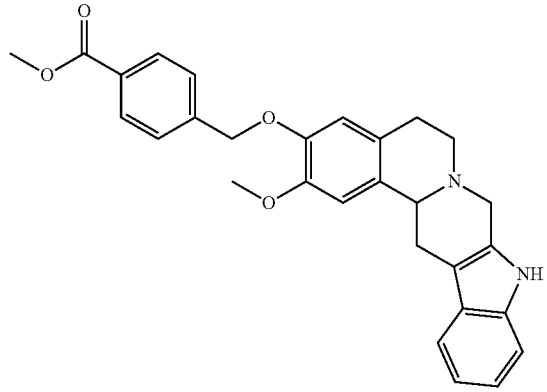<br>C76 |
| C77 | 3-((4-(1H-pyrazol-1-yl)benzyl)oxy)-2,12-dimethoxy-5,6,8,9,14,14a-hexahydroindolo[3',2':4,5]pyridine[2,1-a]isoquinoline | 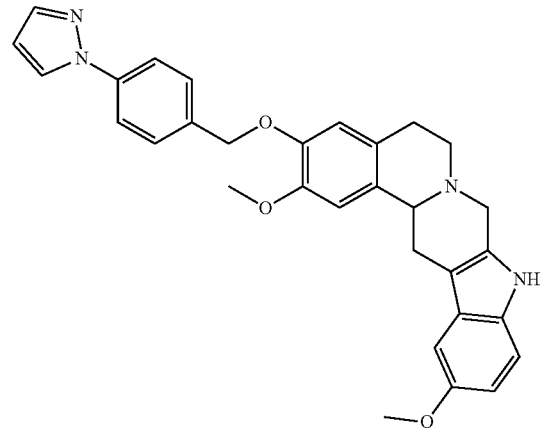<br>C77 |
| C78 | 3-((4-(1H-pyrazol-1-yl)benzyl)oxy)-2-methoxy-5,6,8,9,14,14a-hexahydroindolo[3',2':4,5]pyridine[2,1-a]isoquinoline | 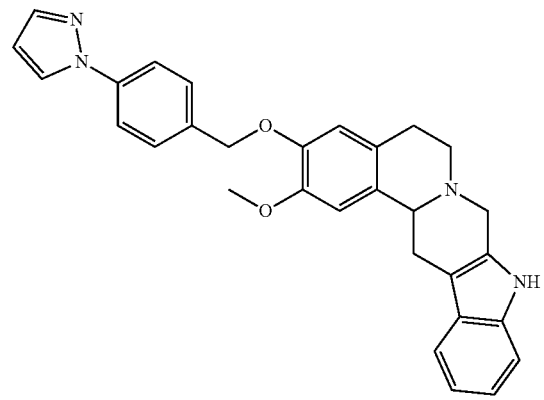<br>C78 |

-continued
| No. | Name | Structure |
|---|---|---|
| C79 | 2,12-dimethoxy-3-((4-(methylsulfonyl)benzyl)oxy)-5,6,8,9,14,14a-hexahydroindolo[3',2':4,5]pyridine[2,1-a]isoquinoline | 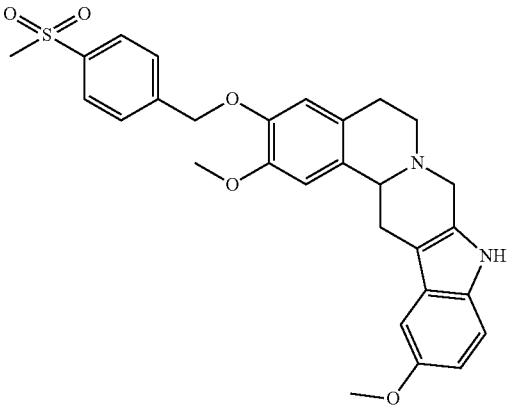<br>C79 |
| C80 | 2-methoxy-3-((4-(methylsulfonyl)benzyl)oxy)-5,6,8,9,14,14a-hexahydroindolo[3',2':4,5]pyridine[2,1-a]isoquinoline | 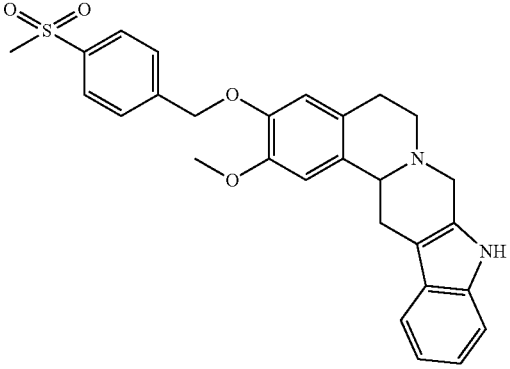<br>C80 |
| C81 | 3-(benzyloxy)-11-fluoro-2-methoxy-5,6,8,9,14,14a-hexahydroindolo[3',2':4,5]pyridine[2,1-a]isoquinoline | 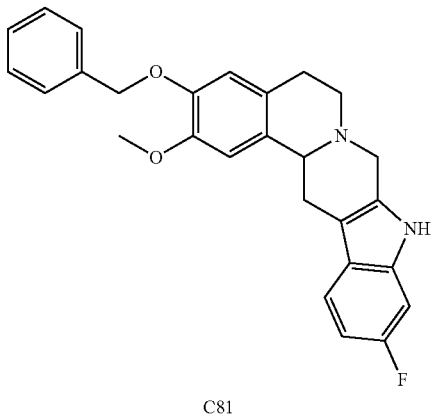 [SMILES: COc1cc2c(cc1OCc1ccccc1)CCN1Cc3[nH]c4cc(F)ccc4c3CC21 ; "C81"]<br>C81 |

-continued
| No. | Name | Structure |
|---|---|---|
| C82 | 3-(benzyloxy)-12-fluoro-2-methoxy-5,6,8,9,14,14a-hexahydroindolo[3',2':4,5]pyridine[2,1-a]isoquinoline | 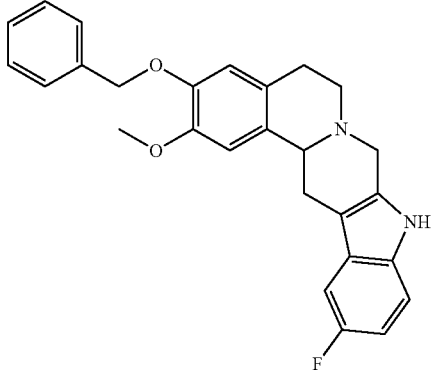<br>C82 |
| C83 | 3-(benzyloxy)-13-fluoro-2-methoxy-5,6,8,9,14,14a-hexahydroindolo[3',2':4,5]pyridine[2,1-a]isoquinoline | 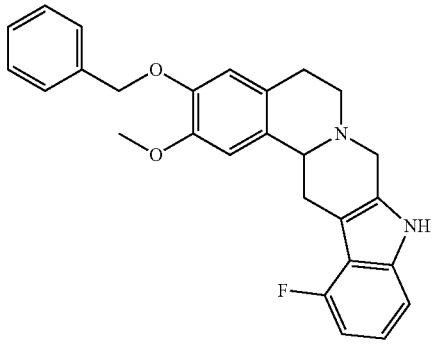<br>C83 |
| C84 | 3-(benzyloxy)-11-chloro-2-methoxy-5,6,8,9,14,14a-hexahydroindolo[3',2':4,5]pyridine[2,1-a]isoquinoline | 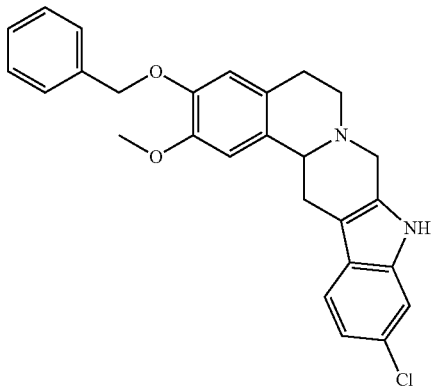<br>C84 |

-continued
| No. | Name | Structure |
|---|---|---|
| C85 | 3-(benzyloxy)-12-chloro-2-methoxy-5,6,8,9,14,14a-hexahydroindolo[3',2':4,5]pyridine[2,1-a]isoquinoline | 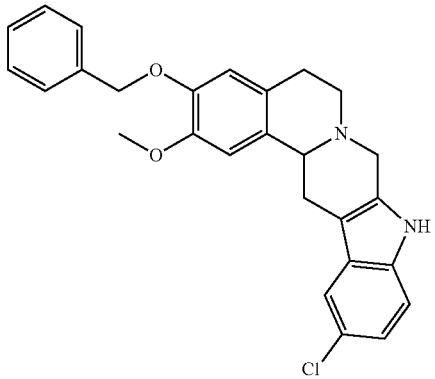<br>C85 |
| C86 | 3-(benzyloxy)-13-chloro-2-methoxy-5,6,8,9,14,14a-hexahydroindolo[3',2':4,5]]pyridine[2,1-a]isoquinoline | 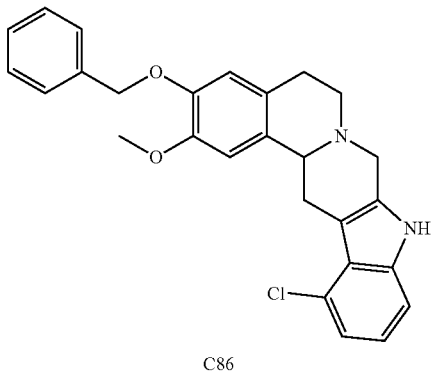 [SMILES: COc1cc2c(cc1OCc1ccccc1)CCN1Cc3[nH]c4cccc(Cl)c4c3CC21 ; "C86"]<br>C86 |
| C87 | 3-(benzyloxy)-11-bromo-2-methoxy-5,6,8,9,14,14a-hexahydroindolo[3',2':4,5]pyridine[2,1-a]isoquinoline | 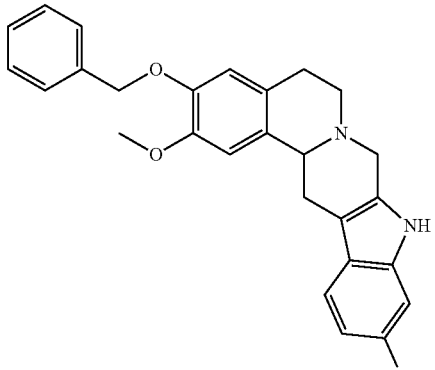<br>C87 |
| C88 | 3-(benzyloxy)-12-bromo-2-methoxy-5,6,8,9,14,14a-hexahydroindolo[3',2':4,5]pyridine[2,1-a]isoquinoline | 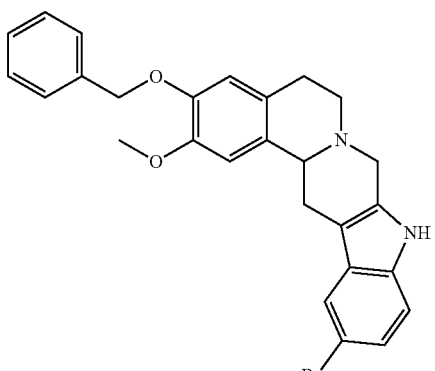<br>C88 |

-continued
| No. | Name | Structure |
|---|---|---|
| C89 | 3-(benzyloxy)-13-bromo-2-methoxy-5,6,8,9,14,14a-hexahydroindolo[3',2':4,5]pyridine[2,1-a]isoquinoline | 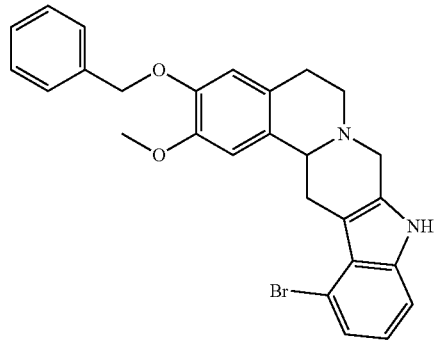<br>C89 |
| C90 | 3-(benzyloxy)-2-methoxy-11-methyl-5,6,8,9,14,14a-hexahydroindolo[3',2':4,5]pyridine[2,1-a]isoquinoline | 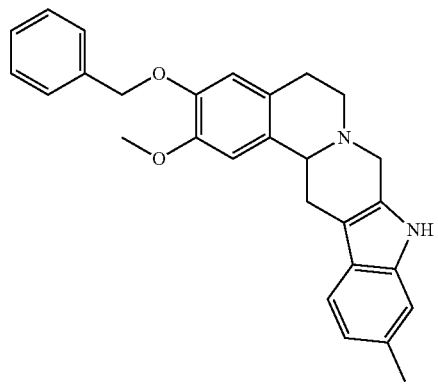<br>C90 |
| C91 | 3-(benzyloxy)-2-methoxy-12-ethyl-5,6,8,9,14,14a-hexahydroindolo[3',2':4,5]pyridine[2,1-a]isoquinoline | 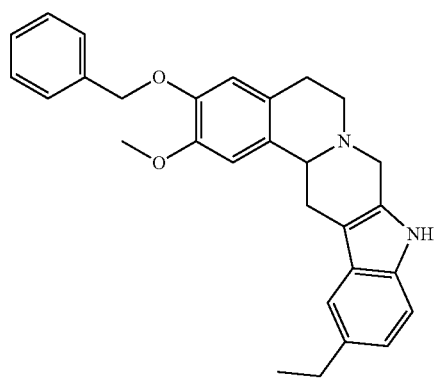<br>C91 |

| No. | Name | Structure |
|---|---|---|
| C92 | 2,12-dimethoxy-5,6,8,9,14,14a-hexahydroindolo[3',2':4,5]pyridine[2,1-a]isoquinoline-3-ylbenzenesulfonate | 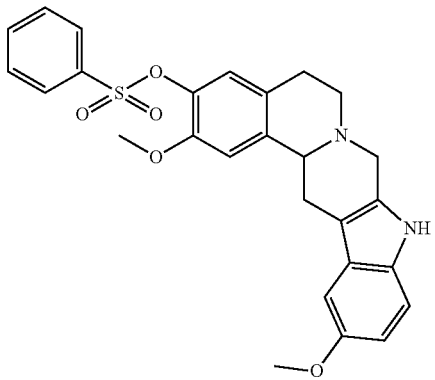 C92 |
| C93 | 3,12-dimethoxy-5,6,8,9,14,14a-hexahydroindolo[3',2':4,5]pyridine[2,1-a]isoquinoline-2-ylbenzenesulfonate | 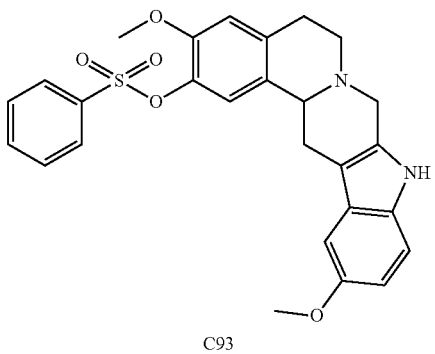 C93 |
| C94 | 2,11,12-trimethoxy-5,6,8,9,14,14a-hexahydroindolo[3',2':4,5]pyridine[2,1-a]isoquinoline-3-ylbenzenesulfonate | 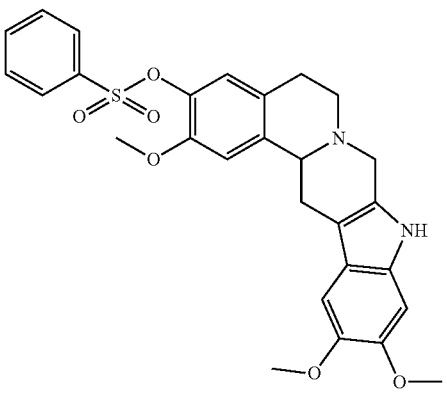 C94 |
| C95 | 3,11,12-trimethoxy-5,6,8,9,14,14a-hexahyoindolo[3',2':4,5]pyridine[2,1-a]isoquinoline-2-ylbenzenesulfonate | 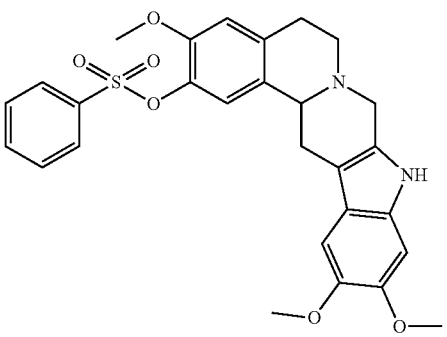 C95 |

| No. | Name | Structure |
|---|---|---|
| C98 | 4-(((2,12-dimethoxy-5,6,8,9,14,14a-hexahydroindolo[3',2':4,5]pyridine[2,1-a]isoquinoline-3-yl)oxy)methyl)benzoic acid | 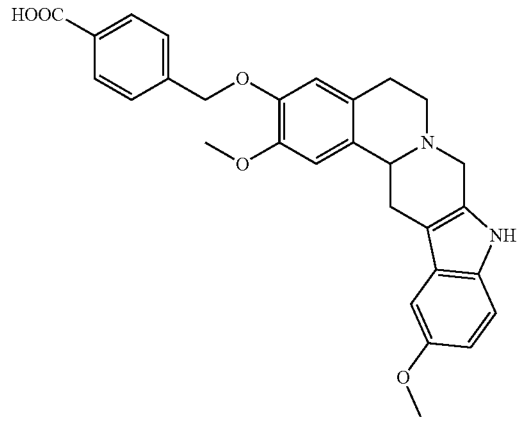 [SMILES: COc1ccc2[nH]c3c(c2c1)CC1c2cc(OC)c(OCc4ccc(C(=O)O)cc4)cc2CCN1C3] |
| C99 | 4-(((3,12-dimethoxy-5,6,8,9,14,14a-hexahydroindolo[3',2':4,5]pyridine[2,1-a]isoquinoline-2-yl)oxy)methyl)aniline | 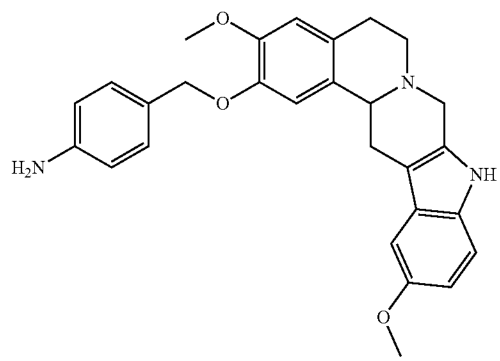 |
| C100 | 4-(((2,12-dimethoxy-5,6,8,9,14,14a-hexahydroindolo[3',2':4,5]pyridine[2,1-a]isoquinoline-3-yl)oxy)methyl)aniline | 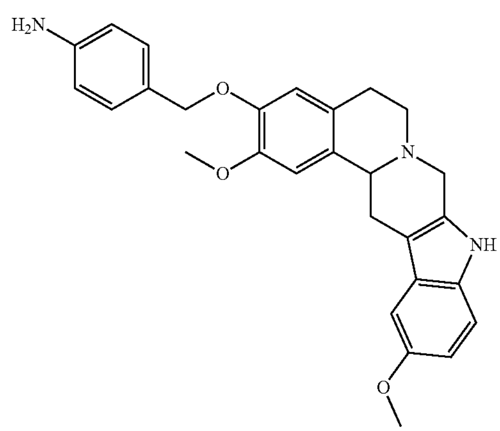 |
| C101 | 4-(((3,12-dimethoxy-5,6,8,9,14,14a-hexahydroindolo[3',2':4,5]pyridine[2,1-a]isoquinoline-2-yl)oxo)methyl)phenol | 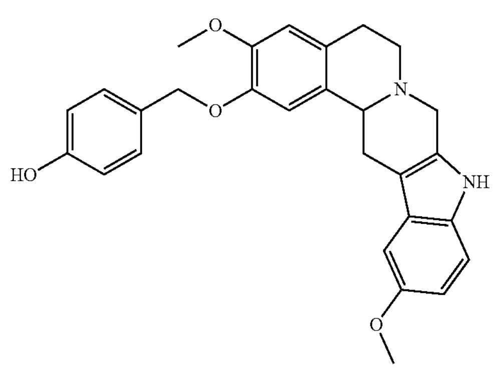 [SMILES: COc1ccc2[nH]c3c(c2c1)CC1c2cc(OCc4ccc(O)cc4)c(OC)cc2CCN1C3] |

-continued

| No. | Name | Structure |
|---|---|---|
| C102 | 4-(((2,12-dimethoxy-5,6,8,9,14,14a-hexahydroindolo[3',2':4,5]pyridine[2,1-a]isoquinoline-3-yl)oxo)methyl)phenol | 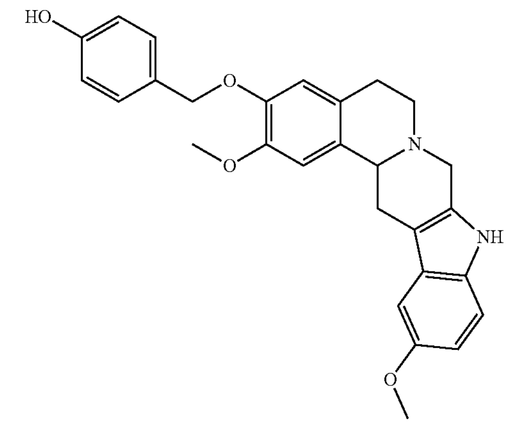 [SMILES: COc1ccc2[nH]c3c(c2c1)CC1c2cc(OC)c(OCc4ccc(O)cc4)cc2CCN1C3] |
| C103 | 4-(((3,12-dimethoxy-5,6,8,9,14,14a-hexahydroindolo[3',2':4,5]pyridine[2,1-a]isoquinoline-2-yl)oxy)methyl)benzoic acid | 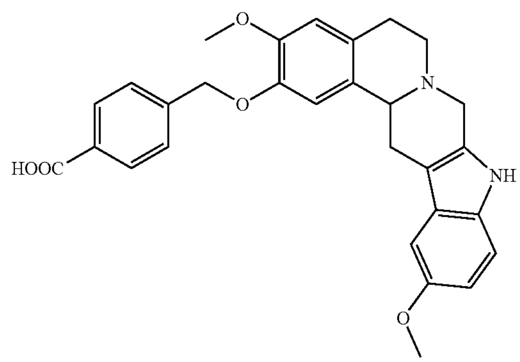 [SMILES: COc1ccc2[nH]c3c(c2c1)CC1c2cc(OCc4ccc(C(=O)O)cc4)c(OC)cc2CCN1C3] |
| (S)-C3 | S)-3,12-dimethoxy-2-((4-(trifluoromethyl)benzyl)oxy)-5,6,8,9,14,14a-hexahydroindolo[3',2':4,5]pyrido[2,1-a]isoquinoline | 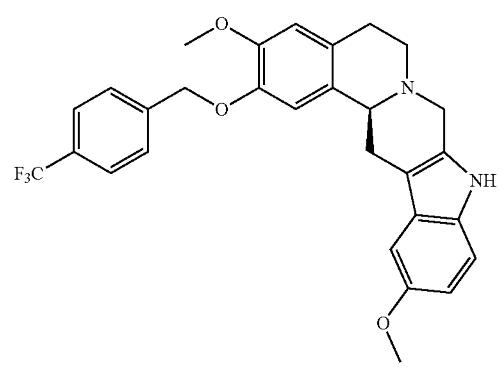 |
| (R)-C3 | R)-3,12-dimethoxy-2-((4-(trifluoromethyl)benzyl)oxy)-5,6,8,9,14,14a-hexahydroindolo[3',2':4,5]pyrido[2,1-a]isoquinoline | 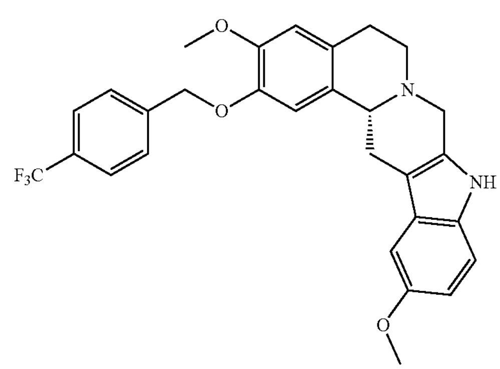 |

-continued

| No. | Name | Structure |
|---|---|---|
| (S)-C47 | S)-2,12-dimethoxy-3-((4-(trifluoromethyl)benzyl)oxy)-5,6,8,9,14,14a-hexahydroindolo[3',2':4,5]pyrido[2,1-a]isoquinoline | 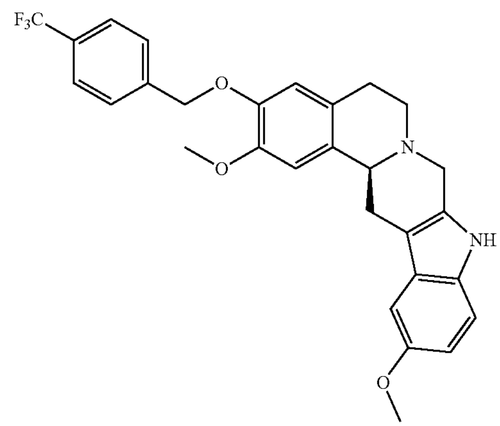 |
| (R)-C47 | R)-2,12-dimethoxy-3-((4-(trifluoromethyl)benzyl)oxy)-5,6,8,9,14,14a-hexahydroindolo[3',2':4,5]pyrido[2,1-a]isoquinoline | 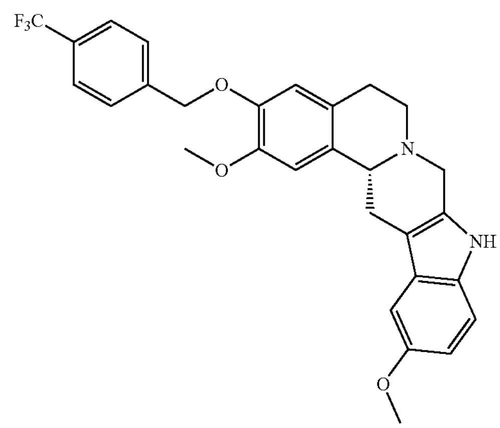 |
| C104 | 2,12-dimethoxy-3-((2-methoxybenzyl)oxy)-5,6,8,9,14,14a-hexahydroindolo[3',2':4,5]pyridine[2,1-a]isoquinoline | 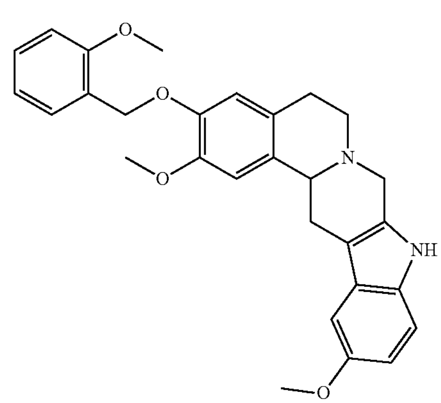 |

-continued
| No. | Name | Structure |
|---|---|---|
| C105 | 2-methoxy-3-((2-methoxybenzyl)oxy)-5,6,8,9,14,14a-hexahydroindolo[3',2':4,5]pyridine[2,1-a]isoquinoline | 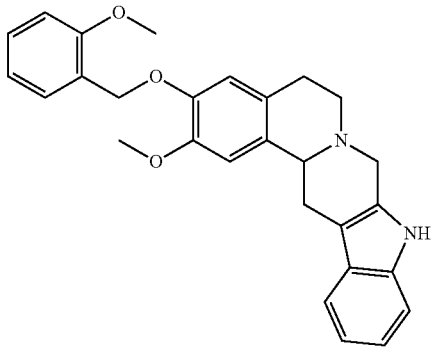<br>C105 |
| C106 | 2,12-dimethoxy-3-((3-methylbenzyl)oxy)-5,6,8,9,14,14a-hexahydroindolo[3',2':4,5]pyridine[2,1-a]isoquinoline | 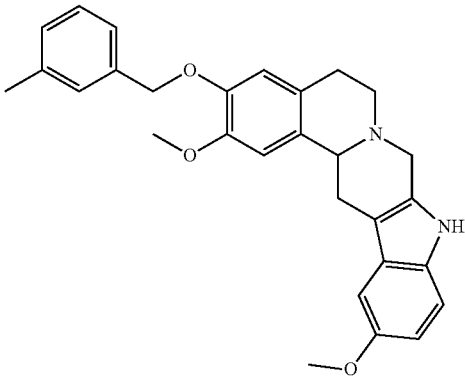<br>C106 |
| C107 | 2-methoxy-3-((3-methylbenzyl)oxy)-5,6,8,9,14,14a-hexahydroindolo[3',2':4,5]pyridine[2,1-a]isoquinoline | 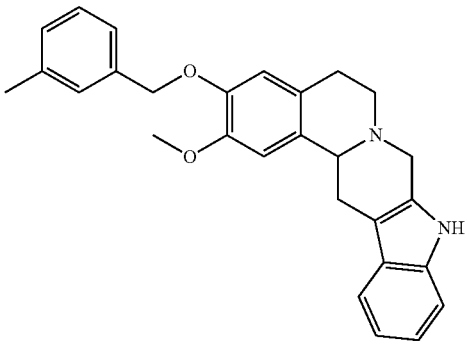<br>C107 |
| C108 | 2,12-dimethoxy-3-((2-methylbenzyl)oxy)-5,6,8,9,14,14a-hexahydroindolo[3',2':4,5]pyridine[2,1-a]isoquinoline | 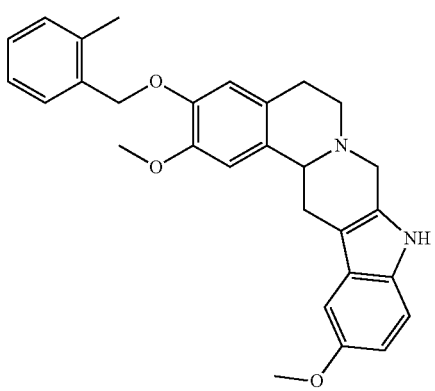<br>C108 |

-continued

| No. | Name | Structure |
|---|---|---|
| C109 | 2-methoxy-3-((2-methylbenzyl)oxy)-5,6,8,9,14,14a-hexahydroindolo[3',2':4,5]pyridine[2,1-a]isoquinoline | C109 |
| C110 | 3,12-dimethoxy-2-((2-methoxybenzyl)oxy)-5,6,8,9,14,14a-hexahydroindolo[3',2':4,5]pyridine[2,1-a]isoquinoline | C110 |
| C111 | 3-methoxy-2-((2-methoxybenzyl)oxy)-5,6,8,9,14,14a-hexahydroindolo[3',2':4,5]pyridine[2,1-a]isoquinoline | C111 |
| C112 | 3,12-dimethoxy-2-((3-methylbenzyl)oxy)-5,6,8,9,14,14a-hexahydroindolo[3',2':4,5]pyridine[2,1-a]isoquinoline | C112 |

-continued

| No. | Name | Structure |
|---|---|---|
| C113 | 3-methoxy-2-((3-methylbenzyl)oxy)-5,6,8,9,14,14a-hexahydroindolo[3',2':4,5]pyridine[2,1-a]isoquinoline | 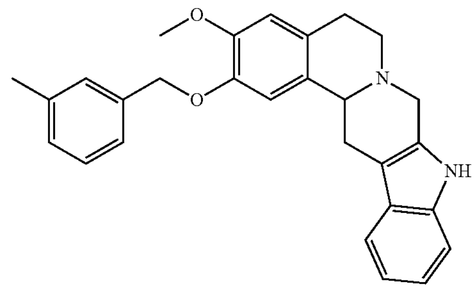 |
| C114 | 3,12-dimethoxy-2-((2-methylbenzyl)oxy)-5,6,8,9,14,14a-hexahydroindolo[3',2':4,5]pyridine[2,1-a]isoquinoline | 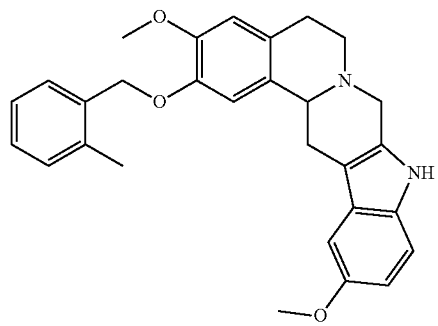 |
| C115 | 3-methoxy-2-((2-methylbenzyl)oxy)-5,6,8,9,14,14a-hexahydroindolo[3',2':4,5]pyridine[2,1-a]isoquinoline | 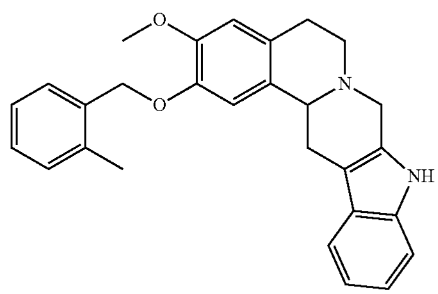 |
| C116 | 2-methoxy-3-((3,4-difluorobenzyl)oxy)-5,6,8,9,14,14a-hexahydroindolo[3',2':4,5]pyridine[2,1-a]isoquinoline | 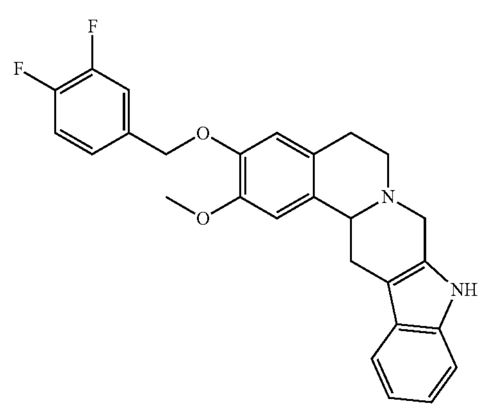 |

-continued
| No. | Name | Structure |
|---|---|---|
| C117 | 2,12-dimethoxy-3-((3,4-difluorobenzyl)oxy)-5,6,8,9,14,14a-hexahydroindolo[3',2':4,5]pyridine[2,1-a]isoquinoline | 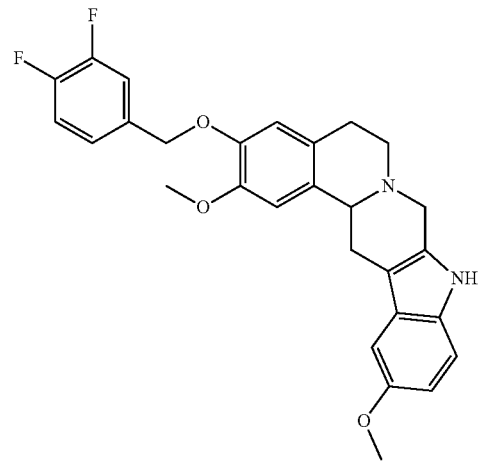 C117 |
| C118 | 2-methoxy-3-((3,5-difluorobenzyl)oxy)-5,6,8,9,14,14a-hexahydroindolo[3',2':4,5]pyridine[2,1-a]isoquinoline | 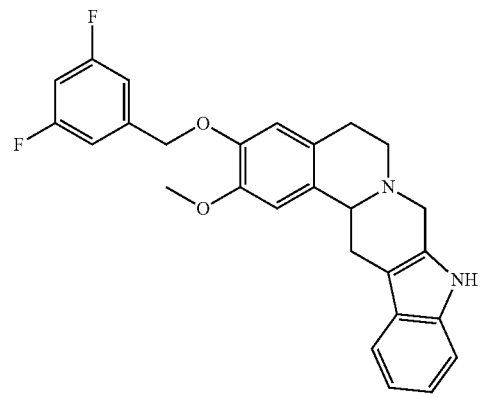 C118 |
| C119 | 2,12-dimethoxy-3-((3,5-((3,5-difluorobenzyl)oxy)-5,6,8,9,14,14a-hexahydroindolo[3',2':4,5]pyridine[2,1-a]isoquinoline | 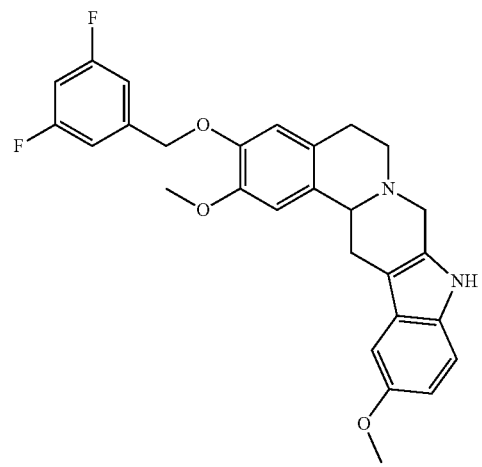 C119 |

-continued

| No. | Name | Structure |
|---|---|---|
| C120 | 2-methoxy-3-((3,4,5-trifluorobenzyl)oxy)-5,6,8,9,14,14a-hexahydroindolo[3',2':4,5]pyridine[2,1-a]isoquinoline | 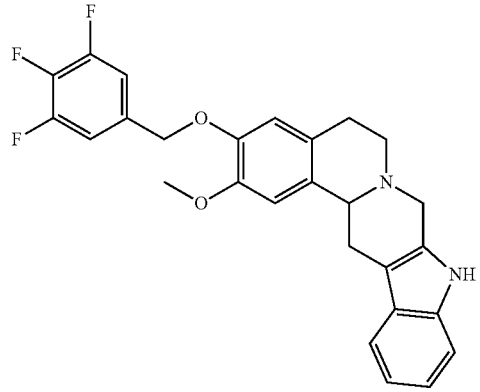<br>C120 |
| C121 | 2,12-dimethoxy-3-((3,4,5-trifluorobenzyl)oxy)-5,6,8,9,14,14a-hexahydroindolo[3',2':4,5]pyridine[2,1-a]isoquinoline | 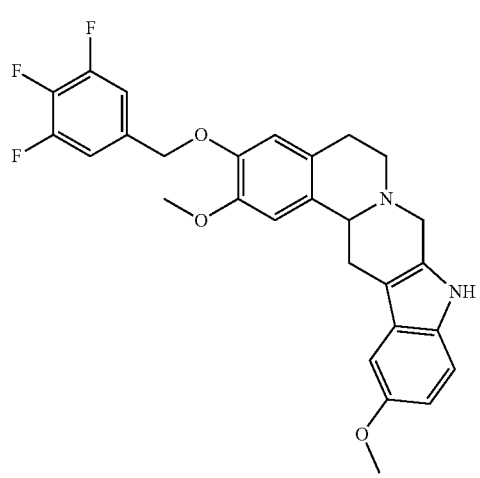<br>C121 |
| C122 | 3-methoxy-2-((3,4-difluorobenzyl)oxy)-5,6,8,9,14,14a-hexahydroindolo[3',2':4,5]pyridine[2,1-a]isoquinoline | 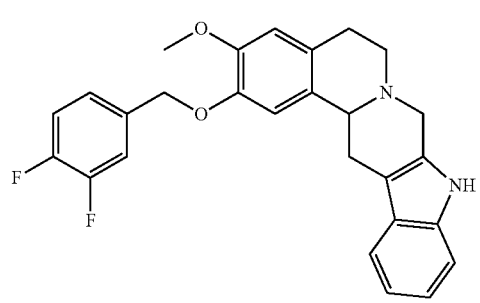<br>C122 |
| C123 | 3,12-dimethoxy-2-((3,4-difluorobenzyl)oxy)-5,6,8,9,14,14a-hexahydroindolo[3',2':4,5]pyridine[2,1-a]isoquinoline | 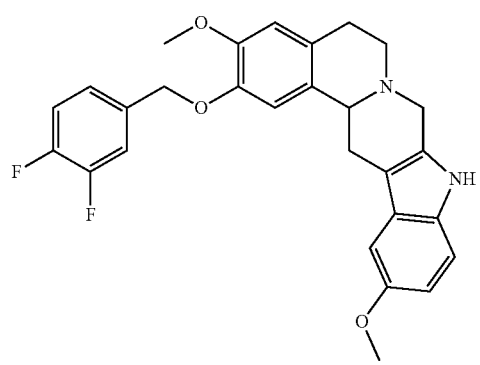<br>C123 |

-continued

| No. | Name | Structure |
|---|---|---|
| C124 | 3-methoxy-2-((3,5-difluorobenzyl)oxy)-5,6,8,9,14,14a-hexahydroindolo[3',2':4,5]pyridine[2,1-a]isoquinoline | 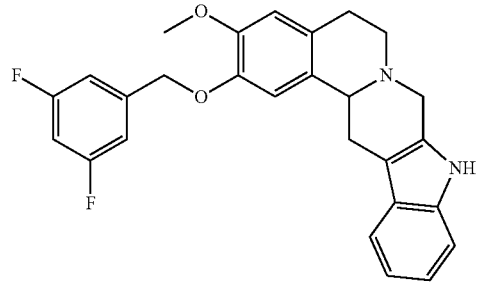<br>C124 |
| C125 | 3,12-dimethoxy-2-((3,5-difluorobenzyl)oxy)-5,6,8,9,14,14a-hexahydroindolo[3',2':4,5]pyridine[2,1-a]isoquinoline | 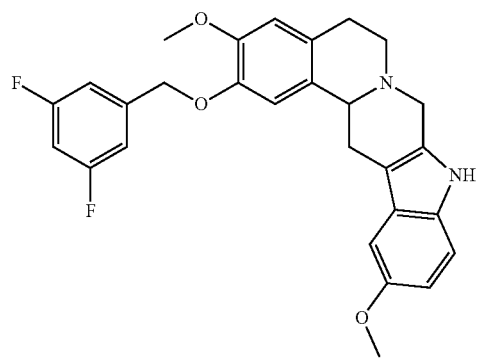<br>C125 |
| C126 | 3-methoxy-2-((3,4,5-trifluorobenzyl)oxy)-5,6,8,9,14,14a-hexahydroindolo[3',2':4,5]pyridine[2,1-a]isoquinoline | 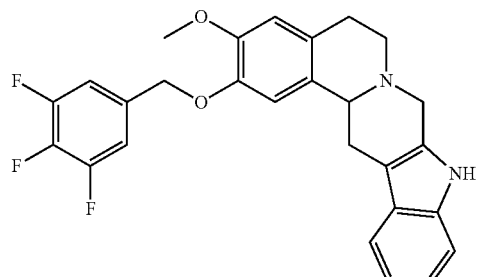<br>C126 |
| C127 | 3,12-dimethoxy-2-((3,4,5-trifluorobenzyl)oxy)-5,6,8,9,14,14a-hexahydroindolo[3',2':4,5]pyridine[2,1-a]isoquinoline | 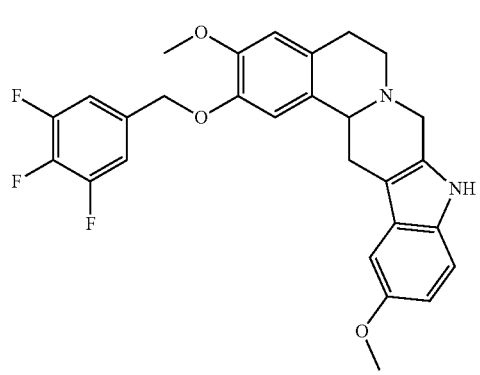<br>C127 | or an enantiomer, diastereomer, racemate, and mixture thereof, a pharmaceutically acceptable salt, crystalline hydrate and solvate thereof.

8. A PCSK9 inhibitor, which comprises a compound of claim 1, or a enantiomer, diastereomer, racemate, or mixture thereof, and a pharmaceutically acceptable salt, crystalline hydrate and solvate thereof.

9. A preparation method of formula I compound of claim 1, wherein comprises the following steps:

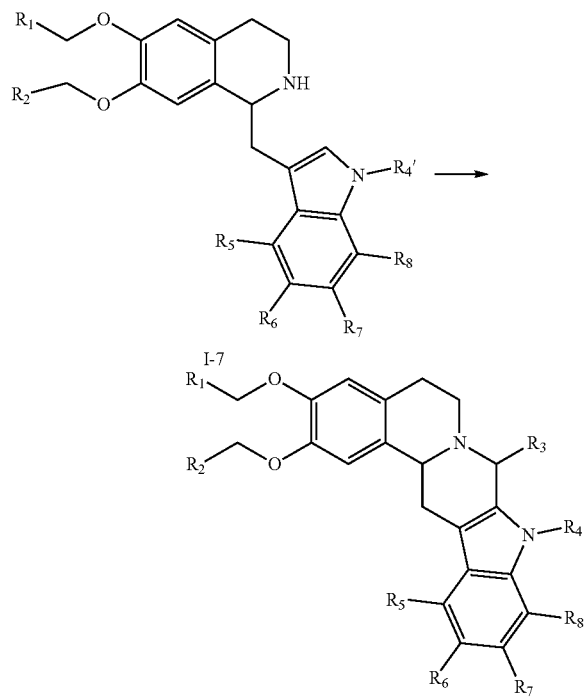

in an inert solvent, with the existence of methanoic acid, reacting $R_3$—CHO reacts with a compound of formula 1-7 to obtain a compound of formula I in the presence of formic acid;

wherein $R_4'$ is of the same definition of $R_4$, while they may be the same or different;

While the remaining groups are defined as in claim 1.

10. A pharmaceutical composition, which comprises (A) therapeutically efficient amount of one or more of a compound of claim 1, a enantiomer, diastereomer, racemate, or mixture thereof, and a pharmaceutically acceptable salt, crystalline hydrate and solvate thereof; and (B) a pharmaceutically acceptable carrier.

11. A method of treating a disease associated with a preprotein convertase subtilisin Kexin-9 (PCSK9), wherein the PCSK9-related diseases include treatment of metabolic diseases hyperlipidemia, hypercholesterolemia, hypertriglyceridemia, fatty liver deformation, atherosclerosis, and obesity, the method comprising administrating to a subject in need thereof the compound of claim 1, or a enantiomer, diastereomer, racemate, or a mixture thereof, and a pharmaceutically acceptable salt, crystalline hydrate and solvate thereof.

12. A compound of formula:

| | | |
|---|---|---|
| A110 | (12-methoxy-5,6,14,14a-tetrahydro-[1,3]dioxazo[4,5-g]indolo[3',2':4,5]pyridine[2,1-a]isoquinoline-9(8H)-yl)methanol | 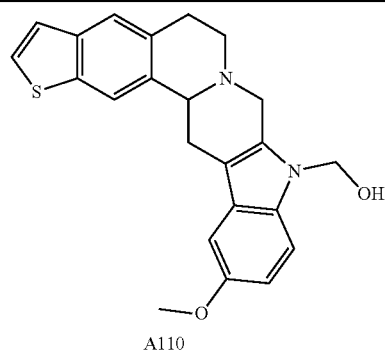 <br> A110 |
| A111 | (5,6,14,14a-tetrahydro-[1,3]dioxazo[4,5-g]indolo[3',2':4,5]pyridine[2,1-a]isoquinoline-9(8H)-yl)methanol | 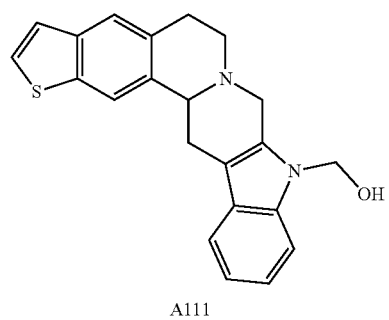 <br> A111 |

-continued
| | | |
|---|---|---|
| B37 | 8-(4-fluorophenyl)-12-methoxy-5,6,8,9,14,14a-hexahydroindole[3',2':4,5]pyridine[2,1-a]thiophene[3,2-g]isoquinoline | 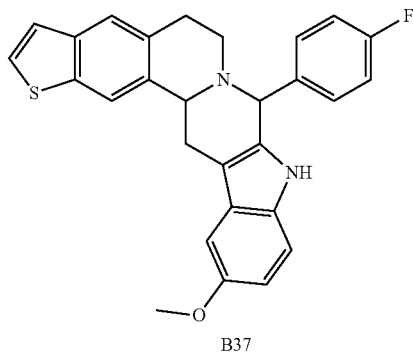 [SMILES: COc1ccc2[nH]c3c(c2c1)CC1c2cc4sccc4cc2CCN1C3c1ccc(F)cc1 ; "B37"]<br>B37 |
| B38 | 8-(4-fluorophenyl)-5,6,8,9,14,14a-hexahydroindole[3',2':4,5]pyridine[2,1-a]thiophene[3,2-g]isoquinoline | 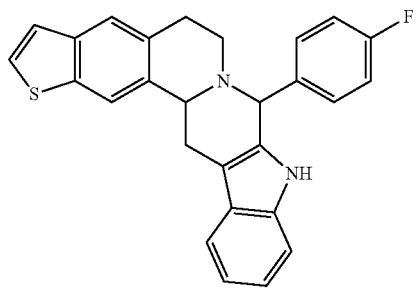<br>B38 |
| C96 | 2,3,11-trimethoxy-5,6,8,9,14,14a-hexahydroindolo[3',2':4,5]pyridine[2,1-a]isoquinoline-12-ylbenzenesulfonate | 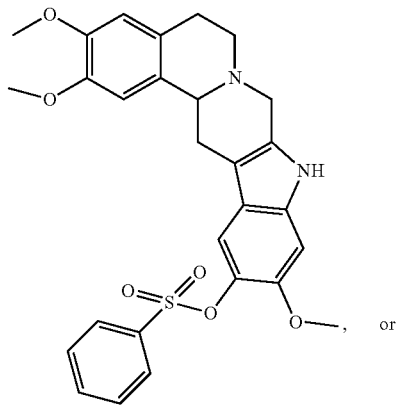, or<br>C96 |
| C97 | 2,3,12-trimethoxy-5,6,8,9,14,14a-hexahydroindolo[3',2':4,5]pyridine[2,1-a]isoquinoline-11-ylbenzenesulfonate | 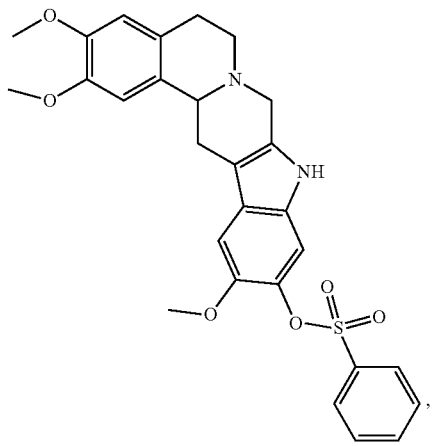,<br>C97 | or an enantiomer, diastereomer, racemate, and mixture thereof, a pharmaceutically acceptable salt, crystalline hydrate and solvate thereof.

13. The compound of claim 1, or enantiomer, diastereomer, racemate, or mixture thereof, and pharmaceutically acceptable salt, crystalline hydrate and solvate thereof, wherein $R_1$ is hydrogen.

14. The compound of claim 1, or enantiomer, diastereomer, racemate, or mixture thereof, and pharmaceutically acceptable salt, crystalline hydrate and solvate thereof, wherein $R_1$ is substituted or unsubstituted phenyl.

15. The compound of claim 1, or enantiomer, diastereomer, racemate, or mixture thereof, and pharmaceutically acceptable salt, crystalline hydrate and solvate thereof, wherein $R_2$ is hydrogen.

16. The compound of claim 1, or enantiomer, diastereomer, racemate, or mixture thereof, and pharmaceutically acceptable salt, crystalline hydrate and solvate thereof, wherein $R_2$ is substituted or unsubstituted phenyl.

17. The compound of claim 1, or enantiomer, diastereomer, racemate, or mixture thereof, and pharmaceutically acceptable salt, crystalline hydrate and solvate thereof, wherein both $R_3$ and $R_4$ are hydrogen, at least one of $R_1$, $R_2$, $R_6$, or $R_7$ is selected from the group consisting of a substituted C6-C10 aryl, substituted 5-7-membered heterocyclic ring, and —$SO_2R_9$.

\* \* \* \* \*

UNITED STATES PATENT AND TRADEMARK OFFICE
CERTIFICATE OF CORRECTION

PATENT NO. : 10,927,107 B2
APPLICATION NO. : 16/089713
DATED : February 23, 2021
INVENTOR(S) : Hong Liu et al.

Page 1 of 1

It is certified that error appears in the above-identified patent and that said Letters Patent is hereby corrected as shown below:

In the Claims

In Claim 7, at Column 370, the structure label "A$_1$" should be replaced with the structure label "A1".

In Claim 7, Column 502, between the row for structure B95 and the row for B98 should insert the following:

| | | |
|---|---|---|
| B96 | 8-fluoro-2-methoxy-3-((4-(methylsulfonyl)benzyl)oxy)-5,6,8,9,14,14a-hexahydroindolo[3',2':4,5]pyridine[2,1-a]isoquinoline | 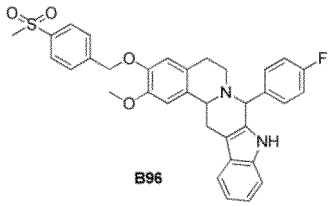 |
| B97 | 3-(benzyloxy)-11-fluoro-8-(4-fluorophenyl)-2-methoxy-5,6,8,9,14,14a-hexahydroindolo[3',2':4,5]pyridine[2,1-a]isoquinoline | 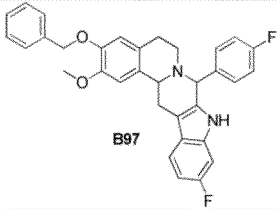 |

--                                                                                                                                                              --.

Signed and Sealed this
Seventh Day of September, 2021

Drew Hirshfeld
*Performing the Functions and Duties of the
Under Secretary of Commerce for Intellectual Property and
Director of the United States Patent and Trademark Office*